US005985869A

United States Patent [19]

Ogawa et al.

[11] Patent Number: 5,985,869

[45] Date of Patent: Nov. 16, 1999

[54] BENZOHETEROCYCLIC COMPOUNDS

[75] Inventors: Hidenori Ogawa, Tokushima-ken; Hisashi Miyamoto, Kyoto-fu; Kazumi Kondo, Tokushima-ken; Hiroshi Yamashita, Tokushima-ken; Kenji Nakaya, Tokushima-ken; Hajime Komatsu, Tokushima-ken; Michinori Tanaka, Tokushima-ken; Shinya Kora, Nagasaki-ken; Michiaki Tominaga, Tokushima-ken; Yoichi Yabuuchi, Tokushima-ken, all of Japan

[73] Assignee: Otsuka Pharmaceutical Company, Limited, Tokyo, Japan

[21] Appl. No.: 08/893,925

[22] Filed: Jul. 15, 1997

Related U.S. Application Data

[62] Division of application No. 08/474,544, Jun. 7, 1995, Pat. No. 5,753,677, which is a division of application No. 08/076,804, Jun. 10, 1993, Pat. No. 5,559,230, which is a division of application No. 07/851,541, Mar. 13, 1992, Pat. No. 5,258,510, which is a continuation-in-part of application No. 07/762,015, filed as application No. PCT/JP90/01340, Oct. 18, 1990.

[30] Foreign Application Priority Data

| | | | |
|---|---|---|---|
| Oct. 20, 1989 | [JP] | Japan | 1-274338 |
| Mar. 15, 1990 | [JP] | Japan | 2-66063 |
| Apr. 20, 1990 | [JP] | Japan | 2-105580 |
| Jul. 9, 1990 | [JP] | Japan | 2-181858 |
| Apr. 19, 1991 | [JP] | Japan | 3-182066 |

[51] Int. Cl.$^6$ .......................... A61K 31/55; A61K 31/33; A61K 31/495; C07D 243/12; C07D 243/14; C07D 245/06; C07D 241/36; C07D 239/72

[52] U.S. Cl. .......................... 514/221; 514/183; 514/220; 514/228.2; 514/228.5; 514/232.8; 514/234.5; 514/248; 514/249; 514/250; 514/259; 514/267; 540/461; 540/471; 540/473; 540/495; 540/510; 540/517; 540/557; 540/567; 540/569; 540/573; 544/60; 544/62; 544/115; 544/116; 544/234; 544/235; 544/237; 544/250; 544/251; 544/283; 544/345; 544/353

[58] Field of Search .................................... 514/183, 220, 514/221, 248, 249, 259, 267, 228.2, 228.5, 234.5, 234.8, 232.8, 250; 540/473, 567, 569, 471, 557, 461, 510, 495, 517, 573; 544/235, 237, 283, 353, 234, 250, 251, 62, 60, 345, 115, 116

[56] References Cited

U.S. PATENT DOCUMENTS

| | | | |
|---|---|---|---|
| 3,035,047 | 5/1962 | Perron et al. | 260/239.1 |
| 4,582,909 | 4/1986 | Butler et al. | 548/486 |
| 4,677,112 | 6/1987 | Butler et al. | 514/312 |
| 4,760,064 | 7/1988 | Tominaga et al. | 514/253 |

OTHER PUBLICATIONS

Yoshitake Yamamura, Hidenori Ogawa, Tomihiko Chihara, Kazumi Kondo, Toshiyuki Onogawa, Shigeki Nakamura, Toyo Mori, Michiaki Tominaga and Youichi Yabucchi, OPC–21268, An Orally Effective, Nonpeptide Vasopressin V1 Receptor Antagonist, *Science*, vol. 252, pp. 572–574 (Apr. 1991).

Ogawa et al., CAS printout of WO 91/05549, May 1991.

*Primary Examiner*—Richard L. Raymond
*Assistant Examiner*—Brenda Coleman
*Attorney, Agent, or Firm*—Sughrue, Mion, Zinn Macpeak & Seas, PLLC

[57] ABSTRACT

Novel benzoheterocyclic compounds of the formula:

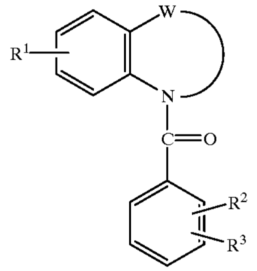

wherein $R^1$ is H, halogen, alkyl, optionally substituted amino, alkoxy; $R^2$ is H, halogen, alkoxy, phenylalkoxy, OH, alkyl, optionally substituted amino, carbamoyl-alkoxy, optionally substituted amino-alkoxy, optionally substituted benzoyloxy; $R^3$ is a group: $-NR^4R^5$ or $-CO-NR^{11}R^{12}$; $R^4$ is H, optionally substitued benzoyl, alkyl; $R^5$ is a group:

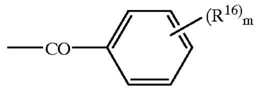

[$R^{16}$ is halogen, optionally substituted alkyl, OH, alkoxy, alkanoyloxy, alkylthio, alkanoyl, carboxy, alkoxycarbonyl, CN, $NO_2$, optionally substituted amino, phenyl, cycloalkyl, etc., or a group: $-O-A-NR^6R^7$; m is 0 to 3], phenylalkoxycarbonyl, alkanoyl, phenylalkanoyl, etc.; $R^{11}$ is H or alkyl; $R^{12}$ is cycloalkyl or optionally substituted phenyl; and W is a group: $-(CH_2)_p$ (p is 3 to 5) or $-CH=CH-(CH_2)_q$ (q is 1 to 3), the carbon atom of these groups beign optionally replaced by O, S, SO, $SO_2$ or a group: $-N(R^{13})-$ and further these groups having optionally 1 to 3 substituents of alkyl, alkoxycarbonyl, carboxy, OH, O, alkanoyloxy, etc., which have excellent vasopressin antagonistic activities and are useful as vasodilator, hypotensive agent, water diuretics, platelet agglutination inhibitor, and a vasopressin antagonistic composition containing the compound as the active ingredient.

9 Claims, 4 Drawing Sheets

BENZOHETEROCYCLIC COMPOUNDS

This is a divisional of application Ser. No. 08/474,544 filed Jun. 7, 1995 (now U.S. Pat. No. 5,753,677 issued May 19, 1998), which is a divisional of application Ser. No. 08/076,804 filed Jun. 10, 1993 (now U.S. Pat. No. 5,559,230 issued Sep. 24, 1996), which is a Divisional of application Ser. No. 07/851,541 filed Mar. 13, 1992 (now U.S. Pat. No. 5,258,510 issued Nov. 2, 1993), which is a Continuation-In-Part of application Ser. No. 07/762,015 filed Jun. 19, 1991 (now Abandoned) which is a national stage of PCT/JP80/01340, filed Oct. 18, 1990, each of which is incorporated in its entirety by reference.

TECHNICAL FIELD

This invention relates to novel benzoheterocyclic compounds which have excellent vasopressin antagonistic activities and are useful as vasodilator, hypotensive agent, water diuretics, platelet aggregation inhibitor.

DISCLOSURE OF THE INVENTION

The benzoheterocyclic compounds of this invention have the following formula:

(1)

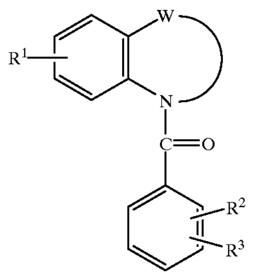

wherein $R^1$ is hydrogen atom, a halogen atom, a lower alkyl, an amino having optionally a lower alkyl substituent, or a lower alkoxy, $R^2$ is hydrogen atom, a halogen atom, a lower alkoxy, a phenyl(lower)alkoxy, hydroxy, a lower alkyl, an amino having optionally a lower alkyl substituent, a carbamoyl-substituted lower alkoxy, an amino-substituted lower alkoxy having optionally a lower alkyl substituent, or a benzoyloxy which has optionally a halogen substituent on the phenyl ring, $R^3$ is a group of the formula:

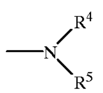

or a group of the formula:

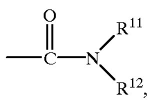

$R^4$ is hydrogen atom, a benzoyl which has optionally a halogen substituent on the phenyl ring, or a lower alkyl, $R^5$ is a group of the formula:

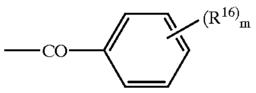

[wherein $R^{16}$ is a halogen atom; a lower alkyl which has optionally a substituent selected from a halogen atom and hydroxy; hydroxy; a lower alkoxy; a lower alkanoyloxy; a lower alkylthio; a lower alkanoyl; carboxy; a lower alkoxycarbonyl; cyano; nitro; an amino which has optionally a substituent selected from a lower alkyl and a lower alkanoyl; phenyl; a cycloalkyl; a lower alkanoyloxy-substituted lower alkoxy; a carboxy-substituted lower alkoxy; a halogen-substituted lower alkoxy; a carbamoyl-substituted lower alkoxy; a hydroxy-substituted lower alkoxy; a lower alkoxycarbonyl-substituted lower alkoxy; a phthalimido-substituted lower alkoxy; an aminocarbonyl-lower alkoxy having a lower alkyl substituent; or a group of the formula:

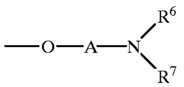

(A is a lower alkylene, and $R^6$ and $R^7$ are the same or different and are each hydrogen atom, a lower alkyl having optionally a hydroxy substituent, a lower alkanoyl, or benzoyl, or $R^6$ and $R^7$ may bind together with nitrogen atom to which they bond to form a 5- or 6-membered saturated heterocyclic group with or without being intervened with nitrogen or oxygen atom wherein the heterocyclic group has optionally a substituent selected from piperidinyl and a lower alkyl); and m is an integer of 0 to 3], a phenyl-lower alkoxycarbonyl, a lower alkanoyl, a phenyl-lower alkanoyl, a cycloalkyl-lower alkanoyl, a cycloalkylcarbonyl, tricyclo[3.3.1.1]-decanylcarbonyl, naphthylcarbonyl, pyridylcarbonyl, furoyl, thenoyl, a phenoxy-lower alkanoyl which phenyl ring has optionally 1 to 3 substituents selected from a lower alkyl, a lower alkoxy and an amino having optionally a lower alkanoyl substituent, a phthalimido-substituted lower alkanoyl, a lower alkoxycarbonyl-lower alkanoyl, a carboxy-lower alkanoyl, a naphthyloxy-lower alkanoyl, a halogen-substituted lower alkanoyl, a group of the formula:

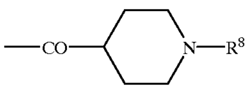

(wherein $R^8$ is hydrogen atom, a lower alkyl, a phenyl-lower alkoxycarbonyl, a carbamoyl-lower alkyl, an amino-lower alkanoyl having optionally a lower alkyl substituent, or a lower alkanoyl), an anilinocarbonyl which has optionally a lower alkyl substituent on the phenyl ring, phenoxycarbonyl, a phenylsulfonyl which has optionally a substituent selected from a halogen atom and a lower alkyl on the phenyl ring, quinolylsulfonyl, or a group of the formula:

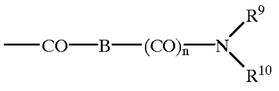

(wherein B is a lower alkylene, n is an integer of 0 or 1, and $R^9$ and $R^{10}$ are the same or different and are each hydrogen atom, a lower alkyl having optionally a hydroxy substituent, a cycloalkyl, a phenyl-lower alkyl, a lower alkanoyl, a lower alkenyl, a phenoxy-lower alkyl, a phenyl which has optionally 1 to 3 substituents selected from an amino-lower alkyl having optionally a lower alkanoyl substituent, a lower alkyl, a lower alkoxy and a halogen atom, a phthalimido-substituted lower alkyl, an amino-lower alkyl having optionally a lower alkanoyl substituent, a lower alkynyl, or an amino-lower alkyl having optionally a lower alkyl substituent, or $R^9$ and $R^{10}$ may bind together with nitrogen atom to which they bond to form a 5- or 6-membered saturated heterocyclic group with or without being intervened with nitrogen or oxygen atom wherein the heterocylic group has optionally a substituent selected from a lower alkyl, a lower alkoxycarboyl and piperidinyl), $R^{11}$ is hydrogen atom or a lower alkyl, $R^{12}$ is a cycloalkyl, or a phenyl which has optionally 1 to 3 substituents selected from a lower alkoxy, a lower alkyl and a halogen atom, W is a group of the formula: $-(CH_2)_p-$ (p is an integer of 3 to 5), or a group of the formula: $-CH{=}CH-(CH_2)_q-$ (q is an integer of 1 to 3), the carbon atom of these groups: $-(CH_2)_p-$ and $-CH{=}CH-(CH_2)_q-$ being optionally replaced by oxygen atom, sulfur atom, sulfinyl, sulfonyl, or a group of the formula:

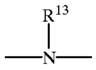

($R^{13}$ is hydrogen atom, a cycloalkyl, or a lower alkyl), and further said $-(CH_2)_p-$ and $-CH{=}CH-(CH_2)_q-$ groups having optionally 1 to 3 substituents selected from a lower alkyl having optionally a hydroxy substituent, a lower alkoxycarbonyl, carboxy, hydroxy, oxo, a lower alkanoyloxy having optionally a halogen substituent, an amino-lower alkyl having optionally a substituent selected from a lower alkyl and a lower alkanoyl, a lower alkanoyloxy-substituted lower alkyl, a lower alkyl sulfonyloxy-lower alkyl, an azido-lower alkyl, a group of the formula:

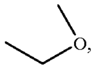

an aminocarbonyloxy having optionally a lower alkyl substituent, a lower alkoxy, a lower alkoxycarbonyl-substituted lower alkoxy, a carboxy-substituted lower alkoxy, an aminocarbonyl-lower alkoxy having optionally a lower alkyl substituent, an amino-lower alkoxy having optionally a substituent selected from a lower alkyl and a lower alkanoyl, a phthalimido-substituted lower alkoxy, hydroxyimino, a lower alkanoyloxyimino, a lower alkylidene, a halogen atom, azido, sulfoxyimino, a group of the formula:

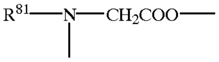

($R^{81}$ is hydrogen atom or a lower alkyl), hydrazino, pyrrolyl, an amino-lower alkanoyloxy having optionally a lower alkyl substituent, a group of the formula:

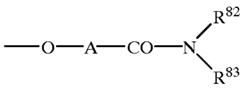

(A is as defined above, and $R^{82}$ and $R^{83}$ are the same or different and are each hydrogen atom, a lower alkyl, a carbamoyl-substituted lower alkyl, a hydroxy-substituted lower alkyl, or a pyridyl-lower alkyl, or $R^{82}$ and $R^{83}$ may bind together with nitrogen atom to which they bond to form a 5- or 6-membered saturated heterocyclic group with or without being intervened with nitrogen, oxygen or sulfur atom wherein the heterocyclic group has optionally a substituent selected from oxo, a lower alkyl, a lower alkanoyl, and carbamoyl), and a group of the formula:

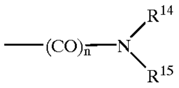

(wherein n is as defined above, and $R^{14}$ and $R^{15}$ are the same or different and are each hydrogen atom, a lower alkyl, a lower alkenyl, a lower alkanoyl, a cycloalkyl, an oxiranyl-substituted lower alkyl, a lower alkyl having optionally 1 to 2 substituents selected from a lower alkoxy, hydroxy and an amino having optionally a lower alkyl substituent, a phenyl-lower alkyl, a pyridyl-lower alkyl, a lower alkylsulfonyl, benzoyl, a lower alkoxy-carbonyl, anilinocarbonyl, an aminocarbonyl having optionally a lower alkyl substituent, a cyano-substituted lower alkyl, a lower alkoxycarbonyl-substituted lower alkyl, a carbamoyl-substituted lower alkyl, a carboxy-substituted lower alkyl, a tetrahydropyranyloxy-substituted lower alkyl, a lower alkanoyloxy-substituted lower alkyl, a piperidinyl having optionally a phenyl-lower alkyl substituent on the piperidinyl ring, a halogen-substituted lower alkanoyl, an imidazolyl-substituted lower alkanoyl, an amino-lower alkanoyl having optionally a substituent selected from a lower alkyl and a lower alkoxycarbonyl, an aminocarbonyl-lower alkyl having optionally a lower alkyl substituent, or a phenyl-lower alkoxycarbonyl, or $R^{14}$ and $R^{15}$ may bind together with nitrogen atom to which they bond to form a 5- or 6-membered saturated heterocyclic group with or without being intervened with nitrogen or oxygen, wherein the heterocyclic group may optionally have a substituent selected from a lower alkyl, a phenyl-lower alkyl or a lower alkanoyl).

The benzoheterocyclic compounds of the formula (1) and their salts have excellent vasopressin antagonistic activities and vasodilating activity, hypotensive activity, activity for inhibiting saccharide release in liver, activity for inhibiting growth of mesangium cells, water diuretic activity, platelet agglutination inhibitory activity and are useful as vasodilator, hypotensive agent, water diuretics, platelet agglutination inhibitor and are used for the prophylaxis and treatment of hypertension, edema, ascites, heart failure, renal function disorder, vasopressin parasecretion syndrome (SIADH), hepatocirrhosis, hyponatremia, hypokaliemia, diabetic, circulation disorder, and the like.

Each group in the above formula (1) includes specifically the following groups.

The "lower alkoxy" includes a straight chain or branched chain alkoxy group having 1 to 6 carbon atoms, for example, methoxy, ethoxy, propoxy, isopropoxy, butoxy, tert-butoxy, pentyloxy, hexyloxy, and the like.

The "lower alkyl" includes a straight chain or branched chain alkyl group having 1 to 6 carbon atoms, for example, methyl, ethyl, propyl, isopropyl, butyl, tert-butyl, pentyl, hexyl, and the like.

The "halogen atom" includes fluorine atom, chlorine atom, bromine atom and iodine atome.

The "amino having optionally a lower alkyl substituent" includes an amino having optionally one or two substituents selected from a straight chain or branched chain alkyl group having 1 to 6 carbon atoms, for example, amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, and the like.

The "lower alkenyl" includes a straight chain or branched chain alkenyl group having 2 to 6 carbon atoms, for example, vinyl, allyl, 2-butenyl, 3-butenyl, 1-methylallyl, 2-pentenyl, 2-hexenyl, and the like.

The "lower alkyl which has optionally a substituent selected from a halogen atom and hydroxy" includes a straight chain or branched chain alkyl group having 1 to 6 carbon atoms which may optionally have 1 to 3 substituents selected from a halogen atom and hydroxy, for example, in addition to the above-mentioned lower alkyl groups, hydroxymethyl, 2-hydroxyethyl, 1-hydroxyethyl, 3-hydroxypropyl, 2,3-dihyroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dichlorohexyl, and the like.

The "lower alkylene" includes a straight chain or branched chain alkylene group having 1 to 6 carbon atoms, for example, methylene, ethylene, trimethylene, 2-methyltrimethylene, 2,2-dimethyltrimethylene, 1-methyltrimethylene, methylmethylene, ethylmethylene, tetramethylene, pentamethylene, hexamethylene, and the like.

The "lower alkanoyloxy" includes a straight chain or branched chain alkanoyloxy group having 1 to 6 carbon atoms, for example, formyloxy, acetyloxy, propionyloxy, butyryloxy, isobutyryloxy, pentanoyloxy, tert-butylcarbonyloxy, hexanoyloxy, and the like.

The "lower alkylthio" includes a straight chain or branched chain alkylthio group having 1 to 6 carbon atoms, for example, methylthio, ethylthio, propylthio, isopropylthio, butylthio, tert-butylthio, pentylthio, hexylthio, and the like.

The "lower alkanoyl" includes a straight chain or branched chain alkanoyl group having 1 to 6 carbon atoms, for example, formyl, acetyl, propionyl, butyryl, isobutyryl, pentanoyl, tert-butylcarbonyl, hexanolyl, and the like.

The "lower alkoxycarbonyl" includes a straight chain or branched chain alkoxycarbonyl group having 1 to 6 carbon atoms in the alkoxy moiety, for example, methoxycarbonyl, ethoxycarbonyl, propoxycarbonyl, isopropoxycarbonyl, butoxycarbonyl, tert-butoxycarbonyl, pentyloxycarbonyl, hexyloxycarbonyl, and the like.

The "amino having optionally a substituent selected from a lower alkyl and a lower alkanoyl" includes an amino having optionally one or two substituents selected from a straight chain or branched chain alkyl group having 1 to 6 carbon atoms and a straight chain or branched chain alkanoyl group having 1 to 6 carbon atoms, for example, amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, N-methyl-N-acetylamino, N-acetylamino, N-formylamino, N-propionylamino, N-butyrylamino, N-isobutyrylamino, N-pentanoylamino, N-tert-butylcarbonylamino, N-hexanoylamino, N-ethyl-N-acetylamino, and the like.

The "cycloalkyl" includes a cycloalkyl having 3 to 8 carbon atoms, for example, cyclopropyl, cyclobutyl, cyclopentyl, cyclohexyl, cycloheptyl, cyclooctyl, and the like.

The "lower alkanoyloxy-substituted lower alkoxy" includes a straight chain or branched chain alkoxy group having 1 to 6 carbon atoms which is substituted by a straight chain or branched chain alkanoyloxy group having 2 to 6 carbon atoms, for example, acetyloxymethoxy, 2-propionyloxyethoxy, 1-butyryloxyethoxy, 3-acetyloxypropoxy, 4-acetyloxybutoxy, 4-isobutyryloxybutoxy, 5-pentanoyloxypentyloxy, 6-acetyloxyhexyloxy, 6-tert-butylcarbonyloxyhexyloxy, 1,1-dimethyl-2-hexanoyloxyethoxy, 2-methyl-3-acetyloxypropoxy, and the like.

The "carbamoyl-substituted lower alkoxy" includes a carbamoyl-substituted alkoxy group wherein the alkoxy moiety is a straight chain or branched chain alkoxy group having 1 to 6 carbon atoms, for example, carbamoylmethoxy, 2-carbamoylethoxy, 1-carbamoylethoxy, 3-carbamoylpropoxy, 4-carbamoylbutoxy, 5-carbamoylpentyloxy, 6-carbamoylhexyloxy, 1,1-dimethyl-2-carbamoylethoxy, 2-methyl-3-carbamoylpropoxy, and the like.

The "hydroxy-substituted lower alkoxy" includes a straight chain or branched chain alkoxy group having 1 to 6 carbon atoms and having 1 to 3 hydroxy substitutents, for example, hydroxymethoxy, 2-hydroxyethoxy, 1-hydroxyethoxy, 3-hydroxypropoxy, 2,3-dihydroxypropoxy, 4-hydroxybutoxy, 3,4-dihydroxybutoxy, 1,1-dimethyl-2-hydroxyethoxy, 5-hydroxypentyloxy, 6-hydroxyhexyloxy, 2-methyl-3-hydroxypropoxy, 2,3,4-trihydroxybutoxy, and the like.

The "lower alkoxycarbonyl-substituted lower alkoxy" includes an alkoxycarbonyl-substituted straight chain or branched chain alkoxy group having 1 to 6 carbon atoms wherein the alkoxycarbonyl moiety is a straight chain or branched chain alkoxycarbonyl group having 1 to 6 carbon atoms, for example, methoxycarbonylmethoxy, 3-methoxycarbonylpropoxy, ethoxycarboxymethoxy, 3-ethoxycarbonylpropoxy, 4-ethoxycarbonylbutoxy, 5-isopropoxycarbonylpentyloxy, 6-propoxycarbonylhexyloxy, 1,1-dimethyl-2- butoxycarbonylethoxy, 2-methyl-3-tertbutoxycarbonylpropoxy, 2-pentyloxycarbonylethoxy, hexyloxycarbonylmethoxy, and the like.

The "carboxy-substituted lower alkoxy" includes a carboxy-substituted alkoxy group wherein the alkoxy moiety is a straight chain or branched chain alkoxy group having 1 to 6 carbon atoms, for example, carboxymethoxy, 2-carboxyethoxy, 1-carboxyethoxy, 3-carboxypropoxy, 4-carboxybutoxy, 5-carboxypentyloxy, 6-carboxyhexyloxy, 1,1-dimethyl-2-carboxyethoxy, 2-methyl-3-carboxypropoxy, and the like.

The "phthalimido-substituted lower alkoxy" includes a straight chain or branched chain alkoxy group having 1 to 6 carbon atoms which is substituted by phthalimido group, for example, phthalimidomethoxy, 2-phthalimidoethoxy, 1-phthalimidoethoxy, 3-phthalimidopropoxy, 4-phthalimidobutoxy, 5-phthalimidopentyloxy, 6-phthalimidohexyloxy, 1,1-dimethyl-2-phthalimidoethoxy, 2-methyl-3-phthalimidopropoxy, and the like.

The "5- or 6-membered saturated heterocyclic group which is formed by binding the groups $R^6$ and $R^7$ together with the nitrogen atom to which they bond with or without being intervened with nitrogen or oxygen atom" includes, for example, pyrrolidinyl, piperidinyl, piperazinyl, morpholino, and the like.

The "heterocyclic group having a substituent selected from piperidinyl and a lower alkyl" includes a heterocyclic group having 1 to 3 substituents selected from piperidinyl and a straight chain or branched chain alkyl group having 1 to 6 carbon atoms, for example, 4-methylpiperiazinyl, 3,4-dimethylpiperazinyl, 3-ethylpyrrolidinyl, 2-propylpyrrolidinyl, 3,4,5-trimethylpiperidinyl, 4-butylpiperidinyl, 3-pentylmorpholino, 4-hexylpiperazinyl, 4-(1-piperidinyl)piperidinyl, 3-(1-piperidinyl)pyrrolidinyl, 3-(1-piperidinyl)-4-methylpiperazinyl, 3-(1-piperidinyl) morpholino, and the like.

The "phenyl(lower)alkanoyl" includes a phenylalkanoyl wherein the alkanoyl moiety is a straight chain or branched chain alkanoyl group having 2 to 6 carbon atoms, for example, phenylacetyl, 3-phenylpropionyl, 2-phenylpropionyl, 4-phenylbutyryl, 2,2-dimethyl-3-phenylpropionyl, 5-phenylpentanoyl, 6-phenylhexanoyl, and the like.

The "cycloalkyl-lower alkanoyl" includes $C_3$–$C_8$ cycloalkyl-alkanoyl group wherein the alkanoyl moiety is a straight chain or branched chain alkanoyl having 2 to 6 carbon atoms, for example, cyclohexylacetyl, 3-cyclopropylpropionyl, 2-cyclopentylpropionyl, 4-cyclohexylbutyryl, 2,2-dimethyl-3-cycloheptylpropionyl, 5-cyclooctylpentanoyl, 6-cyclohexylhexanoyl, and the like.

The "cycloalkylcarbonyl" includes a cycloalkylcarbonyl having 3 to 8 carbon atoms, for example, cyclopropylcarbonyl, cyclobutylcarbonyl, cyclopentylcarbonyl, cyclohexylcarbonyl, cycloheptylcarbonyl, cyclooctylcarbonyl, and the like.

The "amino having optionally a lower alkanoyl substituent" includes an amino having optionally a straight chain or branched chain alkanoyl group having 1 to 6 carbon atoms, for example, amino, formylamino, acetylamino, propionylamino, butyrylamino, isobutyrylamino, pentanoylamino, tert-butylcarbonylamino, hexanoylamino, and the like.

The "phenoxy-lower alkanoyl which phenyl ring has optionally 1 to 3 substituents selected from a lower alkyl, a lower alkoxy and an amino having optonally a lower alkanoyl substituent" includes a phenoxyalkanoyl group wherein the alkanoyl moiety is a straight chain or branched chain alkanoyl having 2 to 6 carbon atoms and the phenyl ring has optionally 1 to 3 substituents selected from a straight chain or branched chain alkyl having 1 to 6 carbon atoms, a straight chain or branched chain alkoxy having 1 to 6 carbon atoms and an amino having optionally a straight chain or branched chain alkanoyl having 1 to 6 carbon atoms, for example, phenoxyacetyl, 3-phenoxypropionyl, 2-phenoxypropionyl, 4-phenoxybutyryl, 2,2-dimethyl-3-phenoxypropionyl, 5-phenoxypentanoyl, 6-phenoxyhexanoyl, (2-aminophenoxy)acetyl, 3-(4-aminophenoxy)propionyl, (2-methylphenoxy)acetyl, (4-methylphenoxy)acetyl, (3-methylphenoxy)acetyl, (3-methoxyphenoxy)acetyl, (3-acetylaminophenoxy)acetyl, 4-(2-propionylaminophenoxy)butyryl, 2,2-dimethyl-3-(4-butyrylaminophenoxy)propionyl, 5-(2-pentanoylaminophenoxy)pentanoyl, 6-(4-hexanoylaminophenoxy)hexanoyl, 3-(2-ethylphenoxy)propionyl, 2-(4-propylphenoxy)propionyl, 4-(4-butylphenoxy)butyryl, 5-(3-pentylphenoxy)pentanoyl, 6-(4-hexylphenoxy)hexanoyl, (2,3-dimethylphenoxy)acetyl, (2,5-dimethylphenoxy)acetyl, (3,4-dimethylphenoxy)acetyl, (3,4,5-trimethylphenoxy)acetyl, 3-(4-ethoxyphenoxy)propionyl, 2-(2-propoxyphenoxy)propionyl, 4-(3-butoxyphenoxy)butyryl, 5-(4-pentyloxyphenoxy)pentanoyl, 6-(4-hexyloxyphenoxy)hexanoyl, (3,4-dimethoxyphenoxy)acetyl, (3,5-dimethoxyphenoxy)acetyl, (2,4-dimethoxyphenoxy)acetyl, (3,4,5-trimethoxyphenoxy)acetyl, (2-acetylamino-4-methylphenoxy)acetyl, (4-acetylamino-3-methoxyphenoxy)acetyl, and the like.

The "phthalimido-substituted lower alkanoyl" includes a straight chain or branched chain alkanoyl group having 2 to 6 carbon atoms which is substituted by phthalimido group, for example, 2-phthalimidoacetyl, 3-phthalimidopropionyl, 2-phthalimidopropionyl, 4-phthalimidobutyryl, 2,2-dimethyl-3-phthalimidopropionyl, 5-phthalimidopentanoyl, 6-phthalimidohexanoyl, 3-methyl-4-phthalimidobutyryl, and the like.

The "lower alkoxycarbonyl-lower alkanoyl" includes an alkoxycarbonyl-alkanoyl group wherein the alkoxy moiety is a straight chain or branched chain alkoxy having 1 to 6 carbon atoms and the alkanoyl moiety is a straight chain or branched chain alkanoyl having 2 to 6 carbon atoms, for example, methoxycarbonylacetyl, 3-methoxycarbonylpropionyl, ethoxycarbonylacetyl, 3-ethoxycarbonylpropionyl, 4-ethoxycarbonylbutyryl, 3-propoxycarbonylpropionyl, 2-methoxycarbonylpropionyl, 6-propoxycarbonylhexanoyl, 5-isopropoxycarbonylpentanoyl, 2,2-dimethyl-3-butoxycarbonylpropionyl, 2-methyl-3-tert-butoxycarbonylpropionyl, pentyloxycarbonylacetyl, hexyloxycarbonylacetyl, and the like.

The "carboxy-lower alkanoyl" includes a carboxyalkanoyl group wherein the alkanoyl moiety is a straight chain or branched chain alkanoyl having 2 to 6 carbon atoms, for example, carboxyacetyl, 3-carboxypropionyl, 2-carboxypropionyl, 4-carboxybutyryl, 2,2-dimethyl-3-carboxypropionyl, 5-carboxypentanoyl, 6-carboxyhexanoyl, and the like.

The "naphthyloxy-lower alkanoyl" includes a naphthyloxy-alkanoyl group wherein the alkanoyl moiety is a straight chain or branched chain alkanoyl having 2 to 6 carbon atoms, for example, naphtyloxyacetyl, 3-naphtyloxypropionyl, 2-naphtyloxypropionyl, 4-naphthyloxybutyryl, 2,2-dimethyl-3-naphthyloxypropionyl, 5-naphthyloxypentanoyl, 6-naphthyloxyhexanoyl, and the like.

The "phenyl-lower alkoxycarbonyl" includes a phenylalkoxycarbonyl wherein the alkoxycarbonyl moiety is a straight chain or branched chain alkoxycarbonyl group having 1 to 6 carbon atoms, for example, benzyloxycarbonyl, 2-phenylethoxycarbonyl, 1-phenylethoxycarbonyl, 3-phenylpropoxycarbonyl, 4-phenylbutoxycarbonyl, 5-phenylpentyloxycarbonyl, 6-phenylhexyloxycarbonyl, 1,1-dimethyl-2-phenylethoxycarbonyl, 2-methyl-3-phenylpropoxycarbonyl, and the like.

The "lower alkyl having optionally a hydroxy substituent" includes a straight chain or branched chain alkyl having 1 to 6 carbon atoms and having optionally 1 to 3 hydroxy substituents, for example, hydroxymethyl, 2-hydroxyethyl, 1-hydroxyethyl, 3-hydroxypropyl, 2,3-dihydroxyethyl, 4-hydroxybutyl, 3,4-dihydroxybutyl, 1,1-dimethyl-2-hydroxyethyl, 5-hydroxypentyl, 6-hydroxyhexyl, 2-methyl-3-hydroxypropyl, 2,3,4-trihydroxybutyl, and the like.

The "phenyl-lower alkyl" includes a phenylalkyl group wherein the alkyl moiety is a straight chain or branched chain alkyl group having 1 to 6 carbon atoms, for example, benzyl, 2-phenylethyl, 1-phenylethyl, 3-phenylpropyl, 4-phenylbutyl, 5-phenylpentyl, 6-phenylhexyl, 1,1-dimethyl-2-phenylethyl, 2-methyl-3-phenylpropyl, and the like.

The "phenoxy-lower alkyl" includes a phenoxyalkyl group wherein the alkyl moiety is a straight chain or branched chain alkyl group having 1 to 6 carbon atoms, for example, phenoxymethyl, 1-phenoxyethyl, 2-phenoxyethyl, 3-phenoxypropyl, 4-phenoxybutyl, 5-phenoxypentyl, 6-phenoxyhexyl, 1,1-dimethyl-2-phenoxyethyl, 2-methyl-3-phenoxypropyl, and the like.

The "phenyl which has optionally 1 to 3 substituents selected from a lower alkyl, a lower alkoxy and a halogen atom" includes a phenyl group which has optionally 1 to 3 substituents selected from a straight chain or branched chain alkyl group having 1 to 6 carbon atoms, a straight chain or branched chain alkoxy group having 1 to 6 carbon atoms and a halogen atom, for example, phenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-pentyloxyphenyl, 2,4-dimethoxyphenyl, 4-hexyloxyphenyl, 3,4-dimethoxyphenyl, 3-ethoxy-4-methoxyphenyl, 2,3-dimethoxyphenyl, 3,4-diethoxyphenyl, 2,5-dimethoxyphenyl, 2,6-dimethoxyphenyl, 3,5-dimethoxyphenyl, 3,4-dipentyloxyphenyl, 3,4,5-trimethoxyphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 3-iodophenyl, 4-iodophenyl, 3,4-dichlorophenyl, 3,5-dichlorophenyl, 2,6-dichlorophenyl, 2,3-dichlorophenyl, 2,4-dichlorophenyl, 3,4-difluorophenyl, 3,5-dibromophenyl, 3,4,5-trichlorophenyl, 2-methoxy-3-chlorophenyl, 2-methylphenyl, 3-methylphenyl, 4-methylphenyl, 2-ethylphenyl, 3-ethylphenyl, 4-ethylphenyl, 4-isopropylphenyl, 3-butylphenyl, 4-pentylphenyl, 4-hexylphenyl, 3,4-dimethylphenyl, 3,4-diethylphenyl, 2,4-dimethylphenyl, 2,5-dimethylphenyl, 2,6-dimethylphenyl, 3,4,5-trimethylphenyl, 3-chloro-4-methylphenyl, 3-methoxy-4-methyl- 5-iodophenyl, 3,4-dimethoxy-5-bromophenyl, 3,5-diiodo-4-methoxyphenyl, and the like.

The "amino-lower alkyl having optionally a lower alkyl substituent" includes a straight chain or branched chain alkyl group having 1 to 6 carbon atoms which is substituted by an amino group having optionally 1 to 2 substituents of a straight chain or branched chain alkyl group having 1 to 6 carbon atoms, for example, aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminomethyl, (N-ethyl-N-propylamino)methyl, 2-(N-methyl-N-hexylamino)ethyl, and the like.

The "5- or 6-membered saturated heterocyclic group which is formed by binding the groups $R^9$ and $R^{10}$ together with the nitrogen atom to which they bond with or without being intervened with nitrogen or oxygen atom" includes, for example, pyrrolidinyl, piperidinyl, piperazinyl, morpholino, and the like.

The "heterocyclic group having a substituent selected from a lower alkyl, a lower alkoxycarbonyl and piperidinyl" includes a heterocyclic group having 1 to 3 substituents selected from a straight chain or branched chain alkyl group having 1 to 6 carbon atoms, a straight chain or branched chain alkoxycarbonyl having 1 to 6 carbon atoms and piperidinyl, for example, in addition to the above-mentioned heterocyclic groups having a substituent of a lower alkyl and piperidinyl, 4-methoxycarbonylpiperazinyl, 4-ethoxycarbonylpiperidinyl, 3-propoxycarbonylpyrrolidinyl, 2-pentyloxycarbonylmorpholino, 4-hexyloxycarbonylpiperidinyl, 4-ethoxycarbonyl-3-methylpiperidinyl, 3-methyl-4-ethoxycarbonylpiperazinyl, and the like.

The "5- or 6-membered saturated heterocyclic group which is formed by binding the groups $R^{14}$ and $R^{15}$ together with the nitrogen atom to which they bond with or without being intervened with nitrogen or oxygen atom" includes, for example, pyrrolidinyl, piperidinyl, piperazinyl, morpholino, and the like.

The "heterocyclic group having a lower alkyl substituent" includes a heterocyclic group having 1 to 3 substituents of a straight chain or branched chain alkyl group having 1 to 6 carbon atoms, for example, 4-methylpiperazinyl, 3,4-dimethylpiperazinyl, 3-ethylpyrrolidinyl, 2-propylpyrrolidinyl, 3,4,5-trimethylpiperidinyl, 4-butylpiperidinyl, 3-pentylmorpholino, 4-hexylpiperazinyl, and the like.

The heterocyclic ring in the formula (1) includes tetrahydroquinolyl, 2,3,4,5-tetrahydro-1H-benzazepinyl, 1,2,3,4,5,6-hexahydrobenzazocinyl, 1,2-dihydroquinolyl, 2,3-dihydro-1H-benzazepinyl, 1,2,3,4-tetrahydrobenzazocinyl, and the like.

The heterocyclic ring in the formula (1) wherein the carbon atom in the group of the formula: $-(CH_2)_p-$ or $-CH{=}CH-(CH_2)_q-$ for W is replaced by oxygen atom, sulfur atom, sulfinyl, sulfonyl, or a group of the formula:

($R^{13}$ is hydrogen atom or a lower alkyl) includes a heterocylic group wherein the carbon atom in the group of the formula: $-(CH_2)_p-$ or $-CH{=}CH-(CH_2)_q-$ for W is replaced by oxygen atom, sulfur atom, sulfinyl, sulfonyl, or a group of the formula:

($R^{13}$ is hydrogen atom or a straight chain or branched chain alkyl having 1 to 6 carbon atoms), for example, 3,4-dihydro- 2H-1,4-benzoxazinyl, 1,2,3,5-tetrahydro-4,1-benzoxazepinyl, 1,2,3,4-tetrahydroquinoxalinyl, 1,2,3,4,5,6-hexahydro-1,5-benzodiazocinyl, 5-methyl-1,2,3,4,5,6-hexahydro-1,5-benzodiazocinyl, 4-methyl-1,2,3,4-tetrahydroquinoxalinyl, 1,2,3,4-tetrahydro-5,1-benzoxazepinyl, 3,4-dihydro-2H-1,4-benzothiazinyl, 2,3,4,5-tetrahydro-1,5-benzothiazepinyl, 1,2,3,5-tetrahydro-4,1-benzothiazepinyl, 4-ethyl-1,2,3,4-tetrahydroquinoxalinyl, 4-propyl-1,2,3,4-tetrahydroquinoxalinyl, 4-butyl-1,2,3,4-tetrahydroquinoxalinyl, 4-pentyl-1,2,3,4-tetrahydroquinoxalinyl, 4-hexyl-1,2,3,4-tetrahydroquinoxalinyl, 2,3,4,5-tetrahydro-1H-1,4-benzodiazepinyl, 4-methyl-2,3,4,5-tetrahydro-1H-1,4-benzodiazepinyl, 4-ethyl-2,3,4,5-tetrahydro-1H-1,4-benzodiazepinyl, 4-propyl-2,3,4,5-tetrahydro-1H-1,4-benzodiazepinyl, 4-butyl-2,3,4,5-tetrahydro-1H-1,4-benzodiazepinyl, 4-pentyl-2,3,4,5-tetrahydro-1H-1,4-benzodiazepinyl, 4-hexyl-2,3,4,5-tetrahydro-1H-1,4-benzodiazepinyl, 2,3,4,5-tetrahydro-1H-1,5-benzodiazepinyl, 5-methyl-2,3,4,5-tetrahydro-1H-1,5-benzodiazepinyl, 5-ethyl-2,3,4,5-tetrahydro-1H-1,5-benzodiazepinyl, 5-propyl-2,3,4,5-tetrahydro-1H-1,5-benzodiazepinyl, 5-butyl-2,3,4,5-tetrahydro-1H-1,5-benzodiazepinyl, 5-pentyl-2,3,4,5-tetrahydro-1H-1,5-benzodiazepinyl, 5-hexyl-2,3,4,5-tetrahydro-1H-1,5-benzodiazepinyl, 3,4-dihydro-1-oxo-2H-1,4-benzothiazepinyl, 3,4-dihydro-1,1-dioxo-2H-1,4-benzothiazepinyl, 1-oxo-2,3,4,5-tetrahydro-1,5-benzothiazepinyl, 1,1-dioxo-2,3,4,5-tetrahydro-1,5-benzothiazepinyl, 4-oxo-1,2,3,5-tetrahydro-4,1-benzothiazepinyl, 4,4-dioxo-1,2,3,5-tetrahydro-4,1-benzothiazepinyl, and the like.

The “halogen-substituted lower alkoxy” includes a straight chain or branched chain alkoxy group having 1 to 6 carbon atoms which has 1 to 3 substituents of a halogen atom, for example, trifluoromethoxy, trichloromethoxy, chloromethoxy, bromomethoxy, fluoromethoxy, iodomethoxy, difluoromethoxy, dibromomethoxy, 2-chloroethoxy, 2,2,2-trifluoroethoxy, 2,2,2-trichloroethoxy, 3-chloropropoxy, 2,3-dichloropropoxy, 4,4,4-trichlorobutoxy, 4-fluorobutoxy, 5-chloropentyloxy, 3-chloro-2-methylpropoxy, 6-bromohexyloxy, 5,6-dichlorohexyloxy, and the like.

The “halogen-substituted lower alkanoyl” includes a straight chain or branched chain alkanoyl group having 1 to 6 carbon atoms which has 1 to 3 substituents of a halogen atom, for example, 2,2,2-trifluoroacetyl, 2,2,2-trichloroacetyl, 2-chloroacetyl, 2-bromoacetyl, 2-fluoroacetyl, 2-iodoacetyl, 2,2-difluoroacetyl, 2,2-dibromoacetyl, 3,3,3-trifluoropropionyl, 3,3,3-trichloropropionyl, 3-chloropropionyl, 2,3-dichloropropionyl, 4,4,4-trichlorobutyryl, 4-fluorobutyryl, 5-chloropentanoyl, 3-chloro-2-methylpropionyl, 6-bromohexanoyl, 5,6-dibromohexanoyl, and the like.

The “aminocarbonyl-lower alkoxy having a lower alkyl substituent” includes a straight chain or branched chain alkoxy group having 1 to 6 carbon atoms which is substituted by an aminocarbonyl group having 1 to 2 substituents of a straight chain or branched chain alkyl group having 1 to 6 carbon atoms, for example, methylaminocarbonylmethoxy, 1-ethylaminocarbonylethoxy, 2-propylaminocarbonylethoxy, 3-isopropylaminocarbonylpropoxy, 4-butylaminocarbonylbutoxy, 5-pentylaminocarbonylpentyloxy, 6-hexylaminocarbonylhexyloxy, dimethylaminocarbonylmethoxy, 3-diethylaminocarbonylpropoxy, diethylaminocarbonylmethoxy, (N-ethyl-N-propylamino)carbonylmethoxy, 2-(N-methyl-N-hexylamino)carbonylethoxy, and the like.

The “carbamoyl-lower alkyl” includes a carbamoyl-substituted alkyl group wherein the alkyl moiety is a straight chain or branched chain alkyl group having 1 to 6 carbon atoms, for example, carbamoylmethyl, 2-carbamoylethyl, 1-carbamoylethyl, 3-carbamoylpropyl, 4-carbamoylbutyl, 5-carbamoylpentyl, 6-carbamoylhexyl, 1,1-dimethyl-2-carbamoylethyl, 2-methyl-3-carbamoylpropyl, and the like.

The “amino-lower alkanoyl having optionally a lower alkyl substituent” includes a straight chain or branched chain alkanoyl having 2 to 6 carbon atoms which is substituted by an amino group having optionally 1 to 2 substituents of a straight chain or branched chain alkyl group having 1 to 6 carbon atoms, for example, 2-aminoacetyl, 3-aminopropionyl, 2-aminopropionyl, 4-aminobutyryl, 5-aminopentanoyl, 6-aminohexanoyl, 2,2-dimethyl-3-aminopropionyl, 2-methyl-3-aminopropionyl, 2-methylaminoacetyl, 2-ethylaminopropionyl, 3-propylaminopropionyl, 3-isopropylaminopropionyl, 4-butylaminobutyryl, 5-pentylaminopentanoyl, 6-hexylaminohexanoyl, 2-dimethylaminoacetyl, 2-diethylaminoacetyl, 2-(N-ethyl-N-propylamino)acetyl, 3-(N-methyl-N-hexylamino)propionyl, and the like.

The “amino-lower alkyl having optionally a lower alkanoyl substituent” includes a straight chain or branched chain alkyl having 1 to 6 carbon atoms which is substituted by an amino group having optionally a substituent of a straight chain or branched chain alkanoyl group having 1 to 6 carbon atoms, for example, aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, acetylaminomethyl, 1-acetylaminoethyl, 2-propionylaminoethyl, 3-isopropionylaminopropyl, 4-butyrylaminobutyl, 5-pentanoylaminopentyl, 6-hexanoylaminohexyl, formylaminomethyl, and the like.

The “anilinocarbonyl having optionally a lower alkyl substituent on the phenyl ring” includes an anilinocarbonyl group having optionally 1 to 3 substituents of a straight chain or branched chain alkyl group having 1 to 6 carbon atoms on the phenyl ring, for example, anilinocarbonyl, 2-methylanilinocarbonyl, 3-methylanilinocarbonyl, 4-methylanilinocarbonyl, 2-ethylanilinocarbonyl, 3-ethylanilinocarbonyl, 4-ethylanilinocarbonyl, 4-isopropylanilinocarbonyl, 3-butylanilinocarbonyl, 4-pentylanilinocarbonyl, 4-hexylanilinocarbonyl, 3,4-dimethylanilinocarbonyl, 3,4-diethylanilinocarbonyl, 2,4-dimethylanilinocarbonyl, 2,5-dimethylanilinocarbonyl, 2,6-dimethylanilinocarbonyl, 3,4,5-trimethylanilinocarbonyl, and the like.

The “phenylsulfonyl which has optionally a substituent selected from a halogen and a lower alkyl on the phenyl ring” includes a phenylsulfonyl group which has optionally 1 to 3 substitutents selected from a straight chain or branched chain alkyl group having 1 to 6 carbon atoms and a halogen atom, for example, phenylsulfonyl, 2-chlorophenylsulfonyl, 3-chlorophenylsulfonyl, 4-chlorophenylsulfonyl, 2-fluorophenylsulfonyl, 3-fluorophenylsulfonyl, 4-fluorophenylsulfonyl, 2-bromophenylsulfonyl, 3-bromophenylsulfonyl, 4-bromophenylsulfonyl, 2-iodophenylsulfonyl, 3-iodophenylsulfonyl, 4-iodophenylsulfonyl, 3,4-dichlorophenylsulfonyl, 3,5-dichlorophenylsulfonyl, 2,6- dichlorophenylsulfonyl, 2,3-dichlorophenylsulfonyl, 2,4-dichlorophenylsulfonyl, 3,4-difluorophenylsulfonyl, 3,5-dibromophenylsulfonyl, 3,4,5-trichlorophenylsulfonyl, 2-ethyl-3-chlorophenylsulfonyl, 2-methylphenylsulfonyl, 3-methylphenylsulfonyl, 4-methylphenylsulfonyl, 2-ethylphenylsulfonyl, 3-ethylphenylsulfonyl, 4-ethylphenylsulfonyl, 4-isopropylphenylsulfonyl, 3-butylphenylsulfonyl, 4-pentylphenylsulfonyl, 4-hexylphenylsulfonyl, 3,4-dimethylphenylsulfonyl, 3,4-diethylphenylsulfonyl, 2,4-dimethylphenylsulfonyl, 2,5-dimethylphenylsulfonyl, 2,6-dimethylphenylsulfonyl, 3,4,6-trimethylphenylsulfonyl, 3,4,5-trimethylphenylsulfonyl, 3-chloro-4-methylphenylsulfonyl, 4-methyl-5-iodophenylsulfonyl, 3,4-dimethyl-5-bromophenylsulfonyl, 3,5-diiodo-4-methylphenylsulfonyl, and the like.

The "phthalimido-substituted lower alkyl" includes a straight chain or branched chain alkyl group having 1 to 6 carbon atoms which is substituted by phthalimido group, for example, phthalimidomethyl, 2-phthalimidoethyl, 1-phthalimidoethyl, 3-phthalimidopropyl, 4-phthalimidobutyl, 5-phthalimidopentyl, 6-phthalimidohexyl, 1,1-dimethyl-2-phthalimidoethyl, 2-methyl-3-phthalimidopropyl, and the like.

The "lower alkynyl" includes a straight chain or branched chain alkynyl having 2 to 6 carbon atoms, for example, ethynyl, 2-propynyl, 2-butynyl, 3-butynyl, 1-methyl-2-propynyl, 2-pentynyl, 2-hexynyl, and the like.

The "benzoyl which has optionally a halogen substituent on the phenyl ring" includes a benzoyl group which has optionally 1 to 3 substituents of a halogen atom on the phenyl ring, for example, benzoyl, 2-chlorobenzoyl, 3-chlorobenzoyl, 4-chlorobenzoyl, 2-fluorobenzoyl, 3-fluorobenzoyl, 4-fluorobenzoyl, 2-bromobenzoyl, 3-bromobenzoyl, 4-bromobenzoyl, 2-iodobenzoyl, 3-iodobenzoyl, 4-iodobenzoyl, 3,4-dichlorobenzoyl, 3,5-dichlorobenzoyl, 2,6-dichlorobenzoyl, 2,3-dichlorobenzoyl, 2,4-dichlorobenzoyl, 3,4-difluorobenzoyl, 3,5-dibromobenzoyl, 3,4,5-trichlorobenzoyl, and the like.

The "phenyl-lower alkoxy" includes a phenylalkoxy group wherein the alkoxy moiety is a straight chain or branched chain alkoxy group having 1 to 6 carbon atoms, for example, benzyloxy, 2-phenylethoxy, 1-phenylethoxy, 3-phenylpropoxy, 4-phenylbutoxy, 5-phenylpentyloxy, 6-phenylhexyloxy, 1,1-dimethyl-2-phenylethoxy, 2-methyl-3-phenylpropoxy, and the like.

The "amino-lower alkoxy having optionally a substituent selected from a lower alkyl and a lower alkanoyl" include a straight chain or branched chain alkoxy group having 1 to 6 carbon atoms which is substituted by an amino group having optionally 1 to 2 substituents selected from a straight chain or branched chain alkyl group having 1 to 6 carbon atoms and a straight chain or branched chain alkanoyl group having 1 to 6 carbon atoms, for example, aminomethoxy, 2-aminoethoxy, 1-aminoethoxy, 3-aminopropoxy, 4-aminobutoxy, 5-aminopentyloxy, 6-aminohexyloxy, 1,1-dimethyl-2-aminoethoxy, 2-methyl-3-aminopropoxy, acetylaminomethoxy, 1-acetylaminoethoxy, 2-propionylaminoethoxy, 3-isopropionylaminopropoxy, 4-butyrylaminobutoxy, 5-pentanoylaminopentyloxy, 6-hexanoylaminohexyloxy, formylaminomethoxy, methylaminomethoxy, 1-ethylaminoethoxy, 2-propylaminoethoxy, 3-isopropylaminopropoxy, 4-butylaminobutoxy, 5-pentylaminopentyloxy, 6-hexylaminohexyloxy, dimethylaminomethoxy, (N-ethyl-N-propylamino)methoxy, 2-(N-methyl-N-hexylamino)ethoxy, and the like.

The "benzoyloxy which has optionally a halogen substituent on the phenyl ring" includes a benzoyloxy group which has optionally 1 to 3 substituents of a halogen atom on the phenyl ring, for example, benzoyloxy, 2-chlorobenzoyloxy, 3-chlorobenzoyloxy, 4-chlorobenzoyloxy, 2-fluorobenzoyloxy, 3-fluorobenzoyloxy, 4-fluorobenzoyloxy, 2-bromobenzoyloxy, 3-bromobenzoyloxy, 4-bromobenzoyloxy, 2-iodobenzoyloxy, 3-iodobenzoyloxy, 4-iodobenzoyloxy, 3,4-dichlorobenzoyloxy, 3,5-dichlorobenzoyloxy, 2,6-dichlorobenzoyloxy, 2,3-dichlorobenzoyloxy, 2,4-dichlorobenzoyloxy, 3,4-difluorobenzoyloxy, 3,5-dibromobenzoyloxy, 3,4,5-trichlorobenzoyloxy, and the like.

The "lower alkanoyloxy-substituted lower alkyl" includes a straight chain or branched chain alkyl group having 1 to 6 carbon atoms which is substituted by a straight chain or branched chain alkanoyloxy group having 2 to 6 carbon atoms, for example, acetyloxymethyl, 2-propionyloxyethyl, 1-butyryloxyethyl, 3-acetyloxypropyl, 4-acetyloxybutyl, 4-isobutyryloxybutyl, 5-pentanoyloxypentyl, 6-acetyloxyhexyl, 6-tert-butylcarbonyloxyhexyl, 1,1-dimethyl-2-hexanoyloxyethyl, 2-methyl-3-acetyloxypropyl, and the like.

The "lower alkylsulfonyloxy-lower alkyl" includes a straight chain or branched chain alkyl group having 1 to 6 carbon atoms which is substituted by a straight chain or branched chain alkylsulfonyloxy group having 1 to 6 carbon atoms, for example, methylsulfonyloxymethyl, 1-ethylsulfonyloxyethyl, 2-propylsulfonyloxyethyl, 3-isopropylsulfonyloxypropyl, 4-butylsulfonyloxybutyl, 5-pentylsulfoyloxypentyl, 6-hexylsulfonyloxyhexyl, 1,1-dimethyl-2-methylsulfoyloxyethyl, 2-methyl-3-ethylsulfonyloxypropyl, and the like.

The "azido-lower alkyl" includes a straight chain or branched chain alkyl group having 1 to 6 carbon atoms which is substituted by an azido group, for example, azidomethyl, 1-azidoethyl, 2-azidoethyl, 3-azidopropyl, 4-azidobutyl, 5-azidopentyl, 6-azidohexyl, 1,1-dimethyl-2-azidoethyl, 2-methyl-3-azidopropyl, and the like.

The "lower alkanoyloxyimino" includes a straight chain or branched chain alkanoyloxyimino group having 1 to 6 carbon atoms, for example, formyloxyimino, acetyloxyimino, propionyloxyimino, butyryloxyimino, isobutyryloxyimino, pentanoyloxyimino, tert-butylcarbonyloxyimino, hexanoyloxyimino, and the like.

The "lower alkylidene" includes a straight chain or branched chain alkylidene group having 1 to 6 carbon atoms, for example, methylidene, ethylidene, propylidene, isopropylidene, butylidene, pentylidene, hexylidene, and the like.

The "oxiranyl-substituted lower alkyl" includes a straight chain or branched chain alkyl group having 1 to 6 carbon atoms which is substituted by oxiranyl group, for example, oxiranylmethyl, 1-oxiranylethyl, 2-oxiranylethyl, 3-oxiranylpropyl, 4-oxiranylbutyl, 5-oxiranylpentyl, 6-oxiranylhexyl, 1,1-dimethyl-2-oxiranylethyl, 2-methyl-3-oxiranylpropyl, and the like.

The "lower alkyl having 1 to 2 substituents selected from a lower alkoxy, hydroxy and an amino having optionally a lower alkyl substituent" includes a straight chain or branched chain alkyl group having 1 to 6 carbon atoms and having 1 to 2 substituents selected from a straight chain or branched chain alkoxy group having 1 to 6 carbon atoms, hydroxy and an amino having optionally a straight chain or branched chain alkyl group having 1 to 6 carbon atoms, for example, methoxymethyl, 1-ethoxyethyl, 2-propoxyethyl, 3-isopropoxypropyl, 4-butoxybutyl, 5-pentyloxypentyl, 6-hexyloxyhexyl, 1,1-dimethyl-2-methoxyethyl, 2-methyl- 3-ethoxypropyl, 3-methoxy-2-hydroxypropyl, hydroxymethyl, 2-hydroxyethyl, 1-hydroxyethyl, 3-hydroxypropyl, 2,3-dihydroxyethyl, 4-hydroxybutyl, 3,4-dihydroxybutyl, 1,1-dimethyl-2-hydroxyethyl, 5,6-dihydroxyhexyl, 5-hydroxypentyl, 6-hydroxyhexyl, 6-(N-ethyl-N-methylamino)-5-methoxyhexyl, 2-methyl-3-hydroxypropyl, aminomethyl, 1-aminoethyl, 2-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, ethylaminomethy, propylaminomethyl, isopropylaminomethyl, butylaminomethyl, tert-butylaminomethyl, pentylaminomethyl, hexylaminomethyl, dimethylaminomethyl, diethylaminomethyl, dipropylaminomethyl, dibutylaminomethyl, dipentylaminomethyl, dihexylaminomethyl, N-methyl-N-ethylaminomethyl, N-methyl-N-propylaminomethyl, N-methyl-N-butylaminomethyl, N-methyl-N-hexylaminomethyl, 1-methylaminoethyl, 2-ethylaminoethyl, 3-propylaminopropyl, 4-butylaminobutyl, 1,1-dimethyl-2-pentylaminoethyl, 5-hexylaminopentyl, 6-dimethylaminohexyl, 4-dimethylaminobutyl, 2-diethylaminoethyl, 1-(N-methyl-N-hexylamino)ethyl, 3-dihexylaminopropyl, 6-diethylaminohexyl, 4-dibutylaminobutyl, 2-(N-methyl-N-pentylamino)ethyl, 2-hydroxy-3-diethylaminopropyl, 3-hydroxy-4-methylaminobutyl, 5-hydroxy-6-diethylaminohexyl, 4-hydroxy-5-dimethylaminopentyl, 4-hydroxy-5-methylaminopentyl, 4-hydroxy-5-diethylaminopentyl, 5-hydroxy-6-ethylaminohexyl, 5-hydroxy-6-isopropylaminohexyl, 5-hydroxy-6-aminohexyl, and the like.

The "aminocarbonyloxy having optionally a lower alkyl substituent" includes an aminocarbonyloxy group having optionally 1 to 2 substituents of a straight chain or branched chain alkyl group having 1 to 6 carbon atoms, for example, aminocarbonyloxy, methylaminocarbonyloxy, ethylaminocarbonyloxy, propylaminocarbonyloxy, isopropylaminocarbonyloxy, butylaminocarbonyloxy, tert-butylaminocarbonyloxy, pentylaminocarbonyloxy, hexylaminocarbonyloxy, dimethylaminocarbonyloxy, diethylaminocarbonyloxy, dipropylaminocarbonyloxy, dibutylaminocarbonyloxy, dipentylaminocarbonyloxy, dihexylaminocarbonyloxy, N-methyl-N-ethylaminocarbonyloxy, N-ethyl-N-propylaminocarbonyloxy, N-methyl-N-butylaminocarbonyloxy, N-methyl-N-hexylaminocarbonyloxy, and the like.

The "lower alkanoyloxy having optionally a halogen substituent" includes a straight chain or branched chain alkanoyloxy group having 1 to 6 carbon atoms which has optionally 1 to 3 substituents of a halogen atom, for example, in addition to the above lower alkanoyl group, 2,2,2-trifluoroacetyloxy, 2,2,2-trichloroacetyloxy, 2-chloroacetyloxy, 2-bromoacetyloxy, 2-fluoroacetyloxy, 2-iodoacetyloxy, 2,2-difluoroacetyloxy, 2,2-dibromoacetyloxy, 3,3,3-trifluoropropionyloxy, 3,3,3-trichloropropionyloxy, 3-chloropropionyloxy, 2,3-dichloropropionyloxy, 4,4,4-trichlorobutyryloxy, 4-fluorobutyryloxy, 5-chloropentanoyloxy, 3-chloro-2-methylpropionyloxy, 6-bromohexanoyloxy, 5,6-dibromohexanoyloxy, and the like.

The "amino-lower alkyl having optionally a substituent selected from a lower alkyl and a lower alkanoyl" include a straight chain or branched chain alkyl group having 1 to 6 carbon atoms which is substituted by an amino group having optionally 1 to 2 substituents selected from a straight chain or branched chain alkyl group having 1 to 6 carbon atoms and a straight chain or branched chain alkanoyl group having 1 to 6 carbon atoms, for example, aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, acetylaminomethyl, 1-acetylaminoethyl, 2-propionylaminoethyl, 3-isopropionylaminopropyl, 4-butyrylaminobutyl, 5-pentanoylaminopentyl, 6-hexanoylaminohexyl, formylaminomethyl, methylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminomethyl, (N-ethyl-N-propylamino)methyl, 2-(N-methyl-N-hexylamino)ethyl, and the like.

The "amino-lower alkanoyloxy having optionally a lower alkyl substituent" includes a straight chain or branched chain alkanoyloxy having 2 to 6 carbon atoms which is substituted by an amino group having optionally 1 to 2 substituents of a straight chain or branched chain alkyl group having 1 to 6 carbon atoms, for example, 2-aminoacetyloxy, 3-aminopropionyloxy, 2-aminopropionyloxy, 4-aminobutyryloxy, 5-aminopentanoyloxy, 6-aminohexanoyloxy, 2,2-dimethyl-3-aminopropionyloxy, 2-methyl-3-aminopropionyloxy, 2-methylaminoacetyloxy, 2-ethylaminopropionyloxy, 3-propylamninopropionyloxy, 3-isopropylaminopropionyloxy, 4-butylaminobutyryloxy, 5-pentylaminopentanoyloxy, 6-hexylaminohexanoyloxy, 2-dimethylaminoacetyloxy, 2-diethylaminoacetyloxy, 2-(N-ethyl-N-propylamino)acetyloxy, 3-(N-methyl-N-hexylamino)propionyloxy, and the like.

The "pyridyl-lower alkyl" include a pyridylalkyl group wherein the alkyl moiety is a straight chain or branched chain alkyl group having 1 to 6 carbon atoms, for example, (4-pyridyl)methyl, 1-(3-pyridyl)ethyl, 2-(2-pyridyl)ethyl, 3-(2-pyridyl)propyl, 4-(3-pyridyl)butyl, 5-(4-pyridyl)pentyl, 6-(2-pyridyl)hexyl, 1,1-dimethyl-2-(3-pyridyl)ethyl, 2-methyl-3-(4-pyridyl)propyl, and the like.

The "5- or 6-membered saturated heterocyclic group which is formed by binding the groups $R^{82}$ and $R^{83}$ together with the nitrogen atom to which they bond with or without being intervened with nitrogen, oxygen or sulfur atom" includes, for example, pyrrolidinyl, piperidinyl, piperazinyl, morpholino, thiomorpholino, and the like.

The above heterocyclic group which has a substituent selected from oxo, a lower alkyl, a lower alkanoyl and carbamoyl includes the above heterocyclic groups which have 1 to 3 substituents selected from oxo, a straight chain or branched chain alkyl group having 1 to 6 carbon atoms, a straight chain or branched chain alkanoyl group having 1 to 6 carbon atoms, and carbamoyl group, for example, 4-methylpiperazinyl, 3,4-dimethylpiperazinyl, 3-ethylpyrrolidinyl, 2-propylpyrrolidinyl, 3,4,5-trimethylpiperidinyl, 4-butylpiperidinyl, 3-pentylmorpholino, 4-hexylpiperazinyl, 2-methylthiomorpholino, 4-acetylpiperazinyl, 2-propionylmorpholino, 3-butyrylthiomorpholino, 3-pentanoylpyrrolidinyl, 4-hexanoylpiperidinyl, 3-methyl-4-acetylpiperazinyl, 2-carbamoylpyrrolidinyl, 4-carbamoylpiperazinyl, 3-carbamoylthiomorpholino, 2-carbamoylmorpholino, 3-carbamoylpiperidinyl, 1-oxo-thiomorpholino, 1,1-dioxothiomorpholino, and the like.

The "lower alkylsulfonyl" includes a straight chain or branched chain alkylsulfonyl group having 1 to 6 carbon atoms, for example, methylsulfonyl, ethylsulfonyl, propylsulfonyl, isopropylsulfonyl, butylsulfonyl, tert-butylsulfonyl, pentylsulfonyl, hexylsulfonyl, and the like.

The "aminocarbonyl having optionally a lower alkyl substituent" includes an aminocarbonyl group having optionally 1 to 2 substituents of a straight chain or branched chain alkyl group having 1 to 6 carbon atoms, for example, aminocarbonyl, methylaminocarbonyl, ethylaminocarbonyl, propylaminocarbonyl, isopropylaminocarbonyl, butylaminocarbonyl, tert-butylaminocarbonyl, pentylaminocarbonyl, hexylaminocarbonyl, dimethylaminocarbonyl, diethylaminocarbonyl, dipropylaminocarbonyl, dibutylaminocarbonyl, dipentylaminocarbonyl, dihexylaminocarbonyl, N-methyl-N-ethylaminocarbonyl, N-ethyl-N-propylaminocarbonyl, N-methyl-N-butylaminocarbonyl, N-methyl-N-hexylaminocarbonyl, and the like.

The "cyano-substituted lower alkyl" includes a straight chain or branched chain alkyl group having 1 to 6 carbon atoms which is substituted by cyano group, for example, cyanomethyl, 2-cyanoethyl, 1-cyanoethyl, 3-cyanopropyl, 4-cyanobutyl, 5-cyanopentyl, 6-cyanohexyl, 1,1-dimethyl-2-caynoethyl, 2-methyl-3-cyanopropyl, and the like.

The "lower alkoxycarbonyl-substituted lower alkyl" includes an alkoxycarbonyl-substituted straight chain or branched chain alkyl group having 1 to 6 carbon atoms wherein the alkoxycarbonyl moiety is a straight chain or branched chain alkoxycarbonyl group having 1 to 6 carbon atoms, for example, methoxycarbonylmethyl, 3-methoxycarbonylpropyl, ethoxycarboxymethyl, 3-ethoxycarbonylpropyl, 4-ethoxycarbonylbutyl, 5-isopropoxycarbonylpentyl, 6-propoxycarbonylhexyl, 1,1-dimethyl-2-butoxycarbonylethyl, 2-methyl-3-tert-butoxycarbonylpropyl, 2-pentyloxycarbonylethyl, hexyloxycarbonylmethyl, and the like.

The "carboxy-substituted lower alkyl" includes a carboxy-substituted alkyl group wherein the alkyl moiety is a straight chain or branched chain alkyl group having 1 to 6 carbon atoms, for example, carboxymethyl, 2-carboxyethyl, 1-carboxyethyl, 3-carboxypropyl, 4-carboxybutyl, 5-carboxypentyl, 6-carboxyhexyl, 1,1-dimethyl-2-carboxyethyl, 2-methyl-3-carboxypropyl, and the like.

The "tetrahydropyranyloxy-substituted lower alkyl" includes a tetrahydropyranyloxy-substituted straight chain or branched chain alkyl group having 1 to 6 carbon atoms, for example, (2-tetrahydropyranyloxy)methyl, 2-(3-tetrahydropyranyloxy)ethyl, 1-(4-tetrahydropyranyloxy) ethyl, 3-(2-tetrahydropyranyloxy)propyl, 4-(3-tetrahydropyranyloxy)butyl, 5-(4-tetrahydropyranyloxy) pentyl, 6-(2-tetrahydropyranyloxy)hexyl, 1,1-dimethyl-2-(3-tetrahydropyranyloxy)ethyl, 2-methyl-3-(4-tetrahydropyranyloxy)propyl, and the like.

The "piperidinyl having optionally a phenyl-lower alkyl substituent" includes a piperidinyl which has optionally a substituent of a phenylalkyl group wherein the alkyl moiety is a straight chain or branched chain alkyl group having 1 to 6 carbon atoms, for example, piperidinyl, 1-benzyl-4-piperidinyl, 1-(2-phenylethyl)-3-piperidinyl, 1-(1-phenylethyl)-2-piperidinyl, 1-(3-phenylpropyl)-4-piperidinyl, 1-(4-phenylbutyl)-4-piperidinyl, 1-(5-phenylpentyl)-4-piperidinyl, 1-(6-phenylhexyl)-4-piperidinyl, 1-(1,1-dimethyl-2-phenylethyl)-3-piperidinyl, 1-(2-methyl-3-phenylpropyl)-2-piperidinyl, and the like.

The "imidazolyl-substituted lower alkanoyl" includes an imidazolyl-substituted alkanoyl group wherein the alkanoyl moiety is a straight chain or branched chain alkanoyl group having 2 to 6 carbon atoms, for example, (1-imidazolyl) acetyl, 3-(2-imidazolyl)propionyl, 2-(4-imidazolyl) propionyl, 4-(1-imidazolyl)butyryl, 2,2-dimethyl-3-(2-imidazolyl)propionyl, 5-(4-imidazolyl)pentanoyl, 6-(1-imidazolyl)hexanoyl, and the like.

The "amino-lower alkanoyl having optionally a substituent selected from a lower alkyl and a lower alkoxycarbonyl" includes a straight chain or branched chain alkanoyl having 2 to 6 carbon atoms which is substituted by an amino group having optionally 1 to 2 substituents selected from a straight chain or branched chain alkyl group having 1 to 6 carbon atoms and a straight chain or branched chain alkoxycarbonyl group having 1 to 6 carbon atoms, for example, 2-aminoacetyl, 3-aminopropionyl, 2-aminopropionyl, 4-aminobutyryl, 5-aminopentanoyl, 6-aminohexanoyl, 2,2-dimethyl-3-aminopropionyl, 2-methyl-3-aminopropionyl, 2-methylaminoacetyl, 2-ethylaminopropionyl, 3-propylaminopropionyl, 3-isopropylaminopropionyl, 4-butylaminobutyryl, 5-pentylaminopentanoyl, 6-hexylaminohexanoyl, 2-dimethylaminoacetyl, 2-diethylaminoacetyl, 2-(N-ethyl-N-propylamino)acetyl, 3-(N-methyl-N-hexylamino)propionyl, 2-methoxycarbonylaminoacetyl, 2-ethoxycarbonylaminoacetyl, 3-propoxycarbonylaminopropionyl, 4-butoxycarbonylaminobutyryl, 2-tert-butoxycarbonylaminoacetyl, 5-pentyloxycarbonylaminopentanoyl, 6-hexyloxycarbonylaminohexanoyl, 2-(N-methyl-N-tert-butoxycarbonylamino)acetyl, and the like.

The "aminocarbonyl-lower alkyl having a lower alkyl substituent" includes a straight chain or branched chain alkyl group having 1 to 6 carbon atoms which is substituted by an aminocarbonyl group having 1 to 2 substituents of a straight chain or branched chain alkyl group having 1 to 6 carbon atoms, for example, methylaminocarbonylmethyl, 1-ethylaminocarbonylethyl, 2-propylaminocarbonylethyl, 3-isopropylaminocarbonylpropyl, 4-butylaminocarbonylbutyl, 5-pentylaminocarbonylpentyl, 6-hexylaminocarbonylhexyl, dimethylaminocarbonylmethyl, 3-diethylaminocarbonylpropyl, diethylaminocarbonylmethyl, (N-ethyl-N-propylamino) carbonylmethyl, 2-(N-methyl-N-hexylamino)carbonylethyl, and the like.

The "amino-substituted lower alkoxy having optionally a lower alkyl substituent" includes an amino-substituted straight chain or branched chain alkoxy having 1 to 6 carbon atoms which has optionally 1 to 2 substituents of a straight chain or branched chain alkyl having 1 to 6 carbon atoms, such as aminomethoxy, 2-aminoethoxy, 1-aminoethoxy, 3-aminopropoxy, 4-aminobutoxy, 5-aminopentyloxy, 6-aminohexyloxy, 1,1-dimethyl-2-aminoethoxy, 2-methyl-3-aminopropoxy, methylaminomethoxy, 1-ethylaminoethoxy, 2-propylaminoethoxy, 3-isopropylaminopropoxy, 4-butylaminobutoxy, 5-pentylaminopentyloxy, 6-hexylaminohexyloxy, dimethylaminomethoxy, (N-ethyl-N-propylamino)methoxy, 2-(N-methyl-N-hexylamino)ethoxy, and the like.

The compounds of the present invention can be prepared by various processes, for example, by the processes shown in the following reaction schemes.

[Reaction Scheme-1]

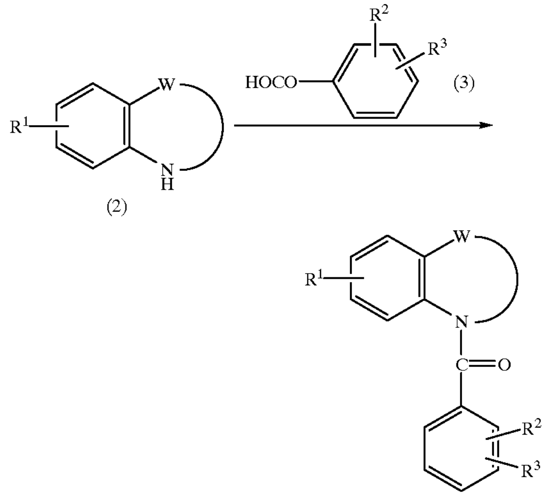

(3)

(2)

(1)

wherein $R^1$, $R^2$, $R^3$, and W are the same as defined above.

The process of Reaction Scheme-1 is carried out by reacting a benzoheterocyclic compound of the formula (2) and a carboxylic acid compound of the formula (3) by a conventional amido bond forming reaction. The amido bond forming reaction can be carried out under the conditions for the conventional amido bond forming reaction, for example, (a) a mixed acid anhydride process, i.e. a process of reacting the carboxylic acid compound (3) with an alkylhalocarboxylic acid to form a mixed acid anhydride and reacting the resultant with the amine compound (2), (b) an activated ester process, i.e. a process of converting the carboxylic acid compound (3) into an activated ester, such as p-nitrophenyl ester, N-hydroxysuccinimide ester, 1-hydroxybenzotriazole ester, etc., and reacting the resultant with the amine compound (2), (c) a carbodiimide process, i.e. a process of condensing the carboxylic acid compound (3) and the amine compound (2) in the presence of an activating agent such as dicyclohexylcarbodiimide, carbonyldiimidazole, etc., (d) other processes, i.e. a process of converting the carboxylic acid compound (3) into a carboxylic anhydride by treatment with a dehydrating agent such as acetic anhydride, and reacting the resultant with the amine compound (2); a process of reacting an ester of the carboxylic acid compound (3) with a lower alcohol and the amine compound (2) at a high temperature under high pressure; a process of reacting an acid halide compound of the carboxylic acid compound (3), i.e. a carboxylic acid halide, with the amine compound (2), and the like.

The mixed acid anhydride used in the above mixed acid anhydride process (a) is obtained by the known Schotten-Baumann reaction, and the reaction product is used without isolation from the reaction mixture for the reaction with the amine compound (2) to give the desired compound of the formula (1). The Schötten-Baumann reaction is usually carried out in the presence of a basic compound. The basic compound is any conventional compounds used for the Sch ötten-Baumann reaction and includes, for example, organic basic compounds such as triethylamine, trimethylamine, pyridine, dimethylaniline, N-methylmorpholine, 1,5-diazabicyclo[4.3.0]nonene-5 (DBN), 1,8-diazabicyclo [5.4.0]undecene-7 (DBU), 1,4-diazabicyclo[2.2.2]octane (DABCO), etc., and inorganic basic compounds such as potassium carbonate, sodium carbonate, potassium hydrogen carbonate, sodium hydrogen carbonate, etc. The reaction is usually carried out at a temperature of from about −20° C. to about 100° C., preferably from about 0° C. to about 50° C., for about 5 minutes to about 10 hours, preferably about 5 minutes to about 2 hours.

The reaction of the thus obtained mixed acid anhydride with the amine compound (2) is usually carried out at a temperature of from about −20° C. to about 150° C., preferably about 10° C. to about 50° C., for about 5 minutes to about 10 hours, preferably about 5 minutes to about 5 hours. The mixed acid anhydride process is usually carried out in an appropriate solvent. The solvent is any conventional solvents which are usually used in the mixed acid anhydride process and includes, for example, halogenated hydrocarbons (e.g. chloroform, dichloromethane dichloroethane, etc.), aromatic hydrocarbons (e.g. benzene, toluene, xylene, etc.), ethers (e.g. diethyl ether, diisopropyl ether, tetrahydrofuran, dimethoxyethane, etc.), esters (e.g. methyl acetate, ethyl acetate, etc.), aprotic polar solvents (e.g. N,N-dimethylformamide, dimethylsulfoxide, hexamethylphosphoric triamide, etc.), or a mixture of these solvents. The alkylhalocarboxylic acid used in the mixed acid anhydride process includes, for example, methyl chloroformate, methyl bromoformate, ethyl chloroformate, ethyl bromoformate, isobutyl chloroformate, and the like. In said process, the carboxylic acid compound (3), the alkylhalocarboxylic acid and the amine (2) are usually used in each equimolar amount, but preferably, the alkylhalocarboxylic acid and the carboxylic acid compound (3) are used each in an amount of about 1 to 1.5 mole to 1 mole of the amine (2).

Among the above other processes (d), in case of the process of reacting the carboxylic acid halide with the amine compound (2), the reaction is usually carried out in the presence of a basic compound in an appropriate solvent. The basic compound is any conventional compounds and includes, in addition to the basic compounds used for the above-mentioned Schotten-Baumann reaction, sodium hydroxide, potassium hydroxide, sodium hydride, potassium hydride. etc. The solvent includes, in addition to the solvents used for the above-mentioned mixed acid anhydride process, alcohols (e.g. methanol, ethanol, propanol, butanol, 3-methoxy-1-butanol, ethylcellosolve, methylcellosolve, etc.), acetonitrile, pyridine, acetone, water, and the like. The amount of the amine compound (2) and the carboxylic acid halide is not critical, but the carboxylic acid halide is usually used at least in equimolar amount, preferably about 1 to 5 moles to 1 mole of the amine compound (2). The reaction is usually carried out at a temperature of from about −20° C. to about 180° C., preferably from about 0° C. to about 150° C., for about 5 minutes to about 30 hours.

The amido bond forming reaction in the above Reaction Scheme-1 may also be carried out by reacting the carboxylic acid compound (3) and the amine (2) in the presence of a condensation agent, i.e. phosphoric compounds such as triphenylphosphine, diphenylphosphinyl chloride, phenyl-N-phenylphosphoramide chloridate, diethyl chlorophosphate, diethyl phosphorocyanidate, diphenylphosphoric azide, bis(2-oxo-3-oxazolidinyl)phosphinic chloride, etc. The reaction is usually carried out in the presence of the solvent and basic compound as used in the above reaction of the carboxylic acid halide and the amine (2) at a temperature of from about −20° C. to about 150° C., preferably about 0° C. to about 100° C., for about 5 minutes to about 30 hours. The condensation agent and the carboxylic acid compound (3) are used at least in equimolar amount, preferably about 1 to 2 moles, to 1 mole of the amine (2).

[Reaction Scheme-2]

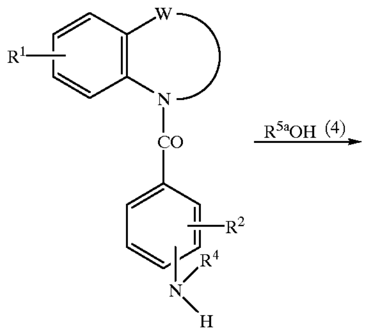

(2b)

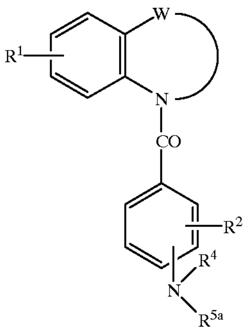

(1b)

wherein $R^1$, $R^2$, $R^4$ and W are as defined above, $R^{5a}$ is the same as $R^5$ as defined above except excluding an anilinocarbonyl having optionally a lower alkyl substituent on the phenyl ring, a phenylsulfonyl having optionally a substituent selected from a halogen atom and a lower alkyl on the phenyl ring and quinolylsulfonyl.

The reaction of the compound (2b) and the compound (4) is carried out in the same manner as in the reaction of the compound (2) and the compound (3) in the above Reaction Scheme-1.

[Reaction Scheme-3]

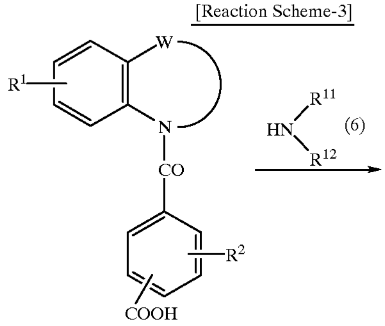

(6)

(5)

-continued

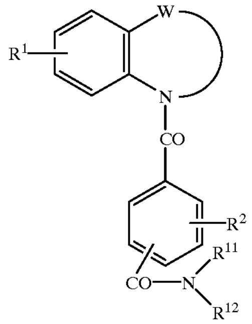

(1c)

wherein $R^1$, $R^2$, $R^{11}$, $R^{12}$ and W are as defined above.

The reaction of the compound (5) and the compound (6) is carried out under the same conditions as used in the reaction of the compound (2) and the compound (3) in the above Reaction Scheme-1.

[Reaction Scheme-4]

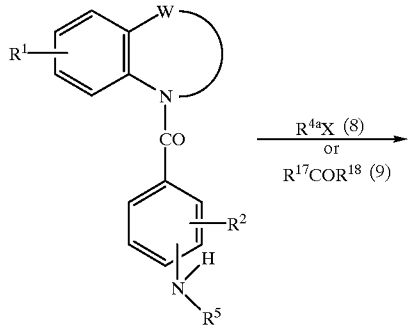

(7)

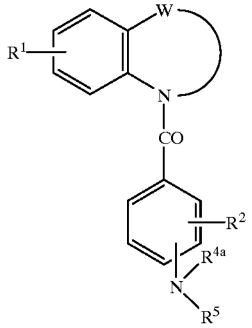

(1d)

wherein $R^1$, $R^2$, $R^5$ and W are as defined above, and $R^{4a}$ is a lower alkyl, $R^{17}$ and $R^{18}$ are each hydrogen atom or a lower alkyl, and X is a halogen atom.

The reaction of the compound (7) and the compound (8) is usually carried out in an inert solvent in the presence or absence of a basic compound. The inert solvent includes, for example, aromatic hydrocarbons (e.g. benzene, toluene, xylene, etc.), ethers (e.g. tetrahydrofuran, dioxane, diethylene glycol dimethyl ether, etc.), halogenated hydrocarbons (e.g. dichloromethane, chloroform, carbon tetrachloride, etc.), lower alcohols (e.g. methanol, ethanol, isopropanol, butanol, tert-butanol, etc.), acetic acid, ethyl acetate, acetone, acetonitrile, pyridine, dimethylsulfoxide, dimethylformamide, hexamethylphosphoric triamide, etc., or a mixture of these solvents. The basic compound includes, for example, carbonates (e.g. sodium carbonate, potassium carbonate, sodium hydrogen carbonate, potassium hydrogen carbonate, etc.), metal hydroxides (e.g. sodium hydroxide, potassium hydroxide, etc.), sodium hydride, potassium, sodium, sodium amide, metal alcoholates (e.g. sodium methoxide, sodium ethoxide, etc.), and organic basic compounds (e.g. pyridine, N-ethyldiisopropylamine, dimethylaminopyridine, triethylamine, 1,5-diazabicyclo[4.3.0]nonene-(5) (DBN), 1,8-diazabicyclo[5.4.0]undecene-7 (DBU), 1,4-diazabicyclo[2.2.2]octane (DABCO), etc.). The amount of the compound (7) and the compound (8) is not critical, but the compound (8) is usually used at least in equivalent amount, preferably 1 to 10 moles, to 1 mole of the compound (7). The reaction is usually carried out at a temperature of from about 0° C. to about 200° C., preferably from about 0° C. to about 170° C., for about 30 minutes to about 30 hours. In the reaction, an alkali metal halide (e.g. sodium iodide, potassium iodide, etc.) may be added to the reaction system.

The reaction of the compound (7) and the compound (9) is carried out in an appropriate solvent or without solvent in the presence of a reducing agent. The solvent includes, for example, water, alcohols (e.g. methanol, ethanol, isopropanol, etc.), acetonitrile, formic acid, acetic acid, ethers (e.g. dioxane, diethyl ether, diglyme, tetrahydrofuran, etc.), aromatic hydrocarbons (e.g. benzene, toluene, xylene, etc.), or a mixture of these solvents. The reducing agent includes, for example, formic acid, fatty acid alkali metal salts (e.g. sodium formate, etc.), hydrogenating reducing agents (e.g. sodium boro hydride, sodium cyanoboro hydride, lithium aluminum hydride, etc.), catalystic reducing agents (e.g. palladium black, palladium-carbon, platinum oxide, platinum black, Raney nickel, etc.).

When formic acid is used as the reducing agent, the reaction is usually carried out at a temperature of from room temperature to about 200° C., peferably about 50° C. to about 150° C., for about 1 to 10 hours. The formic acid is usually used in a large excess amount to the compound (7).

When a hydrogenating reducing agent is used, the reaction is usually carried out at a temperature of about −30° C. to about 100° C., preferably about 0° C. to about 70° C., for about 30 minutes to about 12 hours. The reducing agent is usually used in an amount of 1 to 20 moles, preferably 1 to 6 moles, to 1 mole of the compound (7). When lithium aluminum hydride is used as the reducing agent, it is preferable to use a solvent selected from ethers (e.g. diethyl ether, dioxane, tetrahydrofuran, diglyme, etc.) and aromatic hydrocarbons (e.g. benzene, toluene, xylene, etc.).

When a catalytic reducing agent is used, the reaction is usually carried out under atmospheric pressure to about 20 atm., preferably atmospheric pressure to about 10 atm. under hydrogen atmosphere or in the presence of a hydrogen donor (e.g. formic acid, ammonium formate, cyclohexene, hydrazine hydrate, etc.) at a temperature of about −30° C. to about 100° C., preferably about 0° C. to about 60° C., for about 1 to 12 hours. The catalytic reducing agent is usually used in an amount of about 0.1 to 40% by weight, preferably about 1 to 20% by weight, of the amount of the compound (7). The compound (9) is usually used at least in equivalent amount, preferably equivalent to a large excess amount, to the compound (7).

[Reaction Scheme-5A]

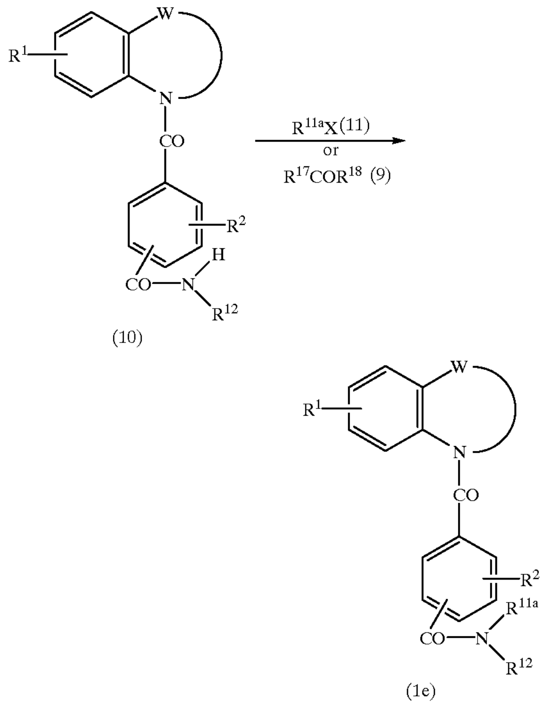

wherein $R^1$, $R^2$, $R^{12}$, $R^{17}$, $R^{18}$, X and W are as defined above, and $R^{11a}$ is a lower alkyl.

[Reaction Scheme-5B]

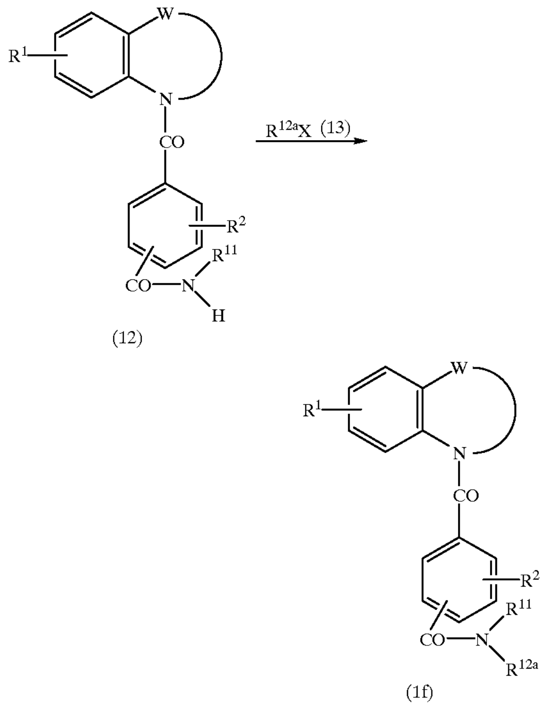

wherein $R^1$, $R^2$, $R^{11}$, X and W are as defined above, and $R^{12a}$ is a cycloalkyl.

The reaction of the compound (10) and the compound (11) in the Reaction Scheme-5A and the reaction of the compound (12) and the compound (13) in the Reaction Scheme-5B are carried out in the same manner as in the reaction of the compound (7) and the compound (8) in the above Reaction Scheme-4.

Besides, the reaction of the compound (10) and the compound (9) in the Reaction Scheme-5A is carried out in the same manner as in the reaction of the compound (7) and the compound (9) in the above Reaction Scheme-4.

[Reaction Scheme-6A]

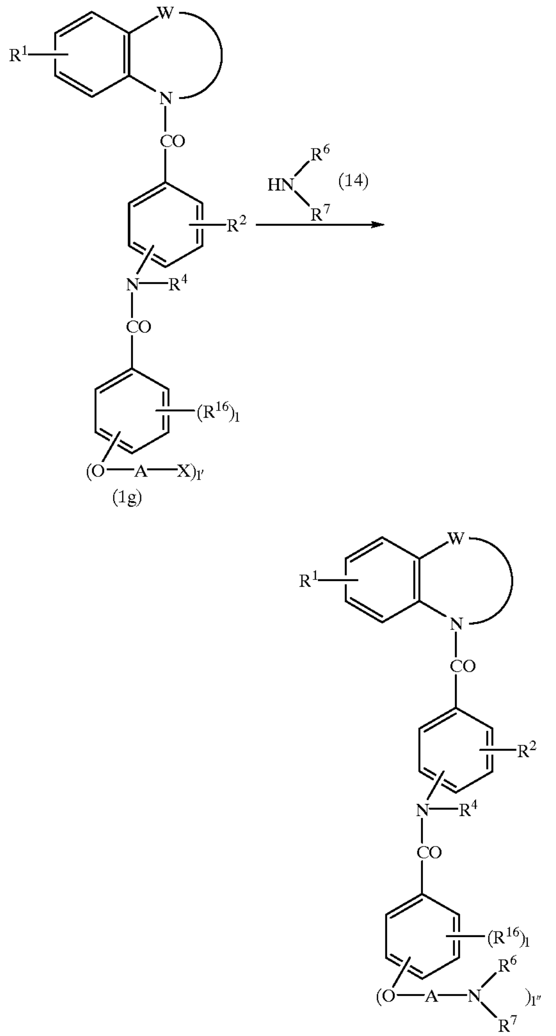

(1g) (14) (1h)

wherein $R^1$, $R^2$, $R^4$, $R^{16}$, $R^6$, $R^7$, X, W, and A are as defined above, l is 0 or an integer of 1 to 3, l' and l'' are each an integer of 1 to 3, provided that l+l' and l+l' are each an integer not more than 3.

[Reaction Scheme-6B]

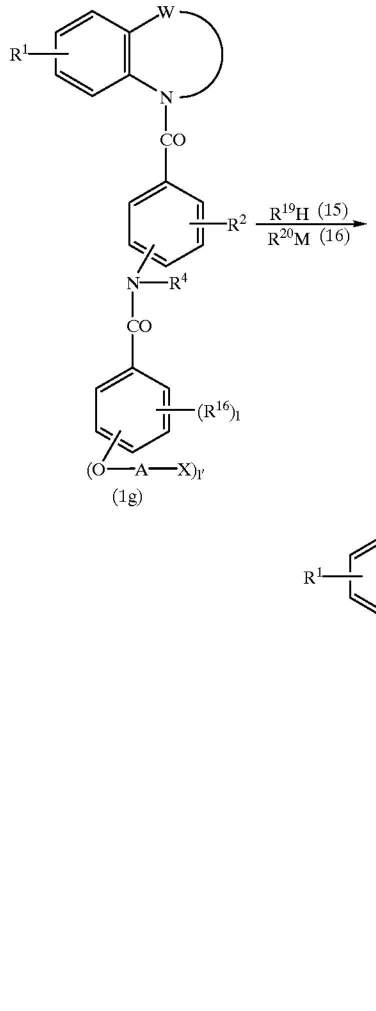

(1g) (1i)

wherein $R^1$, $R^2$, $R^4$, $R^{16}$, X, W, A, l, l', and l'' are as defined above, and $R^{19}$ is a lower alkanoyloxy, $R^{20}$ is a lower alkanoyloxy, hydroxy or phthalimido, $R^{21}$ is the same as as $R^{19}$ and $R^{20}$, and M is an alkali metal (e.g. potassium, sodium, etc.).

The reaction of the compound (1g) and the compound (14) in the Reaction Scheme-6A and the reaction of the compound (1g) and the compound (15) or (16) in the Reaction Scheme-6B can be carried out under the same conditions as in the reaction of the compound (7) and the compound (8) in the above Reaction Scheme-4. In the reaction, an alkali metal halide (e.g. sodium iodide, potassium iodide, etc.) may be added to the reaction system.

[Reaction Scheme-7]

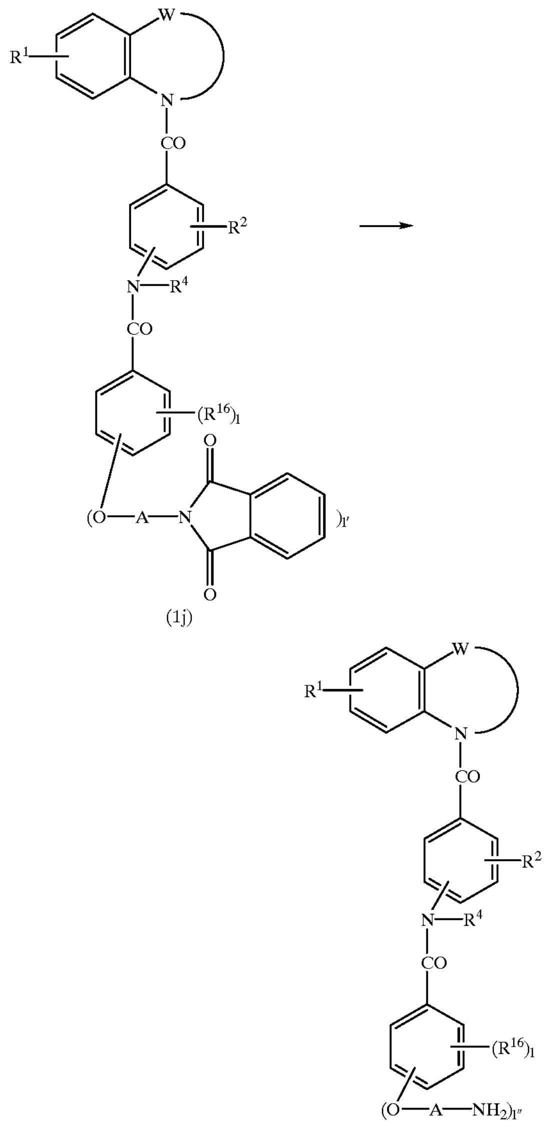

(1j)

(1k)

wherein $R^1$, $R^2$, $R^4$, $R^{16}$, W, l, l', l" and A are as defined above.

The reaction of converting the compound (1j) into the compound (1k) can be carried out by reacting the compound (1j) with hydrazine in an appropriate solvent or by hydrolyzing the compound (1j). The solvent used in the reaction with hydrazine includes water and further the same solvent as used in the reaction of the compound (2b) and the compound (4) in the above Reaction Scheme-2. The reaction is usually carried out at a temperature of from room temperature to about 120° C., preferably about 0° C. to about 100° C., for about 0.5 to 5 hours. Hydrazine is usually used in an amount of at least 1 mole, preferably about 1 to 5 moles, to 1 mole of the compound (1j).

The hydrolysis can be carried out in an appropriate solvent or without solvent in the presence of an acid or a basic compound. The solvent includes, for example, water, lower alcohols (e.g. methanol, ethanol, isopropanol, etc.), ketones (e.g. acetone, methyl ethyl ketone, etc.), ethers (e.g. dioxane, tetrahydrofuran, ethylene glycol dimethyl ether, etc.), fatty acids (e.g. acetic acid, formic acid, etc.), or a mixture of these solvents. The acid includes, for example, mineral acids (e.g. hydrochloric acid, sulfuric acid, hydrobromic acid, etc.) and organic acids (e.g. formic acid, acetic acid, aromatic sulfonic acids, etc.). The basic compound includes, for example, metal carbonates (e.g. sodium carbonate, potassium carbonate, etc.), metal hydroxides (e.g. sodium hydroxide, potassium hydroxide, calcium hydroxide, etc.), and the like. The reaction is usually carried out at a temperature of from room temperature to about 200° C., preferably from room temperature to about 150° C., for about 10 minutes to 25 hours.

[Reaction Scheme-8]

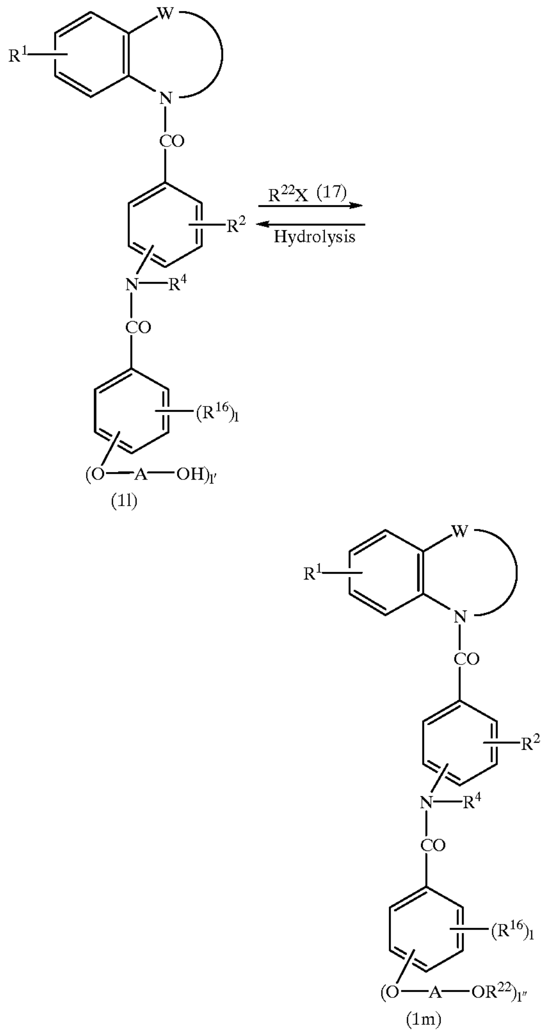

(1l)

(1m)

wherein $R^1$, $R^2$, $R^4$, W, $R^{16}$, l, l', l", X, and A are as defined above, and $R^{22}$ is a lower alkanoyl.

The reaction of the compound (1l) and the compound (17) is carried out under the same conditions as in the reaction of the compound (7) and the compound (8) in the Reaction Scheme-4. In the reaction, an alkali metal halide (e.g. sodium iodide, potassium iodide, etc.) may be added to the reaction system.

The reaction of converting the compound (1m) into the compound (1i) can be carried out under the same condition as in the hydrolysis of the compound (1j) in the Reaction Scheme-7.

[Reaction Scheme-9]

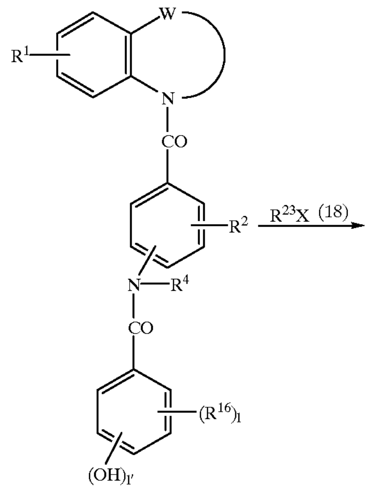

(1n)

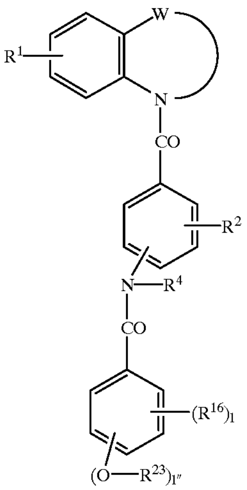

(1o)

wherein $R^1$, $R^2$, $R^4$, W, $R^{16}$, l, l', l'', and X are as defined above, and $R^{23}$ is a lower alkyl, a lower alkanoyloxy-substituted lower alkyl, a halogen-substituted lower alkyl, a carboxy-substituted lower alkyl, a carbamoyl-substituted lower alkyl, a hydroxy-substituted lower alkyl, a lower alkoxycarbonyl-substituted lower alkyl, a phthalimido-substituted lower alkyl, an aminocarbonyl-lower alkyl having optionally a lower alkyl substituent, or a group of the formula:

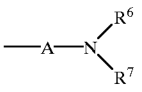

(A, $R^6$ and $R^7$ are as defined above).

The reaction of the compound (1n) and the compound (18) can be carried out under the same conditions as in the reaction of the compound (7) and the compound (8) in the above Reaction Scheme-4. In the reaction, an alkali metal halide (e.g. sodium iodide, potassium iodide, etc.) may be added to the reaction system.

[Reaction Scheme-10]

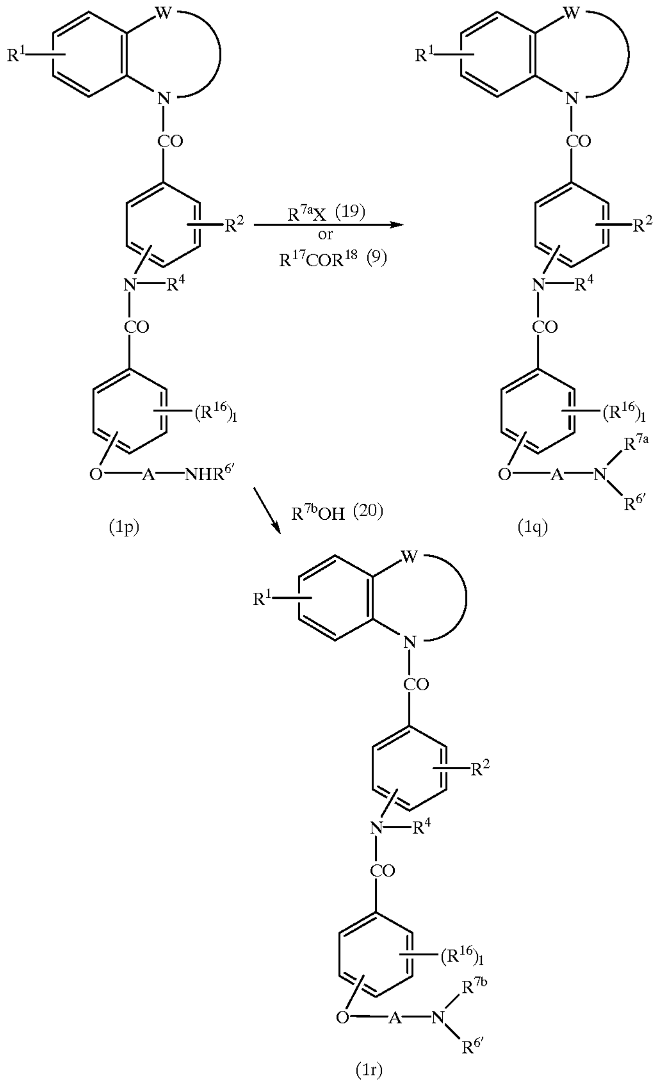

wherein $R^1$, $R^2$, $R^4$, W, $R^{16}$, $R^{17}$, $R^{18}$, l, X, and A are as defined above, and $R^{6'}$ is hydrogen atom, a lower alkyl having optionally a hydroxy substituent, a lower alkanoyl, or benzoyl, $R^{7a}$ is a lower alkyl having optionally a hydroxy substituent, and $R^{7b}$ is a lower alkanoyl or benzoyl.

The reaction of the compound (1p) and the compound (19) or the compound (9) can be carried out under the same conditions as in the reaction of the compound (7) and the compound (8) or the compound (9) in the above Reaction Scheme-4.

The reaction of the compound (1p) and the compound (20) can be carried out under the same conditions as in the reaction of the compound (2) and the compound (3) in the Reaction Scheme-1.

Besides, the compound (1r) can also be obtained by reacting the compound (1p) with a compound of the formula: $(R^{7b})_2O$ ($R^{7b}$ is as defined above). The reaction can be carried out in an appropriate solvent or without solvent in the presence or absence, peferably presence, of a basic compound. The solvent includes, for example, the above-mentioned aromatic hydrocarbons, lower alcohols (e.g. methanol, ethanol, propanol, etc.), dimethylformamide, dimethylsulfoxide, and further halogenated hydrocarbons (e.g. chloroform, methylene chloride, etc.), acetone, pyridine, etc. The basic compound includes, for example, tertiary amines (e.g. triethylamine, pyridine, etc.), sodium hydroxide, potassium hydroxide, sodium hydride, and the like. The above reaction can also be carried out in a solvent such as acetic acid or benzoic acid in the presence of a mineral acid (e.g. sulfuric acid, etc.). The acid anhydride is usually used in an equimolar amount or more, preferably 1 to 10 moles, to 1 mole of the starting compound, and the reaction is usually carried out at a temperature of about 0° C. to about 200° C., preferably from about 0° C. to about 150° C., for about 0.5 to 15 hours.

[Reaction Scheme-11]

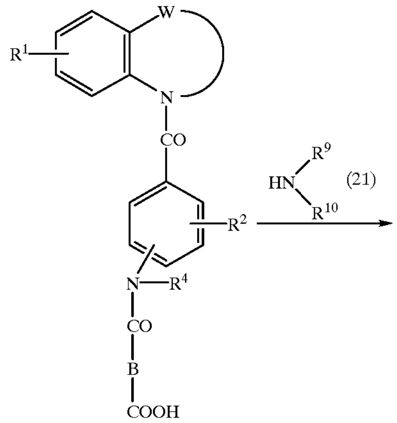

(1s)

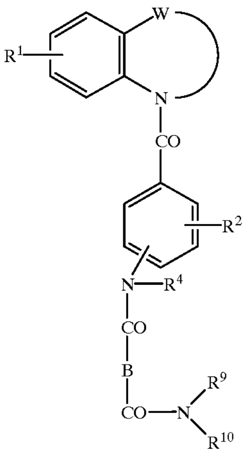

(1t)

wherein $R^1$, $R^2$, $R^4$, $R^{10}$, W, and B are as defined above.

The reaction of the compound (1s) and the compound (21) can be carried out under the same conditions as in the reaction of the compound (2) and the compound (3) in the above Reaction Scheme-1.

[Reaction Scheme-12]

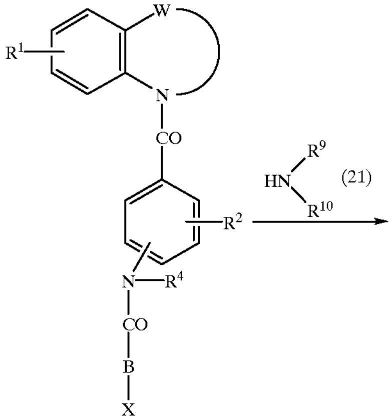

(1u)

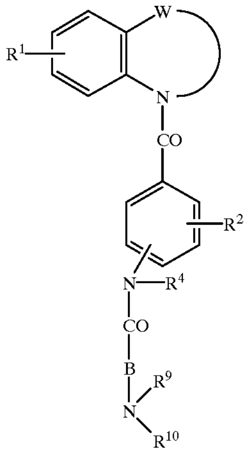

(1v)

wherein $R^1$, $R^2$, $R^4$, W, $R^9$, $R^{10}$, X, and B are as defined above.

The reaction of the compound (1u) and the compound (21) can be carried out under the same conditions as in the reaction of the compound (7) and the compound (8) in the above Reaction Scheme-4. In the reaction, an alkali metal halide (e.g. sodium iodide, potassium iodide, etc.) may be added to the reaction system.

[Reaction Scheme-13]

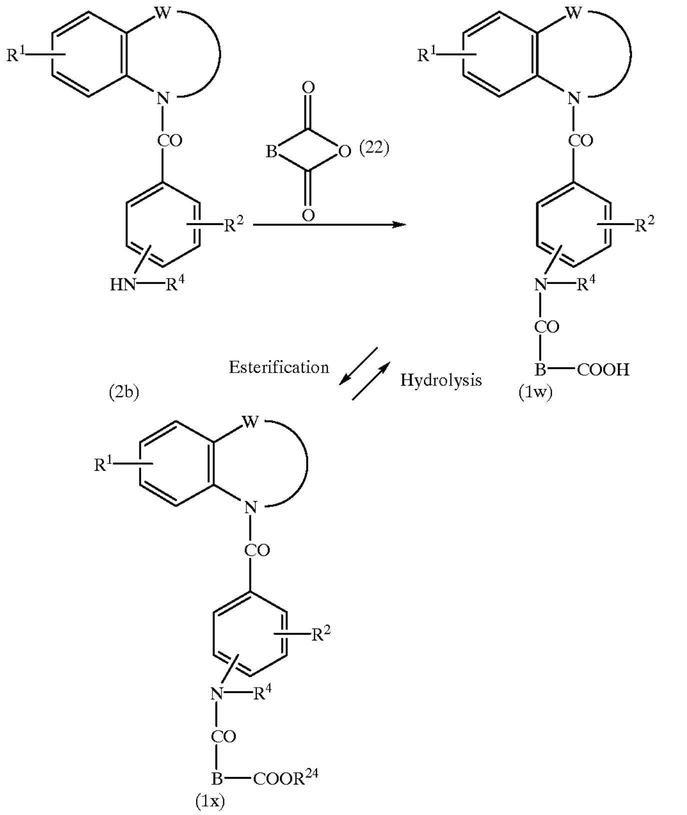

(2b) (22) (1w) (1x)

wherein $R^1$, $R^2$, $R^4$, W, and B are as defined above, and $R^{24}$ is a lower alkyl.

The reaction of the compound (2b) and the compound (22) can be carried out in an appropriate inert solvent. The inert solvent includes, for example, aromatic hydrocarbons (e.g. benzene, toluene, xylene, etc.), ethers (e.g. tetrahydrofuran, dioxane, diethylene glycol dimethyl ether, etc.), lower alcohols (e.g. methanol, ethanol, isopropanol, butanol, etc.), halogenated hydrocarbons (e.g. dichloromethane, chloroform, carbon tetrachloride, etc.), acetic acid, ethyl acetate, acetonitrile, dimethylsulfoxide, dimethylformamide, hexamethylphosphoric triamide, and the like. The amount of the compound (2b) and the compound (22) is not critical, but the compound (22) is usually used in an amount of at least one mole, preferably 1 to 2 moles, to 1 mole of the compound (2b). The reaction is usually carried out at a temperature of from about 0° C. to about 150° C., preferably from about 0° C. to about 100° C., for about 30 minutes to about 10 hours.

The esterification of the compound (1w) is usually carried out by reacting the starting compound with an alcohol (e.g. methanol, ethanol, isopropanol, etc.) in the presence of a mineral acid (e.g. hydrochloric acid, sulfuric acid, etc.) and a halogenating agent (e.g. thionyl chloride, phosphorus oxychloride, phosphorus pentachloride, phosphorus trichloride, etc.) at a temperature of 0° C. to 150° C., preferably 50° C. to 100° C., for about 1 to 10 hours.

The hydrolysis of the compound (1x) can be carried out under the same conditions as in the hydrolysis of the compound (1j) in the Reaction Scheme-7.

[Reaction Scheme-14]

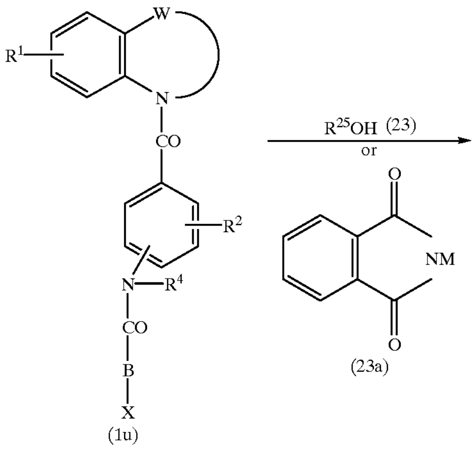

(1u) (23a)

-continued

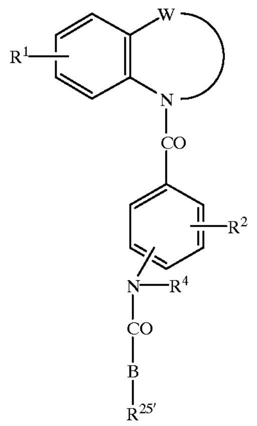

(1y)

wherein $R^1$, $R^2$, $R^4$, W, B, M, and X are as defined above, and $R^{25}$ is a phenyl which has optionally 1 to 3 substituents selected from a lower alkyl, a lower alkoxy and an amino having optionally a lower alkanoyl substituent, or naphthyl, and $R^{25'}$ is a phenoxy which has optionally 1 to 3 substituents selected from a lower alkyl, a lower alkoxy and an amino having optionally a lower alkanoyl substituent, naphthyloxy or phthalimido.

The reaction of the compound (1u) and the compound (23) or (23a) can be carried out under the same conditions as in the reaction of the compound (7) and the compound (8) in the above Reaction Scheme-4.

The compound (1y) wherein $R^{25'}$ is phthalimido can be converted into the compound (1y) wherein $R^{25'}$ is amino under the same conditions as in the reaction of converting the compound (1j) into the compound (1k) in the above Reaction Scheme-7
[Reaction Scheme-15]

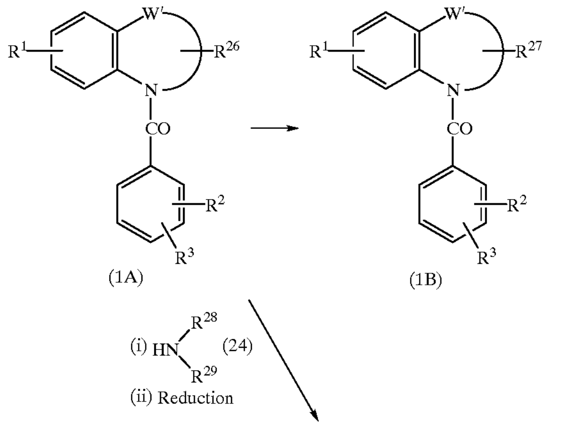

-continued

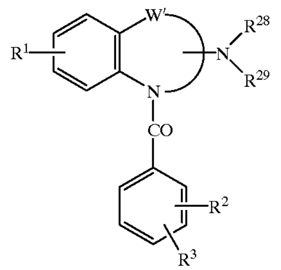

(1C)

wherein $R^1$, $R^2$ and $R^3$ are as defined above, and $R^{26}$ is oxo, $R^{27}$ is hydroxy, and W' is the same as W, provided that the substituents on the group $-(CH_2)_p-$ or $-CH=CH-(CH_2)_q-$ are 0 to 2, and $R^{28}$ and $R^{29}$ are the same or different and are each hydrogen atom, a lower alkenyl, a cycloalkyl, an oxiranyl-substituted lower alkyl, a lower alkyl having 1 to 2 substituents selected from a lower alkoxy, hydroxy and an amino having optionally a lower alkyl substituent, a phenyl-lower alkyl, a pyridyl-lower alkyl, a cyano-substituted lower alkyl, a lower alkoxycarbonyl-substituted lower alkyl, a carbamoyl-substituted lower alkyl, a carboxy-substituted lower alkyl, a tetrahydropyranyloxy-substituted lower alkyl, a lower alkanoyloxy-substituted lower alkyl, a piperidinyl which has optionally a phenyl-lower alkyl substituent, an aminocarbonyl-lower alkyl having optionally a lower alkyl substituent, or a lower alkyl, or $R^{28}$ and $R^{29}$ may bind together with the nitrogen atom to which they bond to form a 5- or 6-membered saturated heterocyclic group with or without being intervened with nitrogen or oxygen atom, which heterocyclic ring may optionally have a substituent selected from a lower alkyl, a phenyl-lower alkyl, or a lower alkanoyl.

The conversion of the compound (1A) into the compound (1B) is carried out by reduction thereof. The reducing reaction is preferably carried out by using a hydrogenating reducing agent (e.g. lithium aluminum hydride, sodium boro hydride, diborane, etc.). The reducing agent is usually used in an amount of at least one mole, preferably 1 to 15 moles, to 1 mole of the starting compound. The reducing reaction is usually carried out in an appropriate solvent, for example, water, alcohols (e.g. methanol, ethanol, isopropanol, etc.), ethers (e.g. tetrahydrofuran, diethyl ether, diisopropyl ether, diglyme, etc.), or a mixture of these solvents, at a temperature of from about −60° C. to about 150° C., peferably about −30° C. to about 100° C., for about 10 minutes to 15 hours. When lithium aluminum hydride or diborane is used as the reducing agent, it is preferable to use an anhydrous solvent such as tetrahydrofuran, diethyl ether, diisopropyl ether, diglyme, etc.

The reaction of converting the compound (1A) into the compound (1C) is usually carried out in an appropriate solvent or without solvent in the presence or absence of a dehydrating agent. The solvent includes, for example, lower alcohols (e.g. methanol, ethanol, isopropanol, etc.), aromatic hydrocarbons (e.g. benzene, toluene, xylene, etc.), halogenated hydrocarbons (e.g. dichloromethane, dichloroethane, chloroform, carbon tetrachloride, etc.), aprotic polar solents (e.g. dimethylformamide, dimethylacetamide, N-methylpyrrolidone, etc.), or a mixture of these solvents. The dehydrating agent includes, for example, conventional drying agent used for dehydrating solvents (e.g. molecular sieves, etc.), mineral acids (e.g. hydrochloric acid, sulfuric acid, borone trifluoride, etc.), organic acids (e.g. p-toluenesulfonic acid, etc.), and the like. The reaction is usually carried out at a temperature of from room temperature to about 250° C., preferably from about 50° C. to about 200° C., for about 1 to 48 hours. The amount of the compound (24) is not critical, but it is usually used at least in an equivalent amount, preferably equimolar to largely excess to the amount of the compound (1A). The dehydrating agent is preferably used in a largely excess amount in case of the drying agent and in a catalytic amount in case of the acid.

The subsequent reducing reaction can be carried out by various methods, for example by catalytically hydrogenating the compound in an appropriate solvent in the presence of a catalyst. The solvent includes, for example, water, acetic acid, alcohols (e.g. methanol, ethanol, isopropanol, etc.), hydrocarbons (e.g. hexane, cyclohexane, etc.), ethers (e.g. diethylene glycol dimethyl ether, dioxane, tetrahydrofuran, diethyl ether, etc.), esters (e.g. ethyl acetate, methyl acetate, etc.), aprotic polar solvents (e.g. dimethylformamide, etc.), or a mixture of these solvents. The catalyst includes, for example, palladium, palladium black, palladium-carbon, platinum, platinum oxide, copper chromite, Raney nickel, and the like. The catalyst is usually used in an amount of 0.02 to 1 part by weight to 1 part by weight of the starting compound. The reaction is usually carried out at a temperature of from about –20° C. to about 100° C., peferably about 0° C. to about 70° C., under a hydrogen atmospheric pressure of 1 to 10 atm. for about 0.5 to 20 hours.

Although the reducting reaction can be carried out under the above conditions, it is preferably carried out by using a hydrogenating reducing agent. The hydrogenating reducing agent includes, for example, lithium aluminum hydride, sodium borohydride, diborane, etc., and it is usually used in an amount of at least one mole, preferably 1 to 10 moles, to 1 mole of the compound (1A). The reaction is usually carried out in an appropriate solvent, such as water, lower alcohols (e.g. methanol, ethanol, isopropanol, etc.), ethers (e.g. tetrahydrofuran, diethyl ether, diglyme, etc.), dimethylformamide, or a mixture of these solvents, at a temperature of about –60° C. to about 50° C., preferably about –30° C. to room temperature, for about 10 minutes to about 5 hours. When lithium aluminum hydride or diborane is used as the reducing agent, it is preferable to use an anhydrous solvent such as diethyl ether, tetrahydrofuran, diglyme, etc.

The compound (1C) wherein at least one of $R^{28}$ and $R^{29}$ is hydrogen atom can be converted into the compound (1C) wherein at least one of $R^{28}$ and $R^{29}$ is a lower alkyl by reacting the compound (1C) with the compound (8) or the compound (9) under the same conditions as in the reaction of the compound (7) and the compound (8) or (9) in the above Reaction Scheme-4.

[Reaction Scheme-16]

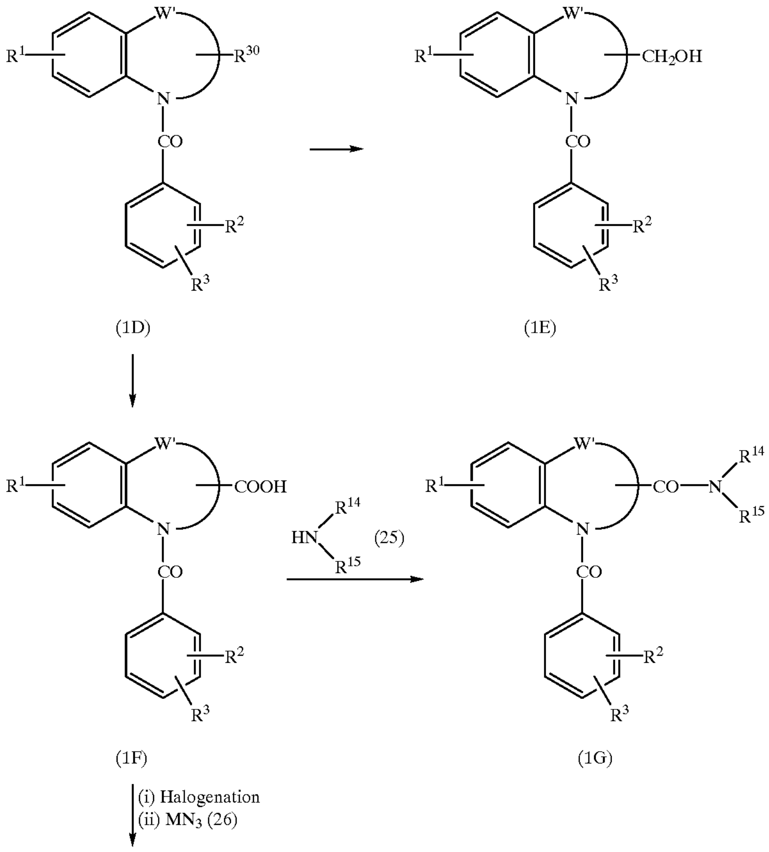

(1D) (1E) (1F) (1G)

-continued

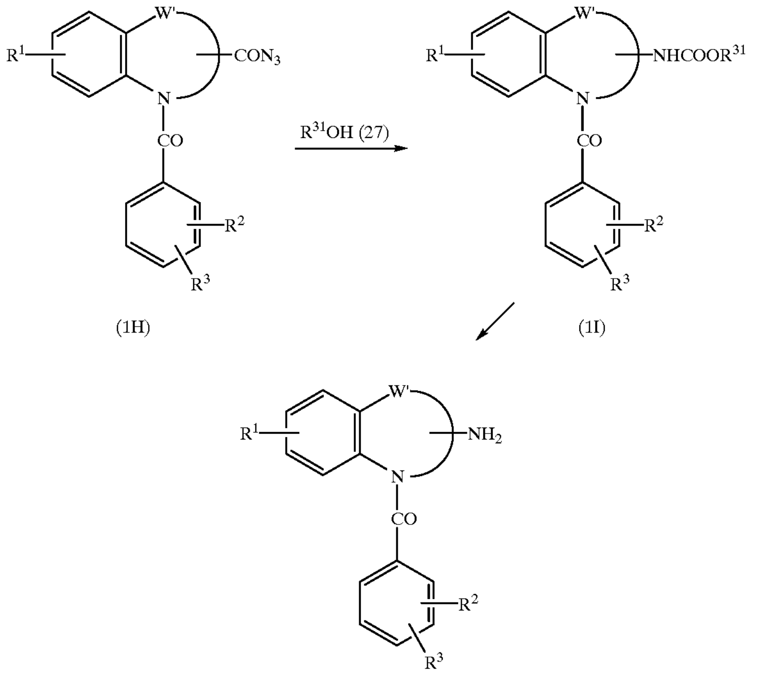

(1H) (1I) (1J)

wherein $R^1$, $R^2$, $R^3$, $R^{14}$, $R^{15}$, W', and M are as defined above, and $R^{31}$ is a phenyl-lower alkyl, and $R^{30}$ is a lower alkoxycarbonyl.

The reaction of converting the compound (1D) into the compound (1E) can be carried out under the same conditions as in the reaction of converting the compound (1A) into the compound (1B) in the above Reaction Scheme-15.

The reaction of converting the compound (1D) into the compound (1F) can be carried out under the same conditions as in the hydrolysis reaction of the compound (1j) in the above Reaction Scheme-7.

The reaction of the compound (1F) and the compound (25) can be carried out under the same conditions as in the reaction of the compound (2) and the compound (3) in the above Reaction Scheme-1.

The halogenation of the compound (1F) can be carried out under a conventional condition for halogenation of a carboxylic acid. The reaction of the thus-obtained carboxylic acid halide of the compound (1F) with the compound (26) is carried out in an appropriate solvent in the presence or absence of a basic compound. The solvent includes, for example, halogenated hydrocarbons (e.g. methylene chloride, chloroform, etc.), aromatic hydrocarbons (e.g. benzene, toluene, xylene, etc.), ethers (e.g. diethyl ether, tetrahydrofuran, dimethoxyethane, etc.), esters (e.g. methyl acetate, ethyl acetate, etc.), aprotic polar solvents (e.g. N,N-dimethylformamide, dimethylsulfoxide, hexamethylphosphoric triamide, etc.), alcohols (e.g. methanol, ethanol, propanol, butanol, 3-methoxy-1-butanol, ethyl cellosolve, methyl cellosolve, etc.), pyridine, acetone, acetonitrile, water, or a mixture of these solvents. The basic compound includes, for example, organic bases such as triethylamine, trimethylamine, pyridine, dimethylaniline, N-methylmorpholine, DBN, DBU, DABCO, etc., inorganic bases such as potassium carbonate, sodium carbonate, potassium hydroxide, sodium hydroxide, potassium hydride, sodium hydride, silver carbonate, alcoholates (e.g. sodium methylate, sodium ethylate, etc.), and the like. The compound (26) is usually used in an amount of at least 1 mole, preferably 1 to 1.5 mole, to 1 mole of the carboxylic acid halide of the compound (1F). The reaction is usually carried out at a temperature of from −30° C. to about 180° C., preferably from about 0° C. to about 150° C., for about 5 minutes to 30 hours.

The reaction of the compound (1H) and the compound (27) is carried out in an appropriate solvent or without solvent at a temperature of from about 0° C. to about 200° C., preferably from room temperature to about 150° C. The solvent includes the same solvents as used in the above reaction of the carboxylic acid halide of the compound (1F) and the compound (26). The compound (27) is preferably used in an amount largely excess to the the compound (1H). The reaction is usually completed in a reaction time of about 1 to 5 hours.

The reaction of converting the compound (1I) into the compound (1J) can be carried out by reducing the compound. The reducing reaction is usually carried out by catalytically hydrogenating the compound in an appropriate solvent in the presence of a catalyst. The solvent includes, for example, water, acetic acid, alcohols (e.g. methanol, ethanol, isopropanol, etc.), hydrocarbons (e.g. hexane, cyclohexane, etc.), ethers (e.g. dioxane, tetra-hydrofuran, diethyl ether, diethylene glycol dimethyl ether, etc.), esters (e.g. ethyl acetate, methyl acetate, etc.), aprotic polar solvents (e.g. N,N-dimethylformamide, etc.), acetic acid, or a mixture of these solvents. The catalyst includes, for example, palladium, palladium black, palladium-carbon, platinum, platinum oxide, copper chromite, Raney nickel, and the like. The catalyst is usually used in an amount of 0.02 to 1 part by weight to 1 part by weight of the starting compound. The reaction is usually carried out at a temperature of from about −20° C. to about 100° C., peferably about 0° C. to about 80° C., under a hydrogen atmospheric pressure of 1 to 10 atm. for about 0.5 to 20 hours.

[Reaction Scheme-17]

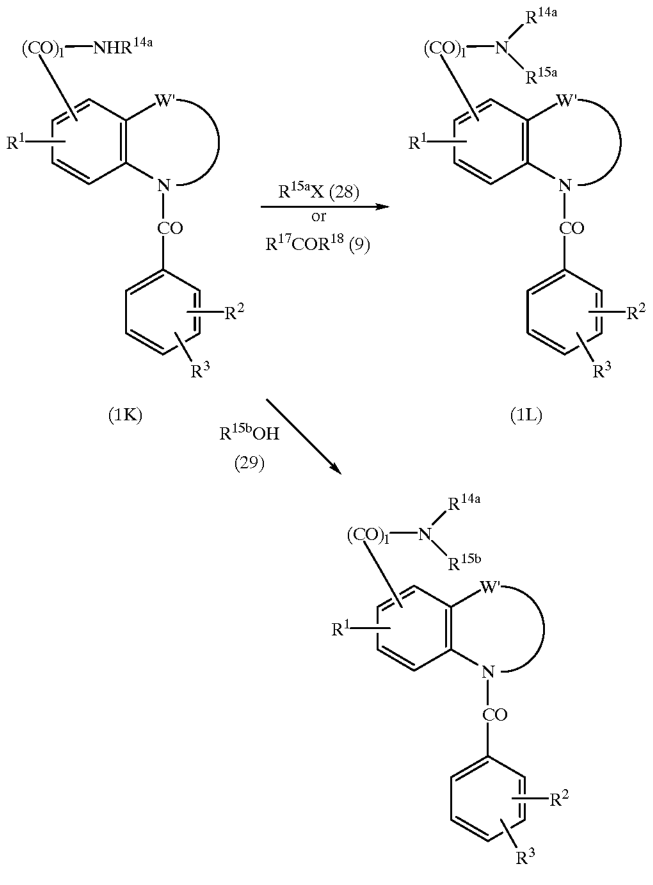

(1M)

wherein $R^1$, $R^2$, $R^3$, W', l, $R^{17}$, $R^{18}$, and X are as defined above, and $R^{14}$a is hydrogen atom, a lower alkyl, a lower alkanoyl, a lower alkenyl, a cycloalkyl, an oxiranyl-substituted lower alkyl, a lower alkyl having 1 to 2 substituents selected from a lower alkoxy, hydroxy and an amino having optionally a lower alkyl substituent, a phenyl-lower alkyl, a pyridyl-lower alkyl, a lower alkylsulfonyl, benzoyl, a lower alkoxycarbonyl, anilinocarbonyl, an aminocarbonyl having optionally a lower alkyl substituent, a cyano-substituted lower alkyl, a lower alkoxycarbonyl-substituted lower alkyl, a carbamoyl-substituted lower alkyl, a carboxy-substituted lower alkyl, a tetrahydropyranyloxy-substituted lower alkyl, a lower alkanoyloxy-substituted lower alkyl, a piperidinyl having optionally a phenyl-lower alkyl substituent, a halogen-substituted lower alkanoyl, an imiazolyl-substituted lower alkanoyl, an amino-lower alkanoyl having optionally a substituent selected from a lower alkyl and a lower alkoxycarbonyl, an aminocarbonyl-lower alkyl having optionally a lower alkyl substituent, or a phenyl-lower alkoxycarbonyl, $R^{15a}$is a lower alkyl, a cycloalkyl, an oxiranyl-substituted lower alkyl, a lower alkyl having 1 to 2 substituents selected from a lower alkoxy, hydroxy and an amino having optionally a lower alkyl substituent, a phenyl-lower alkyl, a pyridyl-lower alkyl, a lower alkylsulfonyl, a cyano-substituted lower alkyl, a lower alkoxycarbonyl-substituted lower alkyl, a carbamoyl-substituted lower alkyl, a carboxy-substituted lower alkyl, a tetrahydropyranyloxy-substituted lower alkyl, a lower alkanoyloxy-substituted lower alkyl, a piperidinyl having optionally a phenyl-lower alkyl substituent, an aminocarbonyl-lower alkyl having optionally a lower alkyl substituent, or a lower alkenyl, and $R^{15b}$ is a lower alkanoyl, a phenyl-lower alkoxycarbonyl, benzoyl, a lower alkoxycarbonyl, a halogen-substituted lower alkanoyl, an imidazolyl-substituted lower alkanoyl, or an amino-lower alkanoyl having optionally a substituent selected from a lower alkyl and a lower alkoxycarbonyl.

The reaction of the compound (1K) and the compound (28) or the compound (9) can be carried out under the same conditions as in the reaction of the compound (7) and the compound (8) or the compound (9) in the above Reaction Scheme-4.

The reaction of the compound (1K) and the compound (29) can be carried out under the same conditions as in the reaction of the compound (2) and the compound (3) in the above Reaction Scheme-1. The compound (1M) can also be obtained by reacting the compound (1K) with a compound of the formula $(R^{15b})_2O$ (wherein $R^{15b}$ is as defined above). The reaction can be carried out under the same conditions as in the reaction of the compound (1p) and the compound of the formula: $(R^{7b})_2O$ as described hereinbefore.

The compound (1M) wherein $R^{15b}$ is formyl can also be prepared by reacting the compound (1K) with a formate of the formula: $HCOOR^{82}$ ($R^{82}$ is a lower alkyl). The reaction is usually carried out in the solvent as used in the reaction of the compound (7) and the compound (8) in the above Reaction Scheme-4 or without solvent, at a temperature of about 0° C. to about 200° C., preferably about 0° C. to about 170° C., for about 30 minutes to about 30 hours. The formate is preferably used in a largely excess amount to the compound (1K).

[Reaction Scheme-18]

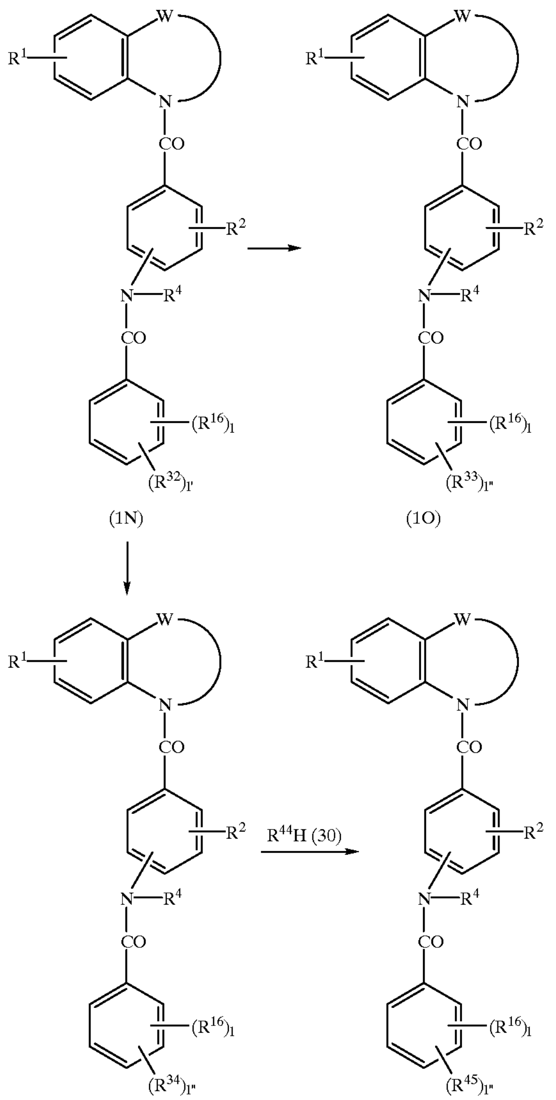

(1N) (1O) (1P) (1P')

wherein $R^1$, $R^2$, $R^4$, $R^{16}$, W, l, l' and l" are as defined above, and $R^{32}$ is a lower alkoxycarbonyl-substituted lower alkoxy, $R^{33}$ is a carbamoyl-substituted lower alkoxy, $R^{34}$ is a carboxy-substituted lower alkoxy, $R^{44}$ is an amino having optionally a lower alkyl substituent, and $R^{45}$ is an aminocarbonyl-lower alkoxy having optionally a lower alkyl substituent.

The conversion of the compound (1N) into the compound (10) can be carried out by reacting the compound with aqueous ammonia in an appropriate solvent in an autoclave. The solvent includes the same solvents as used in the reaction of the carboxylic acid halide and the amine (2) in the above Reaction Scheme-1. The aqueous ammonia is used in a largely excess amount to the compound (1N). The reaction proceeds advantageously by adding an ammonium halide (e.g. ammonium chloride, etc.) to the reaction system. The reaction is usually carried out at a temperature of from room temperature to about 200° C., preferably from room temperature to about 150° C., for about 1 to 10 hours.

The reaction of converting the compound (1N) into the compound (1P) can be carried out under the same conditions as in the hydrolysis of the compound (1j) in the above Reaction Scheme-7.

The reaction of the compound (1P) and the compound (30) can be carried out under the same conditions as in the reaction of the compound (2) and the compound (3) in the above Reaction Scheme-1.

[Reaction Scheme-19]

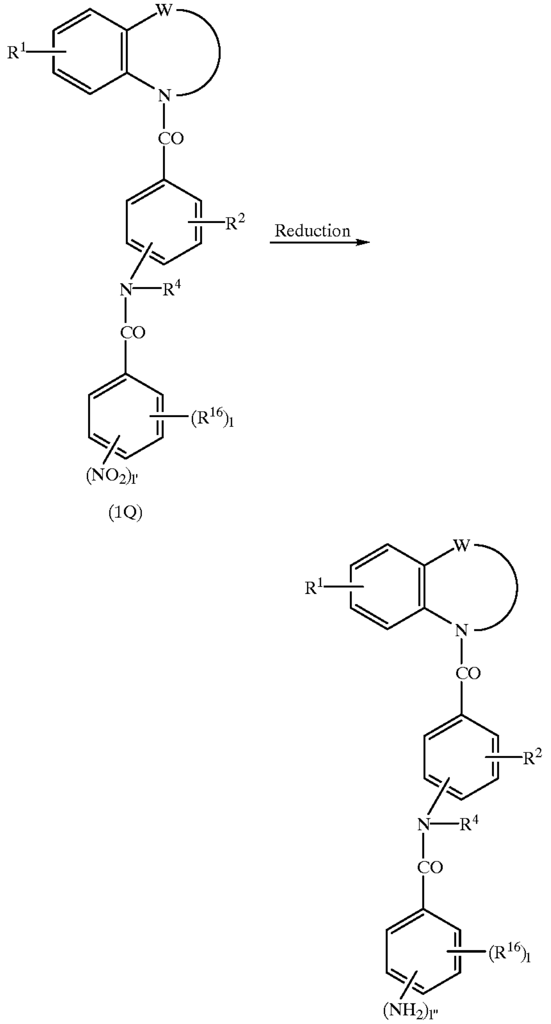

(1Q) (1R)

wherein $R^1$, $R^2$, $R^4$, $R^{16}$, W, l, l' and l" are as defined above.

The reducing reaction in the above reaction scheme is usually carried out, for example, (i) with a reducing catalyst in an appropriate solvent or (ii) with a reducing agent such as a mixture of a metal or metal salt with an acid, or a mixture of a metal or metal salt with an alkali metal hydroxide, a sulfide or an ammonium salt in an appropriate inert solvent.

In case of using a reducing catalyst, the solvent includes, for example, water, acetic acid, alcohols (e.g. methanol, ethanol, isopropanol, etc.), hydrocarbons (e.g. hexane, cyclohexane, etc.), ethers (e.g. dioxane, tetrahydrofuran, diethyl ether, diethylene glycol dimethyl ether, etc.), esters (e.g. ethyl acetate, methyl acetate, etc.), aprotic polar solvents (e.g. N,N-dimethylformamide, etc.), or a mixture of these solvents. The catalyst includes, for example, palladium, palladium black, palladium-carbon, platinum, platinum oxide, copper chromite, Raney nickel, and the like. The catalyst is usually used in an amount of 0.02 to 1 part by weight to 1 part by weight of the starting compound. The reaction is usually carried out at a temperature of from about −20° C. to about 150° C., peferably about 0° C. to about 100° C., under a hydrogen pressure of 1 to 10 atm. for about 0.5 to 10 hours. In the reaction, an acid such as hydrochloric acid may optionally added to the reaction system.

In case of the above method (ii), the reducting agent includes a mixture of iron, zinc, tin or stannous chloride and a mineral acid (e.g. hydrochloric acid, sulfuric acid, etc.), or a mixture of iron, ferrous sulfate, zinc or tin and an alkali metal hydroxide (e.g. sodium hydroxide., etc.), a sulfide (e.g. ammonium sulfide, etc.), aqueous ammonia, or an ammonium salt (e.g. ammonium chloride, etc.). The inert solvent includes, for example water, acetic acid, methanol, ethanol, dioxane, and the like. The reducing reaction conditions are determined depending on the kinds of the reducting agent, but in case of using a reducing agent comprising stannous chloride and hydrochloric acid, for example, it is preferably carried out at a temperature of about 0° C. to room temperature for about 0.5 to 10 hours. The reducing agent is usually used in an amount of at least one mole, preferably 1 to 5 moles, to 1 mole of the starting compound.

[Reaction Scheme-20]

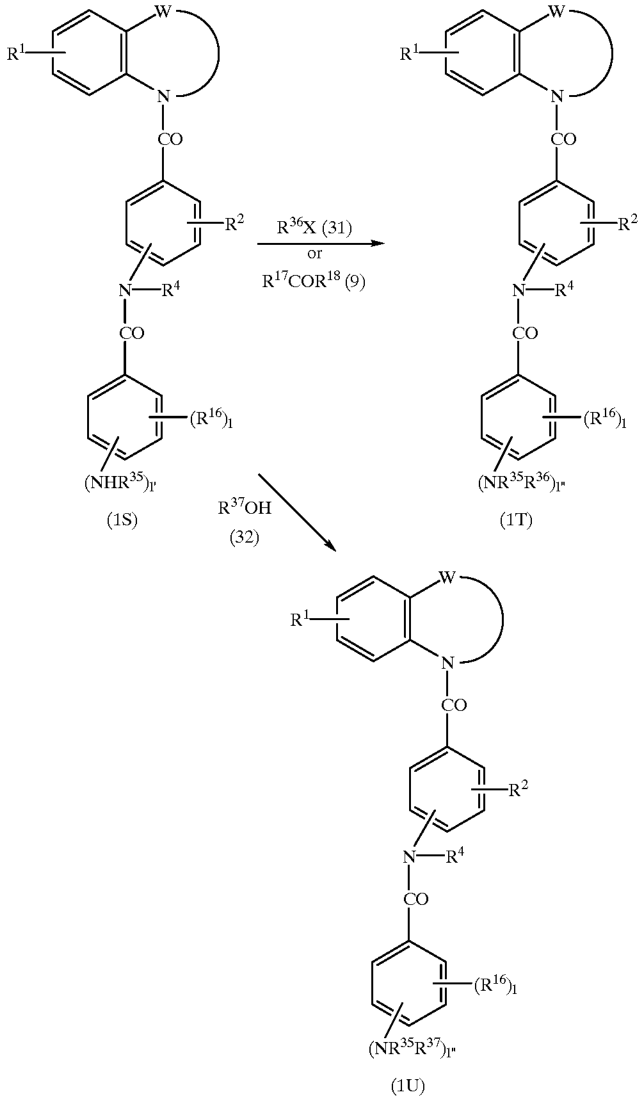

(1S) (1T) (1U)

wherein $R^1$, $R^2$, $R^4$, $R^{16}$, $R^{17}$, $R^{18}$, l, l', l" and W are as defined above, and $R^{36}$ is a lower alkyl, $R^{37}$ is a lower alkanoyl, and $R^{35}$ is hydrogen atom, a lower alkyl or a lower alkanoyl.

The reaction of the compound (1S) and the compound (31) or the compound (9) can be carried out under the same conditions as in the reaction of the compound (7) and the compound (8) or the compound (9) in the above Reaction Scheme-4.

The reaction of the compound (1S) and the compound (32) can be carried out under the same conditions as in the reaction of the compound (2) and the compound (3) in the above Reaction Scheme-1. Besides, the compound (1U) can also be obtained by reacting the compound (1S) with a compound of the formula: $(R^{37})_2O$ ($R^{37}$ is as defined above). The reaction is carried out under the same conditions as in the above reaction of the compound (1p) and a compound of the formula: $(R^{7b})_2O$.

The compound (1) wherein $R^8$ is a phenyl-lower alkoxy-carbonyl can be converted into the compound (1) wherein $R^8$ is hydrogen atom in the same manner as in the reaction of converting the compound (1I) into the compound (1J) in the above Reaction Scheme-16.

Other derivatives of the starting compound (2) can be prepared, for example, by the process as shown in the following reaction scheme.

The reaction of the compound (2) and the compound (33) can be carried out under the same conditions as in the reaction of the compound (2) and the compound (3) in the above Reaction Scheme-1.

The reaction of converting the compound (34) into the compound (2a) can be carried out under the same conditions as in the reducing reaction in the above Reaction Scheme-19.

The starting compound (5) can be prepared, for example, by the process of the following reaction scheme.

[Reaction Scheme-21]

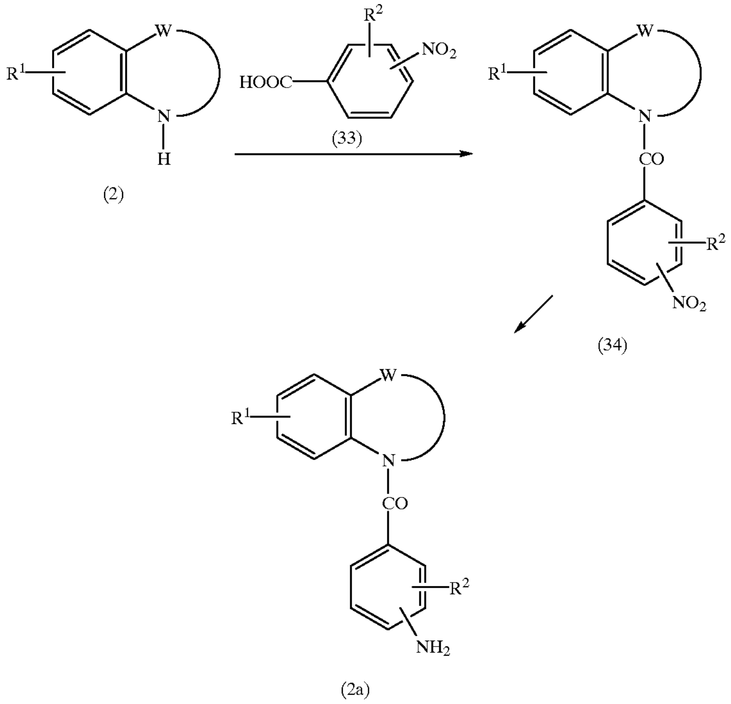

wherein $R^1$, $R^2$, and W are as defined above.

[Reaction Scheme-22]

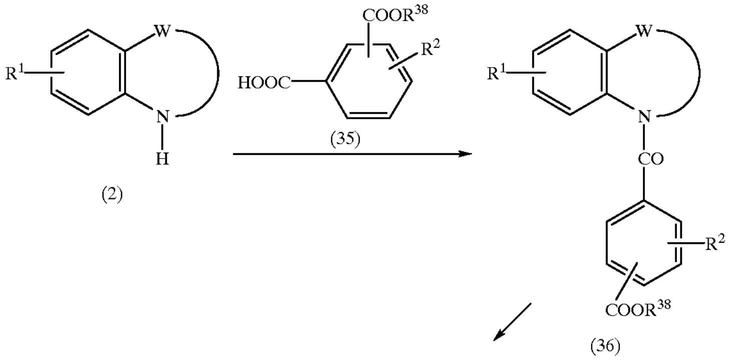

-continued

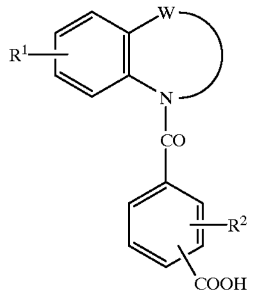

(5)

wherein $R^1$, $R^2$, and W are as defined above, and $R^{38}$ is a lower alkyl.

The reaction of the compound (2) and the compound (35) can be carried out under the same conditions as in the reaction of the compound (2) and the compound (3) in the above Reaction Scheme-1.

The reaction of converting the compound (36) into the compound (5) can be carried out under the same conditions as in the hydrolysis reaction in the above Reaction Scheme-7.

[Reaction Scheme-23]

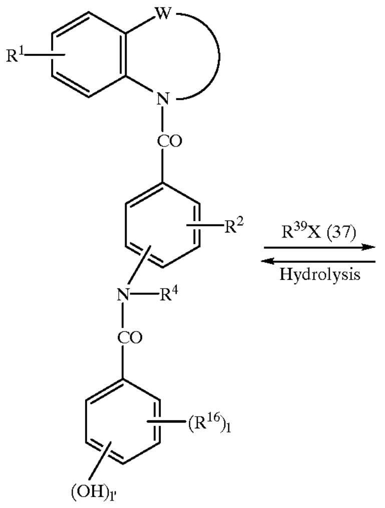

(1W)

-continued

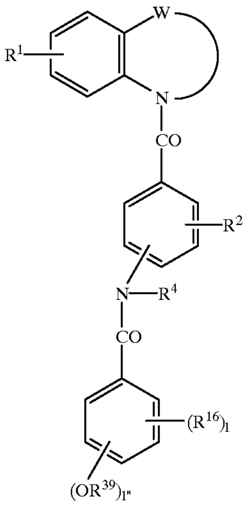

(1X)

wherein $R^1$, $R^2$, $R^4$, $R^{16}$, l, l', l'', X, and W are as defined above, and $R^{39}$ is a lower alkanoyl.

The reaction of the compound (1W) and the compound (37) can be carried out under the same conditions as in the reaction of the compound (1n) and the compound (18) in the above Reaction Scheme-9.

The hydrolysis reaction of the compound (1X) can be carried out under the same conditions as in the hydrolysis of the compound (1j) in the above Reaction Scheme-7.

[Reaction Scheme-24]

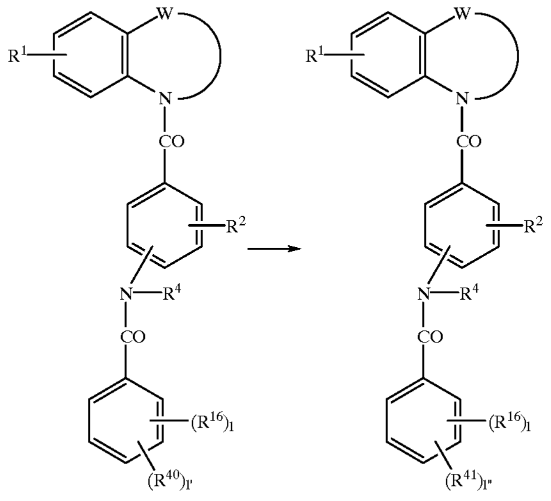

(1Y) (1Z)

wherein $R^1$, $R^2$, $R^4$, $R^{16}$, l, l', l", and W are as defined above, $R^{40}$ is a lower alkanoyl, and $R^{41}$ is a hydroxy-substituted lower alkyl.

The reaction of converting the compound (1Y) into the compound (1Z) can be carried out under the same conditions as in the reaction of converting the compound (1A) into the compound (1B) in the above Reaction Scheme-15.

[Reaction Scheme-25]

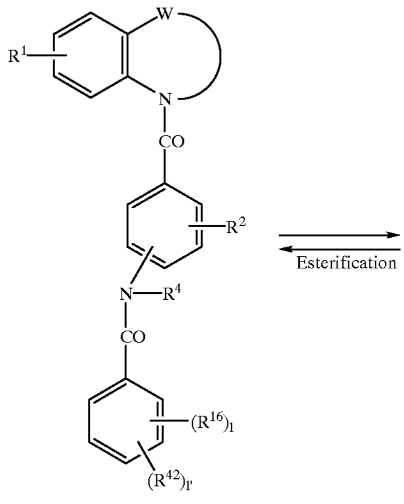

(1aa)

-continued

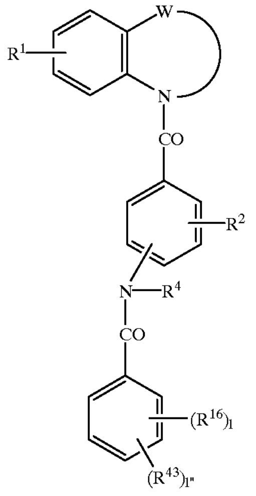

(1bb)

wherein $R^1$, $R^2$, $R^4$, $R^{16}$, l, l', l", and W are as defined above, $R^{42}$ is a lower alkoxycarbonyl and $R^{43}$ is carboxyl.

The reaction of converting the compound (1aa) into the compound (1bb) can be carried out under the same conditions as in the hydrolysis of the compound (1j) in the above Reaction Scheme-7.

The esterification reaction of the compound (1bb) can be carried out under the same conditions as in the esterification of the compound (1w) in the above Reaction Scheme-13.

[Reaction Scheme-26]

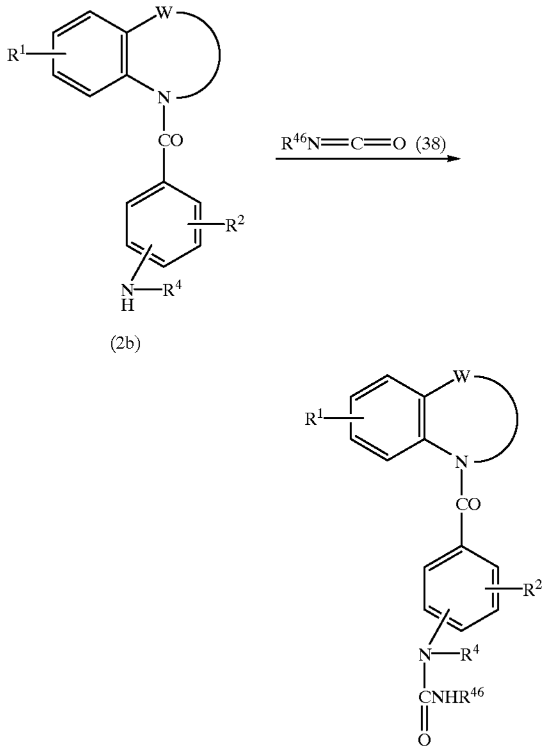

(2b)

(1cc)

wherein $R^1$, $R^2$, $R^4$, and W are as defined above, and $R^{46}$ is a phenyl having optionally a lower alkyl substituent.

The reaction of the compound (2b) and the compound (38) is usually carried out in an appropriate solvent or without solvent in the presence or absence, preferably in the absence, of a basic compound. The solvent and basic compound are the same as those used in the reaction of the carboxylic acid halide and the amine (2) in the above Reaction Scheme-1.

The compound (38) is usually used in an amount of about 1 to 5 moles, preferably about 1 to 3 moles, to 1 mole of the compound (2b). The reaction is usually carried out at a temperature of from about 0° C. to about 200° C., preferably from room temperature to about 150° C., for about 5 minutes to about 30 hours. In the reaction, a boron compound (e.g. boron trifluoride etherate, etc.) may be added to the reaction system.

[Reaction Scheme-27]

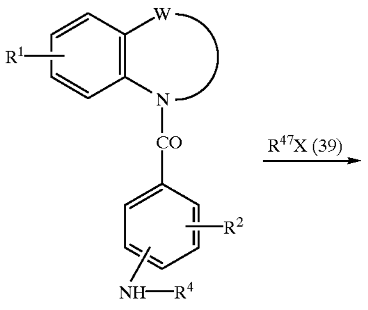

(2b)

-continued

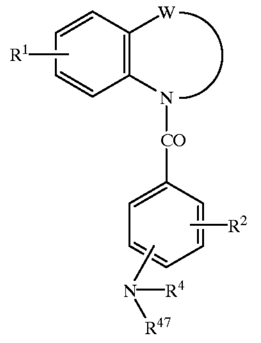

(1dd)

wherein $R^1$, $R^2$, $R^4$, W, and X are as defined above, and $R^{47}$ is a phenylsulfonyl which has optionally a substituent selected from a halogen atom and a lower alkyl on the phenyl ring, or quinolylsulfonyl.

The reaction of the compound (2b) and the compound (39) can be carried out under the same conditions as in the reaction of the compound (7) and the compound (8) in the above Reaction Scheme-4.

[Reaction Scheme-28]

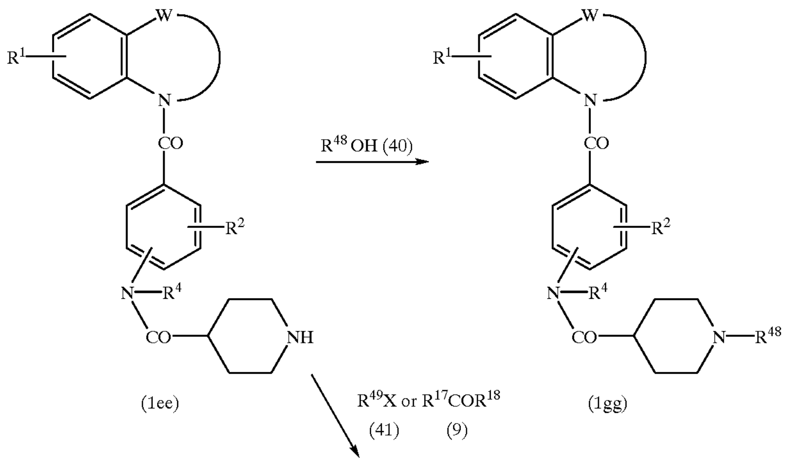

(1ee) (1gg)

-continued

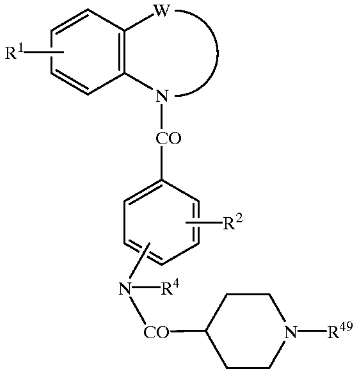

(1ff)

wherein $R^1$, $R^2$, $R^4$, W, $R^{17}$, $R^{18}$, and X are as defined above, $R^{48}$ is a phenyl-lower alkoxycarbonyl, a lower alkanoyl, an amino-lower alkanoyl having optionally a lower alkyl substituent, and $R^{49}$ is a lower alkyl or a carbamoyl-lower alkyl.

The reaction of the compound (1ee) and the compound (40) can be carried out under the same conditions as in the reaction of the compound (2) and the compound (3) in the above Reaction Scheme-1.

The reaction of the compound (1ee) and the compound (41) or the compound (9) can be carried out under the same conditions as in the reaction of the compound (7) and the compound (8) or the compound (9) in the above Reaction Scheme-4, provided that in the reaction product (1ff) produced by the reaction of the compound (1ee) and the compound (9), the group $R^{49}$ is a lower alkyl.

[Reaction Scheme-29]

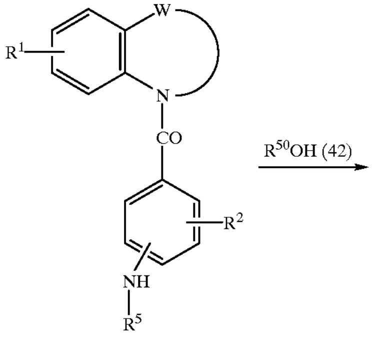

(7)

-continued

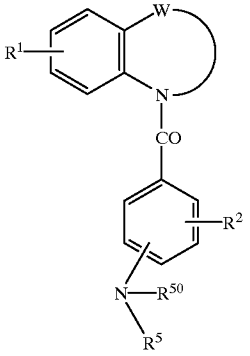

(Ihh)

wherein $R^1$, $R^2$, $R^5$, and W are as defined above, and $R^{50}$ is a benzoyl having optionally a halogen substituent on the phenyl ring.

The reaction of the compound (7) and the compound (42) can be carried out under the same conditions as in the reaction of the compound (2) and the compound (3) in the above Reaction Scheme-1.

[Reaction Scheme-30]

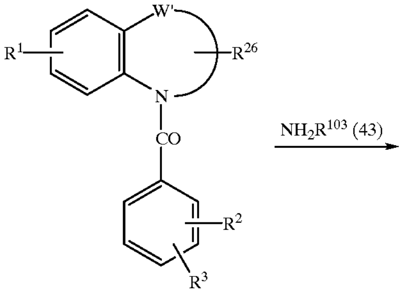

(1A)

-continued

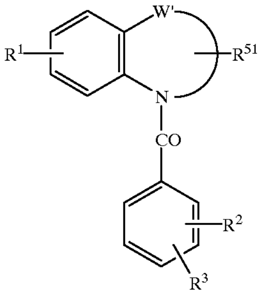

(1ii)

wherein $R^1$, W', $R^{26}$, $R^2$, and $R^3$ are as defined above, $R^{103}$ is hydroxy or sulfoxy, and $R^{51}$ is hydroxyimino or sulfoxyimino.

The reaction of the compound (1A) and the compound (43) is usually carried out in an appropriate inert solvent in the presence or absence of a basic compound. The basic compound includes, for example, inorganic basic compounds such as sodium hydroxide, potassium hydroxide, sodium carbonate, potassium carbonate, etc., and organic basic compounds such as piperidine, pyridine, triethylamine, 1,5-diazabicyclo[4.3.0]nonene-5 (DBN), 1,8-diazabicyclo[5.4.0]undecene-7 (DBU), 1,4-diazabicyclo[2.2.2]octane (DABCO), etc. The inert solvent includes, for example, lower alcohols (e.g. methanol, ethanol, isopropanol, etc.), ethers (e.g. dioxane, tetrahydrofuran, diethyl ether, ethylene glycol monomethyl ether, etc.), aromatic hydrocarbons (e.g. benzene, toluene, xylene, etc.), halogenated hydrocarbons (e.g. dichloromethane, dichloroethane, chloroform, carbon tetrachloride, etc.), pyridine, dimethylformamide, dimethylsulfoxide, hexamethylphosphoric triamide, etc., or a mixture of these solvents. The compound (43) is usually used at least in equivalent amount, preferably 1 to 5 moles, to 1 mole of the compound (1A). The reaction is usually carried out at a temperature of from room temperature to about 200° C., preferably from about 50° C. to 150° C., for about 1 to 10 hours.

[Reaction Scheme-31]

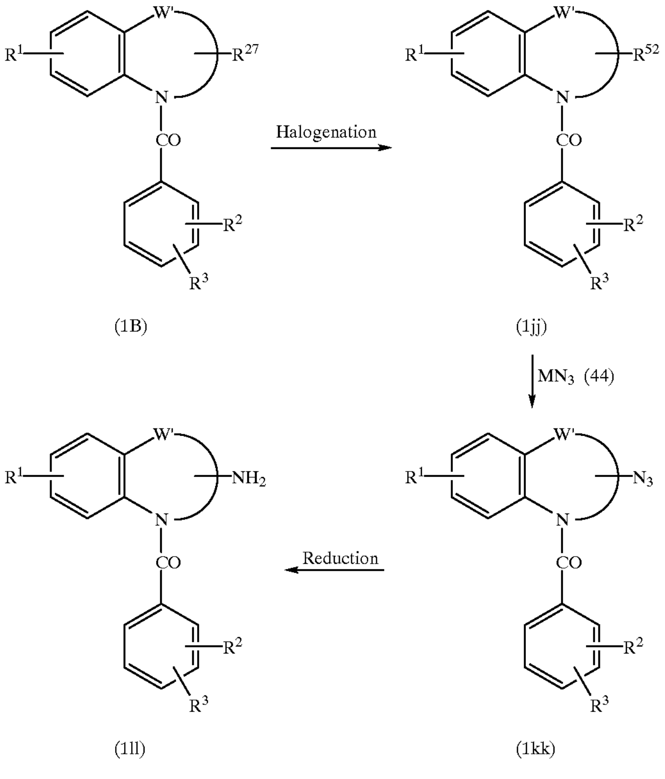

(1B) (1jj) (1kk) (1ll)

wherein $R^1$, W', $R^{27}$, $R^2$, M, and $R^3$ are as defined above, and $R^{52}$ is a halogen atom.

The halogenation of the compound (1B) is usually carried out in an appropriate solvent or without solvent by reacting the compound (1B) with a halogenating agent.

The halogenating agent includes mineral acids (e.g. hydrochloric acid, hydrobromic acid, etc.), N,N-diethyl-1, 2,2-trichlorovinylamide, phosphorus pentachloride, phosphorus pentabromide, phosphorus oxychloride, thionyl chloride, methanesulfonyl chloride, or a combination of a phenyl-lower alkyl halide (e.g. p-toluenesulfonyl chloride, etc.) and a basic compound. The basic compound includes the same compounds as used in the reaction of the compound (1A) and the compound (43) in the above Reaction Scheme-30. The solvent includes, for example, ethers (e.g. dioxane, tetrahydrofuran, etc.), halogenated hydrocarbons (e.g. chloroform, methylene chloride, carbon tetrachloride, etc.), and the like. The amount of the halogenating agent may vary depending on the kinds of the halogenating agents, and in case of a combination of a phenyl-lower alkyl halide (e.g. p-toluenesulfonyl chloride, etc.) and a basic compound, it is used in an amount of at least 1 mole, preferably 1 to 2 moles, to 1 mole of the compound (1B), and in case of other halogenating agents, it is used at least in an equimolar amount, usually in a largely excess amount, to the compound (1B). The reaction is usually carried out at a temperature of from room temperature to about 150° C., preferably from room temperature to about 80° C., for about 1 to 80 hours.

The reaction of the compound (1jj) and the compound (44) can be carried out under the same conditions as in the reaction of the compound (7) and the compound (8) in the above Reaction Scheme-4.

The reducing reaction of the compound (1kk) can be carried out under the same conditions as in the reducing reaction using a reducing catalyst for converting the compound (1A) into the compound (1C) in the above Reaction Scheme-15.

[Reaction Scheme-32A]

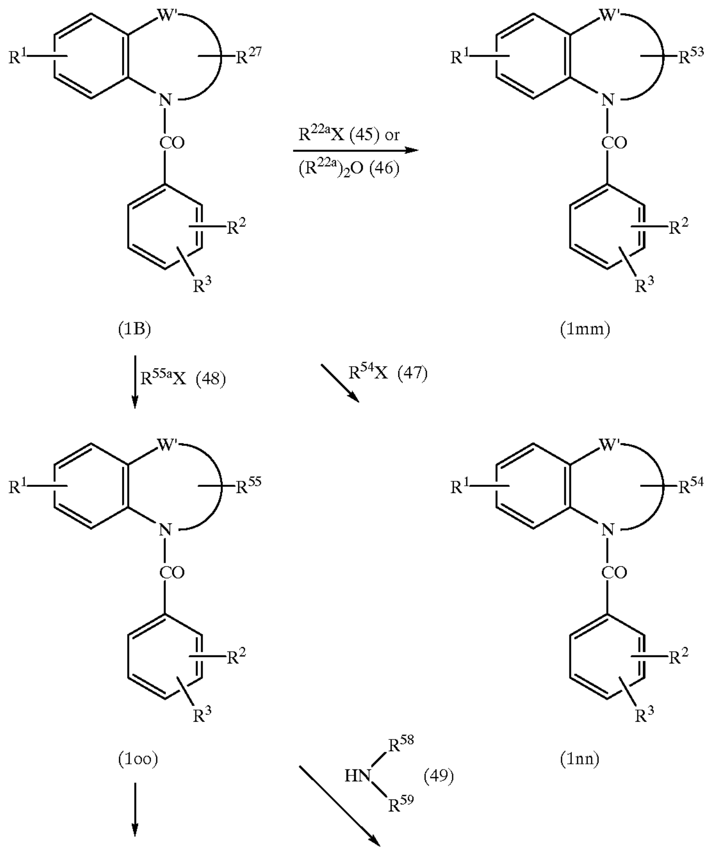

-continued

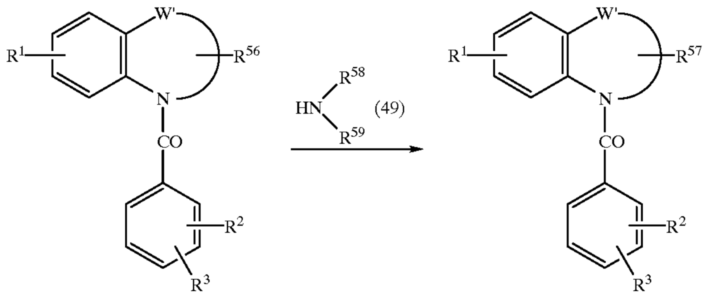

(1pp) (1qq)

wherein $R^1$, W', $R^2$, $R^3$, $R^{27}$, X, and A are as defined above, $R^{53}$ is a lower alkanoyloxy having optionally a halogen substituent, $R^{54}$ is a lower alkoxy, an amino-lower alkanoyloxy having optionally a lower alkyl substituent, or a group of the formula:

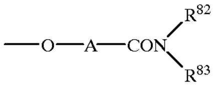

(A, $R^{82}$ and $R^{83}$ are as defined above), $R^{55}$ is a lower alkoxycarbonyl-substituted lower alkoxy, $R^{56}$ is a carboxy-substituted lower alkoxy, $R^{57}$ is an aminocarbonyl-lower alkoxy having optionally a lower alkyl substituent, $R^{54a}$ is a lower alkyl, an amino-lower alkanoyl having optionally a lower alkyl substituent, or a group of the formula:

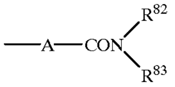

(A, $R^{82}$ and R83 are as defined above), $R^{55a}$ is a lower alkoxycarbonyl-substituted lower alkyl, $R^{58}$ and $R^{59}$ are the same or different and are each hydrogen atom or a lower alkyl, and $R^{22a}$ is a lower alkanoyl having optionally a halogen substituent.

[Reaction Scheme-32B]

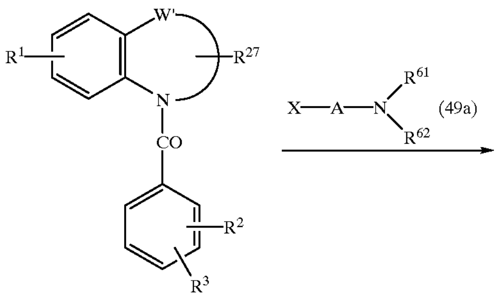

(1B)

-continued

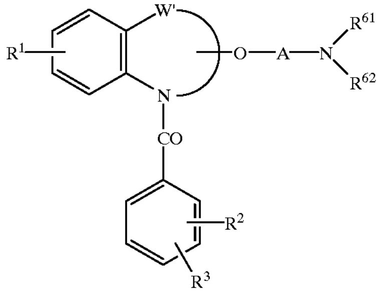

(1qq')

wherein $R^1$, W', $R^2$, $R^3$, X, $R^{27}$, and A are as defined above, and $R^{61}$ and $R^{62}$ are the same or different and are each hydrogen atom, a lower alkyl or a lower alkanoyl.

The reaction of the compound (1B) and the compound (45) or the compound (46) in the Reaction Scheme-32A can be carried out under the same conditions as in the reaction of the compound (1n) and the compound (18) in the above Reaction Scheme-9.

The reaction of the compound (1B) and the compound (47) and the reaction of the compound (1B) and the compound (48) can be carried out under the same conditions as in the reaction of the compound (1n) and the compound (18) in the above Reaction Scheme-9.

The reaction of converting the compound (1oo) into the compound (1pp) can be carried out under the same conditions as in the hydrolysis reaction of the compound (1j) in the above Reaction Scheme-7.

The reaction of the compound (1oo) and the compound (49) and the reaction of the compound (1pp) and the compound (49) can be carried out under the same conditions as in the reaction of the compound (2) and the compound (3) in the above Reaction Scheme-1.

The reaction of the compound (1B) and the compound (49a) in the Reaction Scheme-32B can be carried out under the same conditions as in the reaction of the compound (1n) and the compound (18) in the above Reaction Scheme-9.

[Reaction Scheme-33]

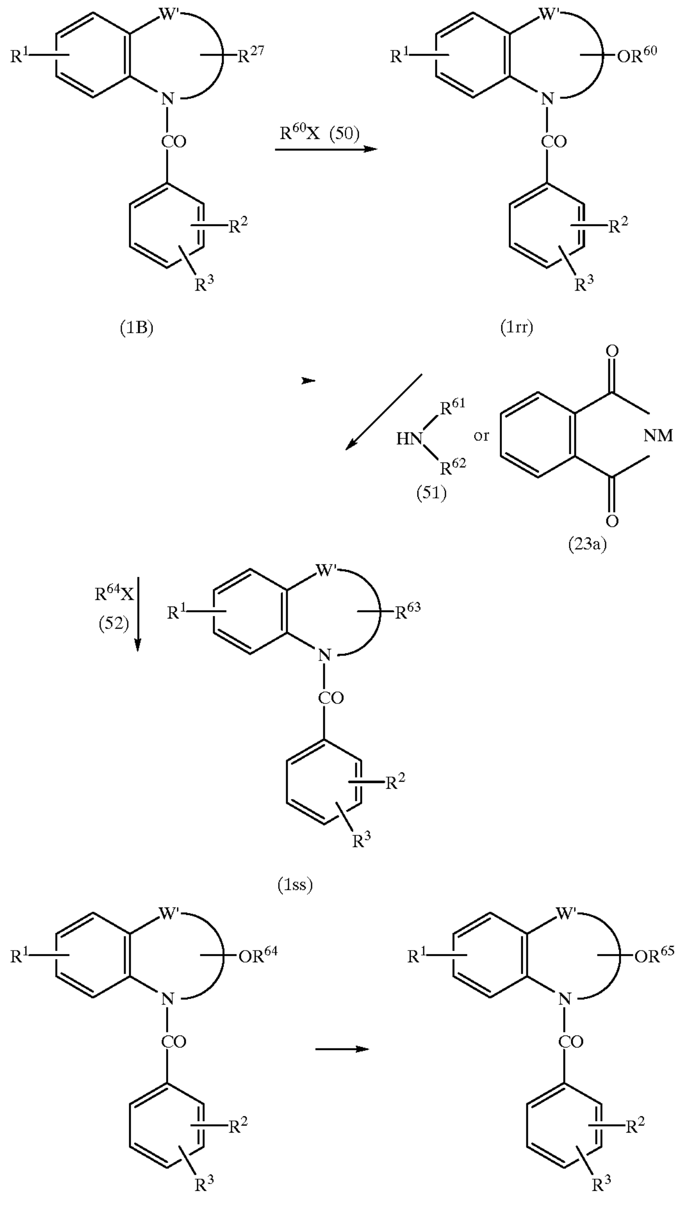

(1B) (1rr)

(1ss)

(1tt) (1uu)

wherein $R^1$, W', $R^2$, $R^3$, $R^{27}$, $R^{61}$, $R^{62}$, M, and X are as defined above, $R^{60}$ is a halogen-substituted lower alkyl, $R^{64}$ is a phthalimido-substituted lower alkyl, $R^{63}$ is an amino-lower alkoxy having optionally a substituent selected from a lower alkyl and a lower alkanoyl, or a phthalimido-substituted lower alkoxy, and $R^{65}$ is an amino-substituted lower alkyl.

The reaction of the compound (1B) and the compound (50) and the reaction of the compound (1B) and the compound (52) can be carried out under the same conditions as in the reaction of the compound (1n) and the compound (18) in the above Reaction Scheme-9.

The reaction of the compound (1rr) and the compound (51) or the compound (23a) can be carried out under the same conditions as in the reaction of the compound (1g) and the compound (14) in the above Reaction Scheme-6.

The reaction of converting the compound (1tt) into the compound (1uu) can be carried out under the same conditions as in the reaction of converting the compound (1j) into the compound (1k) in the above Reaction Scheme-7.

[Reaction Scheme-34]

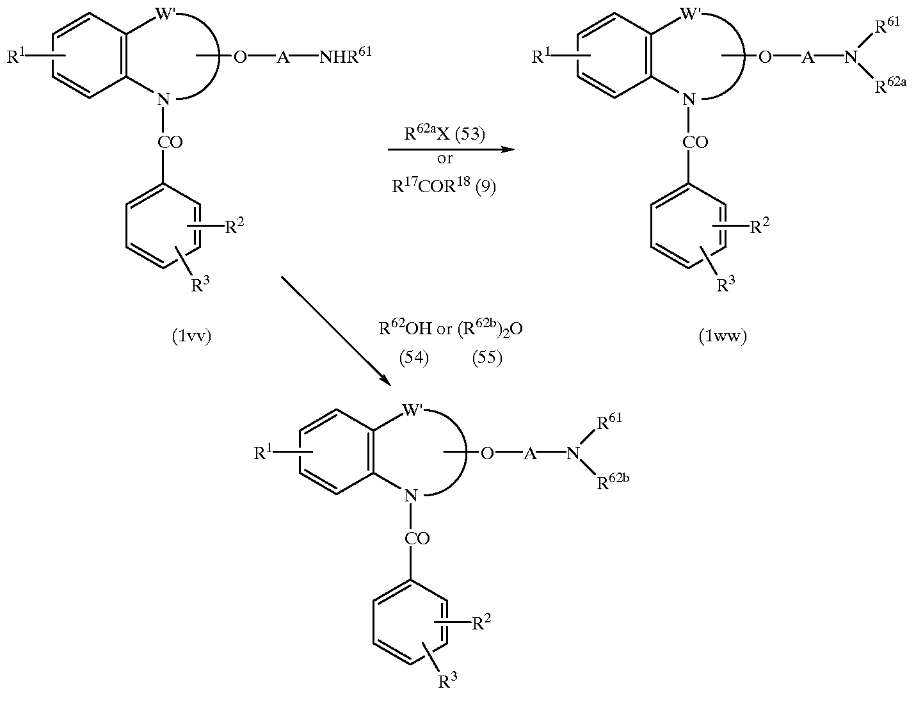

(1vv)

(1ww)

(1xx)

wherein $R^1$, $R^2$, $R^3$, $R^{61}$, W', A, $R^{17}$, $R^{18}$, and X are as defined above, $R^{62a}$ is a lower alkyl, and $R^{62b}$ is a lower alkanoyl.

The reaction of the compound (1vv) and the compound (53) or the compound (9) can be carried out under the same conditions as in the reaction of the compound (7) and the compound (8) or the compound (9) in the above Reaction Scheme-4.

The reaction of the compound (1vv) and the compound (54) can be carried out under the same conditions as in the reaction of the compound (2) and the compound (3) in the above Reaction Scheme-1.

The reaction of the compound (1vv) and the compound (55) can be carried out under the same conditions as in the reaction of the compound (1p) and the compound of the formula: $(R^{7b})_2O$ in the above Reaction Scheme-10.

[Reaction Scheme-35]

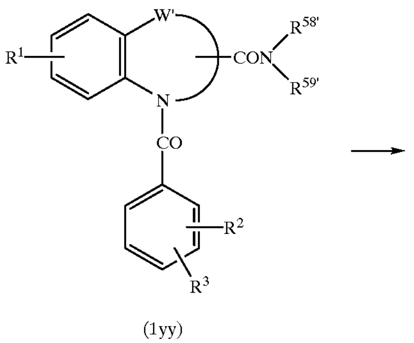

(1yy)

-continued

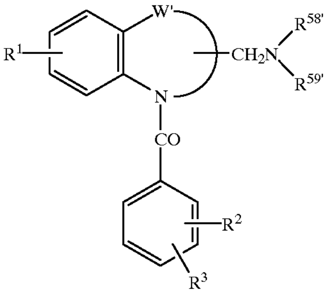

(1zz)

wherein $R^1$, $R^2$, $R^3$, and W' are as defined above, $R^{58'}$ and $R^{59'}$ are the same or different and are each hydrogen atom, a lower alkyl, or a lower alkanoyl.

The reaction of converting the compound (1yy) into the compound (1zz) is usually carried out by reducing the compound (1yy).

The reducting reaction is preferably carried out by using a hydrogenating reducing agent. The hydrogenating reducing agent includes, for example, lithium aluminum hydride, sodium boro hydride, diborane, etc. The reducing agent is usually used in an amount of at least one mole, preferably 1 to 15 moles, to 1 mole of the starting compound. The reducing reaction is usually carried out in an appropriate solvent, such as water, lower alcohols (e.g. methanol, ethanol, isopropanol, etc.), ethers (e.g. tetrahydrofuran, diethyl ether, diisopropyl ether, diglyme, etc.), or a mixture of these soslvents, at a temperature of about −60° C. to about 150° C., preferably about −30° C. to 100° C., for about 10 minutes to about 5 hours. When lithium aluminum hydride or diborane is used as the reducing agent, it is preferable to use an anhydrous solvent such as diethyl ether, tetrahydrofuran, diglyme, etc.

[Reaction Scheme-36]

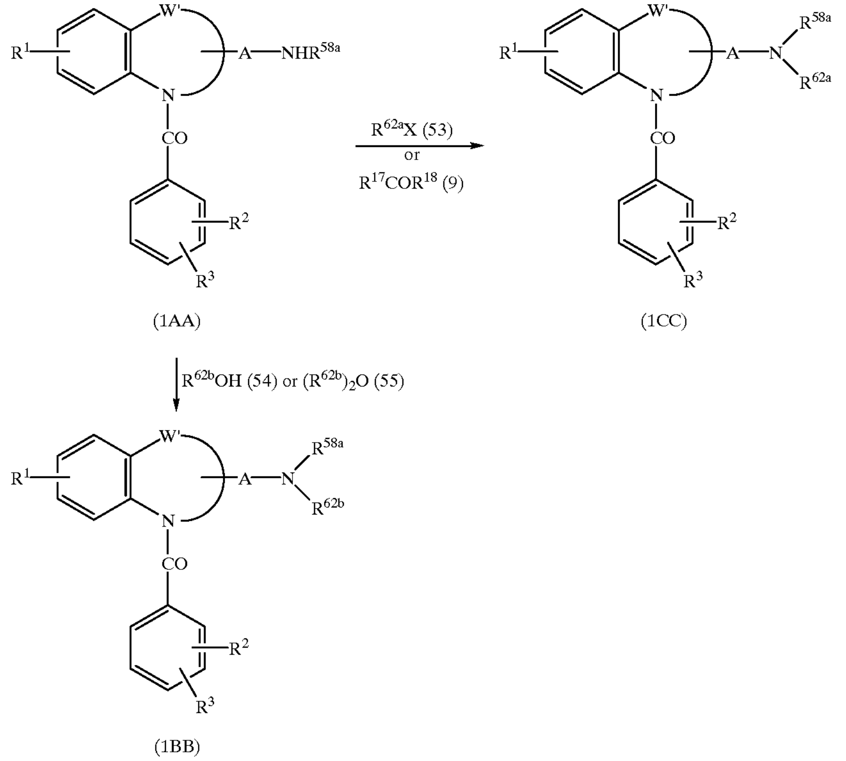

wherein $R^1$, W', $R^2$, $R^3$, $R^{62a}$, $R^{62b}$, X, $R^{17}$, $R^{18}$, and A are as defined above, $R^{58a}$ is hydrogen atom, a lower alkyl or a lower alkanoyl.

The reaction of the compound (1AA) and the compound (53) or the compound (9) can be carried out under the same conditions as in the reaction of the compound (7) and the compound (8) or the compound (9) in the above Reaction Scheme-4.

The reaction of the compound (1AA) and the compound (54) can be carried out under the same conditions as in the reaction of the compound (2) and the compound (3) in the above Reaction Scheme-1.

The reaction of the compound (1AA) and the compound (55) can be carried out under the same conditions as in the reaction of the compound (1p) and the compound of the formula: $(R^{7b})_2O$ in the above Reaction Scheme-10.

The compound (1BB) wherein $R^{62b}$ is formyl can also be prepared by reacting the compound (1AA) with a formate of the formula: $HCOOR^{82}$ under the same conditions as in the reaction of the compound (1K) and the compound of the formula: $HCOOR^{82}$ as described hereinbefore.

The compounds of the formula (1) wherein W is sulfur atom or sulfinyl, or $R^{82}$ and $R^{83}$ bind together with the nitrogen atom to which they bond to form thiomorpholino or 1-oxo-thiomorpholino can be converted into the corresponding compounds of the formula (1) wherein W is sulfinyl or sulfonyl, or $R^{82}$ and $R^{83}$ bind together with the nitrogen atom to which they bond to form 1-oxo-thiomorpholino or 1,1-dioxo-thiomorpholino, respectively, by oxidation thereof.

The oxidation reaction is carried out in an appropriate solvent in the presence of an oxidizing agent. The solvent includes, for example, water, organic acids (e.g. formic acid, acetic acid, trifluoroacetic acid, etc.), alcohols (e.g. methanol, ethanol, etc.), halogenated hydrocarbons (e.g. chloroform, dichloromethane, etc.), or a mixture of these solvents. The oxidizing agent includes, for example, peracids (e.g. performic acid, peracetic acid, trifluoro-peracetic acid, perbenzoic acid, m-chloroperbenzoic acid, o-carboxy-perbenzoic acid, etc.), hydrogen peroxide, sodium metaperiodate, dichromic acid, dichromates (e.g. sodium dichromate, potassium dichromate, etc.), permanganic acid, permanganates (e.g. potassium permanganate, sodium permanganate, etc.), lead salts (e.g. lead tetraacetate, etc.), and the like. The oxidizing agent is usually used in an amount of at least 1 mole, preferably 1 to 2 moles, to 1 mole of the starting compound. Besides, in cases of the oxidation of converting the sulfur atom into sulfonyl group, the oxidizing agent is usually used at least 2 moles, preferably 2 to 4 moles, to 1 mole of the starting compound. The above reaction is usually carried out at a temperature of about −10° C. to about 40° C., preferably from about −10° C. to room temperature, for about 1 to 100 hours.

The compound (1) wherein $R^{16}$ or $R^2$ is a lower alkoxy can be converted into the correspond compound (1) wherein $R^{16}$ or $R^2$ is hydroxy by heating the compound in a mixture of an acid (e.g. hydrobromic acid, hydrochloric acid, etc.) and a solvent (e.g. water, methanol, ethanol, isopropyl alcohol, etc.) at 30 to 150° C., preferably at 50 to 120° C.

Besides, the compound (1) wherein $R^{16}$ or $R^2$ is hydroxy can also be prepared by hydrolysis of the above compound (1) wherein $R^{16}$ or $R^2$ is a lower alkoxy. The hydrolysis can be carried out in an appropriate solvent in the presence of an acid. The solvent includes, for example, water, lower alcohols (e.g. methanol, ethanol, isopropyl alcohol, etc.), ethers (e.g. dioxane, tetrahydrofuran, etc.), halogenated hydrocarbons (e.g. dichloromethane, chloroform, carbon tetrachloride, etc.), polar solvents (e.g. acetonitrile, etc.), or a mixture of these solvents. The acid includes, for example, mineral acids (e.g. hydrochloric acid, hydrobromic acid, etc.), Lewis acids (e.g. boron trifluoride, aluminum chloride, boron tribromide, etc.), iodides (e.g. sodium iodide, potassium iodide, etc.), or a mixture of the above Lewis acid and iodide. The reaction is usually carried out at a temperature of from room temperature to about 150° C., preferably from room temperature to about 100° C., for about 0.5 to 30 hours.

[Reaction Scheme-37]

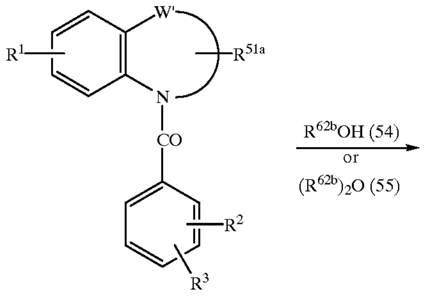

(1ii')

-continued

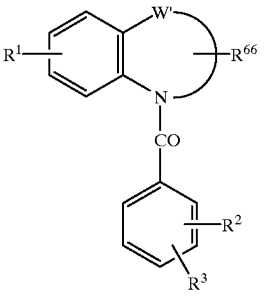

(1DD)

wherein $R^1$, $R^2$, $R^3$, $R^{62}$b, and W' are as defined above, $R^{51a}$ is hydroxyamino, and $R^{66}$ is a lower alkanoyloxyimino.

The reaction of the compound (1ii') and the compound (54) can be carried out under the same conditions as in the reaction of the compound (2) and the compound (3) in the above Reaction Scheme-1.

The reaction of the compound (1ii') and the compound (55) can be carried out under the same conditions as in the reaction of the compound (1p) and the compound of the formula:$(R^{7b})_2O$ in the above Reaction Scheme-10.

[Reaction Scheme-38A]

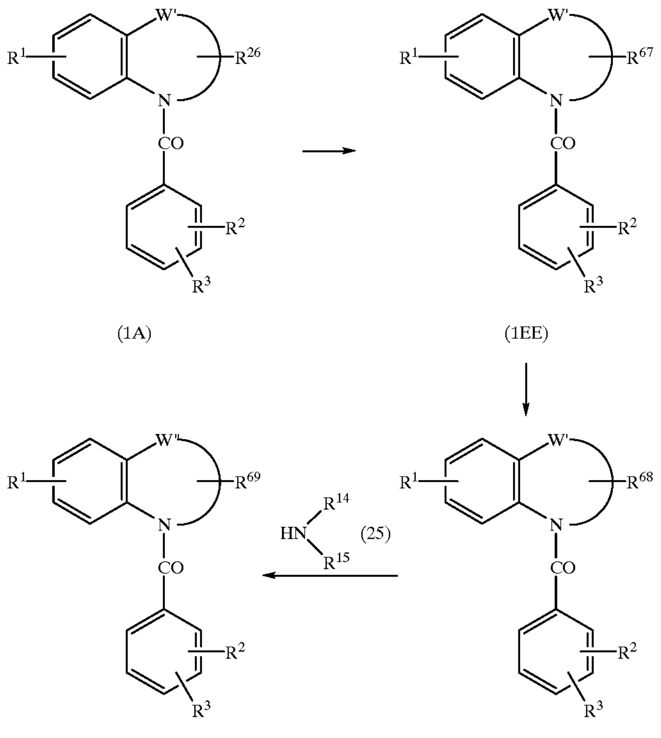

(1A) (1EE)

(1GG) (1FF)

[Reaction Scheme-38B]
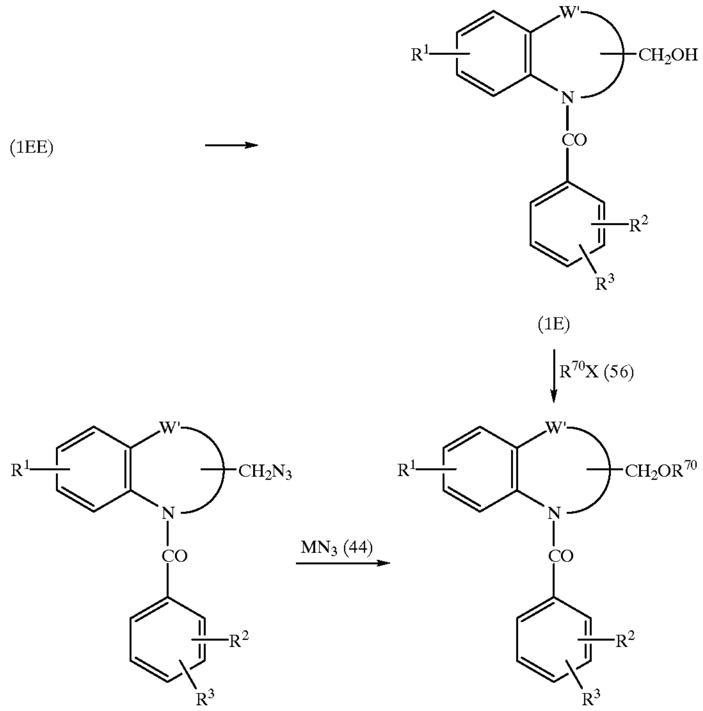
(1EE) (1E)
(1JJ) (1HH)
[Reaction Scheme-38C]
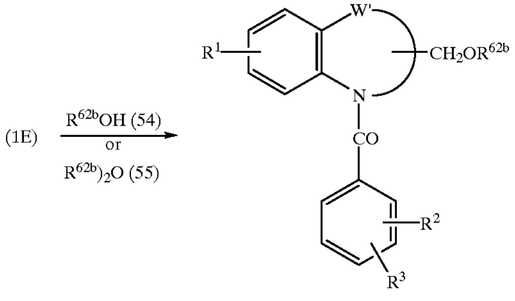
(1E) (1II)
[Reaction Scheme-38D]
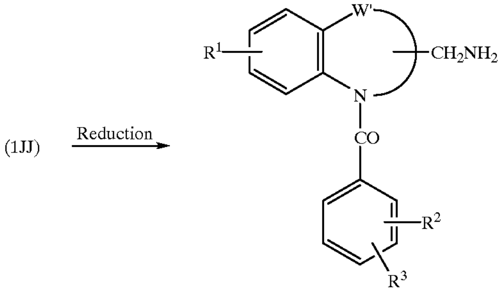
(1JJ) (1KK)

-continued

[Reaction Scheme-38E]

(1EE)

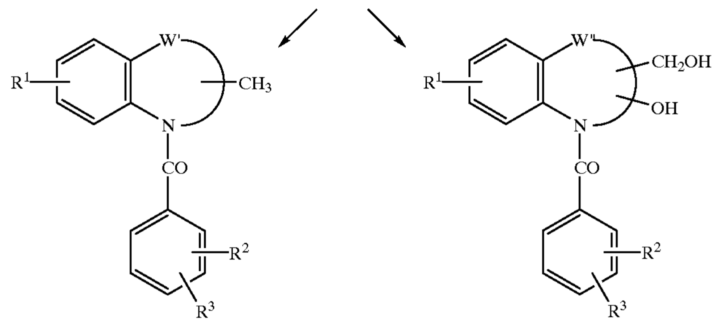

(1LL) (1MM)

wherein $R^1$, $R^2$, $R^3$, W', $R^{26}$, $R^{14}$, $R^{15}$, $R^{62b}$, X and M are as defined above, $R^{67}$ is methylidene, $R^{68}$ is a group of the formula:

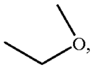

and $R^{69}$ is a group of the formula:

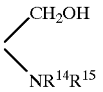

($R^{14}$ and $R^{15}$ are as defined above), or

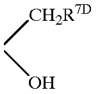

($R^7D$ is an amino having optionally a substituent selected from a lower alkyl and a lower alkanoyl, $R^{70}$ is a lower alkylsulfonyl, and W" is the same as the above W, provided that the number of the substituent in the groups —$(CH_2)_p$— and —CH═CH—$(CH_2)_q$— is 0 or 1.

The reaction of converting the compound (1A) into the compound (1EE) is carried out in an appropriate solvent in the presence of a Wittig reagent and a basic compound. The Wittig reagent includes, for example, a phosphoric compound of the formula:

$$[(R^{71})_3P^+—CH_2—R^{72}]X^- \quad (A)$$

wherein $R^{71}$ is phenyl, $R^{72}$ is hydrogen atom or a lower alkyl, and X is a halogen atom. The basic compound includes inorganic bases (e.g. metallic sodium, metallic potassium, sodium hydride, sodium amide, sodium hydroxide, potassium hydroxide, sodium carbonate, potassium carbonate, sodium hydrogen carbonate, etc.), metal alcoholates (e.g. sodium methylate, sodium ethylate, potassium t-butoxide, etc.), alkyl or aryl lithiums or lithium amides (e.g. methyl lithium, n-butyl lithium, phenyl lithium, lithium diisopropylamide, etc.), organic bases (e.g. pyridine, piperidine, quinoline, triethylamine, N,N-dimethylaniline, etc.). The solvent includes any solvent which does not affect on the reaction, for example, ethers (e.g. diethyl ether, dioxane, tetrahydrofuran, monoglyme, diglyme, etc.), aromatic hydrocarbons (e.g. benzene, toluene, xylene, etc.), aliphatic hydrocarbons (e.g. n-hexane, heptane, cyclohexane, etc.), amines (e.g. pyridine, N,N-dimethylaniline, etc.), aprotic polar solvents (e.g. N,N-dimethylformamide, dimethylsulfoxide, hexamethylphosphoric triamide, etc.), alcohols (e.g. methanol, ethanol, isopropanol, etc.), and the like. The reaction is usually carried out at a temperature of about -80° C. to about 150° C., preferably about -80° C. to about 120° C., for about 0.5 to 15 hours.

The reaction of converting the compound (1EE) into the compound (1LL) can be carried out under the same conditions as in the catalytically hydrogenation reaction for converting the compound (1A) into the compound (1C) in the above Reaction Scheme-15.

The reaction of converting the compound (1EE) into the compound (1FF) is carried out under the same conditions as in the reaction of converting the compound (1) wherein W is sulfur atom or sulfinyl into the corresponding compound (1) wherein W is sulfinyl or sulfonyl respectively as described herebefore.

The reaction of the compound (1FF) and the compound (25) can be carried out under the same conditions as in the reaction of the compound (7) and the compound (8) in the above Reaction Scheme-4.

The reaction of converting the compound (1EE) into the compound (1E) can be carried out by firstly subjecting it to hydroboration reaction and then to oxidation.

The hydroboration reaction is carried out in a solvent such as ethers (e.g. diethyl ether, tetrahydrofuran, dioxane, etc.) in the presence of a hydroborating agent at a temperature of from about 0° C. to about 50° C., preferaly about 0° C. to room temperature, for about 1 to 10 hours. The hydroborating agent includes boron hydride compounds, for example, $BH_3$.tetrahydrofuran, $BH_3.S(CH_3)_2$, $BH_2Cl$, $(CH_3)_2CHC(CH_3)_2BH_2$, $(CH_3)_2CHCH(CH_3)BH$,

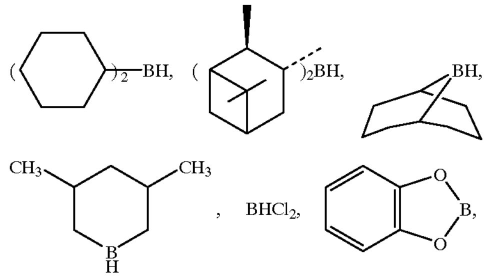

and the like.

The subsequent oxidation is carried out in water in the presence of an oxidizing agent. The oxidizing agent includes, for example, alkaline hydrogen peroxides (e.g. hydrogen peroxide-sodium hydroxide, etc.), and air oxidation is also used. The reaction is usually carried out at a temperature of from room temperature to about 150° C., preferably from room temperature to about 100° C., for 0.5 to 7 hours.

The hydroborating agent and the oxidizing agent are each used in an amount of at least 1 mole, preferably 1 to 2 mole, to 1 mole of the compound (1EE).

The reaction of the compound (1E) and the compound (54) can be carried out under the same conditions as in the reaction of the compound (2) and the compound (3) in the above Reaction Scheme-1.

The reaction of the compound (1E) and the compound (55) can be carried out under the same conditions as in the reaction of the compound (1p) and the compound of the formula: $(R^{7b})_2O$ in the above Reaction Scheme-10.

The reaction of the compound (1E) and the compound (56) can be carried out under the same conditions as in the reaction of the compound (7) and the compound (8) in the above Reaction Scheme-4.

The reaction of the compound (1HH) and the compound (44) can be carried out under the same conditions as in the reaction of the compound (7) and the compound (8) in the above Reaction Scheme-4.

The reducing reaction of the compound (1JJ) can be carried out under the same conditions as in the catalytic hydrogenation reaction for converting the compound (1A) into the compound (1C) in the above Reaction Scheme-15.

The reaction of converting the compound (1EE) into the compound (1MM) can be carried out by reacting with an oxidizing agent in an appropriate solvent in the presence of a co-oxidizing agent.

The solvent used for the reaction with an oxidizing agent includes, for example, pyridine, ethers (e.g. dioxane, tetrahydrofuran, diethyl ether, etc.), aromatic hydrocarbons (e.g. benzene, toluene, xylene, etc.), halogenated hydrocarbons (e.g. dichloromethane, dichloroethane, chloroform, carbon tetrachloride, etc.), esters (e.g. ethyl acetate, etc.), water, alcohols (e.g. methanol, ethanol, isopropanol, t-butanole, etc.), or a mixture of these solvents. The co-oxidizing agent includes, for example, organic amine N-oxides (e.g. pyridine N-oxide, N-ethyldiisopropylamine N-oxide, N-methylmorpholine N-oxide, trimethylamine N-oxide, triethylamine N-oxide, etc.). The oxidizing agent includes, for example, osmium tetraoxide, and the like. The oxidizing agent is usually used in an amount of at least 1 mole, preferably 1 to 5 moles, to 1 mole of the starting compound. The reaction is usually carried out at a temperature of from −20° C. to 150° C., preferably from room temperature to 100° C., for about 1 to 10 hours.

[Reaction Scheme-39]

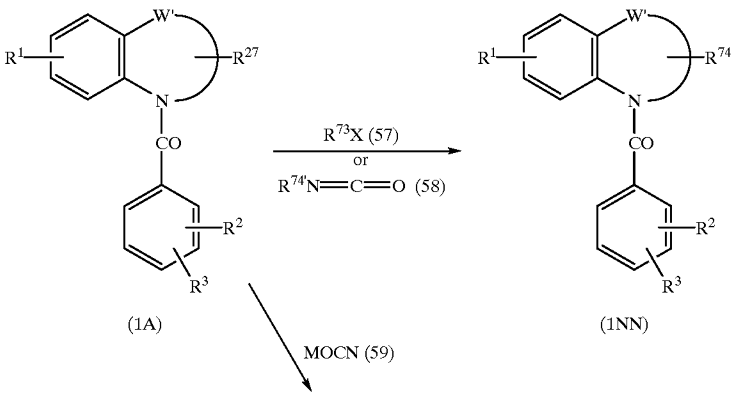

(1A) (1NN)

-continued

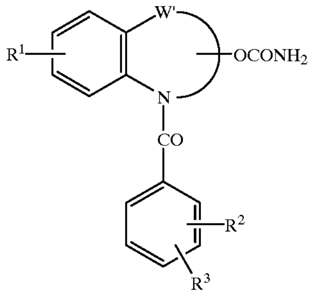

(1NN')

wherein $R^1$, $R^2$, $R^3$, $R^{27}$, W', M, and X are as defined above, $R^{73}$ is an aminocarbonyl having optionally a lower alkyl substituent, $R^{74}$ is an aminocarbonyloxy having optionally a lower alkyl substituent, $R^{74'}$ is a lower alkyl.

The reaction of the compound (1A) and the compound (57) can be carried out under the same conditions as in the reaction of the compound (7) and the compound (8) in the above Reaction Scheme-4.

The reaction of the compound (1A) and the compound (59) is carried out in an appropriate solvent in the presence of an acid. The solvent includes the same solvent as used in the reaction of the compound (7) and the compound (8) in the above Reaction Scheme-4. The acid includes, for example, mineral acids (e.g. hydrochloride acid, sulfuric acid, etc.), sulfonic acids (e.g. methanesulfonic acid, p-toluenesulfonic acid, etc.), alkanoic acids (e.g. trifluoroacetic acid, etc.), and the like. The compound (59) is used in an amount of at least 1 mole, preferably 1 to 5 moles, to 1 mole of the compound (1A). The reaction is usually carried out at a temperature of from room temperature to about 150° C., preferably from room temperature to about 100° C., for about 1 to 7 hours.

The reaction of the compound (1A) and the compound (58) can be carried out under the same conditions as in the reaction of the compound (2b) and the compound (38) in the above Reaction Scheme-26.

[Reaction Scheme-40]

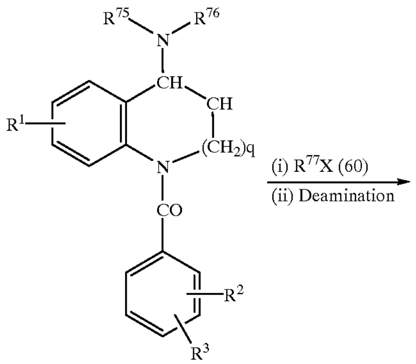

(1OO)

-continued

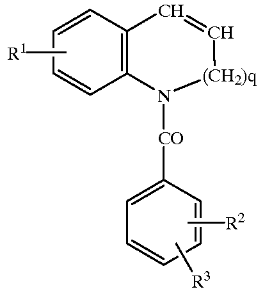

(1PP)

wherein $R^1$, $R^2$, $R^3$, X, and q are as defined above, and $R^{75}$, $R^{76}$ and $R^{77}$ are each a lower alkyl, and the carbon atom in the formula: $-(CH_2)_q-$ may be substituted by oxygen atom, sulfur atom, sulfinyl, sulfonyl, or a group of the formula:

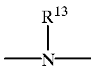

($R^{13}$ is as defined above), and further the group: $-(CH_2)_q-$ may optionally have 1 to 3 substituents selected from a lower alkyl having optionally a hydroxy substituent, a lower alkoxycarbonyl, carboxyl, hydroxy, oxo, a lower alkanoyloxy having optionally a halogen substituent, an amino-lower alkyl having optionally a substituent selected from a lower alkyl and a lower alkanoyl, a lower alkanoyloxy-substituted lower alkyl, a lower alkylsulfonyloxy-lower alkyl, an azido-lower alkyl, a group of the formula:

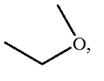

an aminocarbonyloxy having optionally a lower alkyl substituent, a lower alkoxy, a lower alkoxycarbonyl-substituted lower alkoxy, a carboxy-substituted lower alkoxy, an aminocarbonyl-lower alkoxy having optionally a lower alkyl substituent, an amino-lower alkoxy having optionally a substituent selected from a lower alkyl and a lower alkanoyl, a phthalimido-substituted lower alkoxy, hydroxyimino, a lower alkanoyloxyimino, a lower alkylidene, a halogen atom, azido, sulfoxyimino, a group of the formula:

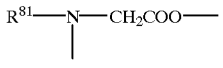

($R^{81}$ is hydrogen atom or a lower alkyl), hydrazino, pyrrolyl, an amino-lower alkanoyloxy having optionally a lower alkyl substituent, a group of the formula:

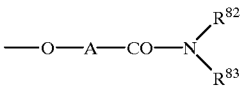

(A is as defined above, and $R^{82}$ and $R^{83}$ are the same or different and are each hydrogen atom, a lower alkyl, a carbamoyl-substituted lower alkyl, a hydroxy-substituted lower alkyl, or a pyridyl-lower alkyl, or $R^{82}$ and $R^{83}$ may bind together with nitrogen atom to which they bond to form a 5- or 6-membered saturated heterocyclic group with or without being intervened with nitrogen, oxygen or sulfur atom wherein the heterocyclic group has optionally a substituent selected from oxo, a lower alkyl, a lower alkanoyl, and carbamoyl), and a group of the formula:

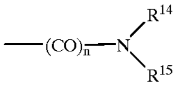

(n is as defined above, and $R^{14}$ and $R^{15}$ are the same or different and are each hydrogen atom, a lower alkyl, a lower alkenyl, a lower alkanoyl, a cycloalkyl, an oxiranyl-substituted lower alkyl, a lower alkyl having 1 to 2 substituents selected from a lower alkoxy, hydroxy and an amino having optionally a lower alkyl substituent, a phenyl-lower alkyl, a pyridyl-lower alkyl, a lower alkylsulfonyl, benzoyl, a lower alkoxycarbonyl, anilinocarbonyl, an aminocarbonyl having optionally a lower alkyl substituent, a cyano-substituted lower alkyl, a lower alkoxycarbonyl-substituted lower alkyl, a carbamoyl-substituted lower alkyl, a carboxy-substituted lower alkyl, a tetrahydropyranyloxy-substituted lower alkyl, a lower alkanoyloxy-substituted lower alkyl, a piperidinyl having optionally a phenyl-lower alkyl substituent on the piperidinyl ring, a halogen-substituted lower alkanoyl, an imidazolyl-substituted lower alkanoyl, an amino-lower alkanoyl having optionally a substituent selected from a lower alkyl and a lower alkoxycarbonyl, an aminocarbonyl-lower alkyl having optionally a lower alkyl substituent, or a phenyl-lower alkoxycarbonyl, or $R^{14}$ and $R^{15}$ may bind together with the nitrogen atom to which they bond to form a 5- or 6-membered saturated heterocyclic group with or without being intervened with nitrogen or oxygen atom, which heterocyclic group may optionally have a substituent selected from a lower alkyl, a phenyl-lower alkyl and a lower alkanoyl.

The reaction of the compound (1OO) and the compound (60) is carried out in an appropriate solvent in an autoclave. The solvent includes any solvent as used in the reaction of the compound (7) and the compound (8) in the above Reaction Scheme-4. The reaction is usually carried out at a temperature of from room temperature to about 200° C., preferably from room temperature to about 150° C., for about 1 to 7 hours.

The subsequent deamination reaction is carried out in an appropriate solvent in the presence of a basic compound. The solvent includes the same solvent as used in the above reaction of the compound (1OO) and the compound (60). The basic compound includes any basic compound as used in the reaction of converting the compound (1A) into the compound (1EE) in the above Reaction Scheme-38. The reaction is usually carried out at a temperature of from room temperature to about 150° C., preferably from room temperature to about 100° C., for about 1 to 10 hours.

[Reaction Scheme-41]

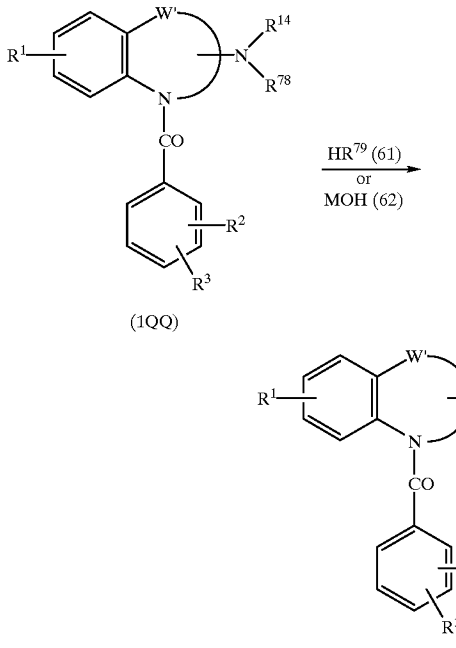

(1QQ)

(1RR)

wherein $R^1$, $R^2$, $R^3$, $R^{14}$, M, and W' are as defined above, $R^{78}$ is an oxiranyl-substituted lower alkyl, $R^{79}$ is a lower alkoxy, or an amino having optionally a lower alkyl substituent, and $R^{80}$ is a lower alkyl having 2 substituents selected from hydroxy, a lower alkoxy, and an amino having optionally a lower alkyl substituent.

The reaction of the compound (1QQ) and the compound (61) can be carried out under the same conditions as in the reaction of the compound (7) and the compound (8) in the above Reaction Scheme-4.

The reaction of the compound (1QQ) and the compound (62) can be carried out by firstly reacting them in trifluoroacetic acid at a temperature of about 0° C. to about 100° C., preferably about 0° C. to about 50° C., for about 1 to 7 hours, followed by hydrolysis of the resultant.

The hydrolysis is carried out in an appropriate solvent or without solvent in the presence of an acid or a basic compound. The solvent includes, for example, water, lower alcohols (e.g. methanol, ethanol, isopropanol, etc.), ketones (e.g. acetone, methyl ethyl ketone, etc.), ethers (e.g. dioxane, tetrahydrofuran, ethylene glycol dimethyl ether, etc.), fatty acids (e.g. acetic acid, formic acid, etc.), or a mixture of these solvents. The acid includes, for example, mineral acids (e.g. hydrochloric acid, sulfuric acid, hydrobromic acid, etc.), organic acids (e.g. formic acid, acetic acid, aromatic sulfonic acid, etc.), and the like. The basic compound includes, for example, metal carbonates (e.g. sodium carbonate, potassium carbonate, etc.), metal hydroxides (e.g. sodium hydroxide, potassium hydroxide, calcium hydroxide, etc.). The reaction is usually carried out at a temperature of from room temperature to about 200° C., preferably from room temperature to about 150° C., for about 0.5 to 25 hours.

[Reaction Scheme-42]

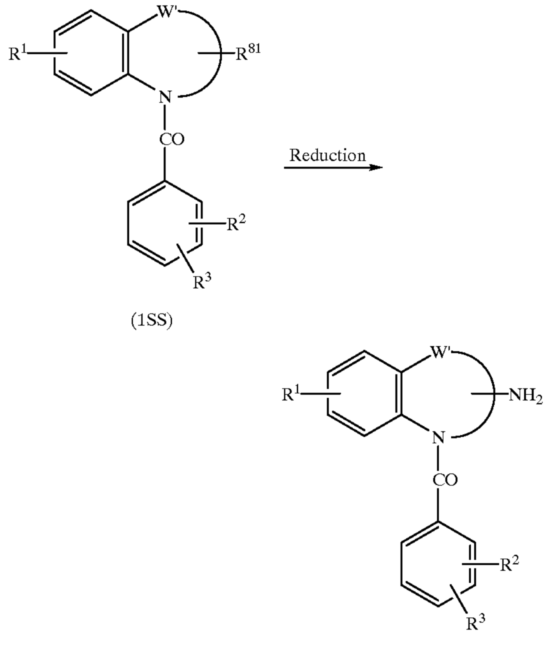

(1SS)

(1ll)

wherein $R^1$, $R^2$, $R^3$, and W' are as defined above, and $R^{81}$ is hydroxyimino or a lower alkanoyloxyimino.

The reaction of converting the compound (1SS) into the compound (1ll) is carried out by catalytically hydrogenating the compound (1SS) in an appropriate solvent in the presence of a catalyst. The solvent includes, for example, water, acetic acid, alcohols (e.g. methanol, ethanol, isopropanol, etc.), hydrocarbons (e.g. hexane, cyclohexane, etc.), ethers (e.g. diethylene glycol dimethyl ether, dioxane, tetrahydrofuran, diethyl ether, etc.), esters (e.g. ethyl acetate, methyl acetate, etc.), aprotic polar solvents (e.g. dimethylformamide, etc.), or a mixture of these solvents. The catalyst includes, for example, palladium, palladium black, palladium-carbon, platinum, platinum oxide, copper chromate, Raney nickel, and the like. The catalyst is usually used in an amount of 0.02 to 1 part by weight to 1 part by weight of the compound (1SS). The reaction is usually carried out at a temperature of from about −20° C. to about 100° C., peferably about 0° C. to about 70° C., under a hydrogen atmospheric pressure of 1 to 10 atm. for about 0.5 to 20 hours.

Alternatively, the reducing reaction can also be carried out by using a hydrogenating reducing agent. The hydrogenating reducing agent includes, for example, lithium aluminum hydride, sodium boro hydride, diborane, etc. The reducing agent is usually used in an amount of at least one mole, preferably 1 to 10 moles, to 1 mole of the compound (1SS). The reaction is usually carried out in an appropriate solvent, such as water, lower alcohols (e.g. methanol, ethanol, isopropanol, etc.), ethers (e.g. tetrahydrofuran, diethyl ether, diglyme, etc.), acetic acid, and the like, at a temperature of about 0° C. to about 200° C., preferably about 0° C. to 170° C., for about 10 minutes to about 10 hours. When lithium aluminum hydride or diborane is used as the reducing agent, it is preferable to use an anhydrous solvent such as diethyl ether, tetrahydrofuran, diglyme, etc.

[Reaction Scheme-43]

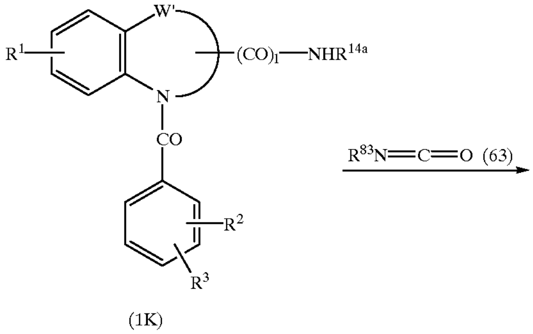

(1K)

-continued

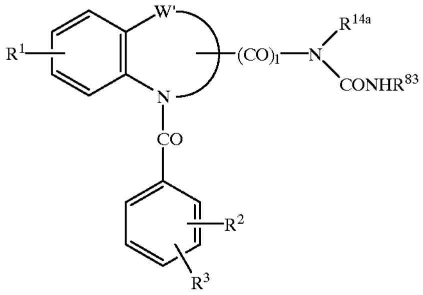

(1TT)

wherein $R^1$, $R^2$, $R^3$, W', l, $R^{14a}$ are as defined above, and $R^{83}$ is phenyl or a lower alkyl.

The reaction of the compound (1K) and the compound (63) can be carried out under the same conditions as in the reaction of the compound (2b) and the compound (38) in the above Reaction Scheme-26.

[Reaction Scheme-44]

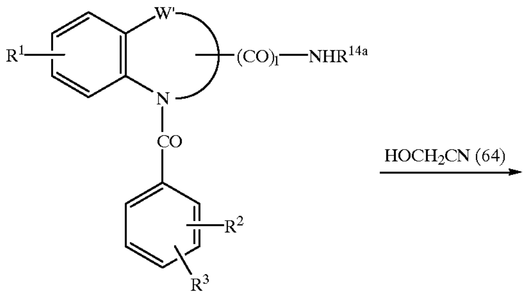

(1K)

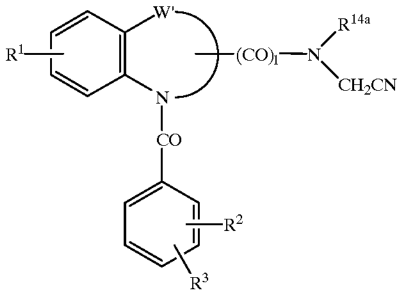

(1UU)

wherein $R^1$, $R^2$, $R^3$, W', l, $R^{14a}$ are as defined above.

The reaction of the compound (1K) and the glyconitrile (64) can be carried out in an appropriate solvent. The solvent includes the same solvent as used in the reaction of the compound (7) and the compound (8) in the above Reaction Scheme-4. The reaction is usually carried out at a temperature of from about 0° C. to about 150° C., preferably about 0° C. to about 100° C., for about 1 to 10 hours. The glyconitrile (64) is used in an amount of at least 1 mole, preferably 1 to 2 moles, to 1 mole of the compound (1K).

[Reaction Scheme-45]

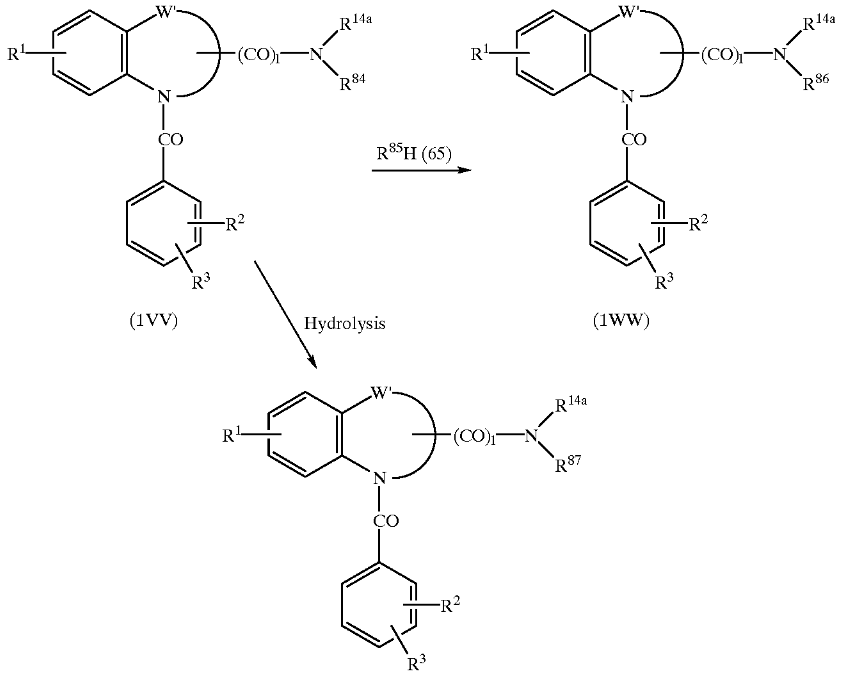

(1VV) (1WW) (1XX)

wherein $R^1$, $R^2$, $R^3$, W', l, $R^{14a}$ are as defined above, $R^{84}$ is a lower alkoxycarbonyl-substituted lower alkyl, $R^{85}$ is an amino having optionally a lower alkyl substituent, $R^{86}$ is an aminocarbonyl-lower alkyl having optionally a lower alkyl substituent, and $R^{87}$ is a carboxy-substituted lower alkyl.

The reaction of the compound (1VV) and the compound (65) can be carried out under the same conditions as in the reaction of the compound (2) and the compound (3) in the above Reaction Scheme-1.

The hydrolysis reaction of the compound (1VV) can be carried out under the same conditions as in the hydrolysis reaction of the compound (1QQ) and the compound (62) in the above Reaction Scheme-41.

[Reaction Scheme-46]

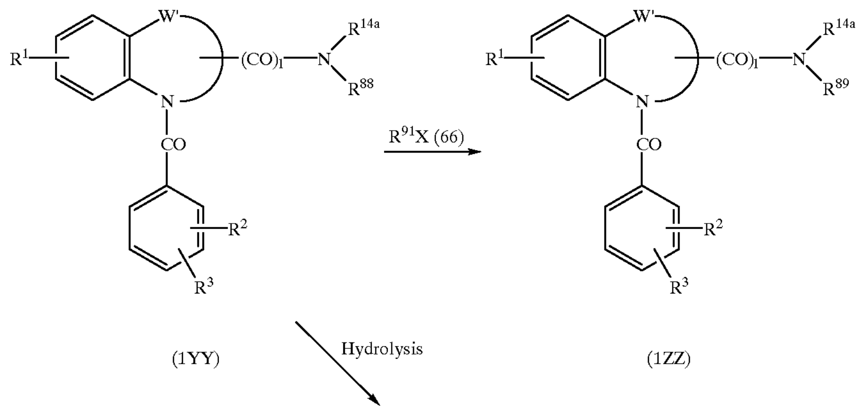

(1YY) (1ZZ)

-continued

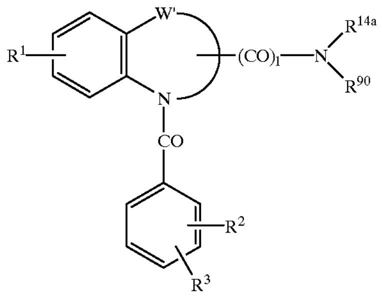

(1aaa)

wherein $R^1$, $R^2$, $R^3$, W', l, X, and $R^{14a}$ are as defined above, $R^{88}$ is a tetrahydropyranyloxy-substituted lower alkyl, $R^{89}$ is a lower alkanoyloxy-substituted lower alkyl, $R^{90}$ is a hydroxy-substituted lower alkyl, and $R^{91}$ is a lower alkanoyl.

The reaction of the compound (1YY) and the compound (66) can be carried out in a solvent such as acetic acid at a temperature of about 0° C. to about 200° C., preferably about 0° C. to about 150° C., for about 0.5 to 15 hours.

The hydrolysis reaction of the compound (1YY) can be carried out under the same conditions as in the hydrolysis reaction of the compound (1QQ) and the compound (62) in the above Reaction Scheme-41, wherein a pyridinium salt (e.g. pyridinium p-toluenesulfonate, etc.) may be used as the acid.

[Reaction Scheme-47]

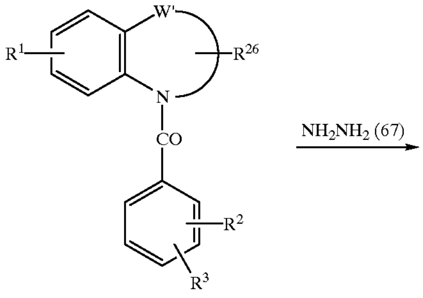

(1A)

-continued

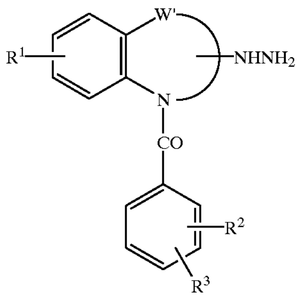

(1bbb)

wherein $R^1$, $R^2$, $R^3$, W', and $R^{26}$ are as defined above.

The reaction of converting the compound (1A) into the compound (1bbb) can be carried out under the same conditions as in the reaction of converting the compound (1A) into the compound (1C) in the above Reaction Scheme-15.

[Reaction Scheme-48]

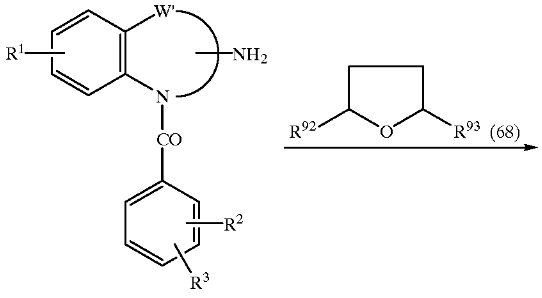

(1ll)

-continued

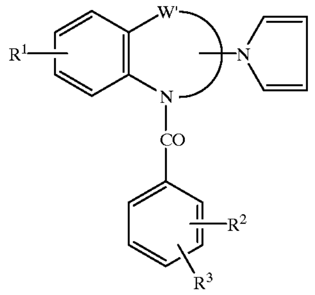

(1ccc)

wherein $R^1$, $R^2$, $R^3$ and W' are as defined above, $R^{92}$ and $R^{93}$ are each a lower alkoxy.

The reaction of the compound (1ll) and the compound (68) is carried out in an appropriate solvent in the presence of an acid. The solvent includes, for example, water, alcohols (e.g. methanol, ethanol, isopropanol, etc.), ketones (e.g. acetone, methyl ethyl ketone, etc.), ethers (e.g. dioxane, tetrahydrofuran, ethylene glycol dimethyl ether, etc.), fatty acids (e.g. acetic acid, formic acid, etc.), or a mixture of these solvents. The acid includes, for example, mineral acids (e.g. hydrochloric acid, sulfuric acid, hydrobromic acid, etc.), organic acids (e.g. formic acid, acetic acid, aromatic sulfonic acids, etc.). The reaction is usually carried out at a temperature of from room temperature to about 200° C., preferably from room temperature to about 150° C., for about 0.5 to 5 hours. The compound (68) is usually used in an amount of at least 1 mole, preferably 1 to 2 moles, to 1 mole of the compound (1ll).

[Reaction Scheme-49]

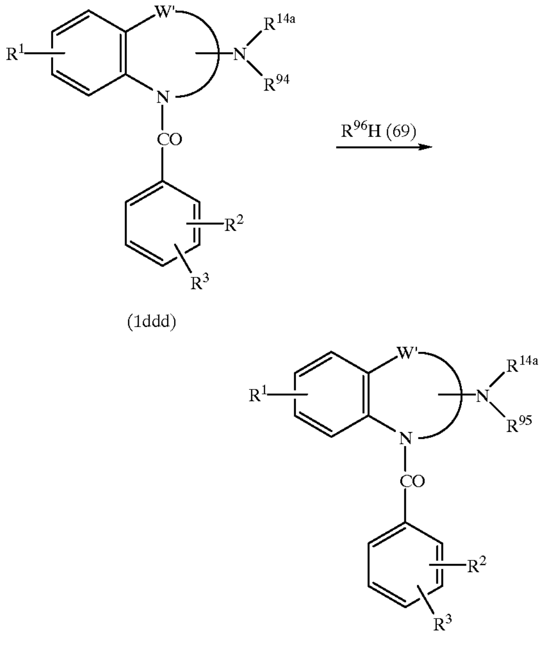

(1ddd)

(1eee)

wherein $R^1$, $R^2$, $R^3$, W', and $R^{14a}$ are as defined above, $R^{94}$ is a halogen-substituted lower alkanoyl, $R^{95}$ is an imidazolyl-substituted lower alkanoyl or an amino-lower alkanoyl having optionally a substituent selected from a lower alkyl and a lower alkoxycarbonyl, and $R^{96}$ is imidazolyl, or an amino having optionally a substituent selected from a lower alkyl and a lower alkoxycarbonyl.

The reaction of the compound (1ddd) and the compound (69) can be carried out under the same conditions as in the reaction of the compound (7) and the compound (8) in the above Reaction Scheme-4.

[Reaction Scheme-50]

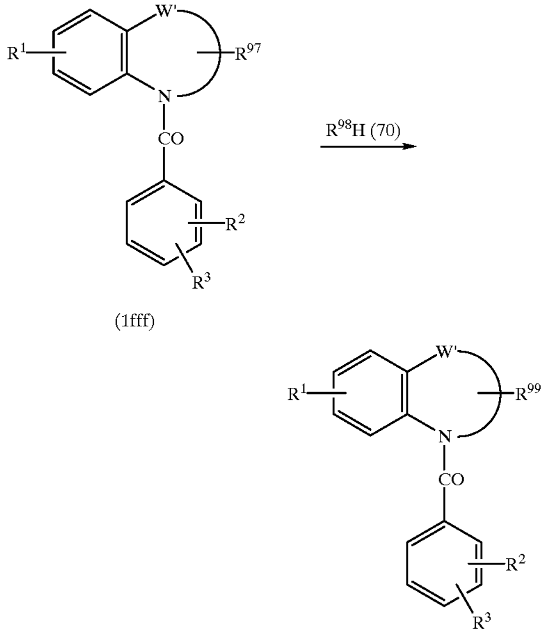

(1fff)

(1ggg)

wherein $R^1$, $R^2$, $R^3$, and W' are as defined above, $R^{97}$ is a lower alkanoyloxy having a halogen substituent, $R^{98}$ is an amino having optionally a lower alkyl substituent, and $R^{99}$ is an amino-lower alkanoyloxy having optionally a lower alkyl substituent.

The reaction of the compound (1fff) and the compound (70) can be carried out under the same conditions as in the reaction of the compound (7) and the compound (8) in the above Reaction Scheme-4.

[Reaction Scheme-51]

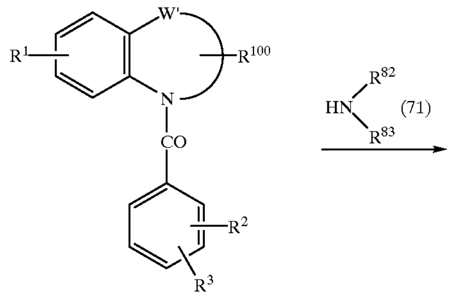

(1hhh)

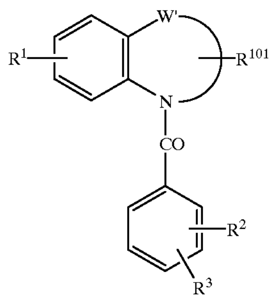

(1iii)

wherein $R^1$, $R^2$, $R^3$, W', $R^{82}$, and $R^{83}$ are as defined above, $R^{100}$ is a carboxy-substituted lower alkoxy, and $R^{101}$ is a group of the formula:

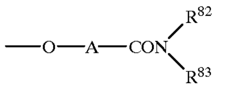

(A, $R^{82}$ and $R^{83}$ are as defined above).

The reaction of the compound (1hhh) and the compound (71) can be carried out under the same conditions as in the reaction of the compound (2) and the compound (3) in the above Reaction Scheme-1.

[Reaction Scheme-52]

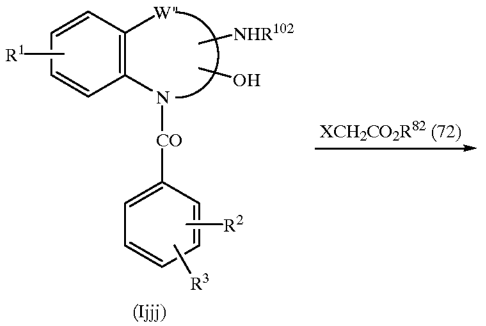

(Ijjj)

-continued

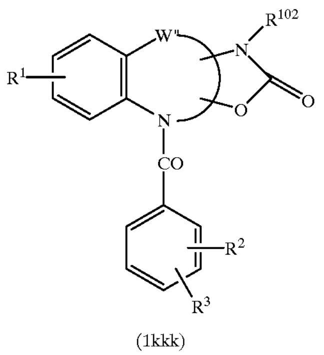

(1kkk)

wherein $R^1$, $R^2$, $R^3$, W", X, and $R^{82}$ are as defined above, and $R^{102}$ is hydrogen atom or a lower alkyl, provided that in the compound (1jjj), the groups of the formulae: —NH—$R^{102}$ and —OH are substituted at the positions adjacent each other.

The reaction of the compound (1jjj) and the compound (72) can be carried out under the same conditions as in the reaction of the compound (7) and the compound (8) in the above Reaction Scheme-4.

[Reaction Scheme-53]

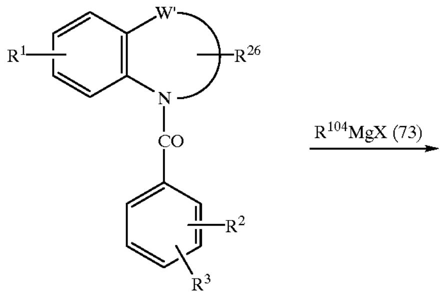

(1A)

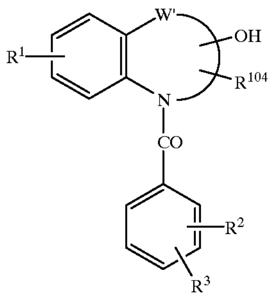

(Illl)

wherein $R^1$, $R^2$, $R^3$, W', $R^{26}$ and X are as defined above, and $R^{104}$ is a lower alkyl.

The reaction of the compound (1A) and the compound (73) can be carried out in an appropriate solvent. The solvent includes, for example, ethers (diethyl ether, dioxane, tetrahydrofuran, etc.), aromatic hydrocarbons (e.g. benzene, toluene, xylene, etc.), saturated hydrocarbons (e.g. pentane, hexane, heptane, cyclohexane, etc.), or a mixture of these solvents. The reaction is usually carried out at a temperature of from about −70° C. to about 50° C., preferably from about −30° C. to room temperature, for about 1 to 6 hours. The compound (73) is used in an amount of at least 1 mole, preferably 1 to 5 moles, to 1 mole of the compound (1A).

[Reaction Scheme-54]

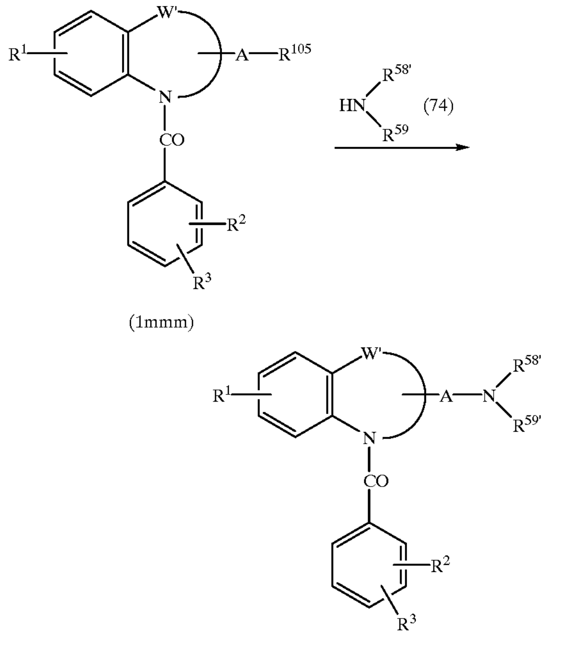

(1mmm)

(1nnn)

wherein $R^1$, $R^2$, $R^3$, W', $R^{58'}$, $R^{59'}$, and A are as defined above, and $R^{105}$ is a lower alkylsulfonyloxy.

The reaction of the compound (1mmm) and the compound (74) can be carried out under the same conditions as in the reaction of the compound (7) and the compound (8) in the above Reaction Scheme-4.

Among the active compounds (1) of this invention, the compounds having an acidic group can easily be converted into salts by treating with a pharmaceutically acceptable basic compound. The basic compound includes, for example, metal hydroxides such as sodium hydroxide, potassium hydroxide, lithium hydroxide, calcium hydroxide, etc., alkali metal carbonates or hydrogen carbonates such as sodium carbonate, sodium hydrogen carbonate, etc., alkali metal alcoholates such as sodium methylate, potassium ethylate, etc. Besides, among the active compounds (1) of this invention, the compounds having a basic group can easily be converted into acid addition salts thereof by treating with a pharmaceutically acceptable acid. The acid includes, for example, inorganic acids such as sulfuric acid,-nitric acid, hydrochloric acid, hydrobromic acid, etc., and organic acids such as acetic acid, p-toluenesulfonic acid, ethanesulfonic acid, oxalic acid, maleic acid, fumaric acid, citric acid, succinic acid, benzoic acid, etc. These salts are useful as an active ingredient as like as the compounds (1) in the free form.

In addition, the compounds (1) of this invention include stereoisomers and optical isomers, and these isomers are also useful as the active ingredient in this invention.

The compounds of this invention thus obtained can easily be isolated and purified by conventional isolation methods. The isolation methods are, for example, distillation method, recrystallization method, column chromatography, ion exchange chromatography, gel chromatography, affinity chromtography, preparative thin layer chromatography, extraction with a solvent, and the like.

The compounds and their salts of this invention are useful as a vasopressin antagonist and are used in the form of a conventional pharmaceutical preparation. The preparation is prepared by using conventional dilutents or carriers such as fillers, thickening agents, binders, wetting agents, disintegrators, surfactants, lubricants, and the like. The pharmaceutical preparations may be selected from various forms in accordance with the desired utilities, and the representative forms are tablets, pills, powders, solutions, suspensions, emulsions, granules, capsules, suppositories, injections (solutions, suspensions, etc.), and the like. In order to form in tablets, there are used carriers such as vehicles (e.g. lactose, white sugar, sodium chloride, glucose, urea, starches, calcium carbonate, kaolin, crystalline cellulose, silicic acid, etc.), binders (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium arginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium base, sodium laurylsulfate, etc.), wetting agents (e.g. glycerin, starches, etc.), adsorbents (e.g. starches, lactose, kaolin, bentonite, colloidal silicates, etc.), lubricants (e.g. purified talc, stearates, boric acid powder, polyethylene glycol, etc.), and the like. Moreover, the tablets may also be in the form of a conventional coated tablet, such as sugar-coated tablets, gelatin-coated tablets, enteric coated tablets, film coating tablets, or double or multiple layer tablets. In the preparation of pills, the carriers include vehicles (e.g. glucose, lactose, starches, cacao butter, hydrogenated vegetable oils, kaolin, talc, etc.), binders (e.g. gum arabic powder, tragacanth powder, gelatin, ethanol, etc.), disintegrators (e.g. laminaran, agar, etc.), and the like. In the preparation of suppositories, the carriers include, for example, polyethylene glycol, cacao butter, higher alcohols, higher alcohol esters, gelatin, semi-synthetic glycerides, and the like. Capsules can be prepared by charging a mixture of the compound of this invention with the above carriers into hard gelatin capsules or soft capsules in a usual manner. In the preparation of injections, the solutions, emulsions or suspendions are sterilized and are preferably made isotonic with the blood. In the preparation of these solutions, emulsions and suspensions, there are used conventional diluents, such as water, ethyl alcohol, macrogol (propylene glycol), ethoxylated isostearyl alcohol, polyoxylated isostearyl alcohol, polyoxyethylene sorbitan fatty acid esters, and the like. In this case, the pharmaceutical preparations may also be incorporated with sodium chloride, glucose, or glycerin in an amount sufficient to make them isotonic, and may also be incorporated with conventional solubilizers, buffers, anesthetizing agents. Besides, the pharmaceutical preparations may optionally be incorporated with coloring agents, preservatives, perfumes, flavors, sweeting agents, and other medicaments, if required.

The amount of the active compound of this invention (active ingredient) to be incorporated into the anti-vasopressin preparations is not specified but may be selected from a broad range, but usually, it is preferably in the range of 1 to 70% by weight, more preferably 5 to 50% by weight.

The anti-vasopressin preparation of this invention may be administered in any method, and suitable method for administration may be determined in accordance with various forms of preparation, ages, sexes and other conditions of the patients, the degree of severity of diseases, and the like. For instance, tablets, pills, solutions, suspensions, emulsions, granules and capsules are administered orally. The injections are intraveneously administered alone or together with a conventional auxiliary liquid (e.g. glucose, amino acid solutions), and further are optionally administered alone in intramuscular, intracutaneous, subcutaneous, or intraperitoneal route, if required. Suppositories are administered in intrarectal route.

The dosage of the anti-vasopressin agent of this invention may be selected in accordance with the usage, ages, sexes and other conditions of the patients, the degree of severity of the diseases, and the like, but is usually in the range of about 0.6 to 50 mg of the active compound of this invention per 1 kg of body weight of the patient per day. The active compound is preferably contained in an amount of 10 to 1000 mg per the dosage unit.

BEST MODE FOR CARRYING OUT THE INVENTION

Figure 1:
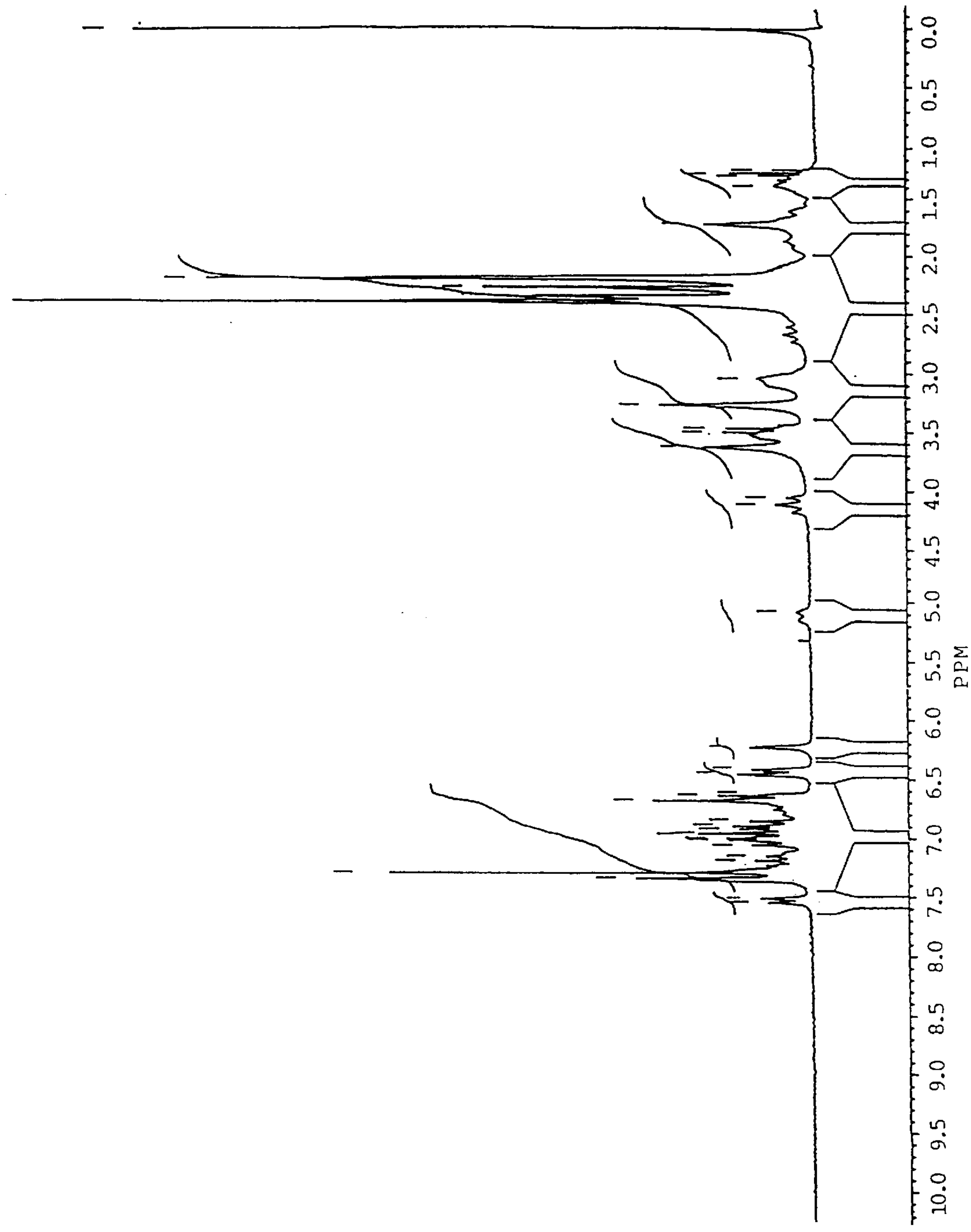
FIG. 1 to FIG. 4 show a chart of NMR ($CDCl_3$) of the compounds in Examples 978 and 979.

The present invention is illustrated by the following Preparations of anti-vasopressin agent, Reference Examples of processes for preparing the starting compounds to be used for preparing the active compounds, Examples of processes for preparing the active compounds, and Experiments of the activities of the active compounds of this invention.

Preparation 1

Film coated tablets are prepared from the following components.

| Components | Amount |
|---|---|
| 4-Methylamino-1-[4-(3,5-dichlorobenzoyl-amino)benzoyl]-1,2,3,4-tetrahydroquinoline | 150 g |
| Avicel (tradename of microcrystalline cellulose, manufactured by Asahi Chemical Industry Co., Ltd., Japan) | 40 g |
| Corn starch | 30 g |
| Magnesium stearate | 2 g |
| Hydroxypropyl methylcellulose | 10 g |
| Polyethylene glycol-6000 | 3 g |
| Castor oil | 40 g |
| Ethanol | 40 g |

The active component of this invention, Avicel, corn starch and magnesium stearate are mixed and kneaded and the mixture is tabletted using a conventional pounder (R 10 mm) for sugar coating. The tablets thus obtained are coated with a film coating agent consisting of hydroxypropyl methylcellulose, polyethylene glycol-6000, castor oil and ethanol to give film coated tablets.

Preparation 2

Tablets are prepared from the following components.

| Components | Amount |
|---|---|
| 1-[4-(N-Butylanilinoacetylamino)benzoyl]-2,3,4,5-tetrahydroy-1H-benzazepine | 150 g |
| Citric acid | 1.0 g |
| Lactose | 33.5 g |
| Dicalcium phosphate | 70.0 g |
| Pullonic F-68 | 30.0 g |
| Sodium laurylsulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium stearate | 3.0 g |
| Dry magnesium stearate | 3.0 g |
| Ethanol | q.s. |

The active compound of this invention, citric acid, lactose, dicalcium phosphate, Pullonic F-68 and sodium laurylstearate are mixed. The mixture is screened with No. 60 screen and is granulated with an alcohol solution containing polyvinylpyrrolidone, carbowax 1500 and 6000. If required, an alcohol is added thereto so that the powder mixture is made a paste-like mass. Corn starch is added to the mixture and the mixture is continuously mixed to form uniform particles. The resulting particles are passed through No. 10 screen and entered into a tray and then dried in an oven at 100° C. for 12 to 14 hours. The dried particles are screened with No. 16 screen and thereto are added dry sodium laurylsulfate and dry magnesium stearate, and the mixture is tabletted to form the desired shape.

The core tablets thus prepared are vanished and dusted with talc in order to guard from wetting. Undercoating is applied to the core tablets. In order to administer the tablets orally, the core tablets are vanished several times. In order to give round shape and smooth surface to the tablets, further undercoating and coating with lubricant are applied thereto. The tablets are further coated with a coloring coating material until the desired colored tablets are obtained. After drying, the coated tablets are polished to obtain the desired tablets having uniform gloss.

Preparation 3

An injection preparation is prepared from the following components.

| Components | Amount |
|---|---|
| 4-Methyl-1-[4-(2,3-dimethylbenzoyl-amino)benzoyl]-2,3,4,5-tetrahydro 1H-1,4-benzodiazepine | 5 g |
| Polyethylene qlycol (molecular weight: 4000) | 0.3 g |
| Sodium chloride | 0.9 g |
| Polyoxyethylene sorbitan monooleate | 0.4 g |
| Sodium metabisulfite | 0.1 g |
| Methyl-paraben | 0.18 g |
| Propyl-paraben | 0.02 g |
| Distilled water for injection | 10.0 ml |

The above parabens, sodium metabisulfite and sodium chloride are dissolved in distilled water of half volume of the above with stirring at 80° C. The solution thus obtained is cooled to 40° C., and the active compound of this invention and further polyethylene glycol and polyoxyethylene sorbitan monooleate are dissolved in the above solution. To the solution is added distilled water for injection to adjust to the desired volume, and the solution is sterilized by filtering with an appropriate filter paper to give an injection preparation.

REFERENCE EXAMPLE 1

To a solution of 1,2,3,4-tetrahydroquinoline (28.7 g) in acetone (400 ml) and water (200 ml) is added potassium carbonate (38.8 g), and thereto is added p-nitrobenzoyl chloride (40 g) under ice-cooling and the mixture is stirred at room temperature overnight. To the reaction mixture is added a suitable amount of water. The precipitated crystal is collected by filtration and dried to give 1-(4-nitrobenzoyl)-1,2,3,4-tetrahydroquinoline (40.8 g) as white powder, m.p. 86–88° C.

REFERENCE EXAMPLE 2

To a solution of 10% Pd-C (5 g) in ethanol (500 ml) is added 1-(4-nitrobenzoyl)-1,2,3,4-tetrahydroquinoline (53.4 g) and the mixture is subjected to catalytic reduction at ordinary temperature under atmospheric pressure of hydrogen. After the reduction, 10% Pd-C is removed by filtration, and the filtrate is concentrated under reduced pressure to give 1-(4-aminobenzoyl)-1,2,3,4-tetrahydroquinoline (46.7 g) as yellow powder, m.p. 185–188° C.

REFERENCE EXAMPLE 3

Using the suitable starting materials, the following compounds are obtained in the same manner as in Reference Example 1.

1-(3-Nitrobenzoyl)-1,2,3,4-tetrahydroquinoline, white powder, m.p. 134–136° C.

1-(2-Nitrobenzoyl)-1,2,3,4-tetrahydroquinoline, yellow powder, m.p. 152–154° C.

3-Methyl-1-(4-nitrobenzoyl)-1,2,3,4-tetrahydroquinoline, yellow powder, m.p. 109–110° C.

4-Methyl-1-(4-nitrobenzoyl)-1,2,3,4-tetrahydroquinoline, yellow powder, m.p. 134–136° C.

2-Methyl-1-(4-nitrobenzoyl)-1,2,3,4-tetrahydroquinoline, yellow powder, m.p. 143–145° C.

1-(4-Nitrobenzoyl)-2,3,4,5-tetrahydro-1H-benzazepine, yellow powder, m.p. 143–145° C.

1-(3-Methyl-4-nitrobenzoyl)-2,3,4,5-tetrahydro-1H-benzazepine, white powder, m.p. 100–102° C.

1-(3-Methoxy-4-nitrobenzoyl)-2,3,4,5-tetrahydro-1H-benzazepine, yellow powder, m.p. 146–148° C.

1-(4-Nitrobenzoyl)-1,2,3,4,5,6-hexahydrobenzazocine, white powder, m.p. 83–85° C.

1-(4-Nitrobenzoyl)-3,4-dihydro-2H-1,4-benzoxazine, yellow powder, m.p. 167–169° C.

1-(4-Nitrobenzoyl)-1,2,3,5-tetrahydro-4,1-benzoxazepine, yellow powder, m.p. 196–198° C.

1-(4-Nitrobenzoyl)-4-methyl-1,2,3,4-tetrahydroquinoxaline, brown powder $^1$H-NMR ($CDCl_3$) δ: 3.03 (3H, s), 3.54 (2H, t, J=5.7 Hz), 4.06 (2H, t, J=5.7 Hz), 6.2–6.5 (2H, m), 6.70 (1H, d, J=8.2 Hz), 6.9–7.1 (1H, m), 7.54 (2H, d, J=8.8 Hz), 8.13 (2H, d, J=8.8 Hz)

1-(4-Nitrobenzoyl)-5-methyl-2,3,4,5-tetrahydro-1H- 1,5-benzodiazepine, yellow oil $^1$H-NMR ($CDCl_3$) δ: 1.7–2.0 (1H, m), 2.0–2.3 (1H, m), 2.8–3.0 (1H, m), 2.98 (3H, s), 3.0–3.2 (1H, m), 3.4–3.6 (1H, m), 4.6–4.8 (1H, m), 6.5–6.7 (2H, m), 6.94 (1H, d, J=8.1 Hz), 7.1–7.2 (1H, m), 7.33 (2H, d, J=8.9 Hz), 7.97 (2H, d, J=8.9 Hz)

1-(4-Nitrobenzoyl)-4-methyl-2,3,4,5-tetrahydro-1H-1,4-benzodiazepine, brown oil $^1$H-NMR ($CDCl_3$) δ: 2.44 (3H, s), 3.0–3.3 (3H, m), 3.77 (1H, d, J=13.7 Hz), 4.06 (1H, d, J=13.6 Hz), 4.9–5.1 (1H, m), 6.59 (1H, d, J=7.7 Hz), 6.97 (1H, t, J=7.6 Hz), 7.15 (1H, t, J=7.4 Hz), 7.2–7.5 (3H, m), 8.03 (2H, d, J=8.8 Hz)

1-(3-Methoxy-4-nitrobenzoyl)-4-methyl-2,3,4,5-tetrahydro-1H-1,4-benzodiazepine, yellow powder, m.p. 146–148° C.

1-(4-Nitrobenzoyl)-4-n-propyl-2,3,4,5-tetrahydro-1H-1,4-benzodiazepine, yellow powder, m.p. 131–133° C.

1-(4-Nitrobenzoyl)-5-chloro-1,2,3,4-tetrahydroquinoline, white powder, m.p. 134–136° C.

1-(4-Nitrobenzoyl)-6-methoxy-1,2,3,4-tetrahydroquinoline, yellow powder, m.p. 149–151° C.

1-(4-Nitrobenzoyl)-6-methyl-1,2,3,4-tetrahydroquinoline, yellow powder, m.p. 109–110° C.

1-(4-Nitrobenzoyl)-7-methoxy-1,2,3,4-tetrahydroquinoline, yellow powder, m.p. 139–141° C.

1-(4-Nitrobenzoyl)-3-(4-methyl-1-piperazinyl)-1,2,3,4-tetrahydroquinoline, yellow amorphous $^1$H-NMR ($CDCl_3$) δ: 2.29 (3H, s), 2.35–3.20 (11H, m), 3.86–4.15 (2H, m), 6.48–6.63 (1H, m), 6.89 (1H, t, J=7.4 Hz), 7.05 (1H, t, J=7.4 Hz), 7.22 (1H, d, J=7.4 Hz), 7.52 (2H, d, J=8.8 Hz), 8.11 (2H, d, J=8.8 Hz)

1-(4-Nitrobenzoyl)-3-(1-pyrrolidinyl)-1,2,3,4-tetrahydroquinoline, yellow amorphous $^1$H-NMR ($CDCl_3$) δ: 1.70–1.95 (4H, m), 2.52–3.30 (7H, m), 3.80–4.22 (2H, m), 6.52 (1H, brs), 6.88 (1H, t, J=7.6 Hz), 6.96–7.11 (1H, m), 7.20 (2H, d, J=7.6 Hz), 7.54 (2H, d, J=8.8 Hz), 8.12 (2H, d, J=8.8 Hz)

1-(4-Nitrobenzoyl)-4-oxo-1,2,3,4-tetrahydroquinoline, yellow powder, m.p. 189–190° C.

1-(4-Nitrobenzoyl)-3-hydroxymethyl-1,2,3,4-tetrahydroquinoline, yellow powder, m.p. 97–100° C.

1-(4-Nitrobenzoyl)-3-ethoxycarbonyl-1,2,3,4-tetrahydroquinoline, pale yellow powder, m.p. 162–163° C.

1-(4-Nitrobenzoyl)-4-dimethylamino-1,2,3,4-tetrahydroquinoline, light brown oil $^1$H-NMR ($CDCl_3$) δ: 1.80–2.02 (1H, m), 2.20–2.50 (7H, m), 3.47 (1H, t, J=4.9 Hz), 3.70–3.88 (1H, m), 4.06–4.25 (1H, m), 6.46 (1H, d, J=7.5 Hz), 6.89 (1H, t, J=7.5 Hz), 7.05 (1H, t, J=7.5 Hz), 7.34 (1H, d, J=7.5 Hz), 7.50 (2H, d, J=7.0 Hz), 8.10 (2H, d, J=7.0 Hz)

REFERENCE EXAMPLE 4

Using the suitable starting materials, the following compounds are obtained in the same manner as in Reference Example 2.

1-(3-Aminobenzoyl)-1,2,3,4-tetrahydroquinoline, white powder, m.p. 128–130° C.

1-(2-Aminobenzoyl)-1,2,3,4-tetrahydroquinoline, yellow powder $^1$H-NMR ($CDCl_3$) δ: 2.01 (2H, quint, J=6.6 Hz), 2.81 (2H, t, J=6.6 Hz), 3.86 (2H, t, J=6.4 Hz), 4.6–4.8 (2H, m), 6.43 (1H, t, J=7 Hz), 6.66 (1H, d, J=8 Hz), 6.79 (1H, dd, J=1.4 Hz, J=7.6 Hz), 6.8–7.2 (5H, m)

3-Methyl-1-(4-aminobenzoyl)-1,2,3,4-tetrahydroquinoline, yellow powder, m.p. 197–200° C.

4-Methyl-1-(4-aminobenzoyl)-1,2,3,4-tetrahydroquinoline, yellow powder, m.p. 197–199° C.

2-Methyl-1-(4-aminobenzoyl)-1,2,3,4-tetrahydroquinoline, yellow powder, m.p. 204–206° C.

1-(4-Aminobenzoyl)-2,3,4,5-tetrahydro-1H-benzazepine, yellow powder, m.p. 172–174° C.

1-(3-Methyl-4-aminobenzoyl)-2,3,4,5-tetrahydro-1H-benzazepine, white powder, m.p. 156–158° C.

1-(3-Methoxy-4-aminobenzoyl)-2,3,4,5-tetrahydro-1H-benzazepine, white powder, m.p. 165–167° C.

1-(4-Aminobenzoyl)-1,2,3,4,5,6-hexahydrobenzazocine, white powder, m.p. 177–179° C.

1-(4-Aminobenzoyl)-3,4-dihydro-2H-1,4-benzoxazine, white powder, m.p. 192–194° C.

1-(4-Aminobenzoyl)-1,2,3,5-tetrahydro-4,1-benzoxazepine, yellow powder, m.p. 196–198° C.

1-(4-Aminobenzoyl)-4-methyl-1,2,3,4-tetrahydroquinoxaline, yellow powder, m.p. 210–212° C.

1-(4-Aminobenzoyl)-5-methyl-2,3,4,5-tetrahydro-1H-1,5-benzodiazepine, white powder, m.p. 159–161° C.

1-(4-Aminobenzoyl)-4-methyl-2,3,4,5-tetrahydro-1H-1,4-benzodiazepine, brown powder, m.p. 169–171° C.

1-(3-Methoxy-4-aminobenzoyl)-4-methyl-2,3,4,5-tetrahydro-1H-1,4-benzodiazepine, yellow oil $^1$H-NMR ($CDCl_3$) δ: 2.41 (3H, s), 2.9–3.2 (3H, m), 3.61 (3H, s), 3.6–4.2 (4H, m), 4.8–5.2 (1H, m), 6.38 (1H, d, J=8.1 Hz), 6.6–6.8 (3H, m), 6.9–7.2 (2H, m), 7.2–7.4 (1H, m)

1-(4-Aminobenzoyl)-4-n-propyl-2,3,4,5-tetrahydro-1H-1,4-benzazepine, brown powder, m.p. 151–153° C.

1-(4-Aminobenzoyl)-5-chloro-1,2,3,4-tetrahydroquinoline, white powder, m.p. 174–175° C.

1-(4-Aminobenzoyl)-6-methoxy-1,2,3,4-tetrahydroquinoline, pale yellow powder, m.p. 159–160° C.

1-(4-Aminobenzoyl)-6-methyl-1,2,3,4-tetrahydroquinoline, white powder, m.p. 145–146° C.

1-(4-Aminobenzoyl)-7-methoxy-1,2,3,4-tetrahydroquinoline, pale yellow powder, m.p. 150–152° C.

1-(4-Aminobenzoyl)-3-(4-methyl-1-piperazinyl)-1,2,3,4-tetrahydroquinoline, light beige powder, m.p. 157–159° C.

1-(4-Aminobenzoyl)-3-(1-pyrrolidinyl)-1,2,3,4-tetrahydroquinoline, pale yellow powder, m.p. 173–174.5° C.

1-(4-Aminobenzoyl)-2,3-dihydro-4(1H)-quinolinone, pale yellow powder, m.p. 178–180° C.

1-(4-Aminobenzoyl)-3-hydroxymethyl-1,2,3,4-tetrahydroquinoline, white powder, m.p. 179–181° C.

1-(4-Aminobenzoyl)-3-ethoxycarbonyl-1,2,3,4-tetrahydroquinoline, pale yellow amorphous $^1$H-NMR ($CDCl_3$) δ: 1.21 (3H, t, J=7.1 Hz), 3.00–3.24 (3H, m), 3.70–4.30 (6H, m), 6.48 (2H, d, J=8.5 Hz), 6.69 (1H, d, J=7.9 Hz), 6.77–7.30 (5H, m)

1-(4-Aminobenzoyl)-4-dimethylamino-1,2,3,4-tetrahydroquinoline, brown oil $^1$H-NMR ($CDCl_3$) δ: 1.83–2.05 (1H, m), 2.13–2.30 (1H, m), 2.34 (6H, m), 3.55–3.83 (2H, m), 3.89 (1H, brs), 3.97–4.18 (1H, m), 6.47 (2H, d, J=7.0 Hz), 6.68 (1H, d, J=7.9 Hz), 6.85–7.05 (2H, m), 7.20 (2H, d, J=7.0 Hz), 7.37 (1H, d, J=7.4 Hz)

REFERENCE EXAMPLE 5

To terephthalic acid monomethyl ester (15 g) is added thionyl chloride (100 ml) and the mixture is refluxed for 2 hours. The thionyl chloride is distilled off under reduced pressure to give terephthalic acid chloride monomethyl ester. Separately, to a solution of 1,2,3,4-tetrahydroquinoline (14.4 g) in dichloromethane (200 ml) is added triethylamine (16.9 g) and further thereto is added slowly terephthalic acid chloride monomethyl ester obtained above under ice-cooling. Then, the mixture is stirred at room temperature for 1 hour. After completion of the reaction, water is added to the reaction mixture. The mixture is extracted with dichloromethane and dried over magnesium sulfate. The solvent is distilled off under reduced pressure and the resulting residue is purified by silica gel column chromatography (eluent; dichloromethane) to give 1-(4-methoxycarbonylbenzoyl)-1,2,3,4-tetrahydroquinoline (22.7 9) as white powder, m.p. 72–74° C.

REFERENCE EXAMPLE 6

To a solution of 1-(4-methoxycarbonylbenzoyl)-1,2,3,4-tetrahydroquinoline (22.7 g) in methanol (300 ml) is added 5% aqueous sodium hydroxide solution (150 ml) and the mixture is refluxed for 2 hours. Methanol is distilled off under reduced pressure and the resulting residue is acidified with diluted hydrochloric acid, extracted with diethyl ether, and dried over magnesium sulfate. The solvent is distilled off under reduced pressure and the resulting crystal is collected by filtration to give 1-(4-carboxybenzoyl)-1,2,3,4-tetrahydroquinoline (13.2 g) as white powder, m.p. 181–183° C.

REFERENCE EXAMPLE 7

Using the suitable starting materials, the following compounds are obtained in the same manner as in Reference Example 1.

5-Dimethylamino-1-(4-nitrobenzoyl)-2,3,4,5-tetrahydro-1H-benzazepine, pale yellow powder, m.p. 139–142° C.

5-Dimethylamino-1-(3-methoxy-4-nitrobenzoyl)-2,3,4,5-tetrahydro-1H-benzazepine, white powder, m.p. 139–141° C.

4-(N-Methyl-N-ethylamino)-1-(4-nitrobenzoyl)-1,2,3,4-tetrahydroquinoline, pale yellow oil $^1$H-NMR ($CDCl_3$) δ: 1.11 (3H, t, J=7.1 Hz), 1.90–2.25 (2H, m), 2.30 (3H, s), 2.57 (2H, q, J=7.1 Hz), 3.55–3.85 (2H, m), 4.00–4.21 (1H, m), 6.35–6.60 (1H, m), 6.80–6.98 (1H, t, J=7.9 Hz), 7.00–7.15 (1H, m), 7.33–7.60 (3H, m), 8.10 (2H, d, J=8.8 Hz)

4-Dimethylamino-1-(3-methoxy-4-nitrobenzoyl)-1,2,3,4-tetrahydroquinoline, brown oil $^1$H-NMR ($CDCl_3$) δ: 1.80–2.05 (1H, m), 2.33 (6H, s), 2.30–2.50 (1H, m), 3.40–3.52 (1H, m), 3.78 (3H, s), 3.70–3.88 (1H, m), 4.04–4.24 (1H, m), 6.52 (1H, d, J=8.2 Hz), 6.85–7.13 (4H, m), 7.28–7.38 (1H, m), 7.71 (1H, d, J=8.2 Hz)

1-(4-Nitrobenzoyl)-4-ethyl-2,3,4,5-tetrahydro-1H-1,4-benzodiazepine, yellow oil $^1$H-NMR ($CDCl_3$) δ: 1.16 (3H, t, J=7.1 Hz), 2.5–2.7 (2H, m), 3.0–3.3 (3H, m), 3.98 (2H, q, J=14 Hz), 4.8–5.0 (1H, m), 6.59 (1H, d, J=7.7 Hz), 6.96 (1H, t, J=7.7 Hz), 7.14 (1H, t, J=7.4 Hz), 7.2–7.4 (3H, m), 8.02 (2H, d, J=8.8 Hz)

1-(4-Nitrobenzoyl)-4-isopropyl-2,3,4,5-tetrahydro-1H-1,4-benzodiazepine, yellow powder, m.p. 222–223° C.

1-(4-Nitrobenzoyl)-4-cyclohexyl-2,3,4,5-tetrahydro-1H-1,4-benzodiazepine, brown oil $^1$H-NMR ($CDCl_3$) δ: 1.0–1.5 (5H, m), 1.5–2.1 (5H, m), 2.4–2.7 (1H, m), 2.9–3.3 (3H, m), 3.94 (2H, s), 4.9–5.1 (1H, m), 6.57 (1H, d, J=7.7 Hz), 6.8–7.0 (1H, m), 7.0–7.2 (1H, m), 7.2–7.4 (3H, m), 8.01 (2H, d, J=8.8 Hz)

1-(4-Nitrobenzoyl)-5-methyl-1,2,3,4,5,6-hexahydro-1,5-benzodiazocine, yellow oil $^1$H-NMR ($CDCl_3$) δ: 1.5–2.1 (2H, m), 2.40 (3H, s), 2.3–2.6 (1H, m), 2.8–3.2 (2H, m), 3.50 (1H, d, J=13.4 Hz), 3.84 (1H, d, J=13.4 Hz), 4.8–5.0 (1H, m), 7.0–7.3 (4H, m), 7.41 (2H, d, J=8.9 Hz), 8.00 (2H, d, J=8.9 Hz)

1-(4-Nitrobenzoyl)-1,2,3,4-tetrahydro-5,1-benzoxazepine, white powder, m.p. 144.5–145.5° C.

1-(2-Nitrobenzoyl)-4-methyl-2,3,4,5-tetrahydro-1H-1,4-benzodiazepine, yellow powder, m.p. 177–180° C.

1-(3-Nitrobenzoyl)-4-methyl-2,3,4,5-tetrahydro-1H-1,4-benzodiazepine, yellow powder, m.p. 145–146° C.

6-Fluoro-1-(4-nitrobenzoyl)-1,2,3,4-tetrahydroquinoline, yellow needles, m.p. 145–146° C.

REFERENCE EXAMPLE 8

Using the suitable starting materials, the following compounds are obtained in the same manner as in Reference Example 2.

5-Dimethylamino-1-(4-aminobenzoyl)-2,3,4,5-tetrahydro-1H-benzazepine, white powder, m.p. 120–122° C.

5-Dimethylamino-1-(3-methoxy-4-amino)-2,3,4,5-tetrahydro-1H-benzazepine, white powder, m.p. 121–123° C.

4-(N-Methy-N-ethylamino)-1-(4-aminobenzoyl)-1,2,3,4-tetrahydroquinoline, orange amorphous $^1$H-NMR ($CDCl_3$) δ: 1.11 (3H, t, J=7.1 Hz), 1.90–2.20 (2H, m), 2.28 (3H, s), 2.26 (2H, q, J=7.1 Hz), 3.60–4.25 (5H, m), 6.48 (2H, d, J=8.5 Hz), 6.69 (1H, d, J=7.9 Hz), 6.80–7.05 (2H, m), 7.24 (2H, d, J=8.5 Hz), 7.46 (1H, d, J=6.2 Hz)

4-Dimethylamino-1-(3-methoxy-4-aminobenzoyl)-1,2,3,4-tetrahydroquinoline, pale yellow amorphous $^1$H-NMR ($CDCl_3$) δ: 1.83–2.04 (1H, m), 2.15–2.32 (1H, m), 2.33 (6H, s), 3.50–3.82 (2H, m), 3.64 (3H, s), 3.95–4.18 (3H, m), 6.50 (1H, d, J=7.9 Hz), 6.65 (1H, dd, J=7.9 Hz, 1.1 Hz), 6.78–7.03 (4H, m), 7.34 (1H, dd, J=7.5 Hz, 1.5 Hz)

1-(4-Aminobenzoyl)-4-ethyl-2,3,4,5-tetrahydro-1H-1,4-benzodiazepine, white powder, m.p. 186–188° C.

1-(4-Aminobenzoyl)-4-isopropyl-2,3,4,5-tetrahydro-1H-1,4-benzodiazepine, white powder, m.p. 191–192° C.

1-(4-Aminobenzoyl)-4-cyclohexyl-2,3,4,5-tetrahydro-1H-1,4-benzodiazepine, white powder, m.p. 149.5–150.5° C.

1-(4-Aminobenzoyl)-5-methyl-1,2,3,4,5,6-hexahydro-1,5-benzodiazocine, yellow powder, m.p. 143–145° C.

1-(4-Aminobenzoyl)-1,2,3,4-tetrahydro-5,1-benzoxazepine, yellow powder, m.p. 163.5–164.5° C.

1-(2-Aminobenzoyl)-4-methyl-2,3,4,5-tetrahydro-1H-1,4-benzodiazepine, yellow powder, m.p. 144–146° C.

1-(3-Aminobenzoyl)-4-methyl-2,3,4,5-tetrahydro-1H-1,4-benzodiazepine, white powder, mp. 153–155° C.

6-Fluoro-1-(4-aminobenzoyl)-1,2,3,4-tetrahydroquinoline, white powder, m.p. 160.5–161.5° C.

REFERENCE EXAMPLE 9

Using the suitable starting materials, the following compounds are obtained in the same manner as in Reference Example 1.

1-(2-Chloro-4-nitrobenzoyl)-4-methyl-2,3,4,5-tetrahydro-1H-1,4-benzodiazepine $^1$H-NMR ($CDCl_3$) δ: 2.40 (3H, s), 2.96–3.33 (3H, m), 3.60–3.79 (1H, m), 3.96–4.23 (1H, m), 4.70–4.91 (1H, m), 6.80–7.43 (5H, m), 7.80–7.99 (1H, m), 8.08–8.21 (1H, m)

1-(3-Methyl-4-nitrobenzoyl)-4-methyl-2,3,4,5-tetrahydro-1H-1,4-benzodiazepine $^1$H-NMR ($CDCl_3$) δ: 2.43 (3H, s), 2.48 (3H, s), 2.92–3.28 (3H, m), 3.91 (2H, AB-q, J=13.9 Hz, 45.5 Hz), 4.77–5.01 (1H, m), 6.54–6.70 (1H, m), 6.88–7.37 (5H, m), 7.62–7.78 (1H, m)

5-Dimethylamino-1-(2-chloro-4-nitrobenzoyl)- 2,3,4,5-tetrahydro-1H-benzazepine $^1$H-NMR ($CDCl_3$) δ: 1.23–2.57 (10H, m), 2.68–5.15 (3H, m), 6.79–7.45 (4H, m), 7.49–8.39 (3H, m)

5-Oxo-1-(4-nitrobenzoyl)-2,3,4,5-tetrahydro-1H-benzazepine, white powder (ethyl acetate/n-hexane), m.p. 147–148° C.

5-Hydroxy-1-(4-nitrobenzoyl)-2,3,4,5-tetrahydro-1H-benzazepine, white powder (ethyl acetate/n-hexane), m.p. 148–150° C.

5-Methoxy-1-(4-nitrobenzoyl)-2,3,4,5-tetrahydro-1H-benzazepine, colorless amorphous $^1$H-NMR ($CDCl_3$) δ: 1.47–2.48 (4H, m), 2.70–3.10 (1H, m), 3.26–3.64 (3H, m), 4.29–5.12 (2H, m), 6.60 (1H, d, J=7.7 Hz), 6.88–7.67 (5H, m), 7.92–8.12 (2H, m)

5-Ethoxycarbonylmethoxy-1-(4-nitrobenzoyl)-2,3,4,5-tetrahydro-1H-benzazepine, white powder, m.p. 107–108° C. (recrystallized from ethyl acetate/n-hexane)

5-(4-Bromobutoxy)-1-(4-nitrobenzoyl)-2,3,4,5-tetrahydro-1H-benzazepine, colorless oil $^1$H-NMR ($CDCl_3$) δ: 1.49–2.55 (8H, m), 2.72–3.07 (1H, m), 3.24–3.77 (4H, m), 4.40–5.15 (2H, m), 6.53–6.66 (1H, m), 6.91–7.06 (1H, m), 7.07–7.80 (4H, m), 7.94–8.13 (2H, m)

5-(4-Dimethylaminobutoxy)-1-(4-nitrobenzoyl)-2,3,4,5-tetrahydro-1H-benzazepine, colorless oil $^1$H-NMR ($CDCl_3$) δ: 1.51–1.88 (6H, m), 2.23–2.61 (4H, m), 2.27 (3H, s), 2.35 (3H, s), 2.74–3.14 (1H, m), 3.55–3.77 (2H, m), 4.48–5.11 (2H, m), 6.54–6.66 (1H, m), 6.91–7.04 (1H, m), 7.06–7.80 (4H, m), 7.93–8.11 (2H, m) 5-[4-(Phthalimid-1-yl)propoxy-1-(4-nitrobenzoyl)-2,3,4,5-tetrahydro-1H-benzazepine, colorless amorphous $^1$H-NMR ($CDCl_3$) δ: 1.48–2.56 (6H, m), 2.71–3.05 (1H, m), 3.40–4.05 (4H, m), 4.47–5.11 (2H, m), 6.50–6.64 (1H, m), 6.84–7.03 (1H, m), 7.03–7.20 (1H, m), 7.20–7.57 (2H, m), 7.57–7.93 (5H, m), 7.97–8.20 (2H, m)

5-Chloro-1-(4-nitrobenzoyl)-2,3,4,5-tetrahydro-1H-benzazepine, light brown powder $^1$H-NMR ($CDCl_3$) δ: 1.75–3.3 (4H, m), 4.6–6.25 (3H, m), 6.45–6.7 (1H, m), 6.8–7.5 (4H, m), 7.55–7.7 (1H, m), 7.9–8.1 (2H, m)

5-Oxo-1-(2-chloro-4-nitorobenzoyl)-2,3,4,5-tetrahydro-1H-benzazepine, pale yellow amorphous $^1$H-NMR ($CDCl_3$) δ: 1.95–2.45 (2H, m), 2.94 (1H, t, J=6 Hz), 3.05–5.3 (2H, m), 6.96–7.1 (1H, m), 7.12–7.5 (3H, m), 7.75–7.85 (1H, m), 7.95–8.1 (1H, m), 8.14 (1H, s)

4-Dimethylaminomethyl-1-(4-nitrobenzoyl)-1,2,3,4-tetrahydroquinoline, white powder, m.p. 117–119° C.

3-Dimethylamino-1-(4-nitrobenzoyl)-2,3,4,5-tetrahydro-1H-benzazepine, yellow oil $^1$H-NMR ($CDCl_3$) δ: 1.5–1.7 (1H, m), 2.1–2.4 (1H, m), 2.42 (6H, s), 2.6–2.7 (1H, m), 2.8–3.0 (3H, m), 5.1–5.3 (1H, m), 6.62 (1H, d, J=7.8 Hz), 6.95 (1H, t, J=7.7 Hz), 7.14 (1H, t, J=7.5 Hz), 7.2–7.4 (3H, m), 8.00 (2H, d, J=8.9 Hz)

3-Dimethylamino-1-(3-methoxy-4-nitrobenzoyl)-2,3,4,5-tetrahydro-1H-benzazepine, yellow oil $^1$H-NMR ($CDCl_3$) δ: 1.5–1.7 (1H, m), 2.0–2.3 (1H, m), 2.41 (6H, s), 2.5–2.8 (1H, m), 2.8–3.0 (3H, m), 3.75 (3H, s), 5.1–5.3 (1H, m), 6.6–6.8 (2H, m), 6.9–7.3 (4H, m), 7.59 (1H, d, J=8.3 Hz)

4-(4-Nitrobenzoyl)-3,4-dihydro-2H-1,4-benzothiazine, yellow powder, m.p. 180–182° C.

5-(4-Nitrobenzoyl)-2,3,4,5-tetrahydro-1,5-benzothiazepine, yellow powder, m.p. 162–163° C.

REFERENCE EXAMPLE 10

Using the suitable starting materials, the following compounds are obtained in the same manner as in Reference Example 2.

1-(2-Chloro-4-aminobenzoyl)-4-methyl-2,3,4,5-tetrahydro-1H-1,4-benzodiazepine, white powder (recrystallized from methanol/diethyl ether), m.p. 194.5–195.5° C.

1-(3-Methyl-4-aminobenzoyl)-4-methyl-2,3,4,5-tetrahydro-1H-1,4-benzodiazepine $^1$H-NMR ($CDCl_3$) δ: 2.01 (3H, s), 2.41 (3H, s), 2.82–3.21 (3H, m), 3.50–4.21 (4H, m), 4.78–5.14 (1H, m), 6.24–6.40 (1H, m), 6.59–6.82 (2H, m), 6.90–7.18 (3H, m), 7.19–7.34 (1H, m)

5-Dimethylamino-1-(2-chloro-4-aminobenzoyl)-2,3,4,5-tetrahydro-1H-benzazepine, white powder (recrystallized from dichloromethane/diethyl ether), m.p. 162–164° C.

5-Dimethylamino-1-(2-methoxy-4-aminobenzoyl)-2,3,4,5-tetrahydro-1H-benzazepine (recrystallized from methanol/diethyl ether)

$^1$H-NMR ($CDCl_3$) δ: 1.23–2.80 (11H, m), 2.90–3.38 (1H, m), 3.50–5.19 (6H, m), 5.87–6.41 (2H, m), 6.65–7.56 (5H, m)

5-Methoxy-1-(4-aminobenzoyl)-2,3,4,5-tetrahydro-1H-benzazepine, white powder (recrystallized from ethyl acetate/n-hexane), m.p. 154–155° C.

5-Ethoxycarbonylmethoxy-1-(4-aminobenzoyl)-2,3,4,5-tetrahydro-1H-benzazepine, white powder (recrystallized from ethyl acetate/n-hexane), m.p. 231–232° C.

5-(4-Dimethylaminobutoxy)-1-(4-aminobenzoyl)-2,3,4,5-tetrahydro-1H-benzazepine, colorless oil $^1$H-NMR ($CDCl_3$) δ: 1.47–1.83 (6H, m), 1.83–2.54 (4H, m), 2.29 (6H, s), 2.61–3.00 (1H, m), 3.36–3.76 (2H, m), 4.35–5.20 (2H, m), 6.27–6.48 (2H, m), 6.57–6.76 (1H, m), 6.90–7.61 (5H, m)

5-[4-(Phthalimid-1-yl)propoxy]-1-(4-aminobenzoyl)-2,3,4,5-tetrahydro-1H-benzazepine, colorless amorphous $^1$H-NMR ($CDCl_3$) δ: 1.30–2.47 (6H, m), 2.57–3.01 (1H, m), 3.30–4.06 (4H, m), 4.34–5.20 (2H, m), 6.30–6.53 (2H, m), 6.57–6.78 (1H, m), 6.87–7.57 (5H, m), 7.62–7.76 (2H, m), 7.76–7.97 (2H, m)

5-Chloro-1-(4-aminobenzoyl)-2,3,4,5-tetrahydro-1H-benzazepine, pale yellow amorphous $^1$H-NMR ($CDCl_3$) δ: 1.35–4.3 (7H, m), 4.55–6.7 (2H, m), 6.3–6.55 (2H, m), 6.6–6.8 (1H, m), 6.85–7.45 (5H, m)

5-Oxo-1-(4-aminobenzoyl)-2,3,4,5-tetrahydro-1H-benzazepine, pale yellow amorphous $^1$H-NMR ($CDCl_3$) δ: 1.95–2.35 (2H, m), 2.89 (2H, t, J=6.3 Hz), 3.0–5.3 (4H, m), 6.35–6.47 (2H, m), 6.72–6.83 (1H, m), 7.0–7.15 (2H, m), 7.18–7.32 (2H, m), 7.81–7.93 (1H, m)

5-Oxo-1-(2-chloro-4-aminobenzoyl)-2,3,4,5-tetrahydro-1H-benzazepine, white powder H-NMR ($CDCl_3$) δ: 1.85–2.3 (2H, m), 2.87 (2H, t, J=6.2 Hz), 3.1–4.75 (4H, m), 6.15–7.5 (6H, m), 7.65–7.9 (1H, m)

4-Dimethylaminomethyl-1-(4-aminobenzoyl)-1,2,3,4-tetrahydroquinoline, white powder, m.p. 123–125° C.

3-Dimethylamino-1-(4-aminobenzoyl)-2,3,4,5-tetrahydro-1H-benzazepine, white powder, m.p. 175–177° C.

3-Dimethylamino-1-(3-methoxy-4-aminobenzoyl)-2,3,4,5-tetrahydro-1H-benzazepine, yellow oil $^1$H-NMR ($CDCl_3$) δ: 1.5–1.7 (1H, m), 2.1–2.3 (1H, m), 2.3–2.6 (1H, m), 2.40 (6H, s), 2.7–3.0 (3H, m), 3.60 (3H, s), 3.8–4.0 (2H, br), 5.2–5.4 (1H, m), 6.37 (1H, d, J=8.2 Hz), 6.5–6.8 (3H, m), 6.9–7.4 (3H, m)

4-(4-Aminobenzoyl)-3,4-dihydro-2H-1,4-benzothiazine, yellow powder, m.p. 207–210° C.

5-(4-Aminobenzoyl)-2,3,4,5-tetrahydro-1,5-benzothiazepine, yellow powder, m.p. 193–195° C.

REFERENCE EXAMPLE 11

Using the suitable starting materials, the following compounds are obtained in the same manner as in Reference Example 1.

5-Carbamoyloxy-1-(4-nitrobenzoyl)-2,3,4,5-tetrahydro-1H-benzazepine, white powder, m.p. 243–244° C. (recrystallized from ethyl acetate/diisopropyl ether)

5-Methylaminocarbonyloxy-1-(4-nitrobenzoyl)-2,3,4,5-tetrahydro-1H-benzazepine, white powder, m.p. 207–208° C. (recrystallized from ethyl acetate/n-hexane)

5-Dimethylaminocarbonyloxy-1-(4-nitrobenzoyl)-2,3,4,5-tetrahydro-1H-benzazepine, white powder, m.p. 155–156° C. (recrystallized from ethyl acetate/diisopropyl ether/n-hexane)

5-Methylidenyl-1-(4-nitrobenzoyl)-2,3,4,5-tetrahydro-1H-benzazepine, colorless prisms, m.p. 133.5–134° C. (recrystallized from ethyl acetate/diisopropyl ether)

5-Oxo-6-methyl-1-(2-chloro-4-nitrobenzoyl)-2,3,4,5-tetrahydro-1H-benzazepine, colorless prisms, m.p. 90–92° C. (recrystallized from ethanol)

1-(4-Nitrobenzoyl)-1,2,3,5-tetrahydro-4,1-benzothiazepine, yellow powder, m.p. 185–187° C. (recrystallized from dichloromethane/diethyl ether)

5-Dimethylamino-1-(2-dimethylamino-4-nitrobenzoyl)-2,3,4,5-tetrahydro-1H-benzazepine, yellow powder, m.p. 123–125° C. (recrystallized from diethyl ether/dichloromethane)

5-Oxo-1-(4-nitrobenzoyl)-2,3,4,5-tetrahydro-1H-1,4-benzodiazepine, white powder, m.p. 201.5–202.5° C. (recrystallized from diethyl ether/dichloromethane)

5-Oxo-4-methyl-1-(4-nitrobenzoyl)-2,3,4,5-tetrahydro-1H-1,4-benzodiazepine, white powder, m.p. 136–138° C. (recrystallized from diethyl ether/dichloromethane)

5-Dimethylamino-1-(3-methyl-4-nitrobenzoyl)-2,3,4,5-tetrahydro-1H-benzazepine, yellow oil $^1$H-NMR ($CDCl_3$) δ: 1.16–3.18 (11H, m), 2.18 (3H, s), 3.40–5.15 (2H, m), 6.50–7.68 (6H, m), 7.70–7.84 (1H, m)

5-Dimethylamino-1-(2-methyl-4-nitrobenzoyl)-2,3,4,5-tetrahydro-1H-benzazepine, colorless amorphous $^1$H-NMR ($CDCl_3$) δ: 1.19–2.86 (11H, m), 2.20 (3H, s), 2.94–3.24 (1H, m), 3.36–5.18 (1H, m), 6.49–8.20 (7H, m)

5-Dimethylamino-1-(2-fluoro-4-nitrobenzoyl)-2,3,4,5-tetrahydro-1H-benzazepine, yellow oil $^1$H-NMR ($CDCl_3$) δ: 1.21–2.66 (10H, m), 2.66–5.11 (3H, m), 6.63–8.25 (7H, m)

5-Dimethylamino-1-(3-fluoro-4-nitrobenzoyl)-2,3,4,5-tetrahydro-1H-benzazepine, white powder, m.p. 152–152.5° C. (recrystallized from chloroform/diethyl ether)

REFERENCE EXAMPLE 12

Using the suitable starting materials, the following compounds are obtained in the same manner as in Reference Example 2.

5-Carbamoyloxy-1-(4-aminobenzoyl)-2,3,4,5-tetrahydro-1H-benzazepine, white powder, m.p. 215–216° C. (recrystallized from ethyl acetate/n-hexane)

5-Methylaminocarbonyloxy-1-(4-aminobenzoyl)-2,3,4,5-tetrahydro-1H-benzazepine, white powder, m.p. 192–195° C. (recrystallized from ethyl acetate/n-hexane)

5-Dimethylaminocarbonyloxy-1-(4-aminobenzoyl)-2,3,4,5-tetrahydro-1H-benzazepine, white powder, m.p. 228–230° C. (recrystallized from ethyl acetate/diisopropyl ether)

5-Methyl-1-(4-aminobenzoyl)-2,3,4,5-tetrahydro-1H-benzazepine, white powder, m.p. 155–156° C. (recrystallized from ethyl acetate/n-hexane)

5-Oxo-6-methyl-1-(2-chloro-4-aminobenzoyl)-2,3,4,5-tetrahydro-1H-benzazepine, white powder, m.p. 193–195° C. (recrystallized from ethanol)

1-(4-Aminobenzoyl)-1,2,3,5-tetrahydro-4,1-benzothiazepine, white powder, m.p. 179–180° C. (recrystallized from dichloromethane/diethyl ether)

5-Dimethylamino-1-(2-dimethylamino-4-aminobenzoyl)-2,3,4,5-tetrahydro-1H-benzazepine, white powder, m.p. 163–165° C. (recrystallized from diethyl ether/dichloromethane)

5-Oxo-1-(4-aminobenzoyl)-2,3,4,5-tetrahydro-1H-benzazepine, yellow powder, m.p. 195–197° C. (recrystallized from diethyl ether/dichloromethane)

5-Oxo-4-methyl-1-(4-aminobenzoyl)-2,3,4,5-tetrahydro-1H-1,4-benzazepine, yellow powder, m.p. 190–192° C. (recrystallized from diethyl ether/dichloromethane)

5-Dimethylamino-1-(2-ethoxy-4-aminobenzoyl)-2,3,4,5-tetrahydro-1H-benzazepine, white powder, m.p. 111–114° C. (recrystallized from diethyl ether)

5-Dimethylamino-1-(3-methyl-4-aminobenzoyl)-2,3,4,5-tetrahydro-1H-benzazepine, yellow oil $^1$H-NMR ($CDCl_3$) δ: 0.66–2.56 (14H, m), 2.93–5.22 (4H, m), 6.23–7.80 (7H, m)

5-Dimethylamino-1-(2-methyl-4-aminobenzoyl)-2,3,4,5-tetrahydro-1H-benzazepine, white powder, m.p. 154–156° C. (recrystallized from methanol/diethyl ether)

5-Dimethylamino-1-(2-fluoro-4-aminobenzoyl)-2,3,4,5-tetrahydro-1H-benzazepine, white powder, m.p. 161–163° C. (recrystallized from dichloromethane/diethyl ether)

5-Dimethylamino-1-(3-fluoro-4-aminobenzoyl)-2,3,4,5-tetrahydro-1H-benzazepine, white powder, m.p. 156–157° C. (recrystallized from methanol/diethyl ether)

5-Oxo-1-(2-methoxy-4-aminobenzoyl)-2,3,4,5-tetrahydro-1H-benzazepine, colorless prisms, m.p. 160–160.5° C. (recrystallized from methanol/diethyl ether)

EXAMPLE 1

To a solution of 1,2,3,4-tetrahydroquinoline (28.7 g) in acetone (400 ml) and water (200 ml) is added potassium carbonate (38.8 g) and further thereto is added 4-benzoylaminobenzoyl chloride (56 g) under ice-cooling. The mixture is stirred at room temperature overnight. Water is added to the reaction mixture, and the mixture is extracted with dichloromethane. The extract is dried over magnesium sulfate, and the solvent is distilled off under reduced pressure. The resulting residue is purified by silica gel column chromatography and recrystallized from methanol to give 1-[4-(benzoylamino)benzoyl-]-1,2,3,4-tetrahydroquinoline (57 g) as white powder, m.p. 202.5–203.5° C.

Using the suitable starting materials, the compounds as shown in the following Table 1 are obtained in the same manner as in Example 1.

TABLE 1

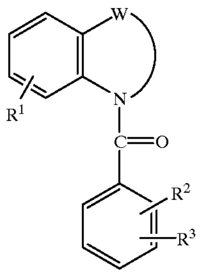

Example 2
Structure

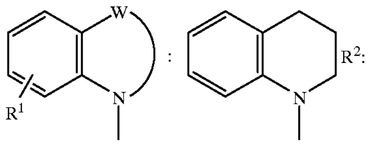

$R^2$: H $R^3$:

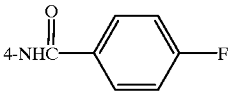

Crystalline form: Light yellow powder
Recrystallization solvent: Methanol
Melting Point: 198.5–199.5° C.
Form: Free Example 3
Structure

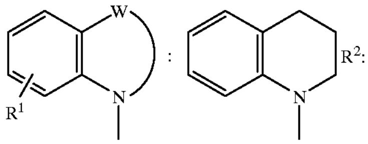

$R^2$: H $R^3$:

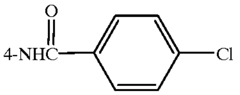

Crystalline form: White powder
Recrystallization solvent: Methanol
Melting Point: 200.5–201.5° C.
Form: Free Example 4
Structure

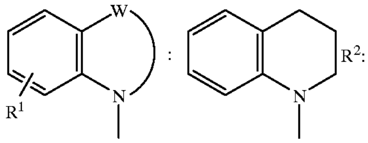

$R^2$: H $R^3$:

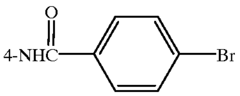

Crystalline form: Yellow powder
Recrystallization solvent: Methanol
Melting Point: 206–207° C.
Form: Free TABLE 1-continued

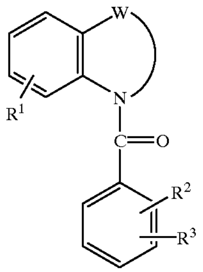

Example 5
Structure

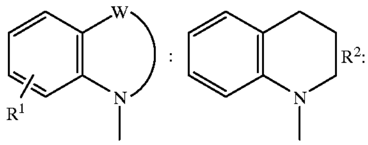
R$^2$: H

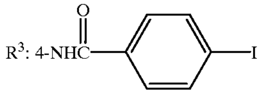

Crystalline form: Yellow powder
Recrystallization solvent: Methanol
Melting Point: 216–217° C.
Form: Free
Example 6
Structure

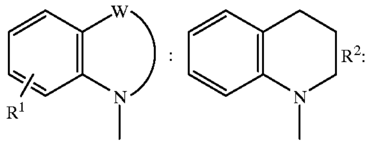
R$^2$: H

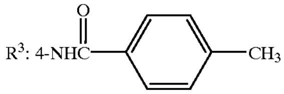

Crystalline form: White powder
Recrystallization solvent: Methanol
Melting Point: 202–203° C.
Form: Free
Example 7
Structure

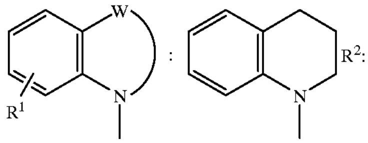
R$^2$: H

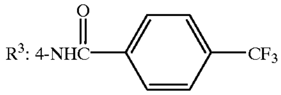

Crystalline form: White powder
Recrystallization solvent: Methanol
Melting Point: 212–213° C.
Form: Free TABLE 1-continued

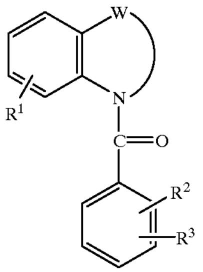

Example 8
Structure

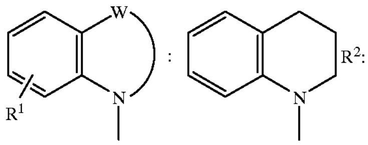
R$^2$: H

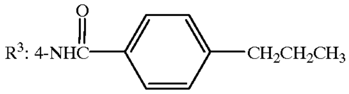

Crystalline form: White powder
Recrystallization solvent: Methanol
Melting Point: 167.5–168.5° C.
Form: Free
Example 9
Structure

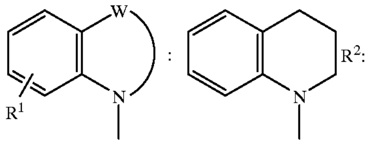
R$^2$: H

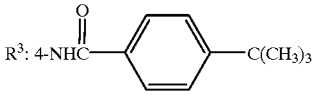

Crystalline form: White powder
Recrystallization solvent: Methanol
Melting Point: 205–206° C.
Form: Free
Example 10
Structure

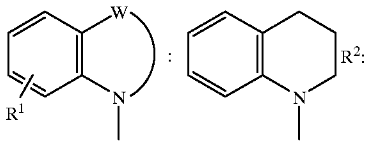
R$^2$: H

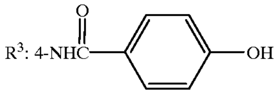

Crystalline form: White powder
Recrystallization solvent: Methanol
Melting Point: >300° C.
NMR analysis: 1)
Form: Free TABLE 1-continued

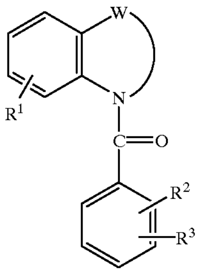

Example 11

Structure

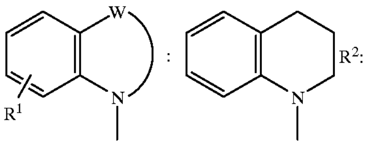

$R^2$: H $R^3$:

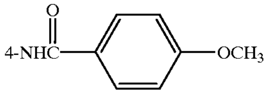

Crystalline form: Yellow powder
Recrystallization solvent: Methanol
Melting Point: 176–177° C.
Form: Free Example 12

Structure

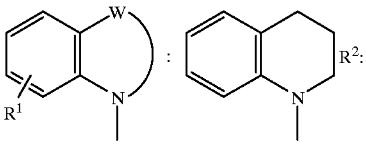

$R^2$: H $R^3$:

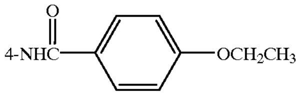

Crystalline form: White powder
Recrystallization solvent: Methanol
Melting Point: 219–220° C.
Form: Free Example 13

Structure

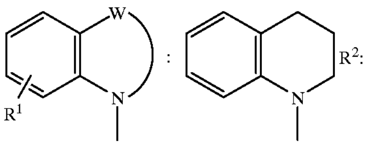

$R^2$: H $R^3$:

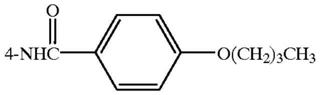

Crystalline form: White powder
Recrystallization solvent: Methanol
Melting Point: 193–194° C.
Form: Free TABLE 1-continued

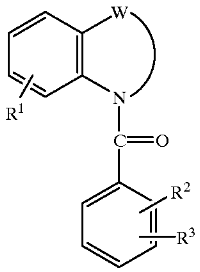

Example 14

Structure

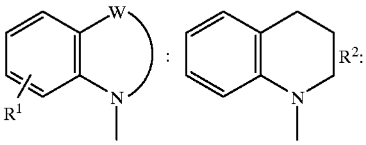

$R^2$: H $R^3$:

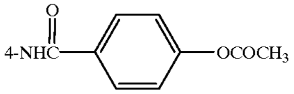

Crystalline form: White powder
Recrystallization solvent: Methanol
Melting Point: 232–233° C.
Form: Free Example 15

Structure

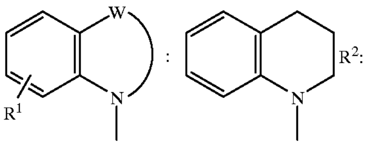

$R^2$: H $R^3$:

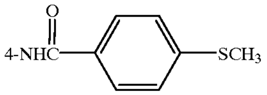

Crystalline form: White powder
Recrystallization solvent: Methanol
Melting Point: 209–210° C.
Form: Free Example 16

Structure

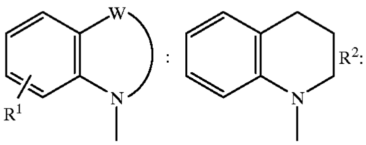

$R^2$: H $R^3$:

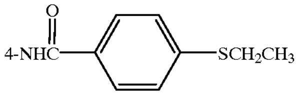

Crystalline form: White powder
Recrystallization solvent: Methanol
Melting Point: 184.5–185.5° C.
Form: Free TABLE 1-continued

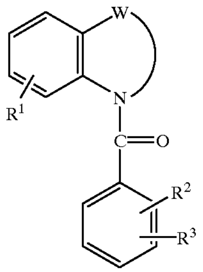

Example 17
Structure

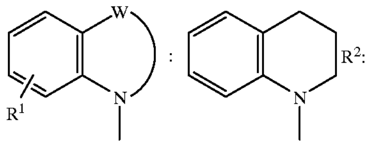

$R^2$: H

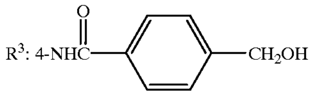

Crystalline form: White powder
Recrystallization solvent: Methanol
Melting Point: 224.5–225.5° C.
Form: Free Example 18
Structure

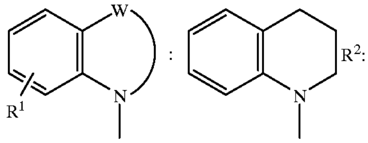

$R^2$: H

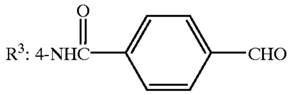

Crystalline form: White powder
Recrystallization solvent: Methanol
Melting Point: 220.5–221.5° C.
Form: Free Example 19
Structure

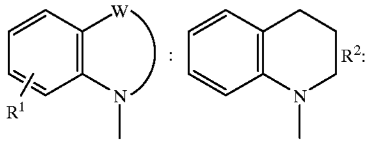

$R^2$: H

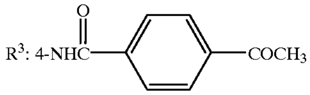

Crystalline form: Yellow powder
Recrystallization solvent: Methanol
Melting Point: 231–232° C.
Form: Free TABLE 1-continued

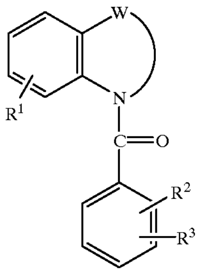

Example 20
Structure

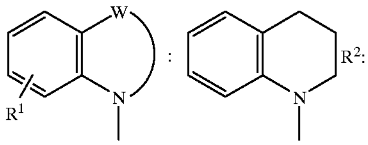

$R^2$: H

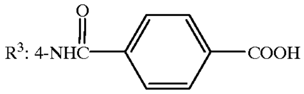

Crystalline form: White powder
Recrystallization solvent: Methanol
Melting Point: >300° C.
NMR analysis: 2)
Form: Free Example 21
Structure

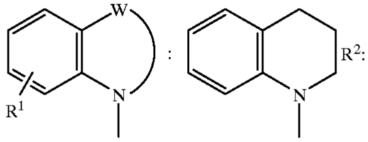

$R^2$: H

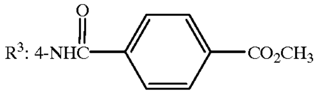

Crystalline form: White powder
Recrystallization solvent: Methanol
Melting Point: 208–209° C.
Form: Free Example 22
Structure

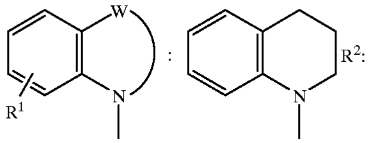

$R^2$: H

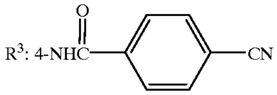

Crystalline form: White powder
Recrystallization solvent: Methanol
Melting Point: 234.5–235.5° C.
Form: Free TABLE 1-continued

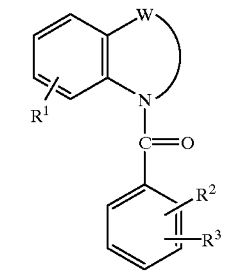

Example 23
Structure

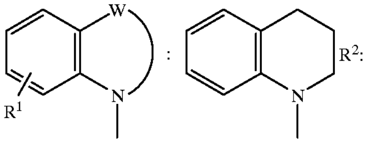

$R^2$: H $R^3$: 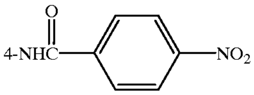

Crystalline form: Yellow powder
Recrystallization solvent: Methanol
Melting Point: 263.5–264.5° C.
Form: Free
Example 24
Structure

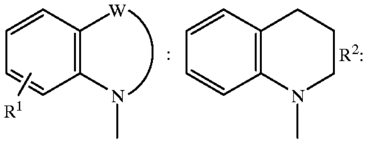

$R^2$: H $R^3$: 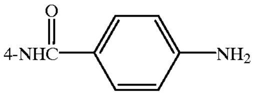

Crystalline form: White powder
Recrystallization solvent: Methanol
Melting Point: 237–238° C.
Form: Free
Example 25
Structure

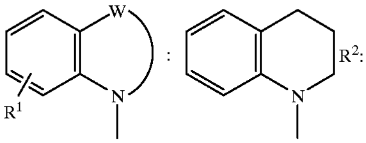

$R^2$: H $R^3$: 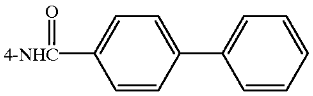

Crystalline form: White powder
Recrystallization solvent: Methanol
Melting Point: 234–235° C.
Form: Free TABLE 1-continued

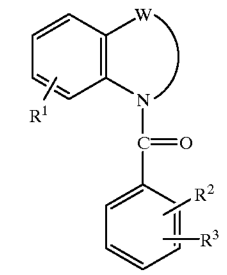

Example 26
Structure

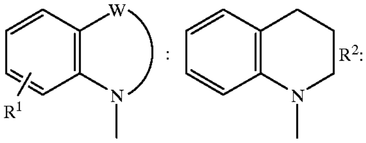

$R^2$: H $R^3$: 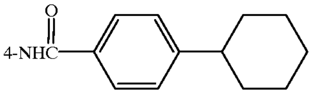

Crystalline form: White powder
Recrystallization solvent: Methanol
Melting Point: 236.5–237.5° C.
Form: Free
Example 27
Structure

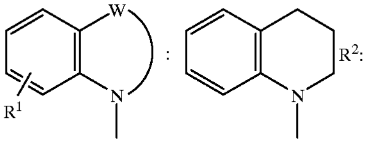

$R^2$: H $R^3$: 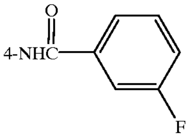

Crystalline form: White powder
Recrystallization solvent: Methanol
Melting Point: 206.5–207.5° C.
Form: Free
Example 28
Structure

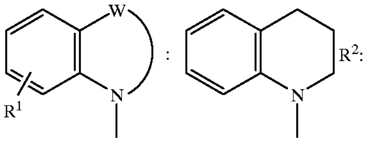

$R^2$: H $R^3$: 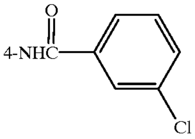

Crystalline form: White powder
Recrystallization solvent: Methanol

TABLE 1-continued

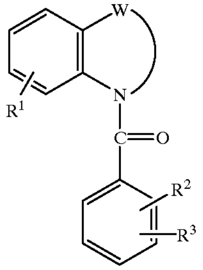

Melting Point: 210–211° C.
Form: Free
Example 29
Structure

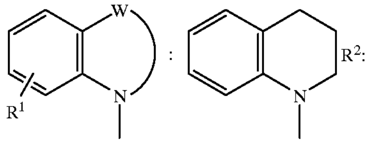 $R^2$: H

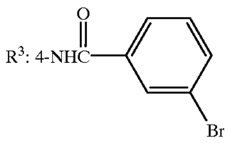

Crystalline form: White powder
Recrystallization solvent: Methanol
Melting Point: 210.5–211.5° C.
Form: Free
Example 30
Structure

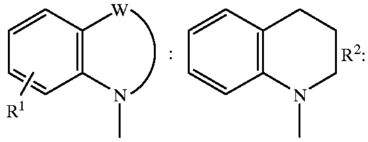 $R^2$: H

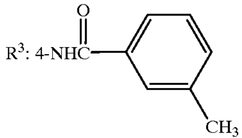

Crystalline form: White powder
Recrystallization solvent: Methanol
Melting Point: 178–179° C.
Form: Free
Example 31
Structure

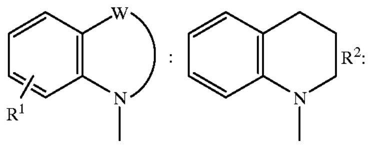 $R^2$: H

TABLE 1-continued

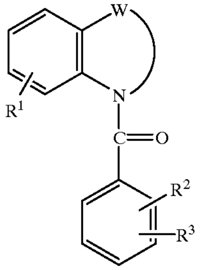

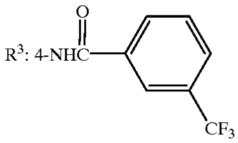

Crystalline form: White powder
Recrystallization solvent: Methanol
Melting Point: 192–193° C.
Form: Free
Example 32
Structure

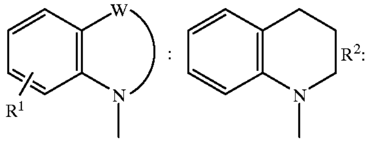 $R^2$: H

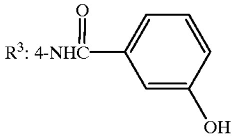

Crystalline form: White powder
Recrystallization solvent: Methanol
Melting Point: 217–218° C.
Form: Free
Example 33
Structure

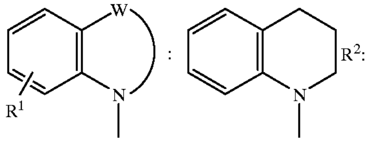 $R^2$: H

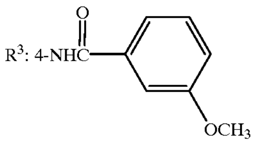

Crystalline form: White powder
Recrystallization solvent: Methanol
Melting Point: 143–144° C.
Form: Free TABLE 1-continued

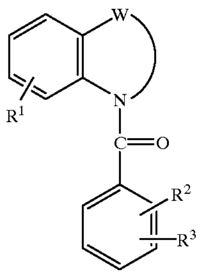

Example 34
Structure

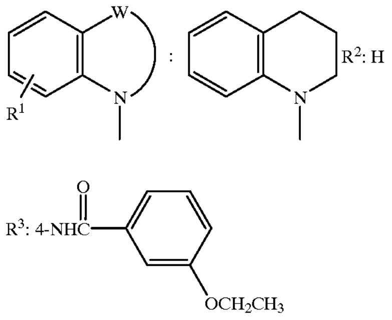

Crystalline form: White powder
Recrystallization solvent: Methanol
Melting Point: 170.5–171.5° C.
Form: Free
Example 35
Structure

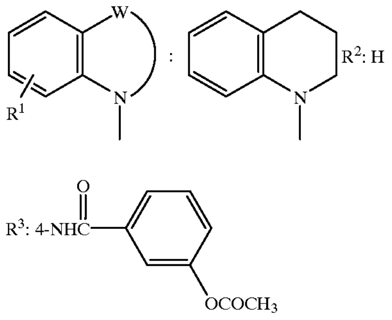

Crystalline form: White powder
Recrystallization solvent: Methanol
Melting Point: 169.5–170.5° C.
Form: Free
Example 36
Structure

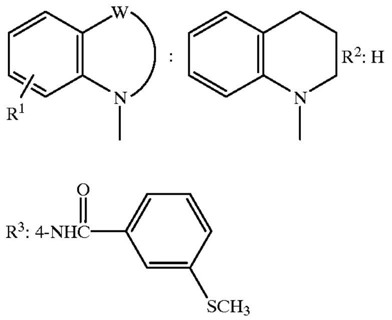

TABLE 1-continued

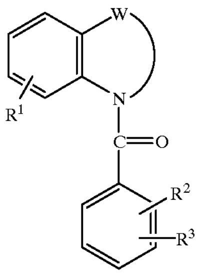

Crystalline form: White powder
Recrystallization solvent: Methanol
Melting Point: 174.5–175.5° C.
Form: Free
Example 37
Structure

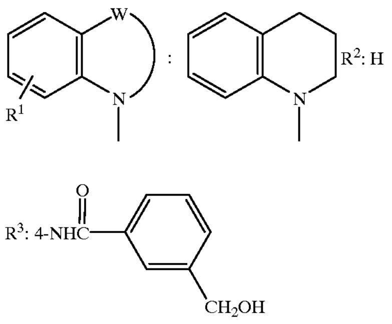

Crystalline form: White powder
Recrystallization solvent: Methanol
Melting Point: 148.5–149.5° C.
Form: Free
Example 38
Structure

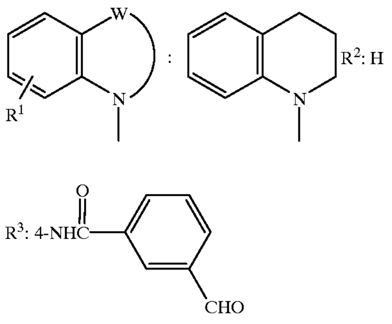

Crystalline form: White powder
Recrystallization solvent: Methanol
Melting Point: 165–166° C.
Form: Free
Example 39
Structure

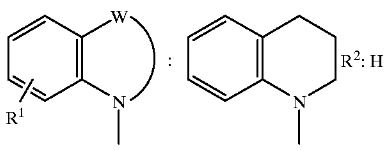

TABLE 1-continued

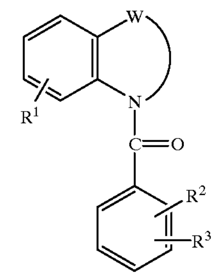

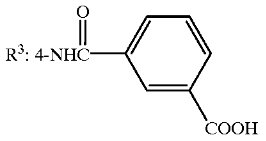

Crystalline form: White powder
Recrystallization solvent: Methanol
Melting Point: 243–244° C.
Form: Free
Example 40
Structure

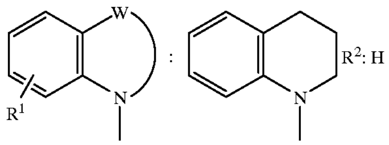

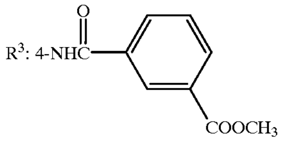

Crystalline form: White powder
Recrystallization solvent: Methanol
Melting Point: 199–200° C.
Form: Free
Example 41
Structure

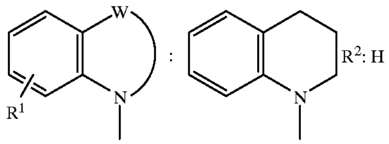

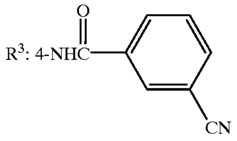

Crystalline form: White powder
Recrystallization solvent: Methanol
Melting Point: 232.5–233.5° C.
Form: Free TABLE 1-continued

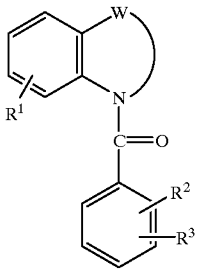

Example 42
Structure

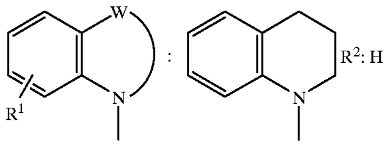

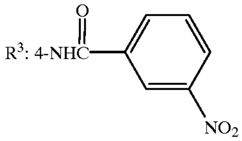

Crystalline form: White powder
Recrystallization solvent: Methanol
Melting Point: 178.5–179.5° C.
Form: Free
Example 43
Structure

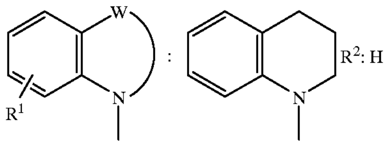

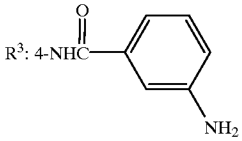

Crystalline form: White powder
Recrystallization solvent: Methanol
Melting point: 205.5–206.5° C.
Form: Free
Example 44
Structure

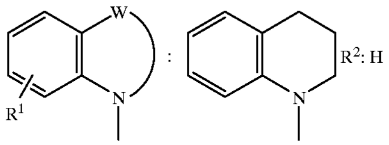

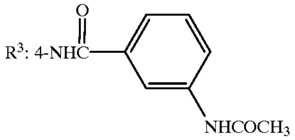

TABLE 1-continued

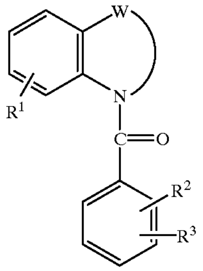

Crystalline form: White powder
Recrystallization solvent: Methanol
Melting Point: 234–235° C.
Form: Free
Example 45
Structure

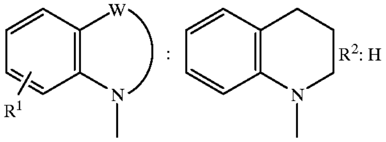

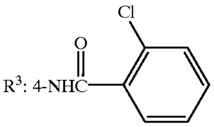

Crystalline form: White powder
Recrystallization solvent: Methanol
Melting Point: 225–226° C.
Form: Free
Example 46
Structure

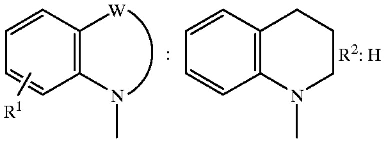

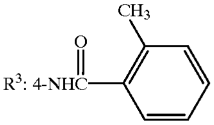

Crystalline form: White powder
Recrystallization solvent: Methanol
Melting Point: 224–225° C.
Form: Free
Example 47
Structure

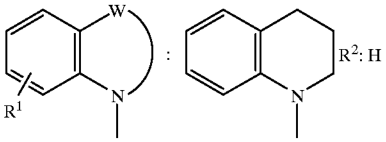

TABLE 1-continued

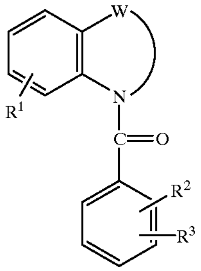

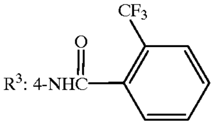

Crystalline form: White powder
Recrystallization solvent: Methanol
Melting Point: 236–237° C.
Form: Free
Example 48
Structure

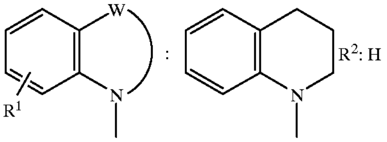

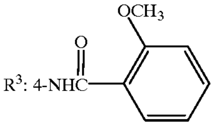

Crystalline form: Yellow powder
Recrystallization solvent: Methanol
Melting Point: 175.5–176.5° C.
Form: Free
Example 49
Structure

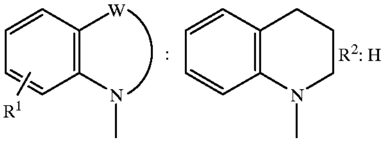

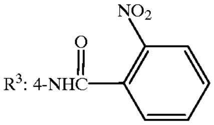

Crystalline form: White powder
Recrystallization solvent: Methanol
Melting Point: 231–232° C.
Form: Free TABLE 1-continued

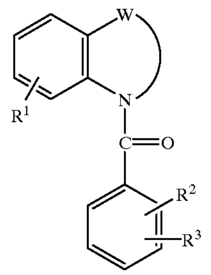

Example 50
Structure

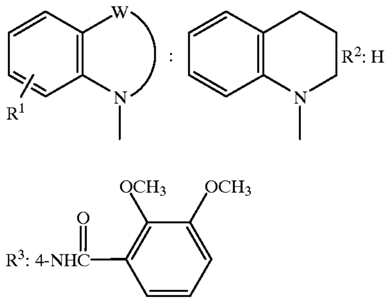

Crystalline form: Yellow powder
Recrystallization solvent: Methanol
Melting Point: 204–205° C.
Form: Free
Example 51
Structure

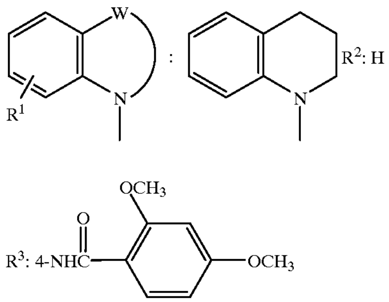

Crystalline form: White powder
Recrystallization solvent: Methanol
Melting point: 190–191° C.
Form: Free
Example 52
Structure

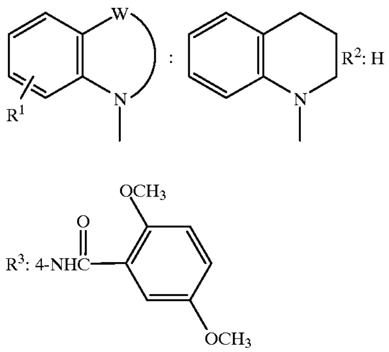

TABLE 1-continued

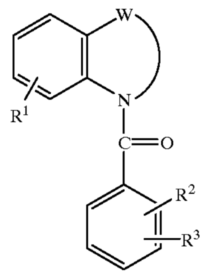

Crystalline form: White powder
Recrystallization solvent: Methanol
Melting point: 156–157° C.
Form: Free
Example 53
Structure

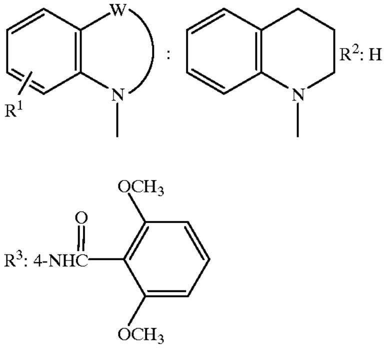

Crystalline form: White powder
Recrystallization solvent: Methanol
Melting Point: 200–201° C.
Form: Free
Example 54
Structure

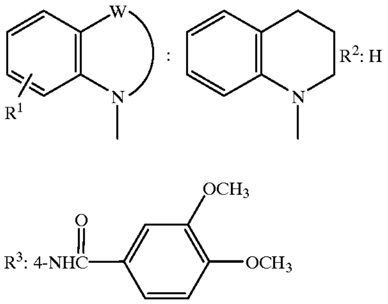

Crystalline form: White powder
Recrystallization solvent: Methanol
Melting Point: 206–207° C.
Form: Free
Example 55
Structure

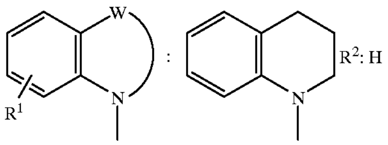

TABLE 1-continued

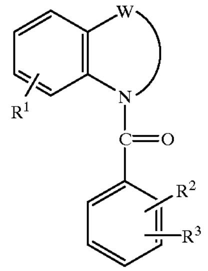

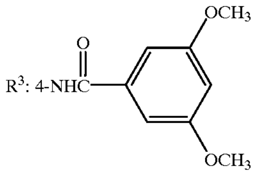

Crystalline form: Colorless amorphous
NMR analysis: 3)
Form: Free
Example 56
Structure

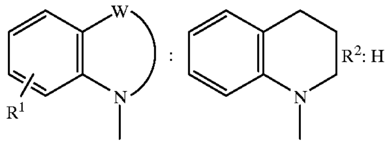

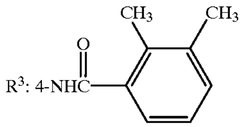

Crystalline form: White powder
Recrystallization solvent: Methanol
Melting point: 215.5–216.5° C.
Form: Free
Example 57
Structure

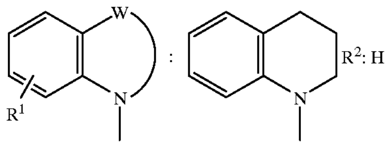

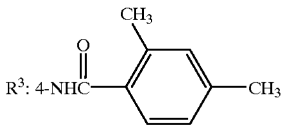

Crystalline form: White powder
Recrystallization solvent: Methanol
Melting Point: 189–190° C.
Form: Free TABLE 1-continued

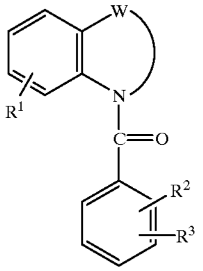

Example 58
Structure

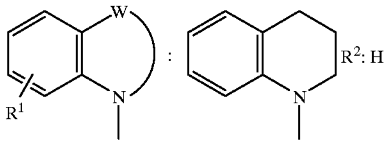

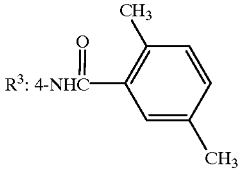

Crystalline form: White powder
Recrystallization solvent: Methanol
Melting Point: 203.5–204.5° C.
Form: Free
Example 59
Structure

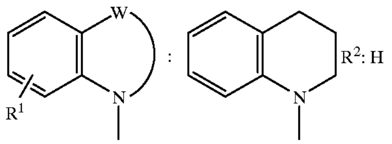

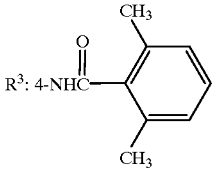

Crystalline form: Yellow powder
Recrystallization solvent: Methanol
Melting Point: 254.5–255.5° C.
Form: Free
Example 60
Structure

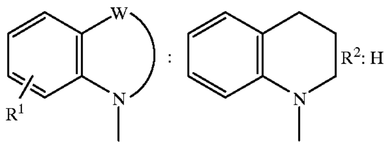

TABLE 1-continued

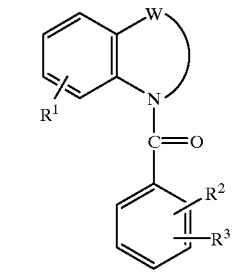

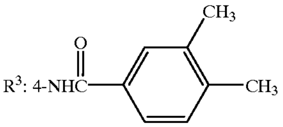

Crystalline form: Brown powder
Recrystallization solvent: Methanol
Melting Point: 182.5–183.5° C.
Form: Free
Example 61
Structure

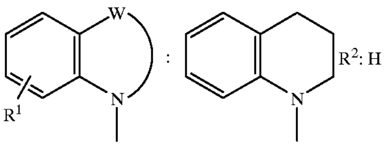

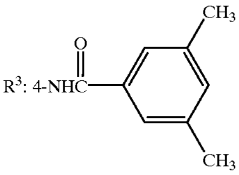

Crystalline form: Colorless amorphous
NMR analysis: 4)
Form: Free
Example 62
Structure

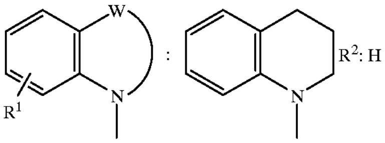

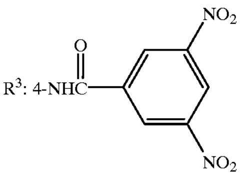

Crystalline form: White powder
Recrystallization solvent: Methanol
Melting Point: 263–264° C.
Form: Free TABLE 1-continued

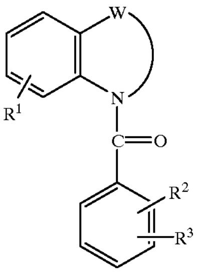

Example 63
Structure

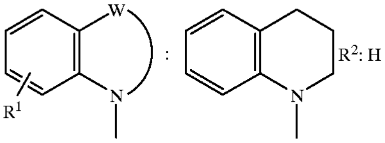

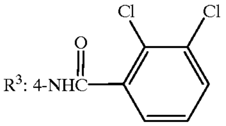

Crystalline form: White powder
Recrystallization solvent: Dichloromethane/ethanol
Melting Point: 217–218° C.
Form: Free
Example 64
Structure

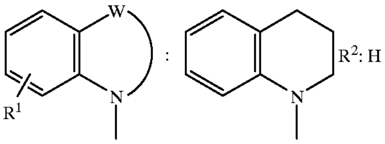

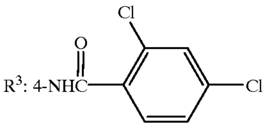

Crystalline form: White powder
Recrystallization solvent: Dichloromethane/ethanol
Melting Point: 183–184° C.
Form: Free
Example 65
Structure

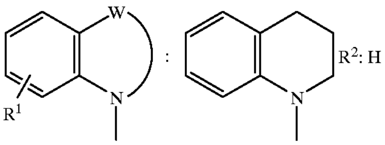

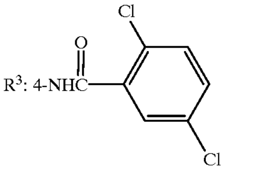

TABLE 1-continued

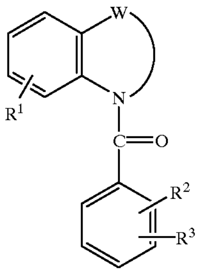

Crystalline form: Yellow powder
Recrystallization solvent: Dichloromethane/ethanol
Melting Point: 207.5–208.5° C.
Form: Free
Example 66
Structure

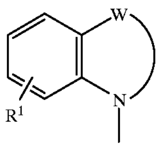 : 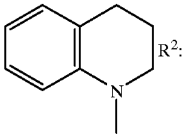 $R^2$: H

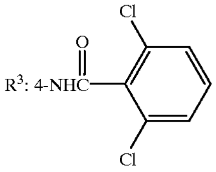

Crystalline form: Yellow powder
Recrystallization solvent: Dichloromethane/ethanol
Melting Point: 251–252° C.
Form: Free
Example 67
Structure

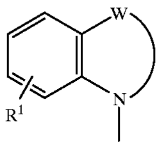 : 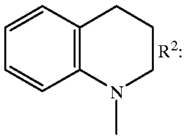 $R^2$: H

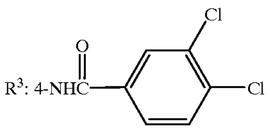

Crystalline form: White powder
Recrystallization solvent: Dichloromethane/ethanol
Melting Point: 208.5–209.5° C.
Form: Free
Example 68
Structure

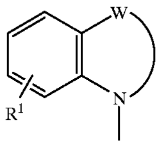 : 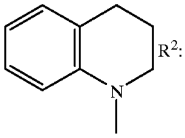 $R^2$: H

TABLE 1-continued

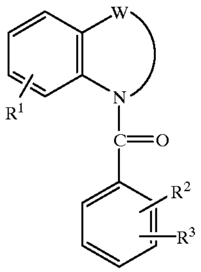

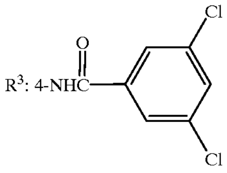

Crystalline form: White powder
Recrystallization solvent: Dichloromethane/ethanol
Melting Point: 231–232° C.
Form: Free
Example 69
Structure

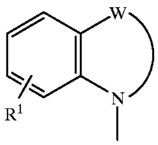 : 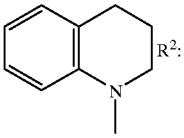 $R^2$: H

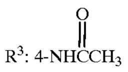

Crystalline form: Colorless amorphous
NMR analysis: 5)
Form: Free
Example 70
Structure

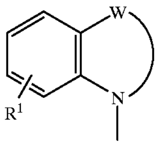 : 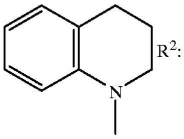 $R^2$: H

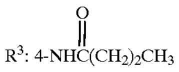

Crystalline form: White powder
Recrystallization solvent: Methanol
Melting Point: 134–135° C.
Form: Free
Example 71
Structure

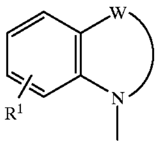 : 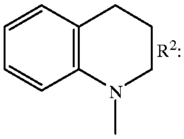 $R^2$: H

TABLE 1-continued

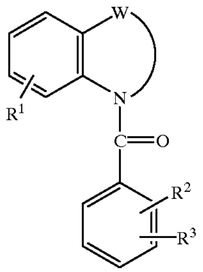

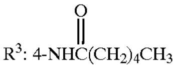

Crystalline form: Yellow powder
Recrystallization solvent: Methanol
Melting point: 115–116° C.
Form: Free
Example 72
Structure

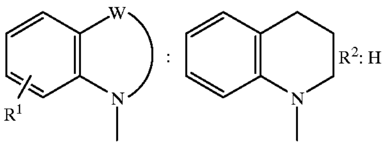

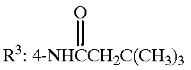

Crystalline form: White powder
Recrystallization solvent: Methanol
Melting Point: 178.5–179.5° C.
Form: Free
Example 73
Structure

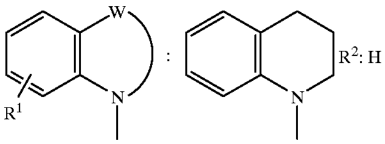

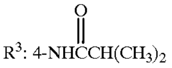

Crystalline form: White powder
Recrystallization solvent: Methanol
Melting Point: 182.5–183.5° C.
Form: Free
Example 74
Structure

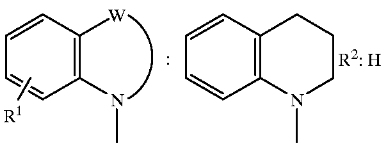

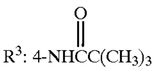

Crystalline form: White powder

TABLE 1-continued

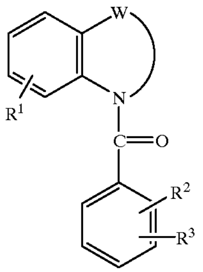

Recrystallization solvent: Methanol
Melting Point: 164–165° C.
Form: Free
Example 75
Structure

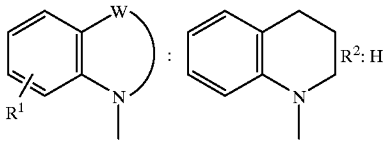

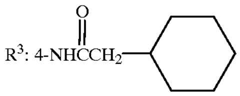

Crystalline form: Colorless amorphous
NMR analysis: 6)
Form: Free
Example 76
Structure

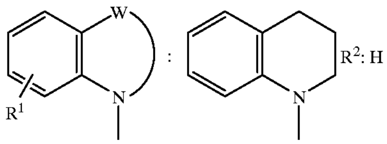

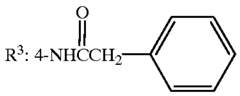

Crystalline form: Yellow amorphous
NMR analysis: 7)
Form: Free
Example 77
Structure

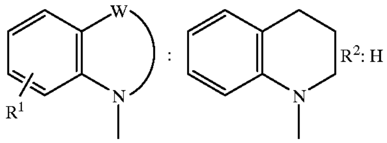

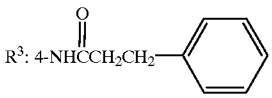

Crystalline form: White powder
Recrystallization solvent: Methanol
Melting Point: 155–156° C.
Form: Free TABLE 1-continued

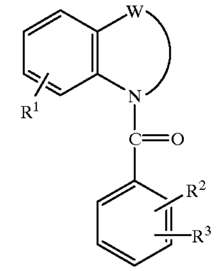

Example 78
Structure

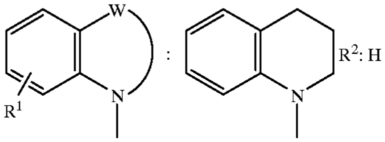

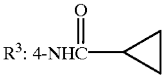

Crystalline form: White powder
Recrystallization solvent: Methanol
Melting Point: 182.5–183. 5° C.
Form: Free
Example 79
Structure

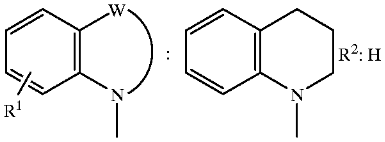

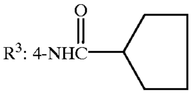

Crystalline form: White powder
Recrystallization solvent: Methanol
Melting Point: 164.5–165.5° C.
Form: Free
Example 80
Structure

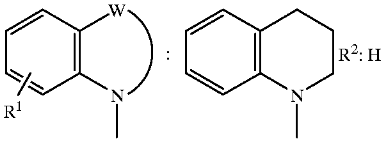

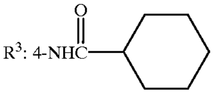

Crystalline form: White powder
Recrystallization solvent: Methanol
Melting Point: 165–167° C.
Form: Free TABLE 1-continued

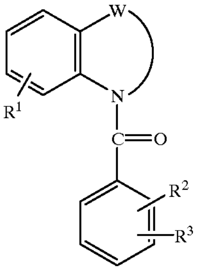

Example 81
Structure

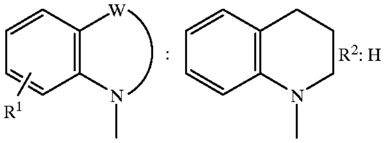

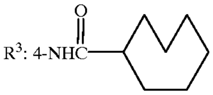

Crystalline form: White powder
Recrystallization solvent: Methanol
Melting Point: 124–125° C.
Form: Free
Example 82
Structure

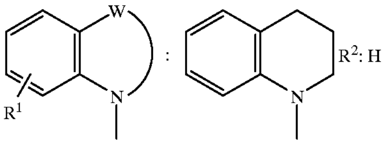

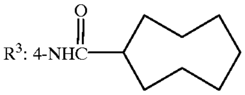

Crystalline form: White powder
Recrystallization solvent: Methanol
Melting Point: 140.5–141.5° C.
Form: Free
Example 83
Structure

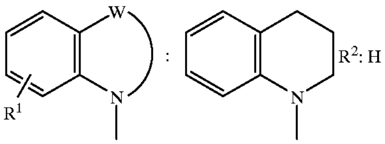

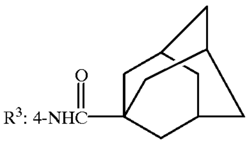

Crystalline form: Colorless amorphous
NMR analysis: 8)
Form: Free

TABLE 1-continued

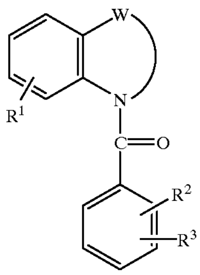

Example 84
Structure

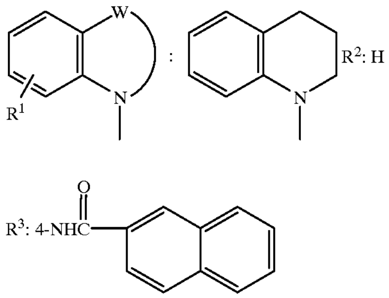

Crystalline form: White powder
Recrystallization solvent: Methanol
Melting Point: 211–212° C.
Form: Free
Example 85
Structure

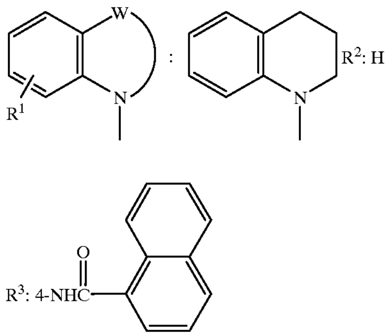

Crystalline form: White powder
Recrystallization solvent: Methanol
Melting Point: 178–179° C.
Form: Free
Example 86
Structure

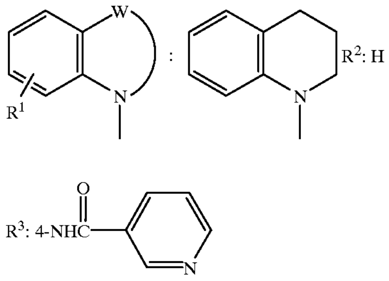

Crystalline form: White powder

TABLE 1-continued

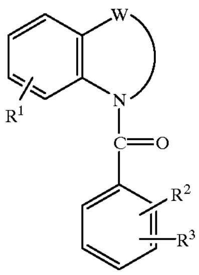

Recrystallization solvent: Methanol
Melting Point: 212.5–213.5° C.
Form: Free
Example 87
Structure

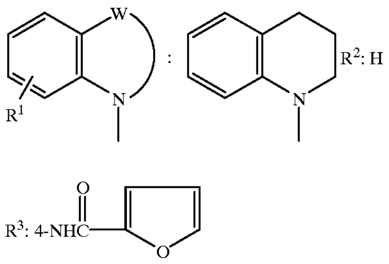

Crystalline form: White powder
Recrystallization solvent: Methanol
Melting Point: 193–194° C.
Form: Free
Example 88
Structure

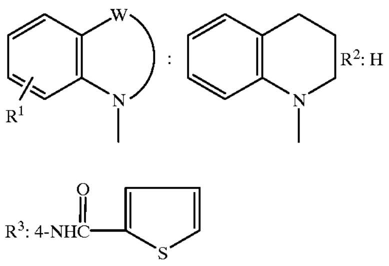

Crystalline form: White powder
Recrystallization solvent: Methanol
Melting Point: 203–204° C.
Form: Free
Example 89
Structure

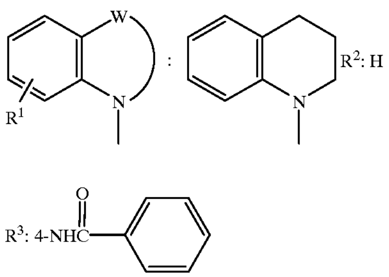

Crystalline form: Colorless amorphous
NMR analysis: 9)
Form: Free

TABLE 1-continued

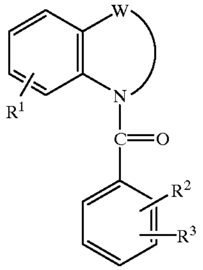

Example 90
Structure

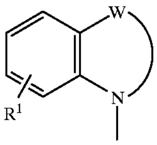 : 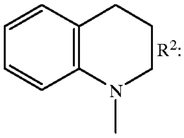 $R^2$: H $R^3$: 4-NHC 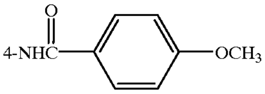

Crystalline form: Colorless amorphous
NMR analysis: 10)
Form: Free
Example 91
Structure

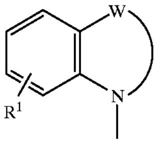 : 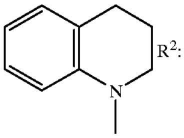 $R^2$: H $R^3$: 4-NHC 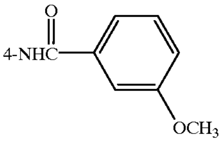

Crystalline form: Colorless amorphous
NMR analysis: 11)
Form: Free
Example 92
Structure

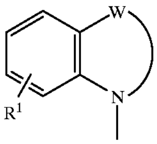 : 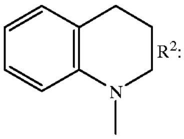 $R^2$: H $R^3$: 4-NHC 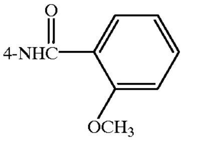

Crystalline form: White powder
Recrystallization solvent: Methanol
Melting Point: 156.5–157.5° C.

TABLE 1-continued

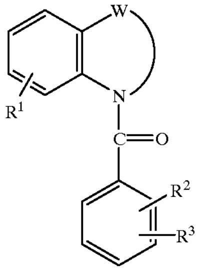

Form: Free
Example 93
Structure

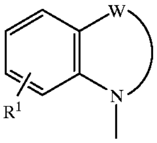 : 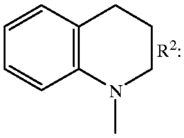 $R^2$: H $R^3$: 4-NHC 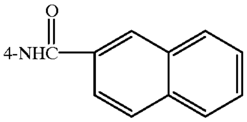

Crystalline form: Colorless amorphous
NMR analysis: 12)
Form: Free
Example 94
Structure

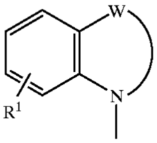 : 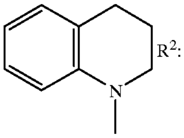 $R^2$: H $R^3$: 4-NHC 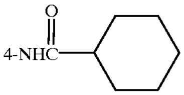

Crystalline form: White powder
Recrystallization solvent: Methanol
Melting Point: 203.5–204.5° C.
Form: Free
Example 95
Structure

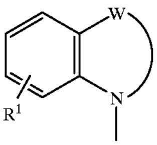 : 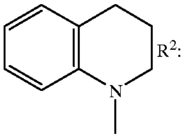 $R^2$: H $R^3$: 4-NHC 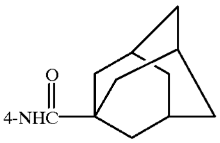

Crystalline form: Colorless amorphous
NMR analysis: 13)

TABLE 1-continued

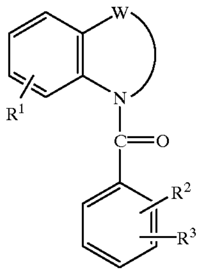

Form: Free

Example 96

Structure

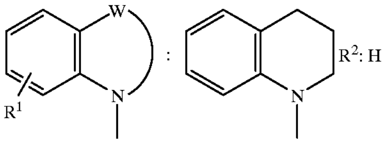

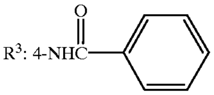

Crystalline form: Yellow powder
Recrystallization solvent: Methanol
Melting Point: 126–127° C.
Form: Free Example 97

Structure

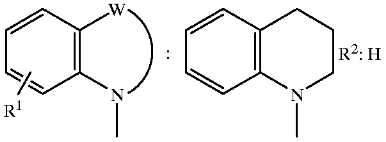

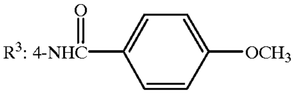

Crystalline form: White powder
Recrystallization solvent: Methanol
Melting Point: 158.5–159.5° C.
Form: Free Example 98

Structure

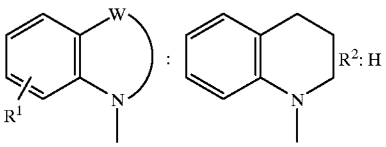

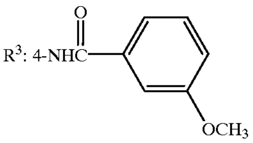

Crystalline form: White powder
Recrystallization solvent: Methanol

TABLE 1-continued

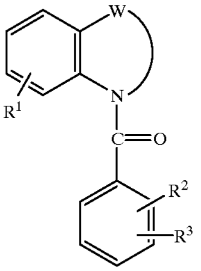

Melting Point: 129–130° C.
Form: Free

Example 99

Structure

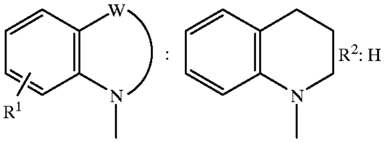

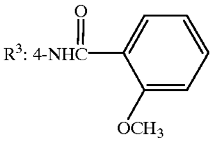

Crystalline form: White powder
Recrystallization solvent: Methanol
Melting Point: 131.5–132.5° C.
Form: Free Example 100

Structure

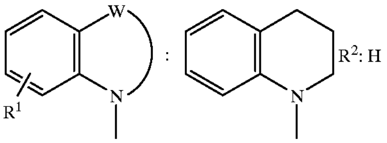

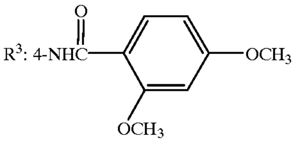

Crystalline form: White powder
Recrystallization solvent: Methanol
Melting Point: 140–141° C.
Form: Free Example 101

Structure

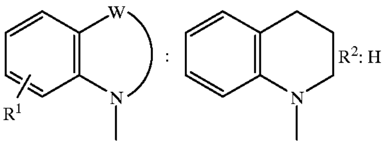

TABLE 1-continued

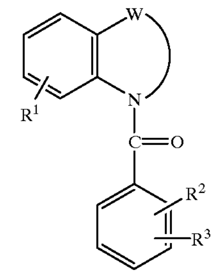

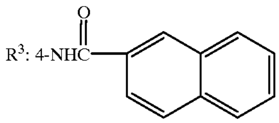

Crystalline form: White powder
Recrystallization solvent: Methanol
Meltinq Point: 138.5–139.5° C.
Form: Free
Example 102
Structure

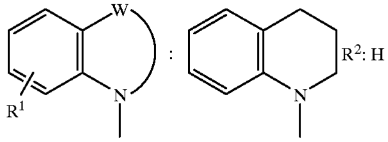

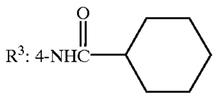

Crystalline form: White powder
Recrystallization solvent: Methanol
Melting Point: 128–129° C.
Form: Free
Example 103
Structure

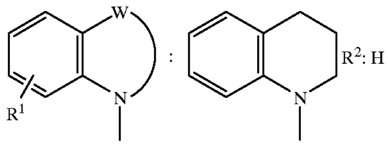

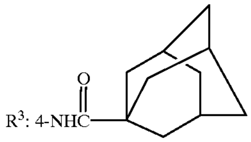

Crystalline form: White powder
Recrystaliization solvent: Methanol
Melting Point: 160–161° C.
Form: Free TABLE 1-continued

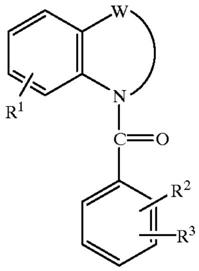

Example 104
Structure

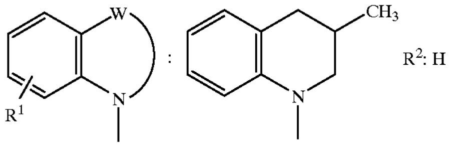

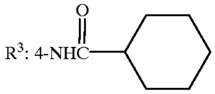

Crystalline form: White powder
Recrystaliization solvent: Methanol
Melting Point: 175–176° C.
Form: Free
Example 105
Structure

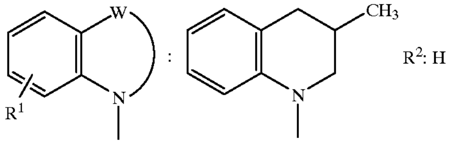

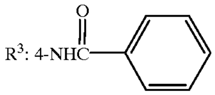

Crystalline form: White powder
Recrystallization solvent: Methanol
Melting Point: 197–198° C.
Form: Free
Example 106
Structure

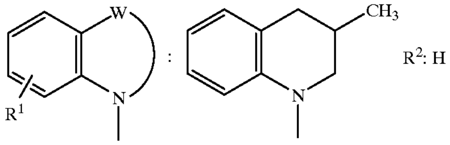

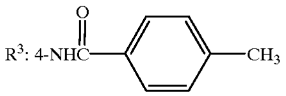

Crystalline form: White powder
Recrystallization solvent: Methanol
Melting Point: 204–2O0° C.
Form: Free TABLE 1-continued

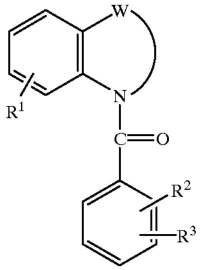

Example 107
Structure

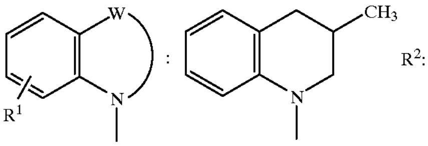

$R^2$: H $R^3$: 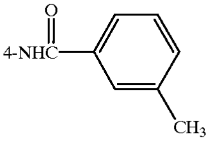

Crystalline form: White powder
Recrystallization solvent: Methanol
Melting Point: 174–175° C.
Form: Free
Example 108
Structure

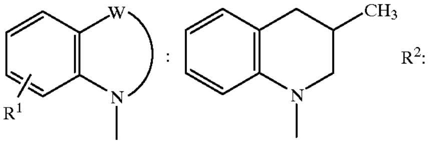

$R^2$: H $R^3$: 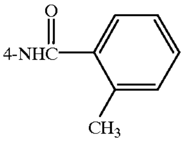

Crystalline form: Yellow powder
Recrystallization solvent: Methanol
Melting Point: 202–203° C.
Form: Free
Example 109
Structure

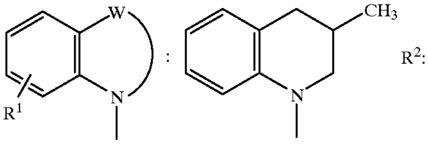

$R^2$: H $R^3$: 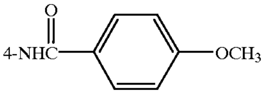

Crystalline form: White powder

TABLE 1-continued

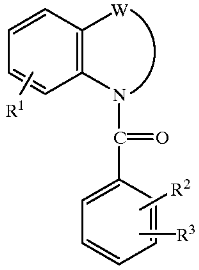

Recrystallization solvent: Methanol
Melting Point: 203–204° C.
Form: Free
Example 110
Structure

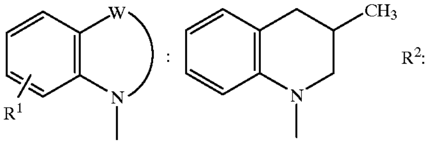

$R^2$: H $R^3$: 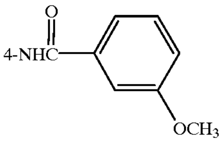

Crystalline form: White powder
Recrystallization solvent: Methanol
Melting Point: 170.5–171.5° C.
Form: Free
Example 111
Structure

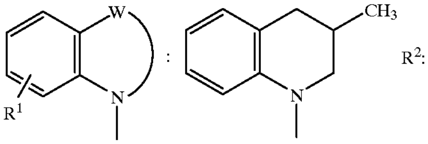

$R^2$: H $R^3$: 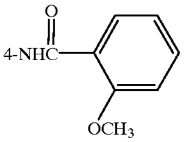

Crystalline form: White powder
Recrystallization solvent: Methanol
Melting Point: 149–150° C.
Form: Free
Example 112
Structure

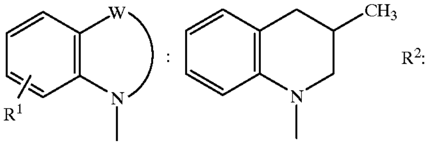

$R^2$: H

TABLE 1-continued

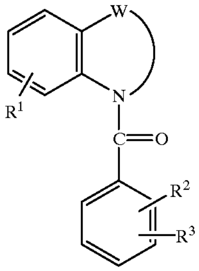

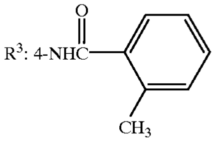

Crystalline form: White powder
Recrystallization solvent: Methanol
Melting Point: 185–186° C.
Form: Free
Example 113
Structure

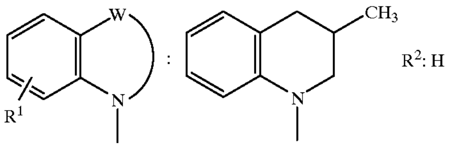

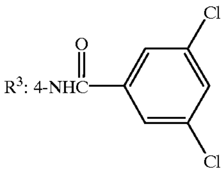

Crystalline form: White powder
Recrystallization solvent: Dichloromethane/ethanoi
Melting Point: 225–226° C.
Form: Free
Example 114
Structure

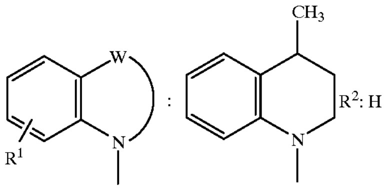

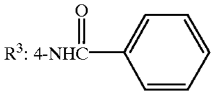

Crystalline form: White powder
Recrystallization solvent: Methanol
Melting Point: 234–235° C.
Form: Free TABLE 1-continued

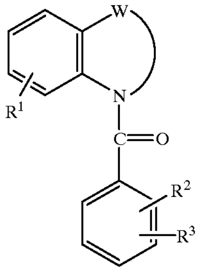

Example 115
Structure

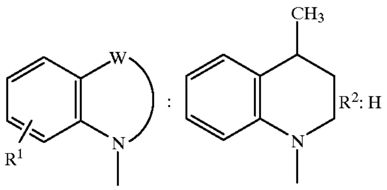

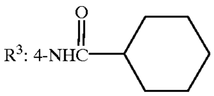

Crystalline form: White powder
Recrystallization solvent: Methanol
Melting Point: 149.5–150.5° C.
Form: Free
Example 116
Structure

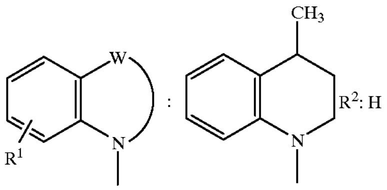

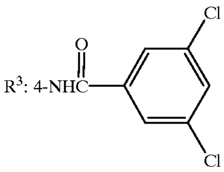

Crystalline form: White powder
Recrystallization solvent: Dichloromethane/ethanol
Melting Point: 197–198° C.
Form: Free
Example 117
Structure

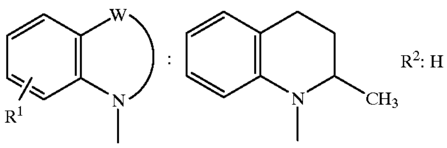

TABLE 1-continued

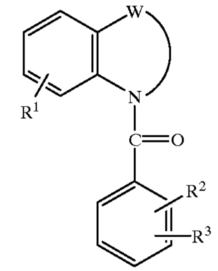

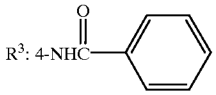

Crystalline form: White powder
Recrystallization solvent: Methanol
Melting Point: 204–205° C.
Form: Free
Example 118
Structure

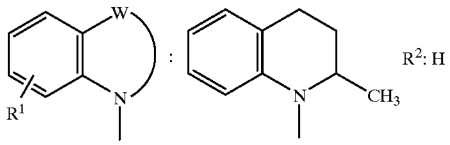

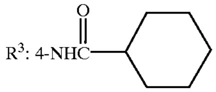

Crystalline form: White powder
Recrystallization solvent: Methanol
Melting Point: 224.5–225.5° C.
Form: Free
Example 119
Structure

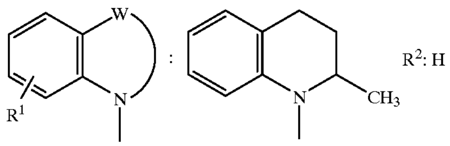

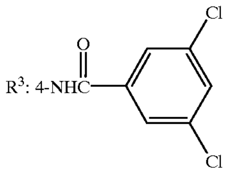

Crystalline form: White powder
Recrystallization solvent: Dichloromethane/ethanol
Melting Point: 189.5–190.5° C.
Form: Free TABLE 1-continued

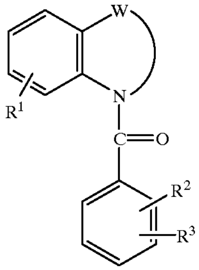

Example 120
Structure

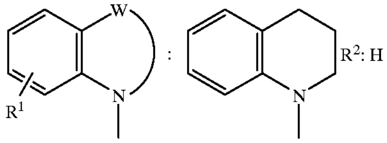

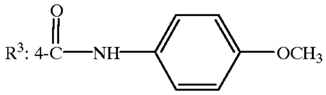

Crystalline form: White powder
Recrystallization solvent: Methanol
Melting Point: 221.5–222.5° C.
Form: Free
Example 121
Structure

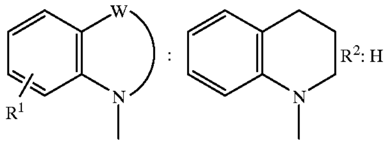

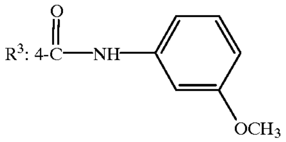

Crystalline form: Colorless needles
Recrystallization solvent: Methanol
Melting Point: 154–155° C.
Form: Free
Example 122
Structure

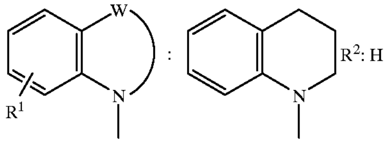

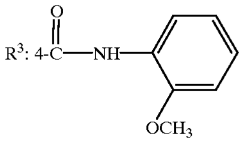

Crystalline form: White powder

TABLE 1-continued

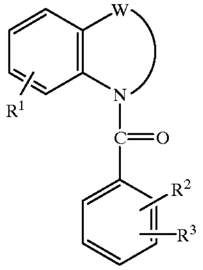

Recrystallization solvent: Methanol
Melting Point: 165–166° C.
Form: Free
Example 123
Structure

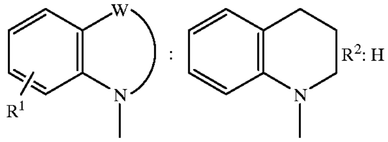

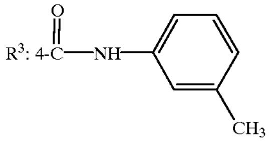

Crystalline form: Colorless needles
Recrystallization solvent: Methanol
Melting Point: 141–142° C.
Form: Free
Example 124
Structure

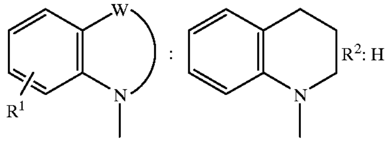

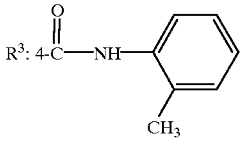

Crystalline form: White powder
Recrystallization solvent: Methanol
Melting Point: 165.5–166.5° C.
Form: Free
Example 125
Structure

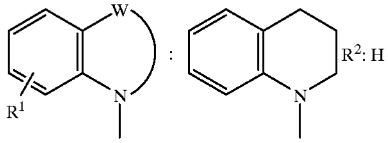

TABLE 1-continued

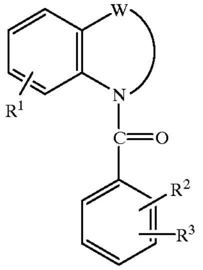

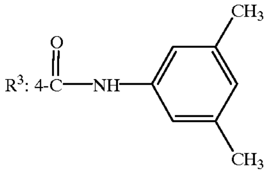

Crystalline form: Colorless needles
Recrystallization solvent: Methanol
Melting point: 164–165° C.
Form: Free
Example 126
Structure

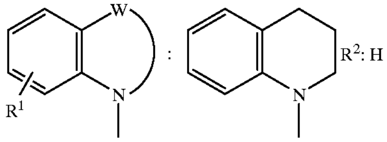

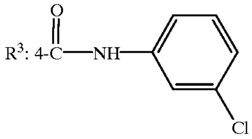

Crystalline form: White powder
Recrystallization solvent: Methanol
Melting Point: 203.5–204.5° C.
Form: Free
Example 127
Structure

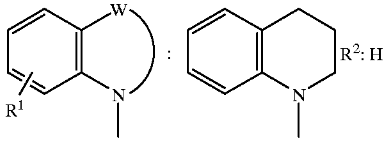

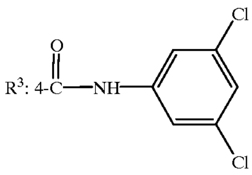

Crystalline form: White powder
Recrystallization solvent: Dichloromethane/ethanol
Melting Point: 236.5–237.5° C.
Form: Free TABLE 1-continued

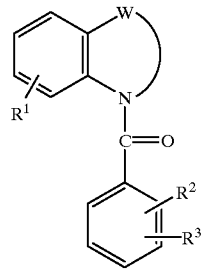

Example 128
Structure

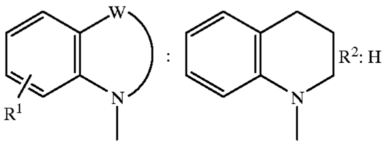

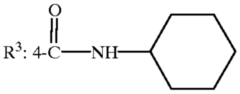

Crystalline form: White powder
Recrystallization solvent: Methanol
Melting Point: 206.5–207.5° C.
Form: Free Example 129
Structure

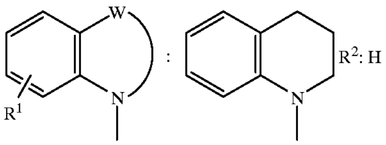

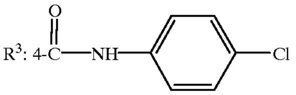

Crystalline form : White powder
Recrystallization solvent: Methanol
Melting Point: 271–272° C.
Form: Free Example 130
Structure

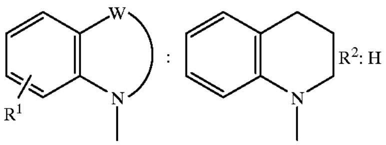

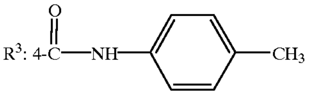

Crystalline form: White powder
Recrystallization solvent: Methanol
Meiting Point: 246–247° C.
Form: Free TABLE 1-continued

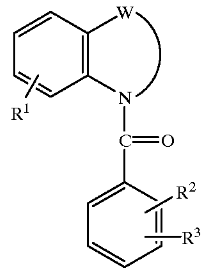

Example 131
Structure

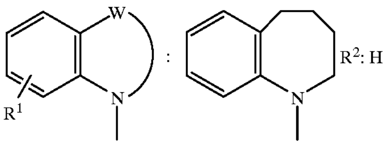

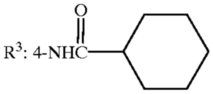

Crystalline form: White powder
Recrystallization solvent: Ethanol/diethyl ether
Melting Point: 210–211° C.
Form: Free Example 132
Structure

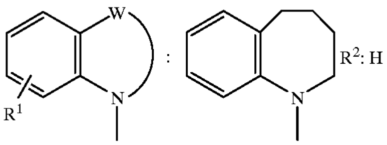

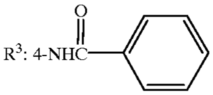

Crystalline form: White powder
Recrystallization solvent: Ethanol/diethyl ether
Melting Point: 230.5–231.5° C.
Form: Free Example 133
Structure

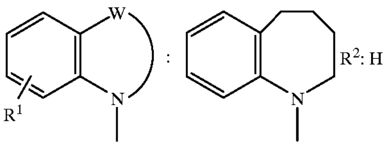

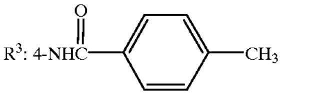

Crystalline form: White powder
Recrystallization solvent: Ethanol/diethyl ether
Melting Point: 203–204° C.
Form: Free TABLE 1-continued

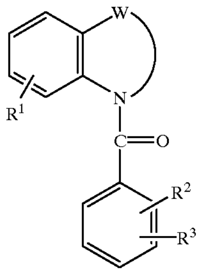

Example 134
Structure

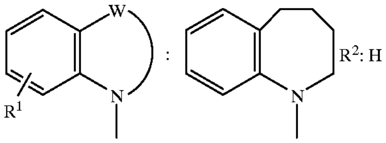

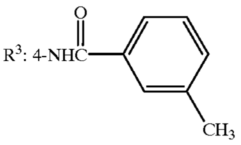

Crystalline form: White powder
Recrystallization solvent: Ethanol/diethyl ether
Melting Point: 170–171° C.
Form: Free
Example 135
Structure

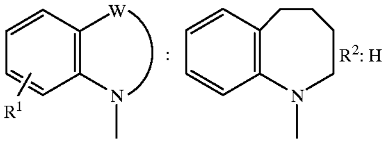

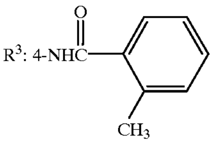

Crystalline form: White powder
Recrystallization solvent: Ethanol/diethyl ether
Melting Point: 225.5–226.5° C.
Form: Free
Example 136
Structure

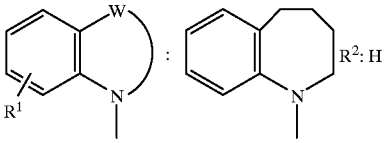

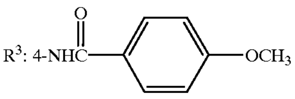

Crystalline form: White powder

TABLE 1-continued

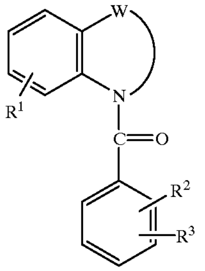

Recrystallization solvent: Ethanol/diethyl ether
Melting Point: 210.5–211.5° C.
Form: Free
Example 137
Structure

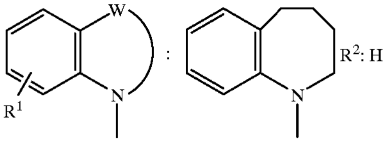

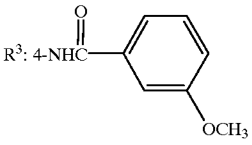

Crystalline form: White powder
Recrystallization solvent: Ethanol/diethyl ether
Melting Point: 183–184° C.
Form: Free
Example 138
Structure

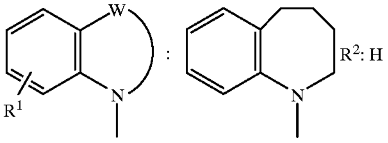

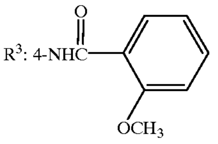

Crystalline form: White powder
Recrystallization solvent: Ethanol/diethyl ether
Melting Point: 191.5–192.5° C.
Form: Free
Example 139
Structure

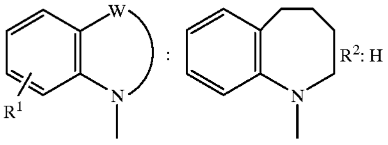

TABLE 1-continued

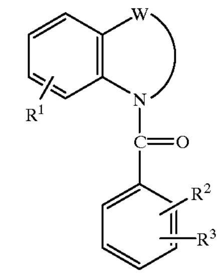

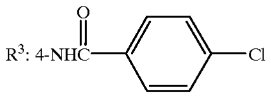

Crystalline form: White powder
Recrystallization solvent: Ethanol/diethyl ether
Melting Point: 203.5–204.5° C.
Form: Free
Example 140
Structure

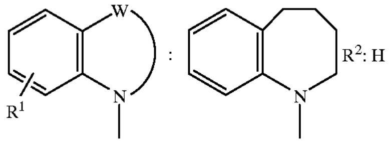

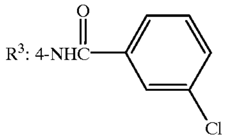

Crystalline form: White powder
Recrystallization solvent: Ethanol/diethyl ether
Melting Point: 215.5–216.5° C.
Form: Free
Example 141
Structure

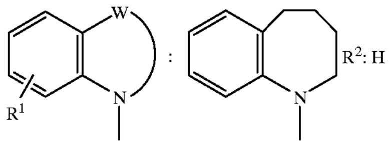

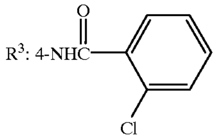

Crystalline form: White powder
Recrystallization solvent: Ethanol/diethyl ether
Melting Point: 211.5–212.5° C.
Form: Free TABLE 1-continued

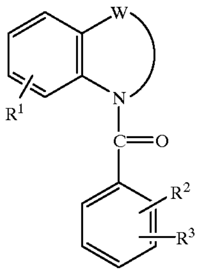

Example 142
Structure

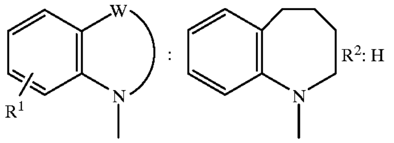

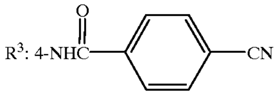

Crystalline form: White powder
Recrystallization solvent: Ethanol/diethyl ether
Melting Point: 280.5–281.5° C.
Form: Free
Example 143
Structure

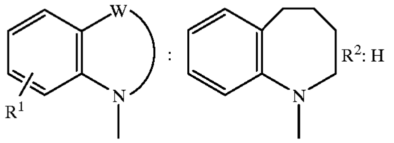

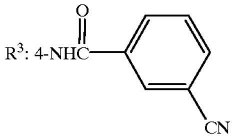

Crystalline form: White powder
Recrystallization solvent: Ethanol/diethyl ether
Melting Point: 235.5–236.5° C.
Form: Free
Example 144
Structure

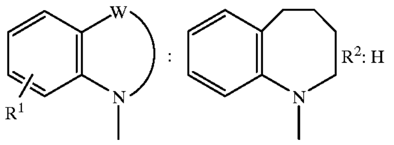

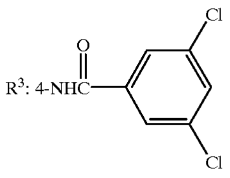

TABLE 1-continued

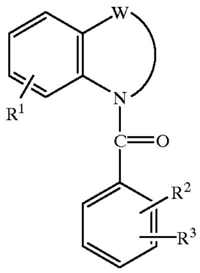

Crystalline form: White powder
Recrystallization solvent: Ethanol/dichloromethane
Melting Point: 249.5–250.5° C.
Form: Free
Example 145
Structure

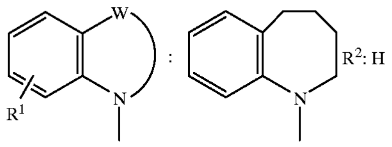

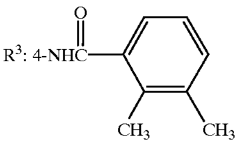

Crystalline form: White powder
Recrystallization solvent: Ethanol/diethyl ether
Melting Point: 217–218° C.
Form: Free
Example 146
Structure

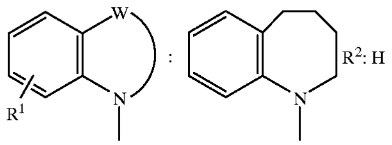

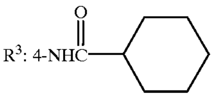

Crystalline form: White powder
Recrystallization solvent: Ethanol/diethyl ether
Melting Point: 201.5–203° C.
Form: Free
Example 147
Structure

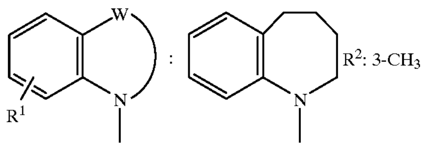

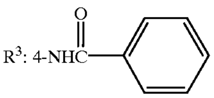

TABLE 1-continued

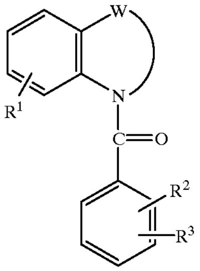

Crystalline form: White powder
Recrystallization solvent: Ethanol/diethyl ether
Melting Point: 221–222° C.
Form: Free
Example 148
Structure

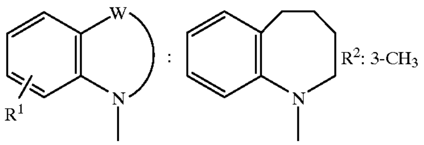

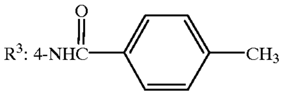

Crystalline form: White powder
Recrystallization solvent: Ethanol/diethyl ether
Melting Point: 193–194° C.
Form: Free
Example 149
Structure

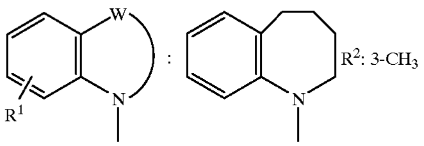

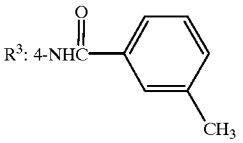

Crystalline form: White powder
Recrystallization solvent: Ethanol/diethyl ether
Melting Point: 176–177° C.
Form: Free
Example 150
Structure

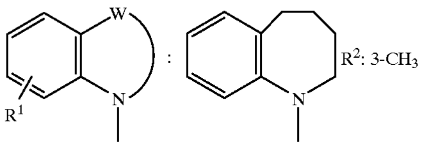

TABLE 1-continued

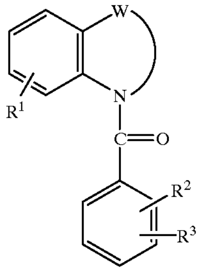

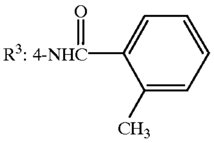

Crystalline form: White powder
Recrystallization solvent: Ethanol/diethyl ether
Melting Point: 188–189.5° C.
Form: Free
Example 151
Structure

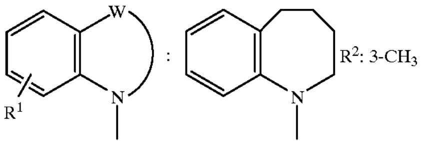

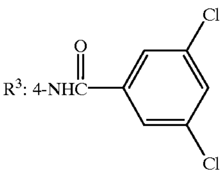

Crystalline form: White powder
Recrystallization solvent: Ethanol/diethyl ether
Melting Point: 227–228° C.
Form: Free
Example 152
Structure

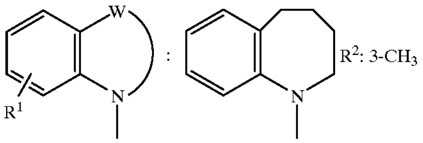

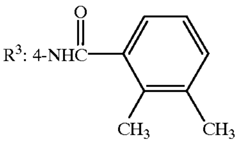

Crystalline form: White powder
Recrystallization solvent: Ethanol/diethyl ether
Melting Point: 186–187° C.
Form: Free TABLE 1-continued

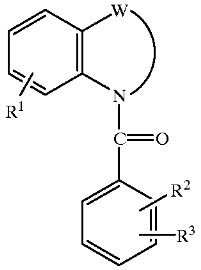

Example 153
Structure

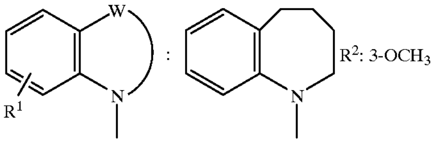

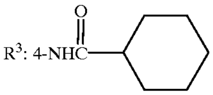

Crystalline form: White powder
Recrystallization solvent: Ethanol/diethyl ether
Melting Point: 135–136° C.
Form: Free
Example 154
Structure

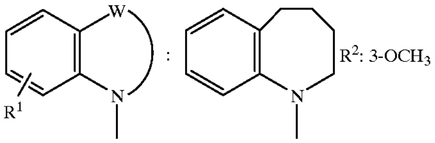

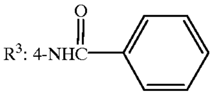

Crystalline form: White powder
Recrystallization solvent: Ethanol/diethyl ether
Melting Point: 173–174° C.
Form: Free
Example 155
Structure

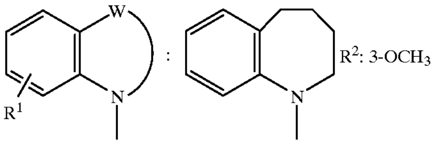

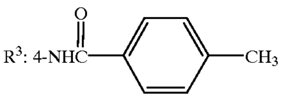

Crystalline form: White powder
Recrystallization solvent: Ethanol/diethyl ether
Melting Point: 174.5–175.5° C.
Form: Free TABLE 1-continued

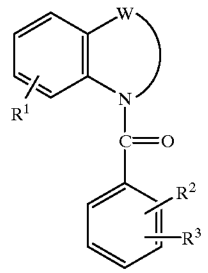

Example 156
Structure

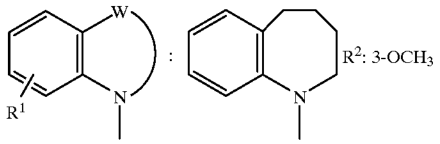

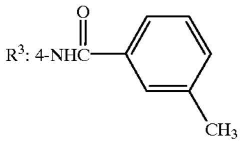

Crystalline form: White powder
Recrystallization solvent: Ethanol/diethyl ether
Melting Point: 156–157° C.
Form: Free
Example 157
Structure

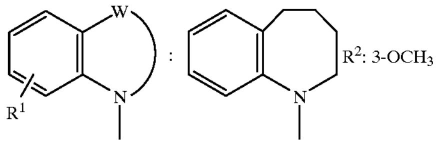

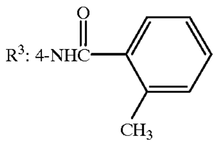

Crystalline form: White powder
Recrystallization solvent: Ethanol/diethyl ether
Melting Point: 153–154° C.
Form: Free
Example 158
Structure

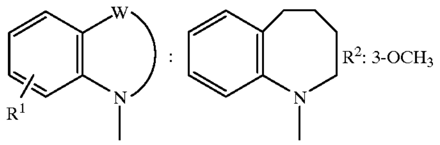

TABLE 1-continued

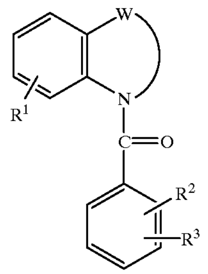

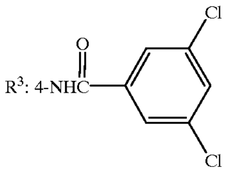

Crystalline form: White powder
Recrystallization solvent: Ethanol/diethyl ether
Melting Point: 169–170° C.
Form: Free
Example 159
Structure

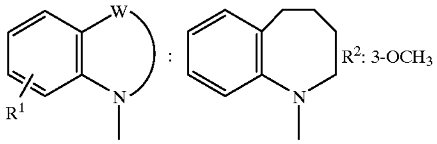

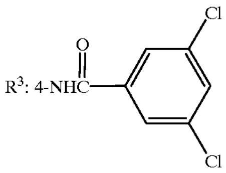

Crystalline form: White powder
Recrystallization solvent: Ethanol/diethyl ether
Melting Point: 185–186° C.
Form: Free
Example 160
Structure

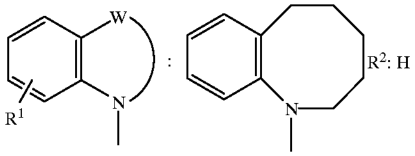

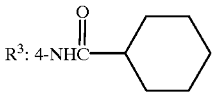

Crystalline form: White powder
Recrystallization solvent: Ethanol/diethyl ether
Melting Point: 213–214° C.
Form: Free TABLE 1-continued

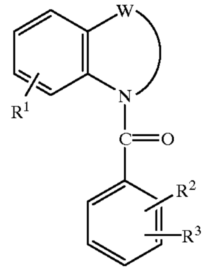

Example 161
Structure

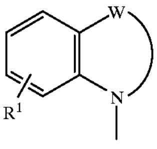 : 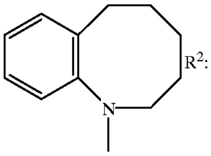 $R^2$: H $R^3$: 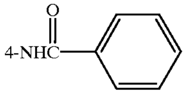

Crystalline form: White powder
Recrystallization solvent: Ethanol/diethyl ether
Melting Point: 240–241° C.
Form: Free
Example 162
Structure

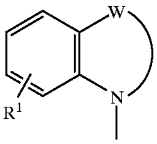 : 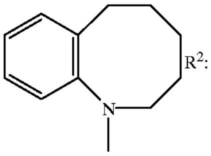 $R^2$: H $R^3$: 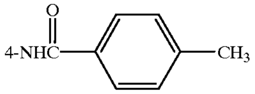

Crystalline form: White powder
Recrystallization solvent: Ethanol/diethyl ether
Melting Point: 225–226° C.
Form: Free
Example 163
Structure

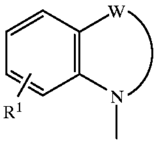 : 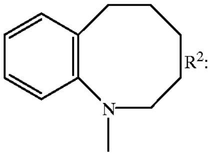 $R^2$: H $R^3$: 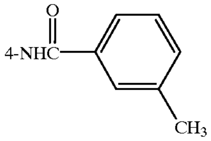

Crystalline form: White powder

TABLE 1-continued

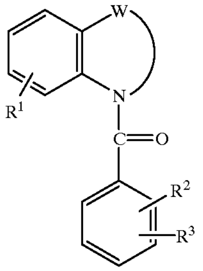

Recrystallization solvent: Ethanol/diethyl ether
Melting Point: 209.5–210.5° C.
Form: Free
Example 164
Structure

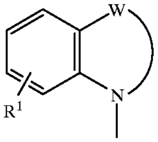 : 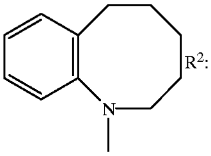 $R^2$: H $R^3$: 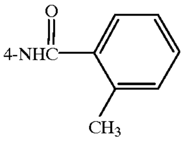

Crystalline form: White powder
Recrystallization solvent: Ethanol/diethyl ether
Melting Point: 198–199° C.
Form: Free
Example 165
Structure

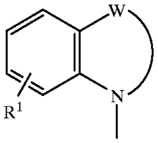 : 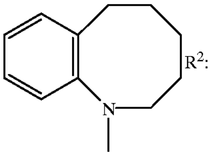 $R^2$: H $R^3$: 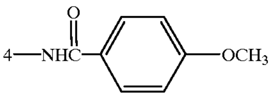

Crystalline form: White powder
Recrystallization solvent: Ethanol/diethyl ether
Melting Point: 214.5–215.5° C.
Form: Free
Example 166
Structure

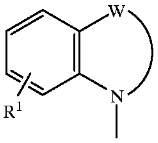 : 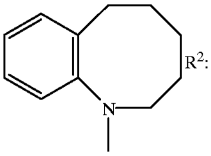 $R^2$: H

TABLE 1-continued

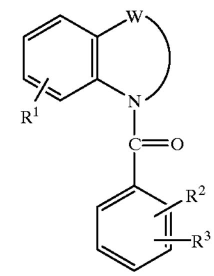

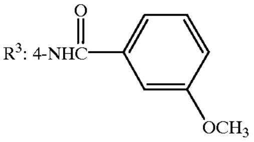

Crystalline form: White powder
Recrystallization solvent: Ethanol/diethyl ether
Melting Point: 196.5–197.5° C.
Form: Free
Example 167
Structure

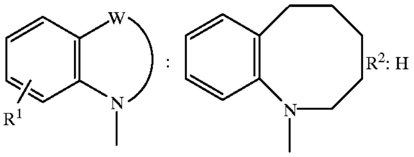

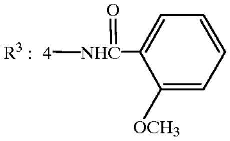

Crystalline form: White powder
Recrystallization solvent: Ethanol/diethyl ether
Melting Point: 194–195° C.
Form: Free
Example 168
Structure

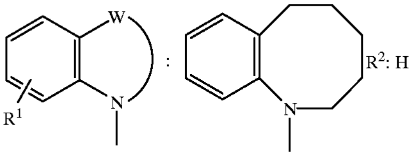

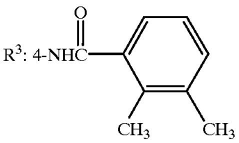

Crystalline form: White powder
Recrystallization solvent: Ethanol/diethyl ether
Melting Point: 191–192° C.
Form: Free TABLE 1-continued

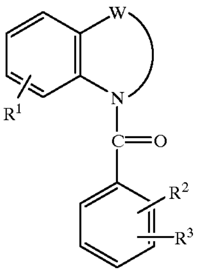

Example 169
Structure

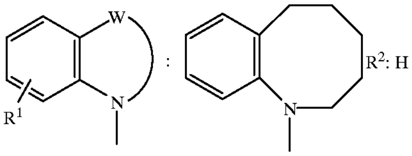

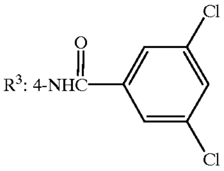

Crystalline form: White powder
Recrystallization solvent: Dichloromethane/ethanol
Melting Point: 227–228° C.
Form: Free
Example 170
Structure

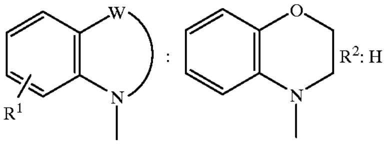

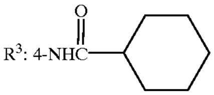

Crystalline form: White powder
Recrystallization solvent: Dichloromethane/diethyl ether
Melting Point: 182–183° C.
Form: Free
Example 171
Structure

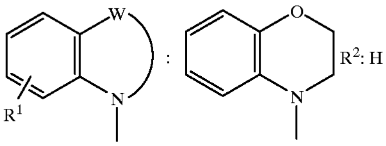

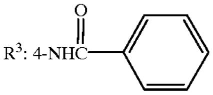

Crystalline form: White powder

TABLE 1-continued

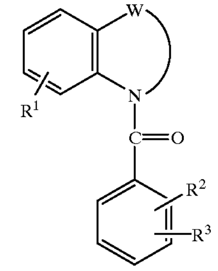

Recrystallization solvent: Dichloromethane/diethyl ether
Melting Point: 222–223° C.
Form: Free
Example 172
Structure

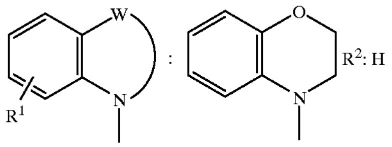

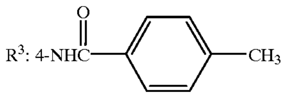

Crystalline form: White powder
Recrystallization solvent: Dichloromethane/diethyl ether
Melting Point: 204–205° C.
Form: Free
Example 173
Structure

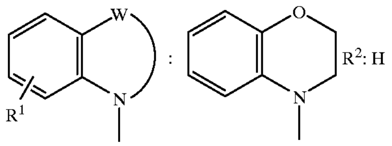

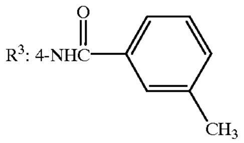

Crystalline form: White powder
Recrystallization solvent: Dichloromethane/diethyl ether
Melting Point: 194–195° C.
Form: Free
Example 174
Structure

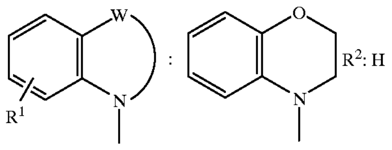

TABLE 1-continued

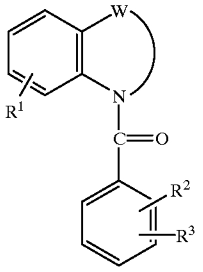

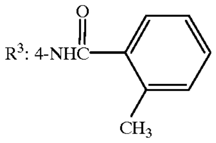

Crystalline form: White powder
Recrystallization solvent: Dichloromethane/diethyl ether
Melting Point: 213–214° C.
Form: Free
Example 175
Structure

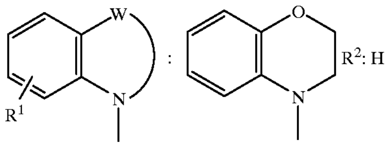

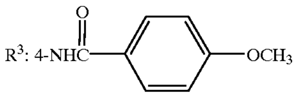

Crystalline form: White powder
Recrystallization solvent: Dichloromethane/diethyl ether
Melting Point: 201–202° C.
Form: Free
Example 176
Structure

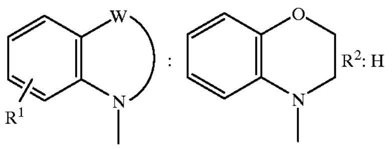

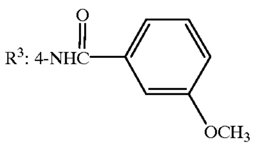

Crystalline form: Colorless needles
Recrystallization solvent: Dichloromethane/diethyl ether
Melting Point: 173–174° C.
Form: Free TABLE 1-continued

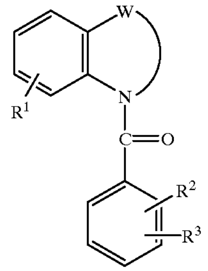

Example 177
Structure

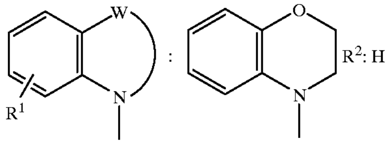

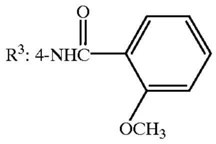

Crystalline form: White powder
Recrystallization solvent: Dichloromethane/diethyl ether
Melting Point: 150.5–151.5° C.
Form: Free
Example 178
Structure

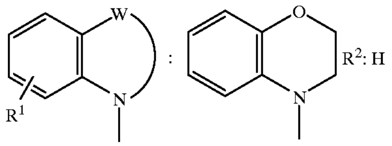

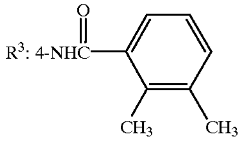

Crystalline form: White powder
Recrystallization solvent: Dichloromethane/diethyl ether
Melting Point: 207.5–208.5° C.
Form: Free
Example 179
Structure

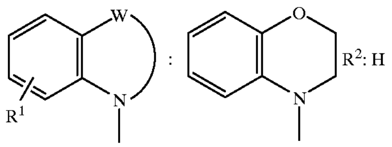

TABLE 1-continued

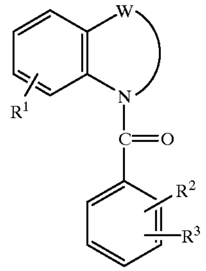

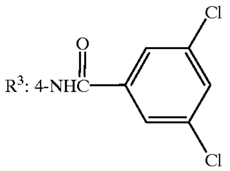

Crystalline form: White powder
Recrystallization solvent: Dichloromethane/diethyl ether
Melting Point: 256.5–257.5° C.
Form: Free
Example 180
Structure

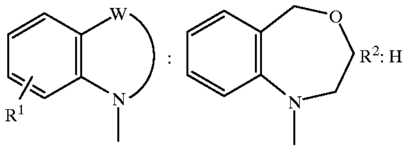

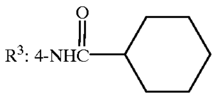

Crystalline form: White powder
Recrystallization solvent: Ethanol/diethyl ether
Melting Point: 199.5–200.5° C.
Form: Free
Example 181
Structure

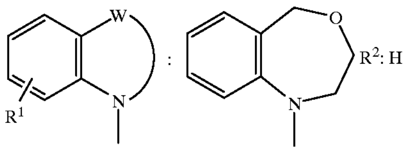

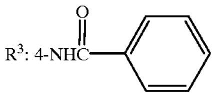

Crystalline form: White powder
Recrystallization solvent: Ethanol/diethyl ether
Melting Point: 211–212° C.
Form: Free TABLE 1-continued

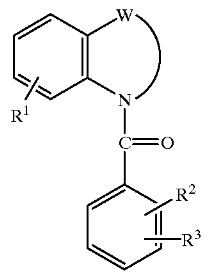

Example 182

Structure

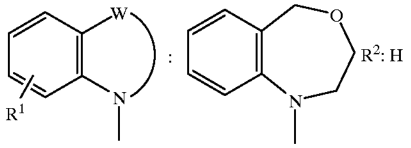

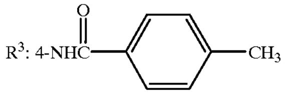

Crystalline form: White powder

Recrystallization solvent: Ethanol/diethyl ether

Melting Point: 189.5–190.5° C.

Form: Free

Example 183

Structure

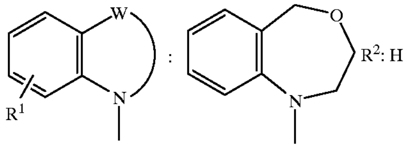

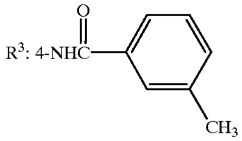

Crystalline form: White powder

Recrystallization solvent: Ethanol/diethyl ether

Melting Point: 176.5–177.5° C.

Form: Free

TABLE 1-continued

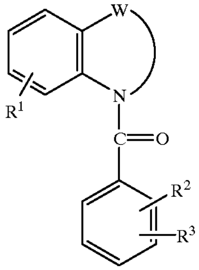

Example 184

Structure

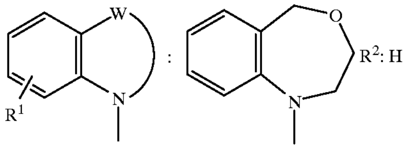

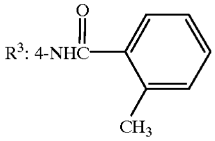

Crystalline form: Yellow powder

Recrystallization solvent: Ethanol/diethyl ether

Melting Point: 202–203° C.

Form: Free

Example 185

Structure

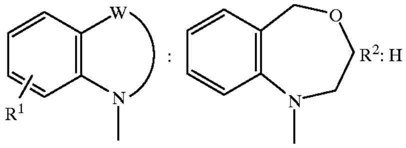

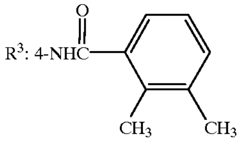

Crystalline form: White powder

Recrystallization solvent: Ethanol/diethyl ether

Melting Point: 219–220° C.

Form: Free

Example 186

Structure

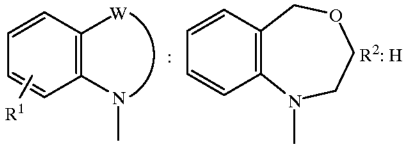

TABLE 1-continued

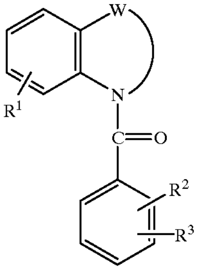

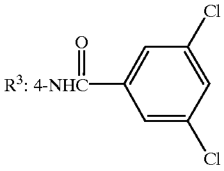

Crystalline form: White powder
Recrystallization solvent: Ethanol/diethyl ether
Melting Point: 272–273° C.
Form: Free Example 187

Structure

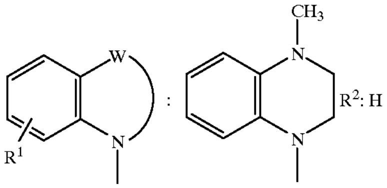

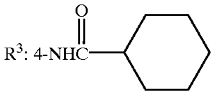

Crystalline form: Yellow powder
Recrystallization solvent: Ethanol/diethyl ether
Melting Point: 146–147° C.
Form: Free Example 188

Structure

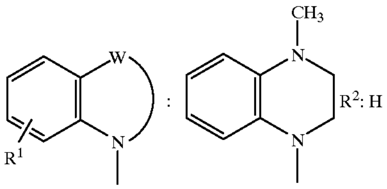

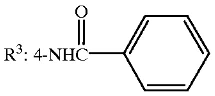

Crystalline form: Yellow powder
Recrystallization solvent: Ethanol/diethyl ether
Melting Point: 229.5–230.5° C.
Form: Free TABLE 1-continued

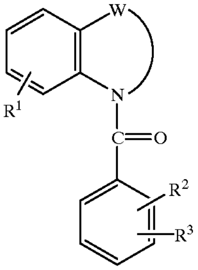

Example 189

Structure

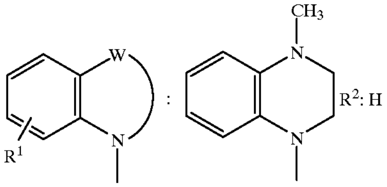

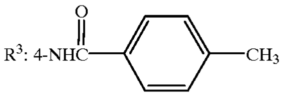

Crystalline form: Yellow powder
Recrystallization solvent: Ethanol/diethyl ether
Melting Point: 119.5–120.5° C.
Form: Free Example 190

Structure

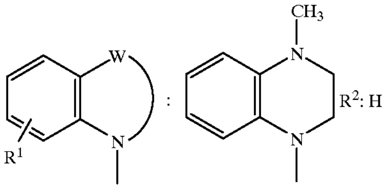

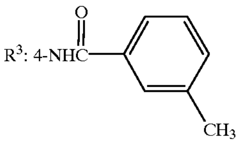

Crystalline form: Yelllow powder
Recrystallization solvent: Ethanol/diethyl ether
Melting Point: 189–190° C.
Form: Free TABLE 1-continued

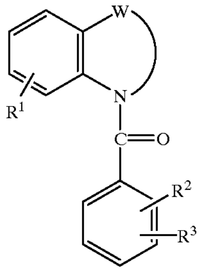

Example 191
Structure

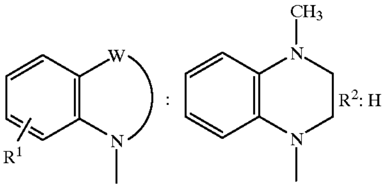

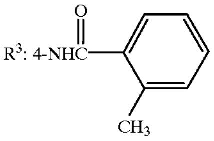

Crystalline form: Yellow powder
Recrystallization solvent: Ethanol/diethyl ether
Melting Point: 207–208° C.
Form: Free
Example 192
Structure

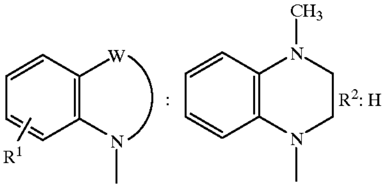

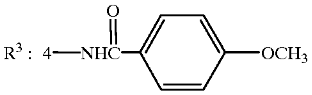

Crystalline form: Yellow powder
Recrystallization solvent: Ethanol/diethyl ether
Melting Point: 196.5–197.5° C.
Form: Free
Example 193
Structure

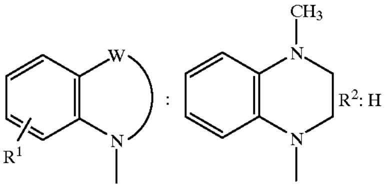

TABLE 1-continued

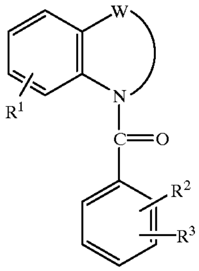

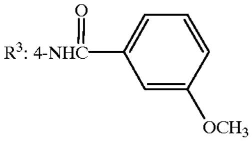

Crystalline form: Yellow powder
Recrystallization solvent: Ethanol/diethyl ether
Melting Point: 182–183° C.
Form: Free
Example 194
Structure

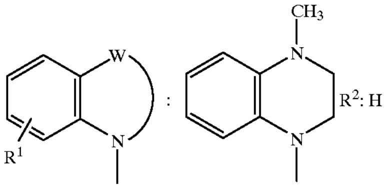

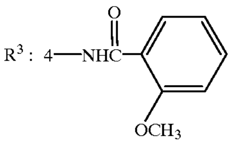

Crystalline form: Yellow powder
Recrystallization solvent: Ethanol/diethyl ether
Melting Point: 172–173° C.
Form: Free
Example 195
Structure

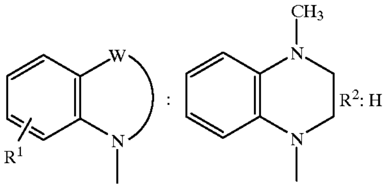

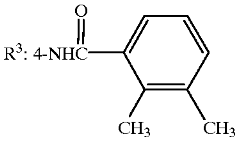

Crystalline form: Yellow powder
Recrystallization solvent: Ethanol/diethyl ether
Melting Point: 197.5–198.5° C.
Form: Free TABLE 1-continued

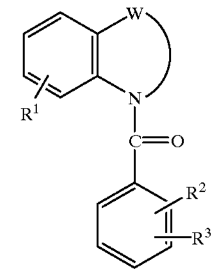

Example 196

Structure

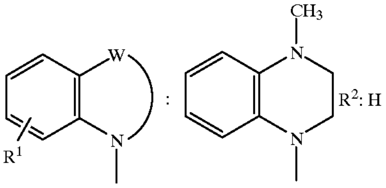

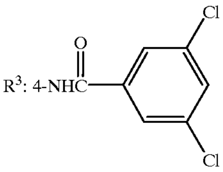

Crystalline form: Yellow powder

Recrystallization solvent: Ethanol/diethyl ether

Melting Point: 227–228° C.

Form: Free

Example 197

Structure

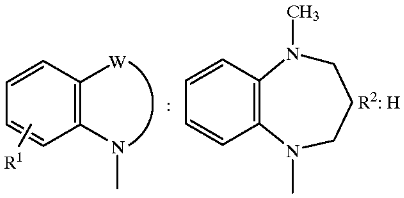

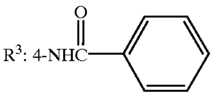

Crystalline form: White powder

Recrystallization solvent: Ethanol/diethyl ether

Melting Point: 216.5–217.5° C.

Form: Free

TABLE 1-continued

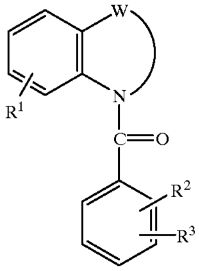

Example 198

Structure

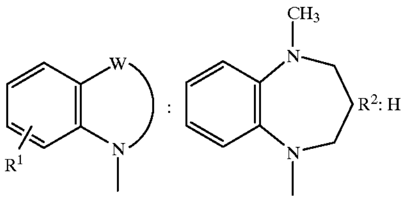

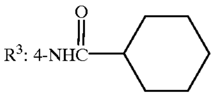

Crystalline form: White powder

Recrystallization solvent: Ethanol/diethyl ether

Melting Point: 207–208° C.

Form: Free

Example 199

Structure

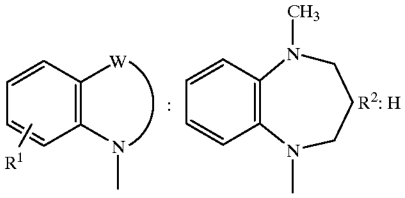

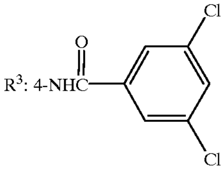

Crystalline form: White powder

Recrystallization solvent: Ethanol/diethyl ether

Melting Point: 236–237° C.

Form: Free

Example 200

Structure

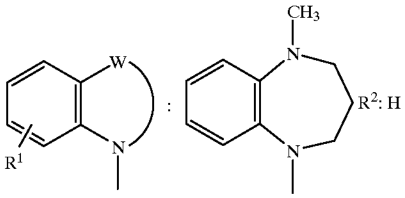

TABLE 1-continued

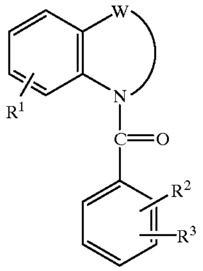

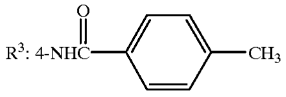

Crystalline form: White powder
Recrystallization solvent: Ethanol/diethyl ether
Melting Point: 199.5–200.5° C.
Form: Free Example 201

Structure

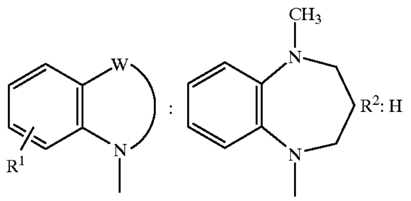

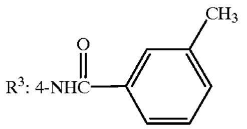

Crystalline form: White powder
Recrystallization solvent: Ethanol/diethyl ether
Melting Point: 171.5–172.5° C.
Form: Free Example 202

Structure

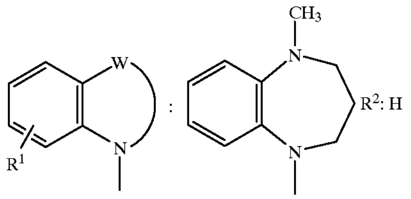

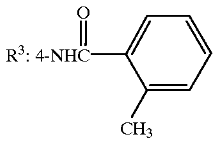

Crystalline form: White powder
Recrystallization solvent: Ethanol/diethyl ether
Melting Point: 222.5–223.5° C.
Form: Free TABLE 1-continued

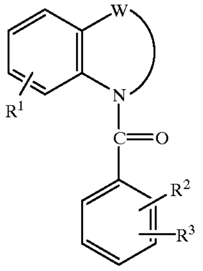

Example 203

Structure

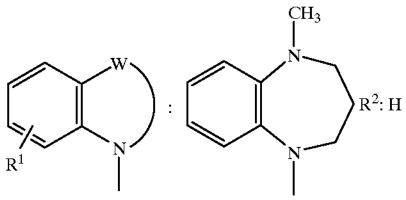

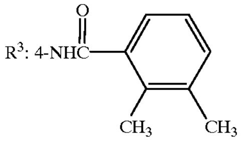

Crystalline form: White powder
Recrystallization solvent: Ethanol/diethyl ether
Melting Point: 209.5–210.5° C.
Form: Free Example 204

Structure

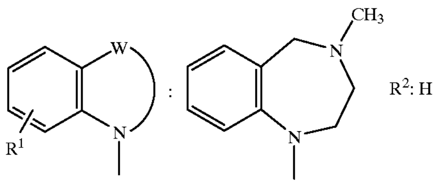

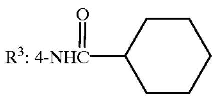

Crystalline form: White powder
Recrystallization solvent: Ethanol/water
NMR analysis: 14)
Form: Hydrochloride TABLE 1-continued

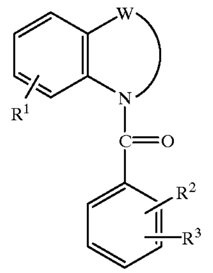

Example 205

Structure

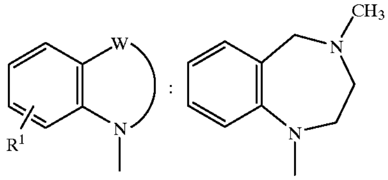

$R^2$: H

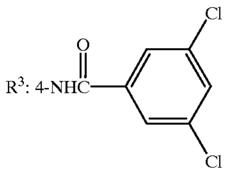

Crystalline form: White powder
Recrystallization solvent: Ethanol/water
NMR analysis: 15)
Form: Hydrochloride Example 206

Structure

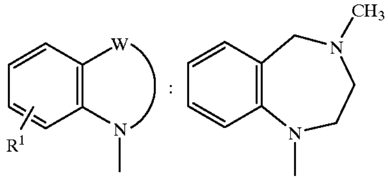

$R^2$: H

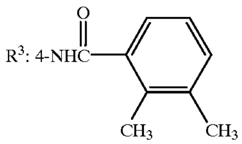

Crystalline form: White powder
Recrystallization solvent: Ethanol/water
NMR analysis: 16)
Form: Hydrochloride TABLE 1-continued

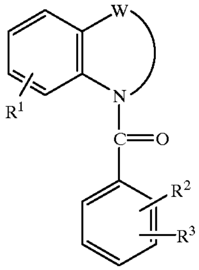

Example 207

Structure

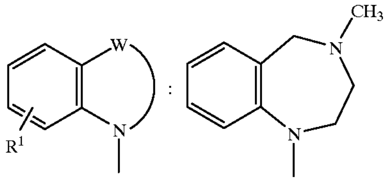

$R^2$: H

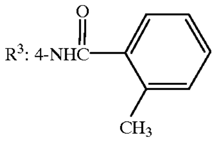

Crystalline form: White powder
Recrystallization solvent: Ethanol/water
NMR analysis: 17)
Form: Hydrochloride Example 208

Structure

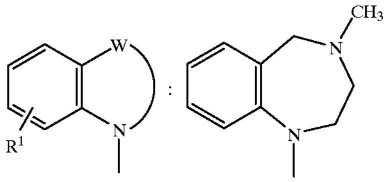

$R^2$: H

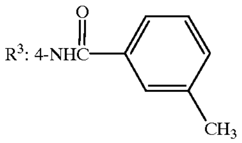

Crystalline form: White powder
Recrystallization solvent: Ethanol/water
NMR analysis: 18)
Form: Hydrochloride Example 209

Structure

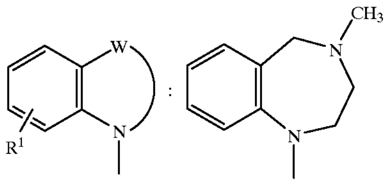

$R^2$: H

TABLE 1-continued

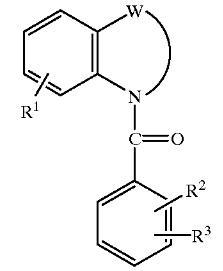

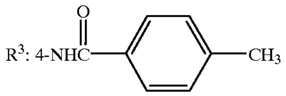

Crystalline form: White powder
Recrystallization solvent: Ethanol/water
NMR analysis: 19)
Form: Hydrochloride
Example 210
Structure

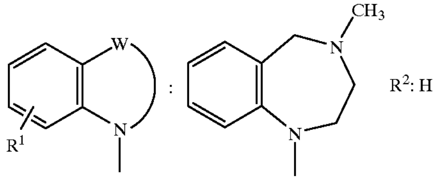

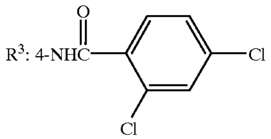

Crystalline form: White powder
Recrystallization solvent: Ethanol/water
NMR analysis: 20)
Form: Hydrochloride
Example 211
Structure

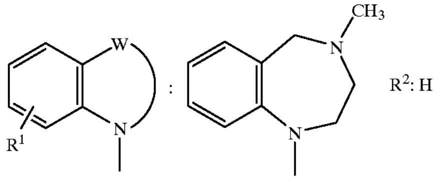

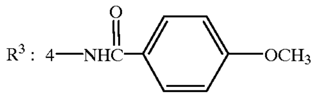

Crystalline form: White powder
Recrystallization solvent: Ethanol/diethyl ether
Melting Point: 159.5–1600.5° C.
Form: Free TABLE 1-continued

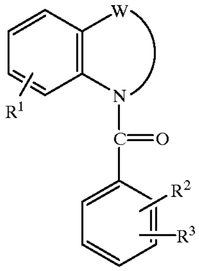

Example 212
Structure

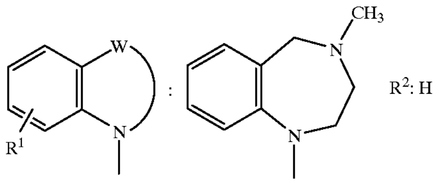

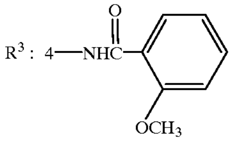

Crystalline form: White powder
Recrystallization solvent: Ethanol/diethyl ether
Melting Point: 189.5–190.5° C.
Form: Free
Example 213
Structure

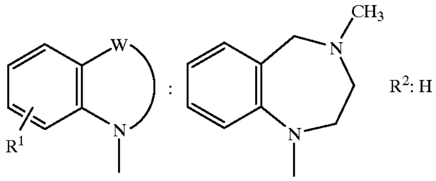

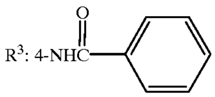

Crystalline form: White powder
Recrystallization solvent: Ethanol/diethyl ether
Melting Point: 170.5–171.5° C.
Form: Free
Example 214
Structure

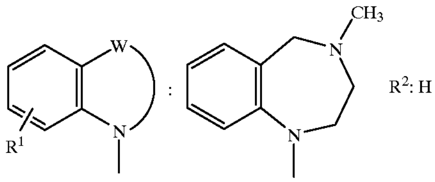

TABLE 1-continued

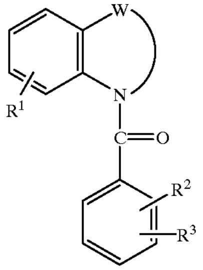

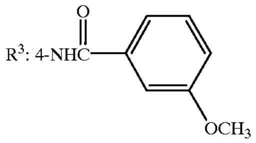

Crystalline form: White powder
Recrystallization solvent: Ethanol/diethyl ether
Melting Point: 165–166° C.
Form: Free
Example 215
Structure

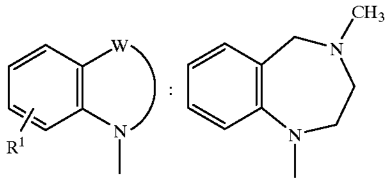

$R^2$: H

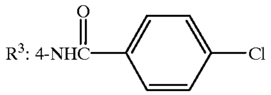

Crystalline form: White powder
Recrystallization solvent: Ethanol/diethyl ether
Melting Point: 173.5–174.5° C.
Form: Free
Example 216
Structure

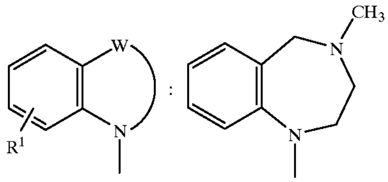

$R^2$: H

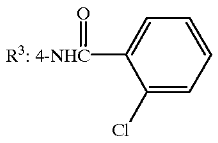

Crystalline form: White powder
Recrystallization solvent: Ethanol/diethyl ether
Melting Point: 182–183° C.
Form: Free TABLE 1-continued

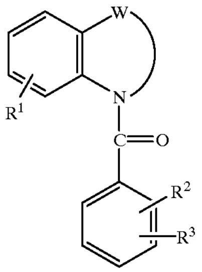

Example 217
Structure

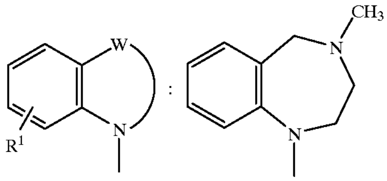

$R^2$: H

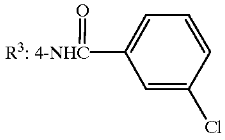

Crystalline form: White powder
Recrystallization solvent: Ethanol/diethyl ether
Melting Point: 225.5–226.5° C.
Form: Free
Example 219
Structure

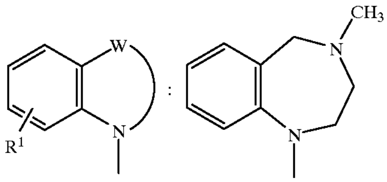

$R^2$: 3-$OCH_3$

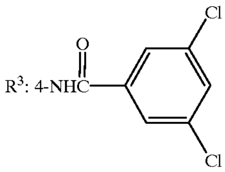

Crystalline form: White powder
Recrystallization solvent: Ethanol/water
NMR analysis: 21)
Form: Hydrochloride TABLE 1-continued

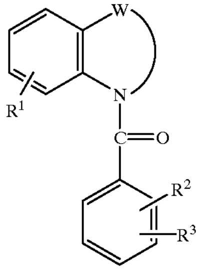

Example 220
Structure

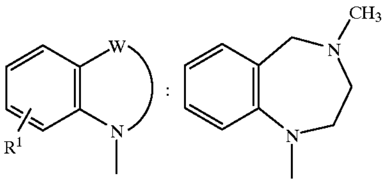

$R^2$: 3-$OCH_3$

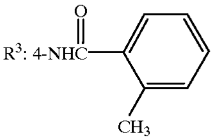

Crystalline form: White powder
Recrystallization solvent: Ethanol/diethyl ether
Melting Point: 147.5–148.5° C.
Form: Free
Example 221
Structure

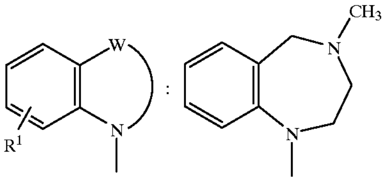

$R^2$: 3-$OCH_3$

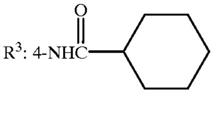

Crystalline form: White powder
Recrystallization solvent: Ethanol/diethyl ether
Melting Point: 136–137° C.
Form: Free
Example 222
Structure

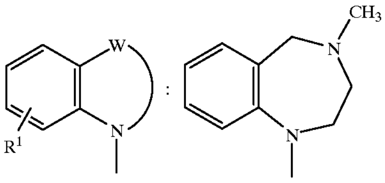

$R^2$: 3-$OCH_3$

TABLE 1-continued

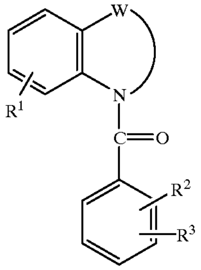

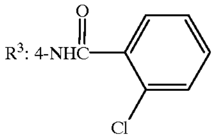

Crystalline form: White powder
Recrystallization solvent: Ethanol/diethyl ether
Melting Point: 191.5–192.5° C.
Form: Free
Example 223
Structure

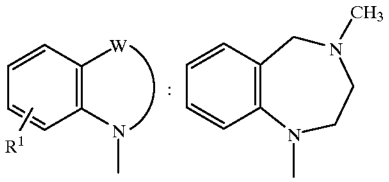

$R^2$: 3-$OCH_3$

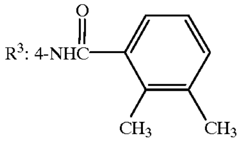

Crystalline form: White powder
Recrystallization solvent: Ethanol/diethyl ether
Melting Point: 145–146° C.
Form: Free
Example 224
Structure

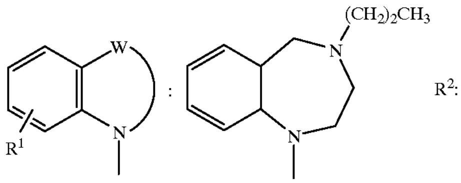

$R^2$: H

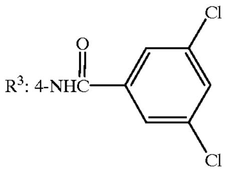

Crystalline form: White powder
Recrystallization solvent: Ethanol/water
NMR analysis: 22)
Form: Hydrochloride TABLE 1-continued

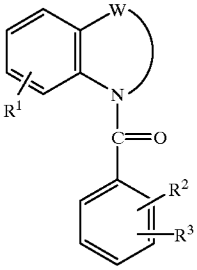

Example 225
Structure

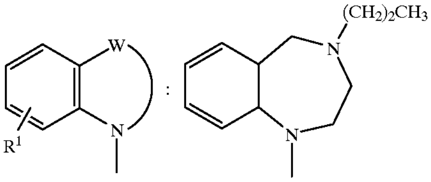

R²: H

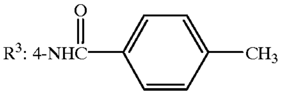

Crystalline form: White powder
Recrystallization solvent: Ethanol/water
NMR analysis: 23)
Form: Hydrochloride
Example 226
Structure

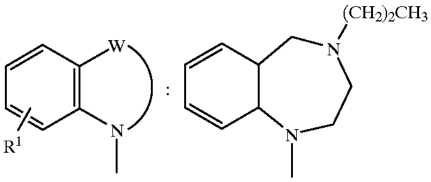

R²: H

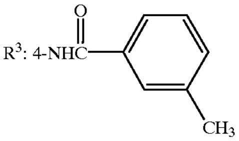

Crystalline form: White powder
Recrystallization solvent: Ethanol/water
NMR analysis: 24)
Form: Hydrochloride
Example 227
Structure

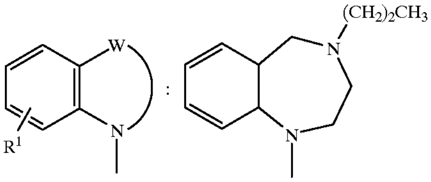

R²: H

TABLE 1-continued

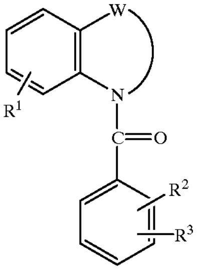

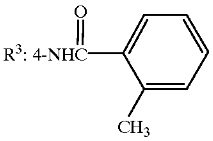

Crystalline form: White powder
Recrystallization solvent: Ethanol/water
NMR analysis: 25)
Form: Hydrochloride
Example 228
Structure

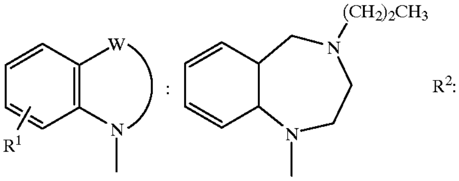

R²: H

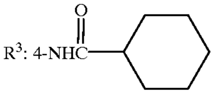

Crystalline form: White powder
Recrystallization solvent: Ethanol/water
NMR analysis: 26)
Form: Hydrochloride
Example 229
Structure

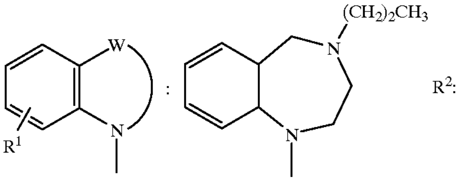

R²: H

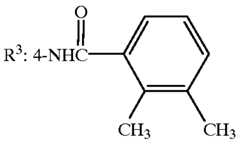

Crystalline form: White powder
Recrystallization solvent: Ethanol/water
NMR analysis: 27)
Form: Hydrochloride TABLE 1-continued

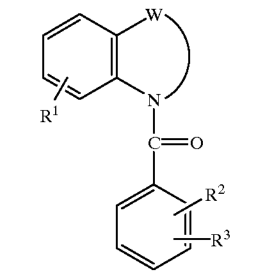

Example 230
Structure

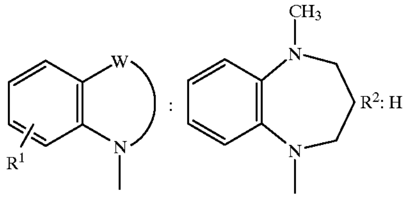

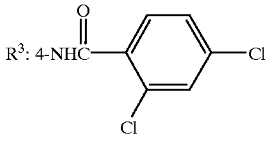

Crystalline form: White powder
Recrystallization solvent: Ethanol/diethyl ether
Melting Point: 206–207° C.
Form: Free
Example 231
Structure

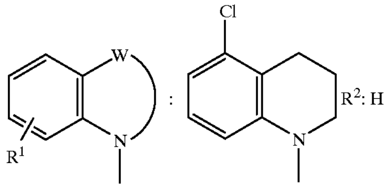

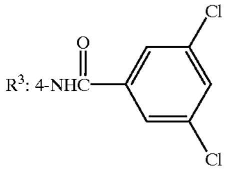

Crystalline form: White powder
Recrystallization solvent: Chloroform/metahnol
Melting Point: 211–213° C.
Form: Free
Example 232
Structure

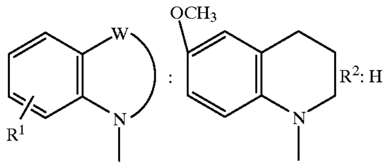

TABLE 1-continued

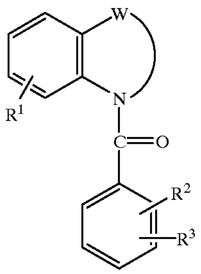

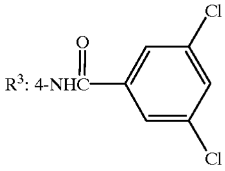

Crystalline form: White powder
Recrystallization solvent: Chloroform/metahnol
Melting Point: 228.5–229.5° C.
Form: Free
Example 233
Structure

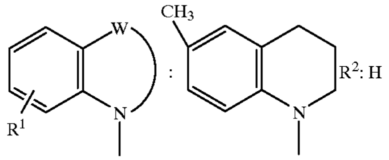

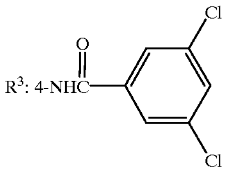

Crystalline form: White powder
Recrystallization solvent: Chloroform/metahnol
Melting Point: 237–238° C.
Form: Free
Example 234
Structure

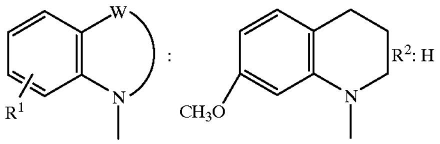

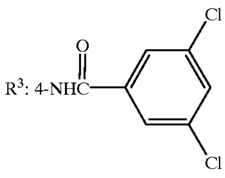

Crystalline form: White powder
Recrystallization solvent: Chloroform/metahnol
Melting Point: 226–228° C.
Form: Free TABLE 1-continued

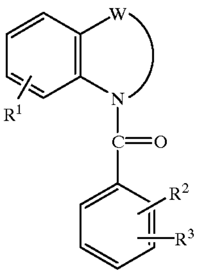

Example 235
Structure

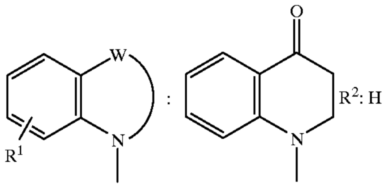

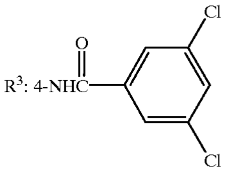

Crystalline form: White powder
Recrystallization solvent: Chloroform/metahnol
Melting Point: 220–222° C.
Form: Free
Example 236
Structure

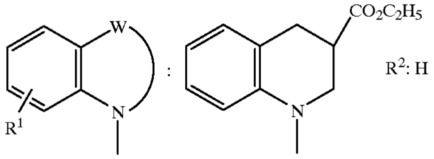

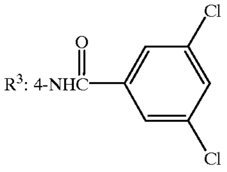

Crystalline form: Colorless amporphous
NMR analysis: 28)
Form: Free
Example 237
Structure

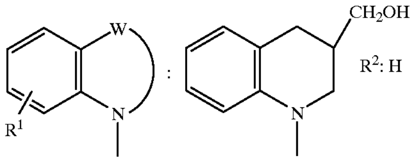

TABLE 1-continued

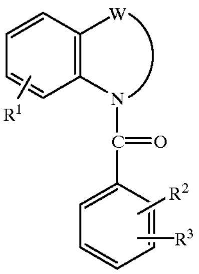

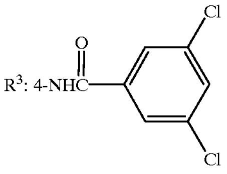

Crystalline form: White powder
Recrystallization solvent: Ethanol
Melting Point: 162–165° C.
Form: Free
Example 238
Structure

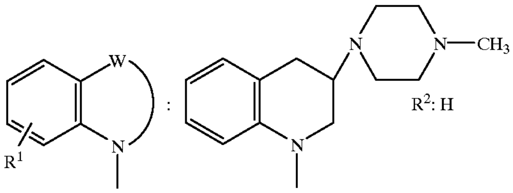

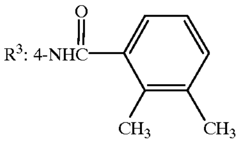

Crystalline form: Light brown amorphous
NMR analysis: 29)
Form: Free
Example 239
Structure

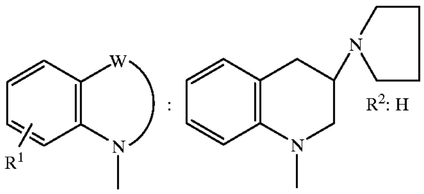

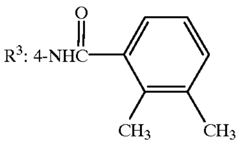

Crystalline form: Light brown amorphous
NMR analysis: 30)
Form: Free

TABLE 1-continued

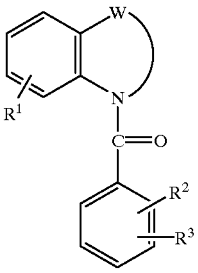

Example 240
Structure

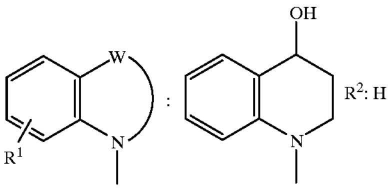

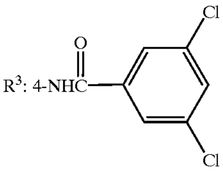

Crystalline form: White powder
Recrystallization solvent: Ethanol
Melting Point: 215–217° C.
Form: Free
Example 241
Structure

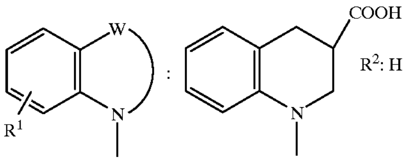

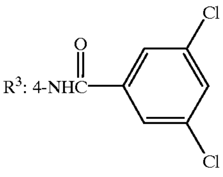

Crystalline form: White powder
Recrystallization solvent: Ethanol
Melting Point: 221–223° C.
Form: Free
Example 242
Structure

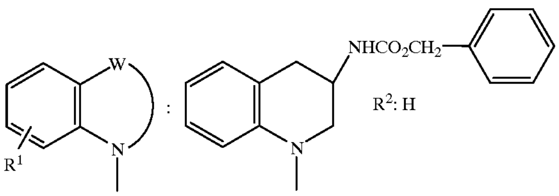

TABLE 1-continued

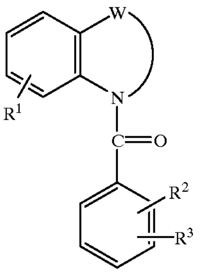

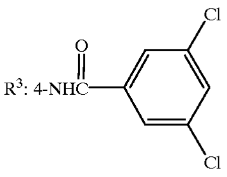

Crystalline form: Colorless amorphous
NMR analysis: 31)
Form: Free
Example 243
Structure

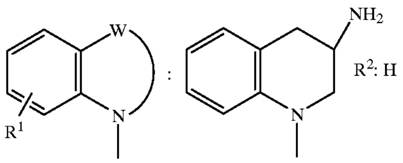

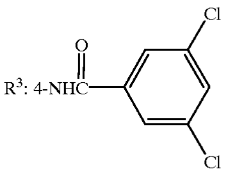

Crystalline form: White powder
Recrystallization solvent: Ethanol
Melting Point: 207–210° C.
Form: Free
Example 244
Structure

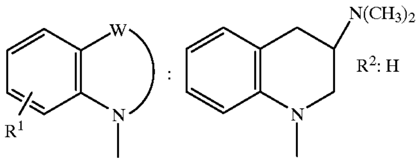

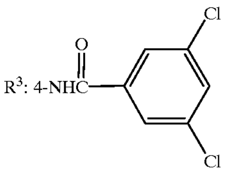

Crystalline form: Colorless amorphous
NMR analysis: 32)
Form: Free

TABLE 1-continued

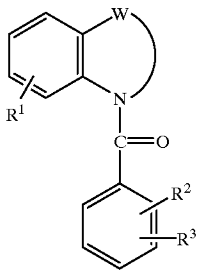

Example 245
Structure

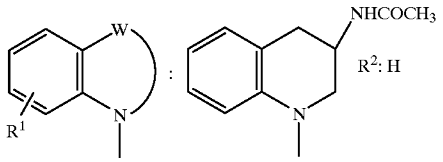

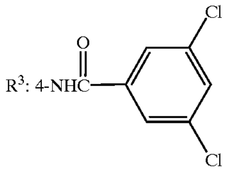

Crystalline form: Colorless amorphous
NMR analyss: 33)
Form: Free
Example 246
Structure

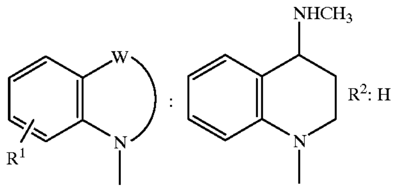

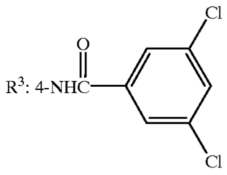

Crystalline form: Colorless amorphous
NMR analysis: 34)
Form: Free
Example 247
Structure

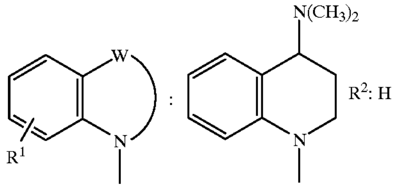

TABLE 1-continued

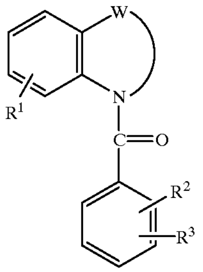

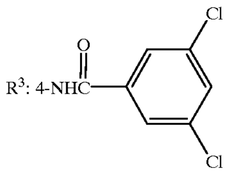

Crystalline form: Colorless amorphous
NMR analysis: 35)
Form: Free
Example 248
Structure

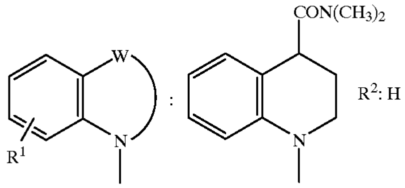

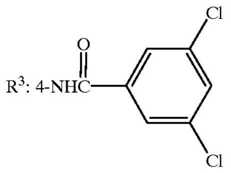

Crystalline form: Light yellow powder
Recrystallization solvent: Ethanol
Melting Point: 186–187° C.
Form: Free
Example 249
Structure

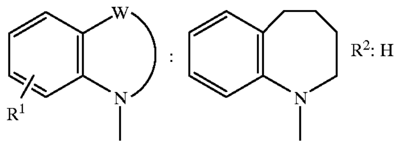

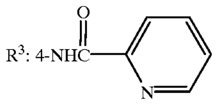

Crystalline form: Colorless needles
Recrystallization solvent: Ethanol
Melting Point: 190–191° C.
Form: Free TABLE 1-continued

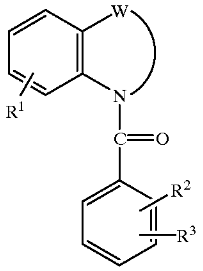

Example 250
Structure

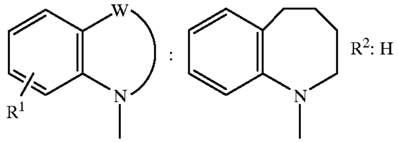

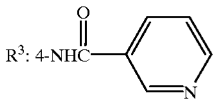

Crystalline form: Light yellow scales
Recrystallization solvent: Ethanol/water
Melting Point: 230–231° C.
Form: Free
Example 251
Structure

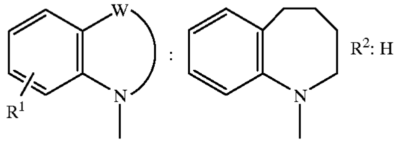

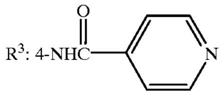

Crystalline form: Light yellow needles
Recrystallization solvent: Ethanol
Melting Point: 227–228° C.
Form: Free
Example 252
Structure

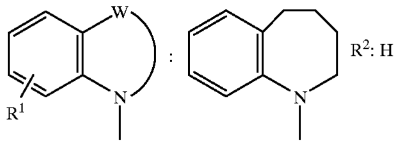

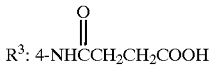

Crystalline form: Colorless needles
Recrystallization solvent: Ethyl acetate
Melting Point: 192° C.
Form: Free TABLE 1-continued

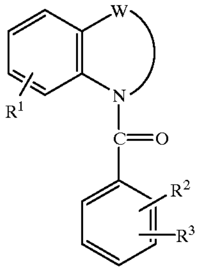

Example 253
Structure

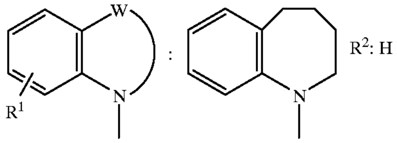

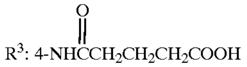

Crystalline form: White powder
Recrystallization solvent: Ethyl acetate
Melting Point: 186.5–189° C.
Form: Free
Example 254
Structure

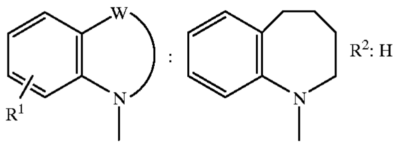

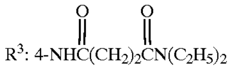

Crystalline form: Light yellow scales
Recrystallization solvent: n-Hexane/ethyl acetate
Melting Point: 165–167° C.
Form: Free
Example 255
Structure

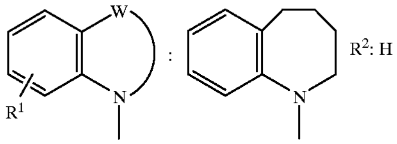

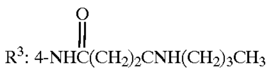

Crystalline form: White powder
Recrystallization solvent: Ethyl acetate
Melting Point: 169–170° C.
Form: Free TABLE 1-continued

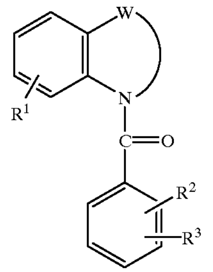

Example 256
Structure

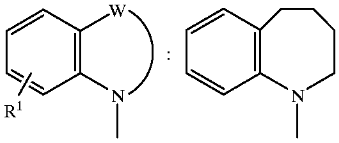

$R^2$: H

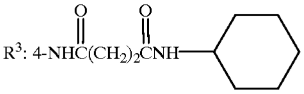

Crystalline form: Colorless scales
Recrystallization solvent: n-Hexane/ethyl acetate
Melting Point: 174–177° C.
Form: Free Example 257
Structure

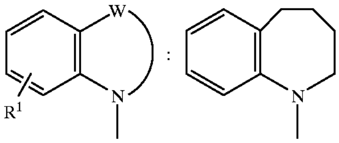

$R^2$: H

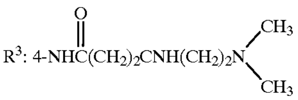

Crystalline form: White powder
Recrystallization solvent: Ethyl acetate
Melting Point: 114–118° C.
Form: Free Example 258
Structure

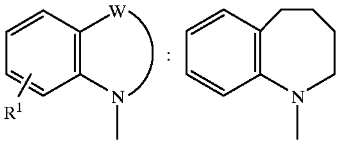

$R^2$: H

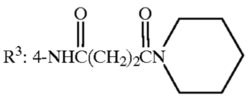

Crystalline form: White powder
Recrystallization solvent: Ethyl acetate
Melting Point: 170–172° C.
Form: Free TABLE 1-continued

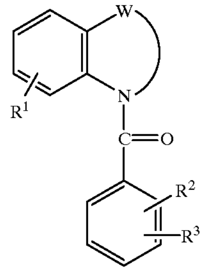

Example 259
Structure

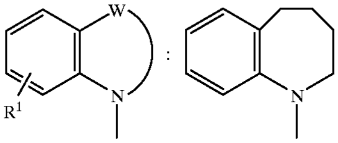

$R^2$: H

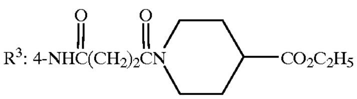

Crystalline form: White powder
Recrystallization solvent: n-Hexane/ethyl acetate
Melting Point: 179–181° C.
Form: Free Example 260
Structure

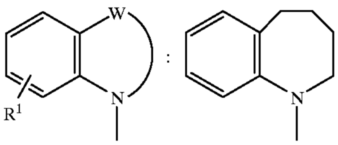

$R^2$: H

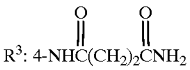

Crystalline form: White powder
Recrystallization solvent: Ethyl acetate
Melting Point: 118–121° C.
Form: Free Example 261
Structure

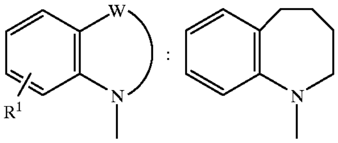

$R^2$: H

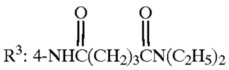

Crystalline form: White powder
Recrystallization solvent: Ethyl acetate
Melting Point: 144–148° C.
Form: Free TABLE 1-continued

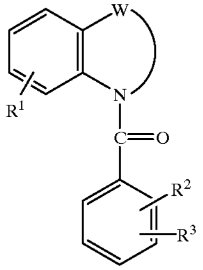

Example 262
Structure

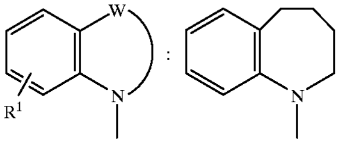

$R^2$: H

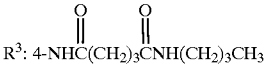

Crystalline form: Colorless scales
Recrystallization solvent: Ethyl acetate
Melting Point: 156–157° C.
Form: Free
Example 263
Structure

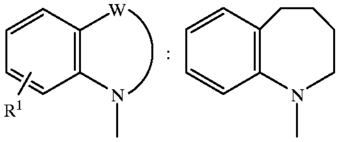

$R^2$: H

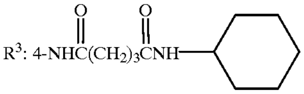

Crystalline form: White powder
Recrystallization solvent: Ethyl acetate
Melting Point: 204–206° C.
Form: Free
Example 264
Structure

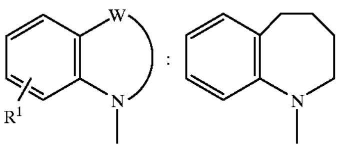

$R^2$: H

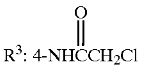

Crystalline form: Light yellow powder
Recrystallization solvent: n-Hexane/ethyl acetate
Melting Point: 165–167° C.
Form: Free TABLE 1-continued

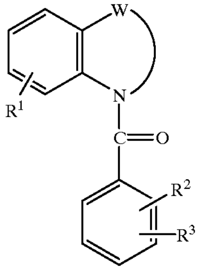

Example 265
Structure

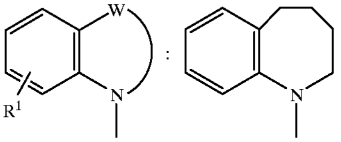

$R^2$: H

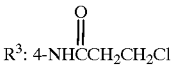

Crystalline form: Light yellow amorphous
NMR analysis: 36)
Form: Free
Example 266
Structure

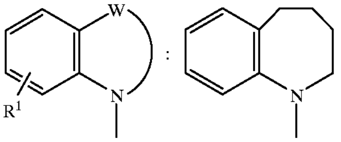

$R^2$: H

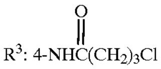

Crystalline form: White powder
Recrystallization solvent: n-Hexane/ethyl acetate
Melting Point: 122–124° C.
Form: Free
Example 267
Structure

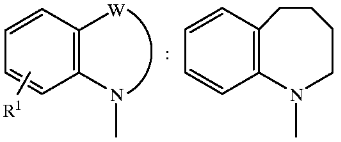

$R^2$: H

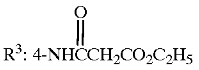

Crystalline form: White powder
Recrystallization solvent: n-Hexane/ethyl acetate
Melting Point: 116–117° C.
Form: Free TABLE 1-continued

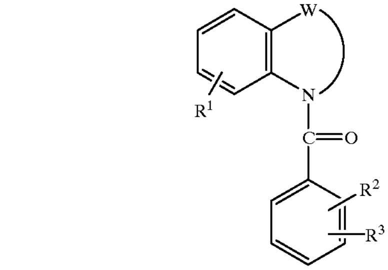

Example 268

Structure

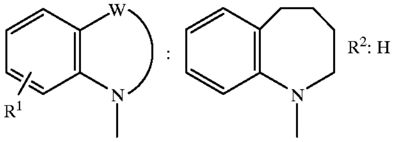

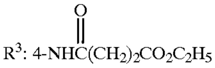

Crystalline form: White powder

Recrystallization solvent: n-Hexane/ethyl acetate

Melting Point: 121–123° C.

Form: Free

Example 269

Structure

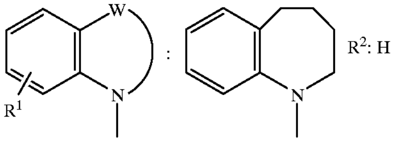

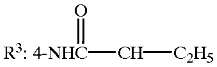

Crystalline form: Colorless needles

Recrystallization solvent: Ethyl acetate

Melting Point: 186–187° C.

Form: Free

Example 270

Structure

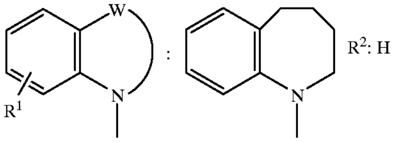

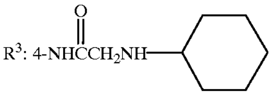

Crystalline form: White powder

Recrystallization solvent: n-Hexane/ethyl acetate

Melting Point: 139–142° C.

Form: Free

TABLE 1-continued

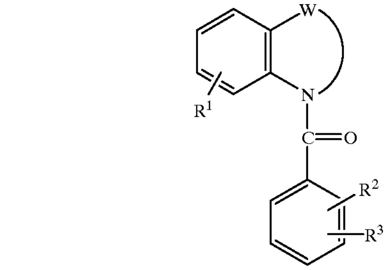

Example 271

Structure

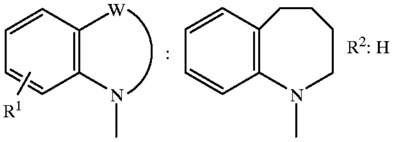

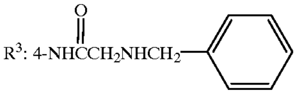

Crystalline form: Light yellow amorphous

NMR analysis: 37)

Form: Free

Example 272

Structure

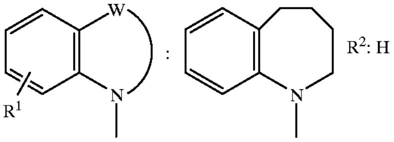

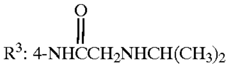

Crystalline form: White powder

Recrystallization solvent: Ethyl acetate

Melting Point: 149.5–152.5° C.

Form: Free

Example 273

Structure

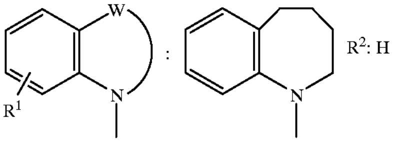

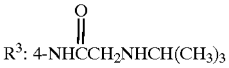

Crystalline form: Colorless needles

Recrystallization solvent: Ethanol

Melting Point: 150–152.5° C.

Form: Free

TABLE 1-continued

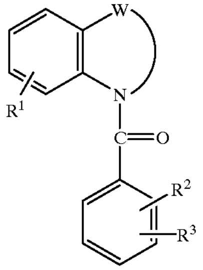

Example 274

Structure

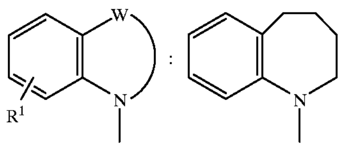

$R^2$: H

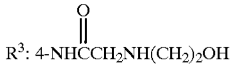

Crystalline form: White powder

Recrystallization solvent: Ethyl acetate

Melting Point: 150° C.

Form: Free

Example 275

Structure

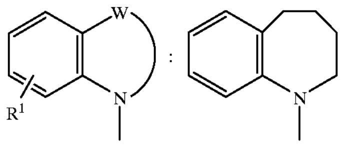

$R^2$: H

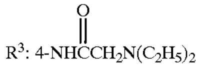

Crystalline form: Colorless needles

Recrystallization solvent: n-Hexane/ethyl acetate

Melting Point: 101–104° C.

Form: Free

Example 276

Structure

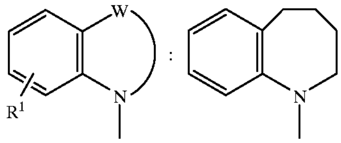

$R^2$: H

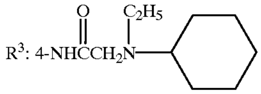

Crystalline form: White powder

Recrystallization solvent: n-Hexane/ethyl acetate

Melting Point: 120–122° C.

Form: Free

TABLE 1-continued

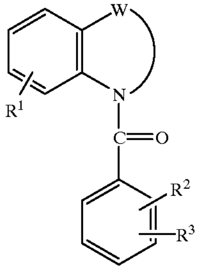

Example 277

Structure

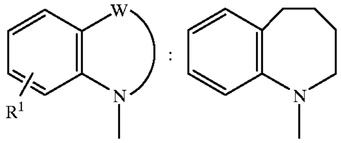

$R^2$: H

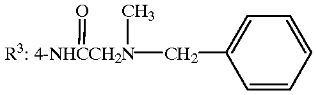

Crystalline form: Light yellow amorphous

NMR analysis: 38)

Form: Free

Example 278

Structure

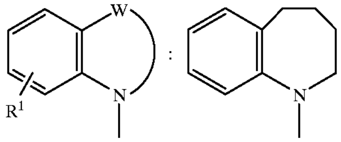

$R^2$: H

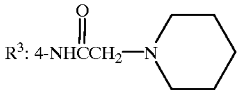

Crystalline form: Colorless needles

Recrystallization solvent: Ethanol

Melting Point: 183–186° C.

Form: Free

Example 279

Structure

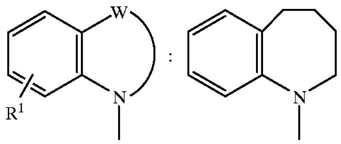

$R^2$: H

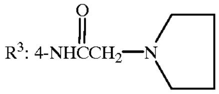

Crystalline form: Light brown powder

Recrystallization solvent: n-Hexane/ethyl acetate

Melting Point: 139–142° C.

Form: Free

TABLE 1-continued

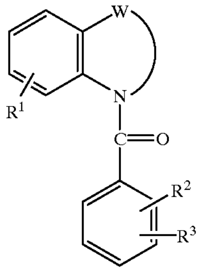

Example 280
Structure

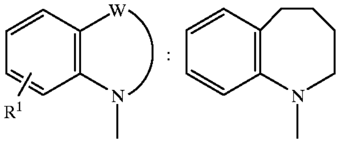

$R^2$: H

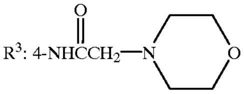

Crystalline form: Light yellow powder
Recrystallization solvent: Ethanol
Melting Point: 162–165° C.
Form: Free Example 281
Structure

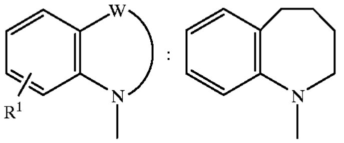

$R^2$: H

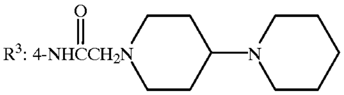

Crystalline form: Light yellow scales
Recrystallization solvent: Ethyl acetate
Melting Point: 224–227° C.
Form: Free Example 282
Structure

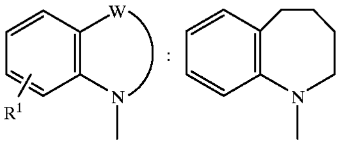

$R^2$: H

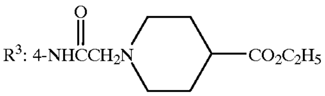

Crystalline form: Light yellow amorphous
NMR analysis: 39)
Form: Free

TABLE 1-continued

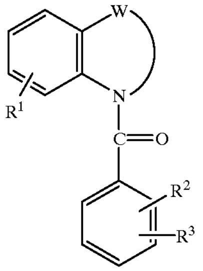

Example 283
Structure

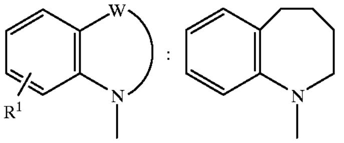

$R^2$: H

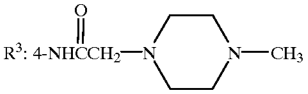

Crystalline form: Light yellow powder
Recrystallization solvent: Ethanol/water
Melting Point: 162–164° C.
Form: Free Example 284
Structure

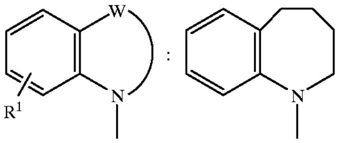

$R^2$: H

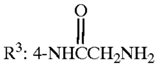

Crystalline form: Light yellow powder
Recrystallization solvent: Ethanol
Melting Point: 238–241° C. (decomposed)
Form: Free Example 285
Structure

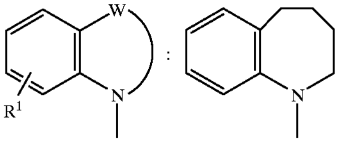

$R^2$: H

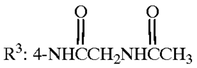

Crystalline form: Light yellow amorphous
NMR analysis: 40)
Form: Free

TABLE 1-continued

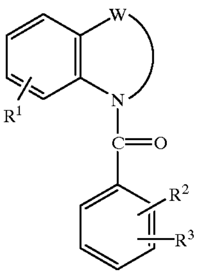

Example 286
Structure

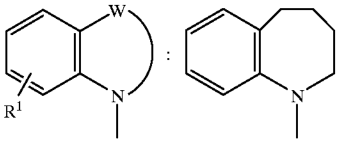

$R^2$: H

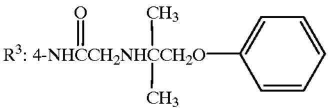

Crystalline form: Colorless amorphous
NMR analysis: 41)
Form: Free
Example 287
Structure

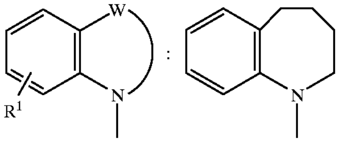

$R^2$: H

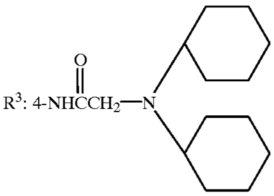

Crystalline form: Colorless needles
Recrystallization solvent: n-Hexane/ethyl acetate
Melting Point: 168–169° C.
Form: Free
Example 288
Structure

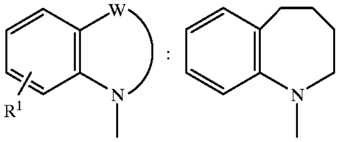

$R^2$: H

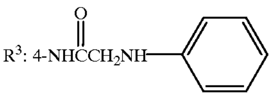

Crystalline form: Light brown powder

TABLE 1-continued

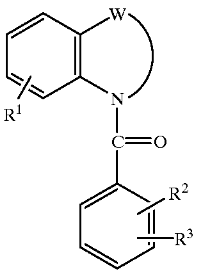

Recrystallization solvent: Ethanol
Melting Point: 189–191° C.
Form: Free
Example 289
Structure

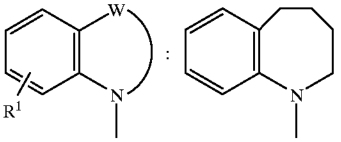

$R^2$: H

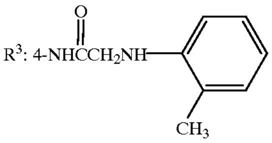

Crystalline form: White powder
Recrystallization solvent: n-Hexane/ethyl acetate
Melting Point: 200–202° C.
Form: Free
Example 290
Structure

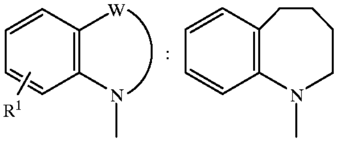

$R^2$: H

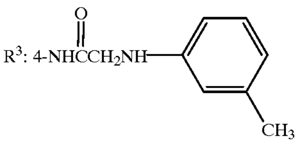

Crystalline form: Colorless scales
Recrystallization solvent: n-Hexane/ethyl acetate
Melting Point: 143–146° C.
Form: Free
Example 291
Structure

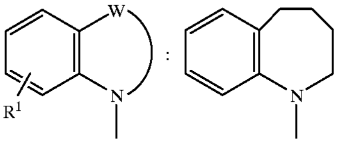

$R^2$: H

TABLE 1-continued

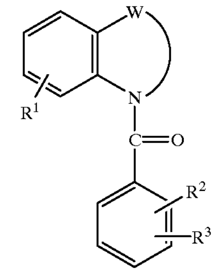

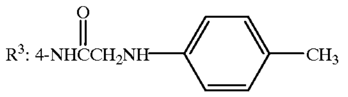

Crystalline form: White powder
Recrystallization solvent: n-Hexane/ethyl acetate
Melting Point: 117–117.5° C.
Form: Free
Example 292
Structure

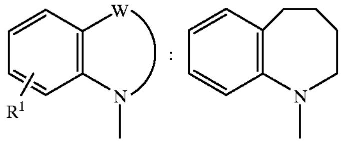

$R^2$: H

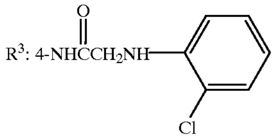

Crystalline form: Light brown powder
Recrystallization solvent: Diethyl ether/ethyl acetate
Melting Point: 225–226° C.
Form: Free
Example 293
Structure

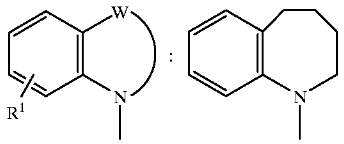

$R^2$: H

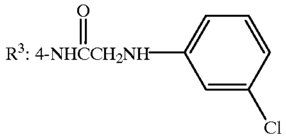

Crystalline form: White powder
Recrystallization solvent: n-Hexane/ethanol
Melting Point: 175–176.5° C.
Form: Free TABLE 1-continued

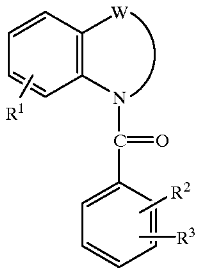

Example 294
Structure

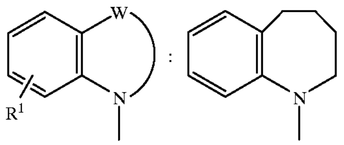

$R^2$: H

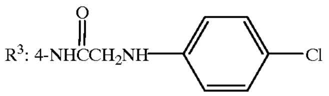

Crystalline form: White powder
Recrystallization solvent: Ethyl acetate
Melting Point: 234–236° C.
Form: Free
Example 295
Structure

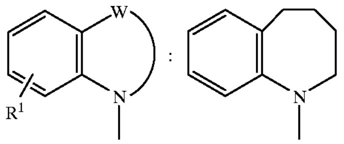

$R^2$: H

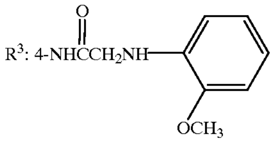

Crystalline form: Colorless scales
Recrystallization solvent: Ethyl acetate
Melting Point: 172–174° C.
Form: Free
Example 296
Structure

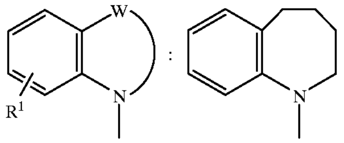

$R^2$: H

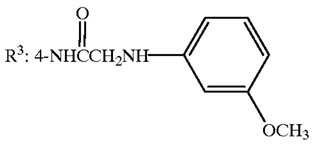

Crystalline form: White powder

TABLE 1-continued

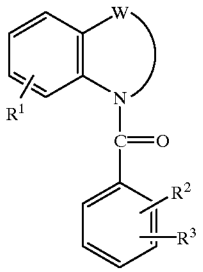

Recrystallization solvent: Ethyl acetate
Melting Point: 154–155° C.
Form: Free
Example 297
Structure

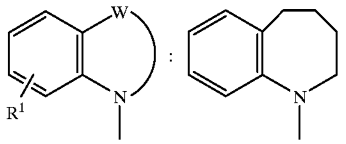

$R^2$: H

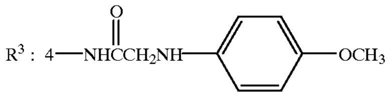

Crystalline form: Light yellow needles
Recrystallization solvent: n-Hexane/ethyl acetate
Melting Point: 181.5–183.5° C.
Form: Free
Example 298
Structure

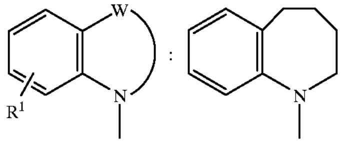

$R^2$: H

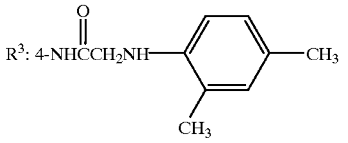

Crystalline form: White powder
Recrystallization solvent: n-Hexane/ethyl acetate
Melting Point: 173–175° C.
Form: Free
Example 299
Structure

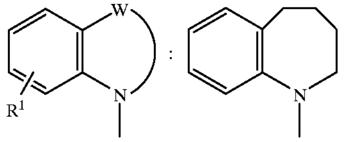

$R^2$: H

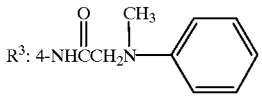

TABLE 1-continued

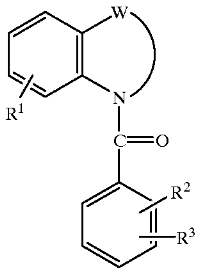

Crystalline form: White powder
Recrystallization solvent: n-Hexane/ethyl acetate
Melting Point: 137–138° C.
Form: Free
Example 300
Structure

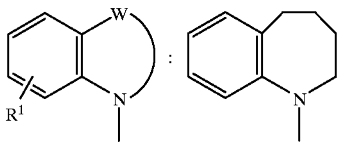

$R^2$: H

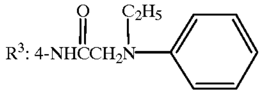

Crystalline form: Light yellow amorphous
NMR analysis: 42)
Form: Free
Example 301
Structure

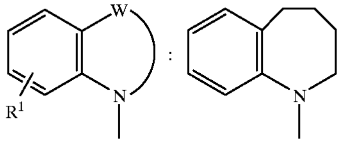

$R^2$: H

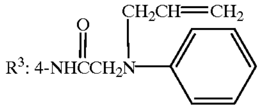

Crystalline form: Colorless needles
Recrystallization solvent: Diethyl ether/ethyl acetate
Melting Point: 129–130° C.
Form: Free
Example 302
Structure

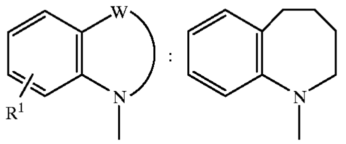

$R^2$: H

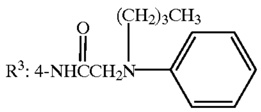

Crystalline form: Colorless needles

TABLE 1-continued

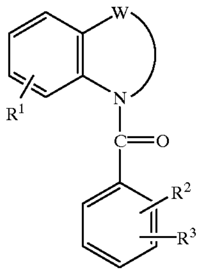

Recrystallization solvent: n-Hexane/ethyl acetate
Melting Point: 181–183° C.
Form: Free
Example 303
Structure

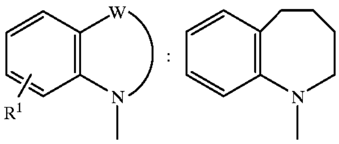

$R^2$: H

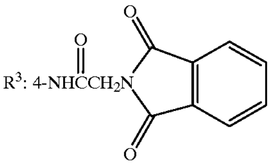

Crystalline form: White powder
Recrystallization solvent: Ethyl acetate
Melting Point: 248–249° C.
Form: Free
Example 304
Structure

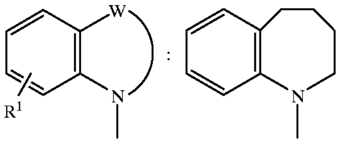

$R^2$: H

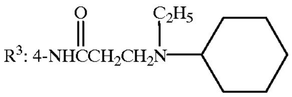

Crystalline form: Light yellow amorphous
NMR analysis: 43)
Form: Free
Example 305
Structure

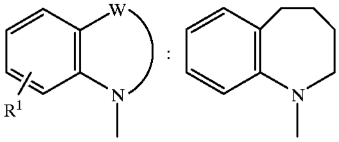

$R^2$: H

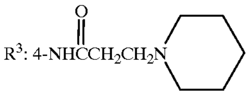

TABLE 1-continued

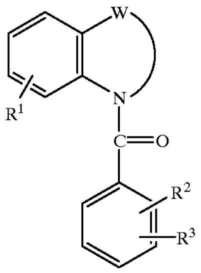

Crystalline form: Light yellow needles
Recrystallization solvent: Ethanol
Melting Point: 94–96° C.
Form: Free
Example 306
Structure

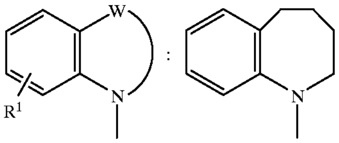

$R^2$: H

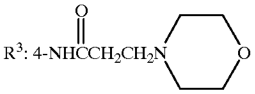

Crystalline form: Light brown powder
Recrystallization solvent: Ethyl acetate
Melting Point: 159–161° C.
Form: Free
Example 307
Structure

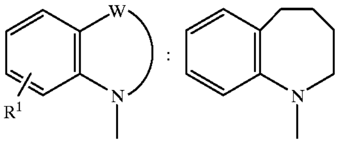

$R^2$: H

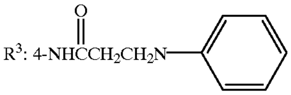

Crystalline form: White powder
Recrystallization solvent: Ethyl acetate
Melting Point: 180–183° C.
Form: Free
Example 308
Structure

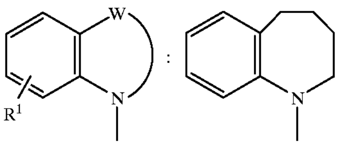

$R^2$: H

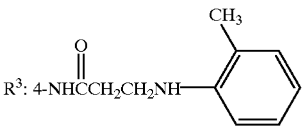

TABLE 1-continued

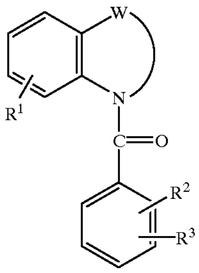

Crystalline form: Light brown powder
Recrystallization solvent: Ethanol
Melting Point: 177–180° C.
Form: Free
Example 309
Structure

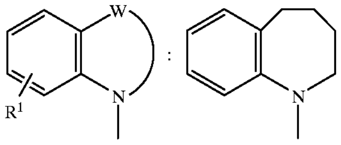

$R^2$: H

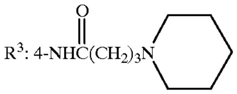

Crystalline form: White powder
Recrystallization solvent: Ethyl acetate
Melting Point: 91–93° C.
Form: Free
Example 310
Structure

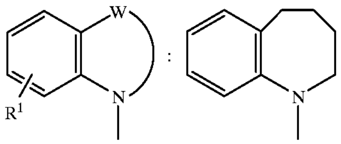

$R^2$: H

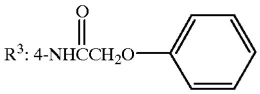

Crystalline form: Light brown scales
Recrystallization solvent: Ethanol
Melting Point: 155–156.5° C.
Form: Free
Example 311
Structure

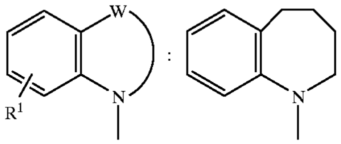

$R^2$: H

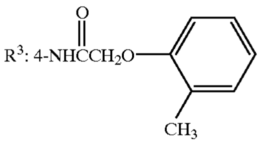

TABLE 1-continued

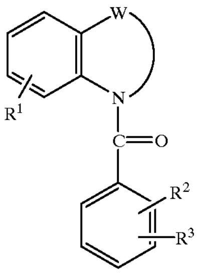

Crystalline form: Colorless scales
Recrystallization solvent: Ethyl acetate
Melting Point: 172.5–175° C.
Form: Free
Example 312
Structure

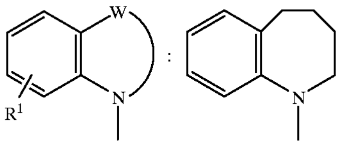

$R^2$: H

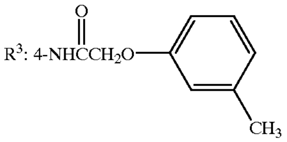

Crystalline form: White powder
Recrystallization solvent: Ethanol
Melting Point: 148–150.5° C.
Form: Free
Example 313
Structure

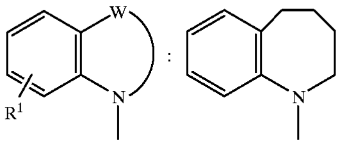

$R^2$: H

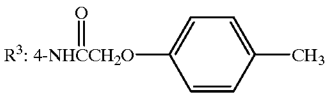

Crystalline form: White powder
Recrystallization solvent: Ethyl acetate
Melting Point: 172–173° C.
Form: Free
Example 314
Structure

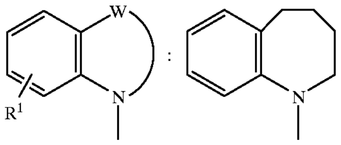

$R^2$: H

TABLE 1-continued

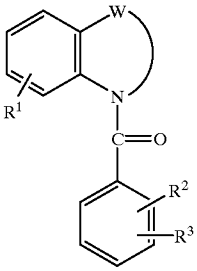

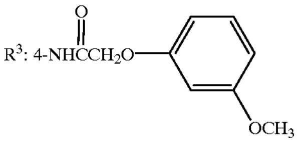

Crystalline form: Colorless scales
Recrystallization solvent: n-Hexane/ethyl acetate
Melting Point: 133–135° C.
Form: Free
Example 315
Structure

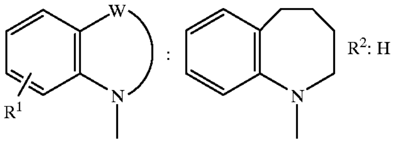

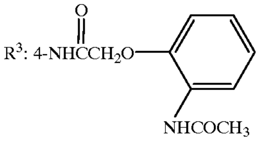

Crystalline form: White powder
Recrystallization solvent: Ethyl acetate
Melting Point: 217–219° C.
Form: Free
Example 316
Structure

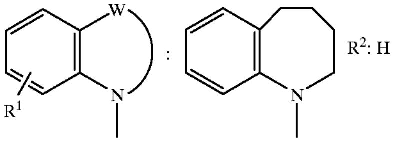

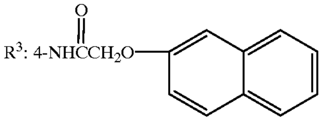

Crystalline form: Colorless needles
Recrystallization solvent: Ethyl acetate
Melting Point: 226–227.5° C.
Form: Free TABLE 1-continued

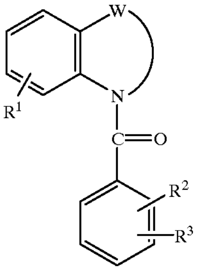

Example 317
Structure

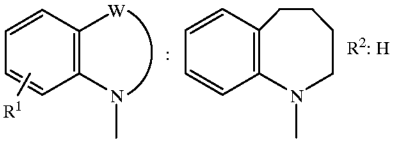

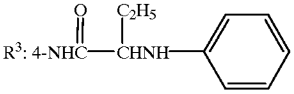

Crystalline form: Colorless amorphous
NMR analysis: 44)
Form: Free
Example 318
Structure

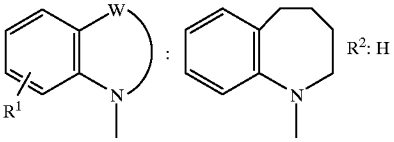

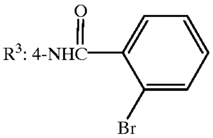

Crystalline form: White powder
Recrystallization solvent: Dichloromethane
Melting Point: 234–235° C.
Form: Free
Example 319
Structure

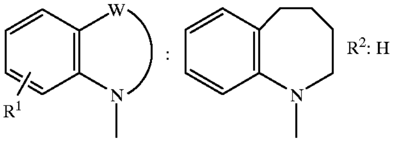

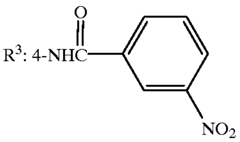

Crystalline form: Colorless prisms
Recrystallization solvent: Methanol

TABLE 1-continued

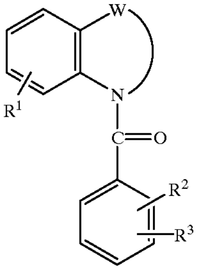

Melting Point: 218–218.5° C.
Form: Free
Example 320
Structure

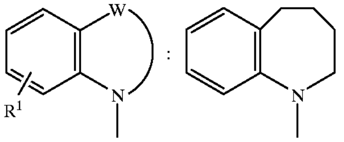
$R^2$: H $R^3$: 4-NHC
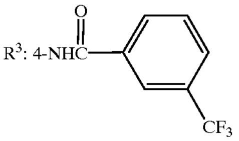

Crystalline form: Colorless prisms
Recrystallization solvent: Ethanol
Melting Point: 202.5–206° C.
Form: Free
Example 321
Structure

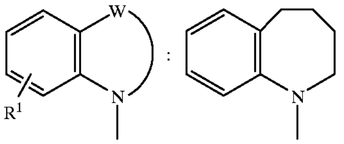
$R^2$: H $R^3$: 4-NHC
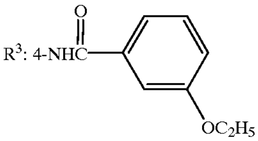

Crystalline form: White powder
Recrystallization solvent: Ethanol
Melting Point: 174–176° C.
Form: Free
Example 322
Structure

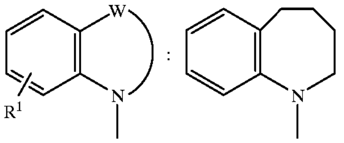
$R^2$: H

TABLE 1-continued

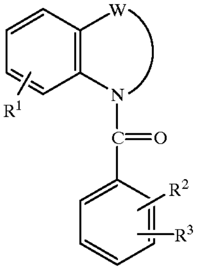

$R^3$: 4-NHC
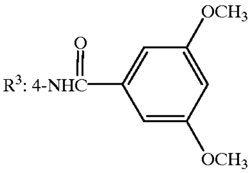

Crystalline form: Colorless prisms
Recrystallization solvent: Ethanol
Melting Point: 216–218° C.
Form: Free
Example 323
Structure

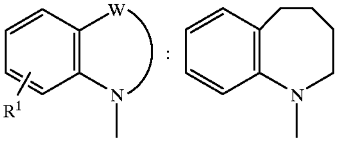
$R^2$: H $R^3$: 4-NHC
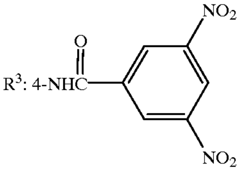

Crystalline form: White powder
Melting Point: >300° C.
NMR analysis: 45)
Form: Free
Example 324
Structure

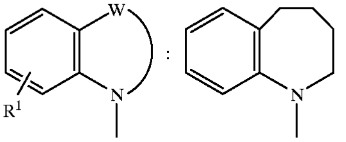
$R^2$: H $R^3$: 4-NHC
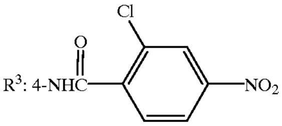

Crystalline form: Colorless prisms
Recrystallization solvent: Ethanol
Melting Point: 250.5–251° C.
Form: Free TABLE 1-continued

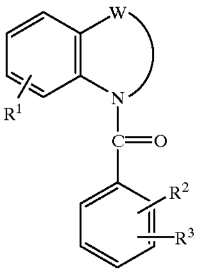

Example 325
Structure

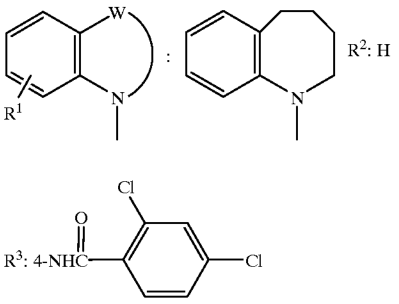

Crystalline form: Colorless prisms
Recrystallization solvent: Ethanol
Melting Point: 223–225° C.
Form: Free
Example 326
Structure

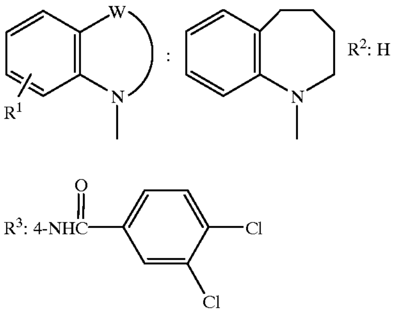

Crystalline form: Colorless prismsr
Recrystallization solvent: Methanol
Melting Point: 213–214° C.
Form: Free
Example 327
Structure

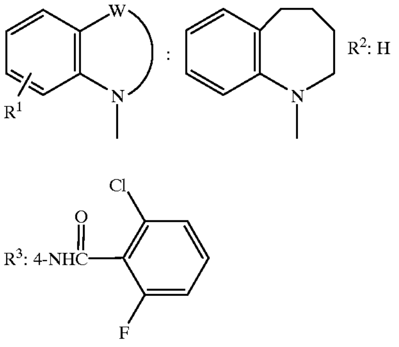

TABLE 1-continued

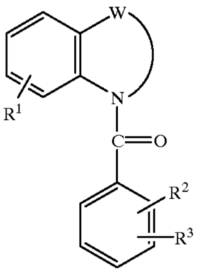

Crystalline form: Colorless prisms
Recrystallization solvent: Ethanol
Melting Point: 246–247° C.
Form: Free
Example 328
Structure

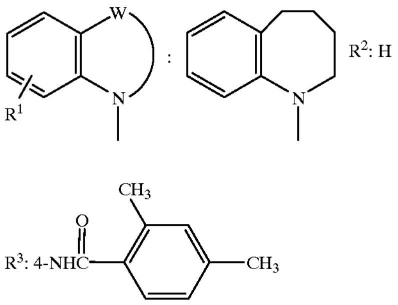

Crystalline form: Colorless prisms
Recrystallization solvent: Methanol
Melting Point: 248–251° C.
Form: Free
Example 329
Structure

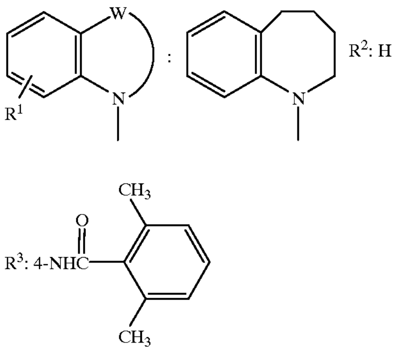

Crystalline form: Colorless prisms
Recrystallization solvent: Ethanol
Melting Point: 268.5–270.5° C.
Form: Free
Example 330
Structure

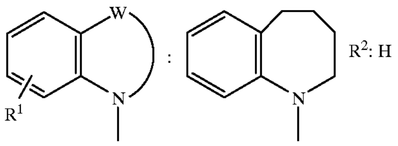

TABLE 1-continued

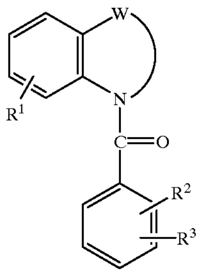

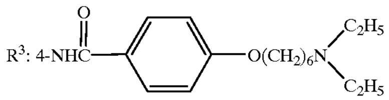

Crystalline form: White powder
Recrystallization solvent: Methano/diethyl ether
Melting Point: 174–176° C.
Form: Free Example 331
Structure

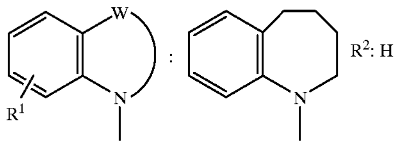

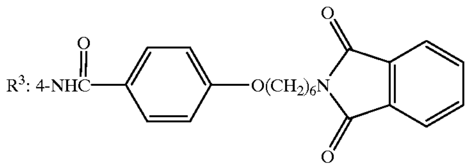

Crystalline form: White powder
Recrystallization solvent: Ethanol
Melting Point: 130–134° C.
Form: Free Example 332
Structure

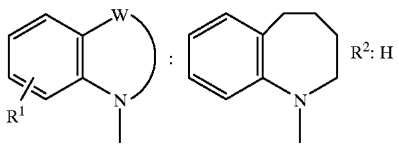

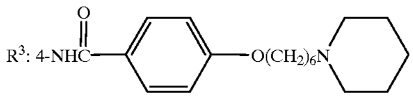

Crystalline form: White powder
Recrystallization solvent: Methanol/diethyl ether
Melting Point: 214–217° C.
Form: Hydrochloride TABLE 1-continued

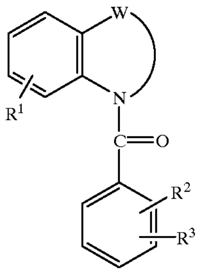

Example 333
Structure

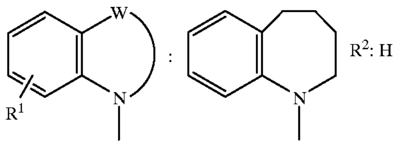

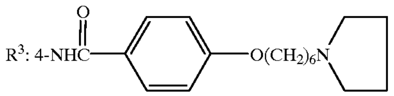

Crystalline form: White powder
Recrystallization solvent: Methanol/diethyl ether
Melting Point: 218–220° C.
Form: Hydrochloride Example 334
Structure

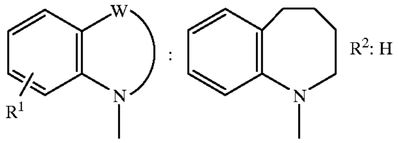

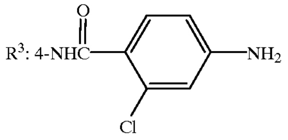

Crystalline form: White powder
Recrystallization solvent: Ethyl acetate
Melting Point: 222–225° C.
Form: Free Example 335
Structure

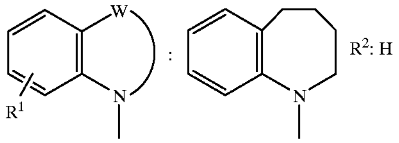

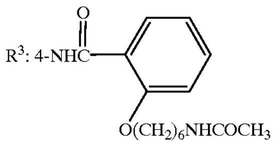

Crystalline form: Colorless needles

TABLE 1-continued

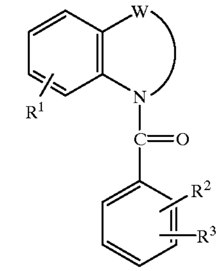

Recrystallization solvent: Methanol/ditehyl ether
Melting Point: 171–172° C.
Form: Free Example 336

Structure

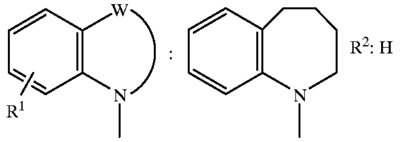

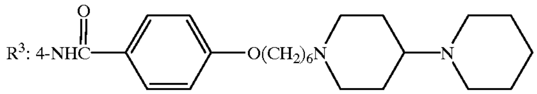

Crystalline form: White powder
Recrystallization solvent: Methanol/diethyl ether
Melting Point: 235.5–236° C.
Form: Dihydrochloride Example 337

Structure

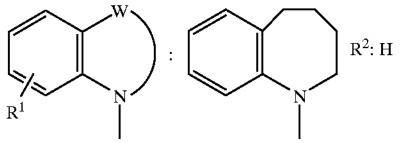

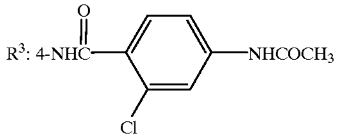

Crystalline form: White powder
Recrystallization solvent: Methanol/diethyl ether
Melting Point: 241–243° C.
Form: Free Example 338

Structure

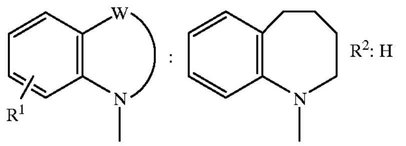

TABLE 1-continued

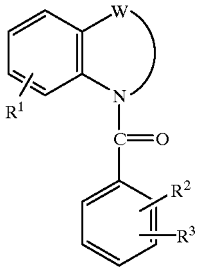

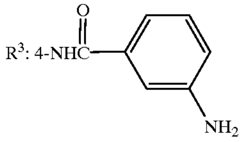

Crystalline form: White powder
Recrystallization solvent: Methanol/diethyl ether
Melting Point: 187–191° C.
Form: Free Example 339

Structure

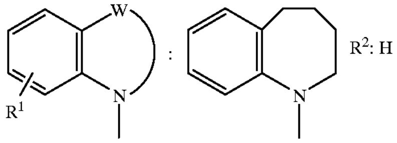

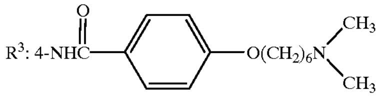

Crystalline form: White powder
Recrystallization solvent: Methanol/diethyl ether
Melting Point: 240–244° C.
Form: Hydrochloride Example 340

Structure

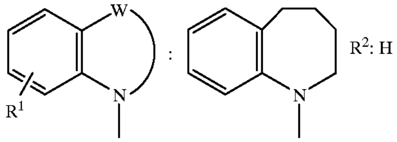

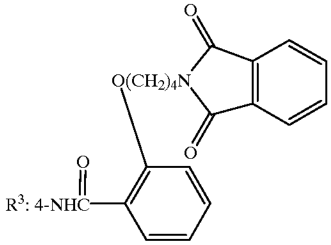

Crystalline form: Colorless prisms
Recrystallization solvent: Methanol/diethyl ether
Melting Point: 181–182° C.
Form: Free TABLE 1-continued

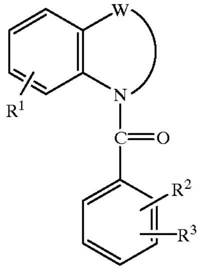

Example 341
Structure

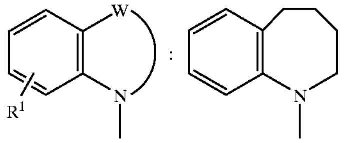

$R^2$: H

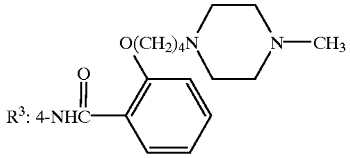

Crystalline form: Colorless prisms
Recrystallization solvent: Methanol/diethyl ether
Melting Point: 188–190° C.
Form: Dihydrochloride
Example 343
Structure

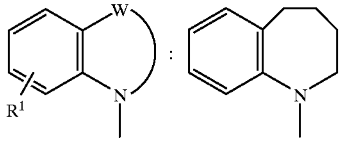

$R^2$: H

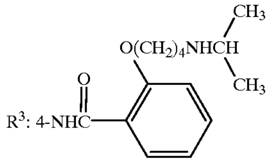

Crystalline form: White powder
Recrystallization solvent: Isopropyl alcohol
Melting Point: 218–218.5° C.
Form: Hydrrochloride
Example 343
Structure

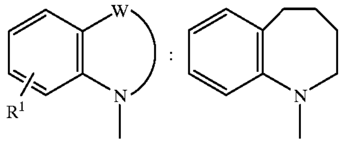

$R^2$: H

TABLE 1-continued

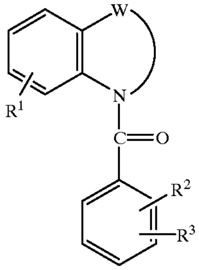

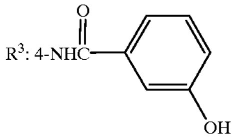

Crystalline form: White powder
Recrystallization solvent: Methanol/diethyl ether
Melting Point: 243–245.5° C.
Form: Free
Example 344
Structure

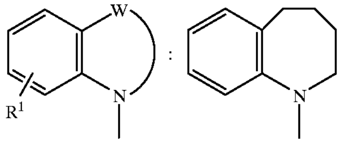

$R^2$: H

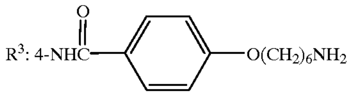

Crystalline form: White powder
Recrystallization solvent: Methanol/diethyl ether
Melting Point: 130–133° C.
Form: Free
Example 345
Structure

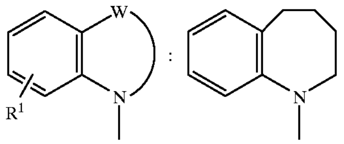

$R^2$: H

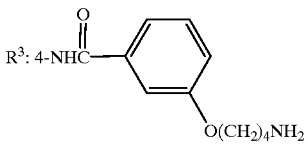

Crystalline form: White powder
Recrystallization solvent: Methanol/diethyl ether
Melting Point: 155–158° C.
Form: Free TABLE 1-continued

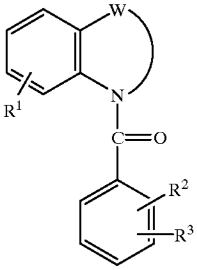

Example 346
Structure

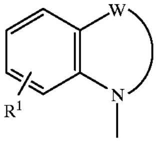
:
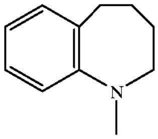
$R^2$: H

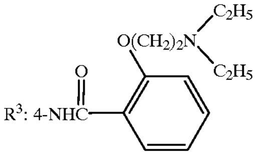

Crystalline form: White powder
Recrystallization solvent: Methanol/diethyl ether
Melting Point: 208–210° C.
Form: Hydrochloride
Example 347
Structure

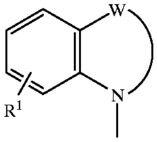
:
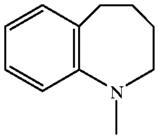
$R^2$: H

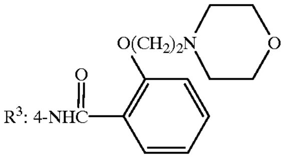

Crystalline form: Colorless prisms
Recrystallization solvent: Methanol/diethyl ether
Melting Point: 154–155° C.
Form: Hydrochloride
Example 348
Structure

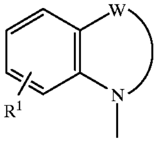
:
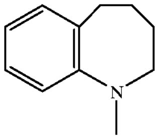
$R^2$: H

TABLE 1-continued

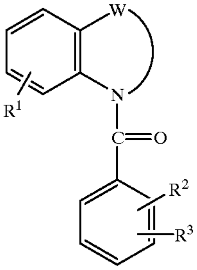

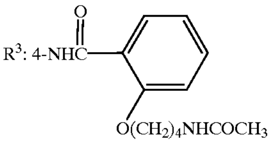

Crystalline form: White powder
Recrystallization solvent: Methanol/diethyl ether
Melting Point: 142–143° C.
Form: Free
Example 349
Structure

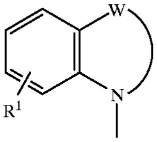
:
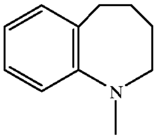
$R^2$: H

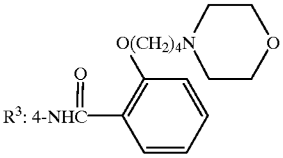

Crystalline form: White powder
Recrystallization solvent: Methanol/diethyl ether
Melting Point: 120–125° C.
Form: Hydrochloride
Example 350
Structure

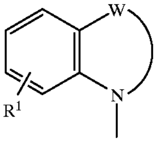
:
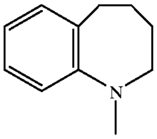
$R^2$: H

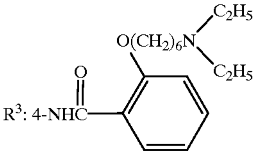

Crystalline form: White powder
Recrystallization solvent: Methanol/diethyl ether
Melting Point: 91–95° C.
Form: Hydrochloride TABLE 1-continued

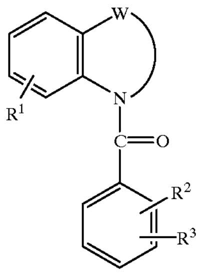

Example 351

Structure

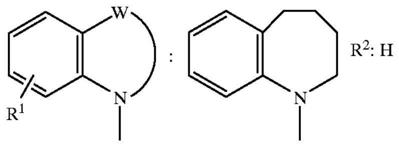

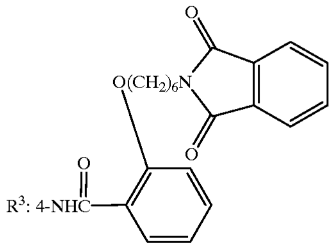

Crystalline form: White powder

Recrystallization solvent: Methanol/diethyl ether

Melting Point: 145–146.5° C.

Form: Free

Example 352

Structure

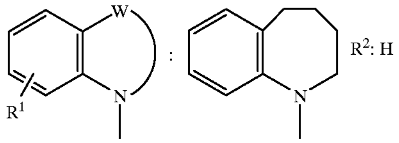

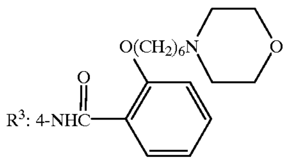

Crystalline form: White powder

Recrystallization solvent: Methanol/diethyl ether

Melting Point: 105–105.5° C.

Form: Free

TABLE 1-continued

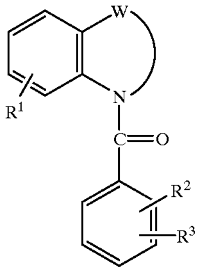

Example 353

Structure

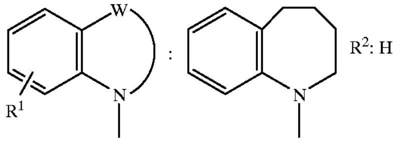

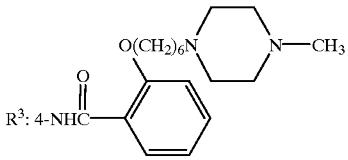

Crystalline form: White powder

Recrystallization solvent: Methanol/diethyl ether

Melting Point: 151–155° C.

Form: Dihydrochloride

Example 354

Structure

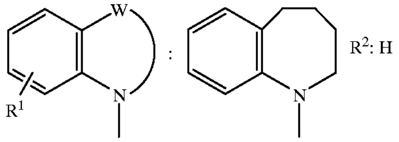

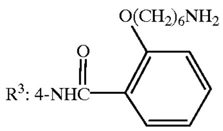

Crystalline form: White powder

Recrystallization solvent: Methanol/diethyl ether

Melting Point: 135.5–137.5° C.

Form: Free

Example 355

Structure

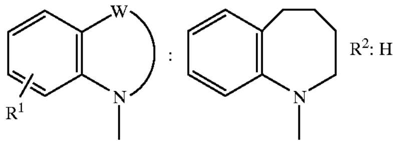

TABLE 1-continued

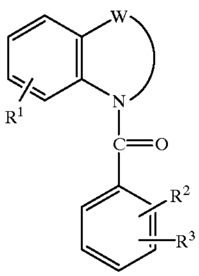

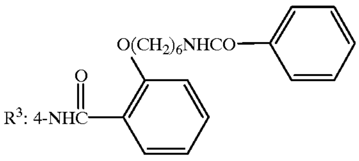

Crystalline form: White powder
Recrystallization solvent: Ethanol
Melting Point: 178–178.5° C.
Form: Free
Example 356
Structure

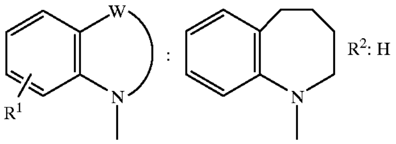

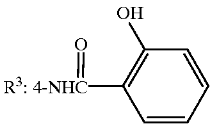

Crystalline form: White powder
Recrystallization solvent: Dichloromethane
Melting Point: 266.5–268° C.
Form: Free
Example 357
Structure

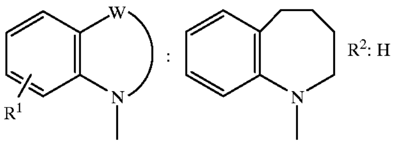

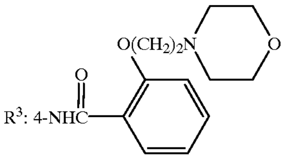

Crystalline form: White powder
Recrystallization solvent: Methanol/diethyl ether
Melting Point: 123–124° C.
Form: Free TABLE 1-continued

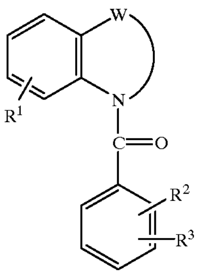

Example 358
Structure

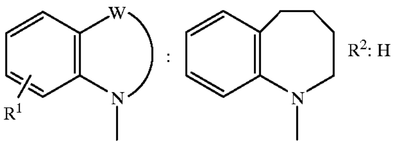

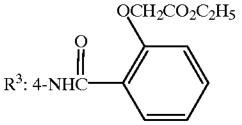

Crystalline form: White powder
Recrystallization solvent: Ethyl acetate
Melting Point: 212–213.5° C.
Form: Free
Example 359
Structure

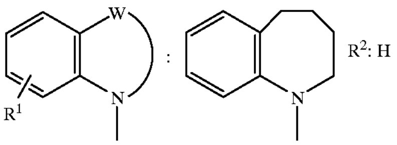

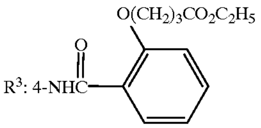

Crystalline form: Colorless scales
Recrystallization solvent: Ethyl acetate
Melting Point: 160.5–162° C.
Form: Free
Example 360
Structure

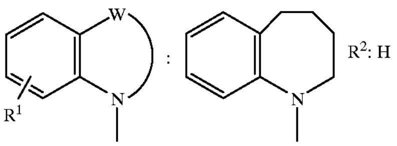

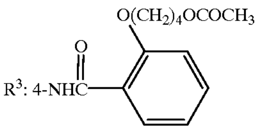

Crystalline form: Colorless needles

TABLE 1-continued

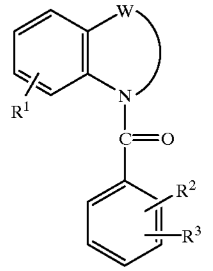

Recrystallization solvent: Ethanol
Melting Point: 103–105° C.
Form: Free
Example 361
Structure

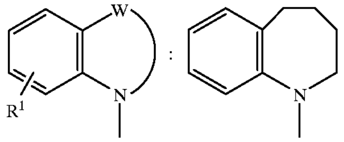

$R^2$: H

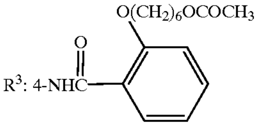

Crystalline form: White powder
Recrystallization solvent: Ethanol
Melting Point: 145–146° C.
Form: Free
Example 362
Structure

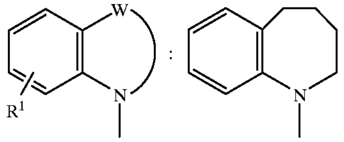

$R^2$: H

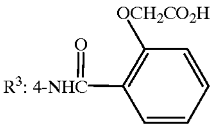

Crystalline form: White powder
Recrystallization solvent: Methanol/diethyl ether
Melting Point: 247–250° C.
Form: Free
Example 363
Structure

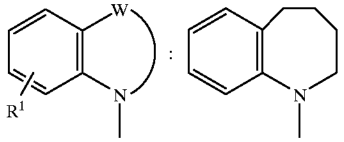

$R^2$: H

TABLE 1-continued

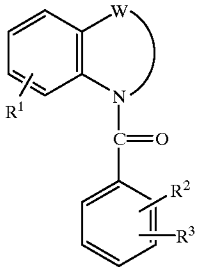

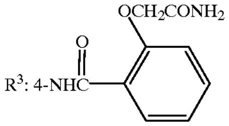

Crystalline form: White powder
Recrystallization solvent: Methanol/diethyl ether
Melting Point: 198–199° C.
Form: Free
Example 364
Structure

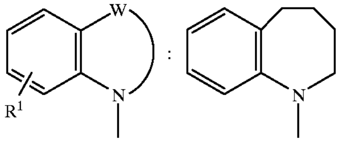

$R^2$: H

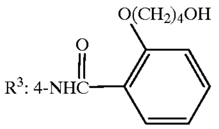

Crystalline form: White powder
Recrystallization solvent: Methanol/diethyl ether
Melting Point: 181.5–182.5° C.
Form: Free
Example 365
Structure

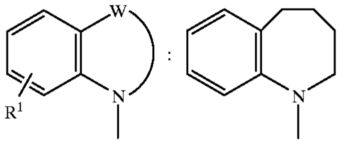

$R^2$: H

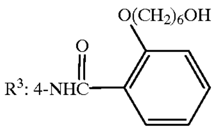

Crystalline form: White powder
Recrystallization solvent: Methanol/diethyl ether
Melting Point: 170–170.5° C.
Form: Free TABLE 1-continued

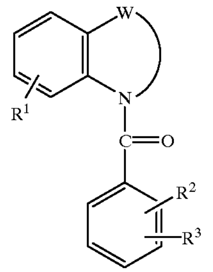

Example 366
Structure

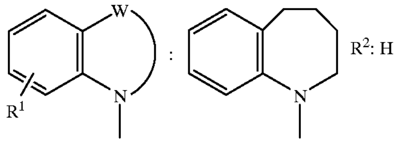

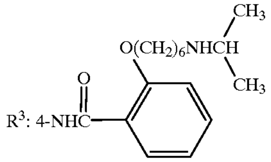

Crystalline form: White powder
Recrystallization solvent: Methanol/diethyl ether
Melting Point: 156–158° C.
Form: Hydrochloride
Example 367
Structure

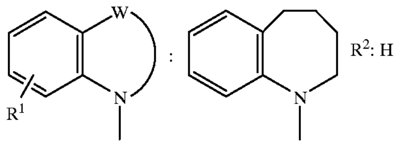

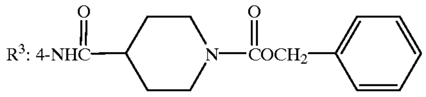

Crystalline form: White powder
Recrystallization solvent: Diethyl ether
Melting Point: 168.5–170.5° C.
Form: Free
Example 368
Structure

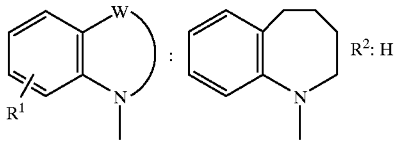

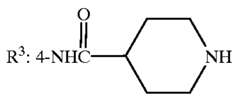

Crystalline form: White powder
Recrystallization solvent: Methanol/diethyl ether TABLE 1-continued

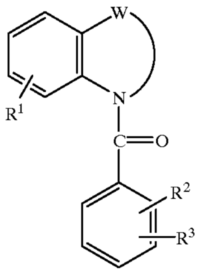

Melting Point: 177–181.5° C.
Form: Hydrochloride
Example 369
Structure

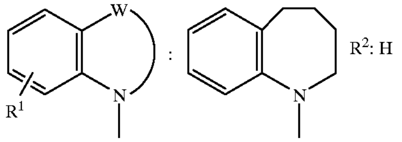

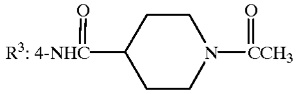

Crystalline form: White powder
Recrystallization solvent: Methanol/diethyl ether
Melting Point: 211–213° C.
Form: Free
Example 370
Structure

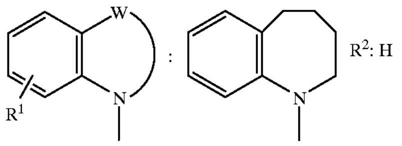

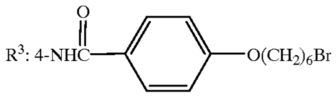

Crystalline form: White powder
NMR analysis: 46)
Form: Free
Example 371
Structure

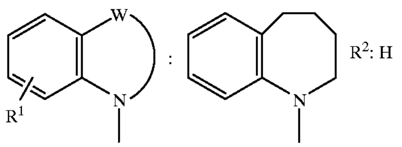

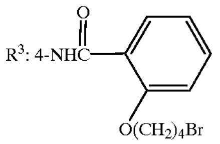

Crystalline form: White powder
Recrystallization solvent: Methanol/diethyl ether TABLE 1-continued

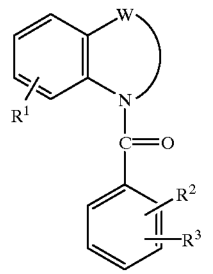

Melting Point: 166–167° C.
Form: Free
Example 372
Structure

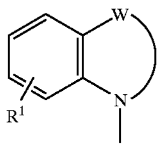
:
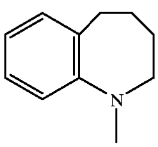
$R^2$: H

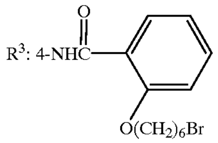

Crystalline form: White powder
Recrystallization solvent: Methanol/diethyl ether
Melting Point: 127–131° C.
Form: Free
Example 373
Structure

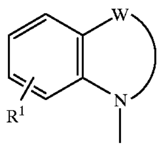
:
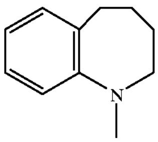
$R^2$: H

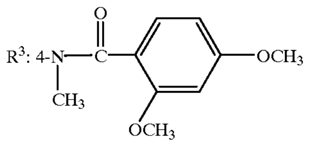

Crystalline form: White powder
Recrystallization solvent: Methanol
Melting Point: 170–171° C.
Form: Free
Example 374
Structure

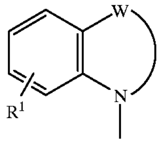
:
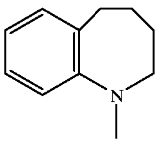
$R^2$: H

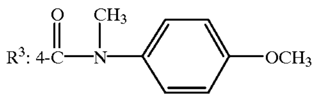

TABLE 1-continued

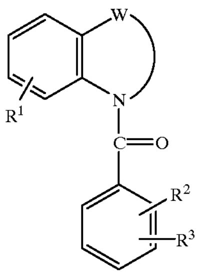

Crystalline form: White powder
Recrystallization solvent: Methanol
Melting Point: 125–126° C.
Form: Free
Example 375
Structure

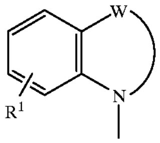
:
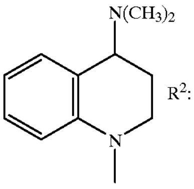
$R^2$: H

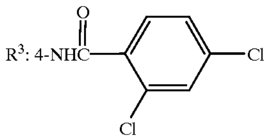

Crystalline form: Light yellow amorphous
NMR analysis: 47)
Form: Hydrochloride
Example 376
Structure

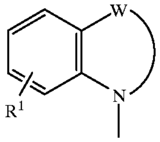
:
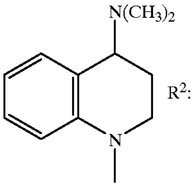
$R^2$: H

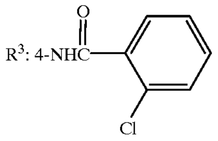

Crystalline form: Colorless amorphous
NMR analysis: 48)
Form: Free

1) $^1$H—NMR($CDCl_3$)δ: 1.92(1H, t, J=6.2Hz), 1.98 (1H, t, J=6.4Hz), 2.8(2H, t, J=6.4Hz), 3.76 (2H, t, J=6.2Hz), 6.75(1H, d, J=7.6Hz), 6.86 (2H, d, J=8.6Hz), 6.8–7.1(2H, m), 7.20(1H, d, J=7Hz), 7.30(2H, d), J=8.6Hz), 7.71(2H, d, J=8.6Hz), 7.84(2H, d, J=8.6Hz), 10.13(1H, s)

2) $^1$H—NMR(DMSO-$d_6$)δ: 2.05(2H, quint, J=6.4Hz), 2.91(2H, t, J=6.4Hz), 3.86(2H, t, J=6.4Hz), 6.85(1H, d, J=7.6Hz), 6.9–7.2(2H, m), 7.30(1H, d, J=7.2Hz), 7.44(2H, d, J=8.5Hz), 7.85(2H, d, TABLE 1-continued

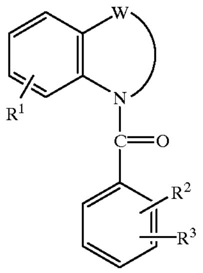

| |
|---|
| J=8.5Hz), 8.1–8.2(4H, m), 10.65(1H, s), 13.2–13.4(1H, br) |
| 3) $^1$H—NMR(CDCl$_3$)δ: 1.9–2.1(2H, m), 2.84(2H, t, J=6.5Hz), 3.82(6H, s), 3.90(2H, t, J=6.6Hz), 6.5–7.2(7H, m), 7.35(2H, d, J=8.7Hz), 7.55(2H, d, J=8.7Hz), 8.05(1H, s) |
| 4) $^1$H—NMR(CDCl$_3$)δ: 1.9–2.1(2H, m), 2.37(6H, s), 2.84(2H, t), J=6.6Hz), 3.90(2H, t, J=6.6Hz), 6.71(1H, d, J=7.9Hz), 6.8–7.2(4H, m), 7.35(2H, d, J=8.6Hz), 7.44(2H, s), 7.56(2H, d), J=8.6Hz), 8.00(1H, s) |
| 5) $^1$H—NMR(CDCl$_3$)δ: 1.9–2.2(2H, m), 2.12(3H, s), 2.84(2H, t, J=6.6Hz), 3.89(2H, t, J=6.5Hz), 6.71(1H, d, J=7.8Hz), 6.87(1H, t, J=7Hz), 6.99 (1H, t, J=7.3Hz), 7.15(1H, d, J=6.5Hz), 7.28 (2H, d, J=8.6Hz), 7.41(2H, d, J=8,6Hz), 8.03 (1H, s) |
| 6) $^1$H—NMR(CDCl$_3$)δ: 0.8–1.3(6H, m), 1.6–2.3(9H, m), 2.83(2H, t, J=6.6Hz), 3.89(2H, t, J=6.5Hz), 6.72(1H, d, J=7.9Hz), 6.8–7.1(2H, m), 7.15(1H, d, J=7.4Hz), 7.28(2H, d, J=8.3Hz), 7.44(2H, d, J=8.4Hz), 7.9–8.1(1H, m) |
| 7) $^1$H—NMR(CDCl$_3$)δ: 2.02(2H, quint, J=6.5Hz), 2.81(2H, t, J=6.6Hz), 3.69(2H, s), 3.87(2H, t, J=6.6Hz), 6.66(1H, d, J=8.2Hz), 6.8–7.0(2H, m), 7.13(1H, d, J=7.3Hz), 7.2–7.4(9H, m), 7.59(1H, s) |
| 8) $^1$H—NMR(CDCl$_3$)δ: 1.7–2.1(17H, m), 2.83(2H, t, J=6.7Hz), 3.90(2H, t, J=6.6Hz), 6.68(1H, d, J=8.1Hz), 6.8–7.1(2H, m), 7.14(1H, d, J=7Hz), 7.32(2H, d, J=8.7Hz), 7.39(1H, s), 7.46(2H, d, J=8.7Hz) |
| 9) $^1$H—NMR(CDCl$_3$)δ: 1.99(2H, quint, J=6.5Hz), 2.82(2H, t, J=6.6Hz), 3.82(2H, t, J=6.5Hz), 6.8–7.1(4H, m), 7.1–7.3(2H, m), 7.4–7.6(3H, m), 7.67(1H, s), 7.8–8.0(3H, m), 8.43(1H, s) |
| 10) $^1$H—NMR(CDCl$_3$)δ: 2.00(2H, quint, J=6.5Hz), 2.83(2H, t, J=6.6Hz), 3.85(2H, t, J=6.6Hz), 3.86(3H, s), 6.8–7.1(6H, m), 7.1–7.3(2H, m), 7.64(1H, s), 7.8–8.0(3H, m), 8.22(1H, s) |
| 11) $^1$H—NMR(CDCl$_3$)δ: 1.98(2H, quint, J=6.5Hz), 2.82(2H, t, J=6.5Hz), 3.81(2H, t, J=6.5Hz), 3.84(3H, s), 6.8–7.5(10H, m), 7.68(1H, s), 7.95 (1H, d, J=8.2Hz), 8.52(1H, s) |
| 12) $^1$H—NMR(CDCl$_3$)δ: 1.7–1.9(2H, m), 2.70(2H, t, J=6.6Hz), 3.70(2H, t, J=6.4Hz), 6.8–7.3(6H, m), 7.4–7.7(2H, m), 7.8–7.9(5H, m), 8.04(1H, d, J=8 Hz), 8.33(1H, s), 8.90(1H, s) |
| 13) $^1$H—NMR(CDCl$_3$)δ: 1.7–2.1(17H, m), 2.84(2H, t, J=6.5Hz), 3.89(2H, t, J=6.4Hz), 6.8–7.2(6H, m), 7.42(1H, s), 7.56(1H, s), 7.81(1H, d, J=8.1Hz) |
| 14) $^1$H—NMR(DMSO-d$_6$)δ: 1.0–1.5(5H, m), 1.5–2.0(5H, m), 2.2–3.8(8H, m), 4.2–5.2(3H, m), 6.77(1H, d, J=7.2Hz), 7.1–7.4(4H, m), 7.47(2H, d, J=8.6Hz), 7.58(1H, d, J=6.2Hz), 10.06(1H, s), 10.9–12.1 (1H, br) |
| 15) $^1$H—NMR(DMSO-d$_6$)δ: 2.5–3.8(6H, m), 4.2–5.2(3H, m), 6.81(1H, d, J=6.8Hz), 7.1–7.3(4H, m), 7.5–7.7(3H, m), 7.8–8.0(1H, m), 7.97(2H, d, J=1.8 Hz), 10.66(1H, s), 11.1–12.3(1H, br) |
| 16) $^1$H—NMR(DMSO-d$_6$)δ: 2.20(3H, s), 2.27(3H, s), 2.5–3.8(6H, m), 4.3–5.3(3H, m), 6.82(1H, d, J=7.2Hz), 7.1–7.4(7H, m), 7.5–7.8(3H, m), 10.43 (1H, s), 11.0–12.2(1H, br) |

TABLE 1-continued

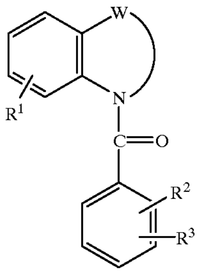

| |
|---|
| 17) $^1$H—NMR(DMSO-d$_6$)δ: 2.34(3H, s), 2.5–3.7(6H, m), 4.3–5.2(3H, m), 6.82(1H, d, J=6.8Hz), 7.2–7.7 (11H, m), 10.41(1H, s), 10.8–12.3(1H, br) |
| 18) $^1$H—NMR(DMSO-d$_6$)δ: 2.38(3H, s), 2.5–3.8(6H, m), 4.3–5.3(3H, m), 6.81(1H, d, J=7.0Hz), 7.1–7.5 (6H, m), 7.5–7.8(5H, m), 10.35(1H, s), 10.9–12.2 (1H, br) |
| 19) $^1$H—NMR(DMSO-d$_6$)δ: 2.37(3H, s), 2.5–3.7(6H, m), 4.3–5.2(3H, m), 6.81(1H, d, J=7.2Hz), 7.2–7.4 (6H, m), 7.5–7.7(3H, m), 7.84(2H, d, J=8.0Hz), 10.31(1H, s), 10.9–12.2(1H, br) |
| 20) $^1$H—NMR(DMSO-d$_6$)δ: 2.5–3.8(6H, m), 4.3–5.2(3H, m), 6.82(1H, d, J=7.4Hz), 7.2–7.3(4H, m), 7.5–7.8(5H, m), 7.75(1H, d, J=1.8Hz), 10.70(1H, s), 10.8–12.2(1H, br) |
| 21) $^1$H—NMR(DMSO-d$_6$)δ: 2.5–3.8(9H, m), 4.3–4.7(1H, m), 4.7–5.1(2H, m), 6.8–7.1(3H, m), 7.1–7.4(2H, m, 7.5–7.7(2H, m), 7.8–8.0(3H, m), 9.79(1H, s), 10.8–12.2(1H, br) |
| 22) $^1$H—NMR(DMSO-d$_6$)δ: 0.8–1.2(3H, m), 1.7–2.2(2H, m), 2.5–3.8(5H, m), 4.3–5.2(32H, m), 6.80(1H, d, J=7.2Hz), 7.1–7.3(4H, m), 7.6–7.7(3H, m), 7.85 (1H, s), 7.96(2H, d, J=1.8Hz), 10.62(1H, s), 10.8–12.0(1H, br) |
| 23) $^1$H—NMR(DMSO-d$_6$)δ: 0.8–1.1(3H, m), 1.7–2.1(2H, m), 2.37(3H, s), 2.7–3.8(5H, m), 4.4–5.2(3H, m), 6.81(1H, d, J=7.6Hz), 7.2–7.4(6H, m), 7.6–7.7 (3H, m), 7.84(2H, d, J=8.2Hz), 10.29(1H, s), 10.5–11.8(1H, br) |
| 24) $^1$H—NMR(DMSO-d$_6$)δ: 0.8–1.2(3H, m), 1.71–2.1(2H, m), 2.38(3H, s), 2.6–3.8(5H, m), 4.3–5.2(3H, m), 6.81(1H, d, J=7.0Hz), 7.2–7.5(6H, m), 7.6–7.8 (5H, m), 10.33(1H, s), 10.5–11.7(1H, br) |
| 25) $^1$H—NMR(DMSO-d$_6$)δ: 0.8–1.2(3H, m), 1.7–2.1(2H, m), 2.6–3.8(5H, m), 3.8–5.2(3H, m), 6.82(1H, d, J=7.2Hz), 7.1–7.5(8H, m), 7.5–7.76(3H, m), 10.42 (1H, s), 10.7–12.0(1H, br) |
| 26) $^1$H—NMR(DMSO-d$_6$)δ: 0.8–2.0(15H, m), 2.2–2.5(1H, m), 2.6–3.7(5H, m), 4.3–5.2(3H, m), 6.76(1H, d, J=7.0Hz), 7.1–7.4(4H, m), 7.46(2H, d, J=8.6Hz), 7.61(1H, d, J=6.4Hz), 10.03(1H, s), 10.5–11.8 (1H, br) |
| 27) $^1$H—NMR(DMSO-d$_6$)δ: 0.8–1.1(3H, m), 1.7–2.0(2H, m), 2.20(3H, s), 2.29(3H, s), 2.6–3.7(5H, m), 4.3–5.2(3H, m), 6.82(1H, d, J=7.0Hz), 7.2–7.4 (7H, m), 7.5–7.7(3H, m), 10.41(1H, s), 10.6–12.0 (1H, br) |
| 28) $^1$H—NMR(CDCl$_3$)δ: 1.21(3H, t, J=7.1Hz), 3.00–3.25(3H, m), 4.00–4.30(4H, m), 6.63(1H, d, J=7.8 Hz), 6.86(1H, t, J=7.3Hz), 7.00(1H, t, J=6.3 Hz), 7.10–7.31(3H, m), 7.40–7.57(3H, m), 7.77 (2H, d, J=1.9Hz), 8.76(1H, brs) |
| 29) $^1$H—NMR(CDCl$_3$)δ: 2.29(3H, s), 2.32(3H, s), 2.34 (3H, s), 2.50–3.15(11H, m), 3.79(1H, dd, J=13.2 Hz), 7.3Hz), 4.05(1H, dd, J=13.2Hz, 5.7Hz), 6.62 (1H, d, J=7.7Hz), 6.82–7.48(8H, m), 7.53(2H, d, J=8.4Hz), 8.05(1H, brs) |
| 30) $^1$H—NMR(CDCl$_3$)δ: 1.65–2.01(4H, m), 2.31(3H, s), 2.35(3H, s), 2.55–3.02(6H, m), 3.09(1H, dd, J=15Hz, 5Hz), 3.70(1H, dd), J=12.5Hz, 8.0Hz), 4.22(1H, dd, J=12.5Hz, 5Hz), 6.67(1H, d, J=7.8 Hz), 6.80–7.32(7H, m), 7.37(2H, d, J=8.6Hz), 7.53(1H, d, J=8.3Hz), 7.66(1H, brs) |

TABLE 1-continued

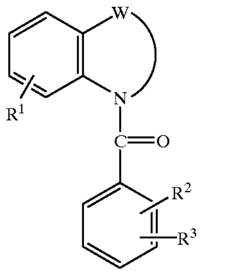

31) $^{1}$H—NMR($CDCl_3$)δ: 2.80(1H, dd, J=16.1Hz, 5.3 Hz), 3.16(1H, dd, J=15.8Hz, 5.3Hz), 3.75–4.50 (3H, m), 4.87–5.10(3H, m), 6.80–7.60(14H, m), 7.74(2H, d, J=1.9Hz), 8.47(1H, brs)

32) $^{1}$H—NMR($CDCl_3$)δ: 2.35(6H, s), 2.72–3.10(3H, m), 3.65–3.78(1H, m), 4.06–4.18(1H, m), 6.60–7.62 (9H, m), 7.74(2H, d, J=1.8Hz), 8.52(1H, brs)

33) $^{1}$H—NMR($CDCl_3$)δ: 1.87(3H, s), 2.68(1H, dd, J=5.6Hz, 16Hz), 3.14(1H, dd, J=5.6Hz, 16Hz), 3.70–3.95(2H, m), 4.32–4.50(1H, m), 6.29(1H, d, J=7.6Hz), 6.90–7.80(11H, m), 9.16(1H, brs)

34) $^{1}$H—NMR($CDCl_3$)δ: 1.62(1H, brs), 1.90–2.25(2H, m), 2.55(3H, s), 3.78(1H, t, J=5.1Hz), 3.95(2H, t, J=6.7Hz), 6.69(1H, t, J=7.9Hz), 6.90–7.13 (2H, m), 7.23–7.40(3H, m), 7.42–7.56(3H, m), 7.77 (2H, d, J=1.9Hz), 8.53(1H, brs)

35) $^{1}$H—NMR($CDCl_3$)δ: 1.80–2.02(1H, m), 2.20–2.35 (1H, m), 2.31(6H, s), 3.52(1H, t, J=5.4Hz), 3.68–3.83(1H, m), 3.95–4.15(1H, m), 6.59(1H, d, J=7.8Hz), 6.81–7.10(2H, m), 7.16–7.50(6H, m), 7.80(2H, d, J=1.8Hz), 9.13(1H, brs)

36) $^{1}$H—NMR($CDCl_3$)δ: 1.35–1.60(1H, m), 1.65–2.20 (3H, m), 2.65–3.20(5H, m), 3.81(2H, d, J=6.5Hz), 4.90–5.10(1H, m), 6.60(1H, d, J=8.0Hz), 6.90 (1H, t, J=8.0Hz), 7.00–7.50(6H, m)

37) $^{1}$H—NMR($CDCl_3$)δ: 1.30–2.25(4H, m), 2.55–3.20 (3H, m), 3.35(2H, s), 3.80(2H, s), 4.90–5.10(1H, m), 6.62(1H, d, J=8.0Hz), 6.85–7.45(12H, m), 9.27(1H, br)

38) $^{1}$H—NMR($CDCl_3$)δ: 1.35–2.25(4H, m), 2.33(3H, s), 2.60–3.20(3H, m), 3.12(2H, s), 3.61(2H, s), 5.00 (1H, brs), 6.50–7.60(13H, m), 9.14(1H, brs)

39) $^{1}$H—NMR($CDCl_3$)δ: 1.27(3H, t, J=7.1Hz), 1.25–2.50(12H, m), 2.70–3.10(4H, m), 3.05(2H, s), 4.15(2H, q, J=7.0Hz), 4.90–5.10(1H, m), 6.63 (1H, d, J=7.5Hz), 6.91(1H, t, J=7.5Hz), 7.00–7.50(6H, m), 9.14(1H, brs)

40) $^{1}$H—NMR($CDCl_3$)δ: 1.30–1.65(1H, m), 1.80–2.25 (5H, m), 2.70–3.20(3H, m), 4.01(2H, d, J=5.0Hz), 4.90–5.10(1H, m), 6.61(1H, d, J=7.7Hz), 6.89 (1H, t, J=7.0Hz), 7.00–7.45(6H, m), 9.05(1H, brs)

41) $^{1}$H—NMR($CDCl_3$)δ: 1.18(6H, s), 1.30–2.20(4H, m), 2.60–3.20(3H, m), 3.30(2H, s), 3.373(2H, s), 4.90–5.10(1H, m), 6.61(1H, d, J=7.3Hz), 6.70–7.45(12H, m), 9.50(1H, brs)

42) $^{1}$H—NMR($CDCl_3$)δ: 1.19(3H, t, J=7.0Hz), 1.30–1.70(1H, m), 1.75–2.20(3H, m), 2.65–3.15(3H, m), 3.46(2H, q, J=7.0Hz), 3.88(2H, s), 4.90–5.10 (1H, m), 6.55–7.45(13H, m), 8.36(1H, brs)

43) $^{1}$H—NMR($CDCl_3$)δ: 1.08(3H, t, J=7.2Hz), 1.05–2.25(14H, m), 2.25–3.25(10H, m), 4.90–5.10(1H, m), 6.64(1H, d, J=7.6Hz), 6.90(1H, t, J=7.2Hz), 6.94–7.50(6H, m), 11.50(1H, brs)

44) $^{1}$H—NMR($CDCl_3$)δ: 1.06(3H, t, J=7.5Hz), 1.30–2.20(6H, m), 2.60–3.20(3H, m), 3.65(1H, m), 3.95 (1H, brs), 4.90–5.10(1H, m), 6.50–6.75(3H, m), 6.75–7.05(2H, m), 7.05–7.55(8H, m), 8.67(1H, brs)

45) $^{1}$H—NMR(DMSO-$d_6$)δ: 1.28–1.57(1H, m), 1.69–2.20 (3H, m), 2.59–3.15(3H, m), 4.74–4.98(1H, m), 6.62–6.80(1H, m), 6.86–7.37(5H, m), 7.50–7.70 (2H, m), 8.95–9.02(1H, m), 9.03–9.15(2H, m), 10.85(1H, s)

TABLE 1-continued

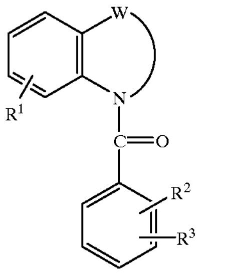

46) $^{1}$H—NMR($CDCl_3$)δ: 1.40–1.66(5H, m), 1.72–2.20 (7H, m), 2.63–3.18(3H, m), 3.42(2H, t, J=6.7Hz), 4.00(2H, t, J=6.3Hz), 4.91–5.13(1H, m), 6.58–6.72(1H, m), 6.82–7.00(3H, m), 7.02–7.30(4H, m), 7.36–7.51(2H, m), 7.70–7.88(2H, m), 7.91(1H, s)

47) $^{1}$H—NMR(DMSO-$d_6$)δ: 2.05–2.95(8H, m), 3.43–3.70 (1H, m), 4.08–4.30(1H, m), 4.72–5.00(1H, m), 6.70–8.08(11H, m), 10.8(1H, s), 11.1(1H, brs)

48) $^{1}$H—NMR(DMSO-$d_6$)δ: 2.10–3.00(8H, m), 3.47–3.70 (1H, m), 4.07–4.33(1H, m), 4.75–4.98(1H, m), 6.78–6.91(1H, m), 7.05–7.22(2H, m), 7.30–7.97 (9H, m), 10.75(1H, s), 10.94(1H, brs)

EXAMPLE 377

To a solution of 1-[4-(4-formylbenzoylamino)benzoyl]-1,2,3,4-tetrahydroquinoline (0.3 g) in methanol (10 ml) is added gradually sodium borohydride (59 mg) under ice-cooling and the mixture is stirred at room temperature for 2 hours. Water is added to the mixture and the solvent is distilled off under reduced pressure. The resulting residue is extracted with dichloromethane, washed with water, and dried over magnesium sulfate. The solvent is distilled off under reduced pressure and the resulting residue is purified by silica gel column chromatography (eluent; dichloromethane:methanol=50:1), and recrystallized from methanol to give 1-[4-(4-hydroxymethylbenzoylamino)benzoyl]-1,2,3,4-tetrahydroquinoline (165 mg) as white powder, m.p. 224.5–225.5° C.

Using the suitable starting materials, the compound of the above Example 37 is obtained in the same manner as in Example 377.

EXAMPLE 378

To a solution of 1-[4-(4-methoxycarbonylbenzoylamino)benzoyl]- 1,2,3,4-tetrahydroquinoline (0.5 g) in methanol (20 ml) is added 5% aqueous sodium hydroxide solution (10 ml) and the mixture is stirred at room temperature overnight. Methanol is distilled off under reduced pressure and the resulting residue is acidified with diluted aqueous hydrochloric acid solution. The precipitated crystal is collected by filtration to give 1-[4-(4-carboxybenzoylamino)benzoyl]-1,2,3,4-tetrahydroquinoline (0.4 g) as white powder, m.p. >300° C.

$^{1}$H-NMR (DMSO-$d_6$) δ: 2.05 (2H, quint, J=6.4 Hz), 2.91 (2H, t, J=6.4 Hz), 3.86 (2H, t, J=6.4 Hz), 6.85 (1H, d, J=7.6 Hz), 6.9–7.2 (2H, m), 7.30 (1H, d, J=7.2 Hz), 7.44 (2H, d, J=8.5 Hz), 7.85 (2H, d, J=8.5 Hz), 8.1–8.2 (4H, m), 10.65 (1H, s), 13.2–13.4 (1H, br)

Using the suitable starting materials, the compounds of the above Examples 39, 241, 252, 253 and 362 are obtained in the same manner as in Example 378.

EXAMPLE 379

To a solution of 1-[4-(3-acetyloxybenzoylamino) benzoyl]-1,2,3,4-tetrahydroquinoline (1.5 g) in methanol (20 ml) is added 5% aqueous sodium hydroxide solution (10 ml) and the mixture is stirred at room temperature overnight. Methanol is distilled off under reduced pressure and the resulting residue is acidified with diluted aqueous hydrochloric acid solution. The precipitated crystal is collected by filtration and recrystallized from methanol to give 1-[4-(3-hydroxybenzoylamino)benzoyl]-1,2,3,4-tetrahydroquinoline (1.22 g) as white powder, m.p. 217–218° C.

Using the suitable starting materials, the compounds of the above Examples 10, 343, 356, 364 and 365 are obtained in the same manner as in Example 379.

EXAMPLE 380

To a solution of 1-[4-(3-hydroxybenzoylamino)benzoyl]-1,2,3,4-tetrahydroquinoline (0.4 g) in acetone (5 ml) are added potassium carbonate (0.22 g) and ethyl iodide (0.34 g), and the mixture is refluxed for 5 hours. Then, acetone is distilled off under reduced pressure and water is added to the residue. The precipitated crystal is collected by filtration, and recrystallized from methanol to give 1-[4-(3-ethoxybenzoylamino)benzoyl]-1,2,3,4-tetrahydroquinoline (0.36 g) as white powder, m.p. 170.5–171.5° C.

Using the suitable starting materials, the compounds of the above Examples 11, 12, 13, 14, 33, 35, 48, 50–55, 90–92, 97–100, 109–111, 120–122, 136–138, 165–167, 175–177, 192–194, 211, 212, 214, 321, 322, 330–333, 335, 336, 339–342, 344–355, 357–366 and 370–374 are obtained in the same manner as in Example 380.

EXAMPLE 381

Ethanol (50 ml) is added to 10% Pd-C (0.1 g) and thereto is added 1-[4-(3-nitrobenzoylamino)benzoyl]-1,2,3,4-tetrahydroquinoline (0.73 g). The mixture is subjected to catalytic reduction at ordinary temperature under atmospheric pressure of hydrogen. After completion of the reduction, 10% Pd-C is removed by filtration and the filtrate is concentrated under reduced pressure. The residue is extracted with dichloromethane and the extract is dried over magnesium sulfate. The solvent is distilled off under reduced pressure and recrystallized from methanol to give 1-[4-(3-aminobenzoylamino)benzoyl]-1,2,3,4-tetrahydroquinoline (0.54 g) as white powder, m.p. 205.5–206.5° C.

Using the suitable starting materials, the compounds of the above Examples 24, 334 and 338 are obtained in the same manner as in Example 381.

EXAMPLE 382

To a solution of 1-(4-aminobenzoyl)-1,2,3,4-tetrahydroquinoline (0.5 g) in dichloromethane (20 ml) is added triethylamine (0.3 g), and thereto is added benzoyl chloride (0.28 g) under ice-cooling. The mixture is stirred at room temperature for 1 hour. To the reaction mixture is added water and extracted with dichloromethane. The extract is dried over magnesium sulfate and the solvent is distilled off under reduced pressure. The resulting residue is purified by silica gel column chromatography (eluent; dichloromethane:methanol=50:1) and recrystallized from methanol to give 1-[4-(benzoylamino)benzoyl]-1,2,3,4-tetrahydroquinoline (245 mg) as white powder, m.p. 202.5–203.5° C.

Using the suitable starting materials, the compounds of the above Examples 2–119, 131–373, 375 and 376 are obtained in the same manner as in Example 382.

EXAMPLE 383

Thionyl chloride (10 ml) is added to 1-(4-carboxybenzoyl)-1,2,3,4-tetrahydroquinoline (0.5 g) and the mixture is refluxed for 1 hour. Thionyl chloride is distilled off under reduced pressure to give 4-[1-(1,2,3,4-tetrahydroquinolyl)carbonyl]benzoyl chloride. Separately, to a solution of m-anisidine (0.27 g) in dichloromethane (20 ml) is added triethylamine (0.34 g), and thereto is added gradually the above obtained 4-[1-(1,2,3,4-tetrahydroquinolyl)carbonyl]benzoyl chloride under ice-cooling and the mixture is stirred at room temperature for 1 hour. Water is added to the reaction mixture and the mixture is extracted with dichloromethane. The extract is dried over magnesium sulfate. The solvent is distilled off under reduced pressure and the resulting residue is purified by silica gel column chromatography (eluent; dichloromethane:methanol=50:1), and recrystallized from methanol to give 1-[4-(3-methoxyanilinocarbonyl)benzoyl]-1,2,3,4-tetrahydroquinoline (203 mg) as colorless needles, m.p. 154–155° C.

Using the suitable starting materials, the compounds of the above Examples 120, 122–130 and 374 are obtained in the same manner as in Example 383.

EXAMPLE 384

To 4-oxo-1-[4-(3,5-dichlorobenzoylamino)benzoyl]-1,2,3,4-tetrahydroquinoline (0.7 g) are added tetrahyrdofuran (10 ml) and methanol (10 ml). To the mixture is added sodium borohydride (0.1 g) in portions and the mixture is stirred at room temperature for 1 hour. Water is added to the reaction mixture and the mixture is extracted with dichloromethane. The solvent is concentrated and the resulting residue is purified by silica gel column chromatography (eluent; dichloromethane→dichloromethane:methanol=20:1), and recrystallized from ethanol to give 4-hydroxy-1-[4-(3,5-dichlorobenzoylamino)benzoyl]-1,2,3,4-tetrahydroquinoline (0.4 g) as white powder, m.p. 215–217° C.

EXAMPLE 385

To 3-ethoxycarbonyl-1-[4-(3,5-dichlorobenzoylamino) benzoyl]-1,2,3,4-tetrahydroquinoline (0.6 g) are added an aqueous solution of sodium hydroxide (0.1 g) in water (1 ml) and ethanol (5 ml). The mixture is stirred at room temperature for 15 minutes, and acidified with diluted hydrochloric acid, extracted with dichloromethane. The solvent is distilled off and the resulting residue is purified by silica gel column chromatography (eluent; dichloromethane→dichloromethane:methanol=50:1), and recrystallized from ethanol to give 3-carboxy-1-[4-(3,5-dichlorobenzoylamino)benzoyl]-1,2,3,4-tetrahydroquinoline (0.4 g) as white powder, m.p. 221–223° C.

EXAMPLE 386

To 3-carboxy-1-[4-(3,5-dichlorobenzoylamino)benzoyl]-1,2,3,4-tetrahydroquinoline (3.7 g) are added tetrahydrofuran (50 ml) and thionyl chloride (5 ml). The mixture is reacted at 60° C. for 1 hour. The reaction mixture is concentrated and to the residue is added acetone (20 ml). To the mixture is added dropwise a solution of sodium azide (1.0 g) in water (5 ml) under ice-cooling. The reaction mixture is stirred at the same temperature for 30 minutes and extracted with dichloromethane, dried over magnesium sulfate. The solvent is concentrated and to the resulting residue are added anhydrous toluene (30 ml) and benzyl alcohol (1.7 g). The mixture is refluxed for 1 hour. The reaction mixture is concentrated and the resulting residue is purified by silica gel column chromatography (eluent; dichloromethane→dichloromethane:methanol=50:1) to give 3-benzyloxycarbonylamino-1-[4-(3,5-dichlorobenzoylamino)benzoyl)-1,2,3,4-tetrahydroquinoline (3.7 g) as colorless amorphous.

$^1$H-NMR ($CDCl_3$) δ: 2.80 (1H, dd, J=16.1 Hz, 5.3 Hz), 3.16 (1H, dd, J=15.8 Hz, 5.3 Hz), 3.75–4.50 (3H, m), 4.87–5.10 (3H, m), 6.80–7.60 (14H, m), 7.74 (2H, d, J=1.9 Hz), 8.47 (1H, brs)

EXAMPLE 387

To 3-benzyloxycarbonylamino-1-[4-(3,5-dichlorobenzoylamino)benzoyl]-1,2,3,4-tetrahydroquinoline (3.3 g) are added acetic acid (40 ml) and 10% Pd-C (0.4 g) and the reaction mixture is subjected to catalytic reduction at ordinary temperature under atmospheric pressure of hydrogen. One hour thereafter, the catalyst is removed by filtration and the filtrate is concentrated. The resulting residue is purified by silica gel column chromatography (eluent; dichloromethane:methanol=20:1), and recrystallized from ethanol to give 3-amino-1-[4-(3,5-dichlorobenzoylamino)benzoyl]-1,2,3,4-tetrahydroquinoline (1.6 g) as white powder, m.p. 207–210° C.

EXAMPLE 388

To 3-amino-1-[4-(3,5-dichlorobenzoylamino)benzoyl]-1,2,3,4-tetrahydroquinoline (0.5 g) are added methanol (10 ml), 37% formaline (0.8 ml) and sodium cyanoborohydride (0.16 g). To the mixture is added acetic acid (0.5 ml) under ice-cooling and the mixture is stirred at room temperature for 1 hour. Water is added to the reaction mixture and the mixture is basified with potassium carbonate and extracted with dichloromethane. The solvent is concentrated and the resulting residue is purified by silica gel column chromatography (eluent; dichloromethane→dichloromethane:methanol=20:1) to give 3-dimethylamino-1-[4-(3,5-dichlorobenzoylamino)benzoyl]-1,2,3,4-tetrahydroquinoline (0.3 g) as colorless amorphous.

$^1$H-NMR ($CDCl_3$) δ: 2.35 (6H, s), 2.72–3.10 (3H, m), 3.65–3.78 (1H, m), 4.06–4.18 (1H, m), 6.60–7.62 (9H, m), 7.74 (2H, d, J=1.8 Hz), 8.52 (1H, brs)

Using the suitable starting materials, the compounds of the above Examples 246, 247, 375 and 376 are obtained in the same manner as in Example 388.

EXAMPLE 389

To 3-amino-1-[4-(3,5-dichlorobenzoylamino)benzoyl]-1,2,3,4-tetrahydroquinoline (0.44 g) are added dichloromethane (5 ml) and acetic anhydride (0.12 g) and the mixture is stirred for 1 hour. The reaction mixture is concentrated and the resulting residue is purified by silica gel column chromatography (eluent; dichloromethane→dichloromethane:methanol=50:1) to give 3-acetylamino-1-[4-(3,5-dichlorobenzoylamino)benzoyl]-1,2,3,4-tetrahydroquinoline (0.3 g) as colorless amorphous.

$^1$H-NMR ($CDCl_3$) δ: 1.87 (3H, s), 2.68 (1H, dd, J=5.6 Hz, 16 Hz), 3.14 (1H, dd, J=5.6 Hz, 16 Hz), 3.70–3.95 (2H, m), 4.32–4.50 (1H, m), 6.29 (1H, d, J=7.6 Hz), 6.90–7.80 (11H, m), 9.16 (1H, brs)

Using the suitable starting materials, the compound of the above Example 242 is obtained in the same manner as in Example 389.

EXAMPLE 390

To 4-oxo-1-[4-(3,5-dichlorobenzoylamino)benzoyl]-1,2,3,4-tetrahydroquinoline (0.5 g) are added 40% solution of methylamine in methanol (5 ml), molecular sieves 4A (1 g) and dimethylformamide (6 ml), and the mixture is refluxed for 4 hours. After cooling, the reaction mixture is filtered and to the filtrate is added sodium borohydride (80 mg), and the mixture is stirred at room temperature for 1 hour. The reaction mixture is concentrated and water is added to the resulting residue, and extracted with ethyl acetate. The solvent is concentrated and the resulting residue is purified by silica gel column chromatography (eluent; dichloromethane:methanol=20:1) to give 4-methylamino-1-[4-(3,5-dichlorobenzoylamino)benzoyl]-1,2,3,4-tetrahydroquinoline (0.2 g) as colorless amorphous.

$^1$H-NMR ($CDCl_3$) δ: 1.62 (1H, brs), 1.90–2.25 (2H, m), 2.55 (3H, s), 3.78 (1H, t, J=5.1 Hz), 3.95 (2H, t, J=6.7 Hz), 6.99 (1H, d, J=7.9 Hz), 6.90–7.13 (2H, m)

Using the suitable starting materials, the compounds of the above Examples 238, 239, 244, 247, 375 and 376 are obtained in the same manner as in Example 390.

EXAMPLE 391

To 3-carboxy-1-[4-(3,5-dichlorobenzoylamino)benzoyl]-1,2,3,4-tetrahydroquinoline (0.7 g) are added dimethylformamide (7 ml), diethyl cyanophosphate (0.3 ml) and dimethylamine hydrochloride (0.15 g). Further thereto is added triethylamine (0.8 ml) and the mixture is stirred at room temperature for 1 hour. Water is added to the reaction mixture and extracted with ethyl acetate. The solvent is concentrated and to the resulting residue is added diethyl ether. The precipitated crystal is collected by filtration to give 3-dimethylamido-1-[4-(3,5-dichlorobenzoylamino)benzoyl]-1,2,3,4-tetrahydroquinoline (0.5 g) as light yellow powder, m.p. 186–187° C.

EXAMPLE 392

To a solution of 1-(4-aminobenzoyl)-2,3,4,5-tetrahydro-1H-benzazepine (3.0 g) in dichloromethane (50 ml) is added succinic anhydride (1.4 g) and the mixture is stirred at room temperature for 4.5 hours. The reaction mixture is evaporated under reduced pressure in order to remove the solvent therefrom, and the resulting crystal is recrystallized from ethyl acetate to give 1-[4-(3-carboxypropionylamino)benzoyl]-2,3,4,5-tetrahydro-1H-benzazepine (3.61 g) as colorless needles, m.p. 192° C.

Using the suitable starting materials, the compound of the above Example 253 is obtained in the same manner as in Example 392.

EXAMPLE 393

1-[4-(3-Carboxypropionylamino)benzoyl]-2,3,4,5-tetrahydro-1H-benzazepine (0.5 g) is dissolved in dimethylformamide (1 ml) and thereto is added dropwise diethyl cyanophosphate (0.25 g) under ice-cooling. The mixture is stirred at room temperature for 30 minutes and then cooled again with ice. Thereto are added dropwise a solution of diethylamine (0.11 g) in dimethylformamide (1 ml) and triethylamine (0.34 g). The mixture is stirred at room temperature for 16 hours. The solvent is distilled off under reduced pressure and water is added to the resulting residue. The mixture is extracted with dichloromethane. The organic layer is washed successively with diluted hydrochloric acid, water, saturated sodium hydrogen carbonate solution, water and saturated saline solution, and dried over magnesium sulfate. The solvent is distilled off under reduced pressure and the resulting residue is purified by silica gel column chromatography (eluent; ethyl acetate), and recrystallized from n-hexane/ethyl acetate to give 1-[4-(3-diethylaminocarbonylpropionylamino)benzoyl]-2,3,4,5-tetrahydro-1H-benzazepine (0.42 g) as colorless scales, m.p. 165–167° C.

Using the suitable starting materials, the compounds of the above Examples 255–263 are obtained in the same manner as in Example 393.

EXAMPLE 394

To a solution of 1-[4-(2-chloroacetylamino)benzoyl]-2,3,4,5-tetrahydro-1H-benzazepine (2.06 g) in dimethylformamide (5 ml) are added sodium iodide (0.90 g), potassium carbonate (1.1 g) and cyclohexylamine (0.89 g), and the mixture is stirred at room temperature for 2 hours. Dimethylformamide is distilled off under reduced pressure and water is added to the resulting residue. The mixture is extracted with dichloromethane. The organic layer is washed successively with water and saturated saline solution, and dried over magnesium sulfate. The solvent is distilled off under reduced pressure and the resulting residue is purified by silica gel column chromatography (eluent; ethyl acetate), and recrystallized from n-hexane/ethyl acetate to give 1-[4-(2-cyclohexylaminoacetylamino)benzoyl]-2,3,4,5-tetrahydro-1H-benzazepine (2.03 g) as white powder, m.p. 139–142° C.

Using the suitable starting materials, the compounds of the above Examples 271–309 and 317 are obtained in the same manner as in Example 394.

EXAMPLE 395 o-Cresol (0.36 g) is dissolved in dimethylsulfoxide (4 ml) containing sodium hydroxide powder (0.18 g) and thereto is added 1-[4-(2-chloroacetylamino)benzoyl]-2,3,4,5-tetrahydro-1H-benzazepine (1.03 g). The mixture is stirred at 90° C. for 7.5 hours. The reaction mixture is poured into ice-water (300 ml) and the precipitated crystal is collected by filtration, washed with water, and purified by silica gel column chromatography (eluent; n-hexane:ethyl acetate=2:1), and recrystallized from ethyl acetate to give 1-{4-[2-(2-methylphenoxy)acetylamino]benzoyl}-2,3,4,5-tetrahydro-1H-benzazepine (546 mg) as colorless scales, m.p. 172.5–175° C.

Using the suitable starting materials, the compounds of the above Examples 310 and 312–316 are obtained in the same manner as in Example 395.

EXAMPLE 396

A mixture of 1-{4-[2-(6-bromohexyloxy)benzoylamino]benzoyl}- 2,3,4,5-tetrahydro-1H-benzazepine (2.00 g), sodium acetate (0.36 g), sodium iodide (0.55 g) and acetic acid (20 ml) is refluxed for 1 day. The solvent is distilled off and the resulting residue is extracted with ethyl acetate. The organic layer is washed successively with 2N aqueous sodium hydroxide solution and saturated saline solution, and dried over magnesium sulfate. The solvent is concentrated and the resulting residue is purified by silica gel column chromatography (eluent; chloroform:methanol=500:1), and recrystallized from ethanol to give 1-{4-[2-(6-acetyloxyhexyloxy)benzoylamino]benzoyl}-2,3,4,5-tetrahydro-1H-benzazepine (1.07 g) as white powder, m.p. 145–146° C.

Using the suitable starting materials, the compound of the above Example 360 is obtained in the same manner as in Example 396.

EXAMPLE 397

A mixture of 1-{4-[2-(6-bromohexyloxy)benzoylamino]benzoyl}-2,3,4,5-tetrahydro-1H-benzazepine (0.70 g), diethylamine (0.16 ml), triethylamine (0.21 ml) and acetonitrile (20 ml) is refluxed overnight. The solvent is distilled off and the resulting residue is dissolved in chloroform, washed successively with water and saturated saline solution, and dried over magnesium sulfate. The solvent is distilled off and the resulting residue is purified by silica gel column chromatography (eluent; chloroform:methanol=200:1→50:1) and converted into the hydrochloride thereof in methanol. The product is recrystallized from methanol/diethyl ether to give 1-{4-[2-(6-diethylaminohexyloxy)benzoylamino]benzoyl}-2,3,4,5-tetrahydro-1H-benzazepine hydrochloride (0.42 g) as white powder, m.p. 91–95° C.

Using the suitable starting materials, the compounds of the above Examples 330, 332, 333, 335, 336, 339, 341, 342, 344–349, 352–355, 357 and 366 are obtained in the same manner as in Example 397.

EXAMPLE 398

A mixture of 1-{4-[2-(6-bromohexyloxy)benzoylamino]benzoyl}-2,3,4,5-tetrahydro-1H-benzazepine (4.00 g), potassium phthalimide (2.02 g) and dimethylformamide (100 ml) is stirred at 100° C. for 5 hours. The reaction mixture is filtered and the filtrate is distilled off. The resulting residue is extracted with ethyl acetate and the organic layer is washed successively with water and saturated saline solution, and dried over magnesium sulfate. The solvent is distilled off and the resulting residue is purified by silica gel column chromatography (eluent; dichloromethane), and recrystallized from methanol/diethyl ether to give 1-{4-[2-(6-phthalimidohexyloxy)benzoylamino]benzoyl}-2,3,4,5-tetrahydro-1H-benzazepine (4.06 g) as white powder, m.p. 145–146.5° C.

Using the suitable starting materials, the compounds of the above Examples 331, 340, 364 and 365 are obtained in the same manner as in Example 398.

EXAMPLE 399

A mixture of 1-{4-[2-[6-phthalimidohexyloxy)benzoylamino]benzoyl}-2,3,4,5-tetrahydro-1H-benzazepine (3.75 g), hydrazine hydrate (0.44 ml) and ethanol (30 ml) is refluxed for 3.5 hours. The precipitated crystal is collected by filtration, dried and purified by silica gel column chromatography (eluent; chloroform:methanol:aqueous ammonia=100:10:1), and recrystallized from methanol/diethyl ether to give 1-{4-[2-(6-aminohexyloxy)benzoylamino]benzoyl}-2,3,4,5-tetrahydro-1H-benzazepine (2.52 g) as white powder, m.p. 135.5–137.5° C.

Using the suitable starting materials, the compounds of the above Examples 284, 344 and 345 are obtained in the same manner as in Example 399.

EXAMPLE 400

A mixture of 1-{4-[2-(6-aminohexyloxy)benzoylamino]benzoyl}-2,3,4,5-tetrahydro-1H-benzazepine (0.70 g), acetic anhydride (20 ml) and two drops of conc. sulfuric acid is stirred at room temperature for 3 hours. To the reaction mixture is added aqueous 2N aqueous sodium hydroxide solution under ice-cooling and the mixture is extracted with chloroform. The organic layer is washed successively with water and saturated saline solution, and dried over magnesium sulfate. The solvent is distilled off and the resulting residue is purified by silica gel column chromatography (eluent; chloroform:methanol=200:1), and recrystallized from methanol/diethyl ether to give 1-{4-[2-(6-acetylaminohexyloxy)benzoylamino]benzoyl}-2,3,4,5-tetrahydro-1H-benzazepine (0.60 g) as colorless needles, m.p. 171–172° C.

EXAMPLE 401

A mixture of 1-{4-[2-(6-aminohexyloxy)benzoylamino]benzoyl}-2,3,4,5-tetrahydro-1H-benzazepine (0.70 g), benzoyl chloride (0.20 ml), triethylamine and dichloromethane (20 ml) is stirred at room temperature for 1 hour. The reaction mixture is washed successively with water and saturated saline solution, and dried over magnesium sulfate. The solvent is concentrated and the resulting residue is recrystallized from ethanol to give 1-{4-[2-(6-benzoylaminohexyloxy)benzoylamino]benzoyl}-2,3,4,5-tetrahydro-1H-benzazepine (0.71 g) as white powder, m.p. 178–178.5° C.

Using the suitable starting materials, the compounds of the above Examples 348 and 357 are obtained in the same manner as in Examples 400 and 401.

EXAMPLE 402

A mixture of 1-[4-(2-ethoxycarbonylmethoxybenzoylamino)benzoyl]-2,3,4,5-tetrahydro-1H-benzazepine (1.00 g), aqueous ammonia (100 ml), ammonium chloride (0.3 g) and methanol (150 ml) is heated at 100° C. for 4 hours in a sealed tube. The solvent is distilled off and the resulting residue is extracted with chloroform, washed successively with water and saturated saline solution, and dried over magnesium sulfate. The solvent is concentrated and the resulting residue is purified by silica gel column chromatography (eluent; chloroform:methanol=50:1), and recrystallized from methanol/diethyl ether to give 1-[4-(2-carbamoylmethoxybenzoylamino)benzoyl]-2,3,4,5-tetrahydro-1H-benzazepine (0.43 g) as white powder, m.p. 198–199° C.

EXAMPLE 403

A mixture of 1-[4-(2-chloro-4-aminobenzoylamino)benzoyl]-2,3,4,5-tetrahydro-1H-benzazepine (0.55 g), acetic anhydride (15 ml), acetic acid (5 ml) and a drop of sulfuric acid is stirred at room temperature for 1 hour. To the reaction mixture is added aqueous 2N aqueous sodium hydroxide solution and the mixture is extracted with chloroform. The extract is washed with saturated saline solution and dried over magnesium sulfate. The solvent is concentrated and the resulting residue is recrystallized from methanol/diethyl ether to give 1-[4-(2-chloro-4-acetylaminobenzoylamino)benzoyl]-2,3,4,5-tetrahydro-1H-benzazepine (0.28 g) as white powder, m.p. 214–243° C.

Using the suitable starting materials, the compound of the above Example 44 is obtained in the same manner as in Example 403.

EXAMPLE 404

A mixture of 1-[4-(1-benzyloxycarbonyl-4-piperidinylcarbonylamino)benzoyl]-2,3,4,5-tetrahydro-1H-benzazepine (8.00 g), 10% Pd-C (0.8 g) and ethanol (250 ml) is subjected to catalytic hydrogenation at 50° C. under 4 atm. of hydrogen pressure for 6 hours. The catalyst is removed by filtration and the filtrate is evaporated under reduced pressure. The resulting residue is extracted with ethyl acetate and washed successively with water and saturated saline solution, and dried over magnesium sulfate. The solvent is distilled off and the resulting residue is purified by silica gel column chromatography (eluent; chloroform-:methanol:ammonium hydroxide=50:10:1) to give 1-{4-[4-(4-piperidinyl)benzoylamino)benzoyl]-2,3,4,5-tetrahydro-1H-benzazepine (4.80 g), and a part (0.5 g) thereof is converted into the hydrochloride thereof in methanol. The hydrochloride is recrystallized from methanol/diethyl ether to give 1-{4-[4-(4-piperidinyl)benzoylamino]benzoyl}-2,3,4,5-tetrahydro-1H-benzazepine hydrochloride (0.42 g) as white powder, m.p. 177–181.5° C.

EXAMPLE 405

Using the suitable starting materials, the following compound is obtained in the same manner as in the above Examples 1, 382 and 388.

1-[4-(4-Dimethylaminobenzoylamino)benzoyl]-1,2,3,4-tetrahydroquinoline, colorless amorphous $^1$H-NMR (DMSO-$d_6$) δ: 1.90–2.00 (2H, m), 2.82 (2H, t, J=6.5 Hz), 2.98 (6H, s), 3.77 (2H, t, J=6.5 Hz), 6.70–7.30 (6H, m), 7.32 (2H, d, J=8.6 Hz), 7.73 (2H, d, J=8.6 Hz), 8.00–8.20 (1H, m), 8.39 (1H, d, J=2.2 Hz), 10.37 (1H, s)

Using the suitable starting materials, the following compounds are obtained in the same manner as in Example 1.

TABLE 2

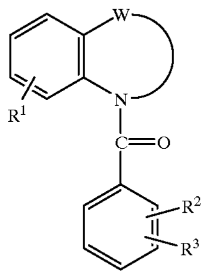

Example 406
Structure

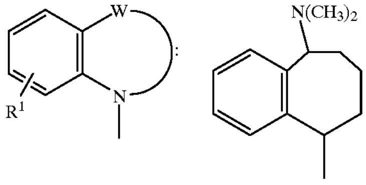

$R^2$: H

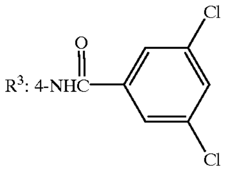

Crystalline form: White powder
Recrystallization solvent: Ethanol
Melting Point: 216–218° C.
Form: Free TABLE 2-continued

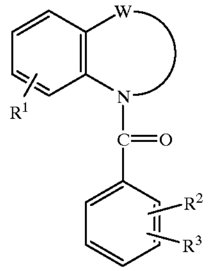

Example 407
Structure

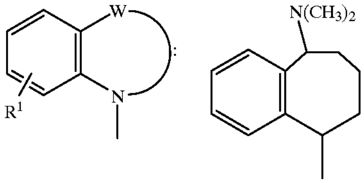

$R^2$: H

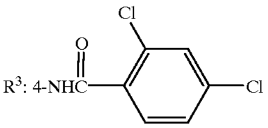

Crystalline form: White powder
Recrystallization solvent: Ethanol
Melting Point: 181–183° C.
Form: Free
Example 408
Structure

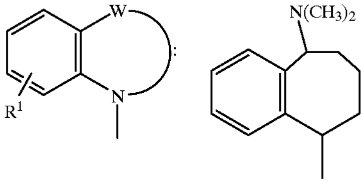

$R^2$: H

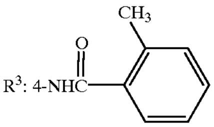

Crystalline form: White powder
Recrystallization solvent: Ethanol
Melting Point: 207–208° C.
Form: Free
Example 409
Structure

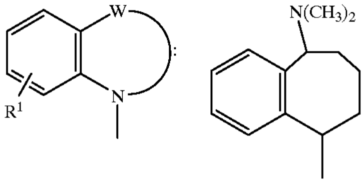

$R^2$: H

TABLE 2-continued

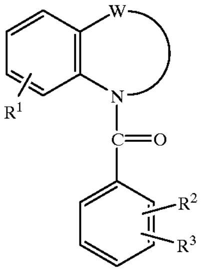

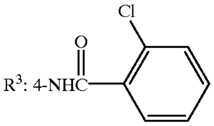

Crystalline form: White powder
Recrystallization solvent: Ethanol
Melting Point: 213–214° C.
Form: Free
Example 410
Structure

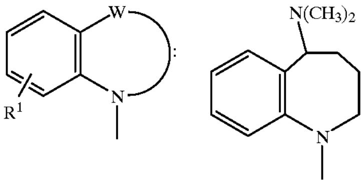

$R^2$: 3-$OCH_3$

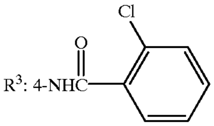

Crystalline form: White powder
Recrystallization solvent: Ethanol
Melting Point: 136–138° C.
Form: Free
Example 411
Structure

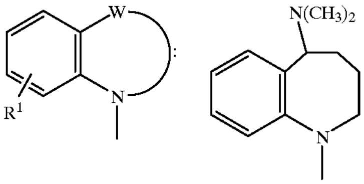

$R^2$: 3-$OCH_3$

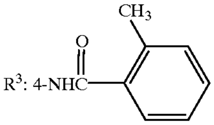

Crystalline form: White powder
Recrystallization solvent: Ethanol
Melting Point: 130–132° C.
Form: Free TABLE 2-continued

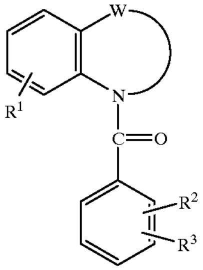

Example 412

Structure

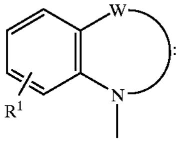

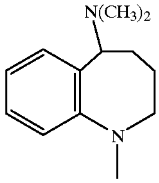

$R^2$: 3-$OCH_3$

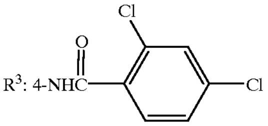

Crystalline form: White powder

Recrystallization solvent: Ethanol

Melting Point: 143–145° C.

Form: Free

Example 413

Structure

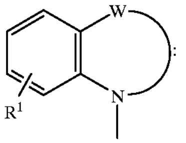

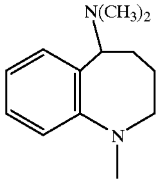

$R^2$: 3-$OCH_3$

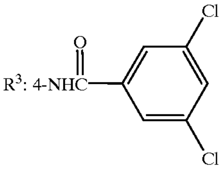

Crystalline form: White powder

Recrystallization solvent: Ethanol

Melting Point: 171–173° C.

Form: Free

TABLE 2-continued

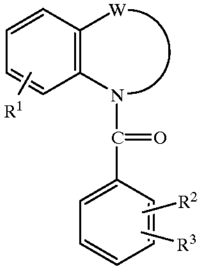

Example 414

Structure

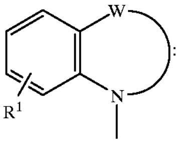

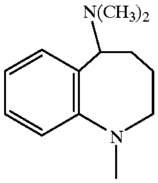

$R^2$: 3-$OCH_3$

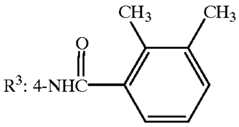

Crystalline form: White powder

Recrystallization solvent: Ethanol

Melting Point: 162–164° C.

Form: Free

Example 415

Structure

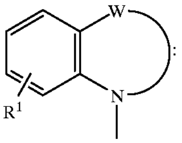

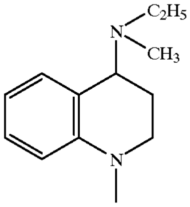

$R^2$: H

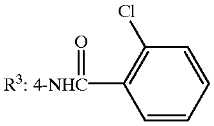

Crystalline form: Colorless amorphous

NMR analysis: 49)

Form: Free

Example 416

Structure

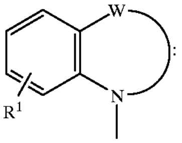

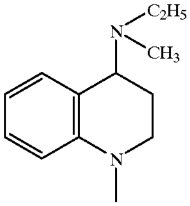

$R^2$: H

TABLE 2-continued

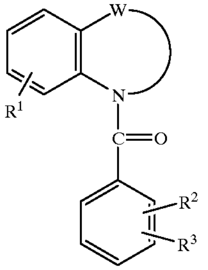

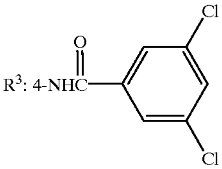

Crystalline form: Colorless amorphous
NMR analysis: 50)
Form: Free
Example 417
Structure

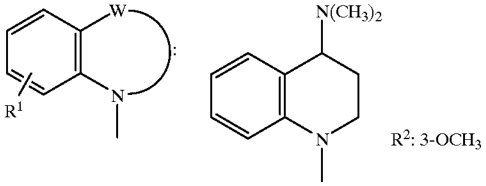

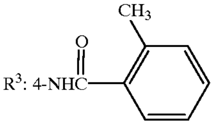

Crystalline form: Colorless amorphous
NMR analysis: 51)
Form: Free
Example 418
Structure

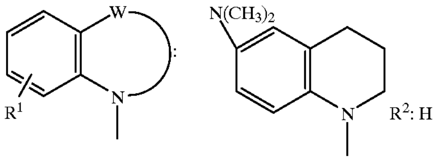

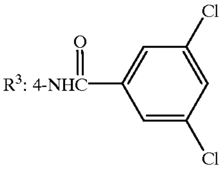

Crystalline form: Colorless needles
Recrystallization solvent: Ethyl acetate/n-hexane
Melting Point: 228.5–230° C.
Form: Free TABLE 2-continued

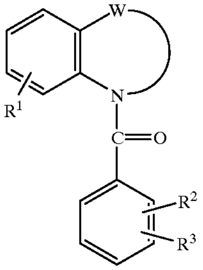

Example 419
Structure

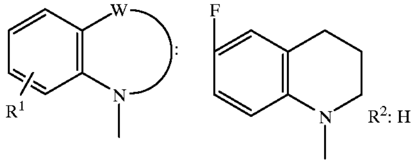

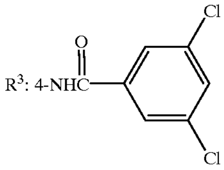

Crystalline form: White powder
Recrystallization solvent: Ethyl acetate/n-hexane
Melting point: 205.5–206.5° C.
Form: Free
Example 420
Structure

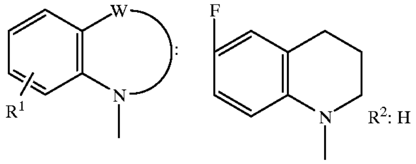

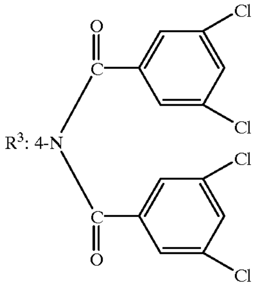

Crystalline form: White powder
Recrystallization solvent: Ethyl acetate/n-hexane
Melting point: 210–212° C.
Form: Free TABLE 2-continued

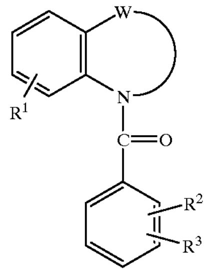

Example 421
Structure

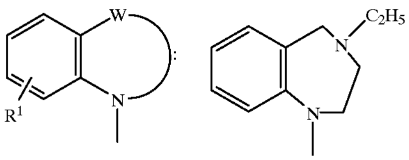

$R^2$: H

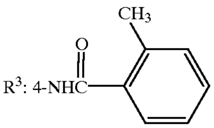

Crystalline form: White powder
Recrystallization solvent: Ethanol
Melting Point: 166–167° C.
Form: Free
Example 422
Structure

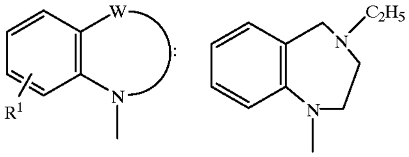

$R^2$: H

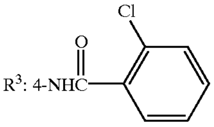

Crystalline form: White powder
Recrystallization solvent: Ethanol
Melting Point: 191.5–192.5° C.
Form: Free
Example 423
Structure

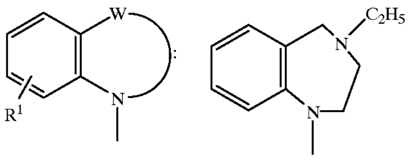

$R^2$: H

TABLE 2-continued

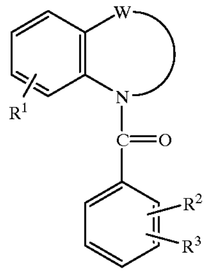

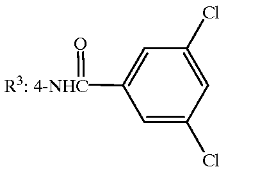

Crystalline form: White powder
Recrystallization solvent: Ethanol
Melting Point: 209–210° C.
Form: Free
Example 424
Structure

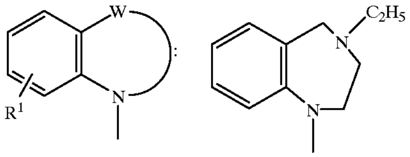

$R^2$: H

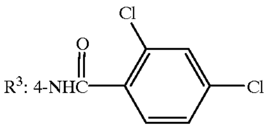

Crystalline form: Colorless amorphous
NMR analysis: 52)
Form: Free
Example 425
Structure

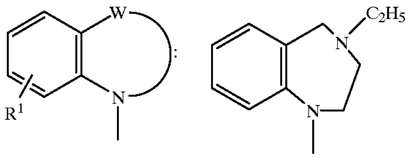

$R^2$: H

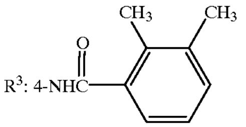

Crystalline form: White powder
Recrystallization solvent: Ethanol
Melting Point: 148–149° C.
Form: Free TABLE 2-continued

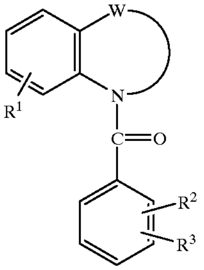

Example 426
Structure

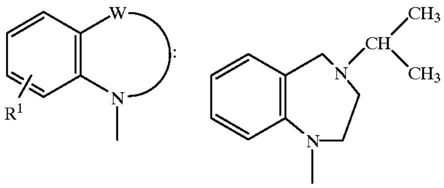

$R^2$: H

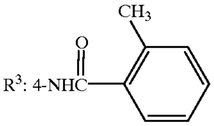

Crystalline form: White powder
Recrystallization solvent: Ethanol
Melting Point: 157–158° C.
Form: Free
Example 427
Structure

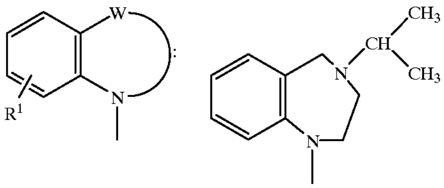

$R^2$: H

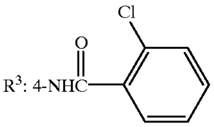

Crystalline form: White powder
Recrystallization solvent: Ethanol
Melting Point: 194.5–195.5° C.
Form: Free
Example 428
Structure

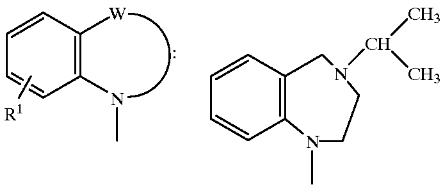

$R^2$: H

TABLE 2-continued

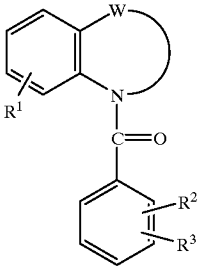

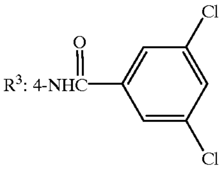

Crystalline form: White powder
Recrystallization solvent: Ethanol
Melting Point: 179.5–180.5° C.
Form: Free
Example 429
Structure

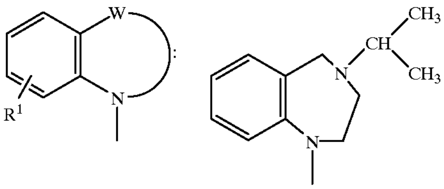

$R^2$: H

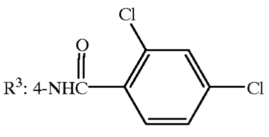

Crystalline form: White powder
Recrystallization solvent: Ethanol
Melting Point: 190–191° C.
Form: Free
Example 430
Structure

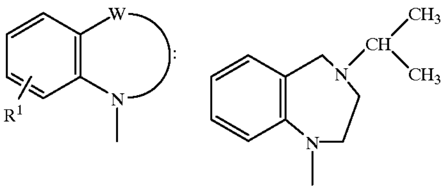

$R^2$: H

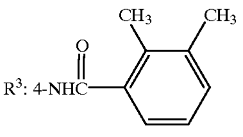

Crystalline form: White powder
Recrystallization solvent: Ethanol
Melting Point: 159–160° C.
Form: Free TABLE 2-continued

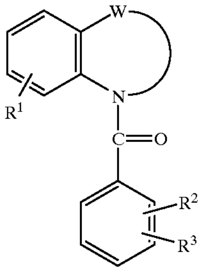

Example 431
Structure

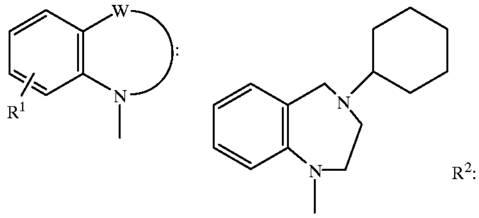

$R^2$: H

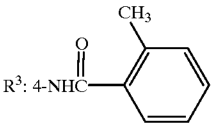

Crystalline form: Colorless amorphous
NMR analysis: 53)
Form: Hydrochloride
Example 432
Structure

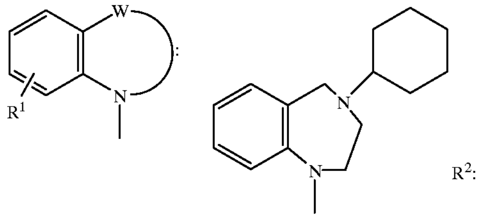

$R^2$: H

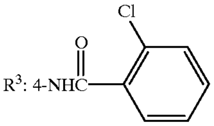

Crystalline form: White powder
Recrystallization solvent: Ethanol
Melting Point: 155–156° C.
Form: Free
Example 433
Structure

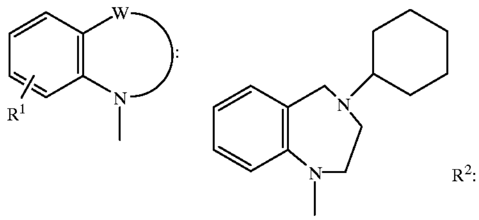

$R^2$: H

TABLE 2-continued

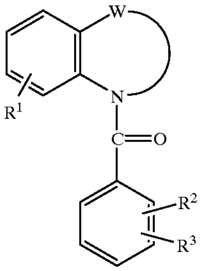

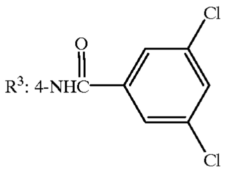

Crystalline form: Colorless amorphous
NMR analysis: 54)
Form: Free
Example 434
Structure

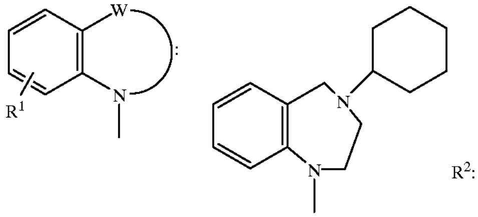

$R^2$: H

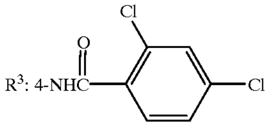

Crystalline form: Colorless amorphous
NMR analysis: 55)
Form: Free
Example 435
Structure

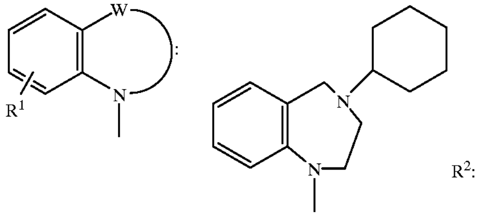

$R^2$: H

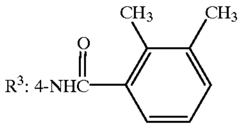

Crystalline form: White powder
Recrystallization solvent: Ethanol
Melting Point: 175–177° C.
Form: Free TABLE 2-continued

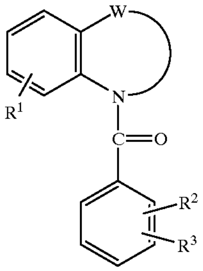

Example 436
Structure

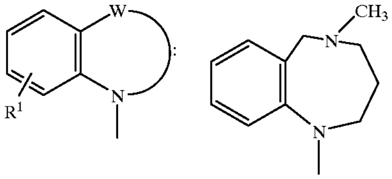

$R^2$: H

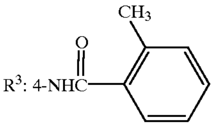

Crystalline form: Colorless amorphous
NMR analysis: 56)
Form: Free
Example 437
Structure

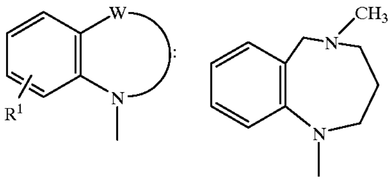

$R^2$: H

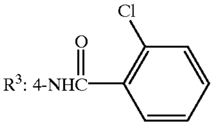

Crystalline form: Colorless amorphous
NMR analysis: 57)
Form: Free
Example 438
Structure

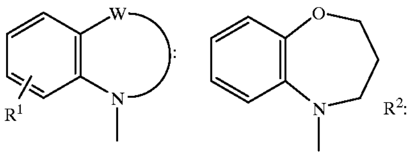

$R^2$: H

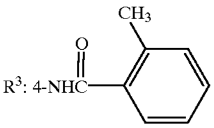

TABLE 2-continued

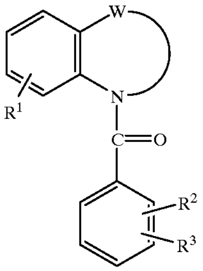

Crystalline form: White powder
Recrystallization solvent: Dichloromethane/diethyl ether
Melting Point: 219–220° C.
Form: Free
Example 439
Structure

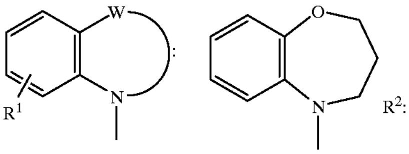

$R^2$: H

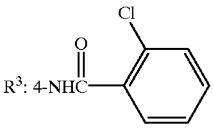

Crystalline form: White powder
Recrystallization solvent: Dichloromethane/diethyl ether
Melting Point: 215–218° C.
Form: Free
Example 440
Structure

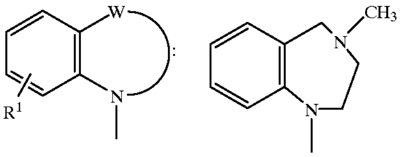

$R^2$: H

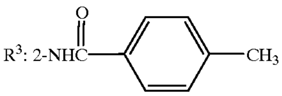

Crystalline form: White powder
Recrystallization solvent: Ethanol
Melting Point: 128.5–129.5° C.
Form: Free
Example 441
Structure

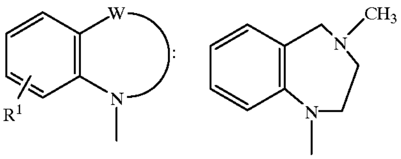

$R^2$: H

TABLE 2-continued

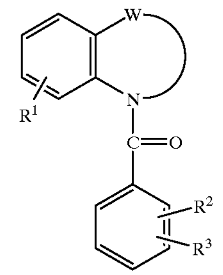

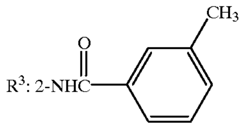

Crystalline form: Colorless amorphous
NMR analysis: 58)
Form: Free
Example 442
Structure

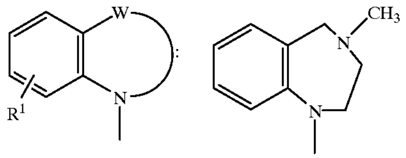

$R^2$: H

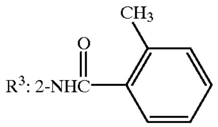

Crystalline form: White powder
Recrystallization solvent: Ethanol
Melting Point: 153–154° C.
Form: Free
Example 443
Structure

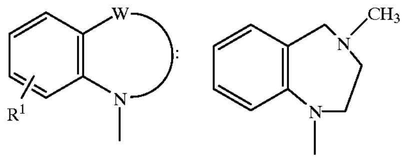

$R^2$: H

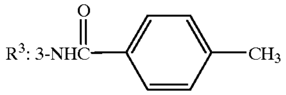

Crystalline form: White powder
Recrystallization solvent: Ethanol
Melting Point: 150–153° C.
Form: Free TABLE 2-continued

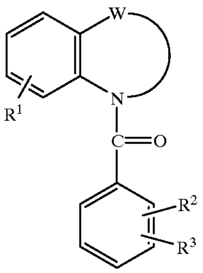

Example 444
Structure

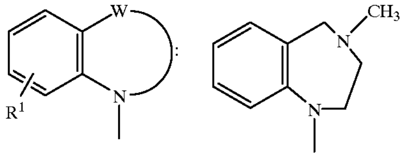

$R^2$: H

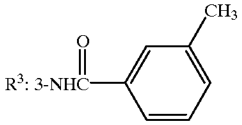

Crystalline form: White powder
Recrystallization solvent: Ethanol
Melting Point: 139–141° C.
Form: Free
Example 445
Structure

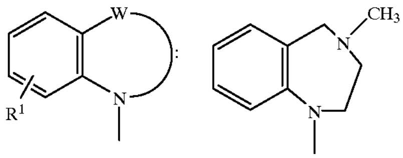

$R^2$: H

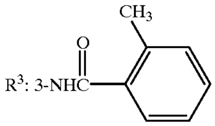

Crystalline form: Colorless amorphous
NMR analysis: 59)
Form: Free
Example 446
Structure

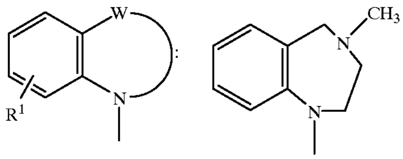

$R^2$: H

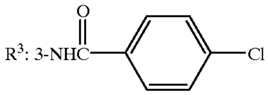

Crystalline form: Colorless amorphous
NMR analysis: 60)

TABLE 2-continued

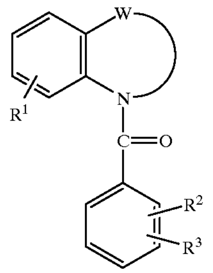

Form: Free
Example 447
Structure

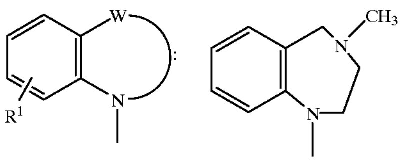

$R^2$: H

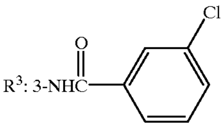

Crystalline form: Colorless amorphous
NMR analysis: 61)
Form: Free
Example 448
Structure

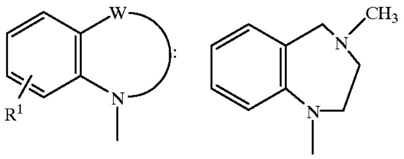

$R^2$: H

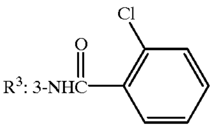

Crystalline form: Colorless amorphous
NMR analysis: 62)
Form: Free
Example 449
Structure

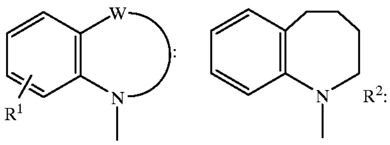

$R^2$: 3-$OCH_3$

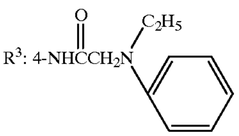

TABLE 2-continued

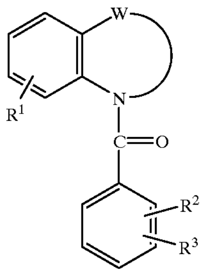

Crystalline form: Colorless amorphous
NMR analysis: 63)
Form: Free
Example 450
Structure

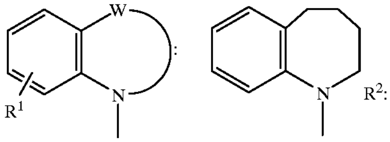

$R^2$: H

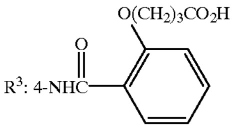

Crystalline form: White powder
Recrystallization solvent: Methanol/diethyl ether
Melting Point: 172.5–173.5° C.
Form: Free
Example 451
Structure

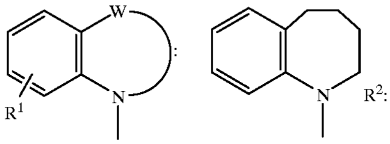

$R^2$: H

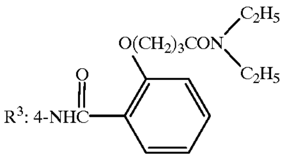

Crystalline form: Colorless prisms
Recrystallization solvent: Methanol/diethyl ether
Melting Point: 122.5–123° C.
Form: Free TABLE 2-continued

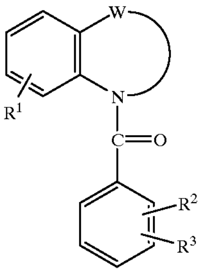

Example 452
Structure

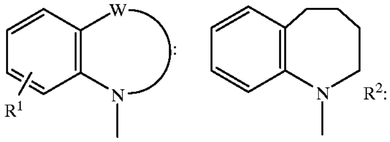 $R^2$: H $R^3$: 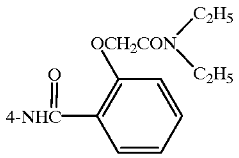

Crystalline form: White powder
Recrystallization solvent: Methanol/diethyl ether
Melting Point: 198–199.5° C.
Form: Free
Example 453
Structure

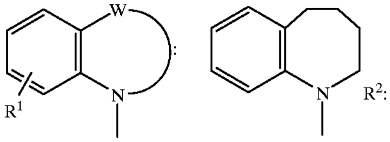 $R^2$: H $R^3$: 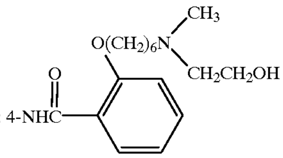

Crystalline from: White powder
Recrystallization solvent: Methanol/diethyl ether
Melting Point: 118–119.5° C.
Form: Hydrochloride
Example 454
Structure

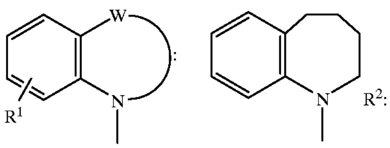 $R^2$: H

TABLE 2-continued

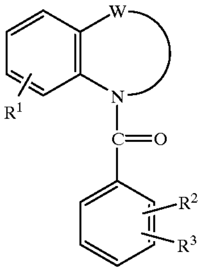

$R^3$: 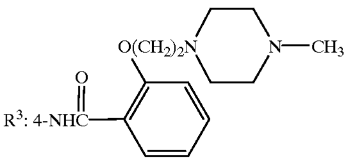

Crystalline form: White powder
Recrystallization solvent: Ethanol
Melting Point: 163–165° C.
Form: Dihydrochloride
Example 455
Structure

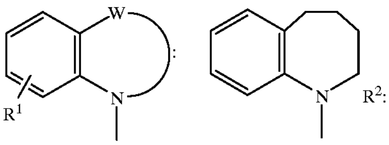 $R^2$: H $R^3$: 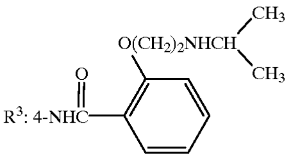

Crystalline form: White powder
Recrystallization solvent: Methanol/diethyl ether
Melting Point: 246–248° C.
Form: Hydrochloride
Example 456
Structure

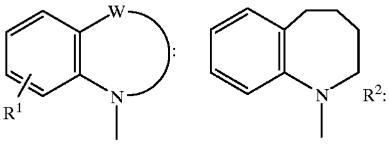 $R^2$: H $R^3$: 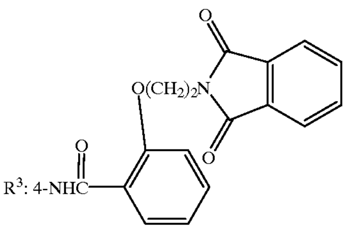

Crystalline form: White powder
Recrystallization solvent: Chloroform/ethanol
Melting Point: 204–205° C.
Form: Free TABLE 2-continued

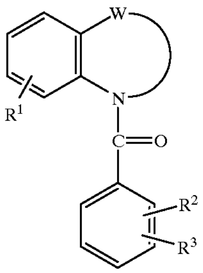

Example 457
Structure

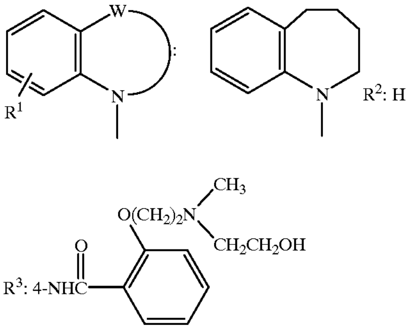

Crystalline form: Colorless prisms
Recrystallization solvent: Methanol/diethyl ether
Melting Point: 127–128° C.
Form: Hydrochloride
Example 458
Structure

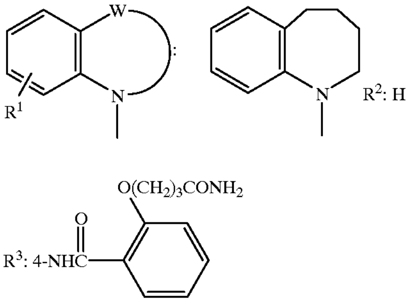

Crystalline form: White powder
Recrystallization solvent: Methanol/diethyl ether
Melting Point: 220–221° C.
Form: Free
Example 459
Structure

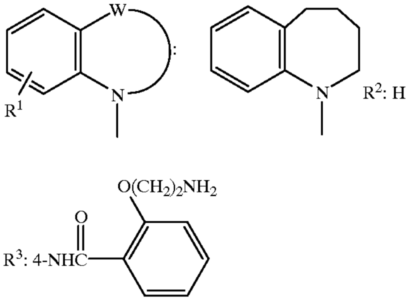

TABLE 2-continued

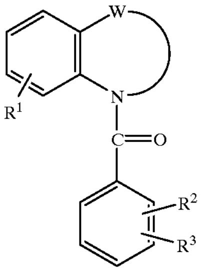

Crystalline form: Colorless needles
Recrystallization solvent: Ethanol
Melting Point: 190–192° C.
Form: Free
Example 460
Structure

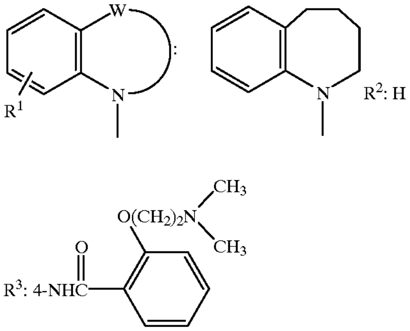

Crystalline form: White powder
Recrystallization solvent: Methanol/diethyl ether
Melting Point: 189–191° C.
Form: Hydrochloride
Example 461
Structure

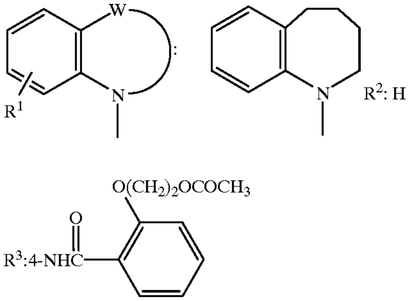

Crystalline form: Colorless needles
Recrystallization solvent: Ethanol
Melting Point: 173–174° C.
Form: Free
Example 462
Structure

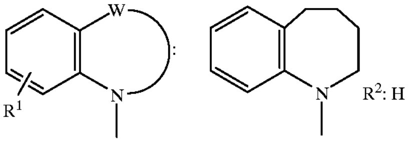

TABLE 2-continued

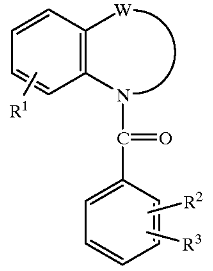

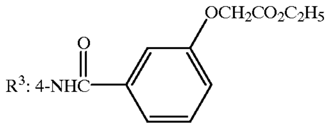

Crystalline form: White powder
Recrystallization solvent: Dichloromethane/ethanol
Melting Point: 129–130° C.
Form: Free
Example 463
Structure

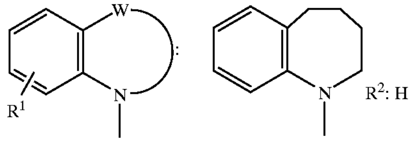

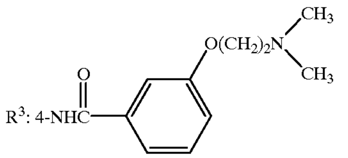

Crystalline form: White powder
Recrystallization solvent: Methanol/diethyl ether
Melting Point: 130–133° C.
Form: Hydrochloride
Example 464
Structure

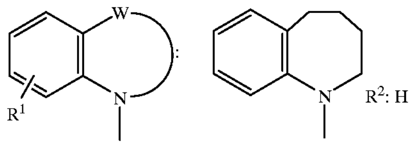

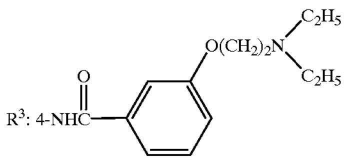

Crystalline form: Light yellow powder
Recrystallization solvent: Methanol/diethyl ether
Melting Point: 170.5–172° C.
Form: Hydrochloride TABLE 2-continued

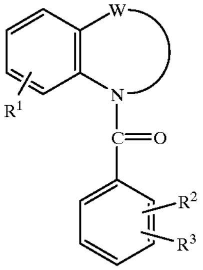

Example 465
Structure

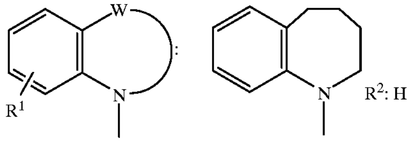

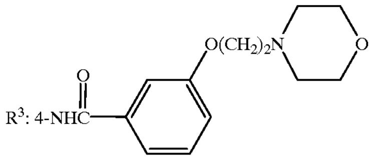

Crystalline form: White powder
Recrystallization solvent: Methanol/diethyl ether
Melting Point: 126–131° C.
Form: Hydrochloride
Example 466
Structure

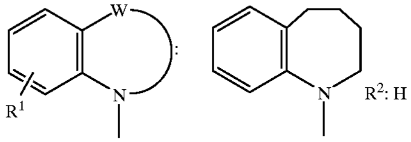

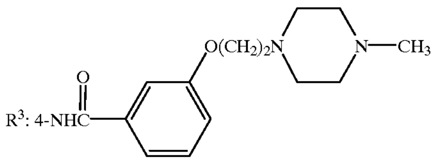

Crystalline form: White powder
Recrystallization solvent: Ethanol
Melting Point: 182–185° C.
Form: Dihydrochloride
Example 467
Structure

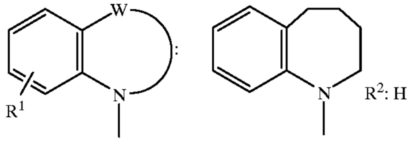

TABLE 2-continued

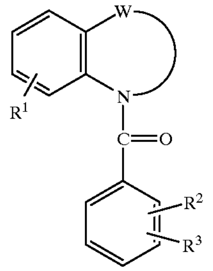

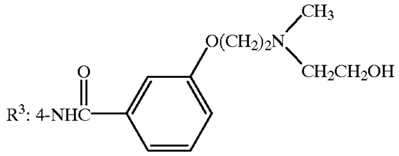

Crystalline form: White powder
Recrystallization solvent: Methanol/diethyl ether
Melting Point: 116–121° C.
Form: Hydrochloride
Example 468
Structure

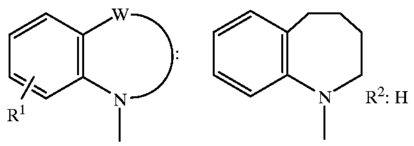

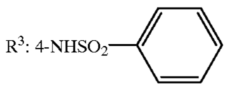

Crystalline form: Colorless prisms
Recrystallization solvent: Methanol/diethyl ether
Melting Point: 178–182.5° C.
Form: Free
Example 469
Structure

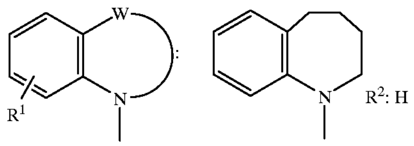

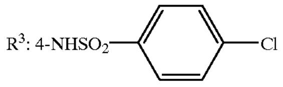

Crystalline form: Colorless particles
Recrystallization solvent: Methanol/diethyl ether
Melting Point: 185–187° C.
Form: Free
Example 470
Structure

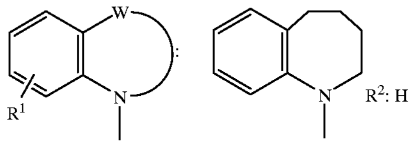

TABLE 2-continued

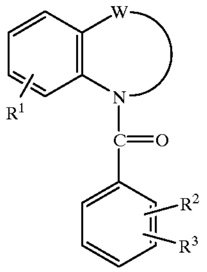

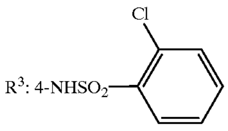

Crystalline form: White powder
Recrystallization solvent: Methanol/diethyl ether
Melting Point: 215–217° C.
Form: Free
Example 471
Structure

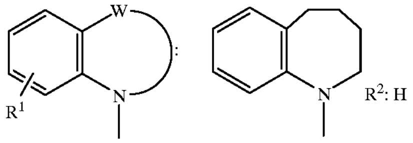

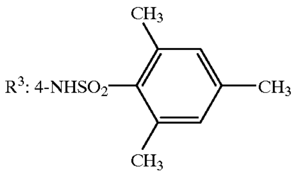

Crystalline form: White powder
Recrystallization solvent: Methanol/diethyl ether
Melting Point: 176–178° C.
Form: Free
Example 472
Structure

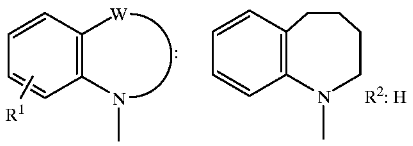

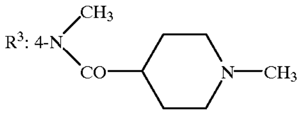

Crystalline form: Light yellow powder
Recrystallization solvent: Methanol/n-hexane
Melting Point: 194.5–197° C.
Form: Free TABLE 2-continued

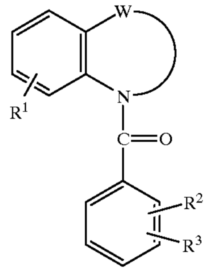

Example 473
Structure

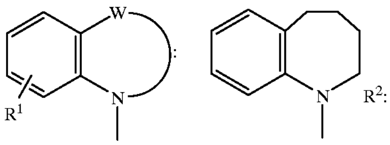 $R^2$: H $R^3$: 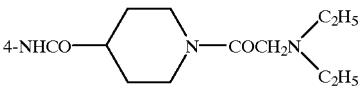

Crystalline form: White powder
Recrystallization solvent: Methanol/diethyl ether
Melting Point: 161.5–165.5° C.
Form: Hydrochloride
Example 474
Structure

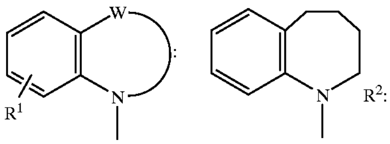 $R^2$: H $R^3$: 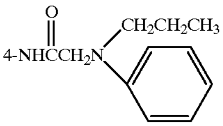

Crystalline form: White powder
Recrystallization solvent: Ethyl acetate
Melting Point 152–153° C.
Form: Free
Example 475
Structure

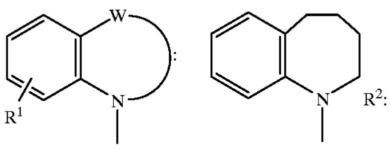 $R^2$: H $R^3$: 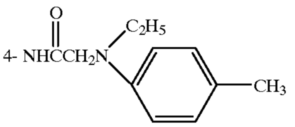

Crystalline form: Colorless needles
Recrystallization solvent: n-Hexane/ethyl acetate
Melting Point: 147–148° C.

TABLE 2-continued

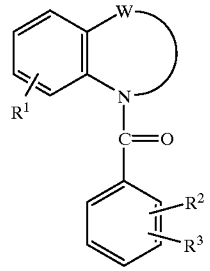

Form: Free
Example 476
Structure

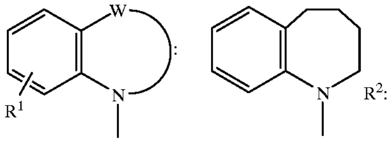 $R^2$: H $R^3$: 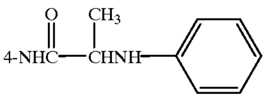

Crystalline form: Light yellow powder
Recrystallization solvent: Ethyl acetate
Melting Point: 25–217° C.
Form: Free
Example 477
Structure

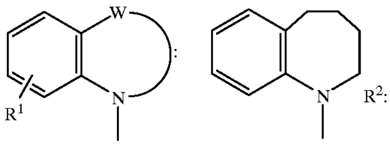 $R^2$: H $R^3$: 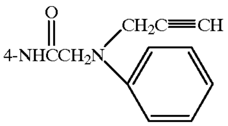

Crystalline form: Colorless amorphous
NMR analysis: 64)
Form: Free
Example 478
Structure

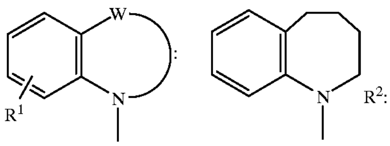 $R^2$: H $R^3$: 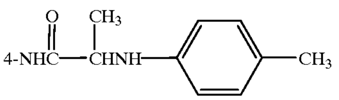

Crystalline form: White powder
Recrystallization solvent: Ethyl acetate
Melting Point: 180–181° C.
Form: Free TABLE 2-continued

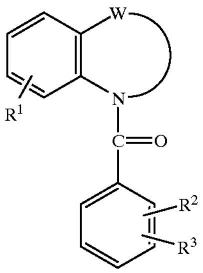

Example 479
Structure

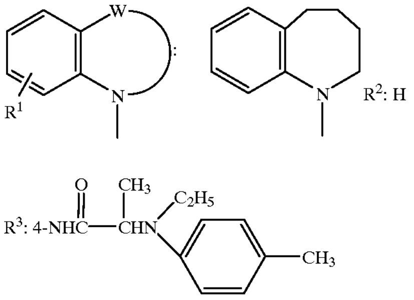

Crystalline form: Colorless amorphous
NMR analysis: 65)
Form: Free
Example 480
Structure

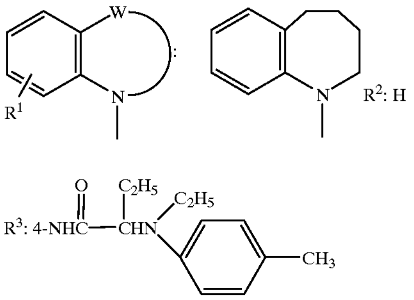

Crystalline form: Colorless amorphous
NMR analysis: 66)
Form: Free
Example 481
Structure

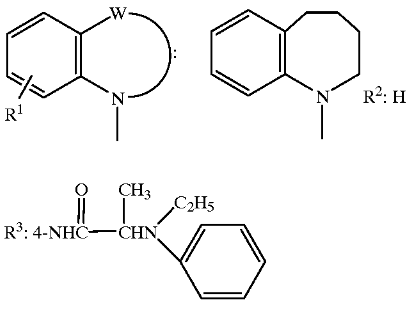

Crystalline form: Colorless amorphous
NMR analysis: 67)
Form: Free

TABLE 2-continued

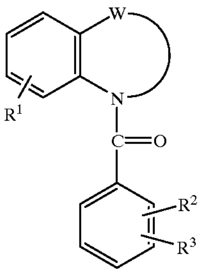

Example 482
Structure

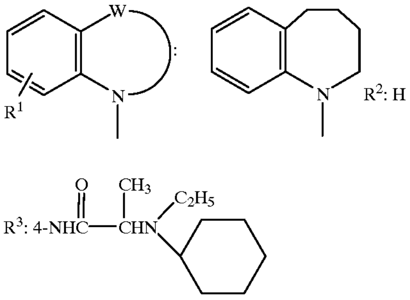

Crystalline form: Colorless scales
Recrystallization solvent: n-Hexane/ethyl acetate
Melting Point: 165–167° C.
Form: Free
Example 483
Structure

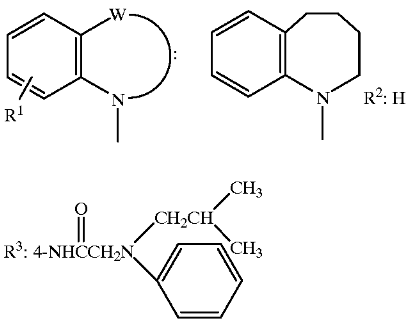

Crystalline form: Colorless amorphous
NMR analysis: 68)
Form: Free
Example 484
Structure

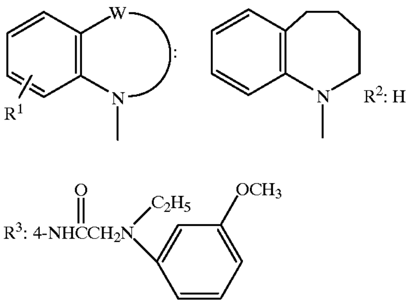

Crystalline form: Colorless amorphous

TABLE 2-continued

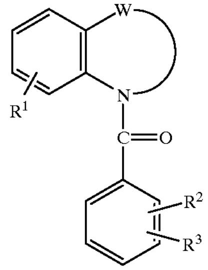

NMR analysis: 69)
Form: Free
Example 485
Structure

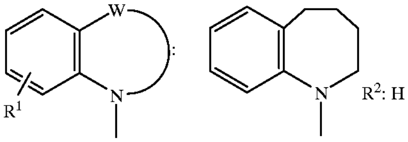

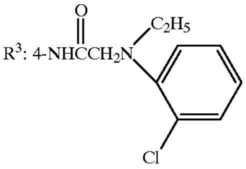

Crystalline form: Colorless amorphous
NMR analysis: 70)
Form: Free
Example 486
Structure

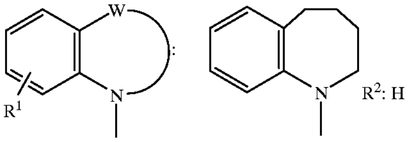

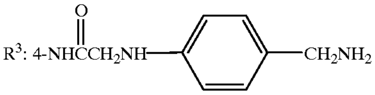

Crystalline form: Colorless amorphous
NMR analysis: 71)
Form: Free
Example 487
Structure

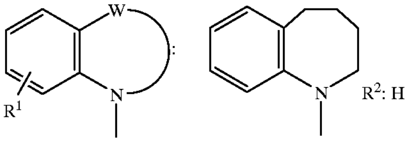

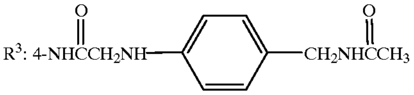

Crystalline form: Colorless amorphous
NMR analysis: 72)

TABLE 2-continued

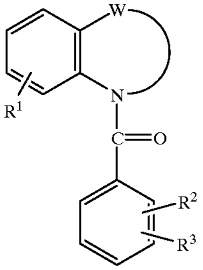

Form: Free
Example 488
Structure

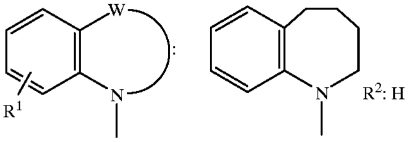

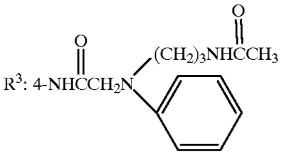

Crystalline form: Colorless amorphous
NMR analysis: 73)
Form: Free
Example 489
Structure

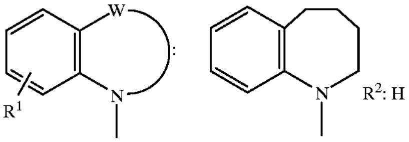

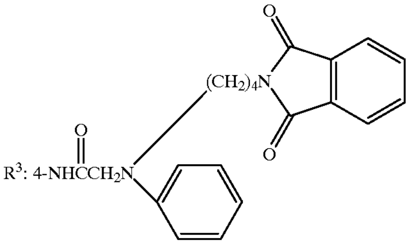

Crystalline form: Light yellow amorphous
NMR analysis: 74)
Form: Free
Example 490
Structure

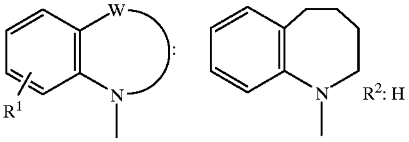

TABLE 2-continued

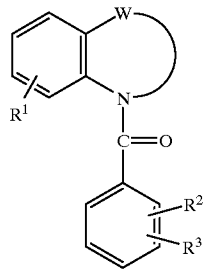

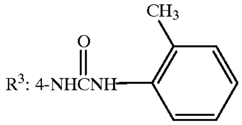

Crystalline form: White powder
Recrystallization solvent: Ethyl acetate
Melting Point: 182–182.5° C.
Form: Free
Example 491
Structure

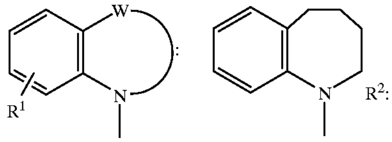
$R^2$: H

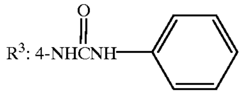

Crystalline form: White powder
Recrystallization solvent: Ethyl acetate
Melting Point: 244–245° C.
Form: Free
Example 492
Structure

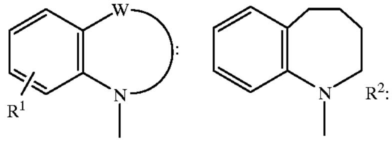
$R^2$: H

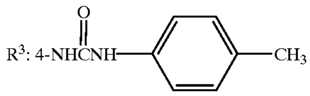

Crystalline form: White powder
Recrystallization solvent: Ethyl acetate
Melting Point: 220–221.5° C.
Form: Free
Example 493
Structure

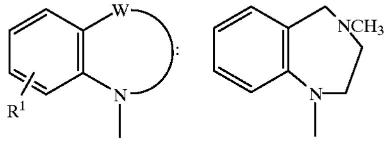
$R^2$: H

TABLE 2-continued

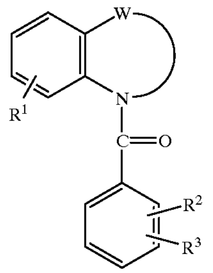

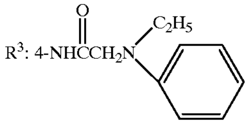

Crystalline form: Light yellow amorphous
NMR analysis: 75)
Form: Free
Example 494
Structure

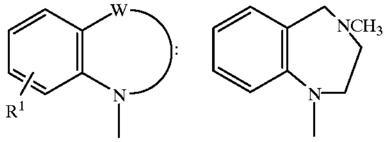
$R^2$: 3-$OCH_3$

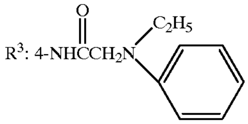

Crystalline form: Light yellow amorphous
NMR analysis: 76)
Form: Free
Example 495
Structure

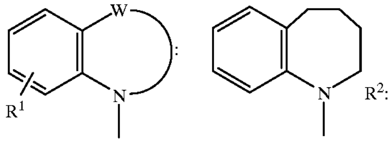
$R^2$: H

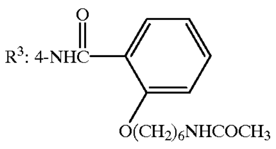

Crystalline form: Colorless needles
Recrystallization solvent: Methanol/diethyl ether
Melting Point: 171–172° C.
Form: Free
Example 496
Structure

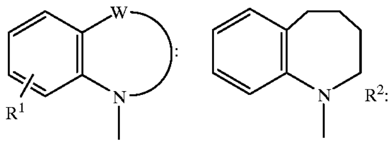
$R^2$: H

TABLE 2-continued
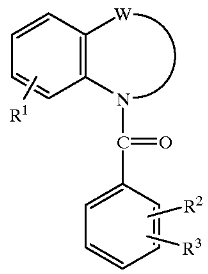
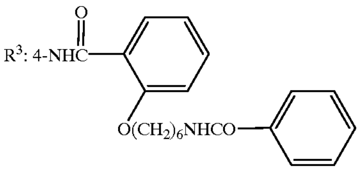
Crystalline form: White powder
Recrystallization solvent: Ethanol
Melting Point: 178–178.5° C.
Form: Free
Example 497
Structure
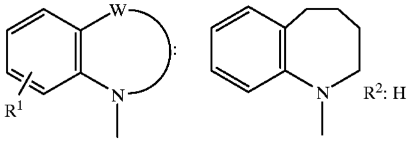
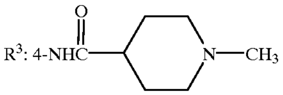
Example 498
Structure
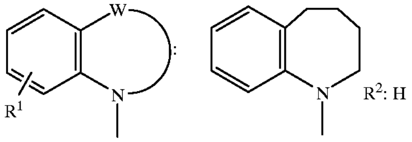
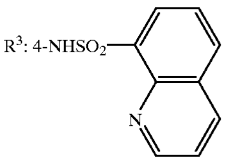
Example 499
Structure
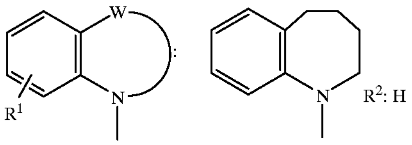
TABLE 2-continued
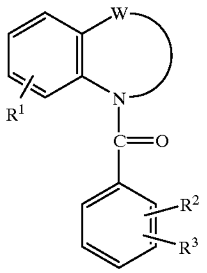
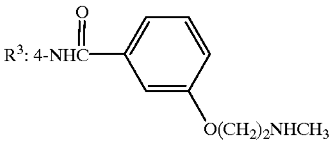
Example 500
Structure
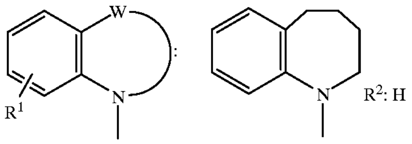
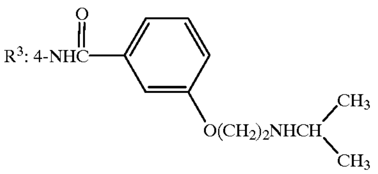
Example 501
Structure
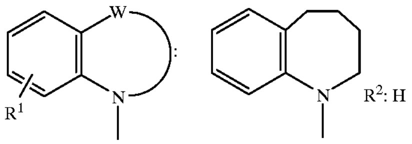
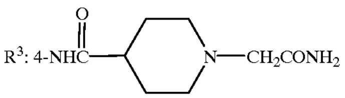
Example 502
Structure
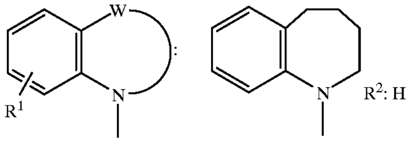
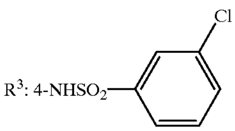

TABLE 2-continued

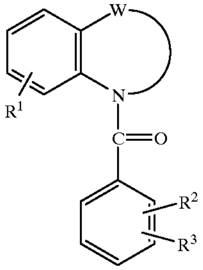

Example 503
Structure

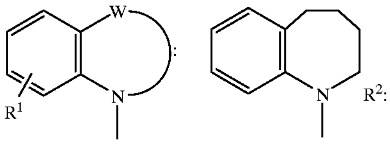

$R^2$: H $R^3$: 4-$NHSO_2$—

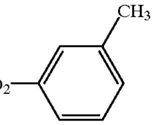

Example 504
Structure

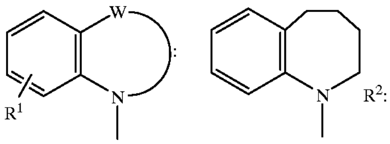

$R^2$: H

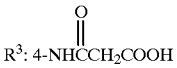

$R^3$: 4-$NHCCH_2COOH$

Crystalline form: Light yellow scales
Recrystallization solvent: Ethanol/water
Melting Point: 129–131° C.
Form: Free
Example 505
Structure

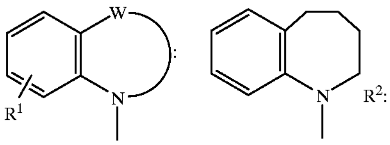

$R^2$: H

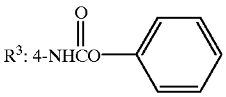

$R^3$: 4-NHCO—

Crystalline form: White powder
Recrystallization solvent: Ethyl acetate
Melting Point: 199–201° C.
Form: Free TABLE 2-continued

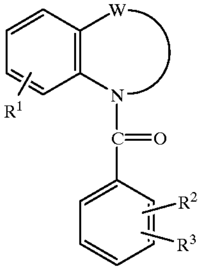

Example 506
Structure

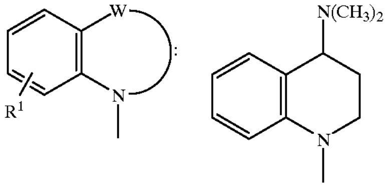

$R^2$: H

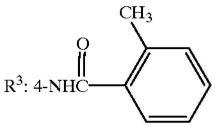

$R^3$: 4-NHC—

Crystalline form: Colorless amorphous
NMR analysis: 77)
Form: Free
Example 507
Structure

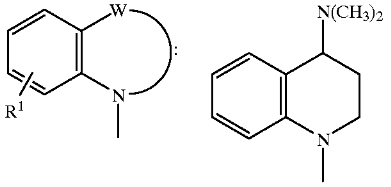

$R^2$: H

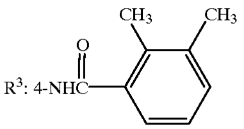

$R^3$: 4-NHC—

Crystalline form: White powder
Recrystallization solvent: n-Hexane/ethyl acetate
Melting Point: 187.5–189° C.
Form: Free
Example 508
Structure

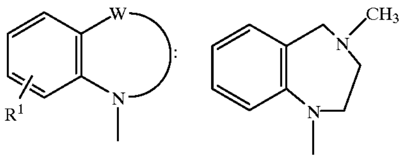

$R^2$: 2-Cl

TABLE 2-continued

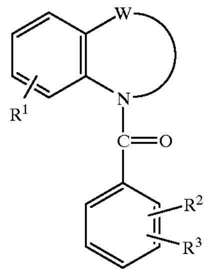

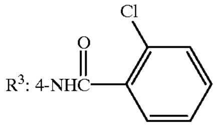

Crystalline form: White powder
Recrystallization solvent: Methanol/diethyl ether
Melting Point: 161–164° C.
Form: Free
Example 509
Structure

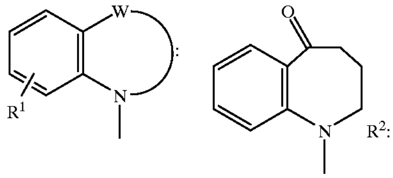

$R^2$: H

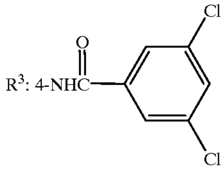

Crystalline form: Colorless prisms
Recrystallization solvent: Ethanol
Melting Point: 242–243° C.
Form: Free
Example 510
Structure

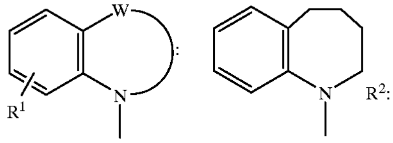

$R^2$: 3-$OCH_3$ $R^3$: 4-$NHCOCH_2Cl$
Crystalline form: White powder
Recrystallization solvent: Dichloroethane/diethyl ether
Melting Point: 186–188° C.
Form: Free
Example 511
Structure

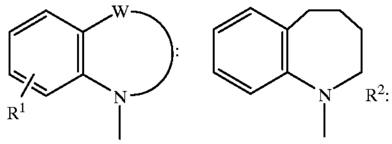

$R^2$: H

TABLE 2-continued

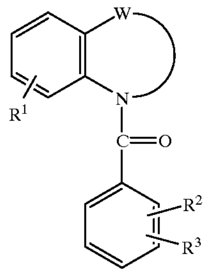

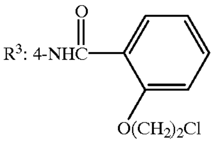

Crystalline form: Colorless amorphous
NMR analysis: 78)
Form: Free
Example 512
Structure

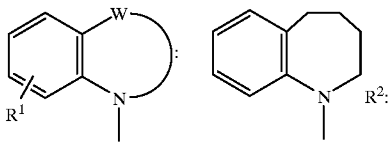

$R^2$: H

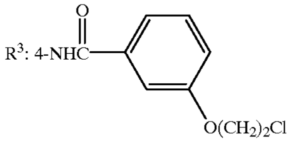

Crystalline form: Colorless amorphous
NMR analysis: 79)
Form: Free

49) $^1$H-NMR($CDCl_3$)δ; 1.11(3H, t, J=7.1Hz), 1.90–2.25 (2H, m), 2.29(3H, s), 2.55(2H, q, J=7.1Hz), 3.62–3.90(2H, m), 4.00–4.20(1H, m), 6.63(1H, d, J=7.9Hz), 6.85–7.10(2H, m), 7.25–7.80(9H, m), 8.25(1H, brs)
50) $^1$H-NMR($CDCl_3$)δ; 1.10(3H, t, J=7.1Hz), 1.90–2.20 (2H, m), 2.28(3H, s), 3.60–3.90(2H, m), 3.95–4.20 (1H, m), 6.62(1H, d, J=7.9Hz), 6.80–7.10(2H, m), 7.20(2H, d, J=8.6Hz), 7.31–7.55(4H, m), 7.80 (2H, d, J=1.9Hz), 9.05(1H, brs)
51) $^1$H-NMR($CDCl_3$)δ; 1.80–2.05(1H, m), 2.15–2.50(1H, m), 2.34(6H, s), 2.51(3H, s), 3.48–3.62(1H, m), 3.72(3H, s), 3.70–3.85(1H, m), 4.00–4.22(1H, m), 6.64(1H, d, J=7.8Hz), 6.84–7.58(9H, m), 8.16 (1H, brs), 8.40(1H, d, J=8.7Hz)
52) $^1$H-NMR($CDCl_3$)δ; 1.16(3H, t, J=7.1Hz), 2.40–2.70 (2H, m), 2.90–3.30(3H, m), 3.80–4.20(2H, m), 4.80–5.00(1H, m), 6.60–6.80(1H, m), 7.00–7.70 (10H, m), 8.24(1H, s)
53) $^1$H-NMR(DMSO-$d_6$)δ; 1.0–2.5(10H, m), 2.34(3H, s), 3.30–3.80(4H, m), 4.50–5.30(3H, m), 6.70–7.00 (1H, m), 7.10–7.80(11H, m), 10.43(1H, s), 10.5–12.0(1H, br)
54) $^1$H-NMR($CDCl_3$)δ; 1.10–2.10(10H, m), 2.40–2.70 (1H, m), 2.80–3.20(3H, m), 3.92(2H, s), 4.90–5.20 (1H, m), 6.50–6.70(1H, m), 6.80–7.60(8H, m), 7.75 (2H, s), 8.73(1H, s)
55) $^1$H-NMR($CDCl_3$)δ; 1.10–2.20(10H, m), 2.40–2.70 (1H, m), 2.90–3.30(3H, m), 3.93(2H, s), 4.90–5.20

TABLE 2-continued

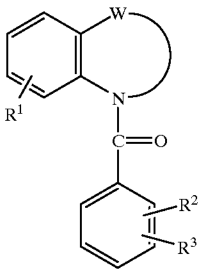

(1H, m), 6.62(1H, d, J=7.6Hz), 6.90–7.70(10H, m), 8.29(1H, s)
56) $^1$H-NMR($CDCl_3$)δ; 1.50–2.10(2H, m), 2.38(6H, s), 2.30–2.70(1H, m), 2.70–3.00(2H, m), 3.45(1H, d, J=13Hz), 3.81(1H, d, J=14Hz), 4.70–5.00(1H, m), 7.0–7.50(12H, m), 8.23(1H, s)
57) $^1$H-NMR($CDCl_3$)δ; 1.50–2.10(2H, m), 2.42(3H, s), 2.40–2.70(1H, m), 2.80–3.00(2H, m), 3.52(1H, d, J=13Hz), 3.85(1H, d, J=13Hz), 4.70–5.00(1H, m), 7.00–7.70(12H, m), 8.54(1H, s)
58) $^1$H-NMR($CDCl_3$)δ; 2.43(3H, s), 2.47(3H, s), 3.00–3.30(3H, m), 3.76(1H, d, J=14Hz), 4.06(1H, d, J=14Hz), 4.90–5.20(1H, m), 6.50–6.80(3H, m), 6.90–7.50(6H, m), 7.70–8.00(2H, m), 8.48(1H, d, J=8Hz), 10.58(1H, s)
59) $^1$H-NMR($CDCl_3$)δ; 2.41(3H, s), 2.44(3H, s), 2.90–3.20(3H, m), 3.74(1H, d, J=13Hz), 4.07(1H, d, J=14Hz), 4.80–5.00(1H, m), 6.67(1H, d, J=7Hz), 6.76(1H, d, J=7Hz), 7.00–7.50(8H, m), 7.55(1H, s), 7.70–7.90(2H, m)
60) $^1$H-NMR($CDCl_3$)δ; 2.41)3H, s), 2.80–3.20(3H, m), 3.73(1H, d, J=13Hz), 4.03(1H, d, J=14Hz), 6.66 (2H, d, J=7.6Hz), 6.90–8.00(10H, m), 8.57(1H, s)
61) $^1$H-NMR($CDCl_3$)δ; 2.40(3H, s), 2.90–3.20(3H, m), 3.73(1H, d, J=13Hz), 4.07(1H, d, J=13Hz), 4.70–5.00(1H, m), 6.60–6.80(2H, m), 6.90–8.00(10H, m), 8.54(1H, s)
62) $^1$H-NMR($CDCl_3$)δ; 2.41(3H, s), 2.90–3.20(3H, m), 3.75(1H, d, J=14Hz), 4.08(1H, d, J=14Hz), 4.80–5.00(1H, m), 6.67(1H, d, J=7.6Hz), 6.82(1H, d, J=7.6Hz), 6.90–7.90(10H, m), 8.08(1H, s)
63) $^1$H-NMR($CDCl_3$)δ; 1.23(3H, t, J=7Hz), 1.40–1.70 (1H, m), 1.90–2.20(3H, m), 2.70–3.30(3H, m), 3.40–3.60(5H, m), 3.91(2H, s), 5.00–5.20(1H, m), 6.60–7.40(11H, m), 8.12(1H, d, J=8Hz), 8.99(1H, s)
64) $^1$H-NMR($CDCl_3$)δ; 1.35–1.70(1H, m), 1.80–2.20(3H, m), 2.25–2.35(1H, m), 2.65–3.20(3H, m), 4.01(2H, s), 4.05–4.17(2H, m), 4.90–5.10(1H, m), 6.61(1H, d, J=7.5Hz), 6.75–7.50(12H, m), 8.44(1H, brs)
65) $^1$H-NMR($CDCl_3$)δ; 1.13(3H, t, J=7.0Hz), 1.30–1.65 (4H, m), 1.80–2.20(3H, m), 2.28(3H, s), 2.65–3.40 (5H, m), 4.90–5.10(1H, m), 6.63(1H, d, J=7.6Hz), 6.75–7.00(3H, m), 7.00–7.45(8H, m), 8.85(1H, brs)
66) $^1$H-NMR($CDCl_3$)δ; 0.88(3H, t, J=7.4Hz), 1.16(3H, t, J=7.0Hz), 1.35–2.20(6H, m), 2.27(3H, s), 2.60–3.20(3H, m), 3.20–3.45(2H, m), 3.85–4.10 (1H, m), 4.90–5.10(1H, m), 6.63(1H, d, J=7.4Hz), 6.67(2H, d, J=8.5Hz), 6.92(1H, t, J=8.0Hz), 7.00–7.45(8H, m), 8.85(1H, brs)
67) $^1$H-NMR($CDCl_3$)δ; 1.17(3H, t, J=7.0Hz), 1.35–1.65 (4H, m), 2.60–3.45(5H, m), 4.20(2H, q, J=7.0Hz), 4.90–5.10(1H, m), 6.63(1H, d, J=7.6Hz), 6.80–7.45(12H, m), 8.66(1H, brs)
68) $^1$H-NMR($CDCl_3$)δ; 0.96(6H, d, J=6.6Hz), 1.35–1.65 (1H, m), 1.80–2.25(4H, m), 2.65–3.15(3H, m), 3.19 (2H, d, J=7.3Hz), 3.99(2H, s), 4.90–5.10(1H, m), 6.60(1H, d, J=7.8Hz), 6.75–7.05(4H, m), 7.05–7.40(8H, m), 8.15(1H, brs)
69) $^1$H-NMR($CDCl_3$)δ; 1.19(3H, t, J=7.0Hz), 1.35–1.65 (1H, m), 1.80–2.25(3H, m), 2.70–3.20(3H, m), 3.44 (2H, q, J=7.0Hz), 3.77(3H, s), 3.87(2H, s), 4.90–5.10(1H, m), 6.25–6.50(3H, m), 6.67(1H, d, J=7.5Hz), 6.85–7.45(8H, m), 8.29(1H, brs)
70) $^1$H-NMR($CDCl_3$)δ; 1.05(3H, t, J=7.1Hz), 1.35–1.65

TABLE 2-continued

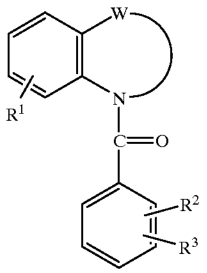

(1H, m), 1.85–2.25(3H, m), 2.65–3.30(5H, m), 3.74 (2H, s), 4.95–5.15(1H, m), 6.63(1H, d, J=7.5Hz), 6.80–7.55(11H, m), 9.51(1H, brs)
71) $^1$H-NMR($CDCl_3$)δ; 1.30–1.65(1H, m), 1.80–2.30(3H, m), 2.65–3.15(3H, m), 3.75(2H, s), 3.74(2H, s), 4.95–5.10(1H, m), 6.45–6.70(3H, m), 6.88(1H, t, J=6.8Hz), 7.00–7.45(8H, m), 8.74(1H, brs)
72) $^1$H-NMR($CDCl_3$)δ; 1.30–1.70(1H, m), 1.75–2.25(6H, m), 2.65–3.15(3H, m), 3.78(2H, d, J=5.4Hz), 4.28 (2H, d, J=5.5Hz), 4.53(1H, brs), 4.90–5.10(1H, m), 5.89(1H, brs), 6.50–6.70(3H, m), 6.89(1H, t, J=7.5Hz), 7.00–7.40(8H, m), 8.61(1H, brs)
73) $^1$H-NMR($CDCl_3$)δ; 1.35–1.65(1H, m), 1.70–2.20(8H, m), 2.65–3.20(3H, m), 3.25–3.55(4H, m), 3.88(2H, s), 4.90–5.10(1H, m), 5.79(1H, brs), 6.55–7.40 (13H, m), 8.37(1H, brs)
74) $^1$H-NMR($CDCl_3$)δ; 1.35–2.00(8H, m), 2.65–3.20(3H, m), 3.30–3.35(2H, m), 3.60–3.85(2H, m), 3.90(2H, s), 4.95–5.15(1H, m), 6.55–7.00(5H, m), 7.00–7.40 (8H, m), 7.65–7.90(4H, m), 8.22(1H, brs)
75) $^1$H-NMR($CDCl_3$)δ; 1.16(3H, t, J=7.0Hz), 2.39(3H, s), 2.80–3.20(3H, m), 3.44(2H, q, J=7.0Hz), 3.65–4.20(4H, m), 4.80–5.05(1H, m), 6.50–7.45 (13H, m), 8.50(1H, brs)
76) $^1$H-NMR($CDCl_3$)δ; 1.23(3H, t, J=7.0Hz), 2.41(3H, s), 2.75–3.20(3H, m), 3.40–3.60(5H, m), 3.65–3.90 (1H, m), 3.92(2H, s), 3.90–4.20(1H, m), 4.85–5.10 (1H, m), 6.65–7.45(11H, m), 8.13(1H, d, J=8.4 Hz), 9.01(1H, brs)
77) $^1$H-NMR($CDCl_3$)δ; 1.80–1.95(1H, m), 2.20–2.70 (10H, m), 3.50–3.60(1H, m), 3.63–3.80(1H, m), 4.00–4.15(1H, m), 6.60(1H, d, J=7.6Hz), 6.92 (1H, t, J=7.6Hz), 7.02(1H, t, J=6.3Hz), 7.20–7.65(9H, m), 7.87(1H, brs)
78) $^1$H-NMR($CDCl_3$)δ; 1.40–1.62(1H, m), 1.84–2.22(3H, m), 2.65–3.19(3H, m), 3.97(2H, t, J=4.9Hz), 4.43 (2H, t, J=4.9Hz), 4.95–5.18(1H, m), 6.60–6.77 (1H, m), 6.85–7.02(2H, m), 7.02–7.30(5H, m), 7.40–7.68(3H, m), 8.20–8.32(1H, m), 9.62–9.81 (1H, m)
79) $^1$H-NMR($CDCl_3$)δ; 1.38–1.65(1H, m), 1.84–2.21(3H, m), 2.64–3.15(3H, m), 3.81(2H, t, J=5.7Hz), 4.25 (2H, t, J=5.7Hz), 4.90–5.13(1H, m), 6.58–6.71 (1H, m), 6.82–7.00(1H, m), 7.00–7.52(10H, m), 8.11(1H, brs)

EXAMPLE 513

To a solution of 1-(4-aminobenzoyl)-2,3,4,5-tetrahydro-1H-benzazepine (1.06 g) in dichloromethane (80 ml) is added o-methylphenyl isocyanate (0.66 g) under ice-cooling. The mixture is stirred at room temperature for 4 hours. After completion of the reaction, the solvent is concentrated under reduced pressure and the resulting residue is purified by silica gel column chromatography (eluent; n-hexane:ethyl acetate=1:1), and recrystallized from ethyl acetate to give 1-[4-(2-methylanilinocarbonylamino) benzoyl]-2,3,4,5-tetrahydro-1H-benzazepine (0.97 g) as white powder, m.p. 182–182.5° C.

Using the suitable starting materials, the compounds of the above Examples 491–492 are obtained in the same manner as in Example 513.

EXAMPLE 514

A mixture of 1-(4-aminobenzoyl)-2,3,4,5-tetrahydro-1H-benzazepine (0.50 g), phenylsulfonyl chloride (0.29 ml), triethylamine (0.32 ml) and dichloromethane (30 ml) is stirred at room temperature overnight. The reaction mixture is washed successively with water and saturated saline solution, and dried over magnesium sulfate. The solvent is distilled off and the resulting residue is purified by silica gel column chromatography (eluent; chloroform), and recrystallized from methanol/diethyl ether to give 1-(4-phenylsulfonylaminobenzoyl)-2,3,4,5-tetrahydro-1H-benzazepine (0.27 g) as colorless prisms, m.p. 178–182.5° C.

Using the suitable starting materials, the compounds of the above Examples 469–471, 498, 502 and 503 are obtained in the same manner as in Example 514.

EXAMPLE 515

To a solution of 1-[4-(4-piperidinylcarbonylamino) benzoyl]-2,3,4,5-tetrahydro-1H-benzazepine (0.70 9) in dimethylformamide (20 ml) is added 60% sodium hydride dispersion in mineral oil (82 mg) and the mixture is stirred at room temperature for 30 minutes. Thereto is added methyl iodide (0.14 ml) and the mixture is stirred ar room temperature overnight. The solvent is distilled off and the resulting residue is extracted with chloroform, and washed successively with water and saturated saline solution, and dried over magnesium sulfate. The solvent is distilled off and the resulting residue is purified by silica gel column chromatography (eluent; chloroform:methanol=10:1), and recrystallized from methanol/n-hexane to give 1-{4-[N-(1-methyl-4-piperidinylcarbonyl)-N-methylamino]benzoyl}-2,3,4,5-tetrahydro-1H-benzazepine (0.03 g) as light yellow powder, m.p. 194.5–197° C.

Using the suitable starting materials, the compounds of the above Examples 497 and 501 are obtained in the same manner as in Example 515.

EXAMPLE 516

6-Fluoro-1-(4-aminobenzoyl)-1,2,3,4-tetrahydroquinoline (0.15 g) is dissolved in dichloromethane (10 ml) and thereto is added triethylamine (0.31 ml). To the mixture is added dropwise a solution of 3,5-dichlorobenzoyl chloride (0.14 g) in dichloromethane (2.0 ml) under ice-cooling, and the mixture is stirred for 30 minutes under ice-cooling, and further, at room temperature for 1 hour. To the mixture are added triethylamine (0.31 ml) and 3,5-dichlorobenzoyl chloride (0.14 ml). The mixture is stirred at room temperature for 4 hours. The reaction mixture is washed with water, and dried over magnesium sulfate. The solvent is distilled off and the resulting residue is purified by silica gel column chromatography (eluent; ethyl acetate:n-hexane=1:5→1:4), and recrystallized from ethyl acetate/n-hexane to give 6-fluoro-1-[4-(3,5-dichlorobenzoylamino) benzoyl]-1,2,3,4-tetrahydroquinoline (0.12 g) and 6-fluoro-1-{4-[bis-(3,5-dichlorobenzoyl)amino]benzoyl}-1,2,3,4-tetrahydroquinoline.

The former: White powder, m.p. 205.5–206.5° C.

The latter: White powder, m.p. 210.5–212° C.

EXAMPLE 517

Using the suitable starting materials, the compounds of the above Examples 450 and 504 are obtained in the same manner as in Example 378.

EXAMPLE 518

Using the suitable starting materials, the compounds of the above Examples 450–467, 495, 496, 499, 500, 511 and 512 are obtained in the same manner as in Example 380.

EXAMPLE 519

Using the suitable starting materials, the compounds of the above Examples 449, 474–489, 493 and 494 are obtained in the same manner as in Example 394.

EXAMPLE 520

Using the suitable starting materials, the compounds of the above Examples 453, 455, 457, 459, 460, 463–467, 495, 496 and 499 are obtained in the same manner as in Example 397.

EXAMPLE 521

Using the suitable starting materials, the compound of the above Example 461 is obtained in the same manner as in Example 396.

EXAMPLE 522

Using the suitable starting materials, the compound of the above Example 456 is obtained in the same manner as in Example 398.

EXAMPLE 523

Using the suitable starting materials, the compound of the above Example 459 is obtained in the same manner as in Example 399.

EXAMPLE 524

Using the suitable starting materials, the compounds of the above Examples 495 and 496 are obtained in the same manner as in Examples 400 and 401.

EXAMPLE 525

Using the suitable starting materials, the compound of the above Example 458 is obtained in the same manner as in Example 402.

Using the suitable starting materials, the compounds of the following Table 3 are obtained in the same manner as in Examples 1 and 382.

TABLE 3

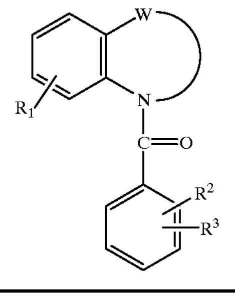

Example 527

Structure

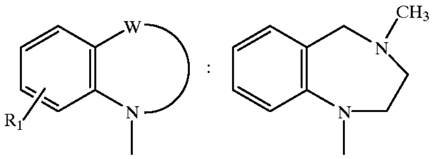

TABLE 3-continued $R^2$: 2-Cl

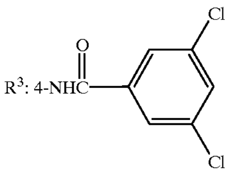

Crystalline form: White powder
Recrystallization solvent: Methanol/diethyl ether
Melting Point: 225–226° C.
Form: Free Example 528

Structure

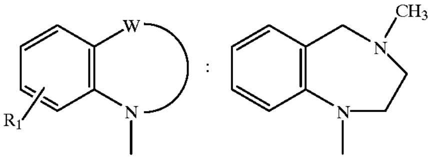

$R^2$: 2-Cl

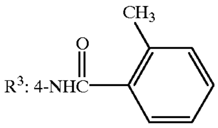

Crystalline form: White powder
Recrystallization solvent: Methanol/diethyl ether
Melting Point: 142.5–145° C.
Form: Free Example 529

Structure

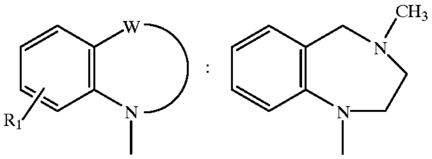

$R^2$: 2-Cl

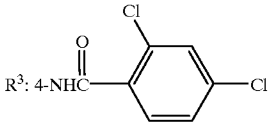

Crystalline form: White powder
Recrystallization solvent: Methanol/diethyl ether
Melting Point: 213–215° C.
Form: Free TABLE 3-continued Example 530

Structure

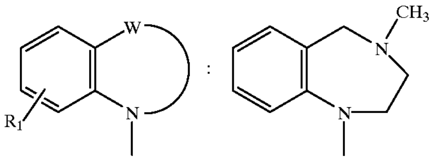

$R^2$: 3-$CH_3$

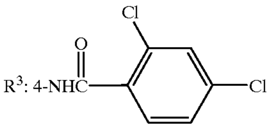

Crystalline form: White powder
Recrystallization solvent: Methanol/diethyl ether
Melting Point: 167–167.5° C.
Form: Free Example 531

Structure

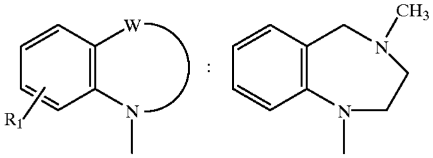

$R^2$: 3-$CH_3$

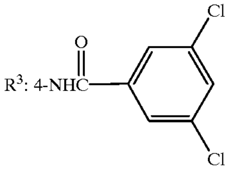

Crystalline form: Colorless scales
Recrystallization solvent: Methanol/diethyl ether
Melting Point: 217–221° C.
Form: Free Example 532

Structure

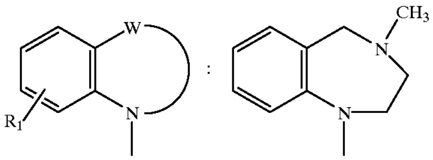

$R^2$: 3-$CH_3$

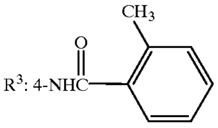

Crystalline form: White powder
Recrystallization solvent: Methanol/diethyl ether TABLE 3-continued Melting Point: 182–184° C.
Form: Free
Example 533

Structure

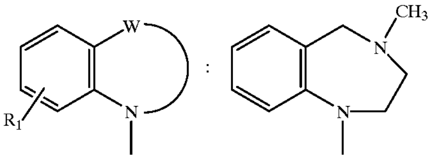

$R^2$: 3-$CH_3$ $R^3$: 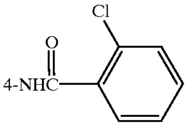

Crystalline form: White powder
Recrystallization solvent: Methanol/diethyl ether
Melting Point: 209–210° C.
Form: Free
Example 534

Structure

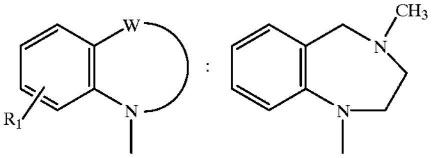

$R^2$: 3-$OCH_3$ $R^3$: 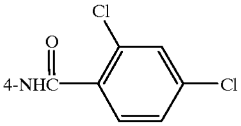

Crystalline form: White powder
Recrystallization solvent: Methanol/diethyl ether
Melting point: 148–149° C.
Form: Free
Example 535

Structure

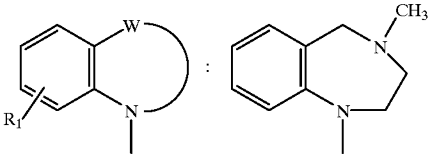

$R^2$: H $R^3$: 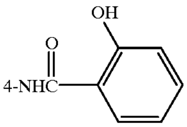

Crystalline form: White powder
Recrystallization solvent: Methanol/diethyl ether TABLE 3-continued Melting point: 202–203° C.
Form: Free
Example 536

Structure

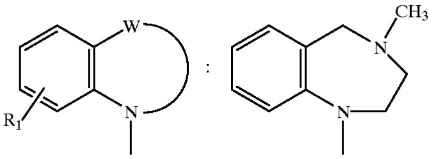

$R^2$: 3-$CH_3$ $R^3$: 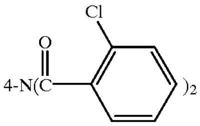

Crystalline form: White powder
Recrystallization solvent: Methanol/diethyl ether
Melting Point: 218–219° C.
Form: Free
Example 537

Structure

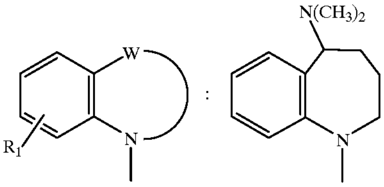

$R^2$: 2-Cl $R^3$: 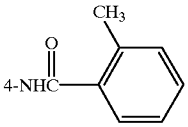

Crystalline form: White powder
Recrystallization solvent: Methanol/n-hexane
Melting Point: 159–160° C.
Form: Free
Example 538

Structure

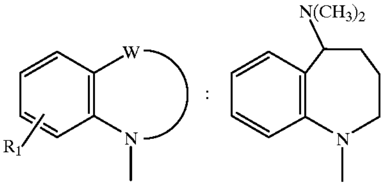

$R^2$: 2-Cl $R^3$: 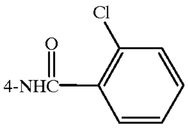

TABLE 3-continued

Crystalline form: White powder
Recrystallization solvent: Methanol/n-hexane
Melting Point: 201–202° C.
Form: Free Example 539

Structure

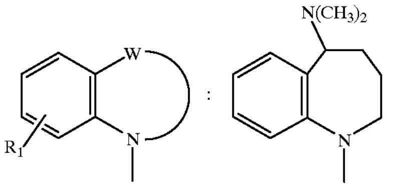

$R^2$: 2-Cl

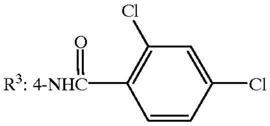

Crystalline form: White powder
Recrystallization solvent: Methanol/n-hexane
Melting Point: 205–207° C.
Form: Free Example 540

Structure

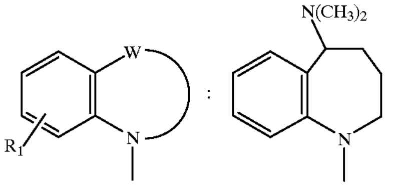

$R^2$: 3-OH

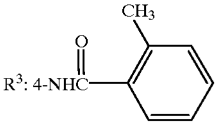

Crystalline form: White powder
Recrystallization solvent: Methanol/diethyl ether
Melting point: 201.5–202.5° C.
Form: Free Example 541

Structure

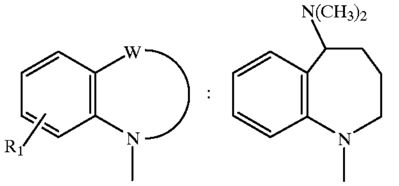

$R^2$: 2-$OCH_3$

TABLE 3-continued

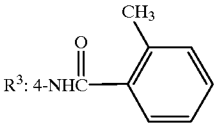

Crystalline form: White powder
Recrystallization solvent: Methanol/diethyl ether
Melting Point: 226–228° C.
Form: Free Example 542

Structure

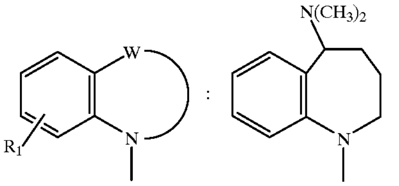

$R^2$: 2-$OCH_3$

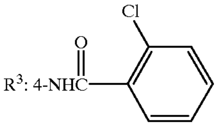

Crystalline form: White powder
Recrystallization solvent: Methanol/diethyl ether
Melting Point: 218–221° C.
Form: Free Example 543

Structure

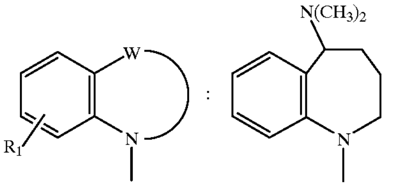

$R^2$: 2-$OCH_3$

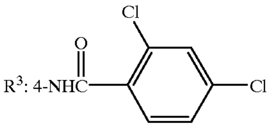

Crystalline form: White powder
Recrystallization solvent: Methanol/diethyl ether
Melting Point: 156–157° C.
Form: Free TABLE 3-continued Example 544

Structure

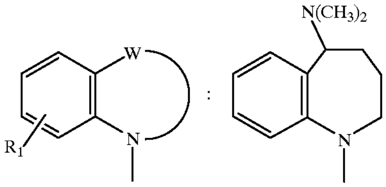

$R^2$: 2-$OCH_3$ $R^3$: 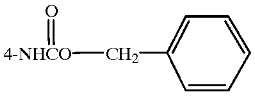

Crystalline form: White powder
NMR analysis: 80)
Form: Free

Example 545

Structure

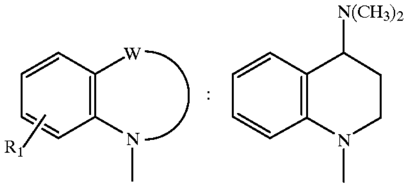

$R^2$: 3-$OCH_3$ $R^3$: 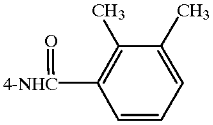

Crystalline form: Colorless amorphous
NMR analysis: 81)
Form: Free

Example 546

Structure

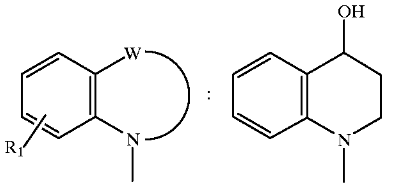

$R^2$: H $R^3$: 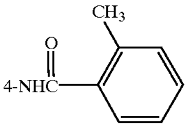

Crystalline form: Colorless amorphous

TABLE 3-continued

NMR analysis: 82)
Form: Free

Example 547

Structure

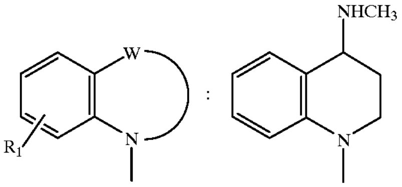

$R^2$: H $R^3$: 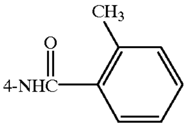

Crystalline form: Light yellow amorphous
NMR analysis: 83)
Form: Free

Example 548

Structure

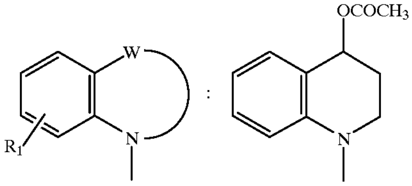

$R^2$: H $R^3$: 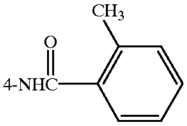

Crystalline form: Colorless amorphous
NMR analysis: 84)
Form: Free

Example 549

Structure

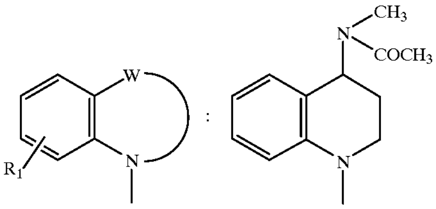

$R^2$: H $R^3$: 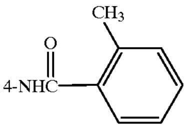

TABLE 3-continued

Crystalline form: Colorless amorphous
NMR analysis: 85)
Form: Free

Example 550

Structure

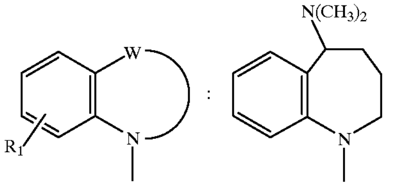

$R^2$: 3-$OCH_2CH_3$

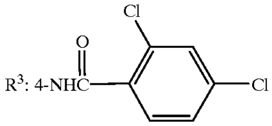

Crystalline form: White powder
Recrystallization solvent: n-Hexane/ethyl acetate
Melting Point: 135–136° C.
Form: Free Example 551

Structure

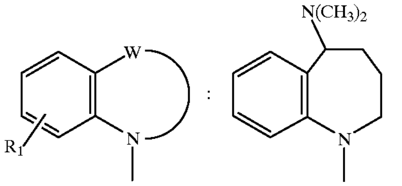

$R^2$: 3-$OCH_2CH_3$

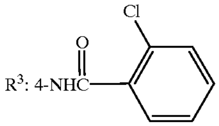

Crystalline form: Colorless prisms
Recrystallization solvent: n-Hexane/ethyl acetate
Melting Point: 122–123° C.
Form: Free Example 552

Structure

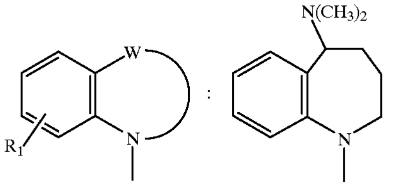

$R^2$: 3-$OCH_2CH_3$

TABLE 3-continued

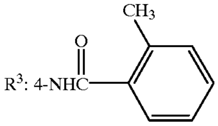

Crystalline form: Colorless prisms
Recrystallization solvent: n-Hexane/ethyl acetate
Melting Point: 118–119° C.
Form: Free Example 553

Structure

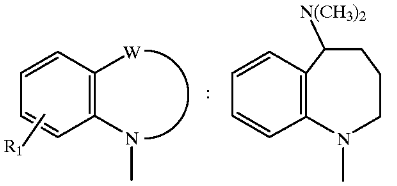

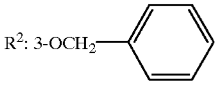

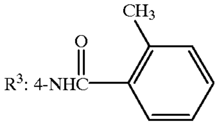

Crystalline form: Colorless prisms
Recrystallization solvent: n-Hexane/ethyl acetate
Melting Point: 145–147° C.
Form: Free Example 554

Structure

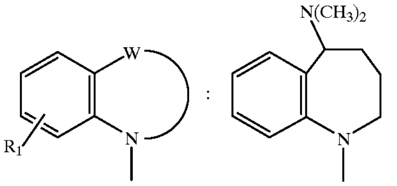

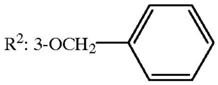

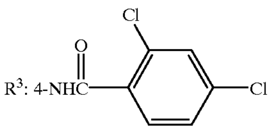

Crystalline form: Light yellow needles
Recrystallization solvent: n-Hexane/ethyl acetate
Melting Point: 169.5–170.5° C.
Form: Free TABLE 3-continued Example 555

Structure

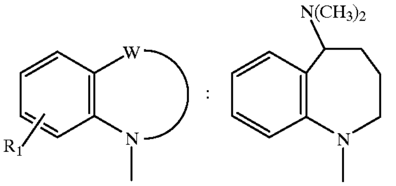

R$^2$: 3-OH

R$^3$: 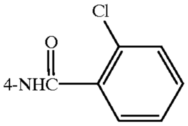

Crystalline form: Colorless prisms
Recrystallization solvent: n-Hexane/ethyl acetate
Melting Point: 194–195° C.
Form: Free Example 556

Structure

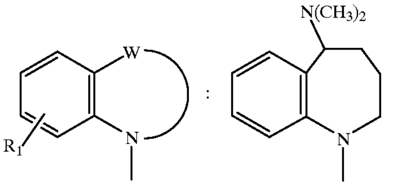

R$^2$: 3-OH

R$^3$: 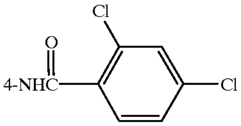

Crystalline form: Colorless needles
Recrystallization solvent: n-Hexane/ethyl acetate
Melting Point: 202–204° C.
Form: Free Example 557

Structure

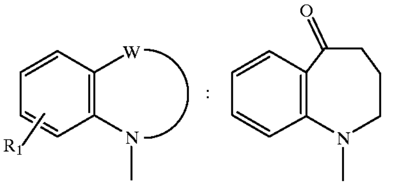

R$^2$: H

TABLE 3-continued

R$^3$: 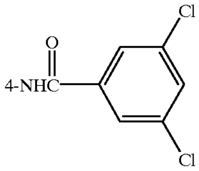

Crystalline form: Colorless prisms
Recrystallization solvent: Ethanol
Melting Point: 242–243° C.
Form: Free Example 558

Structure

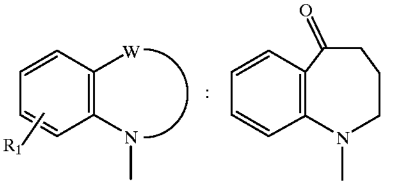

R$^2$: H

R$^3$: 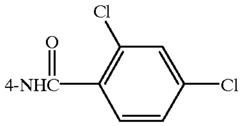

Crystalline form: Light yellow powder
NMR analysis: 86)
Form: Free

Example 559

Structure

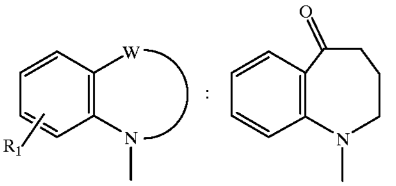

R$^2$: H

R$^3$: 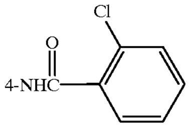

Crystalline form: Light yellow powder
NMR analysis: 87)
Form: Free

TABLE 3-continued

Example 560

Structure

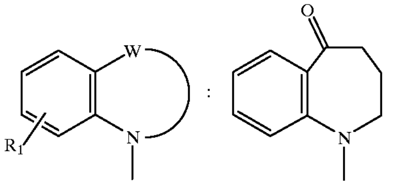

$R^2$: H

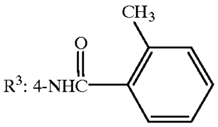

Crystalline form: Colorless needles
Recrystallization solvent: Ethanol
Melting Point: 237–238° C.
Form: Free Example 561

Structure

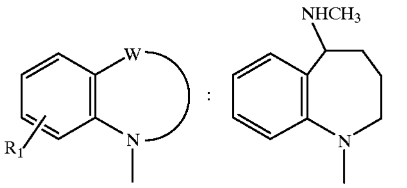

$R^2$: H

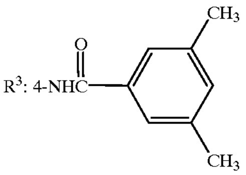

Crystalline form: Colorless prisms
Recrystallization solvent: Dioxane
Melting Point: 258–259° C.
Form: Free Example 562

Structure

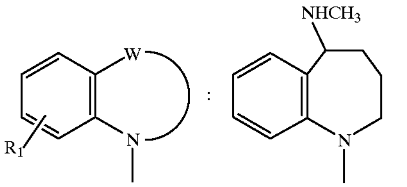

$R^2$: H

TABLE 3-continued

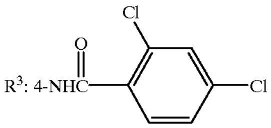

Crystalline form: Colorless prisms
Recrystallization solvent: Ethanol
Melting Point: 182.5–183.5° C.
Form: Free Example 563

Structure

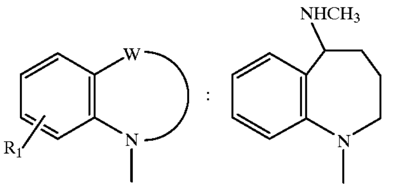

$R^2$: H

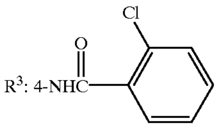

Crystalline form: Colorless prisms
Recrystallization solvent: Ethanol
Melting Point: 209–211° C.
Form: Free Example 564

Structure

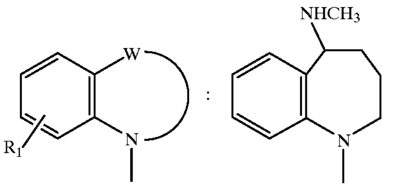

$R^2$: H

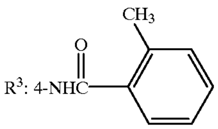

Crystalline form: Colorless prisms
Recrystallization solvent: Dioxane
Melting Point: 210–211° C.
Form: Free TABLE 3-continued Example 565

Structure

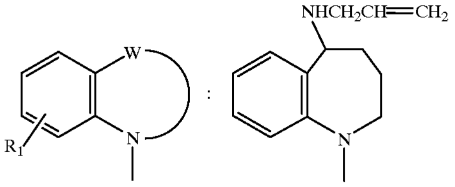

$R^2$: H

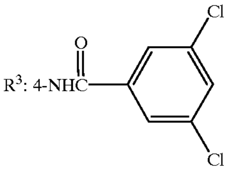

Crystalline form: Colorless needles
Recrystallization solvent: Ethyl acetate/n-hexane
Melting Point: 176–178° C.
Form: Free Example 566

Structure

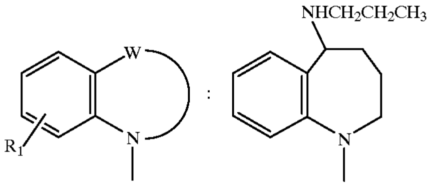

$R^2$: H

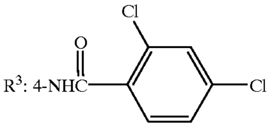

Crystalline form: Light yellow amorphous
NMR analysis: 88)
Form: Free

Example 567

Structure

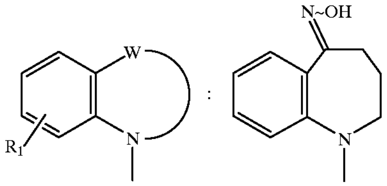

$R^2$: H

TABLE 3-continued

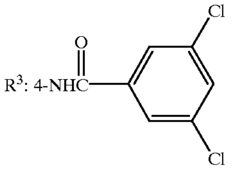

Crystalline form: White powder
Recrystallization solvent: Dioxane/water
Melting Point: 272–273° C.
Form: Free Example 568

Structure

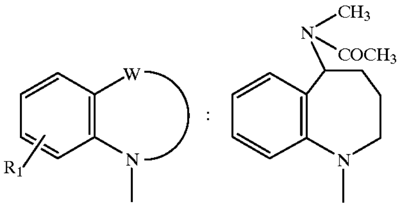

$R^2$: H

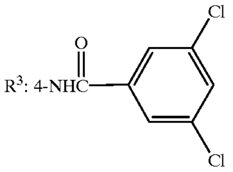

Crystalline form: Colorless prisms
Recrystallization solvent: Dioxane
Melting Point: 253–254° C.
Form: Free Example 569

Structure

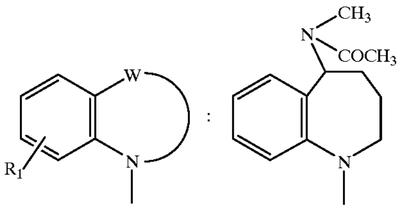

$R^2$: H

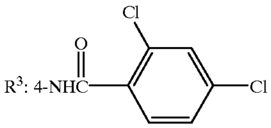

Crystalline form: Colorless prisms
Recrystallization solvent: Ethanol
Melting Point: 248.5–249.5° C.
Form: Free TABLE 3-continued Example 570

Structure

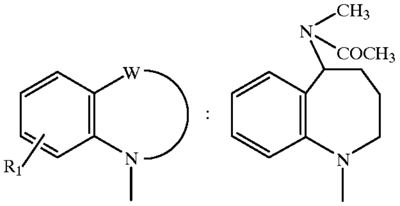

$R^2$: H

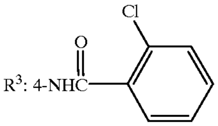

Crystalline form: Colorless needles
Recrystallization solvent: Ethanol
Melting Point: 266.5–267.5° C.
Form: Free Example 571

Structure

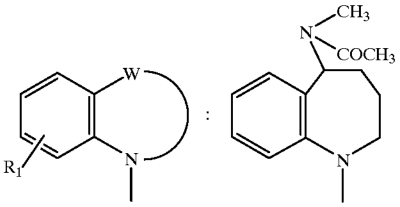

$R^2$: H

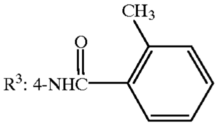

Crystalline form: Colorless needles
Recrystallization solvent: Ethanol
Melting Point: 252–253° C.
Form: Free Example 572

Structure

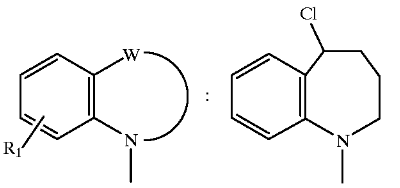

$R^2$: H

TABLE 3-continued

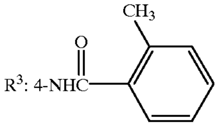

Crystalline form: Light yellow powder
NMR analysis: 89)
Form: Free

Example 573

Structure

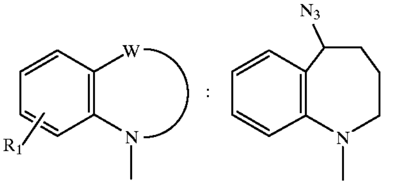

$R^2$: H

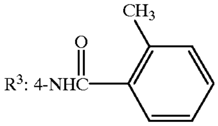

Crystalline form: Light brown powder
NMR analysis: 90)
Form: Free

Example 574

Structure

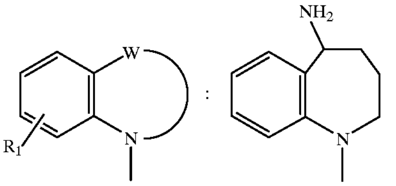

$R^2$: H

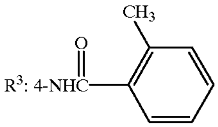

Crystalline form: White powder
Recrystallization solvent: Diethyl ether
Melting Point: 198.5–199.5° C.
Form: Free Example 575

Structure

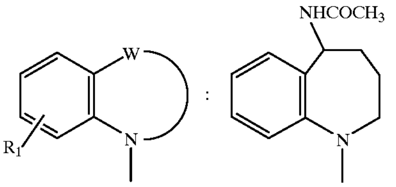

TABLE 3-continued

R$^2$: H

R$^3$: 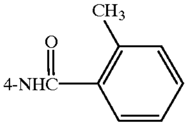

Crystalline form: Colorless needles
Recrystallization solvent: Ethanol
Melting Point: 297–299° C.
Form: Free Example 576

Structure

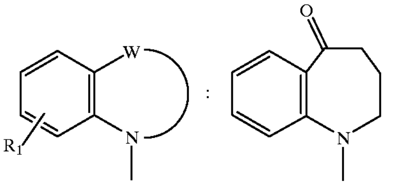

R$^2$: 2-Cl

R$^3$: 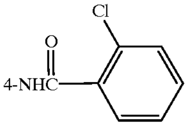

Crystalline form: Colorless amorphous
NMR analysis: 91)
Form: Free

Example 577

Structure

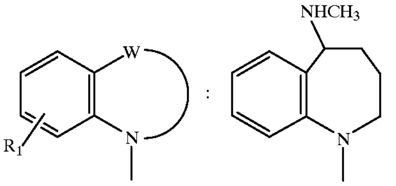

R$^2$: 2-Cl

R$^3$: 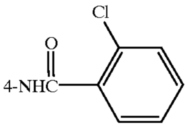

Crystalline form: White powder
Recrystallization solvent: Ethanol/petroleum ether
Melting Point: 202–203° C.
Form: Free TABLE 3-continued Example 578

Structure

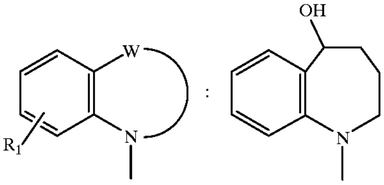

R$^2$: H

R$^3$: 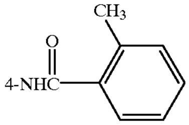

Crystalline form: Colorless amorphous
NMR analysis: 92)
Form: Free

Example 579

Structure

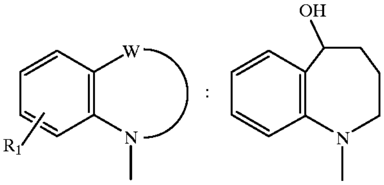

R$^2$: H

R$^3$: 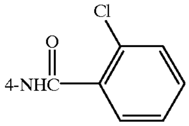

Crystalline form: White powder
Recrystallization solvent: Ethyl acetate/n-hexane
Melting Point: 232–233° C.
Form: Free Example 580

Structure

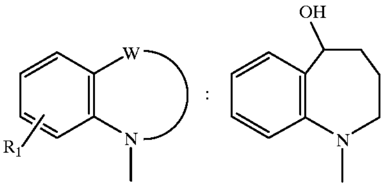

R$^2$: H

R$^3$: 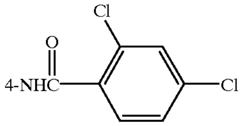

Crystalline form: Colorless amorphous

TABLE 3-continued

NMR analysis: 93)
Form: Free
Example 581

Structure

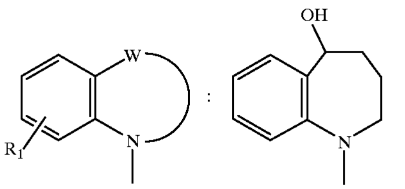

$R^2$: H

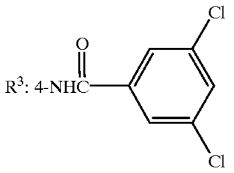

Crystalline form: White powder
Recrystallization solvent: Ethyl acetate/n-hexane
Melting point: 256.5–257° C.
Form: Free
Example 582

Structure

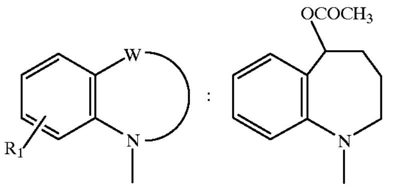

$R^2$: H

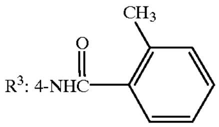

Crystalline form: White powder
Recrystallization solvent: Ethyl acetate/n-hexane
Melting Point: 193–194° C.
Form: Free
Example 583

Structure

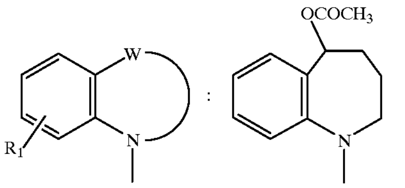

$R^2$: H

TABLE 3-continued

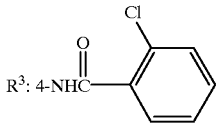

Crystalline form: White powder
Recrystallization solvent: Ethyl acetate/n-hexane
Melting Point: 227–230° C.
Form: Free
Example 584

Structure

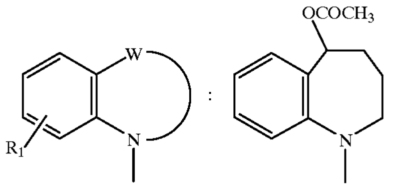

$R^2$: H

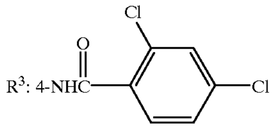

Crystalline form: White powder
Recrystallization soivent: Ethyl acetate/n-hexane
Melting Point: 199.5–202° C.
Form: Free
Example 585

Structure

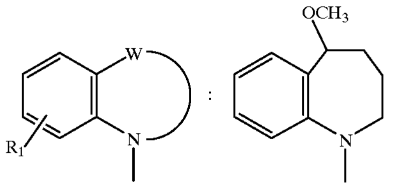

$R^2$: H

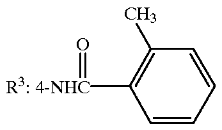

Crystalline form: White powder
Recrystallization solvent: Ethyl acetate/n-hexane
Melting Point: 219–220° C.
Form: Free TABLE 3-continued Example 586

Structure

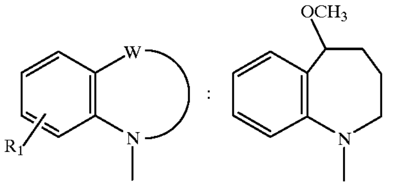

$R^2$: H

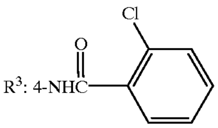

Crystalline form: White powder
Recrystallization solvent: Ethyl acetate/n-hexane
Melting Point: 190–191.5° C.
Form: Free Example 587

Structure

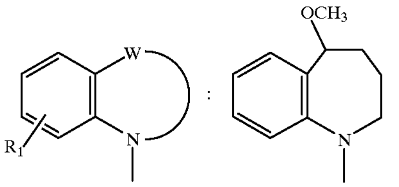

$R^2$: H

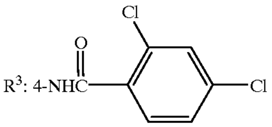

Crystalline form: White powder
Recrystallization solvent: Ethyl acetate/n-hexane
Melting Point: 184–185° C.
Form: Free Example 588

Structure

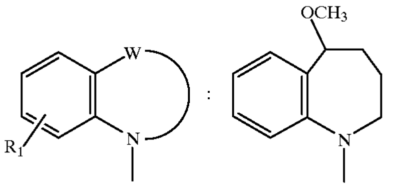

$R^2$: H

TABLE 3-continued

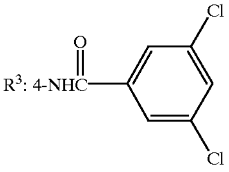

Crystalline form: White powder
Recrystallization solvent: Ethyl acetate/n-hexane
Melting Point: 223–224° C.
Form: Free Example 589

Structure

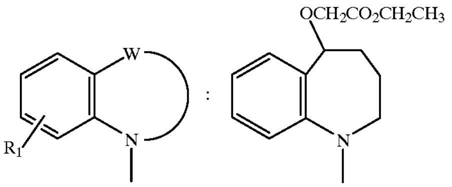

$R^2$: H

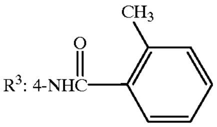

Crystalline form: White powder
Recrystallization solvent: Ethyl acetate/n-hexane
Melting Point: 178–181° C.
Form: Free Example 590

Structure

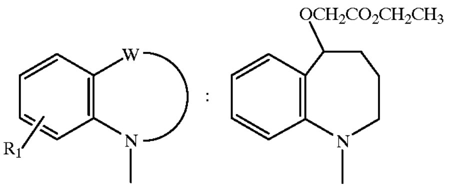

$R^2$: H

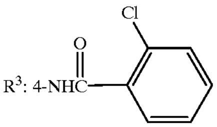

Crystalline form: Colorless needles
Recrystallization solvent: Ethyl acetate/n-hexane
Melting Point: 168–168.5° C.
Form: Free TABLE 3-continued Example 591

Structure

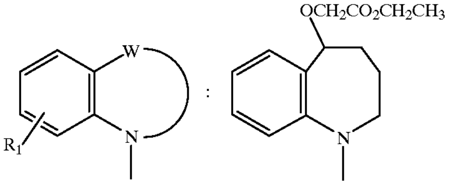

$R^2$: H

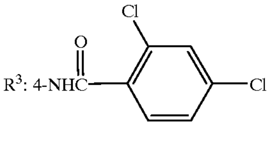

Crystalline form: Colorless amorphous
NMR analysis: 94)
Form: Free

Example 592

Structure

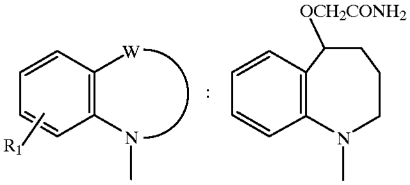

$R^2$: H

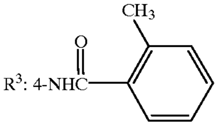

Crystalline form: Colorless amorphous
NMR analysis: 95)
Form: Free

Example 593

Structure

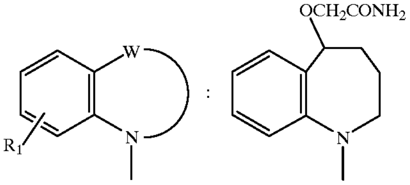

$R^2$: H

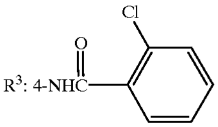

Crystalline form: White powder
Recrystallization solvent: Ethyl acetate/n-hexane TABLE 3-continued Melting Point: 195–197° C.
Form: Free Example 594

Structure

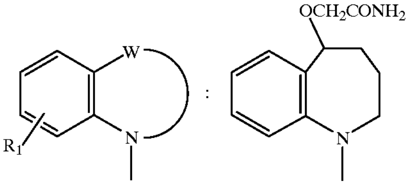

$R^2$: H

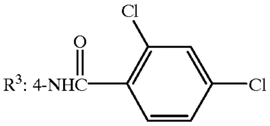

Crystalline form: Colorless amorphous
NMR analysis: 96)
Form: Free

Example 595

Structure

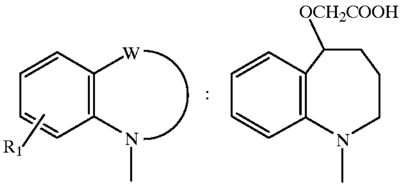

$R^2$: H

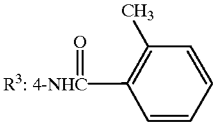

Crystalline form: White powder
Recrystallization solvent: Ethanol/water
Melting Point: 188–189° C.
Form: Free Example 596

Structure

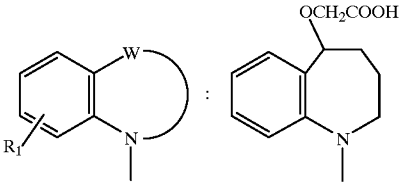

$R^2$: H

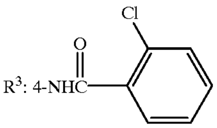

TABLE 3-continued

Crystalline form: Colorless amorphous
NMR analysis: 97)
Form: Free
Example 597

Structure

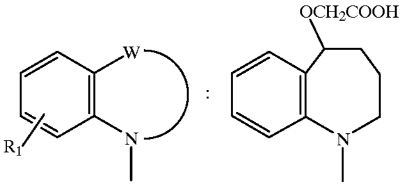

R$^2$: H

R$^3$: 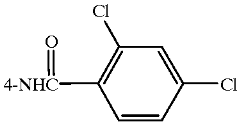

Crystalline form: Colorless amorphous
NMR analysis: 98)
Form: Free
Example 598

Structure

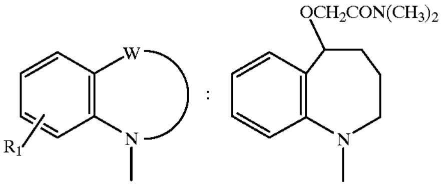

R$^2$: H

R$^3$: 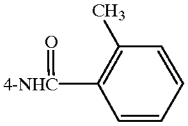

Crystalline form: Colorless prisms
Recrystallization solvent: Ethyl acetate/n-hexane
Melting Point: 203–204° C.
Form: Free
Example 599

Structure

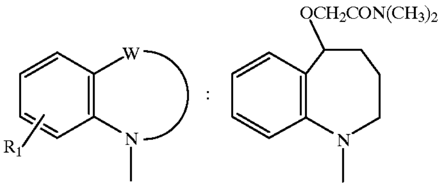

R$^2$: H

TABLE 3-continued

R$^3$: 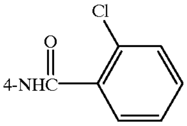

Crystalline form: White powder
Recrystallization solvent: Ethyl acetate/n-hexane
Melting Point: 196–197° C.
Form: Free
Example 600

Structure

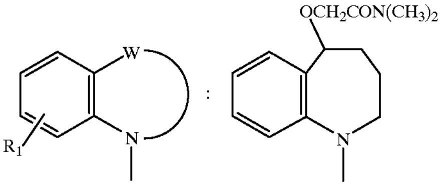

R$^2$: H

R$^3$: 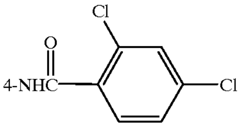

Crystalline form: Colorless amorphous
NMR analysis: 99)
Form: Free
Example 601

Structure

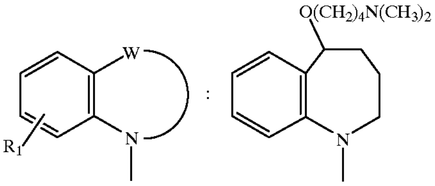

R$^2$: H

R$^3$: 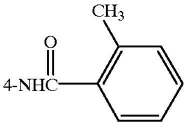

Crystalline form: Colorless amorphous
NMR analysis: 100)
Form: Free
Example 602

Structure

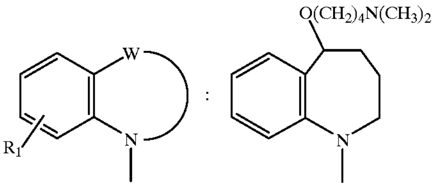

TABLE 3-continued $R^2$: H

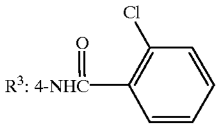

Crystalline form: Colorless amorphous
NMR analysis: 101)
Form: Free

Example 603

Structure

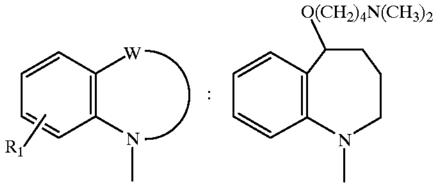

$R^2$: H

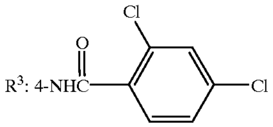

Crystalline form: Colorless amorphous
NMR analysis: 102)
Form: Free

Example 604

Structure

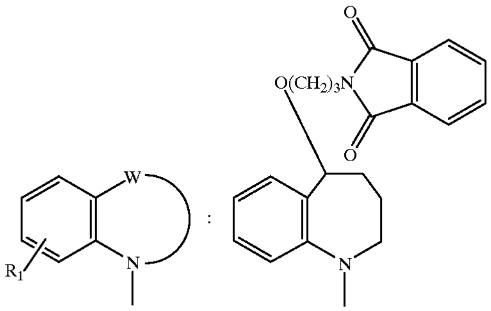

$R^2$: H

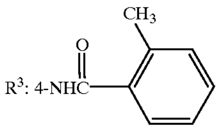

Crystalline form: Colorless amorphous
NMR analysis: 103)
Form: Free

TABLE 3-continued

Example 605

Structure

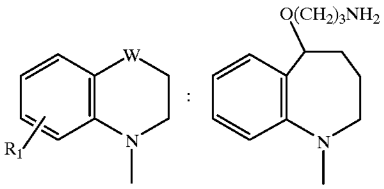

$R^2$: H

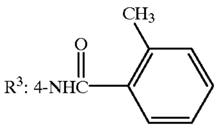

Crystalline form: Colorless amorphous
NMR analysis: 104)
Form: Free

Example 606

Structure

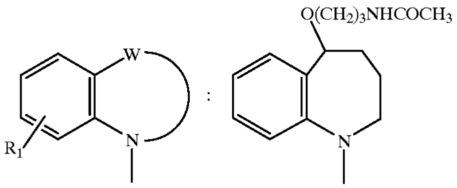

$R^2$: H

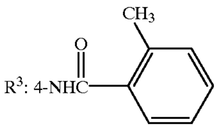

Crystalline form: Colorless amorphous
NMR analysis: 105)
Form: Free

Example 607

Structure

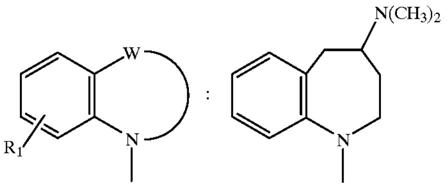

$R^2$: H

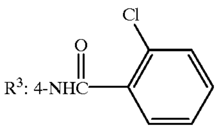

Crystalline form: Cololess needles
Recrystallization solvent: Ethanol

TABLE 3-continued

Melting Point: 169–171° C.
Form: Free
Example 608

Structure

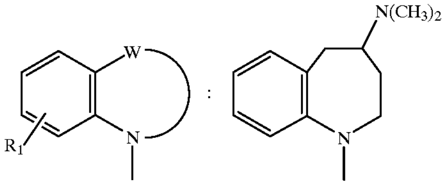

$R^2$: H

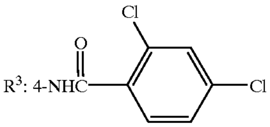

Crystalline form: Colorless needles
Recrystallization solvent: Ethanol/diethyl ether
Melting Point: 178–181° C.
Form: Free
Example 609

Structure

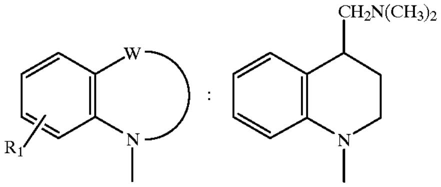

$R^2$: H

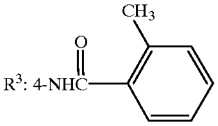

Crystalline form: White powder
Recrystallization solvent: Ethanol
Melting Point: 187–188° C.
Form: Free
Example 610

Structure

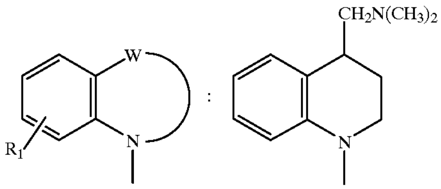

$R^2$: H

TABLE 3-continued

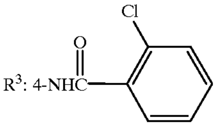

Crystalline form: White powder
Recrystallization solvent: Ethanol
Melting Point: 181–183° C.
Form: Free
Example 611

Structure

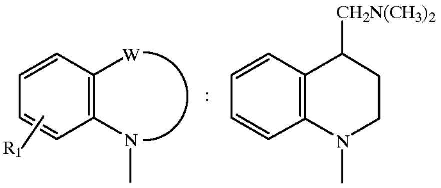

$R^2$: H

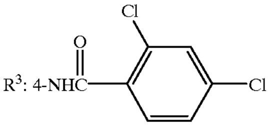

Crystalline form: White powder
Recrystallization solvent: Ethanol
Melting Point: 124–127° C.
Form: Free
Example 612

Structure

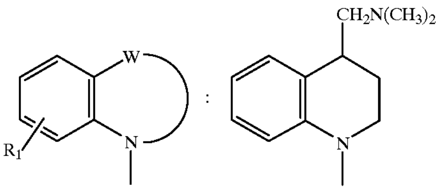

$R^2$: H

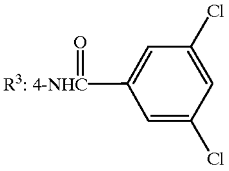

Crystalline form: White powder
Recrystallization solvent: Ethanol
Melting Point: 179–181° C.
Form: Free TABLE 3-continued Example 613

Structure

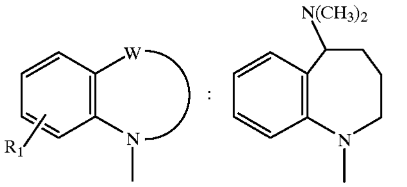

$R^2$: H $R^3$: 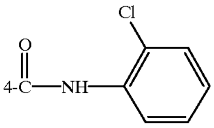

Crystalline form: White powder
Recrystallization solvent: Ethanol
Melting Point: 148–150° C.
Form: Free Example 614

Structure

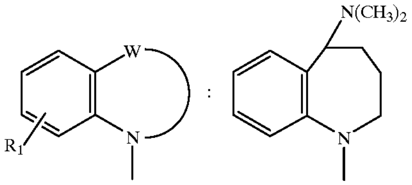

$R^2$: H $R^3$: 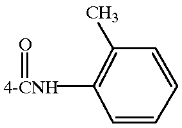

Crystalline form: Colorless amorphous
NMR analysis: 106)
Form: Free

Example 615

Structure

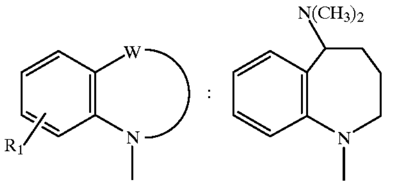

$R^2$: 2-Cl $R^3$: 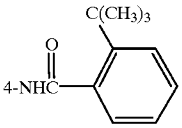

Crystalline form: White powder

TABLE 3-continued

Recrystallization solvent: Ethanol
Melting Point: 219–220° C.
Form: Free

Example 616

Structure

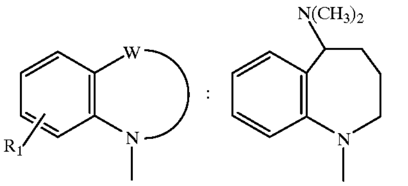

$R^2$: H $R^3$: 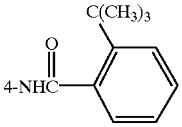

Crystalline form: White powder
Recrystallization solvent: Ethanol
Melting Point: 226–228° C.
Form: Free Example 617

Structure

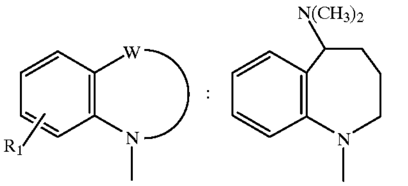

$R^2$: 3-$OCH_3$ $R^3$: 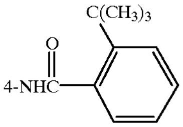

Crystalline form: Colorless amorphous
NMR analysis: 107)
Form: Free

Example 618

Structure

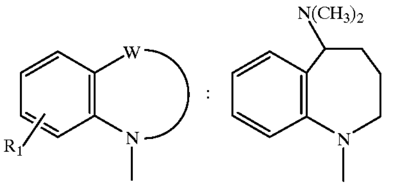

$R^2$: 3-$OCH_3$

TABLE 3-continued

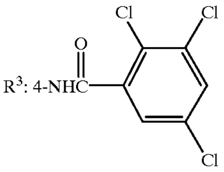

Crystalline form: Colorless amorphous
NMR analysis: 108)
Form: Free
Example 619

Structure

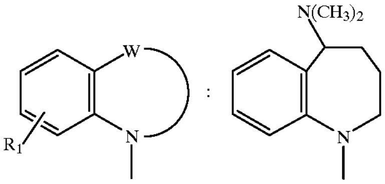

$R^2$: 3-$OCH_3$

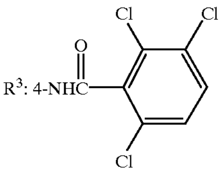

Crystalline form: Colorless amorphous
NMR analysis: 109)
Form: Free
Example 620

Structure

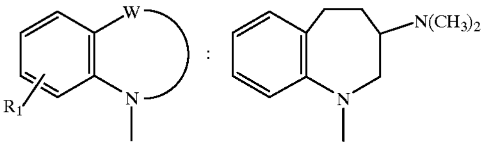

$R^2$: H

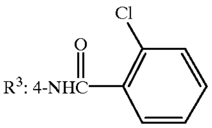

Crystalline form: Colorless amorphous
NMR analysis: 110)
Form: Free
Example 621

Structure

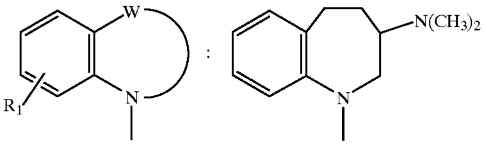

$R^2$: H

TABLE 3-continued

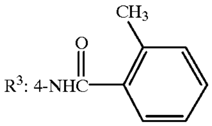

Crystalline form: Colorless amorphous
NMR analysis: 111)
Form: Free
Example 622

Structure

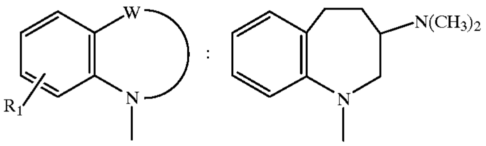

$R^2$: H

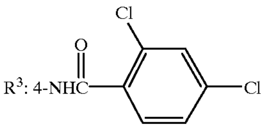

Crystalline form: Colorless amorphous
NMR analysis: 112)
Form: Free
Example 623

Structure

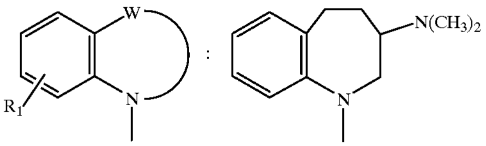

$R^2$: 3-$OCH_3$

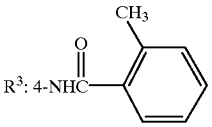

Crystalline form: Colorless amorphous
NMR analysis: 113)
Form: Free
Example 624

Structure

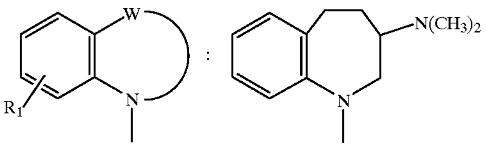

$R^2$: 3-$OCH_3$

TABLE 3-continued

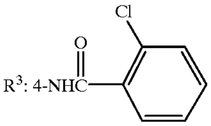

Crystalline form: Colorless amorphous
NMR analysis: 114)
Form: Free
Example 625

Structure

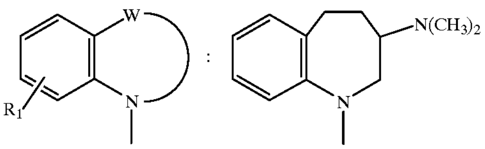

$R^2$: 3-$OCH_3$

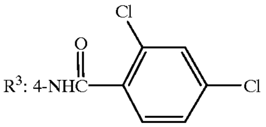

Crystalline form: Colorless amorphous
NMR analysis: 115)
Form: Free
Example 626

Structure

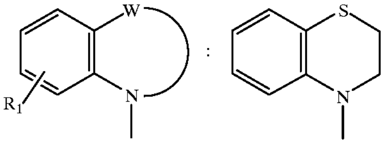

$R^2$: H

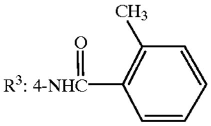

Crystalline form: White powder
Recrystallization solvent: Diethyl ether/dichloromethane
Melting Point: 183–184° C.
Form: Free
Example 627

Structure

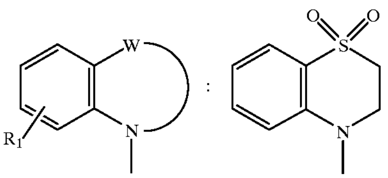

$R^2$: H

TABLE 3-continued

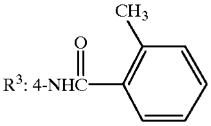

Crystalline form: White powder
Recrystallization solvent: Diethyl ether/dichloromethane
Melting Point: 219–220° C.
Form: Free
Example 628

Structure

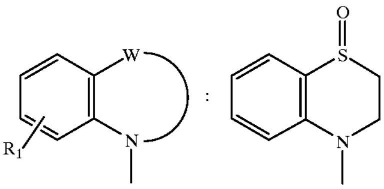

$R^2$: H

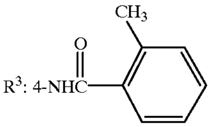

Crystalline form: White powder
Recrystallization solvent: Diethyl ether/dichloromethane
Melting Point: 240–241° C.
Form: Free
Example 629

Structure

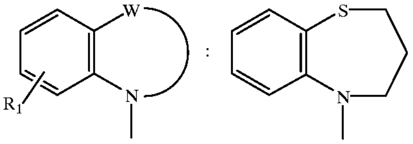

$R^2$: H

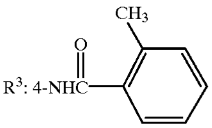

Crystalline form: White powder
Recrystallization solvent: Diethyl ether/dichloromethane
Melting Point: 205–206° C.
Form: Free
Example 630

Structure

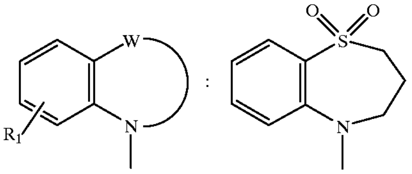

TABLE 3-continued $R^2$: H $R^3$: 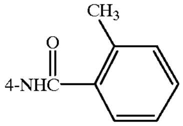

Crystalline form: White powder
Recrystallization solvent: Diethyl ether/dichloromethane
Melting Point: 238–239° C.
Form: Free Example 631

Structure

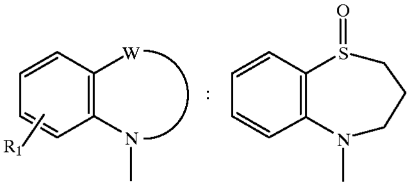

$R^2$: H $R^3$: 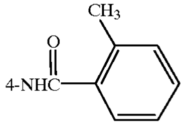

Crystalline form: White powder
Recrystallization solvent: Diethyl ether/dichloromethane
Melting Point: 233–234° C.
Form: Free Example 632

Structure

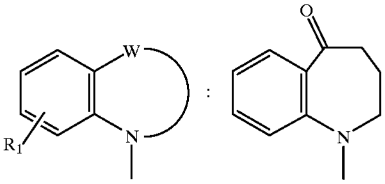

$R^2$: 2-Cl $R^3$: 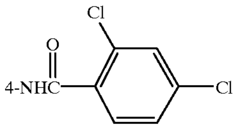

Crystalline form: Colorless amorphous
NMR analysis: 116)
Form: Free

TABLE 3-continued

Example 633

Structure

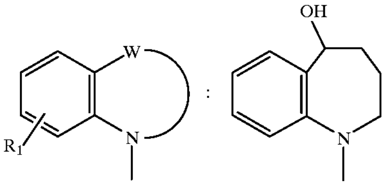

$R^2$: 2-Cl $R^3$: 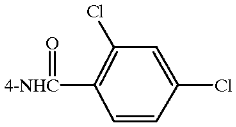

Crystalline form: White powder
Recrystallization solvent: Diethyl ether/dichloromethane
Melting Point: 259.5–260.5° C.
Form: Free 80) $^1$H-NMR($CDCl_3$) δ; 1.24–5.26 (18H, m), 6.39–7.59 (13H, m)

81) $^1$H-NMR($CDCl_3$) δ; 1.70–2.10 (m, 2H), 2.15–2.60 (m, 12H), 3.56 (t, J=5.8 Hz, 1H), 3.65–3.95 (m, 4H) 4.05–4.25 (m, 1H), 6.64 (d, J=7.7 Hz, 1H), 6.85–7.50 (m, 9H), 8.11 (brs, 1H), 8.42 (d, J=8.8 Hz, 1H)

82) $^1$H-NMR($CDCl_3$) δ; 2.00–2.90 (m, 3H), 2.49 (s, 3H), 3.70–3.90 (m, 1H), 4.00–4.20 (m, 1H), 4.80–5.00 (m, 1H), 6.89 (d, J=6.3 Hz, 1H), 6.95–7.65 (m, 11H), 7.70 (brs, 1H)

83) $^1$H-NMR($CDCl_3$) δ; 1.95–2.90 (m, 2H), 2.48 (s, 3H), 2.55 (s, 3H), 3.77 (t, J=5.1 Hz, 1H), 3.92 (t, J=6.7 Hz, 2H), 6.72 (d, J=8.0 Hz, 1H), 6.90–7.15 (m, 2H), 7.15–7.70 (m, 9H), 7.81 (brs, 1H)

84) $^1$H-NMR($CDCl_3$) δ; 2.11 (s, 3H), 2.20–2.40 (m, 2H), 2.50 (s, 3H), 3.80–4.10 (m, 1H), 4.12–4.25 (m, 1H), 6.03 (t, J=4.3 Hz, 1H), 6.80–7.65 (m, 12H), 7.80 (brs, 1H)

85) $^1$H-NMR($CDCl_3$) δ; 1.80–2.40 (m, 5H), 2.45 (s, 3H), 2.81 (s, 3H), 3.55–3.82 (m, 1H), 4.15–4.40 (m, 1H), 5.90–6.10 (m, 1H), 6.80–7.80 (m, 12H), 8.67 (brs, 1H)

86) $^1$H-NMR($CDCl_3$) δ; 1.95–2.35 (2H, m), 2.75–3.0 (2H, m), 3.0–5.4 (2H, m), 6.55–7.95 (11H, m), 8.09 (1H, s)

87) $^1$H-NMR(DMSO-$d_6$) δ; 1.85–2.2 (2H, m), 2.7–2.95 (2H, m), 3.5–5.0 (2H, m), 6.8–7.8 (12H, m), 10.60 (1H, s)

88) $^1$H-NMR($CDCl_3$) δ; 0.8–1.1 (3H, m), 1.2–2.35 (6H, m), 2.35–5.25 (6H, m), 6.63 (1H, d, J=7.7 Hz), 6.8–7.6 (9H, m), 7.67 (1H, d, J=8.2 Hz), 7.9–8.15 (1H, m)

89) $^1$H-NMR($CDCl_3$) δ; 1.7–2.9 (7H, m), 4.5–6.5 (3H, m), 6.55–6.75 (1H, m), 6.85–7.6 (12H, m)

90) $^1$H-NMR($CDCl_3$) δ; 1.65–3.1 (7H, m), 4.7–6.6 (3H, m), 6.6–6.8 (1H, m), 6.85–7.65 (12H, m)

91) $^1$H-NMR($CDCl_3$) δ; 1.8–2.4 (2H, m), 2.86 (2H, t, J=6 Hz), 3.1–5.15 (2H, m), 6.85–7.5 (8H, m), 7.5–7.85 (3H, m), 8.19 (1H, s)

92) $^1$H-NMR($CDCl_3$) δ; 1.46–2.28 (4H, m), 2.37 (3H, s), 2.58–2.90 (1H, m), 4.57–5.10 (2H, m), 6.59 (1H, d, J=7.6 Hz,), 6.91–7.52 (11H, m), 7.62 (1H, d, J=7.6 Hz), 8.10–8.40 (1H, m)

93) $^1$H-NMR($CDCl_3$) δ; 1.45–1.91 (2H, m), 1.91–2.65 (2H, m), 2.65–2.90 (1H, m), 4.63–5.22 (2H, m), 6.63 (1H, d, J=7.4 Hz), 7.34–8.03 (11H, m), 10.16–10.44 (1H, m)

94) $^1$H-NMR($CDCl_3$) δ; 1.08–1.47 (3H, m), 1.50–1.97 (2H, m), 1.97–2.48 (2H, m), 2.65–3.02 (1H, m), 4.00–4.43 (4H, m), 4.52–5.15 (2H, m), 6.50–6.79 (1H, m), 6.90–7.70 (10H, m), 8.26–8.60 (1H, m)

95) $^1$H-NMR($CDCl_3$) δ; 1.56–2.67 (4H, m), 2.46 (3H, s), 2.67–3.03 (1H, m), 3.82–4.32 (2H, m), 4.45–5.15 (2H, m), 5.43–5.83 (1H, m), 6.20–6.45 (1H, m),

TABLE 3-continued

| | |
|---|---|
| | 6.50–6.86 (2H, m), 6.86–7.70 (10H, m), 7.76–8.10 (1H, m) |
| 96) | $^1$H-NMR($CDCl_3$) δ; 1.52–1.90 (2H, m), 1.90–2.54 (2H, m), 2.67–3.05 (1H, m), 3.74–4.32 (2H, m), 4.38–5.17 (2H, m), 5.52–5.98 (1H, brs), 6.20–6.48 (1H, brs), 6.55–6.84 (1H, m), 6.89–7.55 (9H, m), 7.55–7.77 (1H, m), 8.15–8.86 (1H, brs) |
| 97) | $^1$H-NMR(DMSO-$d_6$) δ; 1.26–2.49 (4H, m), 2.57–2.93 (1H, m), 4.07–4.43 (2H, m), 4.44–4.98 (2H, m), 6.62–6.87 (1H, m), 6.92–7.80 (11H, m), 10.57 (1H, s), 12.74 (1H, s) |
| 98) | $^1$H-NMR($CDCl_3$) δ; 1.52–1.89 (2H, m), 1.89–2.56 (2H, m), 2.65–3.02 (1H, m), 3.90–4.40 (2H, m), 4.40–5.07 (2H, m), 6.58–6.78 (1H, m), 6.90–7.70 (10H, m), 8.57–8.81 (1H, brs) |
| 99) | $^1$H-NMR($CDCl_3$) δ; 1.49–1.89 (2H, m), 1.89–2.60 (2H, m), 2.63–3.23 (7H, m), 4.04–4.49 (2H, m), 4.52–5.21 (2H, m), 6.52–6.80 (1H, m), 6.89–7.84 (10H, m), 8.08–8.52 (1H, m) |
| 100) | $^1$H-NMR($CDCl_3$) δ; 1.41–1.86 (6H, m), 1.86–2.53 (4H, m), 2.25 (3H, s), 2.29 (3H, s), 2.43 (3H, s), 2.60–2.97 (1H, m), 3.36–3.77 (2H, m), 4.40–5.10 (2H, m), 6.54–6.72 (1H, m), 6.88–7.67 (11H, m), 8.27–8.58 (1H, m) |
| 101) | $^1$H-NMR($CDCl_3$) δ; 1.44–1.85 (6H, m), 1.85–2.61 (4H, m), 2.32 (3H, s), 2.35 (3H, s), 2.61–3.00 (1H, m), 3.33–3.76 (2H, m), 4.40–5.20 (2H, m), 6.57–6.75 (1H, m), 6.90–7.70 (11H, m), 8.50–8.93 (1H, m) |
| 102) | $^1$H-NMR($CDCl_3$) δ; 1.49–2.04 (6H, m), 2.10–3.02 (5H, m), 2.47 (6H, s), 3.40–3.88 (2H, m), 4.30–5.17 (2H, m), 6.59–6.78 (1H, m), 6.93–7.76 (10H, m), 8.75–9.40 (1H, m) |
| 103) | $^1$H-NMR($CDCl_3$) δ; 1.47–2.47 (6H, m), 2.44 (3H, s), 2.62–3.03 (1H, m), 3.47–4.03 (4H, m), 4.48–5.17 (2H, m), 6.51–6.74 (1H, m), 6.87–7.62 (11H, m), 7.62–7.77 (2H, m), 7.77–8.03 (3H, m) |
| 104) | $^1$H-NMR($CDCl_3$) δ; 1.42–2.32 (6H, m), 2.44 (3H, s), 2.57–2.97 (1H, m), 3.12–3.83 (4H, m), 4.39–5.13 (2H, m), 6.50–6.71 (1H, m), 6.90–7.73 (12H, m) |
| 105) | $^1$H-NMR($CDCl_3$) δ; 1.50–2.63 (9H, m), 2.47 (3H, s), 2.66–3.07 (1H, m), 3.10–3.88 (4H, m), 4.40–5.17 (2H, m), 5.87–6.23 (1H, brs), 6.60–6.79 (1H, m), 6.94–7.60 (11H, m), 7.67 (1H, s) |
| 106) | $^1$H-NMR($CDCl_3$) δ; 1.20–2.53 (13H, m), 2.63–2.82, 3.00–3.13, 3.50–3.67, 4.05–4.23 (total 3H, m), 6.55–8.00 (13H, m) |
| 107) | $^1$H-NMR($CDCl_3$) δ; 1.41 (9H, s), 1.20–2.55 (10H, m), 3.42–4.20 (5.8H, m), 5.00–5.20 (0.2H, m), 6.60–7.67 (10H, m), 7.99 (1H, brs), 8.26 (1H, d, J=8.4 Hz) |
| 108) | $^1$H-NMR($CDCl_3$) δ; 1.2–3.0 (10H, m), 3.0–5.2 (6H, m), 6.5–7.7 (8H, m), 8.22 (1H, d, J=8.4 Hz), 8.36 (1H, s) |
| 109) | $^1$H-NMR($CDCl_3$) δ; 1.2–3.0 (10H, m), 3.0–5.2 (6H, m), 6.3–7.7 (10H, m) |
| 110) | $^1$H-NMR($CDCl_3$) δ; 1.5–1.7 (1H, m), 2.2–2.7 (2H, m), 2.4 (6H, s), 2.7–3.0 (3H, m), 5.1–5.3 (1H, m), 6.67 (1H, d, J=7.7 Hz), 6.9–7.5 (10H, m), 7.69 (1H, d, J=6 Hz), 8.06 (1H, s) |
| 111) | $^1$H-NMR($CDCl_3$) δ; 1.4–1.7 (1H, m), 2.1–2.7 (2H, m), 2.40 (6H, s), 2.44 (3H, s), 2.7–3.0 (3H, m), 5.1–5.2 (1H, m), 6.68 (1H, d, J=7.8 Hz), 6.9–7.5 (11H, m), 7.66 (1H, s) |
| 112) | $^1$H-NMR($CDCl_3$) δ; 1.5–1.8 (1H, m), 2.1–2.7 (2H, m), 2.38 (6H, s), 2.7–3.0 (3H, m), 5.1–5.3 (1H, m), 6.66 (1H, d, J=7.7 Hz), 6.9–7.0 (9H, m), 7.57 (1H, d, J=8.3 Hz), 8.42 (1H, s) |
| 113) | $^1$H-NMR($CDCl_3$) δ; 1.5–1.8 (1H, m), 2.1–2.7 (2H, m), 2.41 (6H, s), 2.48 (3H, s), 2.7–3.0 (3H, m), 3.68 (3H, s), 5.2–5.4 (1H, m), 6.6–6.8 (2H, m), 6.9–7.5 (8H, m), 8.09 (1H, s), 8.26 (1H, d, J=8.1 Hz) |
| 114) | $^1$H-NMR($CDCl_3$) δ; 1.5–1.7 (1H, m), 2.1–2.3 (1H, m), 2.41 (6H, s), 2.4–2.6 (1H, m), 2.8–3.0 (3H, m), 3.71 (3H, s), 5.2–5.4 (1H, m), 6.6–6.8 (2H, m), 6.9–7.5 (7H, m), 7.7–7.8 (1H, m), 8.27 (1H, d, J=8.4 Hz), 8.57 (1H, s) |
| 115) | $^1$H-NMR($CDCl_3$) δ; 1.5–1.7 (1H, m), 2.1–2.7 (2H, m), 2.41 (6H, s), 2.7–3.0 (3H, m), 3.71 (3H, s), 5.2–5.4 (1H, m), 6.6–7.6 (8H, m), 7.70 (1H, d, J=8.3 Hz), 8.24 (1H, d, J=8.5 Hz), 8.59 (1H, s) |
| 116) | $^1$H-NMR($CDCl_3$) δ; 1.8–2.3 (3H, m), 2.7–2.9 (2H, m), 3.5–3.7 (1H, m), 6.8–8.0 (10H, m), 8.7–9.1 (1H, br) |

EXAMPLE 634

To a mixture of 5-oxo-1-[4-(3,5-dichlorobenzoylamino)benzoyl]-2,3,4,5-tetrahydro-1H-benzazepine (4 g) and pyridine (50 ml) is added hydroxylamine hydrochloride (1.84 g) and the mixture is refluxed for 2.5 hours. The reaction solution is concentrated and water is added to the resulting residue. The precipitated crystal is collected by filtration, and recrystallized from dioxane/water to give 5-hydroxyimino-1-[4-(3,5-dichlorobenzoylamino)benzoyl]-2,3,4,5-tetrahydro-1H-benzazepine (2 g) as white powder, m.p. 272–273° C.

EXAMPLE 635

5-Chloro-1-[4-(2-methylbenzoylamino)benzoyl]-2,3,4,5-tetrahydro-1H-benzazepine (0.8 g) is dissolved in dimethylformamide and thereto is added sodium azide (0.18 g) at room temperature. The mixture is stirred at room temperature overnight, and further reacted with heating at 50° C. for 5 hours. Water is added to the reaction mixture and the precipitated crystal is collected by filtration to give 5-azido-1-[4-(2-methylbenzoylamino)benzoyl]-2,3,4,5-tetrahydro-1H-benzazepine (0.68 9) as light brown powder.

$^1$H-NMR($CDCl_3$) δ; 1.65–3.1 (8H, m), 4.7–6.6 (3H, m), 6.6–6.8 (1H, m), 6.85–7.65 (12H, m)

EXAMPLE 636

5-Azido-1-[4-(2-methylbenzoylamino)benzoyl]-2,3,4,5-tetrahydro-1H-benzazepine (0.63 g) is dissolved in ethanol and thereto is added 10% Pd-C (0.1 g). The mixture is subjected to catalytic hydrogenation at room temperature under 1 atm. of hydrogen. Pd-C is removed by filtration and the filtrate is evaporated. The resulting residue is purified by silica gel column chromatography (eluent; dichloromethane:methanol=50:1), and recrystallized from diethyl ether to give 5-amino-1-[4-(2-methylbenzoylamino)benzoyl]-2,3,4,5-tetrahydro-1H-benzazepine (0.34 g) as white powder, m.p. 198.5–199.5° C.

EXAMPLE 637

To 5-hydroxy-1-[4-(2-methylbenzoylamino)benzoyl]-2,3,4,5-tetrahydro-1H-benzazepine (0.58 g) are added acetic anhydride (8.0 ml) and pyridine (2.0 ml). The mixture is stirred at room temperature for 1 hour. Water is added to the reaction mixture and the precipitated crystal is collected by filtration, and recrystallized from ethyl acetate/n-hexane to give 5-acetyloxy-1-[4-(2-methylbenzoylamino)benzoyl]-2,3,4,5-tetrahydro-1H-benzazepine (0.56 g) as white powder, m.p. 193–194° C.

EXAMPLE 638

5-Ethoxycarbonylmethoxy-1-[4-(2-methylbenzoylamino)benzoyl]-2,3,4,5-tetrahydro-1H-benzazepine (1.00 g) is dissolved in methanol (35 ml) and thereto are added aqueous ammonia (20 ml) and ammonium chloride (0.50 g). The mixture is heated at 100° C. for 3.5 hours in a sealed tube. After cooling, the reaction solution is concentrated under reduced pressure and acidified with hydrochloric acid, and extracted with dichloromethane. The extract is dried over magnesium sulfate and the solvent is distilled off. The resulting residue is purified by silica gel column chromatography (eluent; dichloromethane:methanol=15:1) to give 5-carbamoylmethoxy-1-[4-(2-methylbenzoylamino) benzoyl]-2,3,4,5-tetrahydro-1H-benzazepine (0.68 g) as colorless amorphous.

$^1$H-NMR($CDCl_3$) δ; 1.56–2.67 (4H, m), 2.46 (3H, s), 2.67–3.03 (1H, m), 3.82–4.32 (2H, m), 4.45–5.15 (2H, m), 5.43–5.83 (1H, m), 6.20–6.45 (1H, m), 6.50–6.86 (2H, m), 6.86–7.70 (10H, m), 7.76–8.10 (1H, m)

Using the suitable starting materials, the compounds of the above Examples 593 and 594 are obtained in the same manner as in Example 638.

EXAMPLE 639

5-Ethoxycarbonylmethoxy-1-[4-(2,4-dichlorobenzoylamino)benzoyl]-2,3,4,5-tetrahydro-1H-benzazepine (0.94 g) is dissolved in ethanol (100 ml) and thereto is added 5N aqueous sodium hydroxide solution (0.50 ml). The mixture is stirred at room temperature for 2 hours. The reaction solution is concentrated under reduced pressure and to the resulting residue is added diluted hydrochloric acid and then extracted with dichloromethane. The extract is dried over magnesium sulfate and the solvent is distilled off. The resulting residue is washed with n-hexane and collected by filtration to give 5-carboxymethoxy-1-[4-(2,4-dichlorobenzoylamino)benzoyl]-2,3,4,5-tetrahydro-1H-benzazepine (0.79 g) as colorless amorphous.

$^1$H-NMR($CDCl_3$) δ; 1.52–1.89 (2H, m), 1.89–2.56 (2H, m), 2.65–3.02 (1H, m), 3.90–4.40 (2H, m), 4.40–5.07 (2H, m), 6.58–6.78 (1H, m), 6.90–7.70 (10H, m), 8.57–8.81 (1H, brs)

Using the suitable starting materials, the compounds of the above Examples 595 and 596 are obtained in the same manner as in Example 639.

EXAMPLE 640

5-Carboxymethoxy-1-[4-(2-methylbenzoylamino) benzoyl]-2,3,4,5-tetrahydro-1H-benzazepine (0.55 g) is dissolved in dimethylformamide (20 ml) and thereto are added dimethylamine hydrochloride (0.20 g) and diethyl chlorophosphate (0.33 g). To the mixture is added triethylamine (1.0 ml) under ice-cooling, and the mixture is stirred under ice-cooling for 30 minutes, and at room temperature for more 2 hours. Water is added to the reaction solution and the precipitated crystal is collected by filtration and recrystallized from ethyl acetate/n-hexane to give 5-dimethylaminocarbonylmethoxy-1-[4-(2-methylbenzoylamino)benzoyl]-2,3,4,5-tetrahydro-1H-benzazepine (0.50 g) as colorless prisms, m.p. 203–204° C.

Using the suitable starting materials, the compounds of the above Examples 599 and 600 are obtained in the same manner as in Example 640.

EXAMPLE 641

5-[3-(Phthalimid-1-yl)propoxy]-1-[4-(2-methylbenzoylamino)benzoyl]-2,3,4,5-tetrahydro-1H-benzazepine (1.26 g) is dissolved in ethanol (100 ml) and thereto is added hydrazine hydrate (1.0 ml). The mixture is refluxed with stirring for 1 hour. The reaction solution is evaporated under reduced pressure and to the resulting residue is added dichloromethane. The insoluble materials are removed by filtration. The filtrate is purified by silica gel column chromatography (eluent; dichloromethane:methanol:aqueous ammonia=70:10:1) to give 5-(3-aminopropoxy)-1-[4-(2-methylbenzoylamino)benzoyl]-2,3,4,5-tetrahydro-1H-benzazepine (0.70 g) as colorless amorphous.

$^1$H-NMR($CDCl_3$) δ; 1.42–2.32 (6H, m), 2.44 (3H, s), 2.57–2.97 (1H, m), 3.12–3.83 (4H, m), 4.39–5.13 (2H, m), 6.50–6.71 (1H, m), 6.90–7.73 (12H, m)

EXAMPLE 642

A solution of 5-dimethylamino-1-[3-methoxy-4-(2-methylbenzoylamino)benzoyl]-2,3,4,5-tetrahydro-1H-benzazepine (0.50 g) in dichloromethane (30 ml) is added dropwise to a solution of 1M boron tribromide in dichloromethane (5.46 ml) at −45° C. After completion of the dropping, the mixture is stirred for 1 day while the temperature of the reaction mixture is gradually raised to room temperature. To the reaction solution is added water and the mixture is neutralized with sodium hydrogen carbonate, and extracted with dichloromethane. The extract is washed with saturated saline solution and dried over magnesium sulfate. The solvent is distilled off and the resulting residue is purified by silica gel column chromatography (eluent; chloroform:methanol=500:1), and recrystallized from methanol/diethyl ether to give 5-dimethylamino-1-[3-hydroxy-4-(2-methylbenzoylamino)benzoyl]-2,3,4,5-tetrahydro-1H-benzazepine (0.33 g) as white powder, m.p. 201.5–202.5° C.

Using the suitable starting materials, the compounds of the above Examples 10, 32, 343, 356, 535, 555 and 556 are obtained in the same manner as in Example 642.

EXAMPLE 643

To a solution of 4-[4-(2-methylbenzoylamino)benzoyl]-3,4-dihydro-2H-1,4-benzazepine (0.5 g) in dichloromethane (10 ml) is added m-chloroperbenzoic acid (0.58 9) under ice-cooling, and the mixture is stirred at room temperature for 6 hours. The above reaction solution is poured into an aqueous solution of sodium carbonate (0.6 g) in water (10 ml) and the mixture is extracted with dichloromethane. The extract is washed with water, and dried over magnesium sulfate. The solvent is distilled off under reduced pressure and the resulting residue is purified by silica gel column chromatography (eluent; dichloromethane:methanol=100:1), and recrystallized from diethyl ether/dichloromethane to give 4-[4-(2-methylbenzoylamino) benzoyl]-3,4-dihydro-2H-1,4-benzothiazine-1,1-dioxide (0.49 g) as white powder, m.p. 219–220° C.

Using the suitable starting materials, the compound of the above Example 630 is obtained in the same manner as in Example 643.

EXAMPLE 644

To a suspension of 4-[4-(2-methylbenzoylamino) benzoyl]-3,4-dihydro-2H-1,4-benzothiazine (0.5 g) in methanol (15 ml) is added an aqueous solution of sodium metaperiodate (0.28 g) in water (2.5 ml) and the mixture is stirred at room temperature for 72 hours. Water is added to the reaction solution and extracted with dichloromethane. The extract is dried over magnesium sulfate and the solvent is distilled off under reduced pressure. The resulting residue is purified by silica gel column chromatography (eluent; dichloromethane:methanol=100:1), and recrystallized from dichloromethane/diethyl ether to give 4-[4-(2-methylbenzoylamino)benzoyl]-3,4-dihydro-2H-1,4-benzothiazin-1-oxide (0.34 g) as white powder, m.p. 240–241° C.

Using the suitable starting materials, the compound of the above Example 631 is obtained in the same manner as in Example 644.

EXAMPLE 645

5-Hydroxy-1-[4-(2-methylbenzoylamino)benzoyl]-2,3,4,5-tetrahydro-1H-benzazepine (3.57 g) is dissolved in dichloromethane (30 ml) and pyridine (1.1 ml), and thereto is added dropwise methanesulfonyl chloride (0.9 ml) in small portions at 0° C. Then, the mixture is stirred at room temperature for 3 days. The solvent is distilled off and the resulting residue is poured into ice-water. The precipitated crystal is collected by filtration, washed with water, and dried to give 5-chloro-1-[4-(2-methylbenzoylamino) benzoyl]-2,3,4,5-tetrahydro-1H-benzazepine (3.10 g) as light yellow powder.

$^1$H-NMR($CDCl_3$) δ; 1.7–2.9 (8H, m), 4.5–6.5 (3H, m), 6.55–6.75 (1H, m), 6.85–7.6 (12H, m)

EXAMPLE 646

5-Hydroxy-1-[4-(2-methylbenzoylamino)benzoyl]-2,3,4,5-tetrahydro-1H-benzazepine (2.69 g) is dissolved in dimethylformamide (30 ml) and thereto are added 60% sodium hydride dispersion in mineral oil (0.44 9) and ethyl bromoacetate (1.00 ml) under ice-cooling, and the mixture is stirred at room temperature for 4 hours. The reaction solution is poured into an aqueous ammonium chloride solution under ice-cooling, and extracted with ethyl acetate. The extract is dried over magnesium sulfate and the solvent is distilled off. The resulting residue is purified by silica gel column chromatography (eluent; ethyl acetate:n-hexane=1:2), and recrystallized from ethyl acetate/n-hexane to give 5-ethoxycarbonylmethoxy-1-[4-(2-methylbenzoylamino) benzoyl-2,3,4,5-tetrahydro-1H-benzazepine (2.10 g) as white powder, m.p. 178–181° C.

Using the suitable starting materials, the compounds of the above Examples 585–588 and 590–606 are obtained in the same manner as in Example 646.

EXAMPLE 647

Using the suitable starting materials, the compounds of the above Examples 546 and 578–581 are obtained in the same manner as in Example 384.

EXAMPLE 648

Using the suitable starting materials, the compounds of the above Examples 537–545, 547, 549–556, 561–564, 566, 568–571, 577, 601–603 and 607–625 are obtained in the same manner as in Example 388.

EXAMPLE 649

Using the suitable starting materials, the compounds of the above Examples 549, 568–571, 575 and 606 are obtained in the same manner as in Example 389.

EXAMPLE 650

Using the suitable starting materials, the compounds of the above Examples 537–545, 547, 549–556, 561–566, 568–571, 575, 577, 607, 608 and 613–625 are obtained in the same manner as in Example 390.

EXAMPLE 651

Using the suitable starting materials, the compounds of the above Examples 601–603, 605 and 606 are obtained in the same manner as in Example 397.

EXAMPLE 652

Using the suitable starting materials, the compound of the above Example 604 is obtained in the same manner as in Example 398.

EXAMPLE 653

Using the suitable starting materials, the following compound is obtained in the same manner as in Examples 1, 382, 388 and 390.

5-Methylamino-1-[2-chloro-4-(2-methylbenzoylamino) benzoyl]-2,3,4,5-tetrahydro-1H-benzazepine, white powder, m.p. 184.5–185.5° C. (recrystallized from ethanol)

Using the suitable starting materials, the compounds of the following Table 4 are obtained in the same manner as in Examples 1 and 382.

TABLE 4

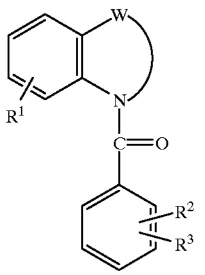

Example 654

Structure

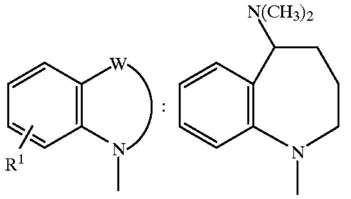

$R^2$: 2-OH $R^3$: 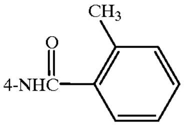

Crystalline form: White powder
Recrystallization solvent: Methanol/n-hexane
Melting Point: 193.5–196° C.
Form: Free Example 655

Structure

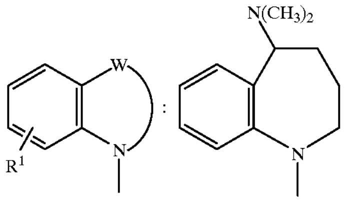

$R^2$: 2-OH

TABLE 4-continued

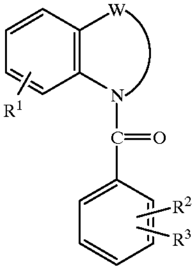

$R^3$: 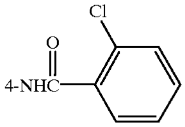

Crystalline form: White powder
Recrystallization solvent: Methanol/n-hexane
Melting Point: 195–198° C.
Form: Free Example 656

Structure

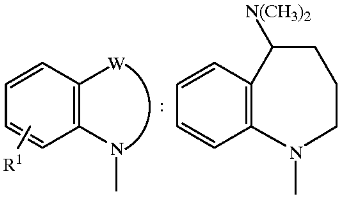

$R^2$: 2-$OC_2H_5$ $R^3$: 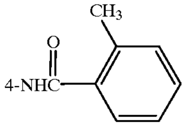

Crystalline form: White powder
Recrystallization solvent: Methanol
Melting Point: 230.5–231.5° C.
Form: Free Example 657

Structure

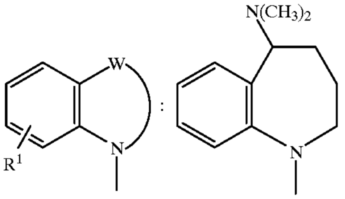

$R^2$: 2-$OC_2H_5$ $R^3$: 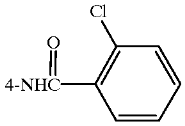

Crystalline form: White powder

TABLE 4-continued

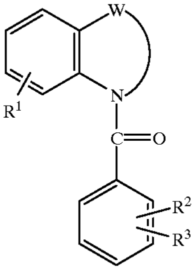

Recrystallization solvent: Methanol/diethyl ether
Melting Point: 223–224.5° C.
Form: Free Example 658

Structure

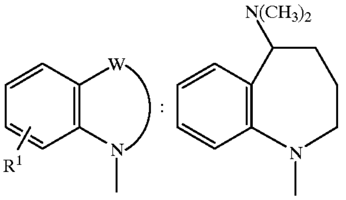

$R^2$: 2-$OC_2H_5$ $R^3$: 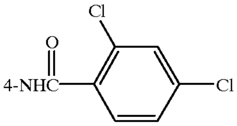

Crystalline form: White powder
Recrystallization solvent: Methanol/diethyl ether
Melting Point: 173–174° C.
Form: Free Example 659

Structure

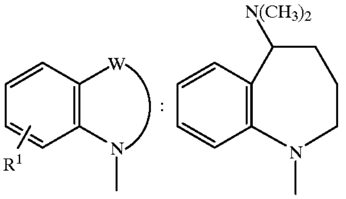

$R^2$: 3-$CH_3$ $R^3$: 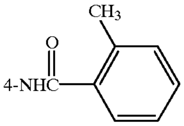

Crystalline form: White powder
Recrystallization solvent: Methanol/diethyl ether
Melting Point: 174–175° C.
Form: Free TABLE 4-continued

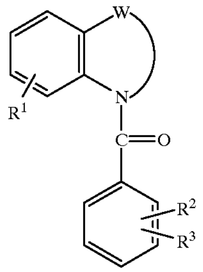

Example 660

Structure

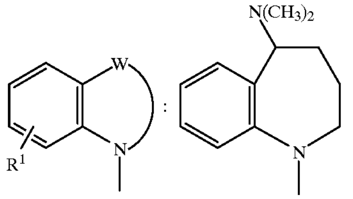

$R^2$: 3-$CH_3$ $R^3$: 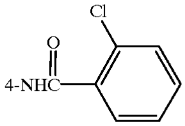

Crystalline form: White powder
Recrystallization solvent: Methanol/diethyl ether
Melting Point: 198–200° C.
Form: Free Example 661

Structure

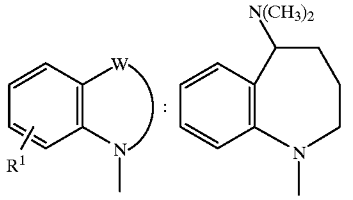

$R^2$: 3-$CH_3$ $R^3$: 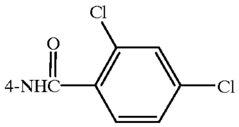

Crystalline form: White powder
Recrystallization solvent: Methanol/n-hexane
Melting Point: 149–150.5° C.
Form: Free TABLE 4-continued

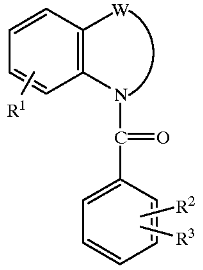

Example 662

Structure

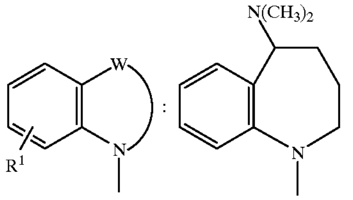

$R^2$: 2-$CH_3$ $R^3$: 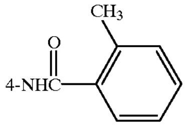

Crystalline form: White powder
Recrystallization solvent: Methanol/diethyl ether
Melting Point: 183–185° C.
Form: Free Example 663

Structure

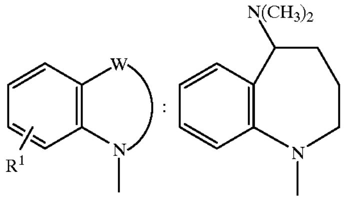

$R^2$: 2-$CH_3$ $R^3$: 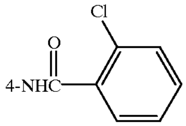

Crystalline form: White powder
Recrystallization solvent: Methanol/diethyl ether
Melting Point: 203–207° C.
Form: Free TABLE 4-continued

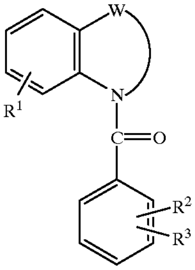

Example 664

Structure

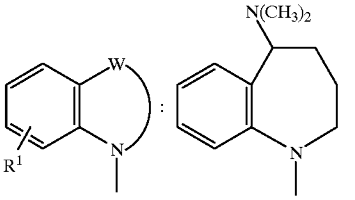

$R^2$: 2-$CH_3$

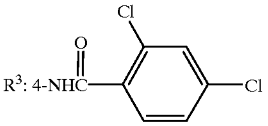

Crystalline form: White powder
Recrystallization solvent: Methanol/diethyl ether
Melting Point: 221–222° C.
Form: Free Example 665

Structure

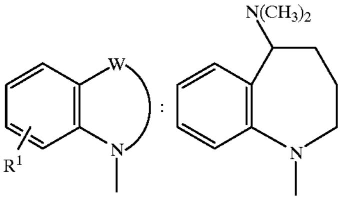

$R^2$: 2-F

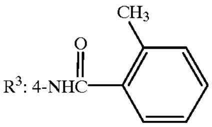

Crystalline form: White powder
Recrystallization solvent: Methanol/diethyl ether
Melting Point: 189–191° C.
Form: Free TABLE 4-continued

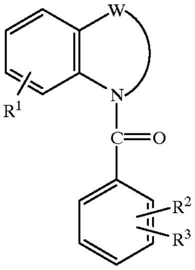

Example 666

Structure

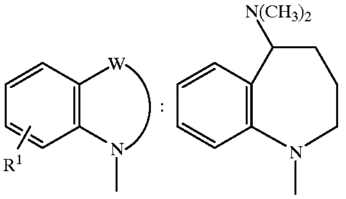

$R^2$: 2-F

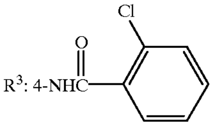

Crystalline form: White powder
Recrystallization solvent: Methanol/diethyl ether
Melting Point: 215.5–217° C.
Form: Free Example 667

Structure

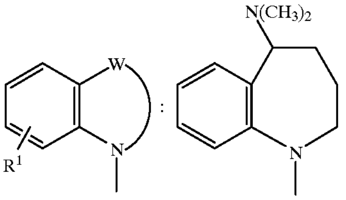

$R^2$: 2-F

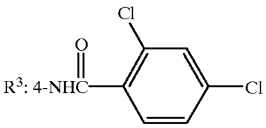

Crystalline form: White powder
Recrystallization solvent: Methanol/n-hexane
Melting Point: 192–194° C.
Form: Free TABLE 4-continued

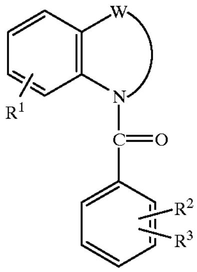

Example 668

Structure

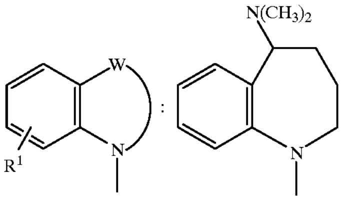

$R^2$: 3-F $R^3$: 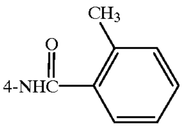

Crystalline form: White powder
Recrystallization solvent: Methanol/diethyl ether
Melting Point: 195–196° C.
Form: Free Example 669

Structure

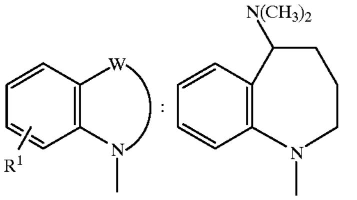

$R^2$: 3-F $R^3$: 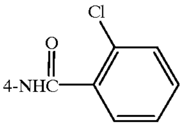

Crystalline form: White powder
Recrystallization solvent: Methanol/diethyl ether
Melting Point: 202–204.5° C.
Form: Free TABLE 4-continued

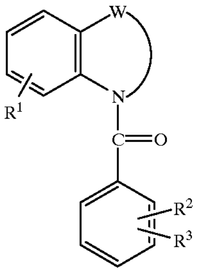

Example 670

Structure

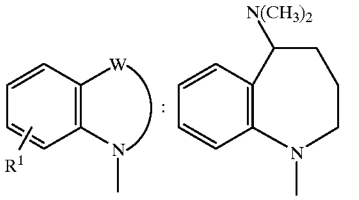

$R^2$: H $R^3$: 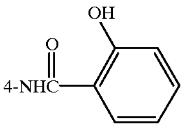

Crystalline form: White powder
Recrystallization solvent: Methanol/diethyl ether
Melting Point: 183–187° C.
Form: Free Example 671

Structure

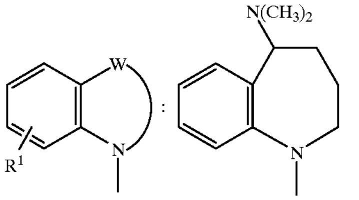

$R^2$: H $R^3$: 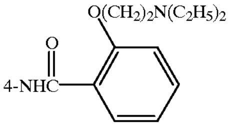

Crystalline form: White powder
Recrystallization solvent: Methanol/diethyl ether
Melting Point: 120–122° C.
Form: Free TABLE 4-continued

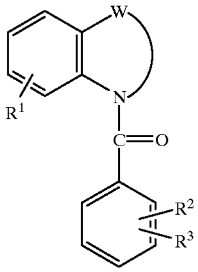

Example 672

Structure

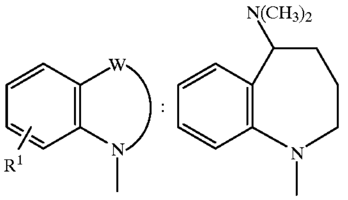

$R^2$: H

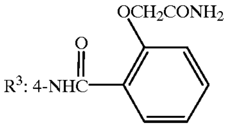

Crystalline form: White powder
Recrystallization solvent: Chloroform/diethyl ether
Melting Point: 208–210° C.
Form: Free Example 673

Structure

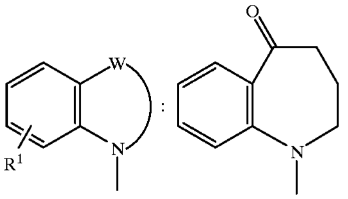

$R^2$: 2-$OCH_3$

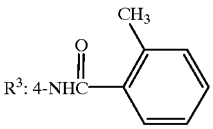

Crystalline form: White powder
Recrystallization solvent: Methanol/diethyl ether
Melting Point: 182–183° C.
Form: Free TABLE 4-continued

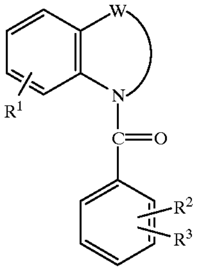

Example 674

Structure

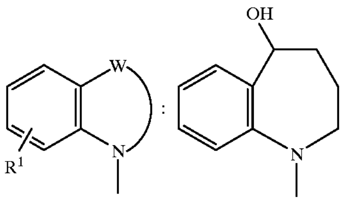

$R^2$: 2-$OCH_3$

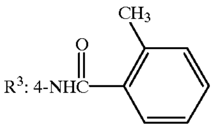

Crystalline form: White powder
Recrystallization solvent: Methanol/diethyl ether
Melting Point: 257–259° C.
Form: Free Example 675

Structure

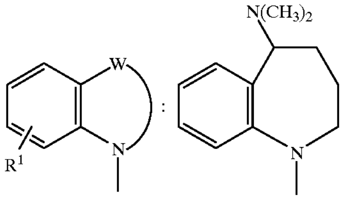

$R^2$: 2-$OC_2H_5$

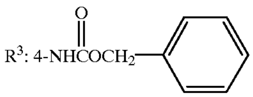

Crystalline form: White powder
Recrystallization solvent: Dichloromethane/diethyl ether
Melting Point: 134–135° C.
Form: Free TABLE 4-continued

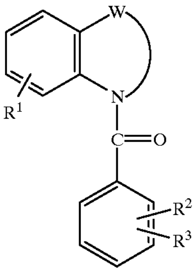

Example 676

Structure

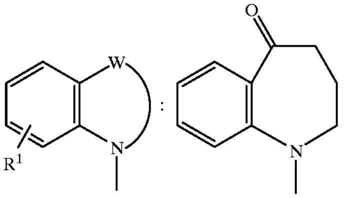

$R^2$: 2-$OCH_3$ $R^3$: 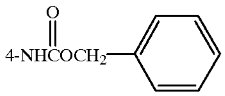

Crystalline form: White powder
Recrystallization solvent: Methanol/diethyl ether
Melting Point: 167–169° C
Form: Free Example 677

Structure

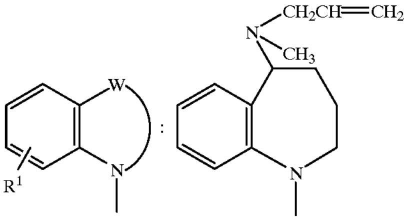

$R^2$: 2-Cl $R^3$: 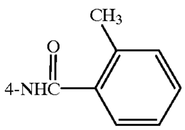

Crystalline form: Light brown prisms
Recrystallization solvent: Ethyl acetate/n-hexane
Melting Point: 170–172° C.
Form: Free TABLE 4-continued

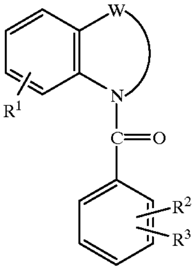

Example 678

Structure

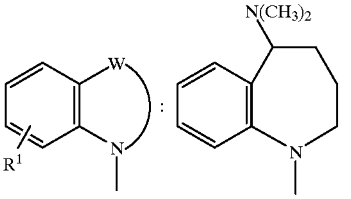

$R^2$: 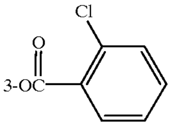

$R^3$: 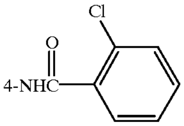

Crystalline form: White powder
Recrystallization solvent: Ethyl acetate/n-hexane
Melting Point: 181.5–182.5° C.
Form: Free Example 679

Structure

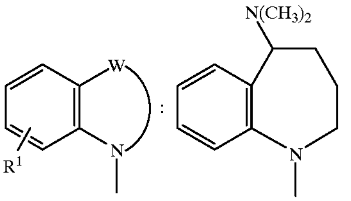

$R^2$: 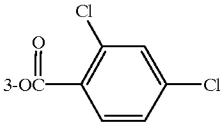

$R^3$: 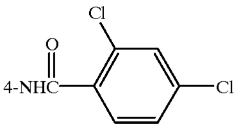

Crystalline form: White powder

TABLE 4-continued

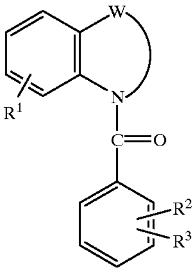

Recrystallization solvent: Ethyl acetate/n-hexane
Melting Point: 176.5–177° C.
Form: Free Example 680

Structure

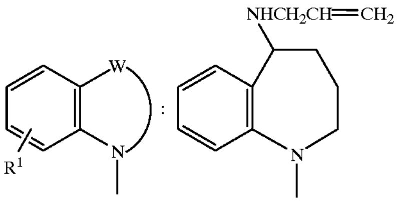

$R^2$: 2-Cl

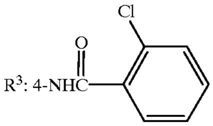

Crystalline form: Yellow amorphous
NMR analysis: 117)
Form: Free

Example 681

Structure

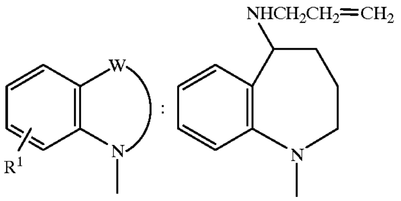

$R^2$: 2-Cl

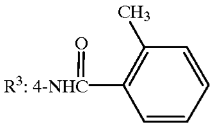

Crystalline form: Yellow amorphous
NMR analysis: 118)
Form: Free

TABLE 4-continued

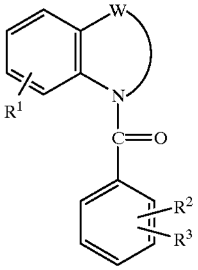

Example 682

Structure

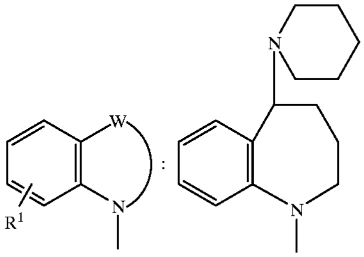

$R^2$: H

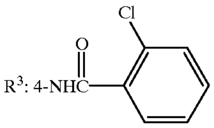

Crystalline form: White powder
Recrystallization solvent: Ethanol
Melting Point: 236–239° C.
Form: Free Example 683

Structure

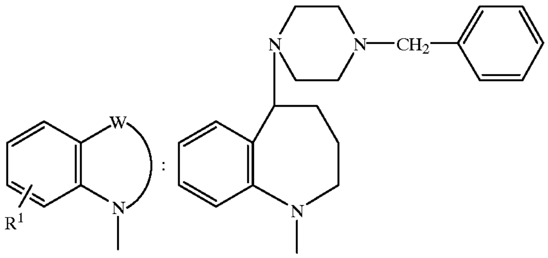

$R^2$: H

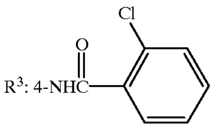

Crystalline form: White powder
Recrystallization solvent: Ethyl acetate/n-hexane
Melting Point: 153–154° C.
Form: Free TABLE 4-continued

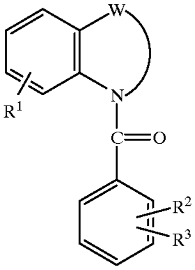

Example 684

Structure

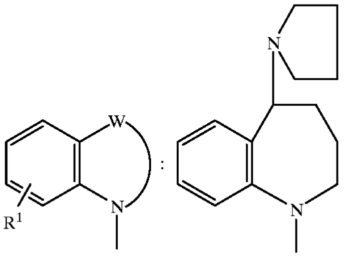

$R^2$: H $R^3$: 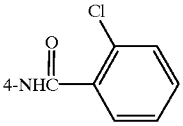

Crystalline form: White powder
Recrystallization solvent: Ethyl acetate
Melting Point: 128–130° C.
Form: Free Example 685

Structure

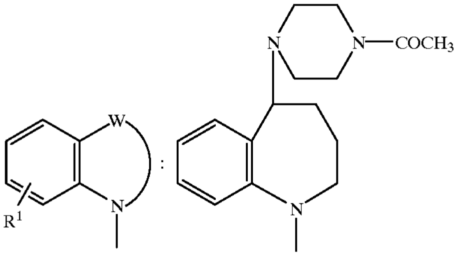

$R^2$: H $R^3$: 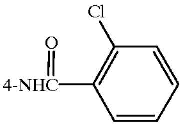

Crystalline form: White powder
Recrystallization solvent: Ethanol/diethyl ether
Melting Point: 231–234° C.
Form: Free TABLE 4-continued

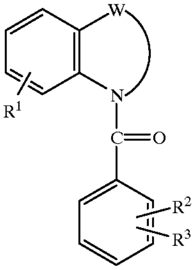

Example 686

Structure

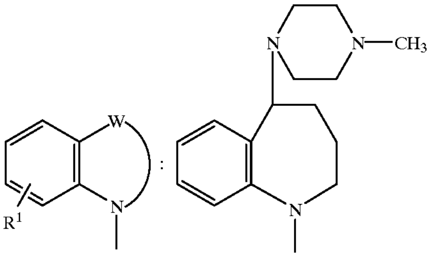

$R^2$: H $R^3$: 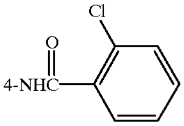

Crystalline form: White powder
Recrystallization solvent: Ethyl acetate
Melting Point: 246–248° C.
Form: Free Example 687

Structure

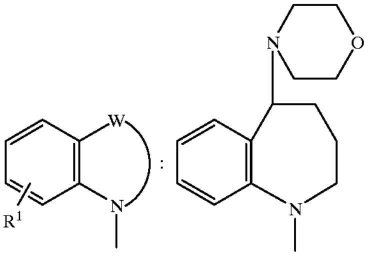

$R^2$: H $R^3$: 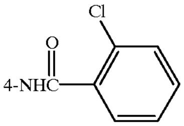

Crystalline form: White powder
Recrystallization solvent: Ethanol/water
Melting Point: 248–248.5° C.
Form: Free TABLE 4-continued

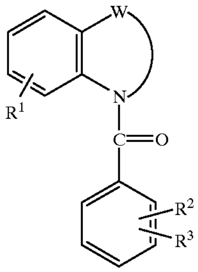

Example 688

Structure

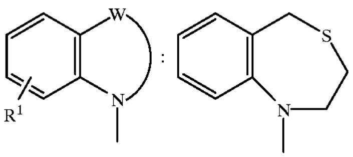

R$^2$: H

R$^3$: 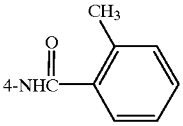

Crystalline form: White powder
Recrystallization solvent: Dichloromethane/diethyl ether
Melting Point: 204–205° C.
Form: Free Example 689

Structure

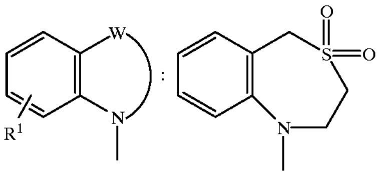

R$^2$: H

R$^3$: 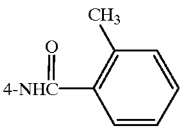

Crystalline form: White powder
Recrystallization solvent: Dichloromethane/diethyl ethyl
Melting Point: >300° C.
NMR analysis: 119)
Form: Free TABLE 4-continued

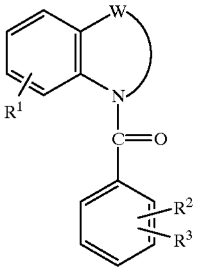

Example 690

Structure

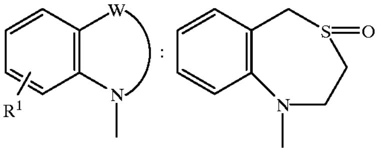

R$^2$: H

R$^3$: 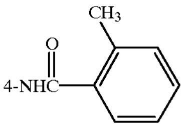

Crystalline form: White powder
Recrystallization solvent: Dichloromethane/diethyl ether
Melting Point: 292–294° C.
Form: Free Example 691

Structure

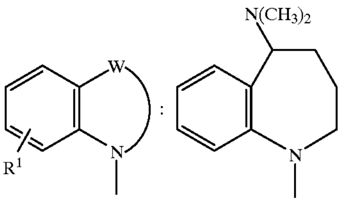

R$^2$: 2-$N(CH_3)_2$

R$^3$: 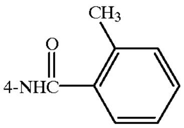

Crystalline form: Colorless amorphous
NMR analysis: 120)
Form: Free

TABLE 4-continued

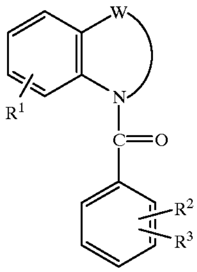

Example 692

Structure

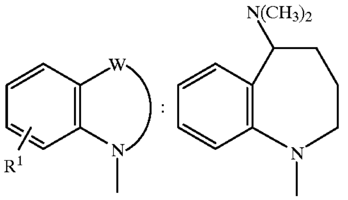

$R^2$: 2-$N(CH_3)_2$ $R^3$: 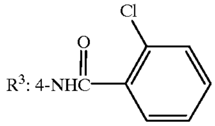

Crystalline form: Colorless amorphous
NMR analysis: 121)
Form: Free

Example 693

Structure

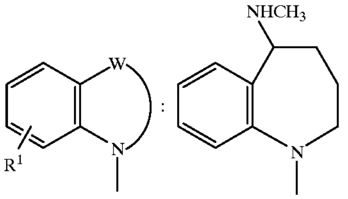

$R^2$: 2-Cl $R^3$: 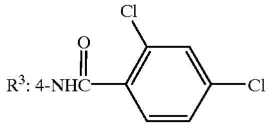

Crystalline form: Colorless amorphous
NMR analysis: 122)
Form: Free

TABLE 4-continued

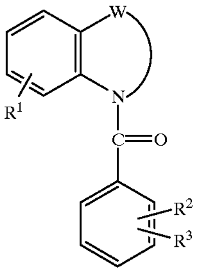

Example 694

Structure

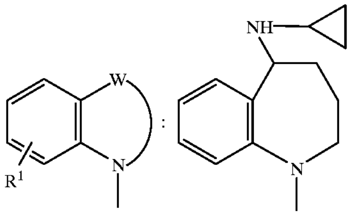

$R^2$: 2-Cl $R^3$: 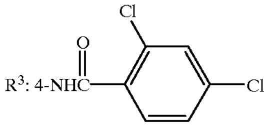

Crystalline form: Colorless amorphous
NMR analysis: 123)
Form: Free

Example 695

Structure

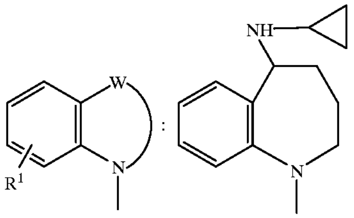

$R^2$: 2-Cl $R^3$: 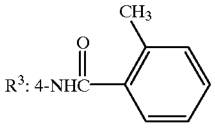

Crystalline form: White powder
Recrystallization solvent: Ethanol
Melting Point: 198.5–199° C.
Form: Free TABLE 4-continued

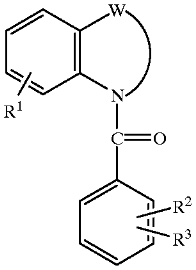

Example 696

Structure

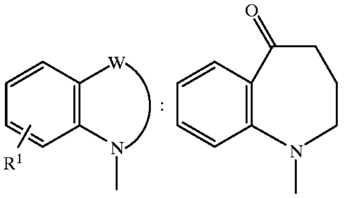

$R^2$: 2-Cl

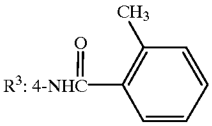

Crystalline form: White powder
Recrystallization solvent: Diethyl ether/dichloromethane
Melting Point: 168–170° C.
Form: Free Example 697

Structure

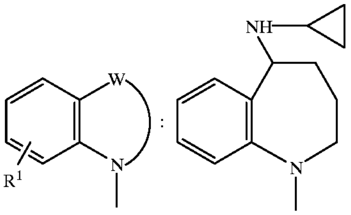

$R^2$: 2-Cl

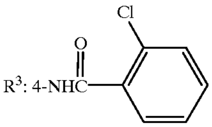

Crystalline form: White powder
Recrystallization solvent: Diethyl ether/dichloromethane
Melting Point: 175–176° C.
Form: Free TABLE 4-continued

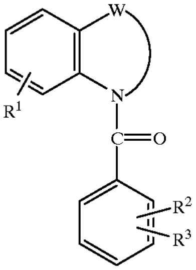

Example 698

Structure

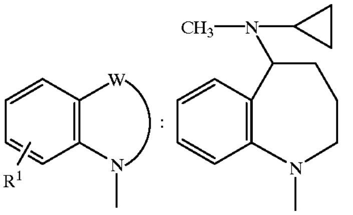

$R^2$: 2-Cl

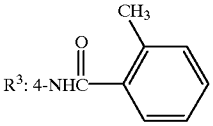

Crystalline form: White powder
Recrystallization solvent: Diethyl ether/dichloromethane
Melting Point: 177–178° C.
Form: Free Example 699

Structure

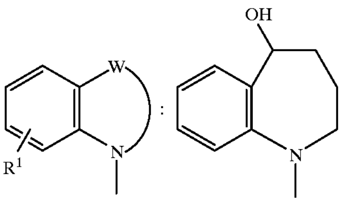

$R^2$: 2-Cl

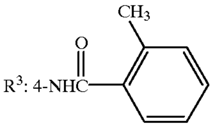

Crystalline form: White powder
Recrystallization solvent: Diethyl ether/dichloromethane
Melting Point: 222–223.5° C.
Form: Free TABLE 4-continued

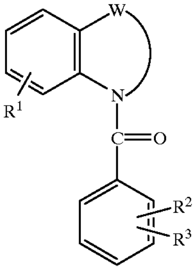

Example 700

Structure

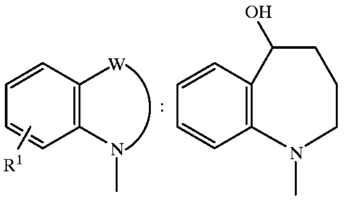

$R^2$: 2-Cl $R^3$: 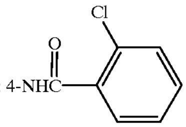

Crystalline form: White powder
Recrystallization solvent: Diethyl ether/dichloromethane
Melting Point: 243–244° C.
Form: Free Example 701

Structure

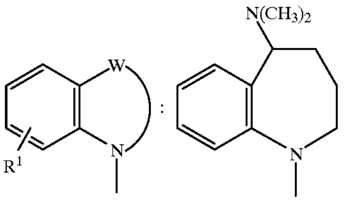

$R^2$: H $R^3$: 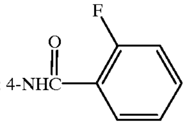

Crystalline form: White powder
Recrystallization solvent: Diethyl ether/dichloromethane
Melting Point: 180–181° C.
Form: Free TABLE 4-continued

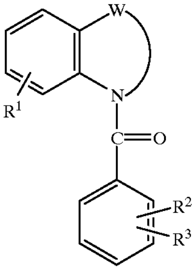

Example 702

Structure

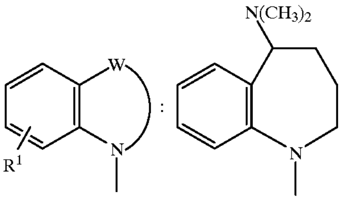

$R^2$: H $R^3$: 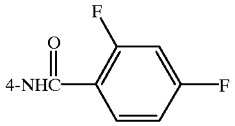

Crystalline form: Colorless amorphous
NMR analysis: 124)
Form: Free

Example 703

Structure

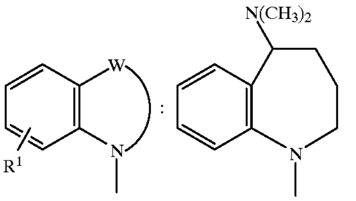

$R^2$: H $R^3$: 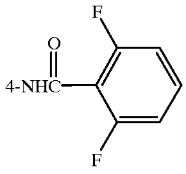

Crystalline form: White powder
Recrystallization solvent: Diethyl ether/dichloromethane
Melting Point: 231–233° C.
Form: Free TABLE 4-continued

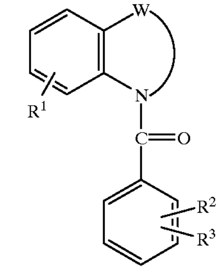

Example 704

Structure

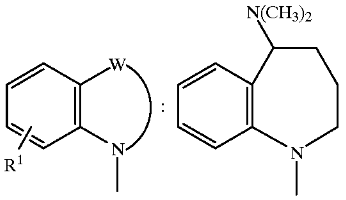

R$^2$: H

R$^3$:
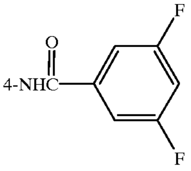

Crystalline form: White powder
Recrystallization solvent: Diethyl ether/dichloromethane
Melting Point: 196–198° C.
Form: Free Example 705

Structure

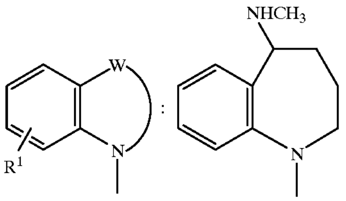

R$^2$: 2-Cl

R$^3$:
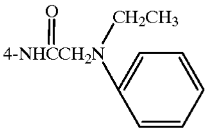

Crystalline form: Colorless amorphous
NMR analysis: 125)
Form: Free

TABLE 4-continued

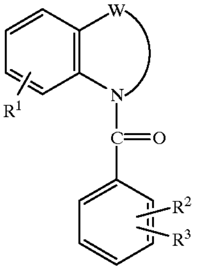

Example 706

Structure

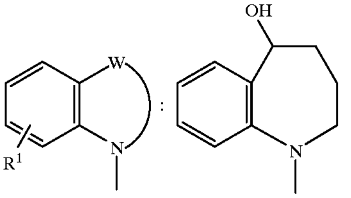

R$^2$: 2-Cl

R$^3$:
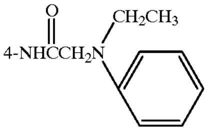

Crystalline form: Yellow amorphous
NMR analysis: 126)
Form: Free

Example 707

Structure

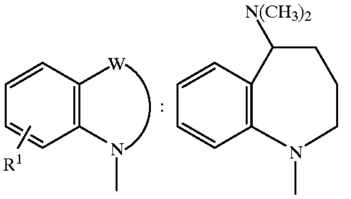

R$^2$: H

R$^3$:
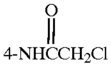

Crystalline form: Yellow powder
Recrystallization solvent: Diethyl ether/dichloromethane
Melting Point: 146–147° C.
Form: Free TABLE 4-continued

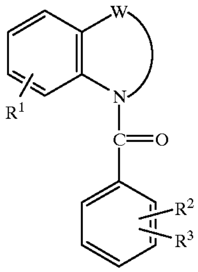

Example 708

Structure

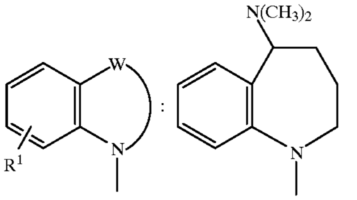

$R^2$: H $R^3$: 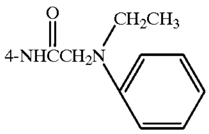

Crystalline form: Colorless amorphous
NMR analysis: 127)
Form: Free

Example 709

Structure

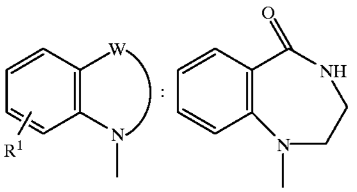

$R^2$: H $R^3$: 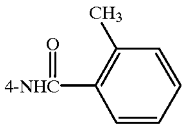

Crystalline form: White powder
Recrystallization solvent: Diethyl ether/dichloromethane
Melting Point: 220–221° C.
Form: Free TABLE 4-continued

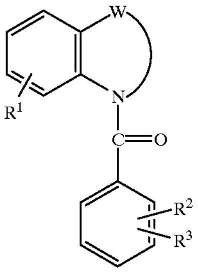

Example 710

Structure

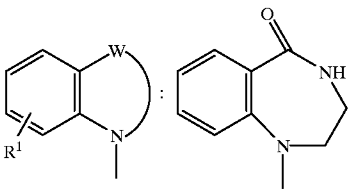

$R^2$: H $R^3$: 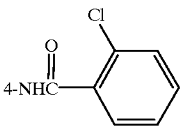

Crystalline form: White powder
Recrystallization solvent: Diethyl ether/dichloromethane
Melting Point: 170–172° C.
Form: Free Example 711

Structure

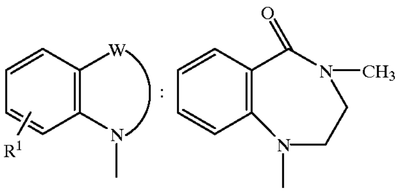

$R^2$: H $R^3$: 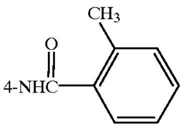

Crystalline form: Colorless amorphous
NMR analysis: 128)
Form: Free

TABLE 4-continued

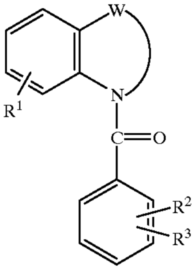

Example 712

Structure

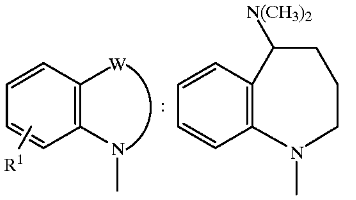

$R^2$: H $R^3$: 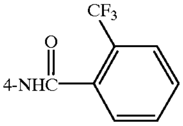

Crystalline form: White powder
Recrystallization solvent: Ethanol
Melting Point: 224–225° C.
Form: Free Example 713

Structure

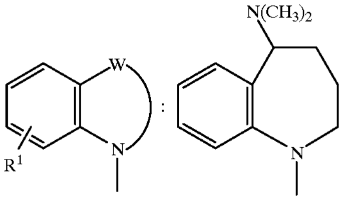

$R^2$: 3-$OCH_3$ $R^3$: 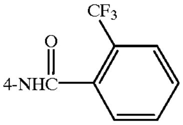

Crystalline form: White powder
Recrystallization solvent: Ethanol
Melting Point: 193–196° C.
Form: Free TABLE 4-continued

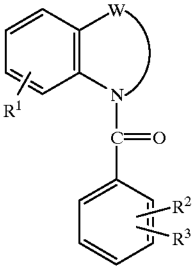

Example 714

Structure

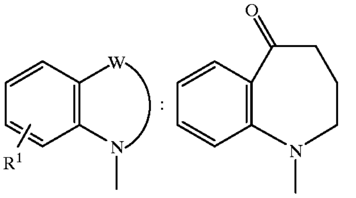

$R^2$: 2-Cl $R^3$: 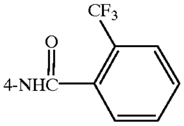

Crystalline form: White powder
Recrystallization solvent: Ethanol
Melting Point: 212–214° C.
Form: Free Example 715

Structure

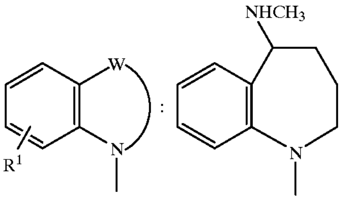

$R^2$: 2-Cl $R^3$: 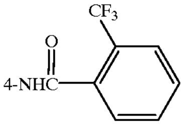

Crystalline form: White powder
Recrystallization solvent: Ethanol
Melting Point: 211–213° C.
Form: Free TABLE 4-continued

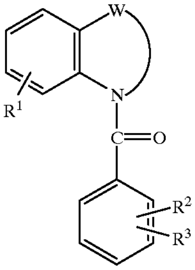

Example 716

Structure

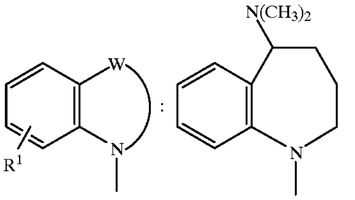

R$^2$: 2-Cl

R$^3$: 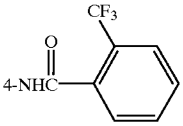

Crystalline form: White powder
Recrystallization solvent: Ethanol
Melting Point: 213–215° C.
Form: Free Example 717

Structure

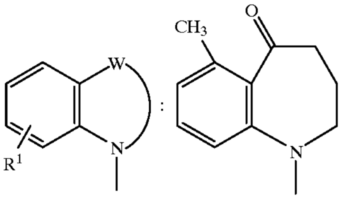

R$^2$: 2-Cl

R$^3$: 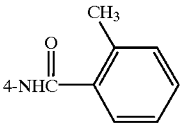

Crystalline form: White powder
Recrystallization solvent: Ethanol
Melting Point: 199–201° C.
Form: Free TABLE 4-continued

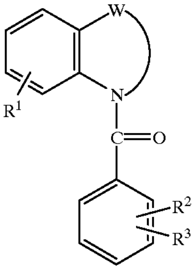

Example 718

Structure

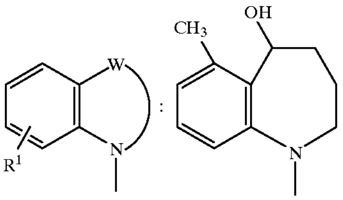

R$^2$: 2-Cl

R$^3$: 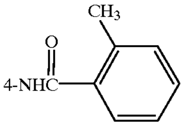

Crystalline form: White powder
Recrystallization solvent: Ethnaol
Melting Point: 238–240° C.
Form: Free Example 719

Structure

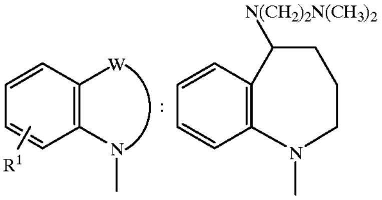

R$^2$: 2-Cl

R$^3$: 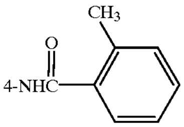

Crystalline form: White powder
Recrystallization solvent: Ethanol
Melting Point: 188–189° C.
Form: Free TABLE 4-continued

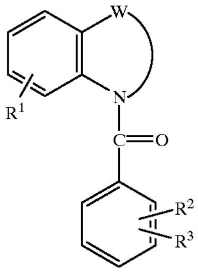

Example 720

Structure

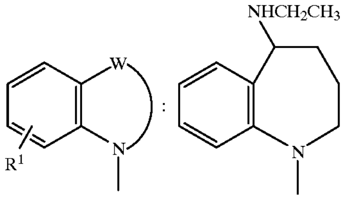

$R^2$: H

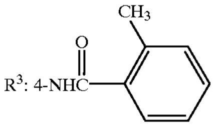

Crystalline form: Colorless prisms
Recrystallization solvent: Dioxane/water
Melting Point: 135.5–137° C.
Form: Free Example 721

Structure

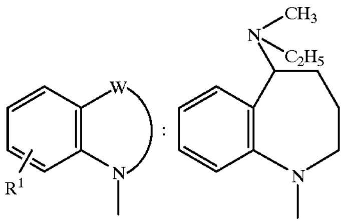

$R^2$: H

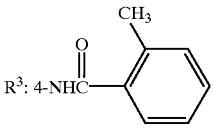

Crystalline form: White powder
Recrystallization solvent: Isopropyl alcohol/petroleum ether
Melting Point: 192–193° C.
Form: Free TABLE 4-continued

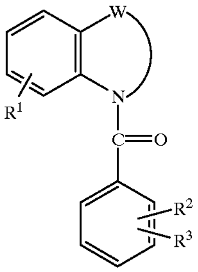

Example 722

Structure

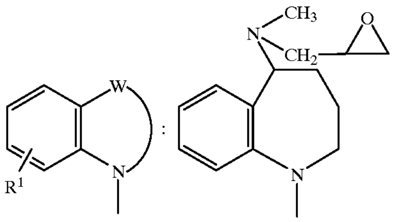

$R^2$: H

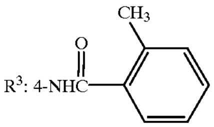

Crystalline form: Colorless needles
Recrystallization solvent: Ethyl acetate
Melting Point: 239–240° C.
Form: Free Example 723

Structure

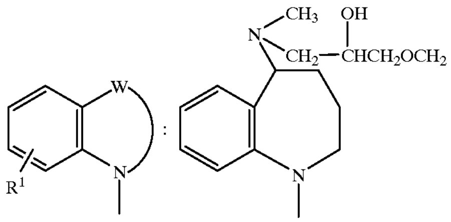

$R^2$: H

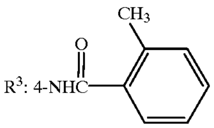

Crystalline form: Colorless amorphous
NMR analysis: 129)
Form: Free

TABLE 4-continued

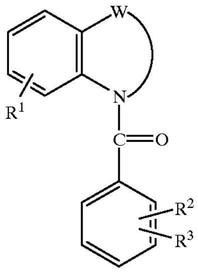

Example 724

Structure

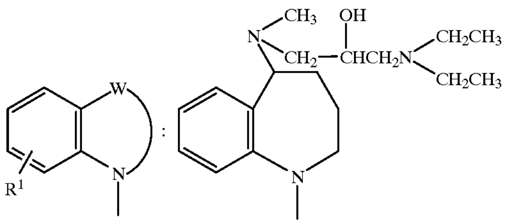

$R^2$: H

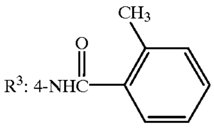

Crystalline form: Colorless amorphous
NMR analysis: 130)
Form: Free

Example 725

Structure

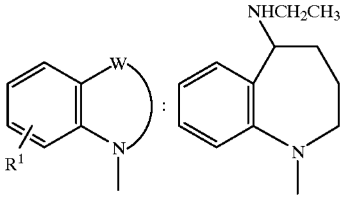

$R^2$: H

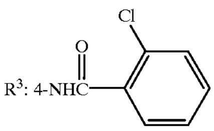

Crystalline form: Colorless needles
Recrystallization solvent: Ethanol/petroleum ether
Melting Point: 193–194° C.
Form: Free TABLE 4-continued

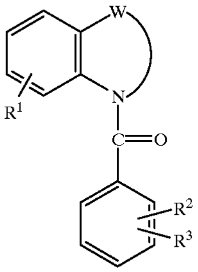

Example 726

Structure

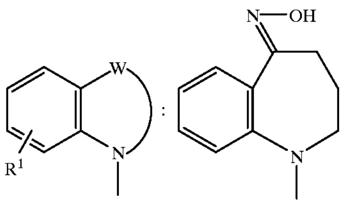

$R^2$: H

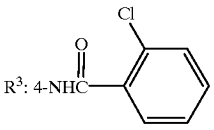

Crystalline form: Light yellow prisms
Recrystallization solvent: Ethanol
Melting Point: 245.5–247° C.
Form: Free Example 727

Structure

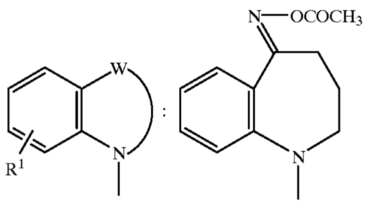

$R^2$: H

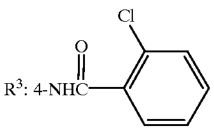

Crystalline form: Colorless prisms
Recrystallization solvent: Ethanol/petroleum ether
Melting Point: 142–144° C.
Form: Free TABLE 4-continued

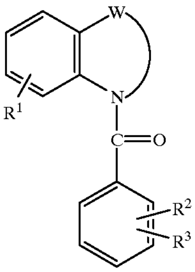

Example 728

Structure

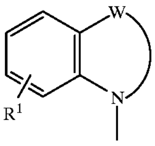 : 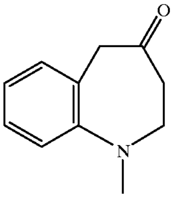

$R^2$: H $R^3$: 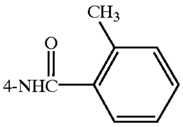

Crystalline form: Light yellow prisms
Recrystallization solvent: Ethanol
Melting Point: 214–217° C.
Form: Free Example 729

Structure

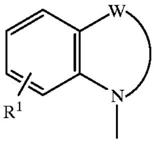 : 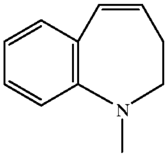

$R^2$: H $R^3$: 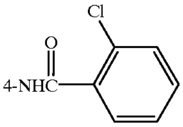

Crystalline form: Colorless needles
Recrystallization solvent: Ethanol
Melting Point: 205–207° C.
Form: Free TABLE 4-continued

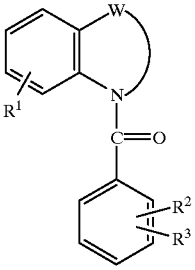

Example 730

Structure

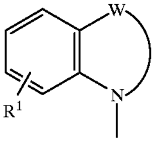 : 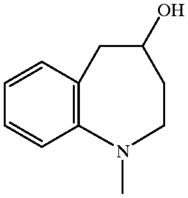

$R^2$: H $R^3$: 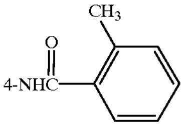

Crystalline form: Colorless needles
Recrystallization solvent: Ethanol/diethyl ether
Melting Point: 201–203° C.
Form: Free Example 731

Structure

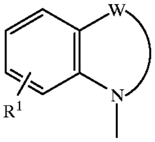 : 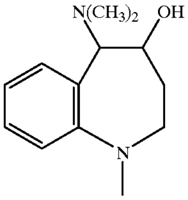

$R^2$: H $R^3$: 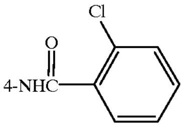

Crystalline form: Colorless needles
Recrystallization solvent: Ethanol/diethyl ether
Melting Point: 180–182° C.
Form: Free TABLE 4-continued

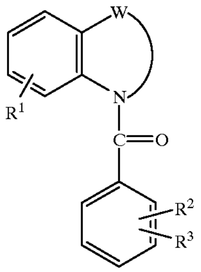

Example 732

Structure

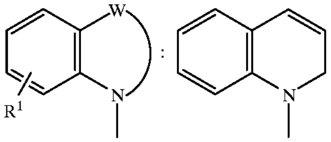

$R^2$: H

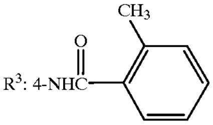

Crystalline form: Light yellow scales
Recrystallization solvent: Ethanol/diethyl ether
Melting Point: 178–180° C.
Form: Free Example 733

Structure

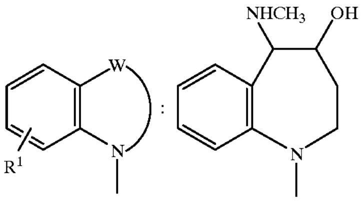

$R^2$: H

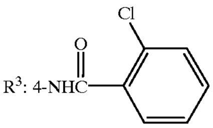

Crystalline form: Colorless needles
Recrystallization solvent: Methanol/diethyl ether
Melting Point: 208–213° C.
Form: Free TABLE 4-continued

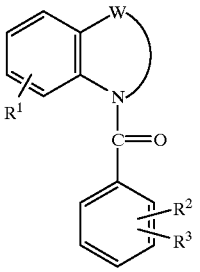

Example 734

Structure

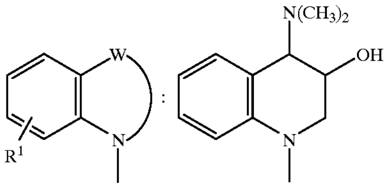

$R^2$: H

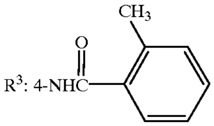

Crystalline form: White powder
Recrystallization solvent: Ethanol/diethyl ether
Melting Point: 175–177° C.
Form: Free Example 735

Structure

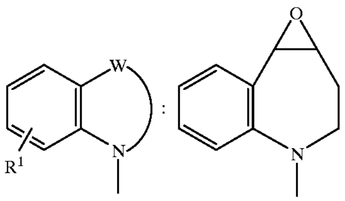

$R^2$: H

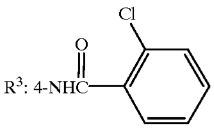

Crystalline form: White powder
NMR analysis: 131)
Form: Free

TABLE 4-continued

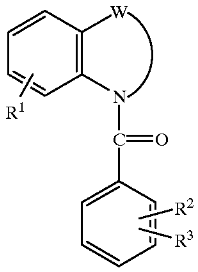

Example 736

Structure

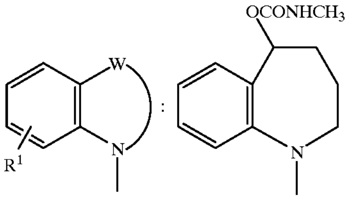

$R^2$: H $R^3$: 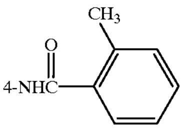

Crystalline form: White powder
Recrystallization solvent: Ethyl acetate/
/n-hexane
Melting Point: 277–279° C.
Form: Free Example 737

Structure

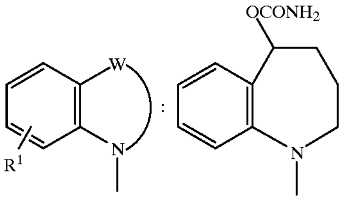

$R^2$: H $R^3$: 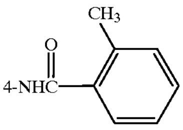

Crystalline form: Colorless amorphous
NMR analysis: 132)
Form: Free

TABLE 4-continued

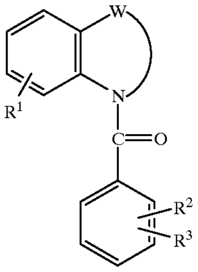

Example 738

Structure

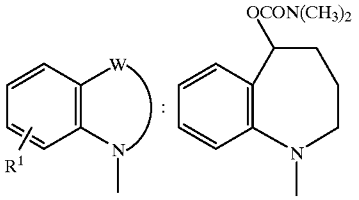

$R^2$: H $R^3$: 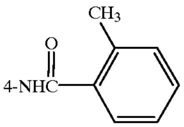

Crystalline form: Colorless amorphous
NMR analysis: 133)
Form: Free

Example 739

Structure

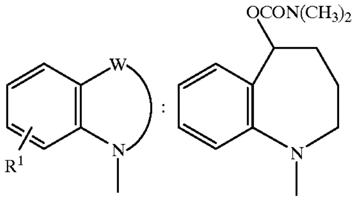

$R^2$: H $R^3$: 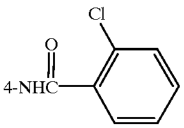

Crystalline form: Colorless amorphous
NMR analysis: 134)
Form: Free

TABLE 4-continued

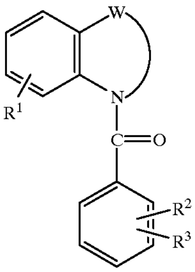

Example 740

Structure

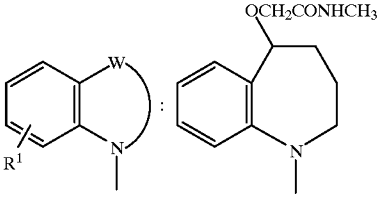

$R^2$: H $R^3$: 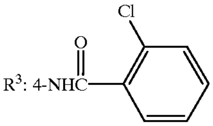

Crystalline form: Colorless amorphous

NMR analysis: 135)

Form: Free

Example 741

Structure

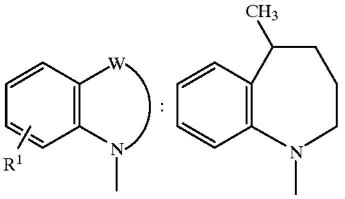

$R^2$: H $R^3$: 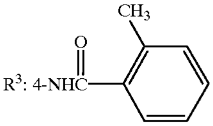

Crystalline form: White powder

Recrystallization solvent: Ethyl acetate/n-hexane

Melting Point: 213–214° C.

Form: Free

TABLE 4-continued

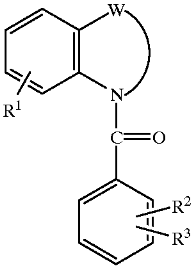

Example 742

Structure

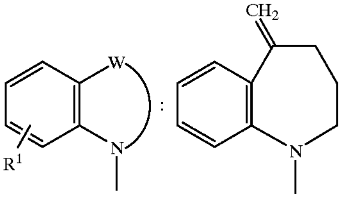

$R^2$: H $R^3$: 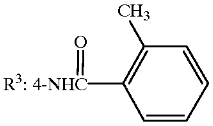

Crystalline form: White powder

Recrystallization solvent: Ethyl acetate/n-hexane

Melting Point: 216–217° C.

Form: Free

Example 743

Structure

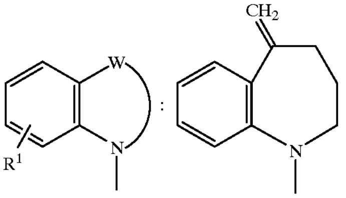

$R^2$: 2-Cl $R^3$: 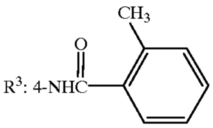

Crystalline form: White powder

Recrystallization solvent: Ethyl acetate/n-hexane

Melting Point: 165–167° C.

Form: Free

TABLE 4-continued

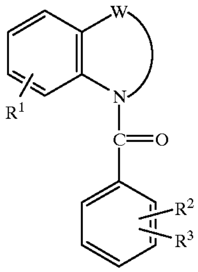

Example 744

Structure

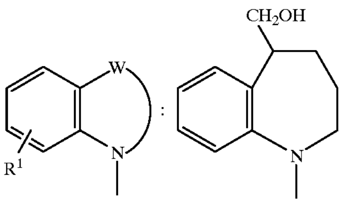

$R^2$: H $R^3$: 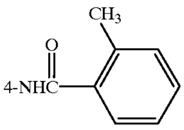

Crystalline form: White powder
Recrystallization solvent: Ethyl acetate/n-hexane
Melting Point: 202–206° C.
Form: Free Example 745

Structure

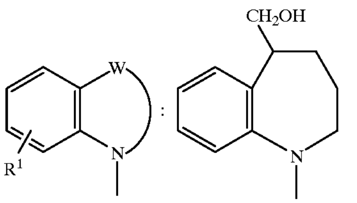

$R^2$: 2-Cl $R^3$: 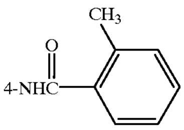

Crystalline form: White powder
Recrystallization solvent: Ethyl acetate/n-hexane
Melting Point: 220–221.5° C.
Form: Free TABLE 4-continued

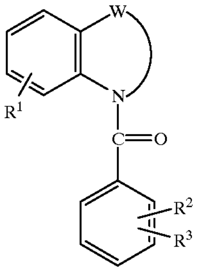

Example 746

Structure

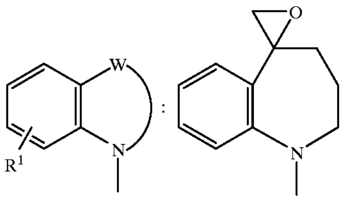

$R^2$: H $R^3$: 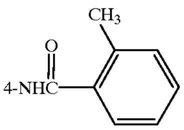

Crystalline form: Colorless needles
Recrystallization solvent: Ethyl acetate/n-hexane
Melting Point: 186–186.5° C.
Form: Free Example 747

Structure

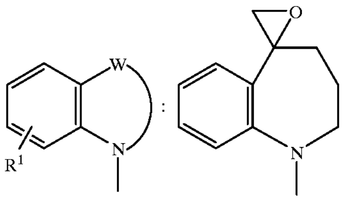

$R^2$: 2-Cl $R^3$: 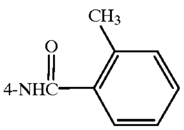

Crystalline form: Colorless amorphous
NMR anaylsis: 136)
Form: Free

TABLE 4-continued

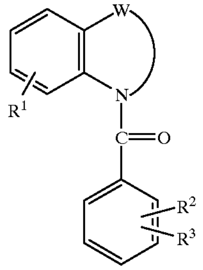

Example 748

Structure

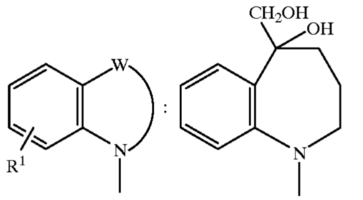

$R^2$: H $R^3$:

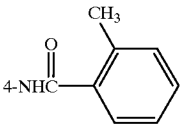

Crystalline form: White powder
Recrystallization solvent: Ethyl acetate/n-hexane
Melting Point: 136–140° C.
Form: Free Example 749

Structure

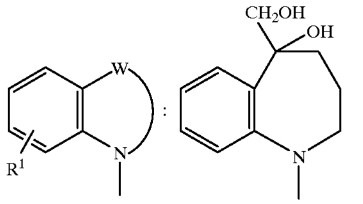

$R^2$: 2-Cl $R^3$:

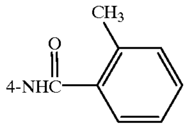

Crystalline form: White powder
Recrystallization solvent: Ethyl acetate/n-hexane
Melting Point: 151–153° C.
Form: Free TABLE 4-continued

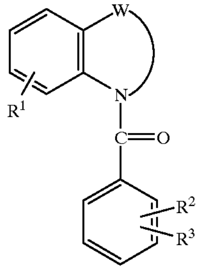

Example 750

Structure

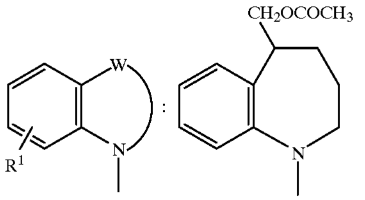

$R^2$: H $R^3$:

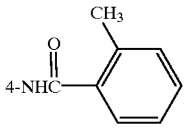

Crystalline form: Colorless needles
Recrystallization solvent: Ethyl acetate/n-hexane
Melting Point: 155–156° C.
Form: Free Example 751

Structure

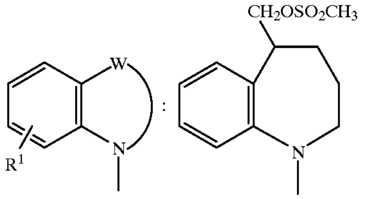

$R^2$: H $R^3$:

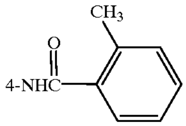

Crystalline form: White powder
Recrystallization solvent: Ethyl acetate/n-hexane
Melting Point: 189–190° C.
Form: Free TABLE 4-continued

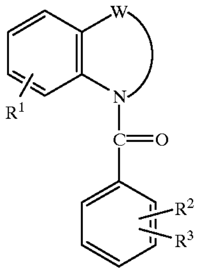

Example 752

Structure

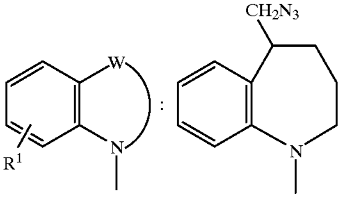

$R^2$: H $R^3$: 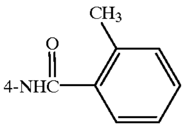

Crystalline form: White powder
Recrystallization solvent: Ethyl acetate/n-hexane
Melting Point: 188–190° C.
Form: Free Example 753

Structure

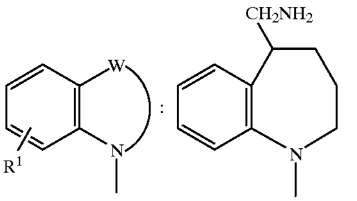

$R^2$: H $R^3$: 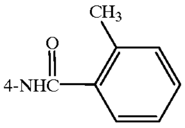

Crystalline form: Colorless needles
Recrystallization solvent: Ethanol
Melting Point: 233–235° C.
Form: Free TABLE 4-continued

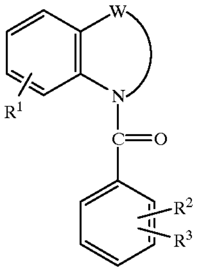

Example 754

Structure

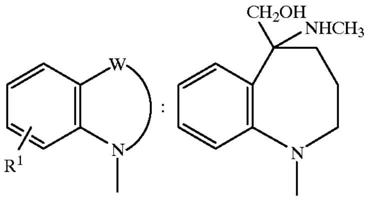

$R^2$: H $R^3$: 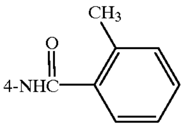

Crystalline form: Colorless amorphous
NMR analysis: 137)
Form: Free

Example 755

Structure

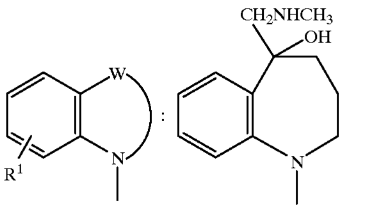

$R^2$: H $R^3$: 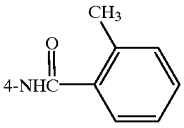

Crystalline form: White powder
Recrystallization solvent: Ethyl acetate/n-hexane
Melting Point: 176–179° C.
Form: Free TABLE 4-continued

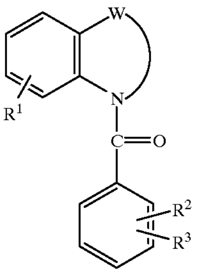

Example 756

Structure

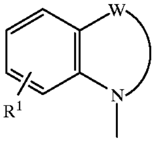 : 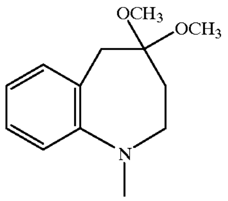

$R^2$: H $R^3$: 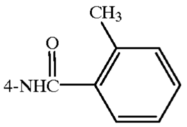

Crystalline form: Colorless needles
Recrystallization solvent: Methanol/diethyl ether
Melting Point: 183–185° C.
Form: Free 117) $^{1}$H-NMR(CDCl$_3$)δ; 1.3–2.3(4H, m), 3.1–3.4(3H, m), 3.8–4.6(2H, m), 5.0–5.3(2H, m), 5.8–6.1(1H, m), 6.8–8.5(11H, m)

118) $^{1}$H-NMR(CDCl$_3$)δ; 1.6–2.2(4H, m), 2.46, 2.53(3H, each s), 3.1–3.5(3H, m), 3.8–4.6(2H, m), 5.0–5.3 (2H, m), 5.8–6.1(1H, m), 6.8–8.8(11H, m)

119) $^{1}$H-NMR(DMSO-d$_6$)δ; 2.33(3H, s), 3.36(2H, m), 3.89(1H, m), 4.41(1H, m), 5.07(1H, m), 5.40(1H, d, J=14.8Hz), 6.85(1H, d, J=7.2Hz), 7.15–7.65 (11H, m), 10.35(1H, s)

120) $^{1}$H-NMR(CDCl$_3$)δ; 1.25–5.05(22H, m), 6.65–7.65 (11H, m), 7.75–8.25(1H, m)

121) $^{1}$H-NMR(CDCl$_3$)δ; 1.15–5.05(19H, m), 6.75–7.85 (11H, m), 7.75–8.25(1H, m)

122) $^{1}$H-NMR(CDCl$_3$)δ; 1.25–2.85(8H, m), 2.95–4.95 (2H, m), 6.75–7.85(10H, m), 9.25–9.75(1H, m)

123) $^{1}$H-NMR(CDCl$_3$)δ; 0.20–0.70(4H, m), 0.95–2.35(6H, m), 2.65–5.00(2H, m), 6.75–7.90(10H, m), 8.65–9.25(1H, m)

124) $^{1}$H-NMR(CDCl$_3$)δ; 1.20–3.15(11H, m), 3.45–3.70 (1H, m), 4.05–5.20(1H, m), 6.60–7.65(10H, m), 8.15–8.45(2H, m)

125) $^{1}$H-NMR(CDCl$_3$)δ; 1.19(3H, t, J=7Hz), 1.25–3.25 (8H, m), 3.46(2H, q, J=7Hz), 3.40–4.10(3H, m), 4.45–5.10(1H, m), 6.65–7.75(12H, m), 8.30–8.60 (1H, m)

126) $^{1}$H-NMR(CDCl$_3$)δ; 1.10–1.30(3H, m), 1.50–2.35(4H, m), 2.65–3.05(2H, m), 3.35–3.60(2H, m), 3.80–4.05 (2H, m), 4.65–5.15(2H, m), 6.55–7.85(12H, m), 8.35–8.65(1H, m)

127) $^{1}$H-NMR(CDCl$_3$)δ; 1.20(3H, t, J=7Hz), 1.10–3.15 (11H, m), 3.45–3.65(3H, m), 3.88(2H, s), 3.95–5.15(1H, m), 6.55–7.65(13H, m), 8.37(1H, s)

128) $^{1}$H-NMR(CDCl$_3$)δ; 2.45(3H, s), 3.40(3H, s), 4.01 (2H, m), 4.38(2H, m), 7.20–7.77(13H, m)

TABLE 4-continued

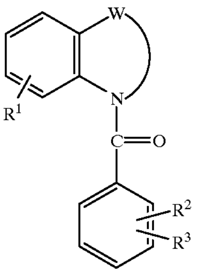

129) $^{1}$H-NMR(CDCl$_3$)δ; 1.35–4.55(22H, m), 6.3–7.8(13H, m)

130) $^{1}$H-NMR(CDCl$_3$)δ; 1.10(6H, t, J=7Hz), 1.35–5.1 (23H, m), 6.55–7.8(13H, m)

131) $^{1}$H-NMR(CDCl$_3$)δ; 1.94–3.21(3H, m), 3.30–4.82(3H, m), 6.57(1H, d, J=7.5Hz), 6.86–8.10(11H, m), 8.72(1H, br)

132) $^{1}$H-NMR(DMSO-d$_6$)δ; 1.57–1.85(2H, m), 1.85–2.28 (2H, m), 2.33(3H, s), 2.64–2.86(1H, m), 4.53–5.07 (1H, m), 5.79–5.94(1H, m), 6.47–7.68(2H, br), 6.64–6.77(1H, m), 6.96–7.62(12H, m)

133) $^{1}$H-NMR(CDCl$_3$)δ; 1.61–1.97(2H, m), 2.00–2.54(2H, m), 2.47(3H, s), 2.60–3.23(7H, m), 4.76–5.22(1H, m), 5.94–6.19(1H, m), 6.61–6.74(1H, m), 6.91–7.62 (12H, m)

134) $^{1}$H-NMR(CDCl$_3$)δ; 1.68–1.97(2H, m), 2.03–2.53(2H, m), 2.61–3.24(7H, m), 4.76–5.22(1H, m), 5.97–6.17 (1H, m), 6.59–6.74(1H, m), 6.92–7.13(1H, m), 7.13–7.58(9H, m), 7.66–7.85(1H, m), 7.85–8.00 (1H, m)

135) $^{1}$H-NMR(CDCl$_3$)δ; 1.57–1.93(2H, m), 1.93–2.54(2H, m), 2.54–2.72(1H, m), 2.79–3.09(3H, m), 3.90–4.32 (2H, m), 4.49–5.18(2H, m), 6.31–6.93(2H, m), 6.96–7.63(10H, m), 7.63–7.89(1H, m), 7.89–8.16 (1H, m)

136) $^{1}$H-NMR(CDCl$_3$)δ; 1.44–1.95(2H, m), 1.95–2.28(2H, m), 2.40–2.67(3H, m), 2.73–3.38(3H, m), 3.40–3.97 (1H, m), 4.50–5.20(1H, m), 6.67–8.11(11H, m)

137) $^{1}$H-NMR(CDCl$_3$)δ; 1.50–2.10(3H, m), 2.10–2.28(1H, m), 2.36(3H, s), 2.48(3H, s), 2.68–2.97(1H, m), 3.26–3.47(1H, m), 4.16(1H, d, J=13.8Hz), 4.25 (1H, d, J=13.8Hz), 5.95(1H, brs), 6.60–6.76(1H, m), 6.97–7.52(8H, m), 7.52–7.73(2H, m), 7.73–7.97 (2H, m)

EXAMPLE 757

A mixture of 5-dimethylamino-1-[4-(2-chlorobenzoylamino)benzoyl]-2,3,4,5-tetrahydro-1H-benzazepine (10 g), methyl iodide (1.7 ml) and chloroform (10 ml) is heated with stirring at 100° C. for 3 hours in an autoclave. After completion of the reaction, the solvent is distilled off under reduced pressure and the resulting residue is dissolved in methanol. The mixture is treated with IRA-400 (trade mark; Organo Co., Ltd., $OH^-$ type). Methanol is distilled off and the resulting residue is suspended in t-butyl alcohol (90 ml), and thereto is added potassium t-butoxide (2.3 g). The mixture is refluxed for 5 hours. The solvent is distilled off under reduced pressure, and the resulting residue is dissolved in dichloromethane. The mixture is washed successively with water and saturated saline solution and dried over magnesium sulfate. The solvent is distilled off and to the resulting residue is added dichloromethane/diethyl ether. The precipitated crude crystal is recrystallized from ethanol to give 1-[4-(2-chlorobenzoylamino)benzoyl]-2,3-dihydro-1H-benzazepine (5.15 g) as colorless needles, m.p. 205–207° C.

EXAMPLE 758

1-[4-(2-Chlorobenzoylamino)benzoyl]-2,3-dihydro-1H-benzazepine (4.7 g) is dissolved in dichloromethane (50 ml)

and thereto is added 80% m-chloroperbenzoic acid (3 g). The mixture is stirred at room temperature overnight. The dichloromethane layer is washed successively with saturated aqueous sodium hydrogen carbonate solution and saturated saline solution, and the solvent is distilled off under reduced pressure. The resulting residue is purified by silica gel column chromatography (eluent; dichloromethane:methanol=50:1) to give 4,5-epoxy-1-[4-(2-chlorobenzoylamino)benzoyl]-2,3,4,5-tetrahydro-1H-benzazepine (4.26 g) as white powder.

$^1$H-NMR($CDCl_3$) δ; 1.94–3.21 (3H, m), 3.30–4.82 (3H, m), 6.57 (1H, d, J=7.5 Hz), 6.86–8.10 (11H, m), 8.72 (1H, brs)

EXAMPLE 759

A mixture of 4,5-epoxy-1-[4-(2-chlorobenzoylamino)benzoyl]-2,3,4,5-tetrahydro-1H-benzazepine (0.5 g), dimethylamine hydrochloride (2.6 g), triethylamine (4.5 g) and methanol (15 ml) is refluxed for 19 hours. After completion of the reaction, the solvent is distilled off and the resulting residue is dissolved in dichloromethane. The mixture is washed successively with water and saturated saline solution. The solvent is distilled off and the resulting residue is purified by silica gel column chromatography (eluent; dichloromethane:methanol=50:1), and recrystallized from ethanol/diethyl ether to give trans-5-dimethylamino-4-hydroxy-1-[4-(2-chlorobenzoylamino)benzoyl]-2,3,4,5-tetrahydro-1H-benzazepine (0.38 g) as colorless needles, m.p. 180–182° C.

Using the suitable starting materials, the compounds of the above Examples 733 and 734 are obtained in the same manner as in Example 759.

EXAMPLE 760

Methyltriphenylphosphonium bromide (4.30 g) is suspended in tetrahydrofuran (100 ml) and thereto is added potassium t-butoxide (1.58 g) under ice-cooling. The mixture is stirred at −5° C. for 1 hour and thereto is added 5-oxo-1-[4-(2-methylbenzoylamino)benzoyl]-2,3,4,5-tetrahydro- 1H-benzazepine (1.60 g) and the mixture is stirred at room temperature for 1 hour. The reaction solution is poured into ice-water (200 ml) and extracted with ethyl acetate. The extract is washed with saturated saline solution and dried over magnesium sulfate. The solvent is distilled off and the resulting residue is purified by silica gel column chromatography (eluent; ethyl acetate:n-hexane=1:2), and recrystallized from ethyl acetate/n-hexane to give 5-methylidene-1-[4-(2-methylbenzoylamino)benzoyl]-2,3,4,5-tetrahydro-1H-benzazepine (1.34 g) as white powder, m.p. 216–217° C.

Using the suitable starting materials, the compound of the above Example 743 is obtained in the same manner as in Example 760.

EXAMPLE 761

5-Methylidene-1-[4-(2-methylbenzoylamino)benzoyl]-2,3,4,5-tetrahydro-1H-benzazepine (2.84 g) is suspended in tetrahydrofuran (50 ml) and thereto is added 1 M solution of boran-tetrahydrofuran complex in tetrahydrofuran (43 ml). The mixture is stirred at room temperature for 6 hours. After completion of the reaction, the reaction solution is cooled with ice, and thereto is added water (70 ml). After termination of the evolution of hydrogen gas, to the reaction solution are added 25% aqueous sodium hydroxide solution (7.0 ml), and subsequently 31% aqueous hydrogen peroxide solution (4.7 ml), and the mixture is heated with stirring at 50° C. for 1 hour. After cooling, to the reaction solution is added saturated saline solution and the tetrahydrofuran layer is collected, washed with saturated saline solution and dried over magnesium sulfate. The solvent is distilled off and the resulting residue is recrystallized from ethyl acetate/n-hexane to give 5-hydroxymethyl-1-[4-(2-methylbenzoylamino)benzoyl]-2,3,4,5-tetrahydro-1H-benzazepine (1.96 g) as white powder, m.p. 202–206° C.

Using the suitable starting materials, the compound of the above Example 745 is obtained in the same manner as in Example 761.

EXAMPLE 762

5-Methylidene-1-[2-chloro-4-(2-methylbenzoylamino)benzoyl]-2,3,4,5-tetrahydro-1H-benzazepine (0.81 g) is dissolved in dichloromethane (30 ml) and thereto is added m-chloroperbenzoic acid (0.57 g). The mixture is stirred at room temperature for 15 hours. After completion of the reaction, the reaction solution is washed successively with aqueous sodium hydrogensulfite solution, aqueous sodium hydrogen carbonate solution and saturated saline solution, and dried over magnesium sulfate. The solvent is distilled off and the resulting residue is purified with silica gel column chromatography (eluent; ethyl acetate:n-hexane=2:3) to give 5,5-epoxy-1-[2-chloro-4-(2-methylbenzoylamino)benzoyl]-2,3,4,5-tetrahydro-1H-benzazepine (0.70 g) as colorless amorphous.

$^1$H-NMR($CDCl_3$) δ; 1.44–1.95 (2H, m), 1.95–2.28 (2H, m), 2.40–2.67 (3H, m), 2.73–3.38 (3H, m), 3.40–3.97 (1H, m), 4.50–5.20 (1H, m), 6.67–8.11 (11H, m)

Using the suitable starting materials, the compound of the above Example 746 is obtained in the same manner as in Example 762.

EXAMPLE 763

To 5-methylidene-1-[4-(2-methylbenzoylamino)benzoyl]-2,3,4,5-tetrahydro-1H-benzazepine (0.60 g) are added successively t-butyl alcohol (6.0 ml), water (1.2 ml), pyridine (0.3 ml), osmium tetroxide (1.2 mg) and trimethylamine N-oxide dihydrate (0.22 9), and the mixture is refluxed with stirring for 2.5 hours. After cooling, to the reaction solution is added 20% aqueous sodium hydrogensulfite solution (10 ml), and the mixture is stirred at room temperature for 1.5 hour. The reaction solution is extracted with a mixture of ethyl acetate/tetrahydrofuran (1:1). The extract is washed successively with diluted hydrochloric acid and saturated saline solution, and dried over magnesium sulfate. The solvent is distilled off and the resulting residue is recrystallized from ethyl acetate/n-hexane to give 5-hydroxymethyl-5-hydroxy-1-[4-(2-methylbenzoylamino)benzoyl]-2,3,4,5-tetrahydro-1H-benzazepine (0.55 g) as white powder, m.p. 136–140° C.

Using the suitable starting materials, the compound of the above Example 749 is obtained in the same manner as in Example 763.

EXAMPLE 764

To 5-hydroxymethyl-1-[4-(2-methylbenzoylamino)benzoyl]-2,3,4,5-tetrahydro-1H-benzazepine (0.40 g) are added acetic anhydride (4.0 ml) and pyridine (0.5 ml), and the mixture is stirred at room temperature for 5 hours. After completion of the reaction, the reaction solution is poured into ice-water and extracted with ethyl acetate. The extract is washed successively with diluted hydrochloric acid and saturated saline solution, and dried over magnesium sulfate. The solvent is distilled off and the resulting residue is recrystallized from ethyl acetate/n-hexane to give 5-acetyloxymethyl-1-[4-(2-methylbenzoylamino)benzoyl]-2,3,4,5-tetrahydro-1H-benzazepine (0.43 g) as colorless needles, m.p. 155–156° C.

EXAMPLE 765

5-Hydroxymethyl-1-[4-(2-methylbenzoylamino) benzoyl]-2,3,4,5-tetrahydro-1H-benzazepine (0.70 g) is dissolved in a mixture (30 ml) of dichloromethane/acetonitrile (1:1) and thereto are added methanesulfonyl chloride (0.8 ml) and pyridine (1.0 ml), and the mixture is refluxed with stirring for 2 hours. After cooling, the reaction solution is evaporated under reduced pressure and to the resulting residue is added water and then extracted with ethyl acetate. The extract is washed successively with diluted hydrochloric acid and saturated saline solution, and dried over magnesium sulfate. The solvent is distilled off and the resulting residue is recrystallized from ethyl acetate/n-hexane to give 5-methanesulfonyloxymethyl-1-[4-(2-methylbenzoylamino)benzoyl]-2,3,4,5-tetrahydro-1H-benzazepine (0.72 g) as white powder, m.p. 189–190° C.

EXAMPLE 766

5-Methanesulfonyloxymethyl-1-[4-(2-methylbenzoylamino)benzoyl]-2,3,4,5-tetrahydro-1H-benzazepine (0.49 g) is dissolved in a mixture (25 ml) of acetonitrile/dimethylformamide (4:1) and thereto is added sodium azide (0.11 g). The mixture is refluxed with stirring for 3.5 hours. After cooling, the reaction solution is poured into ice-water (40 ml), extracted with ethyl acetate, washed with saturated saline solution, and dried over magnesium sulfate. The solvent is distilled off and the resulting residue is purified by silica gel column chromatography (eluent; ethyl acetate:n-hexane=1:2), and recrystallized from ethyl acetate/n-hexane to give 5-azidomethyl-1-[4-(2-methylbenzoylamino)benzoly]-2,3,4,5-tetrahydro-1H-benzazepine (0.29 9) as white powder, m.p. 188–189° C.

EXAMPLE 767

5-Azidomethyl-1-[4-(2-methylbenzoylamino)benzoyl]-2,3,4,5-tetrahydro-1H-benzazepine (0.27 g) is suspended in ethanol (50 ml) and the mixture is subjected to catalytic hydrogenation at room temperature under 3 kg/cm$^2$ for 6 hours by using 10% Pd-C (27 mg). The catalyst is removed by filtration with celite and the filtrate is distilled off and the resulting residue is recrystallized from ethanol to give 5-aminomethyl-1-[4-(2-methylbenzoylamino)benzoyl]-2,3,4,5-tetrahydro-1H-benzazepine (0.12 g) as colorless needles, m.p. 233–235° C.

EXAMPLE 768

To 5,5-epoxy-1-[4-(2-methylbenzoylamino)benzoyl]-2,3,4,5-tetrahydro-1H-benzazepine (0.30 g) is added 30% solution of methylamine in methanol (30 ml), and the mixture is refluxed for 14 hours. After compeltion of the reaction, the reaction solution is evaporated under reduced pressure and the resulting residue is purified by silica gel column chromatography (eluent; ethyl acetate:n-hexane=1:1→dichloromethane:methanol:aqueous ammonia=60 10:1) to give 5-hydroxymethyl-5-methylamino-1-[4-(2-methylbenzoylamino]benzoyl]-2,3,4,5-tetrahydro-1H-benzazepine (A; 35.3 mg) and 5-methylaminomethyl-5-hydroxy-1-[4-(2-methylbenzoylamino)benzoyl]-2,3,4,5-tetrahydro-1H-benzazepine (B; 109 mg).

(A); Colorless amorphous $^1$H-NMR(CDCl$_3$) δ; 1.50–2.10 (3H, m), 2.10–2.28 (1H, m), 2.36 (3H, s), 2.48 (3H, s), 2.68–2.97 (1H, m), 3.26–3.47 (1H, m), 4.16 (1H, d, J=13.8 Hz), 4.25 (1H, d, J=13.8 Hz), 5.95 (1H, brs), 6.60–6.76 (1H, m), 6.97–7.52 (8H, m), 7.52–7.73 (2H, m), 7.73–7.97 (2H, m)

(B); White powder (recrystallized from ethyl acetate/n-hexane)

m.p. 176–179° C.

EXAMPLE 769

5-Methylamino-1-[4-(2-methylbenzoylamino)benzoyl]-2,3,4,5-tetrahydro-1H-benzazepine (1 g) is dissolved in dimethylformamide (10 ml) and thereto are added potassium carbonate (0.5 g) and ethyl iodide (0.45 g). The mixture is stirred at room temperature overnight. After completion of the reaction, the reaction solution is poured into ice-water and the precipitated crystal is collected by filtration, and purified by silica gel column chromatography (eluent; dichloromethane:methanol=90:1), and recrystallized from diisopropyl alcohol/petroleum ether to give 5-(N-methyl-N-ethylamino)-1-[4-(2-methylbenzoylamino)benzoyl]-2,3,4,5-tetrahydro-1H-benzazepine (50 mg) as white powder, m.p. 192–193° C.

Using the suitable starting materials, the compounds of the above Examples 244, 246–248, 330, 339, 342, 346, 350, 366, 375, 376, 406–418, 453, 455, 457, 460, 464, 467, 506, 507, 537–545, 547, 549–556, 561–566, 568–571, 577, 601–603, 607–625, 654–672, 675, 677–681, 691–695, 697, 698, 701–705, 707, 708, 712, 713, 715, 716, 719, 720 and 722–725 are obtained in the same manner as in Example 769.

EXAMPLE 770

To a suspension of 5-methylamino-1-[4-(2-methylbenzoylamino)benzoyl]-2,3,4,5-tetrahydro-1H-benzazepine (3 g) in methanol (30 ml) are added potassium carbonate (1.5 g) and epichlorohydrine (5.7 ml), and the mixture is refluxed for 3 hours. The solvent is distilled off and to the resulting residue is added water and extracted three times with dichloromethane. The extract is washed with saturated saline solution and dried over magnesium sulfate. The resulting residue is purified by silica gel column chromatography (eluent; dichloromethane:methanol=80:1) to give 5-(N-methyl-N-oxiranylmethylamino)-1-[4-(2-methylbenzoylamino)benzoyl]-2,3,4,5-tetrahydro-1H-benzazepine (C; 1.92 g) and 5-[N-methyl-N-(2-hydroxy-3-methoxypropyl)amino]-1-[4-(2-methylbenzoylamino) benzoyl]-2,3,4,5-tetrahydro-1H-benzazepine (D; 0.38 g).

(C); Colorless needles (recrystallization from ethyl acetate) m.p. 239–240° C.

(D); Colorless amorphous $^1$H-NMR(CDCl$_3$) δ; 1.35–4.55 (22H, m), 6.3–7.8 (13H, m)

EXAMPLE 771

5-[N-Methyl-N-oxiranylmethylamino)-1-[4-(2-methylbenzoylamino)benzoyl]-2,3,4,5-tetrahydro-1H-benzazepine (0.5 g) is dissolved in methanol (10 ml) and thereto is added diethylamine (0.13 ml). The mixture is refluxed for 3 hours. After completion of the reaction, the solvent is distilled off and the resulting residue is purified by silica gel column chromatography (eluent; dichloromethane methanol=30:1→dichloromethane:methanol:aqueous ammonia=9:1:0.1) to give 5-[N-methyl-N-(2-hydroxy-3-diethylaminopropyl)amino]-1-[4-(2-methylbenzoylamino)

benzoyl]-2,3,4,5-tetrahydro-1H-benzazepine (0.38 g) as colorless amorphous.

$^1$H-NMR($CDCl_3$) δ; 1.10 (6H, t, J=7 Hz), 1.35–5.1 (23H, m), 6.55–7.8 (13H, m)

EXAMPLE 772

A solution of 5-hydroxyimino-1-[4-(2-chlorobenzoylamino)benzoyl]-2,3,4,5-tetrahydro-1H-benzazepine (1.06 g) in acetic anhydride (10 ml) and pyridine (10 ml) is stirred at room temperature overnight. After completion of the reaction, the reaction solution is concentrated. To the resulting residue is added water and the mixture is extracted with dichloromethane. The extract is washed with saturated saline solution and dried over magnesium sulfate. The solvent is distilled off and the resulting residue is purified by silica gel column chromatography (eluent; dichloromethane:methanol=80:1), and recrystallized from ethanol/petroleum ether to give 5-acetyloxyimino-1-[4-(2-chlorobenzoylamino)benzoyl]-2,3,4,5-tetrahydro-1H-benzazepine (0.75 g) as colorless prisms, m.p. 142–144° C.

EXAMPLE 773

Using the suitable starting materials, the compounds of the above Examples 671 and 672 are obtained in the same manner as in Example 380.

EXAMPLE 774

Using the suitable starting materials, the compounds of the above Examples 674, 699, 700, 706, 718 and 730 are obtained in the same manner as in Example 384.

EXAMPLE 775

Using the suitable starting materials, the compounds of the above Examples 654–672, 675, 677–687, 691–695, 697, 698, 701–705, 707, 708, 712, 713, 715, 716 and 719–725 are obtained in the same manner as in Example 390.

EXAMPLE 776

Using the suitable starting materials, the compounds of the above Examples 654–672, 675, 677–679, 691–693, 698, 701–705, 707, 708, 712, 713, 715, 716 and 719–725 are obtained in the same manner as in Example 388.

EXAMPLE 777

Using the suitable starting materials, the compounds of the above Examples 705, 706 and 708 are obtained in the same manner as in Example 394.

EXAMPLE 778

Using the suitable starting materials, the compound of the above Example 671 is obtained in the same manner as in Example 397.

EXAMPLE 779

Using the suitable starting materials, the compound of the above Example 672 is obtained in the same manner as in Example 402.

EXAMPLE 780

Using the suitable starting materials, the compound of the above Example 726 is obtained in the same manner as in Example 634.

EXAMPLE 781

Using the suitable starting materials, the compound of the above Example 740 is obtained in the same manner as in Examples 638 and 640.

EXAMPLE 782

Using the suitable starting materials, the compound of the above Example 689 is obtained in the same manner as in Example 643.

EXAMPLE 783

Using the suitable starting materials, the compound of the above Example 690 is obtained in the same manner as in Example 644.

EXAMPLE 784

Using the suitable starting materials, the following compound is obtained in the same manner as in Examples 1, 382, 388 and 390.

5-Dimethylamino-1-[4-(2-methylbenzoylamino)benzoyl]-2,3,4,5-tetrahydro-1H-benzazepine hydrochloride, colorless needles (recrystallized from ethanol/water), m.p. 233–237° C.

REFERENCE EXAMPLE 13

Using the suitable starting materials, the following compounds are obtained in the same manner as in Reference Example 1.

5-(2-Chloroacetyloxy)-1-(4-nitrobenzoyl)-2,3,4,5-tetrahydro-1H-benzazepine, white powder, m.p. 156–159° C. (recrystallized from ethyl acetate/n-hexane)

5-(2-Dimethylaminoacetyloxy)-1-(4-nitrobenzoyl)-2,3,4,5-tetrahydro-1H-benzazepine, white powder, m.p. 108–109° C. (recrystallized from ethyl acetate/n-hexane)

5-Oxo-7-chloro-1-(4-nitrobenzoyl)-2,3,4,5-tetrahydro-1H-benzazepine, white powder, m.p. 157.5–159.5° C. (recrystallized from diethyl ether/dichloromethane)

5-Oxo-8-chloro-1-(4-nitrobenzoyl)-2,3,4,5-tetrahydro-1H-benzazepine, white powder, m.p. 151.5–153.5° C. (recrystallized from diethyl ether/dichloromethane)

REFERENCE EXAMPLE 14

Using the suitable starting materials, the following compounds are obtained in the same manner as in Reference Example 2.

5-(2-Dimethylaminoacetyloxy)-1-(4-aminobenzoyl)-2,3,4,5-tetrahydro-1H-benzazepine, colorless amorphous $^1$H-NMR ($CDCl_3$) δ; 1.63–1.98 (2H, m), 1.98–2.25 (1H, m), 2.27 (3H, s), 2.43 (3H, s), 2.65–3.23 (2H, m), 3.38 (2H, s), 3.67 (2H, brs), 4.77–5.28 (1H, m), 6.04–6.31 (1H, m), 6.31–6.56 (2H, m), 6.58–6.86 (1H, m), 6.86–7.46 (5H, m)

5-Oxo-7-chloro-1-(4-aminobenzoyl)-2,3,4,5-tetrahydro-1H-benzazepine, white powder, m.p. 193–193.5° C. (recrystallized from diethyl ether/dichloromethane)

5-Oxo-8-chloro-1-(4-aminobenzoyl)-2,3,4,5-tetrahydro-1H-benzazepine, white powder, m.p. 171–174° C. (recrystallized from diethyl ether/dichloromethane)

REFERENCE EXAMPLE 15

Using the suitable starting materials, the following compounds are obtained in the same manner as in Reference Example 1.

5-Dimethylaminocarbonylmethoxy-1-(4-nitrobenzoyl)-2,3,4,5-tetrahydro-1H-benzazepine, white powder, m.p. 129–131° C. (recrystallized from ethyl acetate/n-hexane)

6-Oxo-1-(4-nitrobenzoyl)-1,2,3,4,5,6-hexahydrobenzazocine, yellow needles $^1$H-NMR ($CDCl_3$) δ; 1.65–2.3 (4H, m), 2.5–5.2 (4H, m), 6.7–6.9 (1H, m), 7.27–7.5 (4H, m), 7.90–8.15 (3H, m)

6-Chloro-5-oxo-1-(4-nitrobenzoyl)-2,3,4,5-tetrahydro-1H-benzazepine, white powder, m.p. 198–202° C. (recrystallized from dichloromethane/diethyl ether)

REFERENCE EXAMPLE 16

Using the suitable starting materials, the following compounds are obtained in the same manner as in Reference Example 2.

5-Dimethylaminocarbonylmethoxy-1-(4-aminobenzoyl)-2,3,4,5-tetrahydro-1H-benzazepine, colorless amorphous $^1$H-NMR ($CDCl_3$) δ; 1.52–2.10 (3H, m), 2.10–3.20 (2H, m), 2.97 (3H, s), 3.05 (3H, s), 4.03–4.48 (2H, m), 4.50–5.35 (2H, m), 6.26–6.57 (2H, m), 6.57–6.88 (1H, m), 6.88–7.76 (5H, m)

6-Oxo-1-(4-aminobenzoyl)-1,2,3,4,5,6-hexahydrobenzazocine, light yellow amorphous $^1$H-NMR ($CDCl_3$) δ; 1.7–2.2 (4H, m), 2.5–5.2 (6H, m), 6.42 (2H, d, J=8.7 Hz), 6.75–6.9 (1H, m), 7.05–7.4 (4H, m), 7.95–8.1 (1H, m)

6-Chloro-5-oxo-1-(4-aminobenzoyl)-2,3,4,5-tetrahydro-1H-benzazepine, white powder, m.p. 166–169° C. (recrystallized from dichloromethane/diethyl ether)

9-Chloro-5-oxo-1-(4-aminobenzoyl)-2,3,4,5-tetrahydro-1H-benzazepine, yellow powder, m.p. 192.5–195° C. (recrystallized from dichloromethane/diethyl ether)

REFERENCE EXAMPLE 17

5-Dimethylamino-1-(2-methyl-4-nitrobenzoyl)-2,3,4,5-tetrahydro-1H-benzazepine (86.0 g) is dissolved in ethanol (800 ml), and thereto is added platinum oxide (10 g). The mixture is subjected to hydrogenation at ordinary temperature under atmospheric pressure of hydrogen for 4 hours. The catalyst is removed by filtration, and the solvent is distilled off. The resulting residue is purified by silica gel column chromatography (eluent; dichloromethane:methanol=200:1→100:1), and further purified by silica gel thin layer chromatography (developer; chloroform:methanol=10:1), and recrystallized from methanol/diethyl ether to give 5-dimethylamino-1-(2-methyl-4-aminobenzoyl)-2,3,4,5-tetrahydro-1H-benzazepine (G) (Rf: 0.52, 27.4 g) and 5-dimethylamino-1-(2-methyl-4-amino-benzoyl)-2,3,4,5-tetrahydro-1H-benzazepine (H) (Rf: 0.48, 12.3 g).

(G): White powder

M.p. 154–156° C.; $[\alpha]_D^{22}$=0° (c=1.0, chloroform)

$^1$H-NMR ($CDCl_3$) δ; 1.10–1.50 (1H, m), 1.50–2.00 (1H, m), 2.00–2.35 (11H, m), 2.90–5.18 (5H, m), 6.00–6.76 (3H, m), 6.81–7.64 (4H, m)

(H): White powder

M.p. 169.5–170° C.; $[\alpha]_D^{22}$=0° (c=1.5, chloroform)

$^1$H-NMR ($CDCl_3$) δ; 1.11–2.90 (13H, m), 2.91–5.23 (5H, m), 6.15–6.53 (1H, m), 6.57–7.62 (6H, m)

Using the suitable starting materials, the compounds of the following Table 5 are obtained in the same manner as in above Examples 1 and 382.

TABLE 5

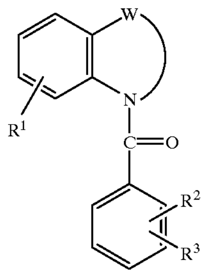

Example 785

Structure

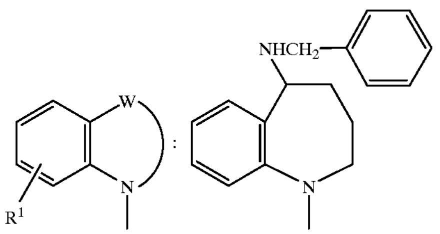

$R^2$: H

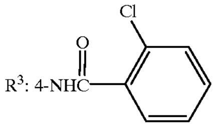

Crystalline form: Colorless needles

Recrystallization solvent: Ethanol

Melting Point: 174–175° C.

Form: Free

Example 786

Structure

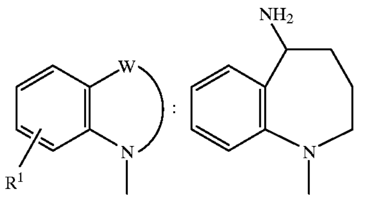

$R^2$: H

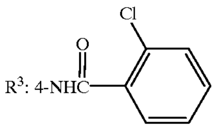

Crystalline form: Colorless prisms

Recrystallization solvent: Ethanol/diethyl ether

Melting Point: 176–178° C.

Form: Free

TABLE 5-continued

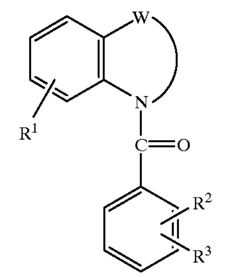

Example 787

Structure

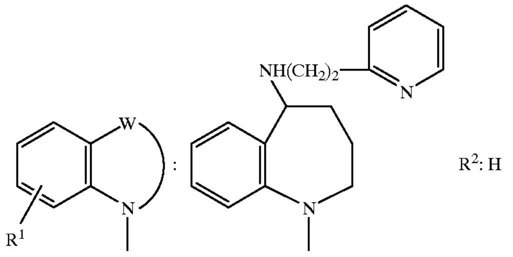

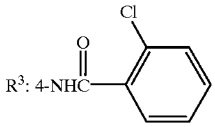

Crystalline form: Colorless prisms

Recrystallization solvent: Ethyl acetate/petroleum ether

Melting Point: 154.5–155° C.

Form: Free

Example 788

Structure

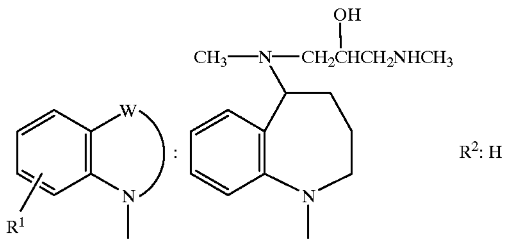

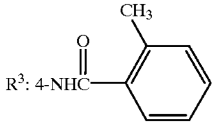

Crystalline form: Colorless amorphous

NMR analysis: 138)

Form: Free

TABLE 5-continued

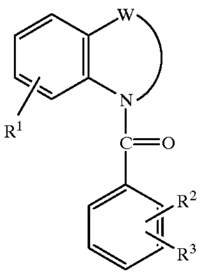

Example 789

Structure

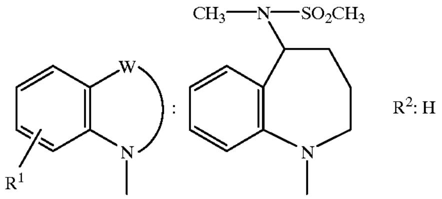

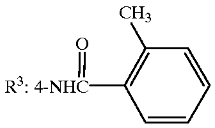

Crystalline form: Colorless scales

Recrystallization solvent: Ethanol

Melting Point: 197–198° C.

Form: Free

Example 790

Structure

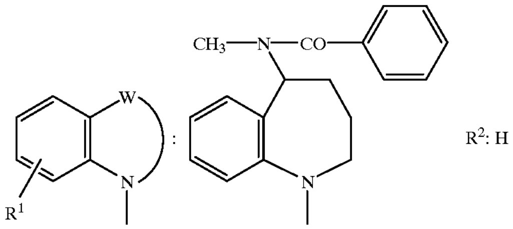

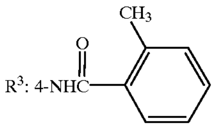

Crystalline form: Colorless needles

Recrystallization solvent: Ethanol

Melting Point: 248–249° C.

Form: Free

Example 791

Structure

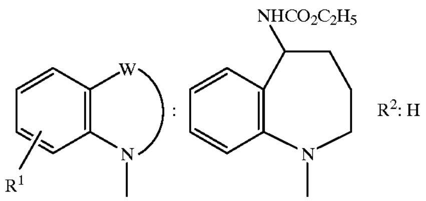

TABLE 5-continued

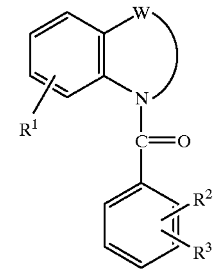

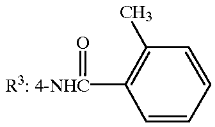

Crystalline form: Colorless needles
Recrystallization solvent: Ethanol/n-hexane
Melting Point: 162–163° C.
Form: Free
Example 792
Structure

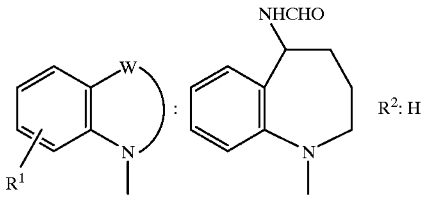

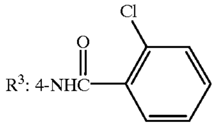

Crystalline form: Colorless prisms
Recrystallization solvent: Ethanol/petroleum ether
Melting Point: 235–236.5° C.
Form: Free
Example 793
Structure

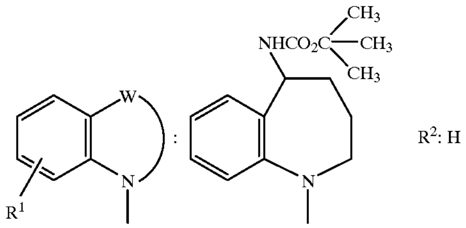

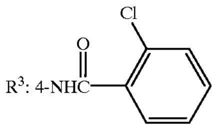

Crystalline form: Colorless amorphous
NMR analysis: 139)
Form: Free

TABLE 5-continued

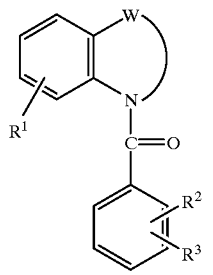

Example 794
Structure

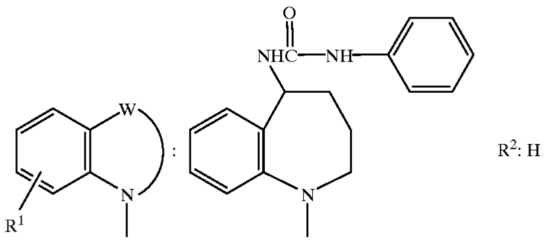

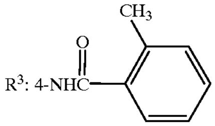

Crystalline form: Colorless prisms
Recrystallization solvent: Dioxane
Melting Point: 269–271° C.
Form: Free
Example 795
Structure

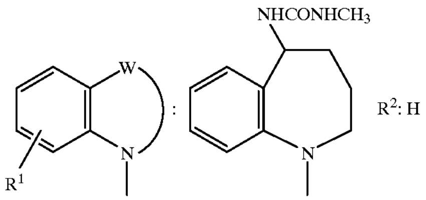

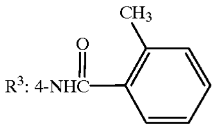

Crystalline form: Colorless prisms
Recrystallization solvent: Dimethylformamide
Melting Point: 286–287° C.
Form: Free TABLE 5-continued

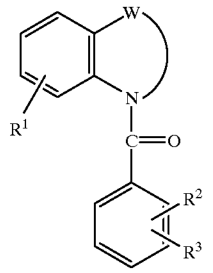

Example 796
Structure

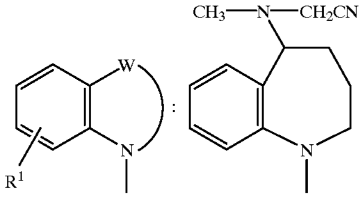

$R^2$: H

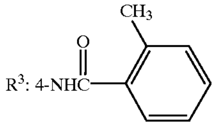

Crystalline form: Colorless needles
Recrystallization solvent: Acetonitrile
Melting Point: 227–228° C.
Form: Free
Example 797
Structure

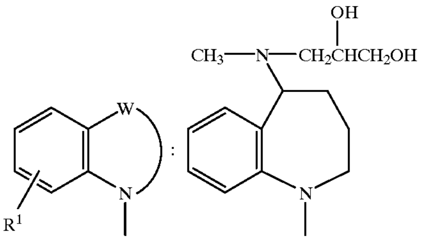

$R^2$: H

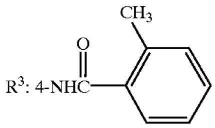

Crystalline form: Colorless amorphous
NMR analysis: 140)
Form: Free
Example 798
Structure

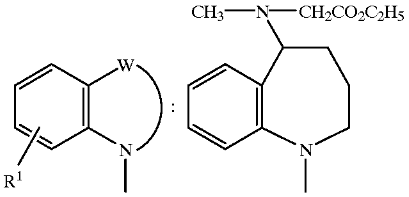

$R^2$: H

TABLE 5-continued

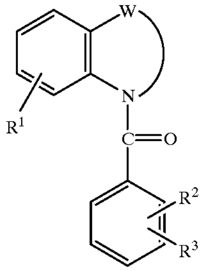

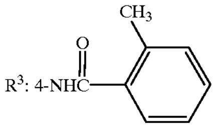

Crystalline form: Colorless prisms
Recrystallization solvent: Ethyl acetate/petroleum ether
Melting Point: 167–168° C.
Form: Free
Example 799
Structure

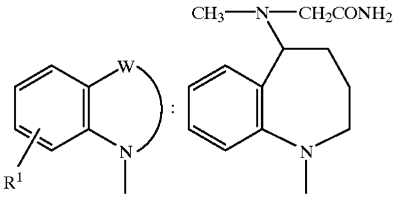

$R^2$: H

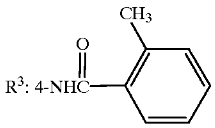

Crystalline form: Colorless amorphous
NMR analysis: 141)
Example 800
Structure

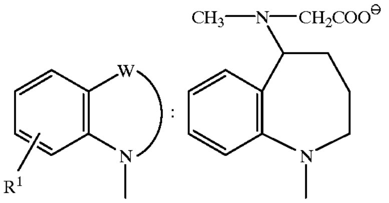

$R^2$: H

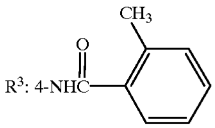

Crystalline form: Colorless needles
Recrystallization solvent: Diethyl ether
Melting Point: 164–171° C.
Form: $K^{\oplus}$ TABLE 5-continued

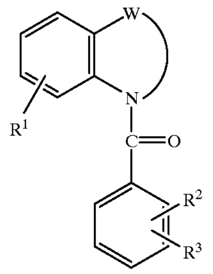

Example 801

Structure

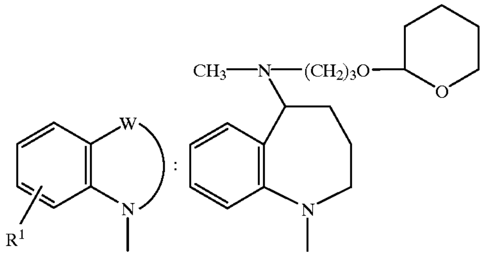

$R^2$: H

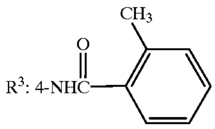

Crystalline form: Colorless amorphous

NMR analysis: 142)

Form: Free

Example 802

Structure

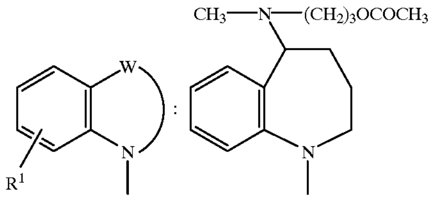

$R^2$: H

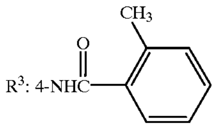

Crystalline form: Colorless amorphous

NMR analysis: 143)

Form: Free

TABLE 5-continued

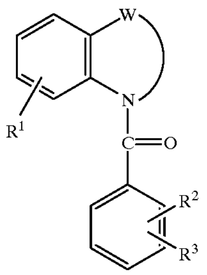

Example 803

Structure

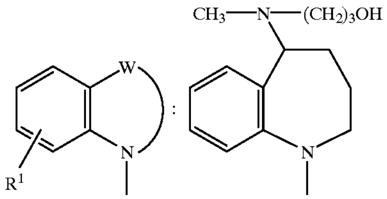

$R^2$: H

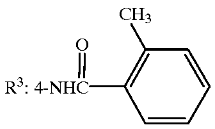

Crystalline form: Colorless amorphous

NMR analysis: 144)

Form: Free

Example 804

Structure

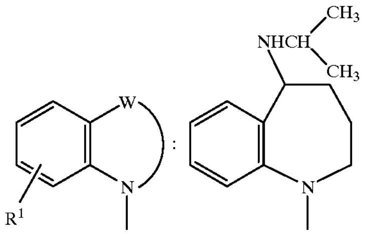

$R^2$: H

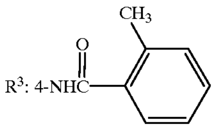

Crystalline form: Colorless amorphous

NMR analysis: 145)

Form: Free

Example 805

Structure

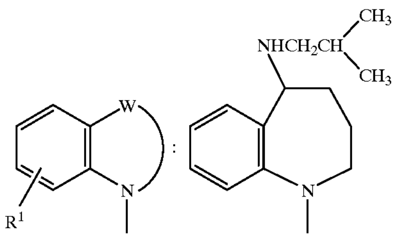

$R^2$: H

TABLE 5-continued

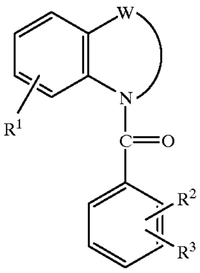

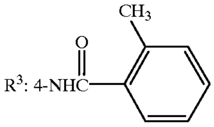

Crystalline form: Colorless needles
Recrystallization solvent: Ethanol
Melting Point: 207–208° C.
Form: Free
Example 806
Structure

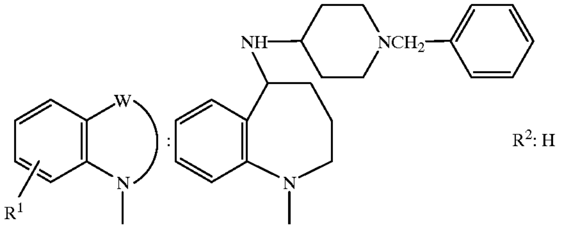

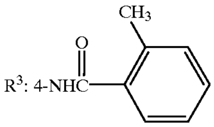

Crystalline form: White powder
Recrystallization solvent: Dichloromethane/diethyl ether
Melting Point: 187–189° C.
Form: Free
Example 807
Structure

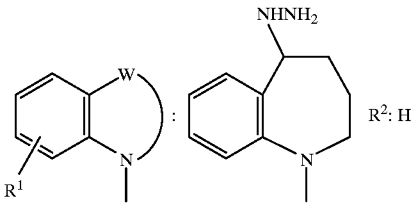

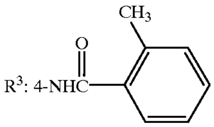

Crystalline form: Colorless prisms
Recrystallization solvent: Ethanol/petroleum ether
Melting Point: 217–218° C.
Form: Free TABLE 5-continued

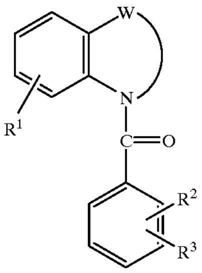

Example 808
Structure

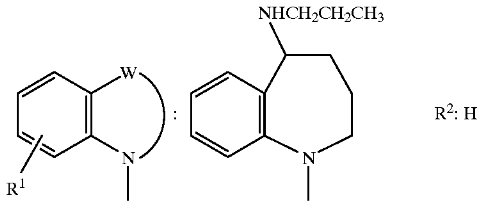

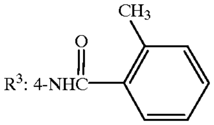

Crystalline form: Colorless needles
Recrystallization solvent: Ethyl acetate
Melting Point; 170–171° C.
Form: Free
Example 809
Structure

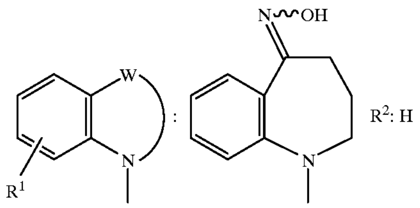

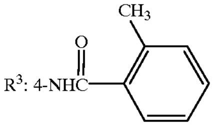

Crystalline form: Colorless prisms
Recrystallization solvent: Ethanol
Melting Point: 239.5–241° C.
Form: Free
Example 810
Structure

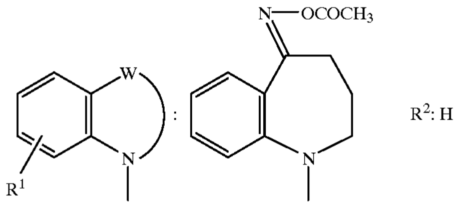

TABLE 5-continued

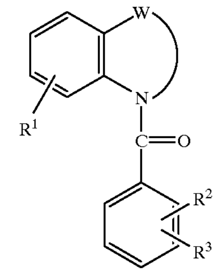

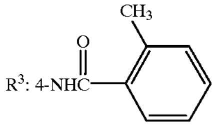

Crystalline form: Colorless needles
Recrystallization solvent: Ethanol
Melting Point: 190–191° C.
Form: Free
Example 811
Structure

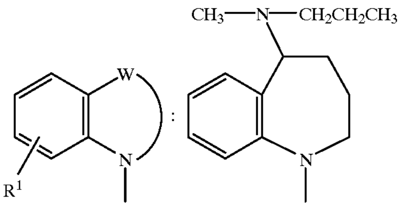

$R^2$: H

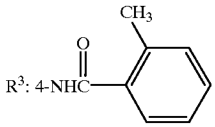

Crystalline form: Colorless prisms
Recrystallization solvent: Diethyl ether
Melting Point: 163–163.5° C.
Form: Free
Example 812
Structure

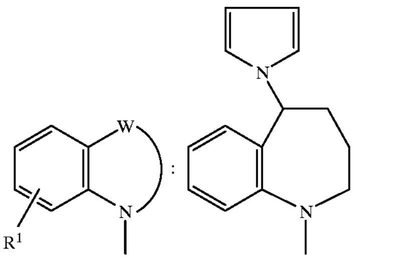

$R^2$: H

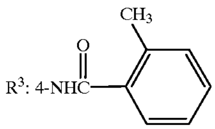

Crystalline form: Colorless prisms
Recrystallization solvent: Ethyl acetate/n-hexane
Melting Point: 208–210° C.

TABLE 5-continued

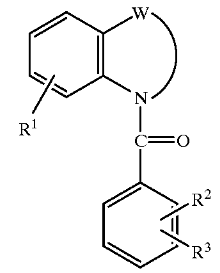

Form: Free
Example 813
Structure

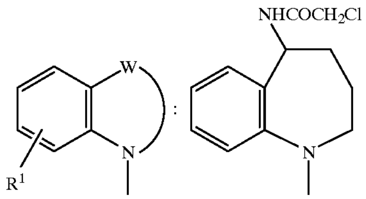

$R^2$: H

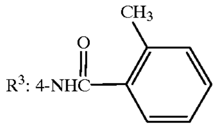

Crystalline form: White powder
NMR analysis: 146)
Form: Free
Example 814
Structure

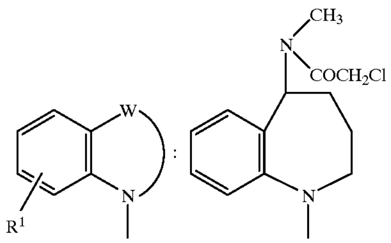

$R^2$: H

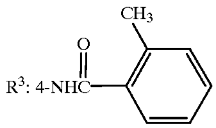

Crystalline form: Colorless amorphous
NMR analysis: 147)
Form: Free

TABLE 5-continued

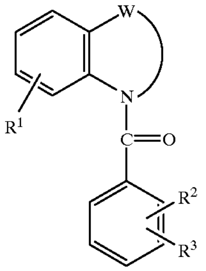

Example 815
Structure

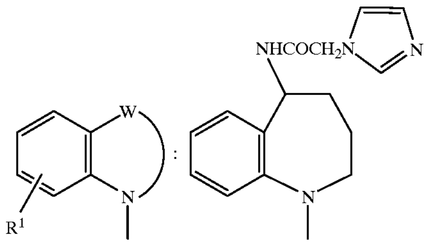

$R^2$: H $R^3$: 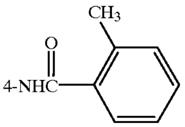

Crystalline form: Colorless needles
Recrystallization solvent: Ethanol/n-hexane
Melting Point: 250–252° C.
Form: Free Example 816
Structure

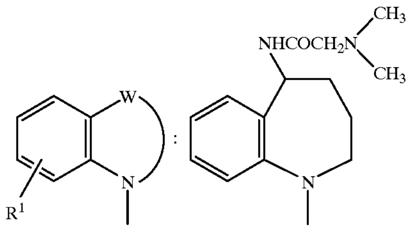

$R^2$: H $R^3$: 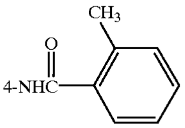

Crystalline form: Colorless prisms
Recrystallization solvent: Ethyl acetate
Melting Point: 214–216° C.
Form: Free TABLE 5-continued

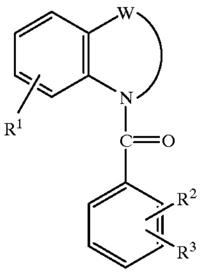

Example 817
Structure

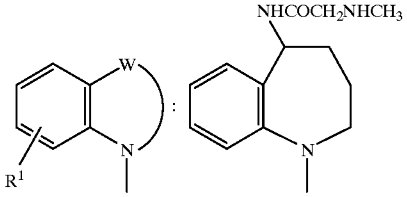

$R^2$: H $R^3$: 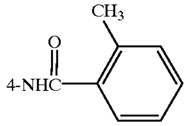

Crystalline form: Colorless prisms
Recrystallization solvent: Ethanol/n-hexane
Melting Point: 243–245° C.
Form: Free Example 818
Structure

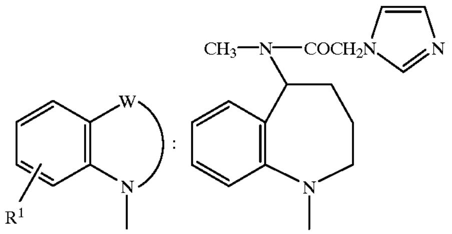

$R^2$: H $R^3$: 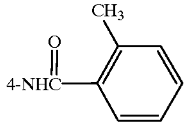

Crystalline form: Colorless prisms
Recrystallization solvent: Diethyl ether
Melting Point: 159–162° C.
Form: Free TABLE 5-continued

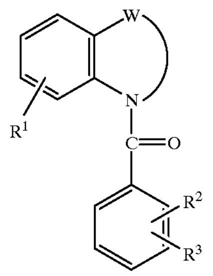

Example 819

Structure

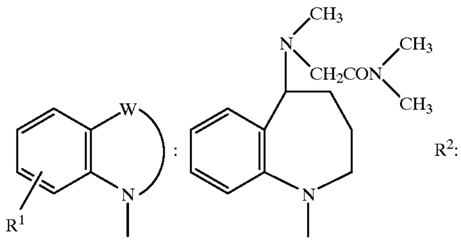

$R^2$: H

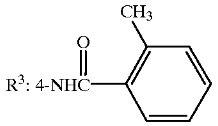

Crystalline form: Colorless amorphous

NMR analysis: 148)

Form: Free

Example 820

Structure

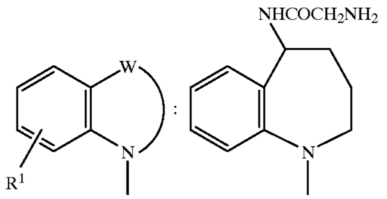

$R^2$: H

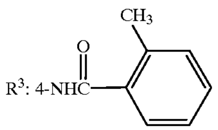

Crystalline form: Colorless prisms

Recrystallization solvent: Ethyl acetate

Melting Point: 287–289° C.

Form: Free

TABLE 5-continued

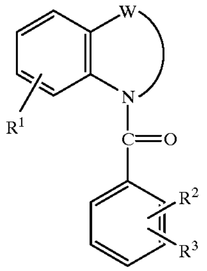

Example 821

Structure

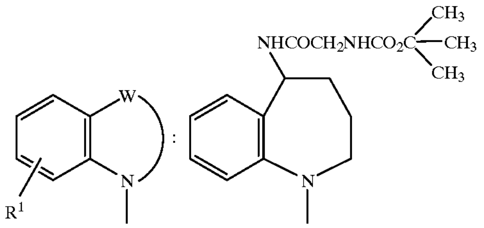

$R^2$: H

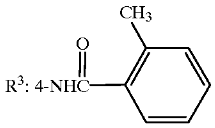

Crystalline form: Colorless prisms

Recrystallization solvent: Diethyl ether

Melting Point: 170–171° C.

Form: Free

Example 822

Structure

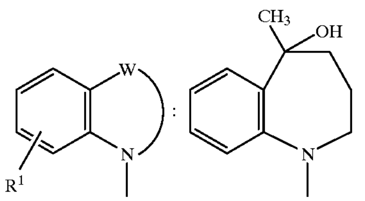

$R^2$: H

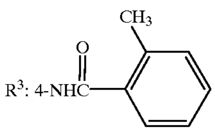

Crystalline form: White powder

Recrystallization solvent: Ethyl acetate/n-hexane

Melting Point: 204–205° C.

Form: Free

TABLE 5-continued

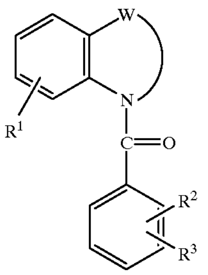

Example 823
Structure

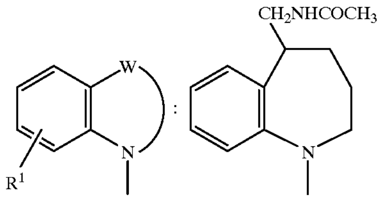

$R^2$: H

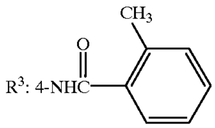

Crystalline form: White powder
Recrystallization solvent: Ethyl acetate/n-hexane
Melting Point: 273–273.5° C.
Form: Free
Example 824
Structure

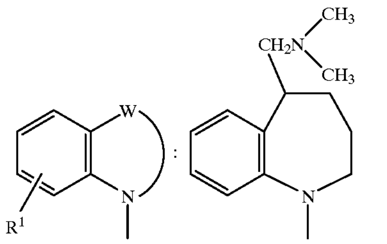

$R^2$: H

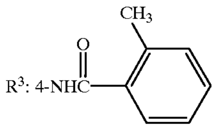

Crystalline form: Colorless amorphous
NMR analysis: 149)
Form: Free
Example 825
Structure

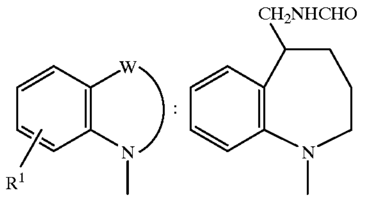

$R^2$: H

TABLE 5-continued

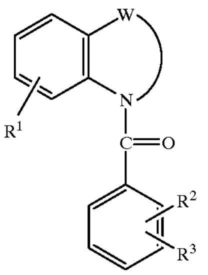

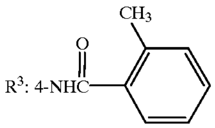

Crystalline form: White powder
Recrystallization solvent: Ethyl acetate/n-hexane
Melting Point: 240–241° C.
Form: Free
Example 826
Structure

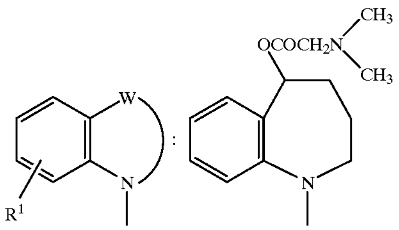

$R^2$: H

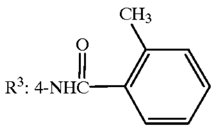

Crystalline form: White powder
Recrystallization solvent: Acetonitrile/ethanol
Melting Point: 231–232° C.
Form: Free
Example 827
Structure

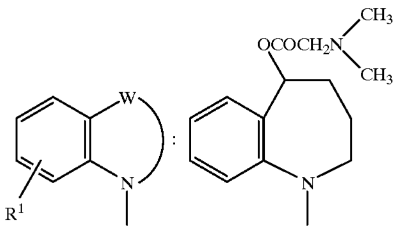

$R^2$: H

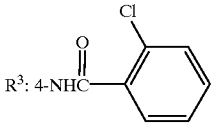

Crystalline form: White powder
Recrystallization solvent: Acetonitrile/ethanol
Melting Point: 222–224° C.
Form: Free TABLE 5-continued

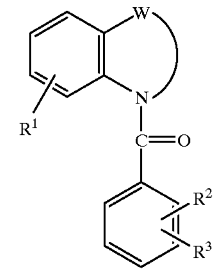

Example 828

Structure

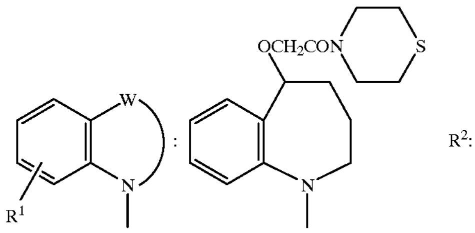

$R^2$: H

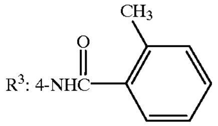

Crystalline form: White powder

Recrystallization solvent: Ethyl acetate/n-hexane

Melting Point: 235–237° C.

Form: Free

Example 829

Structure

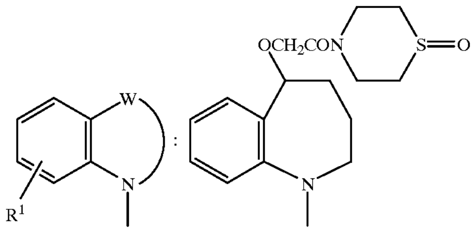

$R^2$: H

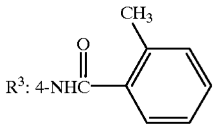

Crystalline form: Colorless amorphous

NMR analysis: 150)

Form: Free

TABLE 5-continued

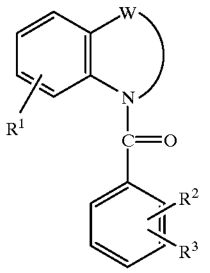

Example 830

Structure

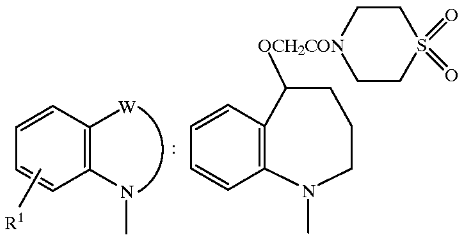

$R^2$: H

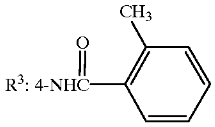

Crystalline form: Colorless amorphous

NMR analysis: 151)

Form: Free

Example 831

Structure

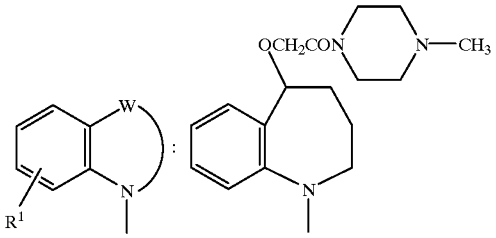

$R^2$: H

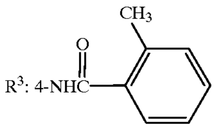

Crystalline form: Colorless amorphous

NMR analysis: 152)

Form: Free

TABLE 5-continued

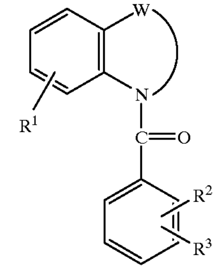

Example 832

Structure

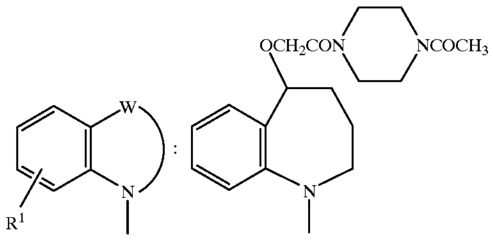

$R^2$: H

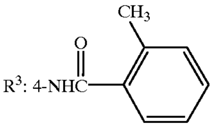

Crystalline form: Colorless amorphous

NMR analysis: 153)

Form: Free

Example 834

Structure

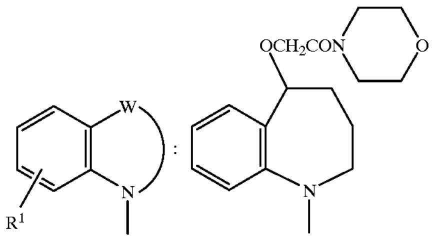

$R^2$: H

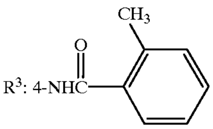

Crystalline form: White powder

Recrystallization solvent: Ethyl acetate/n-hexane

Melting Point: 247–248° C.

Form: Free

TABLE 5-continued

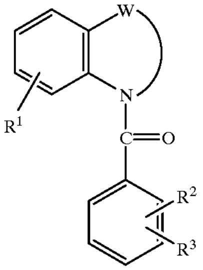

Example 835

Structure

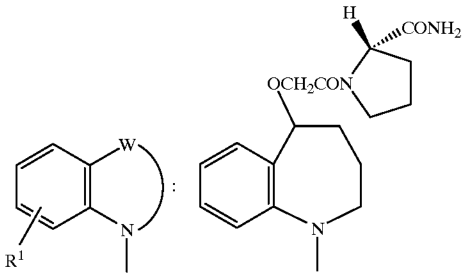

$R^2$: H

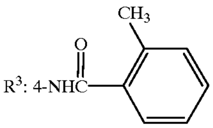

Crystalline form: Colorless amorphous

NMR analysis: 154)

Form: Free

Example 836

Structure

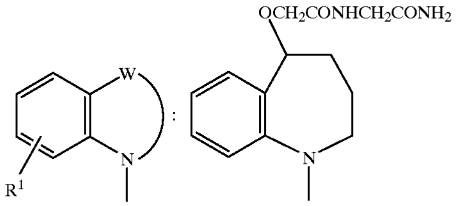

$R^2$: H

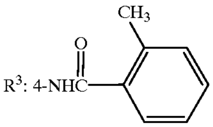

Crystalline form: Colorless amorphous

NMR analysis: 155)

Form: Free

TABLE 5-continued

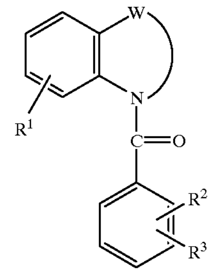

Example 837
Structure

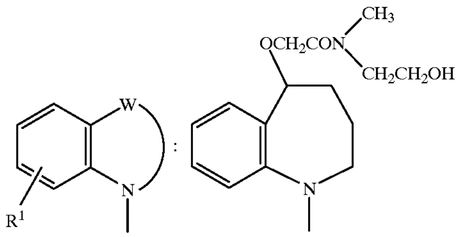

$R^2$: H

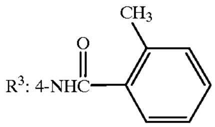

Crystalline form: Colorless amorphous
NMR analysis: 156)
Form: Free
Example 838
Structure

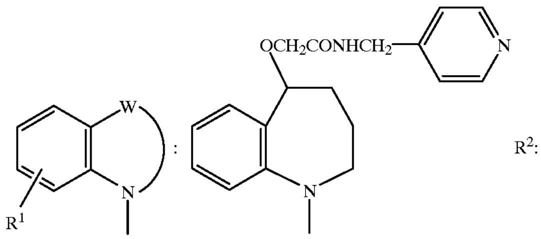

$R^2$: H

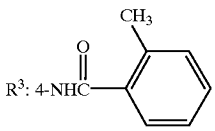

Crystalline form: Colorless amorphous
NMR analysis: 157)
Form: Free
Example 839
Structure

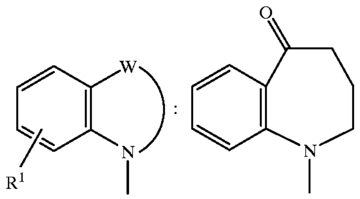

$R^2$: H

TABLE 5-continued

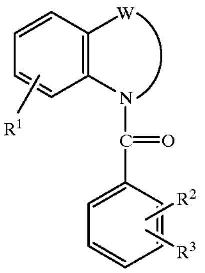

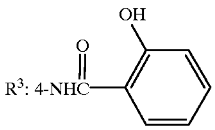

Crystalline form: White powder
Recrystallization solvent: Ethyl acetate/n-hexane
Melting Point: 234–235° C.
Form: Free
Example 840
Structure

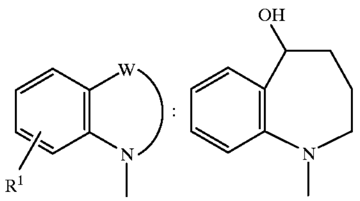

$R^2$: H

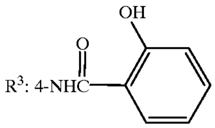

Crystalline form: White powder
Recrystallization solvent: Ethyl acetate/n-hexane
Melting Point: 234–235° C.
Form: Free
Example 841
Structure

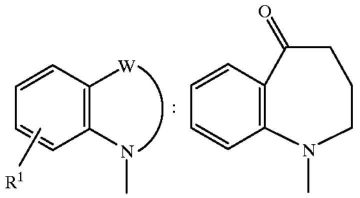

$R^2$: H

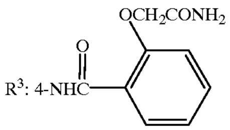

Crystalline form: White powder
Recrystallization solvent: Ethyl acetate/n-hexane
Melting Point: 226–228° C.
Form: Free TABLE 5-continued

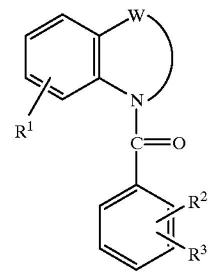

Example 842

Structure

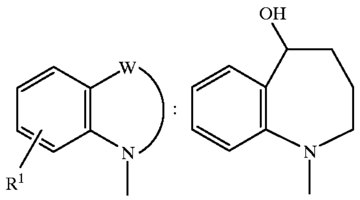

$R^2$: H

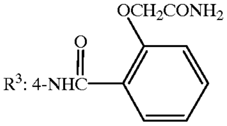

Crystalline form: White powder

Recrystallization solvent: Ethyl acetate/n-hexane

Melting Point: 230–231° C.

Form: Free

Example 843

Structure

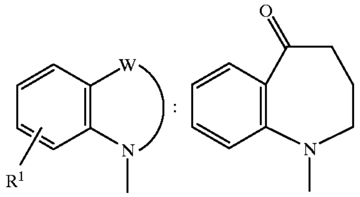

$R^2$: H

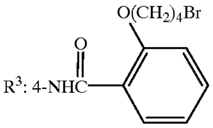

Crystalline form: White powder

Recrystallization solvent: Ethyl acetate/n-hexane

Melting Point: 186–188° C.

Form: Free

TABLE 5-continued

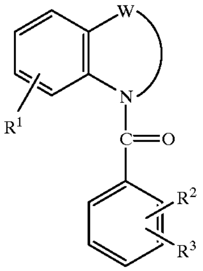

Example 844

Structure

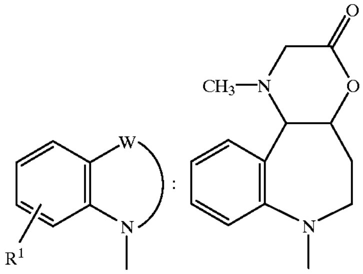

$R^2$: H

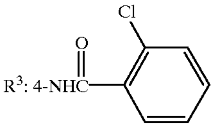

Crystalline form: Colorless prisms

Recrystallization solvent: Chloroform/methanol

Melting Point: 286–290° C.

Form: Free

Example 845

Structure

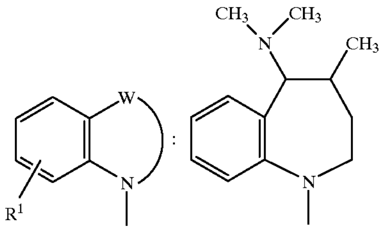

$R^2$: H

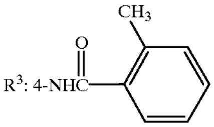

Crystalline form: Colorless needles

Recrystallization solvent: Ethanol

Melting Point: 186–188.5° C.

Form: Free

TABLE 5-continued

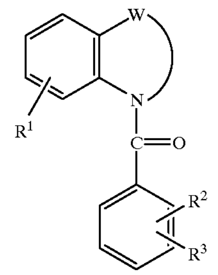

Example 846
Structure

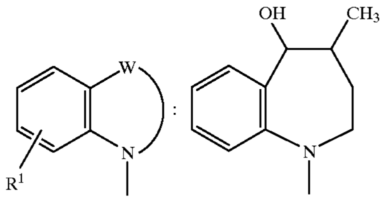

$R^2$: H

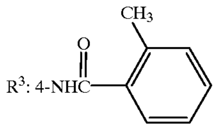

Crystalline form: Colorless prisms
Recrystallization solvent: Ethanol
Melting Point: 220–222° C.
Form: Free
Example 847
Structure

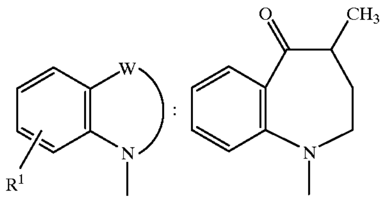

$R^2$: H

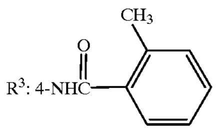

Crystalline form: White powder
NMR analysis: 158)
Form: Free
Example 848
Structure

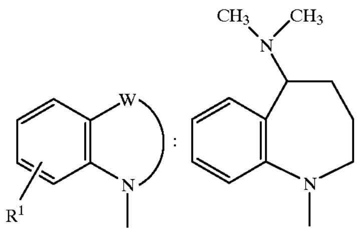

$R^2$: H

TABLE 5-continued

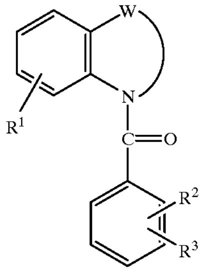

$R^3$: 4-$NHCOCH_2CONH_2$
Crystalline form: Colorless prisms
Recrystallization solvent: Dichloromethane/diethyl ether
Melting Point: 189–192° C.
Form: Free
Example 849
Structure

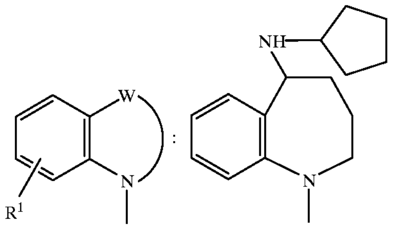

$R^2$: 2-Cl

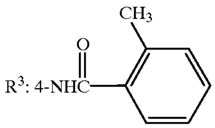

Crystalline form: Colorless amorphous
NMR analysis: 159)
Form: Free
Example 850
Structure

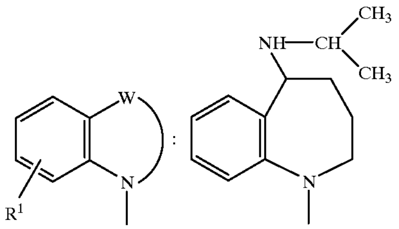

$R^2$: 2-Cl

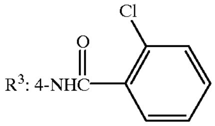

Crystalline form: White powder
Recrystallization solvent: Dichloromethane/diethyl ether
Melting Point: 207–209° C. (decomposed)
Form: Free TABLE 5-continued

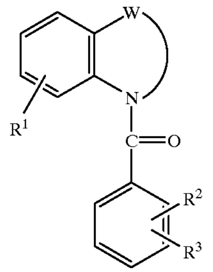

Example 851
Structure

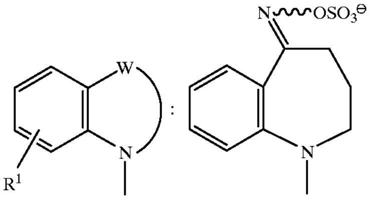

R$^2$: 2-Cl

R$^3$: 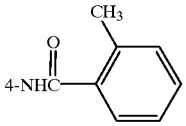

Crystalline form: White powder
NMR analysis: 160)
Form: K$^{\oplus}$
Example 852
Structure

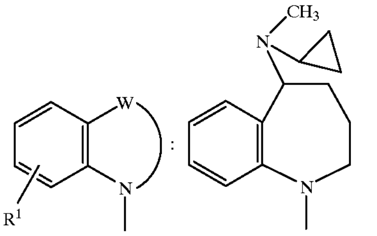

R$^2$: 2-Cl

R$^3$: 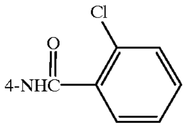

Crystalline form: White powder
Recrystallization solvent: Dichloromethane/diethyl ether
Melting Point: 193–194° C.
Form: Free
Example 853
Structure

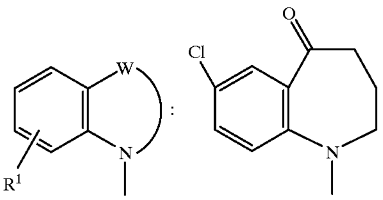

R$^2$: H

TABLE 5-continued

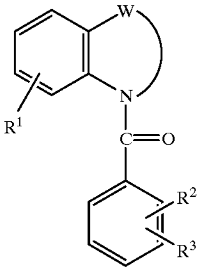

R$^3$: 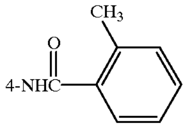

Crystalline form: White powder
Recrystallization solvent: Diethyl ether/dichloromethane
Melting Point: 185.5–186° C.
Form: Free
Example 854
Structure

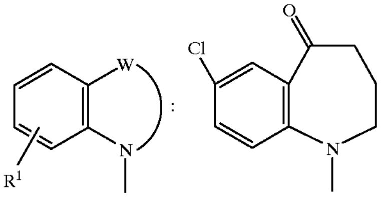

R$^2$: H

R$^3$: 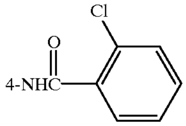

Crystalline form: White powder
Recrystallization solvent: Diethyl ether/dichloromethane
Melting Point: 223.5–226° C. (decomposed)
Form: Free
Example 855
Structure

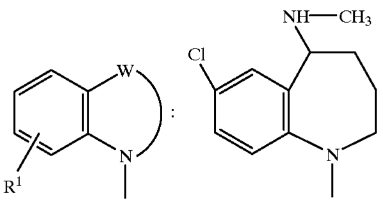

R$^2$: H

R$^3$: 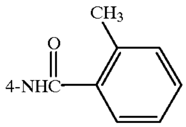

Crystalline form: Colorless amorphous
NMR analysis: 161)
Form: Free

TABLE 5-continued

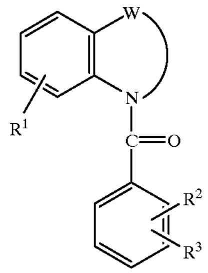

Example 856

Structure

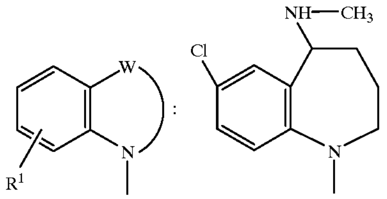

$R^2$: H

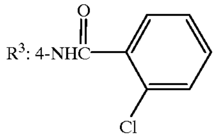

Crystalline form: White powder

Recrystallization solvent: Diethyl ether/dichloromethane

Melting Point: 225.5–227° C.

Form: Free

Example 857

Structure

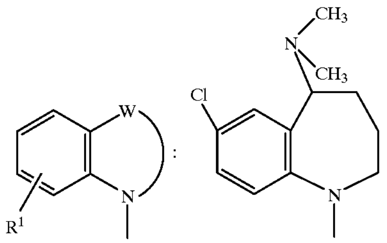

$R^2$: H

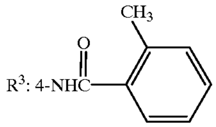

Crystalline form: White powder

Recrystallization solvent: Diethyl ether/dichloromethane

Melting Point: 212–214° C.

Form: Free

TABLE 5-continued

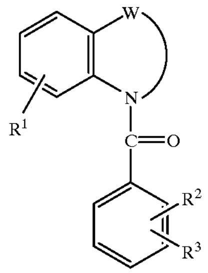

Example 858

Structure

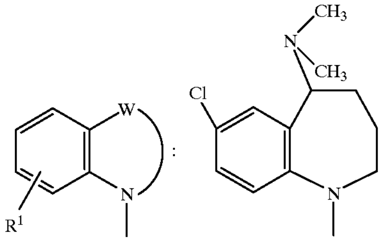

$R^2$: H

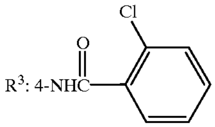

Crystalline form: White powder

Recrystallization solvent: Diethyl ether/dichloromethane

Melting Point: 230.5–233° C.

Form: Free

Example 859

Structure

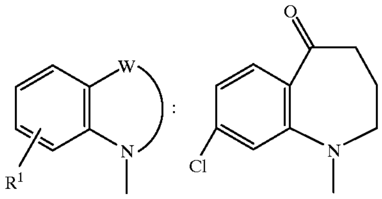

$R^2$: H

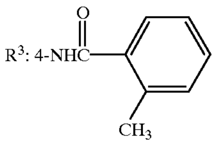

Crystalline form: White powder

Recrystallization solvent: Diethyl ether/dichloromethane

Melting Point: 212.5–215° C. (decomposed)

Form: Free

TABLE 5-continued

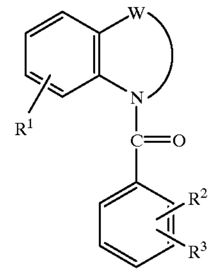

Example 860
Structure

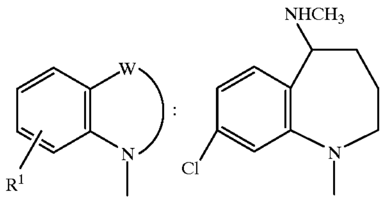

$R^2$: H

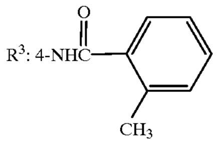

Crystalline form: White powder
Recrystallization solvent: Diethyl ether/dichloromethane
Melting Point: 192–194.5° C.
Form: Free Example 861
Structure

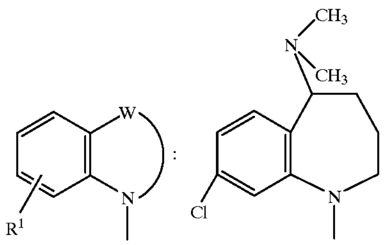

$R^2$: H

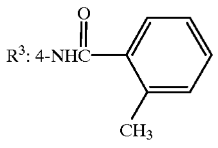

Crystalline form: White powder
Recrystallization solvent: Diethyl ether/dichloromethane
Melting Point: 175–177° C.
Form: Free TABLE 5-continued

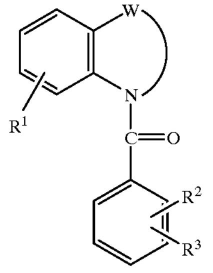

Example 862
Structure

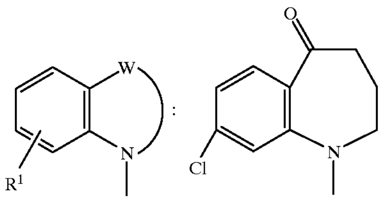

$R^2$: H

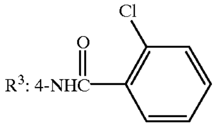

Crystalline form: White powder
Recrystallization solvent: Diethyl ether/dichloromethane
Melting Point: 208.5–209.5° C.
Form: Free Example 863
Structure

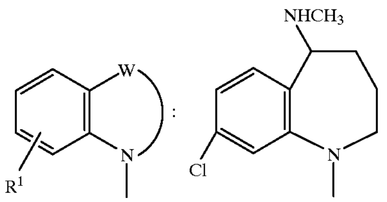

$R^2$: H

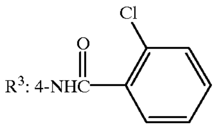

Crystalline form: White powder
Recrystallization solvent: Diethyl ether/dichloromethane
Melting Point: 191–193.5° C.
Form: Free TABLE 5-continued

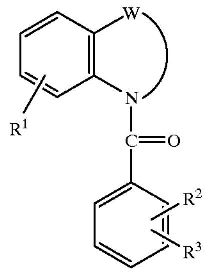

Example 864

Structure

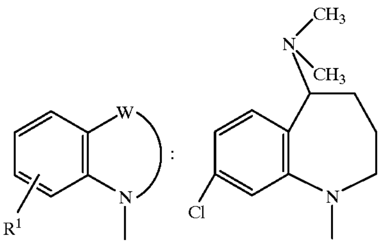

$R^2$: H $R^3$: 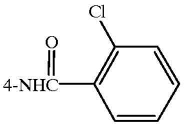

Crystalline form: White powder

Recrystallization solvent: Diethyl ether/dichloromethane

Melting Point: 204–205.5° C.

Form: Free

Example 865

Structure

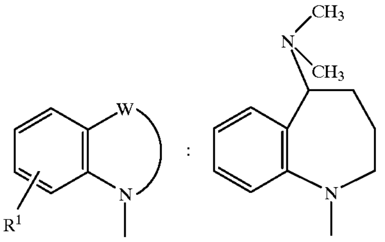

$R^2$: H $R^3$: 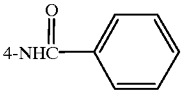

Crystalline form: Light yellow prisms

Recrystallization solvent: Ethanol

Melting Point: 221–223° C.

Form: Free

TABLE 5-continued

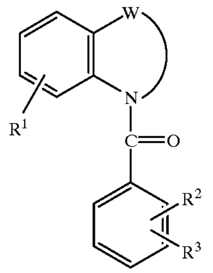

Example 866

Structure

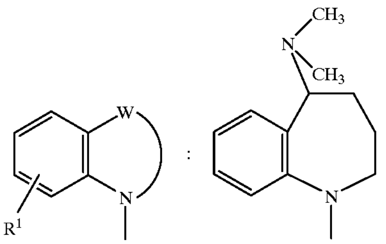

$R^2$: H $R^3$: 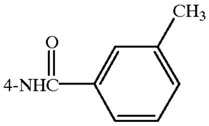

Crystalline form: Colorless prisms

Recrystallization solvent: Ethyl acetate

Melting Point: 171–173° C.

Form: Free

Example 867

Structure

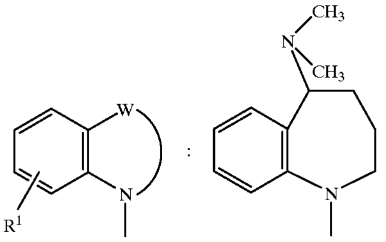

$R^2$: H $R^3$: 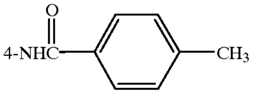

Crystalline form: Colorless prisms

Recrystallization solvent: Ethyl acetate

Melting Point: 185–187° C.

Form: Free

TABLE 5-continued

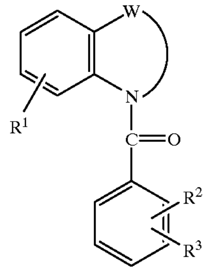

Example 868
Structure

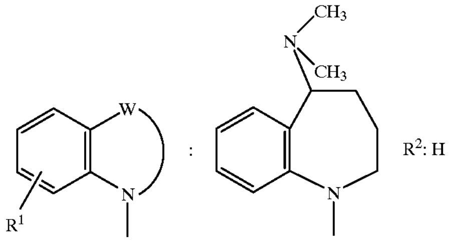

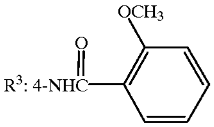

Crystalline form: Colorless prisms
Recrystallization solvent: Ethanol
Melting Point: 190–192° C.
Form: Free Example 869
Structure

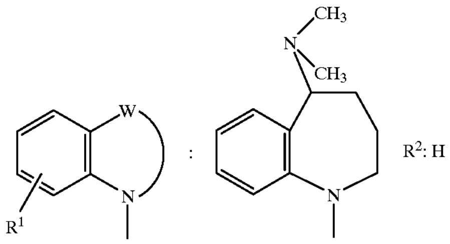

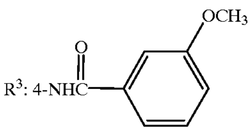

Crystalline form: Colorless prisms
Recrystallization solvent: Ethanol
Melting Point: 175–177° C.
Form: Free TABLE 5-continued

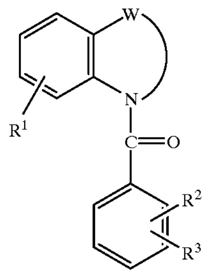

Example 870
Structure

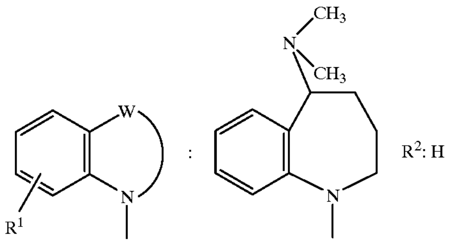

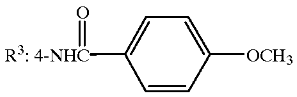

Crystalline form: Colorless powder
Recrystallization solvent: Ethyl acetate/n-hexane
Melting Point: 148–151° C.
Form: Free Example 871
Structure

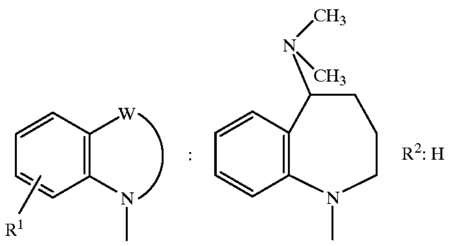

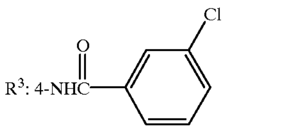

Crystalline form: Colorless prisms
Recrystallization solvent: Ethanol
Melting Point: 200–202° C.
Form: Free TABLE 5-continued

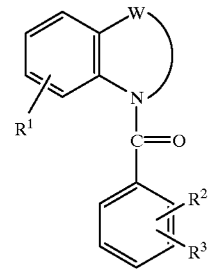

Example 872

Structure

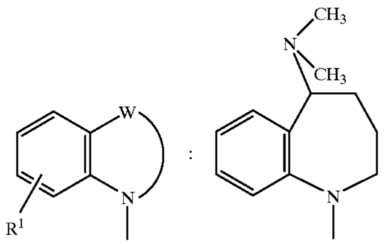

$R^2$: H $R^3$: 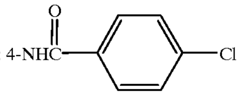

Crystalline form: Colorless prisms

Recrystallization solvent: Ethanol

Melting Point: 200–202° C.

Form: Free

Example 873

Structure

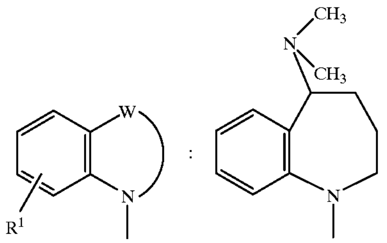

$R^2$: H $R^3$: 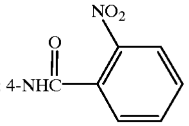

Crystalline form: Light yellow powder

Recrystallization solvent: Acetone

Melting Point: 235–238° C.

Form: Free

TABLE 5-continued

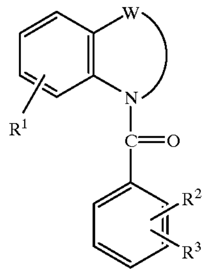

Example 874

Structure

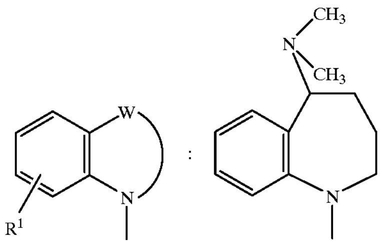

$R^2$: H $R^3$: 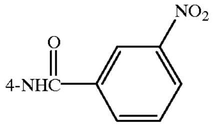

Crystalline form: Light yellow powder

Recrystallization solvent: Acetone

Melting Point: 198–201° C.

Form: Free

Example 875

Structure

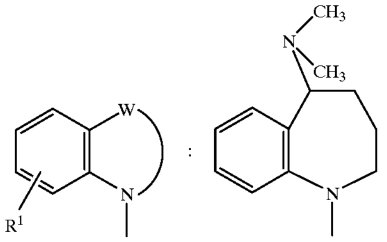

$R^2$: H $R^3$: 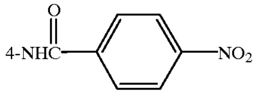

Crystalline form: Light yellow needles

Recrystallization solvent: Chloroform/ethyl acetate

Melting Point: 232–237° C.

Form: Free

TABLE 5-continued

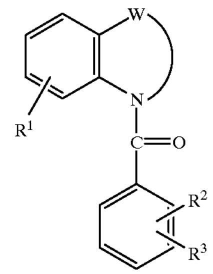

Example 876

Structure

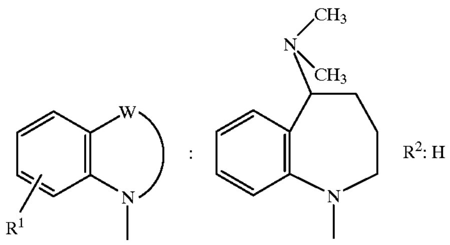

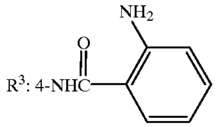

Crystalline form: Colorless prisms

Recrystallization solvent: Chloroform/ethyl acetate

Melting Point: 224–227° C.

Form: Free

Example 877

Structure

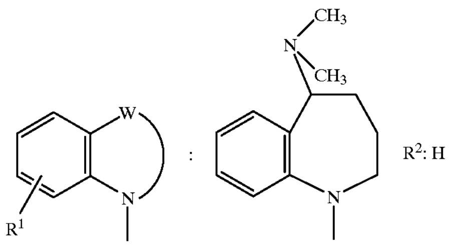

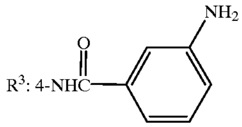

Crystalline form: Colorless prisms

Recrystallization solvent: Ethanol

Melting Point: 211–214° C.

Form: Free

TABLE 5-continued

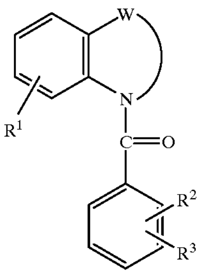

Example 878

Structure

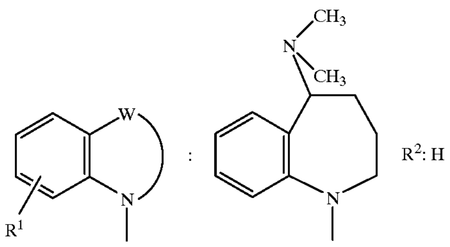

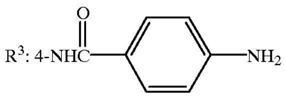

Crystalline form: Colorless powder

Recrystallization solvent: Dichloromethane/n-hexane

Melting Point: 238–243° C.

Form: Free

Example 879

Structure

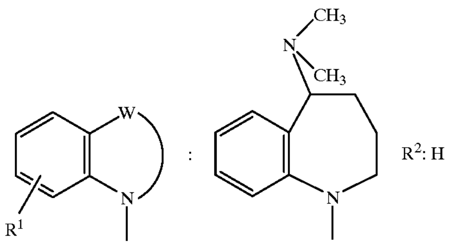

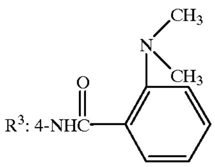

Crystalline form: Colorless amorphous

NMR analysis: 162)

Form: Free

TABLE 5-continued

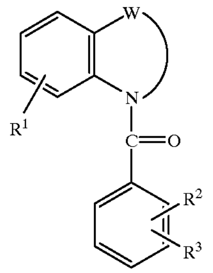

Example 880
Structure

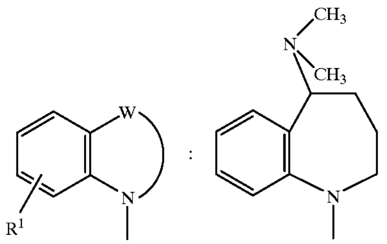

$R^2$: H

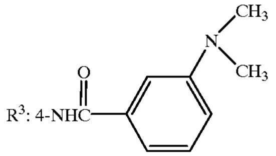

Crystalline form: Colorless amorphous
NMR analysis: 163)
Form: Free

Example 881
Structure

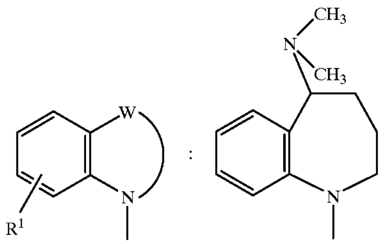

$R^2$: H

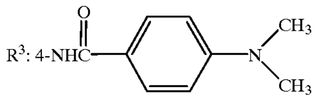

Crystalline form: Colorless prisms
Recrystallization solvent: Dichloromethane/diethyl ether
Melting Point: 198–202° C.
Form: Free TABLE 5-continued

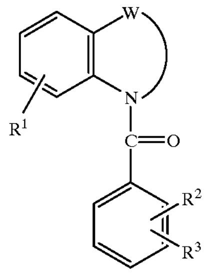

Example 882
Structure

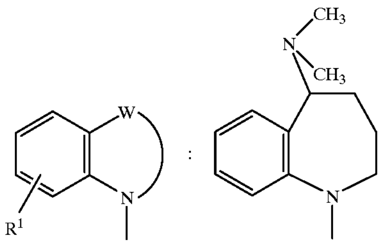

$R^2$: H

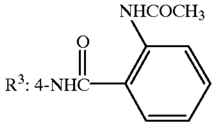

Crystalline form: Colorless prisms
Recrystallization solvent: Chloroform/ethyl acetate
Melting Point: 226–229° C.
Form: Free Example 883
Structure

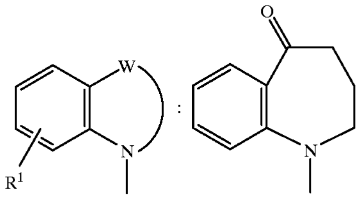

$R^2$: 2-$CH_3$

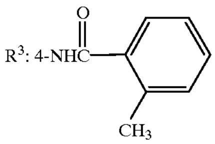

Crystalline form: White powder
Recrystallization solvent: Methanol/diethyl ether
Melting Point: 139–140° C.
Form: Free TABLE 5-continued

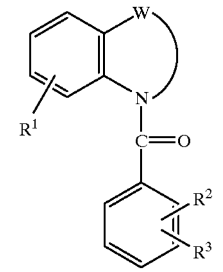

Example 884
Structure

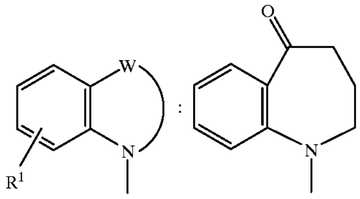

$R^2$: 2-$CH_3$

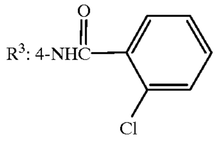

Crystalline form: White powder
Recrystallization solvent: Methanol/diethyl ether
Melting Point: 149–152° C.
Form: Free
Example 885
Structure

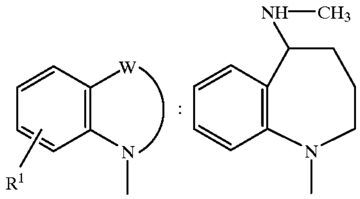

$R^2$: 2-$CH_3$

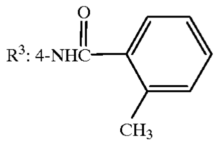

Crystalline form: White powder
Recrystallization solvent: Methanol/diethyl ether
Melting Point: 180.5–182° C.
Form: Free
Example 886
Structure

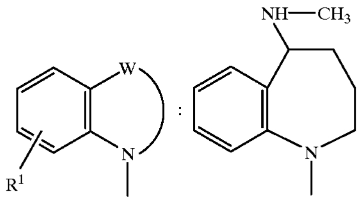

$R^2$: 2-$CH_3$

TABLE 5-continued

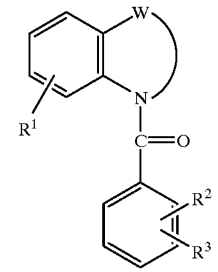

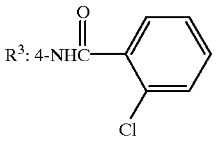

Crystalline form: White powder
Recrystallization solvent: Chloroform/diethyl ether
Melting Point: 211–214° C.
Form: Free
Example 887
Structure

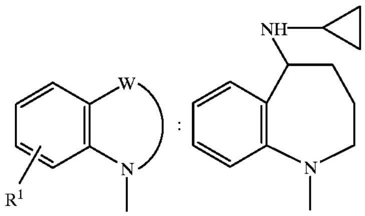

$R^2$: 2-$CH_3$

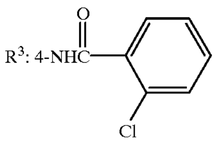

Crystalline form: White powder
Recrystallization solvent: Chloroform/diethyl ether
Melting Point: 171–174.5° C.
Form: Free
Example 888
Structure

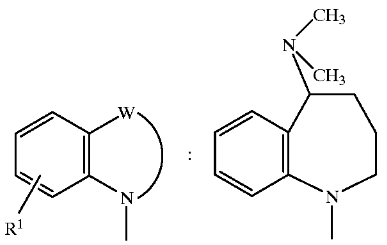

$R^2$: H

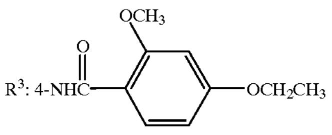

Crystalline form: White powder
Recrystallization solvent: Methanol/diethyl ether
Melting Point: 203–205° C.

TABLE 5-continued

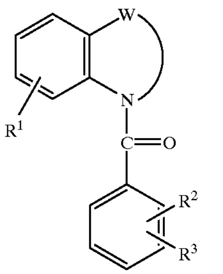

Form: Free

Example 889

Structure

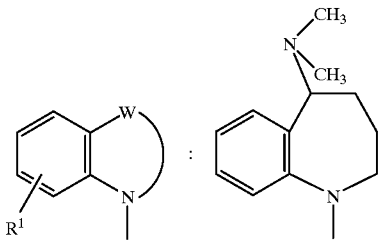

$R^2$: 3-$OCH_3$

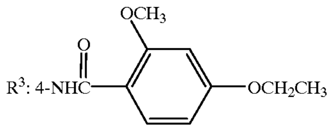

Crystalline form: White powder

Recrystallization solvent: Ethanol

Melting Point: 202–202.5

Form: Free

Example 890

Structure

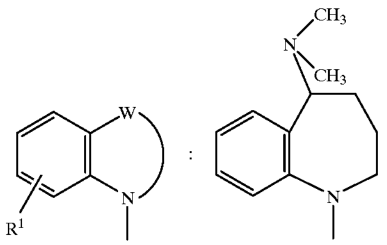

$R^2$: 3-$OCH_2CONH_2$

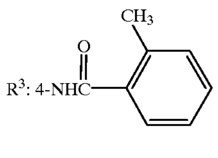

Crystalline form: White powder

Recrystallization solvent: Methanol/diethyl ether

Melting Point: 130–133° C.

Form: Free

TABLE 5-continued

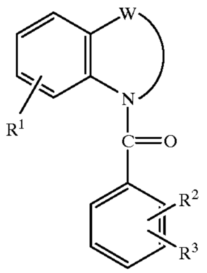

Example 891

Structure

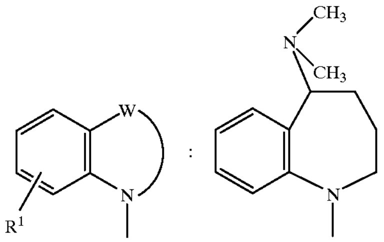

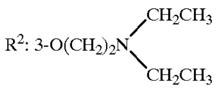

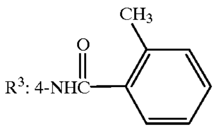

Crystalline form: White powder

Recrystallization solvent: Methanol/n-hexane

Melting Point: 104.5–106° C.

Form: Free

Example 892

Structure

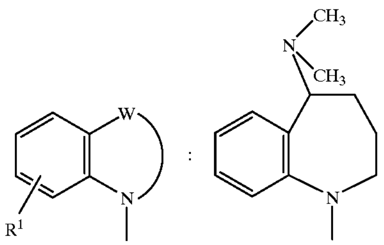

$R^2$: H

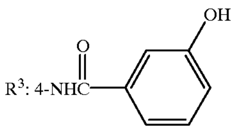

Crystalline form: White powder

Recrystallization solvent: Methanol/diethyl ether

Melting Point: 197–198° C.

Form: Free

TABLE 5-continued

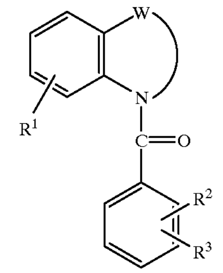

Example 893

Structure

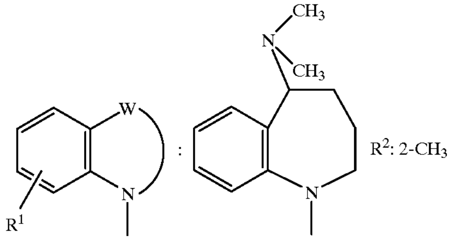

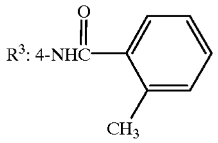

Crystalline form: White powder

Recrystallization solvent: Dichloromethane/ethyl acetate

Melting Point: 191–192° C.

Form: Free

Example 894

Structure

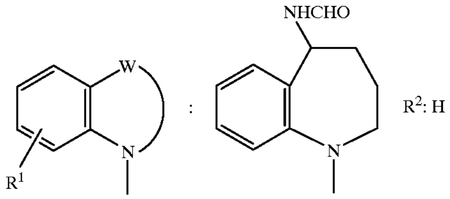

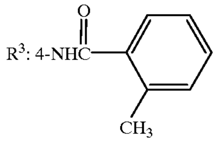

Crystalline form: Colorless columnar

Recrystallization solvent: Ethanol/petroleum ether

Melting Point: 211–213° C.

Form: Free

TABLE 5-continued

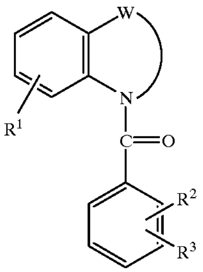

Example 895

Structure

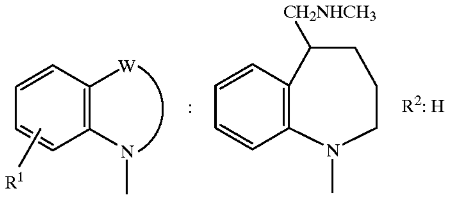

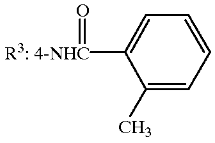

Crystalline form: Colorless amorphous

NMR analysis: 164)

Form: Free

Example 896

Structure

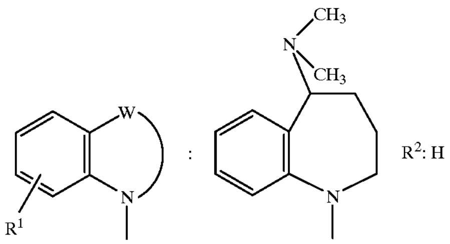

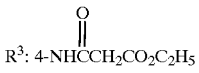

Crystalline form: Colorless amorphous

NMR analysis: 165)

Form: Free

Example 897

Structure

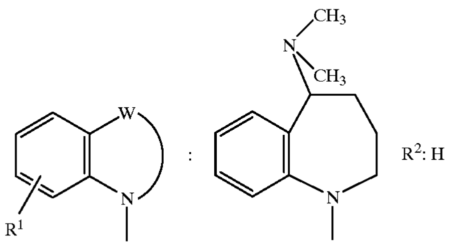

TABLE 5-continued

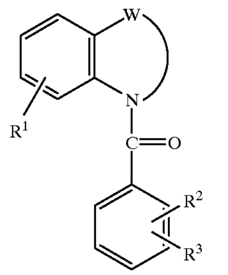

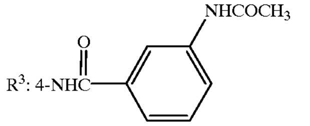

Crystalline form: Colorless amorphous
NMR analysis: 166)
Form: Free
Example 898
Structure

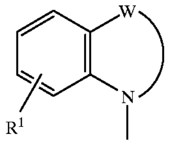 : 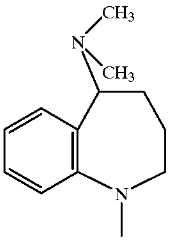 $R^2$: H

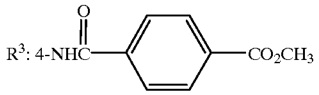

Crystalline form: Colorless prisms
Recrystallization solvent: Ethanol
Melting Point: 224–228° C.
Form: Free 138) $^1$H-NMR(CDCl$_3$)δ; 1.3–2.95(19H, m), 3.05–3.3(1H, m), 3.85–4.1(2H, m), 4.3–4.6(1H, m), 6.64(1H, d, J=7.8Hz), 6.9–7.8(12H, m)
139) $^1$H-NMR(CDCl$_3$)δ; 1.1–2.3(13H, m), 2.65–3.2(1H, m), 4.55–5.6(3H, m), 6.55–6.7(1H, m), 6.9–7.6 (12H, m)
140) $^1$H-NMR(CDCl$_3$)δ; 1.3–4.15(19H, m), 4.3–5.0(1H, m), 6.65(1H, d, J=7.7Hz), 6.9–8.05(12H, m)
141) $^1$H-NMR(CDCl$_3$)δ; 1.4–3.0(9H, m), 3.05–3.6(3H, m), 3.9–4.1(1H, m), 4.35–4.55(1H, m), 4.9–5.65 (1H, m), 6.67(1H, d, J=7.4Hz), 6.85–7.6(12H, m), 7.6–7.85(2H, m)
142) $^1$H-NMR(CDCl$_3$)δ; 1.3–2.85(21H, m), 3.2–4.0(4H, m), 4.3–4.4(1H, m), 4.45–5.2(2H, m), 6.61(1H, d, J=7.6Hz), 6.9–7.65(12H, m)
143) $^1$H-NMR(CDCl$_3$)δ; 1.3–3.45(17H, m), 3.8–5.7(5H, m), 6.5–7.65(13H, m)
144) $^1$H-NMR(CDCl$_3$)δ; 1.25–3.1(14H, m), 3.3–4.0(4H, m), 4.15–4.4(1H, m), 4.45–5.2(1H, m), 6.64(1H, d, J=7.4Hz), 6.9–7.7(12H, m)
145) $^1$H-NMR(CDCl$_3$)δ; 0.9–3.25(16H, m), 3.9–5.9(2H, m), 6.65(1H, d, J=7.4Hz), 6.85–7.5(11H, m), 7.9–8.3(1H, m)
146) $^1$H-NMR(DMSO-d$_6$)δ; 1.3–2.15(4H, m), 2.32(3H, s), 2.8–3.05(1H, m), 4.24(2H, AB-q, J=12.8, 15.4 Hz), 4.35–4.55(1H, m), 4.9–5.25(1H, m), 6.68(1H, d, J=7.6Hz), 6.9–7.45(9H, m), 7.52(2H, d, J=8.6

TABLE 5-continued

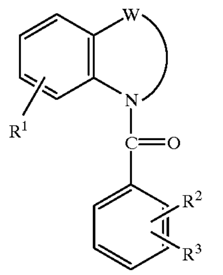

Hz), 8.9–9.05(1H, m), 10.31(1H, s)
147) $^1$H-NMR(CDCl$_3$)δ; 1.5–2.35(4H, m), 2.45(3H, s), 2.6–2.85(1H, m), 3.32(3H, s), 4.19(2H, AB-q, J=12.2Hz, 15.6Hz), 5.0–5.2(1H, m), 5.82(1H, d, J=10.3Hz), 6.69(1H, d, J=7.8Hz), 6.75–7.95(12H, m)
148) $^1$H-NMR(CDCl$_3$)δ; 1.2–3.3(17H, m), 3.45(2H, AB-q, J=14.7, 22.9Hz), 3.9–4.35(2H, m), 6.60(2H, d, J=7.7Hz), 6.8–8.0(11H, m), 8.39(1H, s)
149) $^1$H-NMR(CDCl$_3$)δ; 1.45–3.40(8H, m), 2.23(3H, s), 2.33(3H, s), 2.46(3H, s), 4.44–5.23(1H, m), 6.54–6.78(1H, m), 6.84–7.94(12H, m)
150) $^1$H-NMR(CDCl$_3$)δ; 1.50–1.92(3H, m), 1.92–2.05 (1H, m), 2.47(3H, s), 2.55–3.06(5H, m), 3.43–5.76 (8H, m), 6.63–6.82(1H, m), 6.97–8.08(12H, m)
151) $^1$H-NMR(CDCl$_3$)δ; 1.43–2.65(4H, m), 2.48(3H, s), 2.69–3.25(5H, m), 3.90–5.40(8H, m), 6.64–6.94 (1H, m), 6.94–7.77(12H, m)
152) $^1$H-NMR(CDCl$_3$)δ; 1.50–1.90(3H m), 1.90–2.20 (1H, m), 2.20–2.64(4H, m), 2.32(3H, s), 2.47(3H, s), 2.64–3.27(1H, m), 3.36–3.83(4H, m), 3.93—4.52 (2H, m), 4.52–5.27(2H, m), 6.57–6.82(1H, m), 6.93–7.87(12H, m)
153) $^1$H-NMR(CDCl$_3$)δ; 1.52–1.93(2H, m), 1.93–2.23 (4H, m), 2.23–2.57(1H, m), 2.45(3H, s), 2.72–3.02 (1H, m), 3.02–3.77(8H, m), 3.93–4.50(2H, m), 4.50–5.20(2H, m), 6.60–6.80(1H, m), 6.94–7.64 (11H, m), 8.16(1H, brs)
154) $^1$H-NMR(CDCl$_3$)δ; 1.48–2.60(8H, m), 2.46(3H, s), 2.65–3.01(1H, m), 3.20–3.74(2H, m), 3.80–5.14 (4H, m), 5.30–5.84(1H, m), 6.51–8.14(13H, m)
155) $^1$H-NMR(CDCl$_3$)δ; 1.54–1.91(2H, m), 1.91–2.20 (1H, m), 2.22–2.64(1H, m), 2.44(3H, s), 2.70–3.13 (1H, m), 3.60–4.40(4H, m), 4.50–5.20(2H, m), 6.07–8.00(13H, m), 9.93(1H, s)
156) $^1$H-NMR(CDCl$_3$)δ; 1.56–1.92(2H, m), 1.92–2.19(1H, m), 2.19–2.60(1H, m), 2.46(3H, s), 2.66–3.26(4H, m), 3.33–3.95(4H, m). 4.00–5.20(4H, m), 6.58–6.82 (1H, m), 6.93–8.21(12H, m)
157) $^1$H-NMR(CDCl$_3$)δ; 1.57–2.17(3H, m), 2.21–2.68 (1H, m), 2.47(3H, s), 2.73–3.04(1H, m), 3.92–4.42 (4H, m), 4.50–5.17(2H, m), 6.61–6.99(2H, m), 6.99–8.10(14H, m), 8.21–8.71(2H, m)
158) $^1$H-NMR(CDCl$_3$)δ; 1.31(3H, d, J=6.7Hz), 1.53–1.90(1H, m), 2.29–2.58(1H, m), 2.47(3H, s), 2.94–3.63(2H, m), 4.57–5.05(1H, m), 6.68–6.82 (1H, m), 7.10–7.59(10H, m), 7.72(1H, s), 7.78–7.96(1H, m)
159) $^1$H-NMR(CDCl$_3$)δ; 1.20–2.60(17H, m), 2.65–5.10 (3H, m), 6.85–3.85(12H, m)
160) $^1$H-NMR(DMSO-d$_6$)δ; 1.40–1.75(1H, m), 1.90–2.15 (1H, m), 2.33(3H, s), 2.50–2.80(2H, m), 3.10–3.50 (1H, m), 4.40–4.65(1H, m), 6.85–7.60(10H, m), 7.85(1H, s), 10.44(1H, s)
161) $^1$H-NMR(CDCl$_3$)δ; 1.30–2.70(11H, m), 3.00–5.20 (3H, m), 6.58(1H, d, J=8Hz), 6.90–7.05(1H, m), 7.10–7.70(10H, m)
162) $^1$H-NMR(CDCl$_3$)δ; 1.25–2.90(4H, m), 2.44(6H, s), 2.79–3.57(2H, m), 2.79(6H, s), 4.10–5.25(1H, m), 6.60–6.80(1H, m), 6.94–7.60(10H, m), 8.23(1H, d, J=6.2Hz), 12.41(1H, m)
163) $^1$H-NMR(CDCl$_3$)δ; 1.25–3.00(4H, m), 2.42(6H, s), 2.99(6H, s), 3.40–3.65(2H, m), 4.01–5.15(1H, m), 6.58–7.59(12H, m), 7.94(1H, brs)

TABLE 5-continued

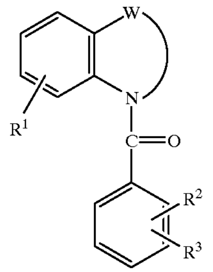

| | |
|---|---|
| 164) | $^1$H-NMR(DMSO-$d_6$)δ; 1.40–2.18(4H, m), 2.34(3H, s), 2.47(3H, s), 2.54–3.50(4H, m), 4.30–5.08(1H, m), 6.56–6.82(1H, m), 6.87–7.48(10H, m), 7.48–7.75(2H, m), 10.35(1H, s) |
| 165) | $^1$H-NMR($CDCl_3$)δ; 1.08–5.20[20H, m, 1.30(3H, t, J=7.2Hz), 3.41(2H, s), 4.22(2H, q, J=7.2Hz)], 6.49–7.73(8H, m), 9.25–9.58(1H, m) |
| 166) | $^1$H-NMR($CDCl_3$)δ; 1.17–2.80(4H, m), 2.05(3H, s), 2.42(6H, s), 3.02–3.53(2H, m), 4.06–5.15(1H, m), 6.55–7.80(12H, m), 8.53–8.74(2H, m) |

EXAMPLE 899

To a solution of 5-acetyloxyimino-1-[4-(2-chlorobenzoylamino)benzoyl]-2,3,4,5-tetrahydro-1H-benzazepine (0.48 g) in acetic acid (20 ml) is added platinum oxide (0.05 9) and the mixture is subjected to catalytic reduction under hydrogen atmosphere. After completion of the reaction, the catalyst is removed by filtration, and the filtrate is concentrated. The resulting residue is purified by silica gel column chromatography (eluent; dichloromethane:methanol=20:1→10:1), and recrystallized from ethanol/diethyl ether to give 5-amino-1-[4-(2-chlorobenzoylamino)benzoyl]-2,3,4,5-tetrahydro-1H-benzazepine (0.19 g) as colorless prisms, m.p. 176–178° C.

EXAMPLE 900

To a solution of 5-methylamino-1-[4-(2-methylbenzoylamino)benzoyl]-2,3,4,5-tetrahydro-1H-benzazepine (0.6 g) in dichloromethane (10 ml) is added triethylamine (0.24 ml). Subsequently, thereto is added methanesulfonyl chloride (0.14 ml) under ice-cooling, and then, the mixture is warmed to room temperature and stirred overnight. Water is added to the reaction solution, extracted three times with dichloromethane. The extract is washed with saturated saline solution, and dried over magnesium sulfate. The solvent is distilled off and the resulting residue is purified by silica gel column chromatography (eluent; dichloromethane:methanol=20:1), and recrystallized from ethanol to give 5-(N-methyl-N-methanesulfonylamino)-1-[4-(2-methylbenzoylamino)benzoyl]-2,3,4,5-tetrahydro-1H-benzazepine (0.48 9) as colorless scales, m.p. 197–198° C.

EXAMPLE 901

To a solution of 5-methylamino-1-[4-(2-methylbenzoylamino)benzoyl]-2,3,4,5-tetrahydro-1H-benzazepine (0.6 g) in dichloromethane is added triethylamine (0.24 ml). Subsequently, thereto is added benzoyl chloride (0.2 ml) under ice-cooling, and the temperature thereof is raised to room temperature, and the mixture is stirred overnight. Water is added to the reaction solution and extracted three times with dichloromethane. The extract is washed with saturated saline solution and dried over magnesium sulfate. The solvent is distilled off and the resulting residue is purified by silica gel column chromatography (eluent; dichloromethane:methanol=20:1), and recrystallized from ethanol to give 5-(N-methyl-N-benzoylamino)-1-[4-(2-methylbenzoylamino)benzoyl]-2,3,4,5-tetrahydro-1H-benzazepine (0.64 g) as colorless needles, m.p. 248–249° C.

EXAMPLE 902

A mixture of 5-amino-1-[4-(2-methylbenzoylamino)benzoyl]-2,3,4,5-tetrahydro-1H-benzazepine (0.6 g) and ethyl formate (10 ml) is refluxed for 4 hours. The reaction solution is concentrated and the resulting residue is recrystallized from ethanol/petroleum ether to give 5-formylamino-1-[4-(2-methylbenzoylamino)benzoyl]-2,3,4,5-tetrahydro-1H-benzazepine (0.38 g) as colorless columnar crystal, m.p. 211–213° C.

Using the suitable starting materials, the compounds of above Examples 825 and 894 are obtained in the same manner as in above Example 902.

EXAMPLE 903

To a solution of 5-amino-1-[4-(2-chlorobenzoylamino)benzoyl]-2,3,4,5-tetrahydro-1H-benzazepine (0.6 g) in dichloromethane (10 ml) is added triethylamine (0.22 ml). Subsequently, thereto is added di-tert-butyl dicarbonate (0.34 g) at room temperature and the mixture is stirred for 2 hours. Then, thereto is added additional di-tert-butyl dicarbonate (0.1 g) and the mixture is stirred for 1 hour. The reaction mixture is concentrated and the resulting residue is purified by silica gel column chromatography (eluent; n-hexane:ethyl aceate=1:1) to give 5-t-butoxycarbonylamino-1-[4-(2-chlorobenzoylamino)benzoyl]-2,3,4,5-tetrahydro-1H-benzazepine (0.66 g) as colorless amorphous.

$^1$H-NMR ($CDCl_3$) δ; 1.1–2.3 (13H, m), 2.65–3.2 (1H, m), 4.55–5.6 (3H, m), 6.55–6.7 (1H, m), 6.9–7.6 (12H, m)

Using the suitable starting materials, the compound of above Example 791 is obtained in the same manner as in above Example 903.

EXAMPLE 904

To a solution of 5-amino-1-[4-(2-methylbenzoylamino)benzoyl]-2,3,4,5-tetrahydro-1H-benzazepine (0.6 g) in dichloromethane (10 ml) is added phenyl isocyanate (0.2 g) under ice-cooling. The mixture is stirred at the same temperature for 30 minutes, and the temperature thereof is raised to room temperature and then the mixture is stirred overnight. The reaction solution is distilled off and the resulting residue is recrystallized from dioxane to give 5-anilinocarbonylamino-1-[4-(2-methylbenzoylamino)benzoyl]-2,3,4,5-tetrahydro-1H-benzazepine (0.65 g) as colorless prisms, m.p. 269–271° C.

Using the suitable starting materials, the compound of above Example 795 is obtained in the same manner as in above Example 904.

EXAMPLE 905

To a solution of 5-methylamino-1-[4-(2-methylbenzoylamino)benzoyl]-2,3,4,5-tetrahydro-1H-benzazepine (0.6 g) in methanol (10 ml) is added glycolonitrile (50%, 0.19 ml) and the mixture is stirred at room temperature for 20 minutes, and then refluxed for 30 minutes. Thereto is added additional glycolonitrile (0.5 ml) and the mixture is refluxed for 5.5 hours. The reaction solution is concentrated and to the resulting residue is added ethyl acetate. The precipitated crystal is collected by filtration, and recrystallized from acetonitrile to give 5-(N-methyl-N-cyanomethylamino)-1-[4-(2-methylbenzoylamino) benzoyl]-2,3,4,5-tetrahydro-1H-benzazepine (0.32 g) as colorless needles, m.p. 227–228° C.

EXAMPLE 906

To 5-(N-methyl-N-oxiranylmethylamino)-1-[4-(2-methylbenzoylamino)benzoyl]-2,3,4,5-tetrahydro-1H-benzazepine (0.62 g) is added trifluoroacetic acid (1.22 ml) under ice-cooling and the mixture is stirred for 4 hours. The reaction solution is neutralized with aqueous sodium carbonate solution, and extracted three times with dichloromethane. The extract is washed with saturated saline solution and dried over magnesium sulfate. The solvent is distilled off and the resulting residue is dissolved in methanol (10 ml). Thereto is added 40% aqueous sodium hydroxide solution (10 ml) and water (10 ml), and the mixture is stirred at room temperature overnight. Methanol is distilled off and the resulting residue is purified by silica gel column chromatography (eluent; dichloromethane:methanol=30:1) to give 5-[N-methyl-N-(2,3-dihydroxypropyl)amino)-1-[4-(2-methylbenzoylamino)benzoyl]-2,3,4,5-tetrahydro-1H-benzazepine (0.23 g) as colorless amorphous.

$^1$H-NMR ($CDCl_3$) δ; 1.3–4.15 (19H, m), 4.3–5.0 (1H, m), 6.65 (1H, d, J=7.7 Hz), 6.9–8.05 (12H, m)

EXAMPLE 907

A mixture of 5-methylamino-1-[4-(2-methylbenzoylamino)benzoyl]-2,3,4,5-tetrahydro-1H-benzazepine (1.64 g), acetonitrile (20 ml), potassium carbonate (0.6 g) and ethyl bromoacetate (0.44 ml) is refluxed for 3 hours. The reaction solution is concentrated and water is added to the resulting residue, and the mixture is extracted three times with dichloromethane. The extract is washed with saturated saline solution, and dried over magnesium sulfate. The solvent is distilled off and the resulting residue is purified by silica gel column chromatography (eluent; dichloromethane:methanol=30:1), and recrystallized from ethyl acetate/petroleum ether to give 5-(N-methyl-N-ethoxycarbonylmethylamino)-1-[4-(2-methylbenzoylamino)benzoyl]-2,3,4,5-tetrahydro-1H-benzazepine (0.82 g) as colorless prisms, m.p. 167–168° C.

Using the suitable starting materials, the compounds of above Examples 785, 787, 799, 800, 802–806, 808, 811, 819, 824, 826, 827, 845, 848, 849, 850, 852, 855–858, 860, 861, 863–882, 885–893 and 895–898 are obtained in the same manner as in above Example 907.

EXAMPLE 908

5-(N-Methyl-N-ethoxycarbonylmethylamino)-1-[4-(2-methylbenzoylamino)benzoyl]-2,3,4,5-tetrahydro-1H-benzazepine (0.6 g) is dissolved in saturated solution of ammonia in methanol (20 ml), and the mixture is heated at 100° C. for 8 hours in a sealed tube. The reaction solution is concentrated and the resulting residue is purified by silica gel column chromatography (eluent; dichloromethane:methanol=30:1) to give 5-(N-methyl-N-carbamoylmethylamino)-1-[4-(2-methylbenzoylamino) benzoyl]-2,3,4,5-tetrahydro-1H-benzazepine (0.4 g) as colorless amorphous.

$^1$H-NMR ($CDCl_3$) δ; 1.4–3.0 (9H, m), 3.05–3.6 (3H, m), 3.9–4.1 (1H, m), 4.35–4.55 (1H, m), 4.9–5.65 (1H, m), 6.67 (1H, d, J=7.4 Hz), 6.85–7.6 (12H, m), 7.6–7.85 (2H, m)

EXAMPLE 909

To a solution of 5-(N-methyl-N-ethoxycarbonylmethylamino)-1-[4-(2-methylbenzoylamino)benzoyl]-2,3,4,5-tetrahydro-1H-benzazepine (0.6 g) in dioxane (10 ml) is added aqueous solution (1 ml) of sodium hydroxide (0.07 g) and the mixture is stirred at room temperature for 2 days. The reaction solution is concentrated and to the resulting residue is added water. The insoluble materials are removed by filtration. The filtrate is neutralized with 10% hydrochloric acid and extracted three times with dichloromethane. The extract is washed with saturated saline solution and dried over magnesium sulfate. The solvent is distilled off and to the resulting residue is added a solution of potassium ethylhexanoate (0.2 g) in dichloromethane (20 ml). The solvent is distilled off, and diethyl ether is added to the resulting residue. The precipitated crystal is collected by filtration, and recrystallized from diethyl ether to give potassium 2-[N-methyl-N-{1-[4-(2-methylbenzoylamino)benzoyl]-2,3,4,5-tetrahydro-1H-benzazepin-5-yl}amino]acetate (0.6 g) as colorless needles, m.p. 164–171° C.

EXAMPLE 910

To a solution of 5-methylamino-1-[4-(2-methylbenzoylamino)benzoyl]-2,3,4,5-tetrahydro-1H-benzazepine (1.5 g) in dimethyformamide (20 ml) are added potassium carbonate (0.6 g), potassium iodide (0.72 g) and 2-(3-bromopropyloxy)-3,4,5,6-tetrahydro-2H-pyrane (0.97 g) and the mixture is stirred at room temperature overnight. The reaction solution is concentrated and to the resulting residue is added water. The mixture is extracted three times with dichloromethane. The extract is washed with saturated saline solution, and dried over magnesium sulfate. The solvent is distilled off and the resulting residue is purified by silica gel column chromatography (eluent; dichloromethane→dichloromethane:methanol=50:1) to give 5-{N-methyl-N-[3-(3,4,5,6-tetrahydro-2H-pyran-2-yloxy) propyl]amino}-1-[4-(2-methylbenzoylamino)benzoyl]-2,3,4,5-tetrahydro-1H-benzazepine (1.3 g) as colorless amorphous.

$^1$H-NMR ($CDCl_3$); 1.3–2.85 (21H, m), 3.2–4.0 (4H, m), 4.3–4.4 (1H, m), 4.45–5.2 (2H, m), 6.61 (1H, d, J=7.6 Hz), 6.9–7.65 (12H, m)

EXAMPLE 911

To 5-{N-methyl-N-[3-(3,4,5,6-tetrahydro-2H-pyran-2-yloxy)propyl]amino}-1-[4-(2-methylbenzoylamino) benzoyl]-2,3,4,5-tetrahydro-1H-benzazepine (0.4 g) is added a mixture of acetyl chloride (0.5 ml) and acetic acid (5 ml) at room temperature, and the mixture is stirred overnight. The reaction solution is concentrated and the resulting residue is purified by silica gel column chromatography (eluent; dichloromethane:methanol=30:1), and further purified again by silica gel column chromatography (eluent; n-hexane:ethyl acetate=1:2) to give 5-[N-methyl-N-(3-acetyloxypropyl)amino]-1-[4-(2-methylbenzoylamino) benzoyl]-2,3,4,5-tetrahydro-1H-benzazepine (0.06 g) as colorless amorphous.

$^1$H-NMR ($CDCl_3$) δ; 1.3–3.45 (17H, m), 3.8–5.7 (5H, m), 6.5–7.65 (13H, m)

EXAMPLE 912

To a solution of 5-{N-methyl-N-[3-(3,4,5,6-tetrahydro-2H-pyran-2-yloxy)propyl]amino}-1-[4-(2-methylbenzoylamino)benzoyl]-2,3,4,5-tetrahydro-1H- benzazepine (0.55 g) in ethanol (10 ml) is added pyridinium p-toluenesulfonate (0.03 g) and the mixture is heated at 60° C. overnight. After the mixture is refluxed for more 2 hours, water and pyridinium p-toluenesulfonate (0.03 g) are added thereto. The mixture is refluxed for 4 hours. The reaction solution is concentrated and to the resulting residue is added dichloromethane. The mixture is basified with aqueous sodium hydrogen carbonate solution and extracted three times with dichloromethane. The extract is washed with saturated saline solution and dried over magnesium sulfate. The solvent is distilled off and the resulting residue is purified by silica gel column chromatography (eluent; dichloromethane:methanol=30:1) to give 5-[N-methyl-N-(3-hydroxypropyl)amino]-1-[4-(2-methylbenzoylamino)benzoyl]-2,3,4,5-tetrahydro-1H-benzazepine (0.26 g) as colorless amorphous.

$^1$H-NMR ($CDCl_3$) δ; 1.25–3.1 (14H, m), 3.3–4.0 (4H, m), 4.15–4.4 (1H, m), 4.45–5.2 (1H, m), 6.64 (1H, d, J=7.4 Hz), 6.9–7.7 (12H, m)

EXAMPLE 913

To a solution of 5-amino-1-[4-(2-methylbenzoylamino)benzoyl]-2,3,4,5-tetrahydro-1H-benzazepine (0.6 g) in acetic acid (10 ml) is added dropwise 2,5-dimethoxytetrahydrofuran (0.19 ml), and the mixture is refluxed for 1 hour. The reaction solution is concentrated and the resulting residue is purified by silica gel column chromatography (eluent; dichloromethane:methanol=50:1), and recrystallized from ethyl acetate/n-hexane to give 5-(1-pyrrolyl)-1-[4-(2-methylbenzoylamino)benzoyl]-2,3,4,5-tetrahydro-1H-benzazepine (0.31 g) as colorless prisms, m.p. 208–210° C.

EXAMPLE 914

To a solution of 5-amino-1-[4-(2-methylbenzoylamino)benzoyl]-2,3,4,5-tetrahydro-1H-benzazepine (2.5 g) in dichloromethane (30 ml) is added triethylamine (0.96 ml) and further thereto is added dropwise chloroacetyl chloride (0.55 ml) under ice-cooling. The mixture is stirred for 5 minutes. The reaction solution is concentrated and to the resulting residue is added water. The precipitated crystal is collected by filtration, washed with water, and dried to give 5-(2-chloroacetylamino)-1-[4-(2-methylbenzoylamino)benzoyl]-2,3,4,5-tetrahydro-1H-benzazepine (1.4 g) as white powder.

$^1$H-NMR (DMSO-$d_6$) δ; 1.3–2.15 (4H, m), 2.32 (3H, s), 2.8–3.05 (1H, m), 4.24 (2H, AB-q, J=12.8, 15.4 Hz), 4.35–4.55 (1H, m), 4.9–5.25 (1H, m), 6.68 (1H, d, J=7.6 Hz), 6.9–7.45 (9H, m), 7.52 (2H, d, J=8.6 Hz), 8.9–9.05 (1H, m), 10.31 (1H, s)

Using the suitable starting materials, the compound of above Example 814 is obtained in the same manner as in above Example 914.

EXAMPLE 915

A mixed solution of 5-(2-chloroacetylamino)-1-[4-(2-methylbenzoylamino)benzoyl]-2,3,4,5-tetrahydro-1H-benzazepine (0.6 g), imidazole (0.1 g) and potassium carbonate (0.19 g) in acetonitrile (30 ml) is refluxed for 8 hours. The reaction solution is concentrated and the resulting residue is washed with water and separated by decantation. The remainder is purified by silica gel column chromatography (eluent; dichloromethane:methanol=20:1→15:1), and recrystallized from ethanol/n-hexane to give 5-[2-(1-imidazolyl)acetylamino]-1-[4-(2-methylbenzoylamino)benzoyl]-2,3,4,5-tetrahydro-1H-benzazepine (0.15 g) as colorless needles, m.p. 250–252° C.

Using the suitable starting materials, the compound of above Example 818 is obtained in the same manner as in above Example 915.

EXAMPLE 916

To a solution of 5-(2-chloroacetylamino)-1-[4-(2-methylbenzoylamino)benzoyl]-2,3,4,5-tetrahydro-1H-benzazepine (0.6 g) in dimethylformamide (20 ml) are added dimethylamine hydrochloride (0.21 g) and potassium carbonate (0.54 g), and the mixture is stirred at room temperature for 2 days. The reaction solution is concentrated and water is added to the resulting residue. The precipitated crystal is collected by filtration, and recrystallized from ethyl acetate to give 5-(2-dimethylaminoacetylamino)-1-[4-(2-methylbenzoylamino)benzoyl]-2,3,4,5-tetrahydro-1H-benzazepine (0.24 g) as colorless prisms, m.p. 214–216° C.

Using the suitable starting materials, the compounds of above Examples 816, 817, 820, 821, 826 and 827 are obtained in the same manner as above Example 916.

EXAMPLE 917

A mixture of 5-methylamino-1-[4-(2-methylbenzoylamino)benzoyl]-2,3,4,5-tetrahydro-1H-benzazepine (0.6 g), N,N-dimethyl-2-chloroacetamide (0.19 g) and potassium carbonate (0.22 g) is refluxed for 24 hours. The reaction solution is concentrated and water is added to the resulting residue. The mixture is extracted three times with dichloromethane. The extract is washed with saturated saline solution, and dried over magnesium sulfate. The solvent is distilled off and the resulting residue is purified by silica gel column chromatography (eluent; dichloromethane:methanol=30:1) to give 5-[N-methyl-N-(dimethylaminocarbonylmethyl)amino]-1-[4-(2-methylbenzoylamino)benzoyl]-2,3,4,5-tetrahydro-1H-benzazepine (0.05 g) as colorless amorphous.

$^1$H-NMR ($CDCl_3$) δ; 1.2–3.3 (17H, m), 3.45 (2H, AB-q, J=14.7, 22.9 Hz), 3.9–4.35 (2H, m), 6.60 (1H, d, J=7.7 Hz), 6.8–8.0 (11H, m), 8.39 (1H, s)

EXAMPLE 918

To a solution of t-butoxycarbonylglycine (0.84 g) in dimethylformamide (20 ml) are added diethyl cyanophosphate (0.73 ml) and 5-amino-1-[4-(2-methylbenzoylamino)benzoyl]-2,3,4,5-tetrahydro-1H-benzazepine (1.74 g), and further thereto is added triethylamine (1.8 ml) under ice-cooling. The mixture is stirred for 30 minutes, and then stirred at room temperature overnight. The reaction solution is concentrated and water is added to the resulting residue. The precipitated crystal is collected by filtration, washed with water, and recrystallized from ethyl acetate to give 5-(2-aminoacetylamino)-1-[4-(2-methylbenzoylamino)benzoyl]-2,3,4,5-tetrahydro-1H-benzazepine (E) (0.16 g). Separately, the filtrate is concentrated and purified by silica gel column chromatography (eluent; dichloromethane:methanol=50:1), and recrystallized from diethyl ether to give 5-[2-(t-butoxycarbonylamino)acetylamino]-1-[4-(2-methylbenzoylamino)benzoyl]-2,3,4,5-tetrahydro-1H-benzazepine (F) (0.19 g).

(E): Colorless prisms, m.p. 287–289° C.

(F): Colorless prisms, m.p. 170–171° C.

EXAMPLE 919

5-Oxo-1-[4-(2-methylbenzoylamino)benzoyl]-2,3,4,5-tetrahydro-1H-benzazepine (0.50 g) is suspended in tetrahydrofuran (20 ml), and thereto is added dropwise a 3.0 M solution of methyl magnesium bromide in diethyl ether (1.5 ml) at room temperature. The mixture is stirred at room temperature for 1 hour. The reaction solution is poured into ice-water (20 ml), and extracted with ethyl acetate. The extract is dried over magnesium sulfate, and the solvent is distilled off. The resulting residue is purified by silica gel column chromatography (eluent; ethyl acetate:n-hexane=2:3→1:1), and recrystallized from ethyl acetate/n-hexane to give 5-methyl-5-hydroxy-1-[4-(2-methylbenzoylamino)benzoyl]-2,3,4,5-tetrahydro-1H-benzazepine (0.23 g) as white powder, m.p. 204–205° C.

EXAMPLE 920

To a solution of 5-carboxymethoxy-1-[4-(2-methylbenzoylamino)benzoyl]-2,3,4,5-tetrahydro-1H-benzazepine (1.50 g) in dimethylformamide (60 ml) are added successively thiomorpholine (0.66 ml), diethyl cyanophosphate (0.89 g) and triethylamine (1.37 ml) with stirring under ice-cooling. The mixture is stirred for 30 minutes under ice-cooling, and at room temperature for 20 minutes. Water (60 ml) is added to the reaction solution, and extracted with dichloromethane. The extract is dried over magnesium sulfate, and the solvent is distilled off. The resulting residue is purified by silica gel column chromatography (eluent; ethyl acetate:n-hexane=5:2→3:1), and recrystallized from ethyl acetate/n-hexane to give 5-(thiomorpholinocarbonylmethoxy)-1-[4-(2-methylbenzoylamino)benzoyl]-2,3,4,5-tetrahydro-1H-benzazepine (1.60 g) as white powder, m.p. 235–237° C.

Using the suitable starting materials, the compounds of above Examples 829–838 are obtained in the same manner as in above Example 920.

EXAMPLE 921

To a solution of 5-(thiomorpholinocarbonylmethoxy)-1-[4-(2-methylbenzoylamino)benzoyl]-2,3,4,5-tetrahydro-1H-benzazepine (0.40 g) in dichloromethane (40 ml) is added 80% m-chloroperbenzoic acid (175 mg) with stirring at −8° C., and the mixture is stirred at −8° C. for 1 hour. To the reaction solution is added 20% aqueous sodium hydrogensulfite solution (40 ml) and the mixture is stirred at room temperature for 30 minutes. The dichloromethane layer is collected, washed with saturated saline solution and dried over magnesium sulfate. The solvent is distilled off and the resulting residue is purified by silica gel column chromatography (eluent; dichloromethane:methanol=20:1) to give 5-[(1-oxothiomorpholino)carbonylmethoxy]-1-[4-(2-methylbenzoylamino)benzoyl]-2,3,4,5-tetrahydro-1H-benzazepine (0.32 g) as colorless amorphous.

$^1$H-NMR ($CDCl_3$) δ; 1.50–1.92 (3H, m), 1.92–2.05 (1H, m), 2.47 (3H, s), 2.55–3.06 (5H, m), 3.43–5.76 (8H, m), 6.63–6.82 (1H, m), 6.97–8.08 (12H, m)

EXAMPLE 922

To a solution of 5-(thiomorpholinocarbonylmethoxy)-1-[4-(2-methylbenzoylamino)benzoyl]-2,3,4,5-tetrahydro-1H-benzazepine (0.40 g) in dichloromethane (40 ml) is added 80% m-chloroperbenzoic acid (0.35 g), and the mixture is stirred at room temperature for 1 hour. The reaction solution is washed successively with an aqueous sodium hydrogensulfite solution and saturated saline solution, and dried over magnesium sulfate. The solvent is distilled off to give 5-[(1,1-dioxothiomorpholino)carbonylmethoxy]-1-[4-(2-methylbenzoylamino)benzoyl]-2,3,4,5-tetrahydro-1H-benzazepine (0.41 g) as colorless amorphous.

$^1$H-NMR ($CDCl_3$) δ; 1.43–2.65 (4H, m), 2,48 (3H, s), 2.69–3.25 (5H, m), 3.90–5.40 (8H, m), 6.64–6.94 (1H, m), 6.94–7.77 (12H, m)

EXAMPLE 923

To a solution of 5-oxo-1-[4-(2-hydroxybenzoylamino)benzoyl)-2,3,4,5-tetrahydro-1H-benzazepine (400 mg) in acetone (20 ml) are added potassium carbonate (210 mg), potassium iodide (250 mg) and 2-chloroacetamide (120 mg), and the mixture is refluxed for 2 hours. The insoluble materials are removed by filtration, and the filtrate is distilled off. Dichloromethane is added to the resulting residue, and the mixture is washed with saturated saline solution, and dried over magnesium sulfate. The solvent is distilled off and the resulting residue is recrystallized from ethyl acetate/n-hexane to give 5-oxo-1-[4-(2-carbamoylmethoxybenzoylamino)benzoyl]-2,3,4,5-tetrahydro-1H-benzazepine (436 mg) as white powder, m.p. 226–228° C.

Using the suitable starting materials, the compound of above Example 842 is obtained in the same manner as above Example 923.

EXAMPLE 924

A mixture of 5-methylamino-4-hydroxy-1-[4-(2-chlorobenzoylamino)benzoyl]-2,3,4,5-tetrahydro-1H-benzazepine (0.13 g), ethyl α-bromoacetate (58 mg), diisopropylethylamine (49 mg) and acetonitrile (5 ml) is refluxed for 10 hours. Acetonitrile is distilled off under reduced pressure, and the resulting residue is dissolved in dichloromethane, washed with water, dried over magnesium sulfate, and distilled off under reduced pressure. The resulting residue is purified by silica gel column chromatography (eluent; dichloromethane:methanol=50:1), and recrystallized from chloroform/methanol to give 7-[4-(2-chlorobenzoylamino)benzoyl]-1-methyl-1,2,3,4a, 5,6,7,11b-octahydro-3-oxo[1]benzazepino[4,5-b][1,4]oxazine (80 mg) as colorless prisms, m.p. 286–290° C.

EXAMPLE 925

To a solution of 5-oxo-1-[2-chloro-4-(2-methylbenzoylamino)benzoyl]-2,3,4,5-tetrahydro-1H-benzazepine (1 g) in methanol (20 ml) and dichloromethane (20 ml) is added hydroxylamine-O-sulfonic acid (0.28 g) with stirring at room temperature, and the mixture is stirred at the same temperature for 1 hour. Subsequently, to the reaction solution is added with stirring an aqueous solution of patassium carbonate (0.34 g) in water (1 ml) at room temperature, and the mixture is stirred at the same temperature for 2 hours. The precipitated crystal is removed by filtration, and the filtrate is concentrated under reduced pressure. The resulting residue is purified by silica gel column chromatography to give potassium {1-[2-chloro-4-(2-methylbenzoylamino)benzoyl]-2,3,4,5-tetrahydro-1H-benzazepin-5-yl}imino-O-sulfonate (0.4 g) as white powder.

$^1$H-NMR (DMSO-$d_6$) δ; 1.40–1.75 (1H, m), 1.90–2.15 (1H, m), 2.33 (3H, s), 2.50–2.80 (2H, m), 3.10–3.50 (1H, m), 4.40–4.65 (1H, m), 6.85–7.60 (10H, m), 7.85 (1H, s), 10.44 (1H, s)

EXAMPLE 926

Using the suitable starting materials, the compounds of above Examples 841–843, 868–870, 888 and 889 are obtained in the same manner as in above Example 380.

EXAMPLE 927

Using the suitable starting materials, the compounds of above Examples 876–878 are obtained in the same manner as in above Example 381.

EXAMPLE 928

Using the suitable starting materials, the compounds of above Examples 840, 842 and 846 are obtained in the same manner as in above Example 384.

EXAMPLE 929

Using the suitable starting materials, the compounds of above Examples 788–790, 796–804, 805, 808, 811, 814, 818, 819, 824, 826, 827, 837, 845, 848, 850, 852, 855, 856–858, 860, 861, 863–882, 885, 886, 888–893 and 895–898 are obtained in the same manner as in above Example 388.

EXAMPLE 930

Using the suitable starting materials, the compound of above Example 848 is obtained in the same manner as in above Example 393.

EXAMPLE 931

Using the suitable starting materials, the compounds of above Examples 841 and 842 are obtained in the same manner as in above Example 402.

EXAMPLE 932

Using the suitable starting materials, the compounds of above Examples 882 and 897 are obtained in the same manner as in above Example 403.

EXAMPLE 933

Using the suitable starting materials, the compound of above Example 809 is obtained in the same manner as in above Example 634.

EXAMPLE 934

Using the suitable starting materials, the compounds of above Examples 828–838 are obtained in the same manner as in above Example 640.

EXAMPLE 935

Using the suitable starting materials, the compound of above Example 810 is obtained in the same manner as in above Example 772.

EXAMPLE 936

Using the suitable starting materials, the compound of above Example 788 is obtained in the same manner as in above Example 771.

EXAMPLE 937

Using the suitable starting materials, the compounds of above Examples 785, 787, 788–790, 796–805, 806, 807, 808, 811, 814, 818, 819, 845, 848, 849, 850, 852, 855, 856–858, 860, 861, 863–882, 885, 886, 888–893 and 896–898 are obtained in the same manner as in above Example 390.

EXAMPLE 938

To 5-methanesulfonyloxymethyl-1-[4-(2-methylbenzoylamino)benozyl]-2,3,4,5-tetrahydro-1H-benzazepine (0.50 g) is added a 30% solution of methylamine in methanol (50 ml), and the mixture is heated at 100° C. for 3 hours in a sealed tube. After cooling, the reaction solution is evaporated under reduced pressure, and the resulting residue is purified by silica gel column chromatography (eluent; dichloromethane:methanol:aqueous ammonia=100:10:1) to give 5-methylaminomethyl-1-[4-(2-methylbenzoylamino)benzoyl]-2,3,4,5-tetrahydro-1H-benzazepine (0.07 g).

$^1$H-NMR (DMSO-$d_6$) δ; 1.40–2.18 (4H, m), 2.34 (3H, s), 2.47 (3H, s), 2.54–3.50 (4H, m), 4.30–5.08 (1H, m), 6.56–6.82 (1H, m), 6.87–7.48 (10H, m), 7.48–7.75 (2H, m), 10.35 (1H, s)

Using the suitable starting materials, the compounds of above Examples 823–825 are obtained in the same manner as in above Example 938.

Using the above suitable starting materials, the compounds of the following Table 6 are obtained in the same manner as in Examples 1 and 382.

TABLE 6

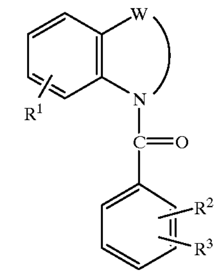

Example 939
Structure

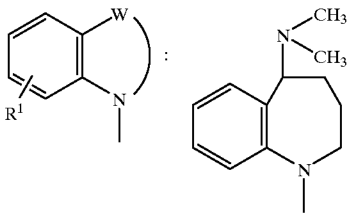

$R^2$: H

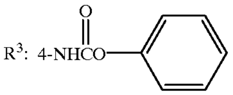

Crystalline form: White powder
Recrystallization solvent: Ethanol
Melting Point: 208–211° C.
Form: Free Example 940
Structure

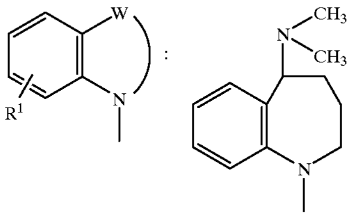

$R^2$: H

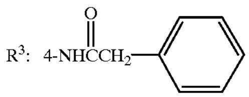

TABLE 6-continued

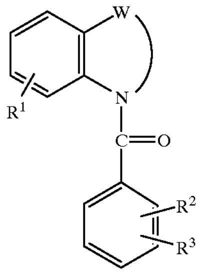

Crystalline form: White powder

Recrystallization solvent: Methanol/diethyl ether

Melting Point: 171.5–172.5° C.

Form: Free

Example 941

Structure

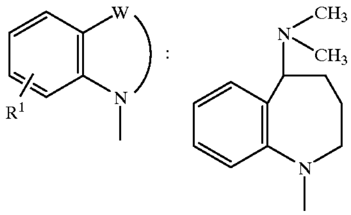

$R^2$: H

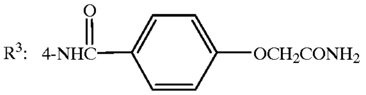

Crystalline form: White powder

Recrystallization solvent: Methanol/diethyl ether

Melting Point: 151–154° C.

Form: Free

Example 942

Structure

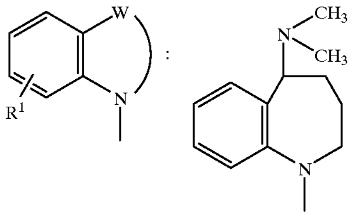

$R^2$: H

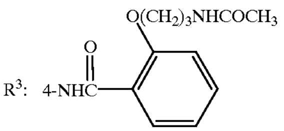

Crystalline form: Colorless amorphous

NMR analysis: 167)

Form: Free

TABLE 6-continued

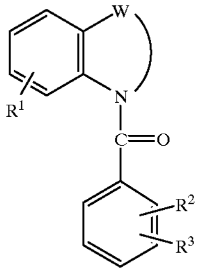

Example 943

Structure

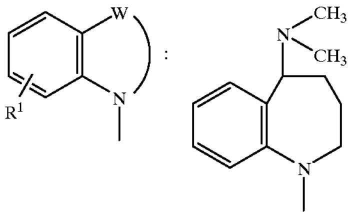

$R^2$: H

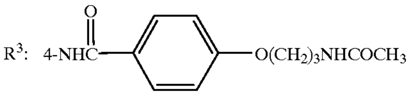

Crystalline form: White powder

Recrystallization solvent: Methanol/diethyl ether

Melting Point: 180–183° C.

Form: Free

Example 944

Structure

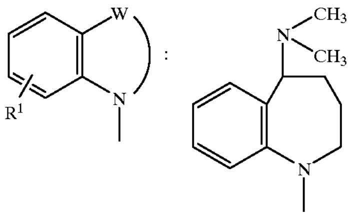

$R^2$: H

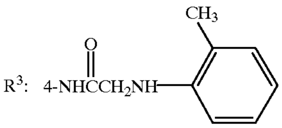

Crystalline form: White powder

Recrystallization solvent: Methanol/diethyl ether

Melting Point: 109–110° C.

Form: Free

TABLE 6-continued

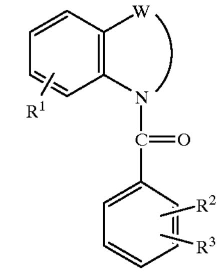

Example 945

Structure

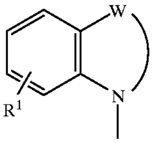 : 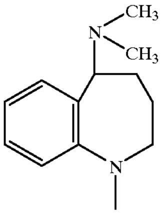 $R^2$: H $R^3$: 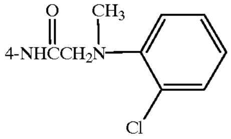

Crystalline form: Colorless oil

NMR analysis: 168)

Form: Free

Example 946

Structure

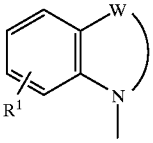 : 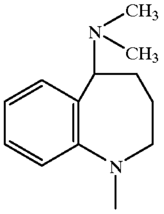 $R^2$: H $R^3$: 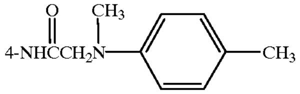

Crystalline form: Colorless oil

NMR analysis: 169)

Form: Free

Example 947

Structure

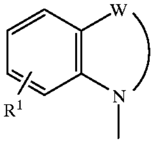 : 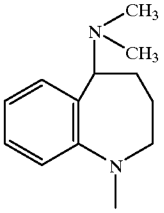 $R^2$: H

TABLE 6-continued

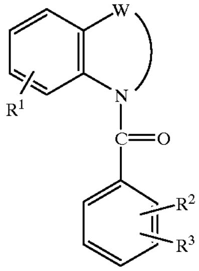

$R^3$: 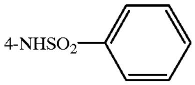

Crystalline form: White powder

Recrystallization solvent: Methanol/diethyl ether

Melting Point: 177–178.5° C.

Form: Free

Example 948

Structure

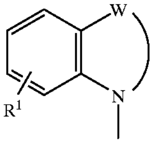 : 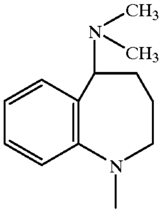 $R^2$: H $R^3$: 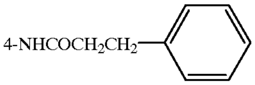

Crystalline form: Colorless amorphous

NMR analysis: 170)

Form: Free

Example 949

Structure

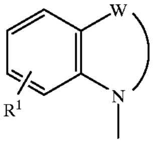 : 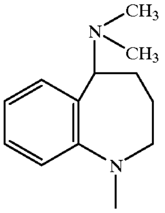 $R^2$: H $R^3$: 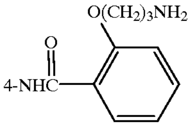

Crystalline form: White powder

Recrystallization solvent: Methanol/diethyl ether

Melting Point: 162–165° C.

Form: Free

TABLE 6-continued

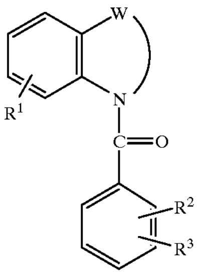

Example 950
Structure

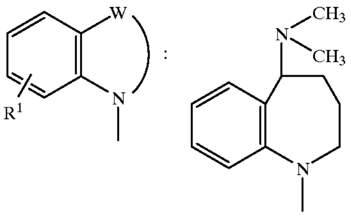

R$^2$: H

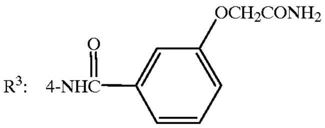

Crystalline form: White powder
Recrystallization solvent: Methanol/diethyl ether
Melting Point: 212–215° C.
Form: Free
Example 951
Structure

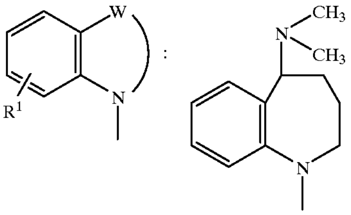

R$^2$: H

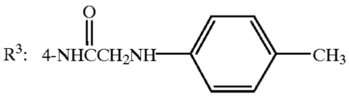

Crystalline form: Colorless oil
NMR analysis 171)
Form: Free
Example 952
Structure

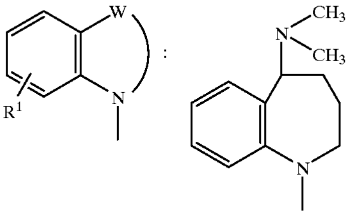

R$^2$: H

TABLE 6-continued

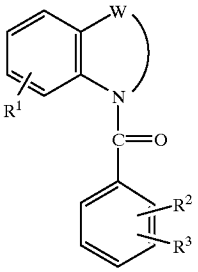

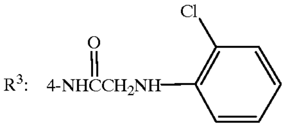

Crystalline form: White powder
Recrystallization solvent: Methanol/diethyl ether
Melting Point: 112–114° C.
Form: Free
Example 953
Structure

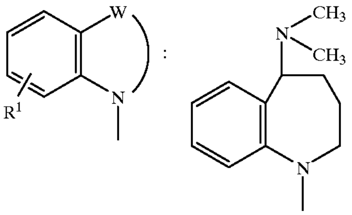

R$^2$: H

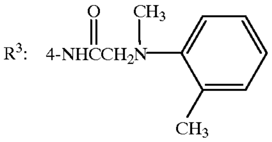

Crystalline form: Colorless oil
NMR analysis: 172)
Form: Free
Example 954
Structure

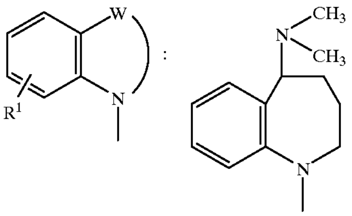

R$^2$: H

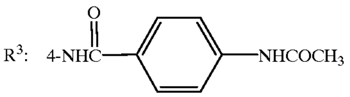

Crystalline form: Colorless amorphous
NMR analysis: 173)
Form: Free

TABLE 6-continued

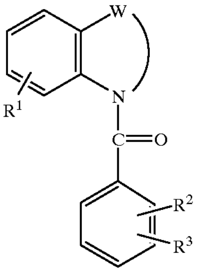

Example 955

Structure

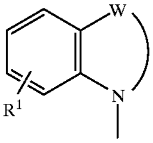 : 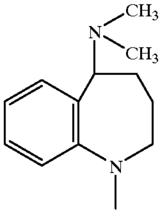 $R^2$: H

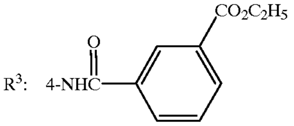

Crystalline form: Light yellow amorphous

NMR anlaysis: 174)

Form: Free

Example 956

Structure

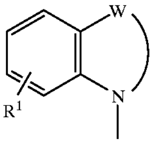 : 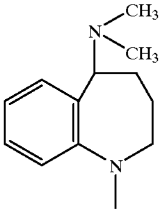 $R^2$: H

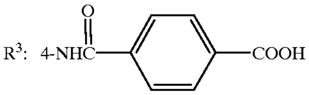

Crystalline form: White powder

Recrystallization solvent: Diethyl ether

Melting Point: 189–193° C.

Form: Free

TABLE 6-continued

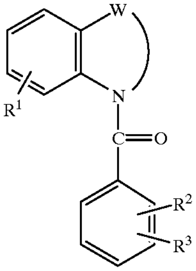

Example 957

Structure

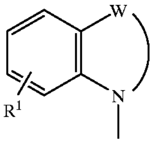 : 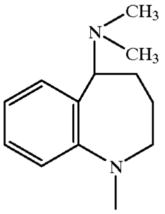 $R^2$: H

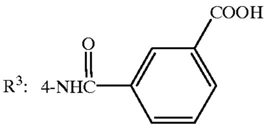

Crystalline form: Colorless amorphous

NMR analysis: 175)

Form: Free

Example 958

Structure

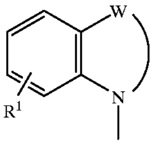 : 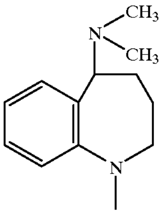 $R^2$: H

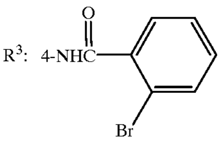

Crystalline form: Colorless prisms

Recrystallization solvent: Ethanol

Melting Point: 234–238° C.

Form: Free

Example 959

Structure

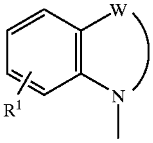 : 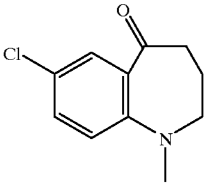 $R^2$: H

TABLE 6-continued

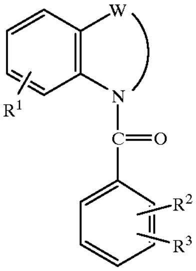

$R^3$: 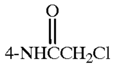

Crystalline form: White powder
Recrystallization solvent: Diethyl ether/dichloromethane
Melting Point: 183–184.5° C.
Form: Free Example 960
Structure

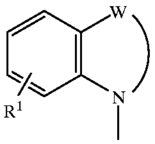 : 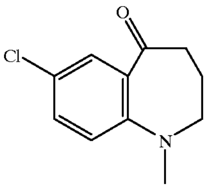 $R^2$: H $R^3$: 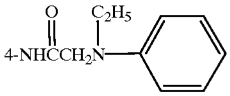

Crystalline form: Brown oil
NMR analysis: 176)
Form: Free

Example 961
Structure

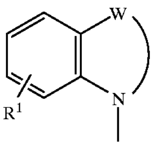 : 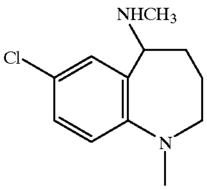 $R^2$: H $R^3$: 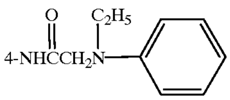

Crystalline form: Colorless amorphous
NMR analysis: 177)
Form: Free

TABLE 6-continued

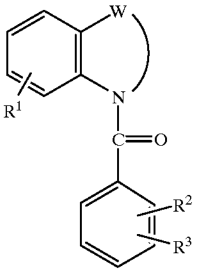

Example 962
Structure

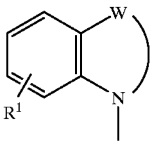 : 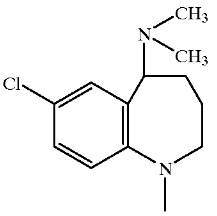 $R^2$: H $R^3$: 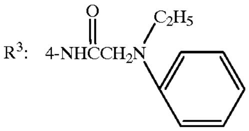

Crystalline form: Colorless amorphous
NMR analysis: 178)
Form: Free

Example 963
Structure

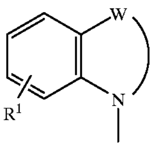 : 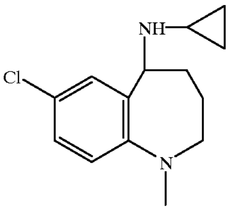 $R^2$: H $R^3$: 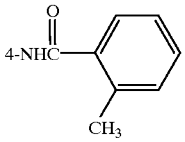

Crystalline form: White powder
Recrystallization solvent: Dichloromethane/diethyl ether
Melting Point: 202.5–204.5° C.
Form: Free Example 964
Structure

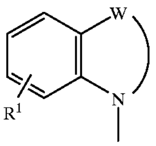 : 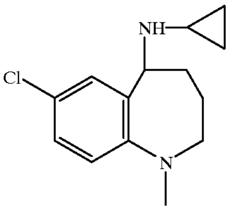 $R^2$: H

TABLE 6-continued

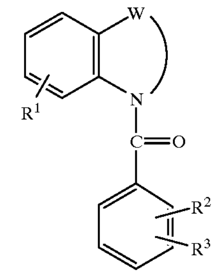

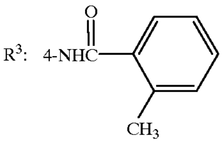

Crystalline form: White powder
Recrystallization solvent: Dichloromethane/diethyl ether
Melting Point: 199.5–201° C.
Form: Free
Example 965
Structure

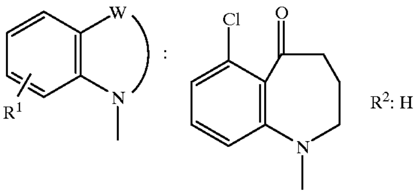

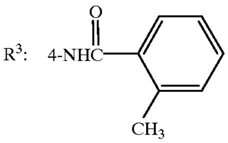

Crystalline form: White powder
Recrystallization solvent: Dichloromethane/diethyl ether
Melting Point: 196.5–197° C.
Form: Free
Example 966
Structure

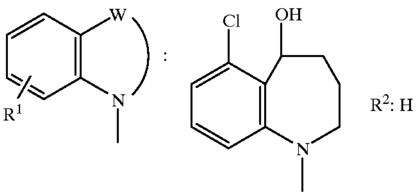

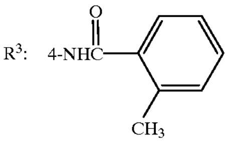

Crystalline form: White powder
Recrystallization solvent: Dichloromethane/diethyl ether
Melting Point: 204–205° C.
Form: Free TABLE 6-continued

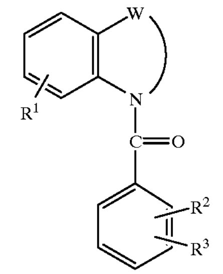

Example 967
Structure

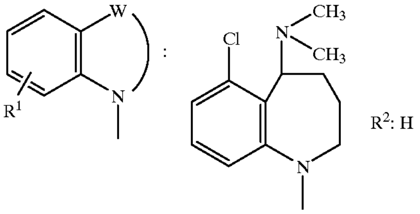

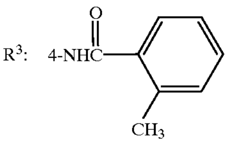

Crystalline form: White powder
Recrystallization solvent: Dichloromethane/diethyl ether
Melting Point: 175–177° C.
Form: Free
Example 968
Structure

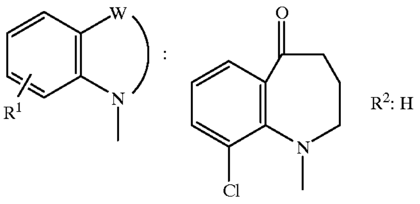

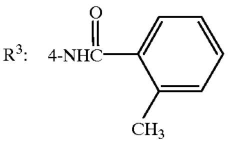

Crystalline form: Pink amorphous
NMR analysis: 179)
Form: Free
Example 969
Structure

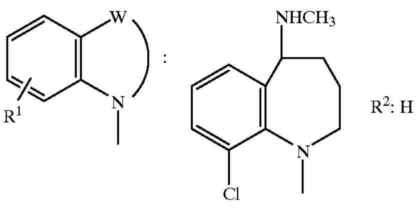

TABLE 6-continued

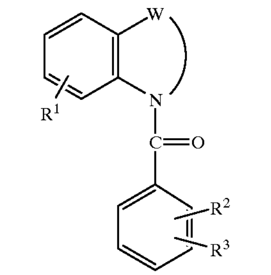

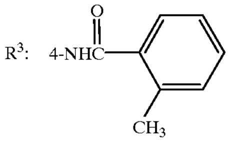

Crystalline form: White powder
Recrystallization solvent: Dichloromethane/diethyl ether
Melting Point: 186–189° C.
Form: Free
Example 970
Structure

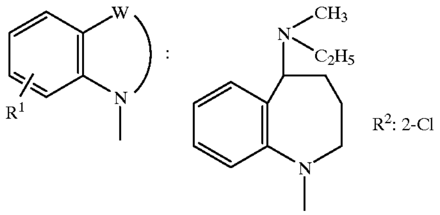

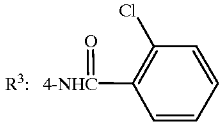

Crystalline form: Colorless prisms
Recrystallization solvent: Ethyl acetate/n-hexane
Melting Point: 211–212° C.
Form: Free
Example 971
Structure

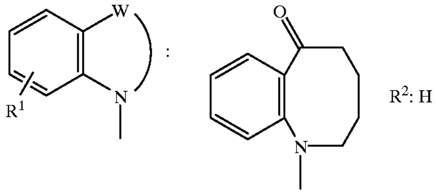

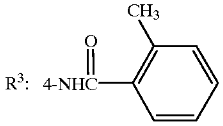

Crystalline form: Colorless amorphous
NMR analysis: 180)
Form: Free

TABLE 6-continued

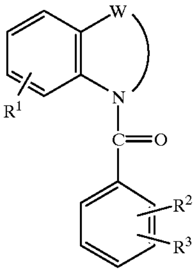

Example 972
Structure

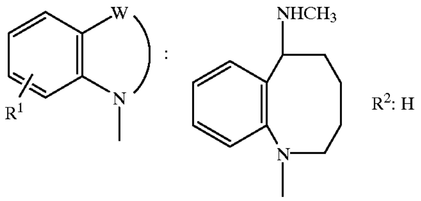

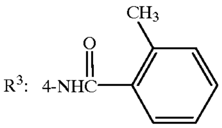

Crystalline form: Colorless needles
Recrystallization solvent: Ethanol
Melting Point: 206–207° C.
Form: Free
Example 973
Structure

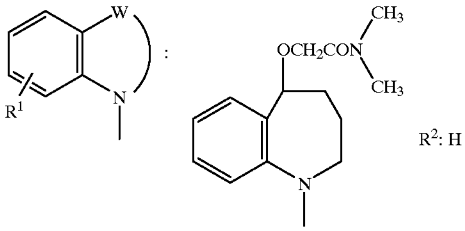

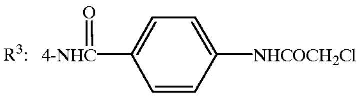

Crystalline form: Colorless amorphous
NMR analysis: 181)
Form: Free
Example 974
Structure

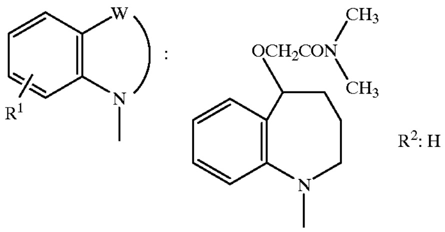

TABLE 6-continued

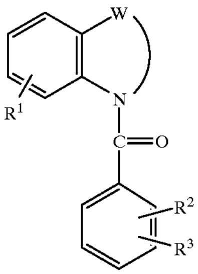

$R^3$: 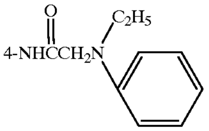

Crystalline form: White powder
Recrystallization solvent: Ethyl acetate/n-hexane
Melting Point: 152–154° C.
Form: Free Example 975
Structure

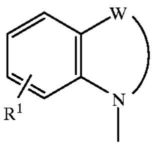 : 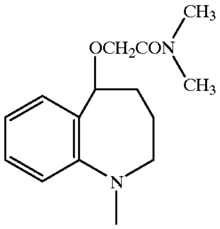 $R^2$: H $R^3$: 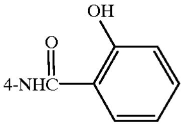

Crystalline form: Colorless amorphous
NMR analysis: 182)
Form: Free

Example 976
Structure

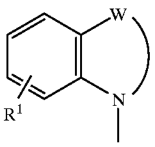 : 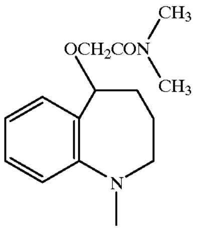 $R^2$: H $R^3$: 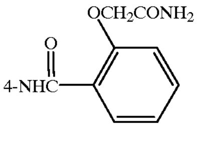

Crystalline form: White powder
Recrystallization solvent: Ethyl acetate/n-hexane
Melting Point: 204–206° C.
Form: Free TABLE 6-continued

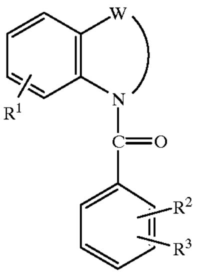

Example 977
Structure

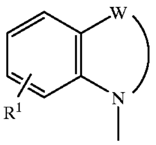 : 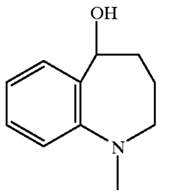 $R^2$: H $R^3$: 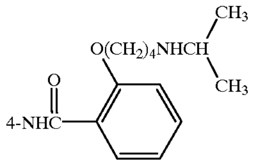

Crystalline form: Colorless needles
Recrystallization solvent: Ethyl acetate/n-hexane
Melting Point: 162–163° C.
Form: Free 167) $^1$H-NMR($CDCl_3$)δ; 1.14–2.83(13H, m), 2.43(3H, s), 2.95–5.19(4H, m), 4.12(2H, t, J=6.2Hz), 6.27–6.83(2H, m), 6.83–7.36(6H, m), 7.36–7.67 (4H, m), 7.93–8.11(1H, m), 9.77(1H, brs)

168) $^1$H-NMR($CDCl_3$)δ; 1.11–2.98(11H, m), 2.80(3H, s), 3.69(2H, s), 2.98–5.24(2H, m), 6.50–7.71 (12H, m), 9.37(1H, brs)

169) $^1$H-NMR($CDCl_3$)δ; 1.10–2.80(14H, m), 2.99(3H, s), 3.39–5.20(2H, m), 4.00(2H, s), 6.49–7.67 (12H, m), 8.51(1H, brs)

170) $^1$H-NMR($CDCl_3$)δ; 1.10–1.98(3H, m), 1.98–2.82 (10H, m), 2.82–3.20(2H, m), 3.34–5.15(2H, m), 6.48–7.68(15H, m), 7.86(1H, brs)

171) $^1$H-NMR($CDCl_3$)δ; 1.10–2.84(10H, m), 2.40(3H, s), 2.90–5.20(2H, m), 3.79(2H, d, J=2.7Hz), 4.33 (1H, br), 6.30–7.68(12H, m), 8.67(1H, brs)

172) $^1$H-NMR($CDCl_3$)δ; 1.10–2.85(14H, m), 2.72(3H, s), 2.98–5.20(2H, m), 3.62(2H, s), 6.50–7.75 (12H, m), 9.18(1H, brs)

173) $^1$H-NMR(DMSO-$d_6$)δ; 1.28–2.62(4H, m), 2.07(3H, s), 2.34(6H, s), 3.04–3.57(2H, m), 3.99–4.86(1H, m), 6.62–7.88(12H, m), 10.12–10.20(2H, m)

174) $^1$H-NMR($CDCl_3$)δ; 1.39(3H, t, J=7.1Hz), 1.64–2.68(4H, m), 2.42(6H, s), 3.04–3.58(2H, m), 3.98–5.01(1H, m), 4.38(2H, q, J=7.1Hz), 6.57–8.57(13H, m)

175) $^1$H-NMR(DMSO-$d_6$)δ; 1.67–5.02(7H, m), 3.35(6H, s), 6.75–8.17(12H, m), 8.46(1H, s), 10.54(1H, s)

176) $^1$H-NMR($CDCl_3$)δ; 1.21(3H, t, J=7.1Hz), 1.95–2.30(2H, m), 2.88(2H, t, J=6.2Hz), 3.40–3.65 (2H, m), 3.70–4.50(2H, m), 3.91(2H, s), 6.66(1H, d, J=8.5Hz), 6.70–7.00(3H, m), 7.10–7.50(7H, m), 7.81(1H, d, J=2.5Hz), 8.44(1H, s)

177) $^1$H-NMR($CDCl_3$): 1.21(3H, t, J=7Hz), 1.30–5.20 (11H, m), 3.48(2H, q, J=7Hz), 3.90(2H, s), 6.53 (1H, d, J=8.3Hz), 6.65–7.00(4H, m), 7.00–7.40 (6H, m), 7.51(1H, d, J=2.5Hz), 8.40(1H, s)

TABLE 6-continued

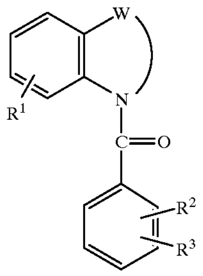

178) $^1$H-NMR($CDCl_3$)δ; 1.21(3H, t, J=7Hz), 1.20–5.20 (15H, m), 3.90(2H, s), 6.48(1H, d, J=8.3Hz), 6.50–7.70(11H, m), 8.39(1H, s)
179) $^1$H-NMR($CDCl_3$)δ; 1.60–2.20(1H, m), 2.10–2.35 (1H, m), 2.45(3H, s), 2.70–2.95(2H, m), 3.25–3.45 (1H, m), 4.60–4.85(1H, m), 7.10–7.80(12H, m)
180) $^1$H-NMR($CDCl_3$)δ; 1.65–2.15(4H, m), 2.46(3H, s), 2.6–5.15(4H, m), 6.75–6.95(1H, m), 7.15–7.55 (10H, m), 7.61(1H, s), 7.95–8.1(1H, m)
181) $^1$H-NMR($CDCl_3$)δ; 1.60–2.15(3H, m), 2.15–2.90 (2H, m), 2.90–3.22(6H, m), 4.00–4.50(2H, m), 4.13 (2H, s), 4.58–5.22(2H, m), 6.53–6.80(1H, m), 6.90–7.90(7H, m), 8.48(1H, s)
182) $^1$H-NMR($CDCl_3$)δ; 1.48–2.20(3H, m), 2.20–2.85 (2H, m), 2.85–3.27(6H, m), 4.05–4.47(2H, m), 4.47–5.22(2H, m), 6.50–6.76(1H, m), 6.76–6.91 (1H, m), 6.91–7.69(9H, m), 7.69–8.13(1H, m), 9.28 (1H, s), 11.87(1H, brs)

EXAMPLE 978

5-Dimethylamino-1-(2-methyl-4-aminobenzoyl)-2,3,4,5-tetrahydro-1H-benzazepine (H) (1.00 g) is dissolved in dichloromethane (30 ml), and thereto is added triethylamine (0.48 ml) under ice-cooling, and further added dropwise 2-methylbenzoyl chloride (0.44 ml). The mixture is stirred at room temperature for 1 hour. The reaction solution is washed with water, and dried over magnesium sulfate. The solvent is distilled off, and the resulting residue is crystallized by adding thereto ethyl acetate. The precipitated crystal is recrystallized from dichloromethane/ethyl acetate to give 5-dimethylamino-1-[2-methyl-4-(2-methylbenzoylamino) benzoyl]-2,3,4,5-tetrahydro-1H-benzazepine (0.92 g) as white powder, m.p. 191–192° C.

HPLC retention time: 7.5 minutes

Column; Wakosil II $5C_{18}$ (trade mark; Wako Pure Chemical Co., Ltd.)

Solvent; acetonitrile: 50 mN aqueous $Na_2SO_4$ solution: acetic acid=27:73:1

Rate; 1.0 ml/min.

$[\alpha]_D^{22}$=0° (c=1.0, chloroform); $^1$H-NMR ($CDCl_3$) δ; 1.15–3.25 (17H, m), 3.35–5.14 (2H, m), 6.62–8.05 (12H, m)

Figure 2:
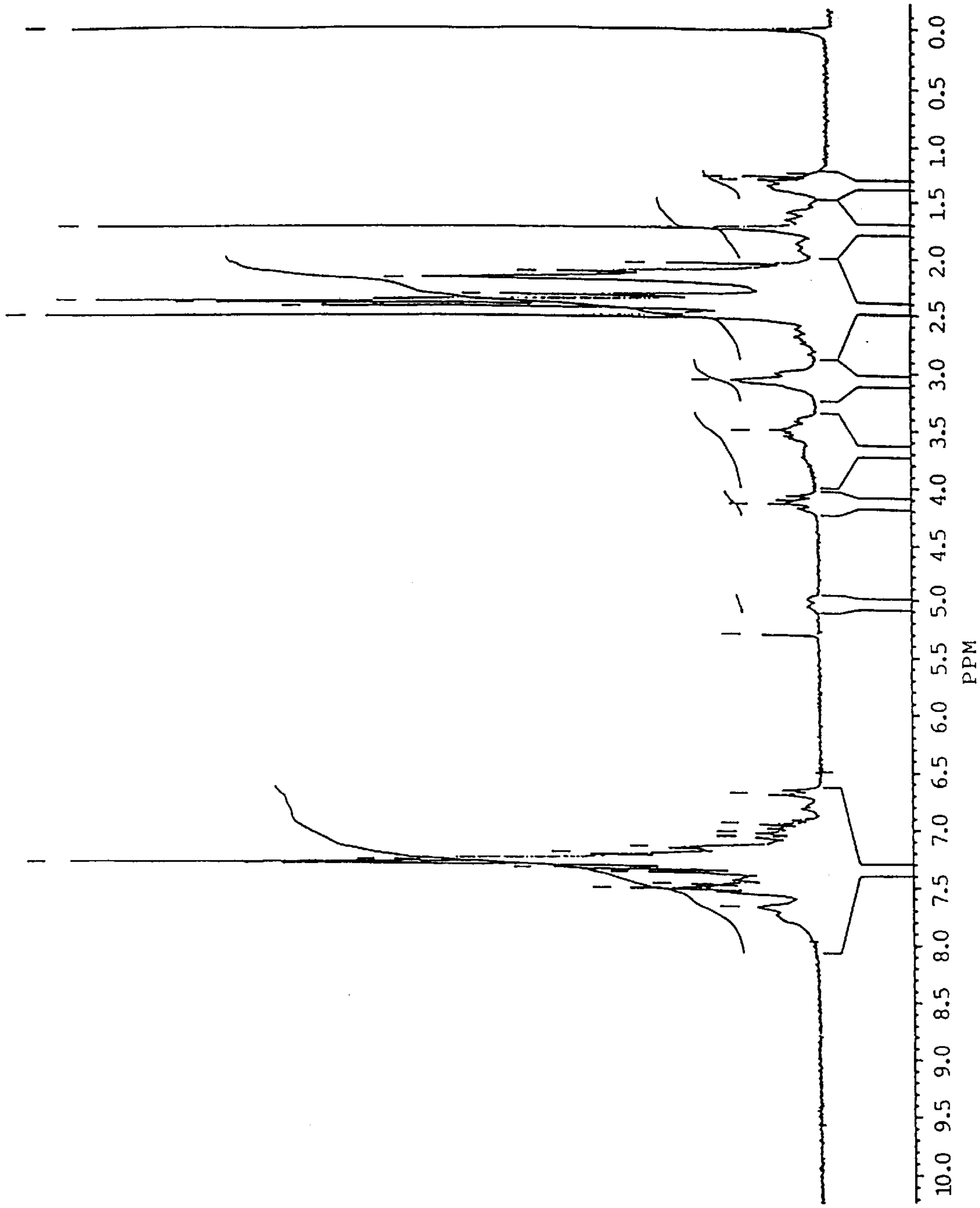

Charts of $^1$H-NMR ($CDCl_3$) of the starting compound (H) and the compound obtained in Exmaple 978 are shown in FIG. 1 and FIG. 2, respectively.

EXAMPLE 979

Using 5-dimethylamino-1-(2-methyl-4-aminobenzoyl)-2,3,4,5-tetrahydro-1H-benzazepine (G) (1.00 g), 5-dimethylamino-1-(2-methyl-4-(2-methylbenzoylamino) benzoyl]-2,3,4,5-tetrahydro-1H-benzazepine (0.48 g) is obtained in the same manner as in Example 978 except that methanol/diethyl ether is used instead of ethyl acetate as recrystallization solvent, as white powder, m.p. 183–185° C.

HPLC retention time: 8.1 minutes (the conditions of HPLC are same as those in Example 978)

$[\alpha]_D^{22}$=0° (c=1.3, chloroform); $^1$H-NMR ($CDCl_3$) δ; 1.10–3.20 (17H, m), 3.35–5.15 (2H, m), 6.50–6.80 (1H, m), 6.86–7.62 (10H, m), 7.65–8.09 (1H, m)

Figure 3:
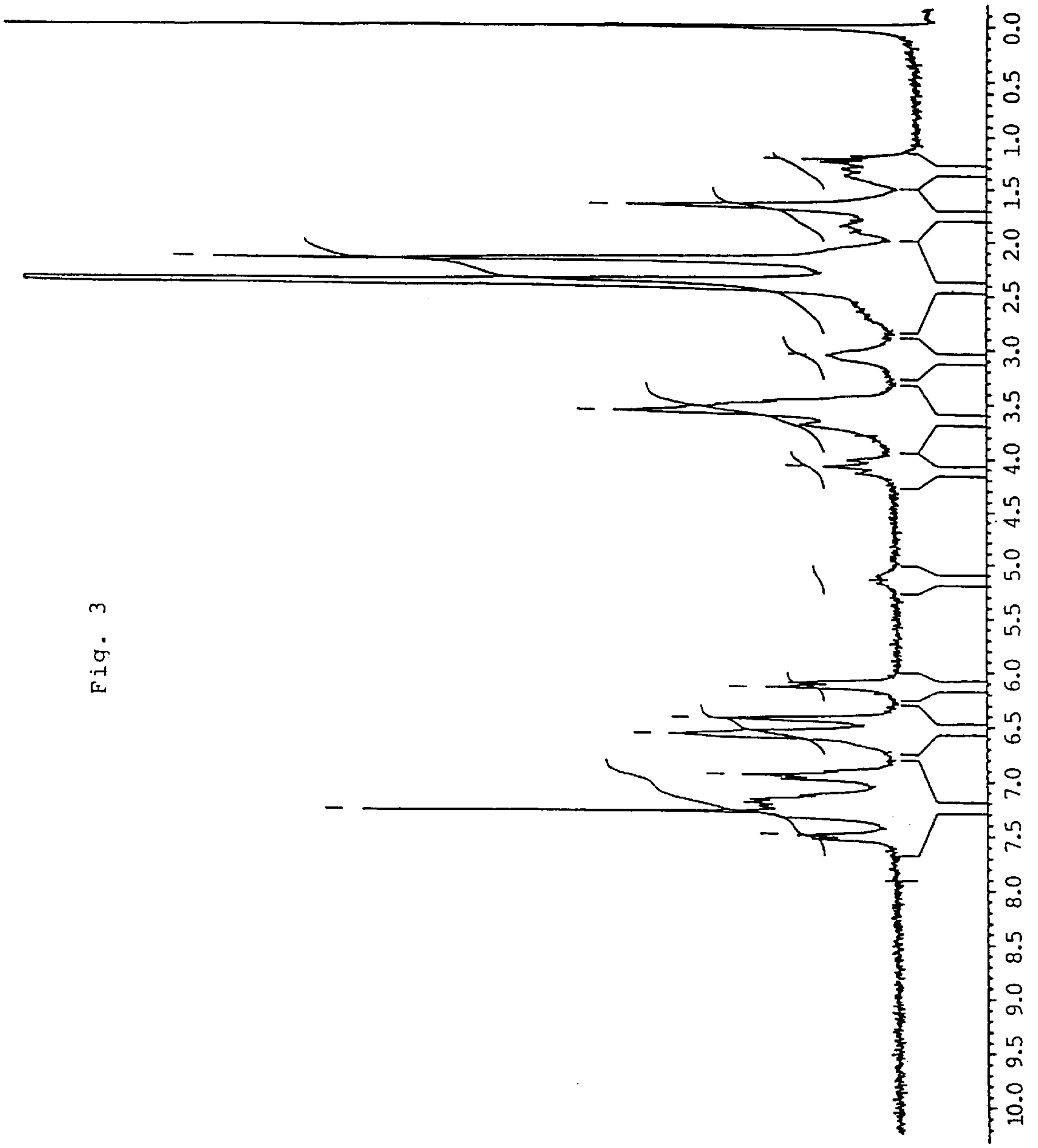
Figure 4:
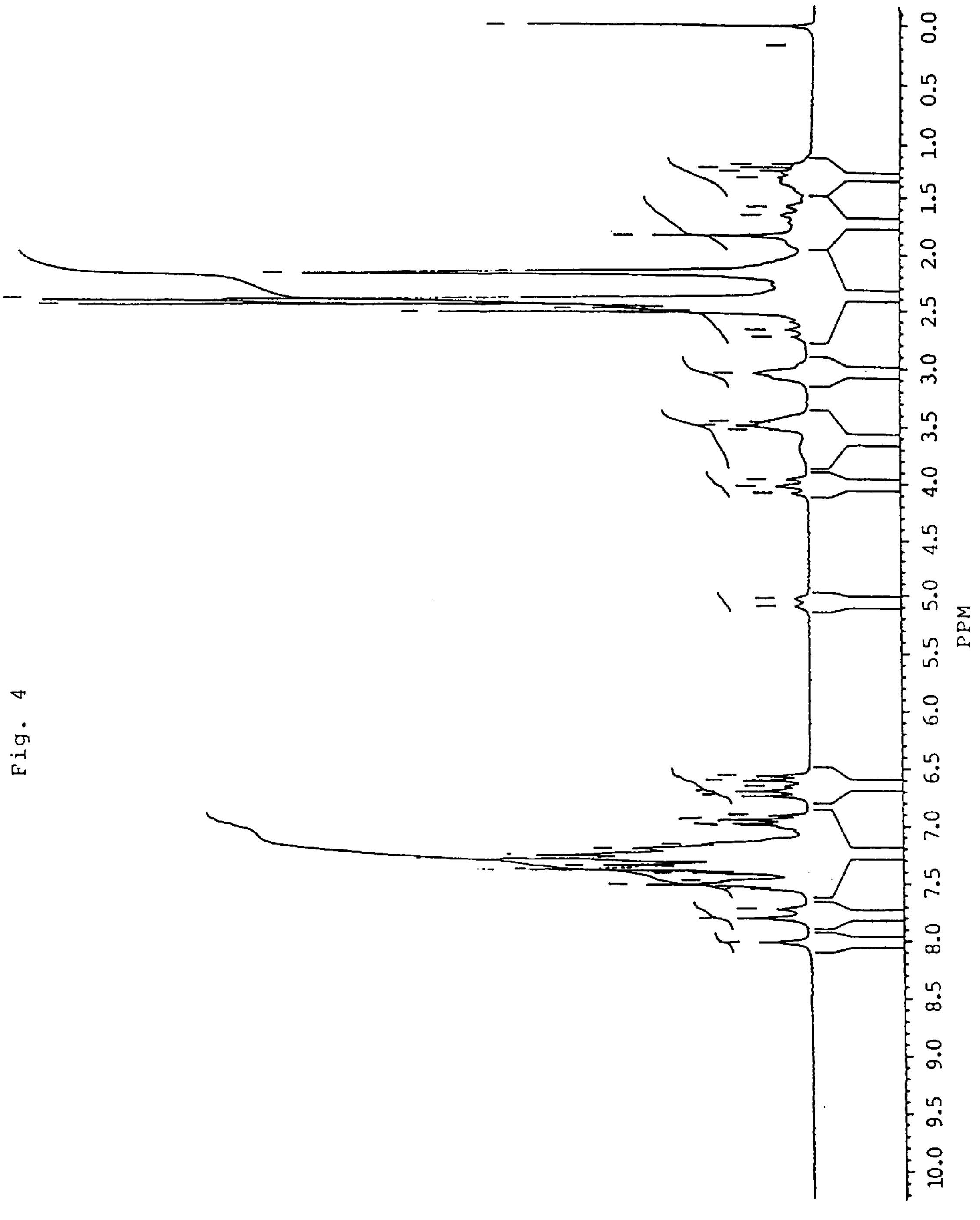

Charts of $^1$H-NMR ($CDCl_3$) of the starting compound (G) and the compound obtained in Exmaple 979 are shown in FIG. 3 and FIG. 4, respectively.

REFERENCE EXAMPLE 18

Using the suitable starting materials, the following compounds are obtained in the same manner as in Reference Example 1.

7-Methoxy-5-oxo-1-(4-nitrobenzoyl)-2,3,4,5-tetrahydro-1H-benzazepine, colorless needles, m.p. 178–178.5° C. (recrystallized from ethyl acetate/n-hexane)

7-Methoxy-5-oxo-1-(2-chloro-4-nitrobenzoyl)-2,3,4,5-tetrahydro-1H-benzazepine, white powder, m.p. 150–151° C. (recrystallized from ethyl acetate/n-hexane)

7-Methoxy-5-oxo-1-(3-methoxy-4-nitrobenzoyl)-2,3,4,5-tetrahydro-1H-benzazepine, white powder, m.p. 116–118° C. (recrystallized from ethyl acetate/n-hexane)

7-Chloro-5-oxo-1-(3-methoxy-4-nitrobenzoyl)-2,3,4,5-tetrahydro-1H-benzazepine, yellow powder, m.p. 156–158° C. (recrystallized from diethyl ether/dichloromethane)

REFERENCE EXAMPLE 19

Using the suitable starting materials, the following compounds are obtained in the same manner as in Reference Example 2.

7-Methoxy-5-oxo-1-(4-aminobenzoyl)-2,3,4,5-tetrahydro-1H-benzazepine, white powder, m.p. 172.5–173.5° C. (recrystallized from ethyl acetate/n-hexane)

7-Methoxy-5-oxo-1-(2-chloro-4-aminobenzoyl)-2,3,4,5-tetrahydro-1H-benzazepine, white powder, m.p. 153–155° C. (recrystallized from ethyl acetate/n-hexane)

7-Methoxy-5-oxo-1-(3-methoxy-4-aminobenzoyl)-2,3,4,5-tetrahydro-1H-benzazepine, colorless needles, m.p. 170–171° C. (recrystallized from ethyl acetate/n-hexane)

7-Chloro-5-oxo-1-(3-methoxy-4-aminobenzoyl)- 2,3,4,5-tetrahydro-1H-benzazepine, yellow oil $^1$H-NMR ($CDCl_3$) δ; 2.05–2.30 (2H, m), 2.85–3.00 (2H, m), 3.70 (3H, s), 3.85–4.30 (4H, m), 6.42 (1H, d, J=8.1 Hz), 6.64 (1H, dd, J=1.7 Hz, 8.1 Hz), 6.72 (1H, d, J=8.5 Hz), 6.80 (1H, d, J=1.8 Hz), 7.19 (1H, dd, J=2.6 Hz, 8.5 Hz), 7.81 (1H, d, J=2.5 Hz)

Using the suitable starting materials, the compounds of the following Table 7 are obtained in the same manner as in above Examples 1 and 382.

TABLE 7

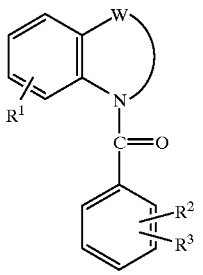

Example 980

Structure

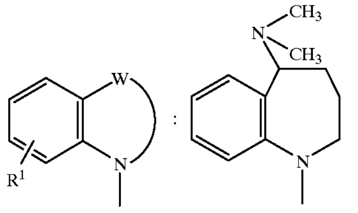

$R^2$: H $R^3$: 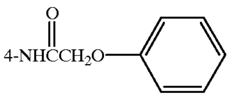

Crystalline form: Colorless amorphous
NMR analysis: 183)
Form: Free

Example 981

Structure

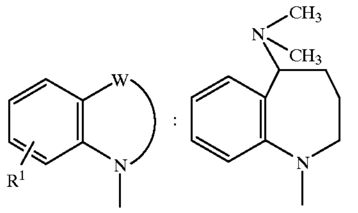

$R^2$: H $R^3$: 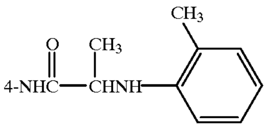

Crystalline form: Colorless amorphous
NMR analysis: 184)
Form: Free

TABLE 7-continued

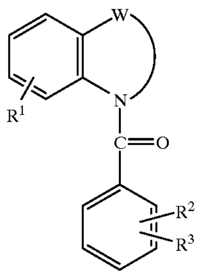

Example 982

Structure

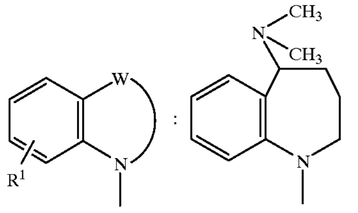

$R^2$: H $R^3$: 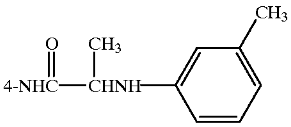

Crystalline form: Colorless amorphous
NMR analysis: 185)
Form: Free

Example 983

Structure

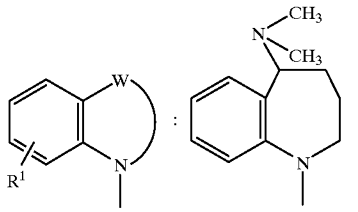

$R^2$: H $R^3$: 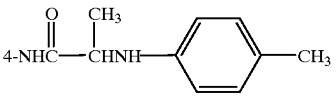

Crystalline form: Colorless amorphous
NMR analysis: 186)
Form: Free

TABLE 7-continued

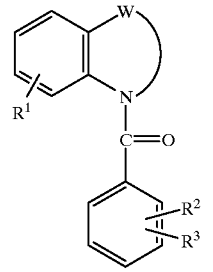

Example 984

Structure

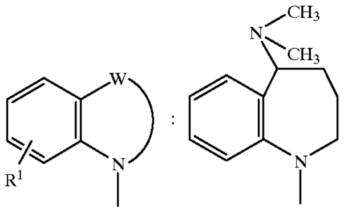

$R^2$: H $R^3$: 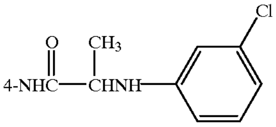

Crystalline form: Colorless amorphous
NMR analysis: 187)
Form: Free

Example 985

Structure

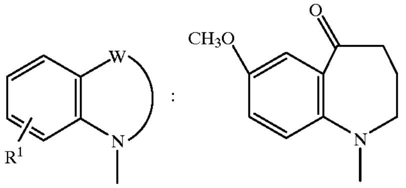

$R^2$: 2-Cl $R^3$: 4-NHCO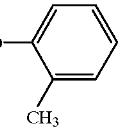

Crystalline form: Colorless amorphous
NMR analysis: 188)
Form: Free

Example 986

Structure

TABLE 7-continued

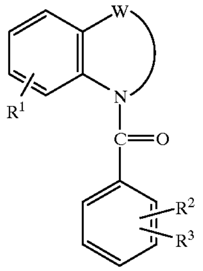

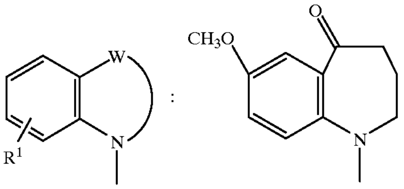

$R^2$: 2-Cl $R^3$: 4-NHCO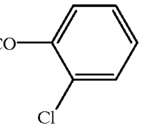

Crystalline form: Colorless amorphous
NMR analysis: 189)
Form: Free

Example 987

Structure

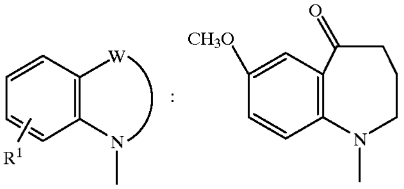

$R^2$: H $R^3$: 4-NHCO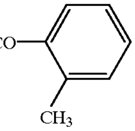

Crystalline form: White powder
Recrystallization solvent: Ethanol/water
Melting Point: 267–268° C.
Form: Free Example 988

Structure

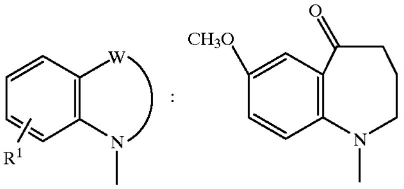

TABLE 7-continued

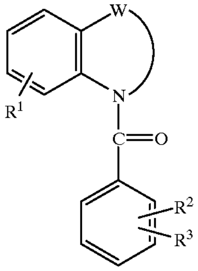

$R^2$: H $R^3$: 4-NHCO
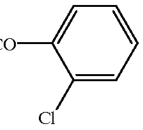

Crystalline form: White powder
Recrystallization solvent: Ethanol/water
Melting Point: 264–266° C.
Form: Free Example 989

Structure

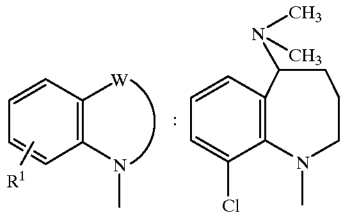

$R^2$: H $R^3$: 4-NHCO
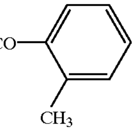

Crystalline form: White powder
Recrystallization solvent: Dichloromethane/diethyl ether
Melting Point: 218–220° C.
Form: Free Example 990

Structure

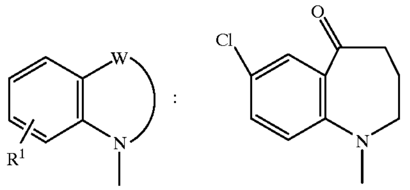

$R^2$: 3-$OCH_3$

TABLE 7-continued

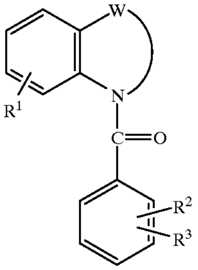

$R^3$: 4-NHCO
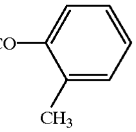

Crystalline form: Yellow oil
NMR analysis: 190)
Form: Free

Example 991

Structure

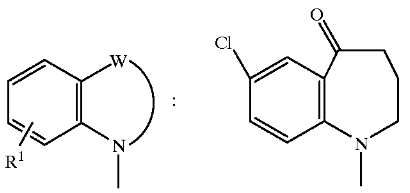

$R^2$: 3-$OCH_3$ $R^3$: 4-NHCO
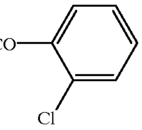

Crystalline form: Yellow oil
NMR analysis: 191)
Form: Free

Example 992

Structure

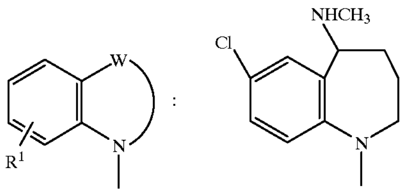

$R^2$: 3-$OCH_3$ $R^3$: 4-NHCO
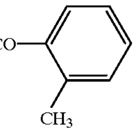

Crystalline form: Yellow powder
Recrystallization solvent: Dichloromethane/diethyl ether
Melting Point: 174–177° C.

TABLE 7-continued

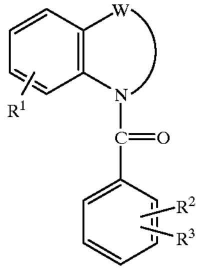

Form: Free

Example 993

Structure

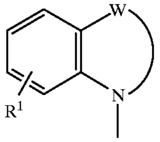
:
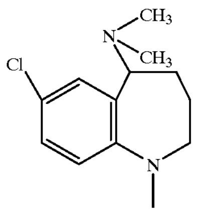

$R^2$: 3-$OCH_3$ $R^3$: 4-NHCO—
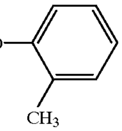

Crystalline form: Yellow amorphous
NMR analysis: 192)
Form: Free

Example 994

Structure

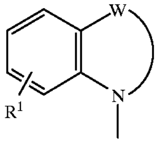
:
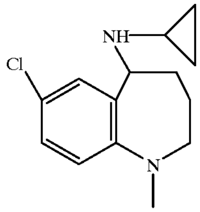

$R^2$: 3-$OCH_3$ $R^3$: 4-NHCO—
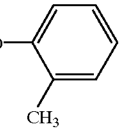

Crystalline form: Colorless amorphous
NMR analysis: 193)
Form: Free

TABLE 7-continued

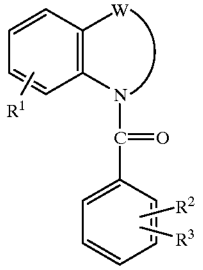

Example 995

Structure

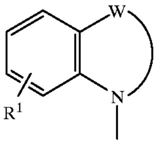
:
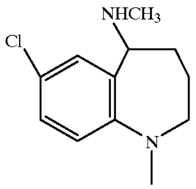

$R^2$: 3-$OCH_3$ $R^3$: 4-NHCO—
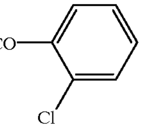

Crystalline form: White powder
Recrystallization solvent: Diethyl ether/dichloromethane
Melting Point: 163–165° C.
Form: Free Example 996

Structure

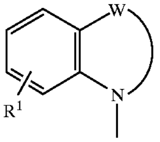
:
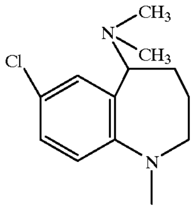

$R^2$: 3-$OCH_3$ $R^3$: 4-NHCO—
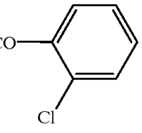

Crystalline form: Colorless amorphous
NMR analysis: 194)
Form: Free

TABLE 7-continued

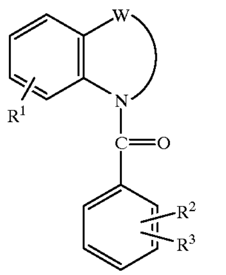

Example 997

Structure

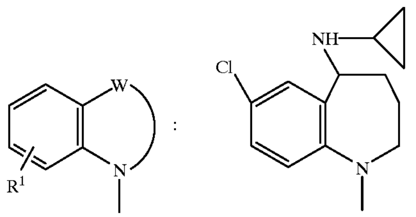

$R^2$: 3-$OCH_3$ $R^3$: 4-NHCO—

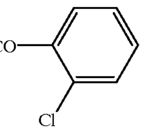

Crystalline form: Colorless amorphous
NMR analysis: 195)
Form: Free

183) $^1$H-NMR($CDCl_3$)δ; 1.10–2.83(11H, m), 2.96–5.21(2H, m), 4.55(2H, s), 6.48–7.72(13H, m), 8.30(1H, brs)
184) $^1$H-NMR($CDCl_3$)δ; 1.10–2.85(11H, m), 1.58(3H, d, J=6.8Hz), 2.23(3H, s), 2.95–5.19(4H, m), 6.38–7.70(12H, m), 8.69(1H, brs)
185) $^1$H-NMR($CDCl_3$)δ; 1.10–2.85(14H, m), 2.26(3H, s), 2.96–5.19(4H, m), 6.36–7.68(12H, m), 8.72(1H, brs)
186) $^1$H-NMR($CDCl_3$)δ; 1.09–2.72(11H, m), 1.53(3H, d, J=6.9Hz), 2.24(3H, s), 2.93–5.21(4H, m), 6.30–7.78(12H, m), 8.76(1H, brs)
187) $^1$H-NMR($CDCl_3$)δ; 1.10–2.82(14H, m), 2.96–5.20(4H, m), 6.38–7.70 (12H, m), 8.54(1H, brs)
188) $^1$H-NMR($CDCl_3$)δ; 1.64–2.28(2H, m), 2.41(3H, s), 2.60–2.90(2H, m), 2.90–3.70(1H, m), 3.76(3H, s), 4.10–5.10(1H, m), 6.60–7.70(10H, m), 8.51 (1H, s)
189) $^1$H-NMR($CDCl_3$)δ; 1.64–2.43(2H, m), 2.67–2.97(2H, m), 3.00–3.70 (1H, m), 3.77(3H, s), 4.20–5.10(1H, m), 6.60–7.75(10H, m), 8.51(1H, s)
190) $^1$H-NMR($CDCl_3$)δ; 2.00–2.35(2H, m), 2.49(3H, s), 2.89(2H, t, J=6.2Hz), 3.72(3H, s), 3.40–4.80(2H, m), 6.74(2H, d, J=8.5Hz), 6.80–7.00 (2H, m), 7.25–7.60(5H, m), 7.80(1H, d, J=2.6Hz), 8.16(1H, s), 8.37(1H, d, J=8.6 Hz)
191) $^1$H-NMR($CDCl_3$)δ; 1.90–2.40(2H, m), 2.90(2H, t, J=6.2Hz), 3.75(3H, s), 3.40–4.80(2H, m), 6.74(1H, d, J=8.5Hz), 6.80–7.00(2H, m), 7.10–7.50 (4H, m), 7.73(1H, dd, J=2.3Hz, 6Hz), 7.80(1H, d, J=2.5Hz), 8.38(1H, d, J=8.8Hz), 8.65(1H, s)
192) $^1$H-NMR($CDCl_3$)δ; 1.10–2.10(13H, m), 2.80–5.20(6H, m), 6.56(1H, d, J=8.4Hz), 6.69(1H, d, J=7Hz), 6.85–7.70(7H, m), 8.15(1H, s), 8.31(1H, d, J=8.4Hz)
193) $^1$H-NMR($CDCl_3$)δ; 0.30–0.65(4H, m), 1.20–2.50(7H, m), 2.50(3H, s), 3.10–5.20(2H, m), 3.75(3H, s), 6.60(1H, d, J=8.3Hz), 6.70–7.60(8H, m), 8.14(1H, s), 8.20–8.40(1H, m)
194) $^1$H-NMR($CDCl_3$)δ; 0.80–2.50(10H, m), 2.90–4.10(6H, m), 6.50–7.80 (9H, m), 8.32(1H, d, J=8Hz), 8.62(1H, s)
195) $^1$H-NMR($CDCl_3$)δ; 0.30–0.65(4H, m), 0.70–2.40(6H, m), 2.60–5.20 (6H, m), 6.50–7.80(9H, m), 8.30(1H, d, J=8Hz), 8.62(1H, s)

REFERENCE EXAMPLE 20

Using the suitable starting materials, the following compounds are obtained in the same manner as in Reference Example 1.

7-Methyl-5-oxo-1-(4-nitrobenzoyl)-2,3,4,5-tetrahydro-1H-benzazepine, white needles $^1$H-NMR ($CDCl_3$) δ; 2.20 (2H, brs), 2.32 (3H, s), 2.88 (2H, t, J=6.3 Hz), 3.40–4.79 (2H, m), 6.57 (1H, d, J=8.0 Hz), 7.04 (1H, d, J=7.7 Hz), 7.36 (2H, d, J=8.6 Hz), 7.62 (1H, d, J=1.7 Hz), 8.04 (2H, d, J=8.7 Hz)

7-Dimethylamino-5-oxo-1-(4-nitrobenzoyl)-2,3,4,5-tetrahydro-1H-benzazepine, red brown prisms (recrystallized from dichloromethane/diethyl ether)

$^1$H-NMR ($CDCl_3$) δ; 1.75–2.47 (2H, m), 2.60–3.62, 4.51–4.92 (total 4H, m), 2.93 (6H, s), 6.46 (1H, dd, J=2.2 Hz, 7.0 Hz), 6.52 (1H, d, J=7.0 Hz), 7.33 (2H, d, J=7.0 Hz), 8.00 (2H, d, J=7.0 Hz)

7-Bromo-5-oxo-1-(4-nitrobenzoyl)-2,3,4,5-tetrahydro-1H-benzazepine, white powder (recrystallized from dichloromethane/diethyl ether), m.p. 177–182° C.

7-Chloro-5-oxo-1-(2-methyl-4-nitrobenzoyl)-2,3,4,5-tetrahydro-1H-benzazepine, white powder (recrystallized from dichloromethane/diethyl ether)

$^1$H-NMR ($CDCl_3$) δ;1.78–2.37 (2H, m), 2.48 (3H, s), 2.88 (2H, t, J=6.1 Hz), 3.30–5.12 (2H, m), 6.47–6.82 (1H, m), 6.82–7.09 (1H, m), 7.09–7.27 (1H, m), 7.48–8.35 (3H, m)

6-Oxo-1-(2-chloro-4-nitrobenzoyl)-1,2,3,4,5,6-hexahydrobenzazocine, yellow amorphous $^1$H-NMR ($CDCl_3$) δ; 1.7–2.1 (4H, m), 2.85–4.7 (4H, m), 7.12 (1H, d, J=8.4 Hz), 7.17–7.51 (4H, m), 7.89 (1H, dd, J=7.8 Hz, 2.1 Hz), 8.11 (1H, d, J=2.2 Hz)

8-Chloro-6-oxo-1-(2-chloro-4-nitrobenzoyl)- 1,2,3,4,5,6-hexahydrobenzazocine, yellow amorphous $^1$H-NMR ($CDCl_3$) δ; 1.7–2.15 (4H, m), 2.85–4.8 (4H, m), 7.14 (1H, d, J=8.5 Hz), 7.16 (1H, d, J=8.4 Hz), 7.34 (1H, dd, J=8.3 Hz, 2.5 Hz), 7.85 (1H, d, J=2.5 Hz), 7.94 (1H, dd, J=8.4 Hz, 2.2 Hz), 8.13 (1H, d, J=2.1 Hz)

8-Methyl-6-oxo-1-(2-chloro-4-nitrobenzoyl)-1,2,3,4,5,6-hexahydrobenzazocine, yellow amorphous $^1$H-NMR ($CDCl_3$) δ; 1.65–2.2 (4H, m), 2.33 (3H, s), 2.7–5.0 (4H, m), 7.0–7.25 (3H, m), 7.67 (1H, d, J=2.0 Hz), 7.89 (1H, dd, J=8.4 Hz, 2.2 Hz), 8.10 (1H, d, J=2.1 Hz)

8-Methoxy-6-oxo-1-(2-chloro-4-nitrobenzoyl)-1,2,3,4,5,6-hexahydrobenzazocine, light yellow amorphous $^1$H-NMR ($CDCl_3$) δ; 1.6–2.05 (4H, m), 2.8–5.2 (4H, m), 3.78 (3H, s), 6.88 (1H, dd, J=8.6 Hz, 3.1 Hz), 7.11 (1H, d, J=8.4 Hz), 7.12 (1H, d, J=8.6 Hz), 7.38 (1H, d, J=3.0 Hz), 7.90 (1H, dd, J=8.4 Hz, 2.2 Hz), 8.11 (1H, d, J=2.2 Hz)

7-Chloro-5-oxo-1-(2-chloro-4-nitrobenzoyl)-2,3,4,5-tetrahydro-1H-benzazepine, yellow powder (recrystallized from diethyl ether/dichloromethane), m.p. 125–126.5° C.

REFERENCE EXAMPLE 21

Using the suitable starting materials, the following compounds are obtained in the same manner as in Reference Example 2.

7-Methyl-5-oxo-1-(4-aminobenzoyl)-2,3,4,5-tetrahydro-1H-benzazepine, yellow powder $^1$H-NMR ($CDCl_3$) δ; 2.13 (2H, brs), 2.32 (3H, s), 2.86 (2H, t, J=6.2 Hz), 2.89–5.29 (2H, m), 3.86 (2H, brs), 6.41 (2H, m), 6.65 (1H, d, J=8.1 Hz), 7.06 (3H, m), 7.65 (1H, d, J=1.7 Hz)

7-Dimethylamino-5-oxo-1-(4-aminobenzoyl)-2,3,4,5-tetrahydro-1H-benzazepine, yellow needles (recrystallized from dichloromethane/diethyl ether)

$^1$H-NMR ($CDCl_3$) δ; 1.78–2.49 (2H, m), 2.64–3.78, 4.07–5.02 (total 4H, m), 2.93 (6H, m), 3.96 (2H, m), 6.38

(2H, d, J=8.7 Hz), 6.55 (1H, dd, J=2.7, 8.7 Hz), 6.62 (1H, d, J=8.7 Hz), 6.96–7.18 (3H, m)

7-Bromo-5-oxo-1-(4-aminobenzoyl)-2,3,4,5-tetrahydro-1H-benzazepine, white powder (recrystallized from methanol/diethyl ether)

$^1$H-NMR ($CDCl_3$) δ; 1.98–2.37 (2H, m), 2.88 (2H, t, J=6.3 Hz), 3.52–4.55 (4H, m), 6.28–6.57 (2H, m), 6.57–6.76 (1H, m), 6.92–7.20 (2H, m), 7.28–7.42 (1H, m), 7.90–8.09 (1H, m)

7-Chloro-5-oxo-1-(2-methyl-4-aminobenzoyl)-2,3,4,5-tetrahydro-1H-benzazepine, white powder (recrystallized from dichloromethane/diethyl ether), m.p. 190–191° C.

6-Oxo-1-(2-chloro-4-aminobenzoyl)-1,2,3,4,5,6-hexahydrobenzazocine, light yellow amorphous $^1$H-NMR ($CDCl_3$) δ; 1.3–2.25 (4H, m), 2.8–4.4 (6H, m), 6.1–6.9 (3H, m), 6.95–7.75 (3H, m), 7.8–8.3 (1H, m)

8-Chloro-6-oxo-1-(2-chloro-4-aminobenzoyl)-1,2,3,4,5,6-hexahydrobenzazocine, light yellow amorphous $^1$H-NMR ($CDCl_3$) δ; 1.59–2.2 (4H, m), 2.6–4.4 (6H, m), 6.1–6.9 (3H, m), 6.95–7.5 (2H, m), 7.8–8.05 (1H, m)

7-Chloro-5-oxo-1-(2-chloro-4-aminobenzoyl)-2,3,4,5-tetrahydro-1H-benzazepine, yellow powder (recrystallized from diethyl ether/dichloromethane), m.p. 188–191.5° C.

Using the suitable starting materials, the compounds of the following Table 8 are obtained in the same manner as in above Examples 1 and 382.

TABLE 8

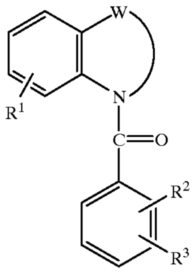

Example 998

Structure

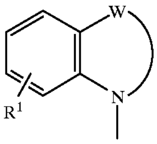
:
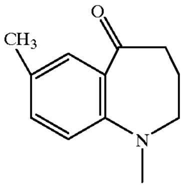

$R^2$: H $R^3$ : 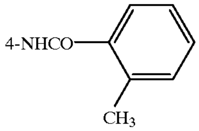

Crystalline form: White powder
NMR analysis: 196)
Form: Free

TABLE 8-continued

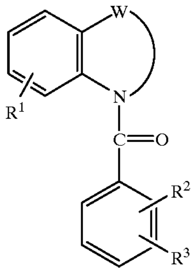

Example 999

Structure

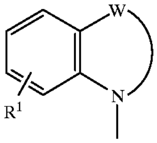
:
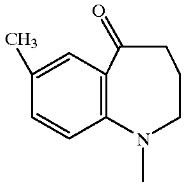

$R^2$: H $R^3$ : 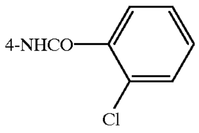

Crystalline form: White powder
NMR analysis: 197)
Form: Free

Example 1000

Structure

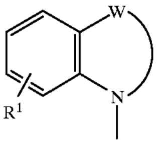
:
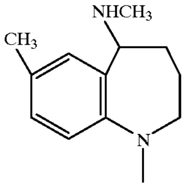

$R^2$: H $R^3$ : 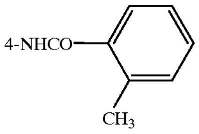

Crystalline form: White powder
Recrystallization solvent: Dichloromethane/diethyl ether
Melting Point: 200–205° C.
Form: Free TABLE 8-continued

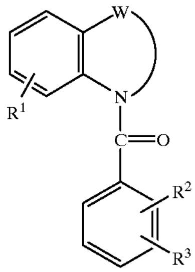

Example 1001

Structure

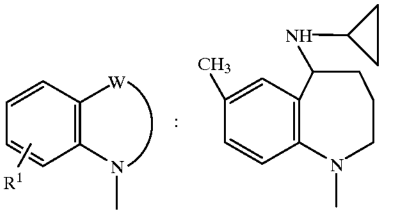

$R^2$: H $R^3$ : 4-NHCO 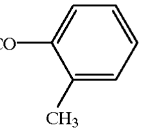

Crystalline form: Colorless amorphous
NMR analysis: 198)
Form: Free

Example 1002

Structure

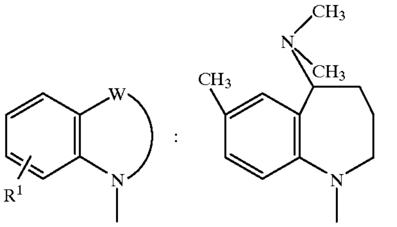

$R^2$: H $R^3$ : 4-NHCO 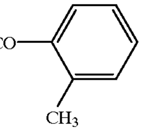

Crystalline form: White powder
Recrystallization solvent: Dichloromethane/diethyl ether
Melting Point: 234–238° C.
Form: Free TABLE 8-continued

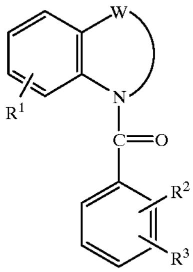

Example 1003

Structure

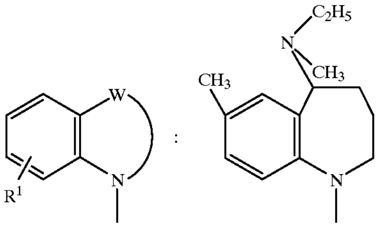

$R^2$: H $R^3$ : 4-NHCO 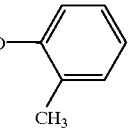

Crystalline form: White powder
Recrystallization solvent: Ethyl acetate/n-hexane
Melting Point: 174–178° C.
Form: Free Example 1004

Structure

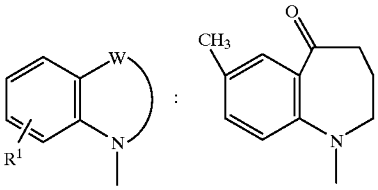

$R^2$: 2-Cl $R^3$ : 4-NHCO 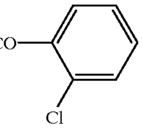

Crystalline form: Light yellow amorphous
NMR analysis: 199)
Form: Free

TABLE 8-continued

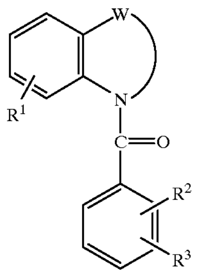

Example 1005

Structure

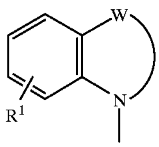 : 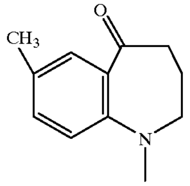

$R^2$: 2-Cl $R^3$ : 4-NHCO 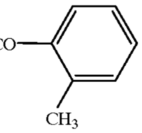

Crystalline form: Light yellow amorphous
NMR analysis: 200)
Form: Free

Example 1006

Structure

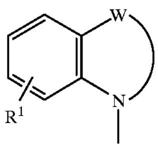 : 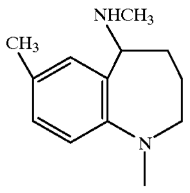

$R^2$: 2-Cl $R^3$ : 4-NHCO 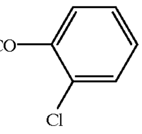

Crystalline form: Light yellow amorphous
NMR analysis: 201)
Form: Free

TABLE 8-continued

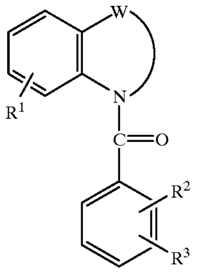

Example 1007

Structure

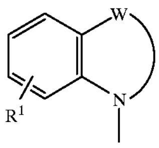 : 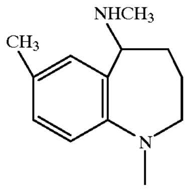

$R^2$: 2-Cl $R^3$ : 4-NHCO 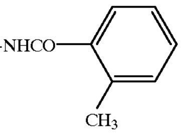

Crystalline form: Light yellow amorphous
NMR analysis: 202)
Form: Free

Example 1008

Structure

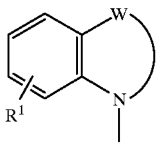 : 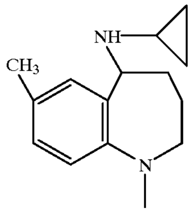

$R^2$: 2-Cl $R^3$ : 4-NHCO 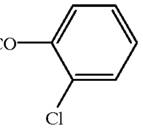

Crystalline form: Light yellow amorphous
MNR analysis: 203)
Form: Free

TABLE 8-continued

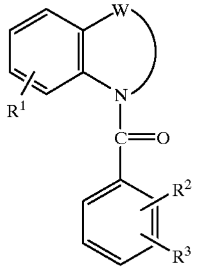

Example 1009

Structure

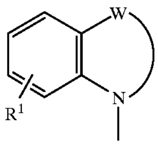
:
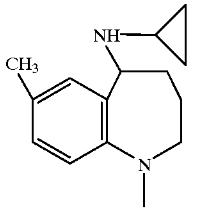

$R^2$: 2-Cl

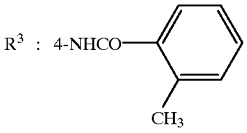

Crystalline form: Light yellow amorphous
NMR analysis: 204)
Form: Free

Example 1010

Structure

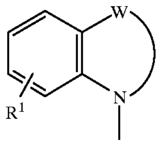
:
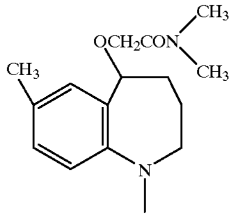

$R^2$: H

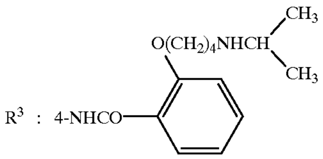

Crystalline form: Colorless amorphous
NMR analysis: 205)
Form: Free

TABLE 8-continued

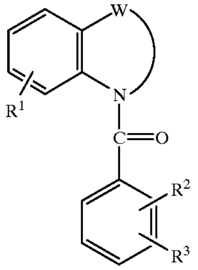

Example 1011

Structure

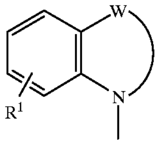
:
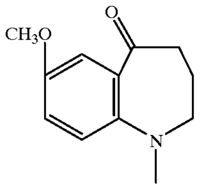

$R^2$: 3-$OCH_3$

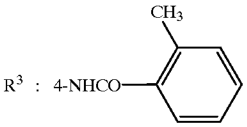

Crystalline form: White powder
Recrystallization solvent: Ethyl acetate/n-hexane
Melting Point: 153–155° C.
Form: Free Example 1012

Structure

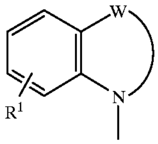
:
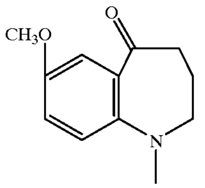

$R^2$: 3-$OCH_3$

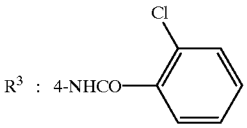

Crystalline form: White powder
Recrystallization solvent: Ethyl acetate/n-hexane
Melting Point: 142–143° C.
Form: Free TABLE 8-continued

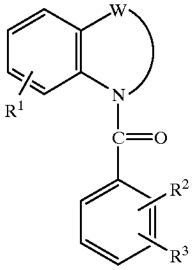

Example 1013

Structure

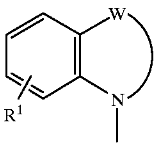 : 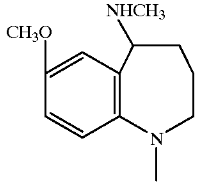

R$^2$: H

R$^3$ : 4-NHCO 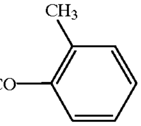

Crystalline form: White powder
Recrystallization solvent: Ethyl acetate/n-hexane
Melting Point: 176–178° C.
Form: Free Example 1014

Structure

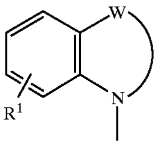 : 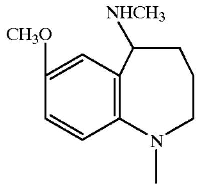

R$^2$: H

R$^3$ : 4-NHCO 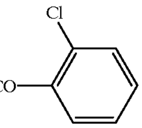

Crystalline form: White powder
Recrystallization solvent: Ethyl acetate/n-hexane
Melting Point: 186–188° C.
Form: Free TABLE 8-continued

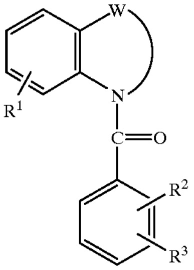

Example 1015

Structure

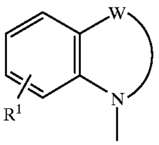 : 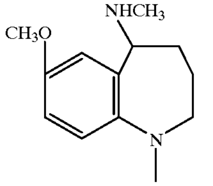

R$^2$: 2-Cl

R$^3$ : 4-NHCO 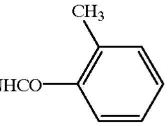

Crystalline form: Colorless amorphous
NMR analysis: 206)
Form: Free

Example 1016

Structure

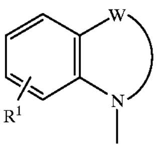 : 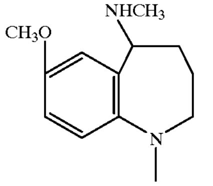

R$^2$: 2-Cl

R$^3$ : 4-NHCO 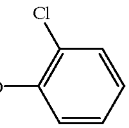

Crystalline form: Colorless amorphous
NMR analysis: 207)
Form: Free

TABLE 8-continued

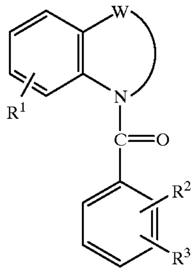

Example 1017

Structure

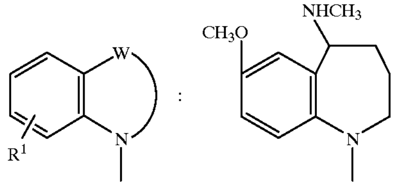

$R^2$: 3-$OCH_3$ $R^3$ : 4-NHCO 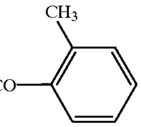

Crystalline form: White powder
Recrystallization solvent: Ethyl acetate/n-hexane
Melting Point: 191–191.5° C.
Form: Free Example 1018

Structure

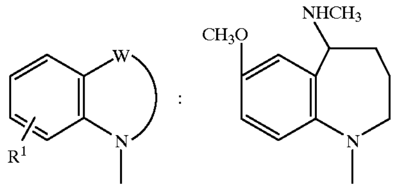

$R^2$: 3-$OCH_3$ $R^3$ : 4-NHCO 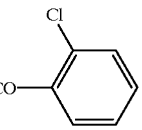

Crystalline form: White powder
Recrystallization solvent: Ethyl acetate/n-hexane
Melting Point: 210–212° C.
Form: Free TABLE 8-continued

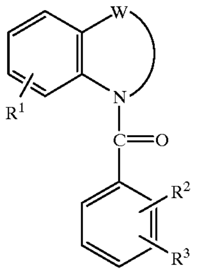

Example 1019

Structure

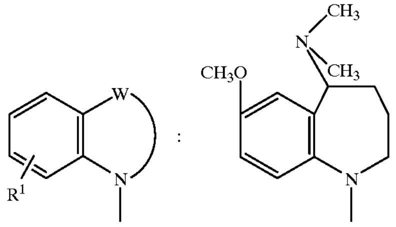

$R^2$: H $R^3$ : 4-NHCO 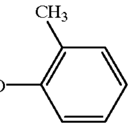

Crystalline form: White powder
Recrystallization solvent: Ethyl acetate/n-hexane
Melting Point: 196–198° C.
Form: Free Example 1020

Structure

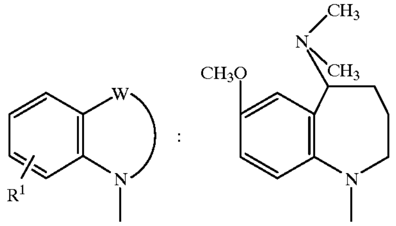

$R^2$: H $R^3$ : 4-NHCO 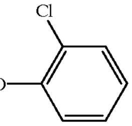

Crystalline form: Colorless amorphous
NMR analysis: 208)
Form: Free

TABLE 8-continued

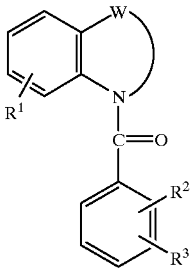

Example 1021

Structure

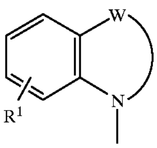
:
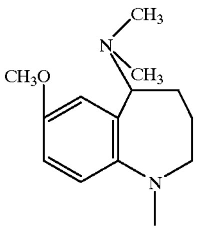

$R^2$: 2-Cl $R^3$ : 4-NHCO
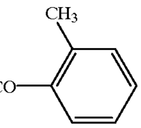

Crystalline form: Colorless amorphous
NMR analysis: 209)
Form: Free

Example 1022

Structure

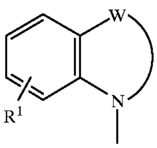
:
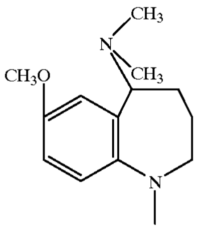

$R^2$: 2-Cl $R^3$ : 4-NHCO
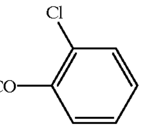

Crystalline form: Colorless amorphous
NMR analysis: 210)
Form: Free

TABLE 8-continued

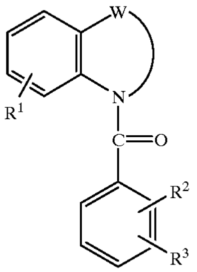

Example 1023

Structure

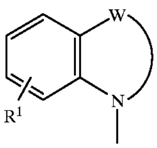
:
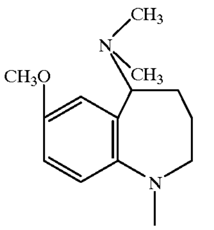

$R^2$: 3-$OCH_3$ $R^3$ : 4-NHCO
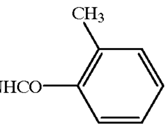

Crystalline form: Colorless amorphous
NMR analysis: 211)
Form: Free

Example 1024

Structure

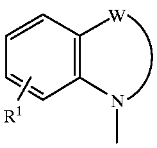
:
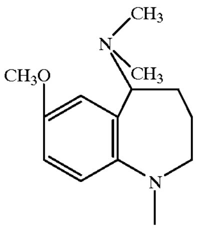

$R^2$: 3-$OCH_3$ $R^3$ : 4-NHCO
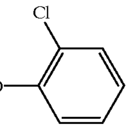

Crystalline form: Colorless amorphous
NMR analysis: 212)
Form: Free

TABLE 8-continued

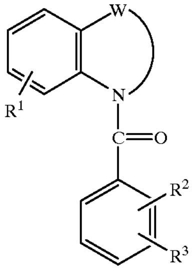

Example 1025

Structure

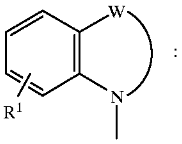
:
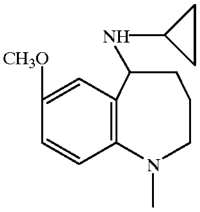

$R^2$: 2-Cl $R^3$ : 4-NHCO
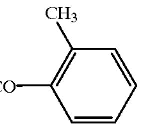

Crystalline form: Colorless amorphous
NMR analysis: 213)
Form: Free

Example 1026

Structure

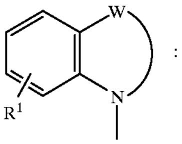
:
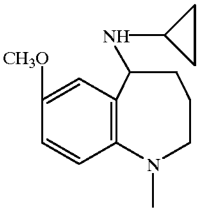

$R^2$: 2-Cl $R^3$ : 4-NHCO
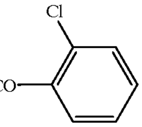

Crystalline form: Colorless amorphous
NMR analysis: 214)
Form: Free

TABLE 8-continued

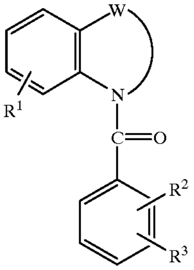

Example 1027

Structure

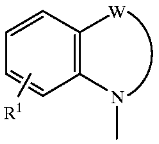
:
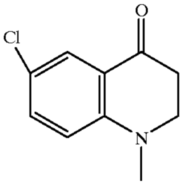

$R^2$: 2-Cl $R^3$ : 4-NHCO
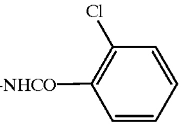

Crystalline form: Colorless prisms
Recrystallization solvent: Ethanol
Melting Point: 207–208° C.
Form: Free Example 1028

Structure

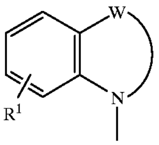
:
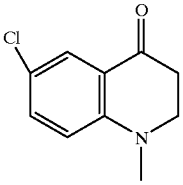

$R^2$: 2-Cl $R^3$ : 4-NHCO
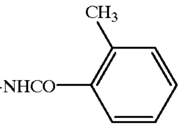

Crystalline form: White powder
Recrystallization solvent: Ethanol
Melting Point: 201–202° C.
Form: Free TABLE 8-continued

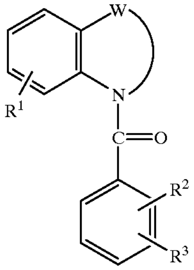

Example 1029

Structure

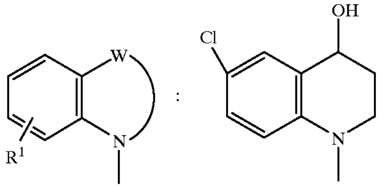

$R^2$: 2-Cl $R^3$ : 4-NHCO

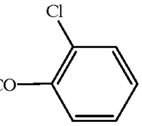

Crystalline form: White powder
Recrystallization solvent: Ethanol
Melting Point: 193–194° C.
Form: Free Example 1030

Structure

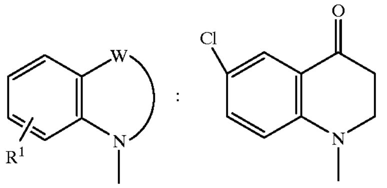

$R^2$: H $R^3$ : 4-NHCO

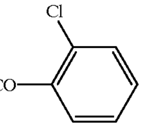

Crystalline form: White powder
Recrystallization solvent: Ethanol
Melting Point: 205–208° C.
Form: Free TABLE 8-continued

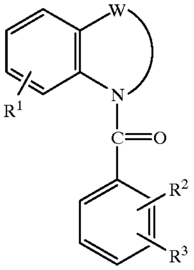

Example 1031

Structure

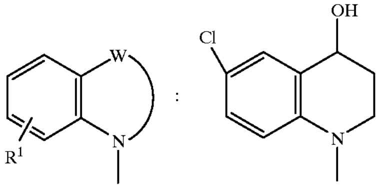

$R^2$: H $R^3$ : 4-NHCO

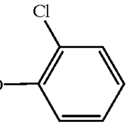

Crystalline form: White powder
Recrystallization solvent: Ethanol
Melting Point: 214–216° C.
Form: Free Example 1032

Structure

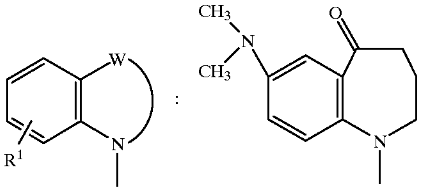

$R^2$: H $R^3$ : 4-NHCO

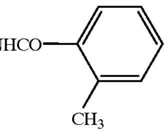

Crystalline form: Yellow needles
Recrystallization solvent: Ethanol
Melting Point: 223–226° C.
Form: Free TABLE 8-continued

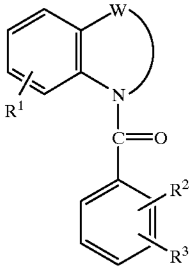

Example 1033

Structure

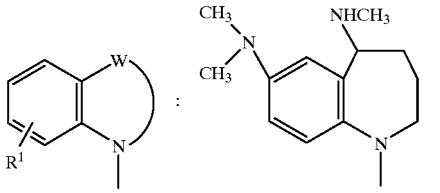

$R^2$: H $R^3$ : 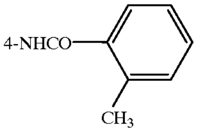

Crystalline form: Colorless needles
Recrystallization solvent: Ethanol/diethyl ether
Melting Point: 203–206° C.
Form: Free Example 1034

Structure

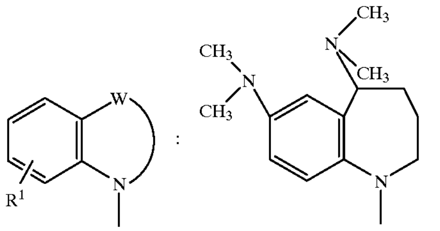

$R^2$: H $R^3$ : 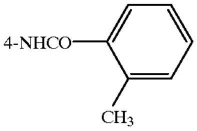

Crystalline form: Colorless needles
Recrystallization solvent: Ethanol/diethyl ether/n-hexane
Melting Point: 168–171° C.
Form: Free TABLE 8-continued

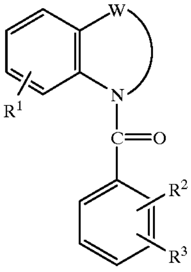

Example 1035

Structure

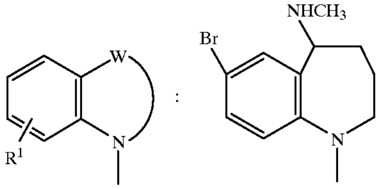

$R^2$: H $R^3$ : 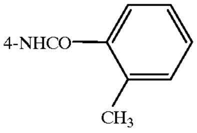

Crystalline form: White powder
Recrystallization solvent: Methanol/diethyl ether
Melting Point: 206–208° C.
Form: Free Example 1036

Structure

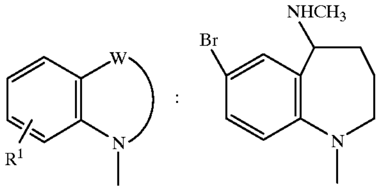

$R^2$: H $R^3$ : 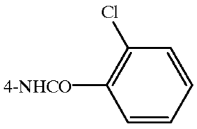

Crystalline form: White powder
Recrystallization solvent: Methanol/diethyl ether
Melting Point: 229–232° C.
Form: Free TABLE 8-continued

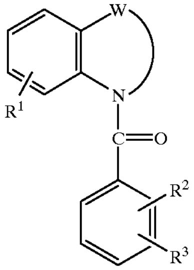

Example 1037

Structure

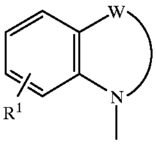
:
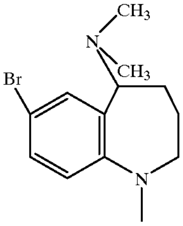

$R^2$: H $R^3$ : 4-NHCO 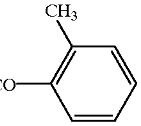

Crystalline form: White powder
Recrystallization solvent: Methanol/diethyl ether
Melting Point: 220–222° C.
Form: Free Example 1038

Structure

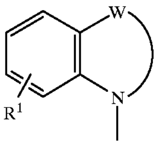
:
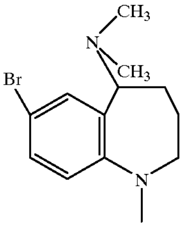

$R^2$: H $R^3$ : 4-NHCO 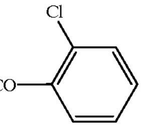

Crystalline form: White powder
Recrystallization solvent: Methanol/diethyl ether
Melting Point: 232–233.5° C.
Form: Free TABLE 8-continued

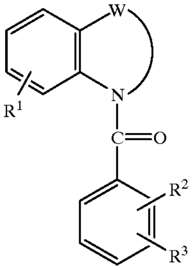

Example 1039

Structure

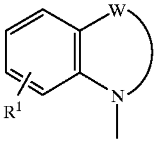
:
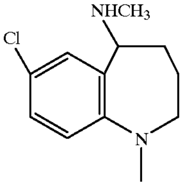

$R^2$: 2-$CH_3$ $R^3$ : 4-NHCO 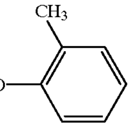

Crystalline form: Colorless amorphous
NMR analysis: 215)
Form: Free

Example 1040

Structure

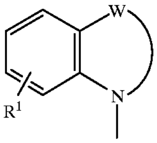
:
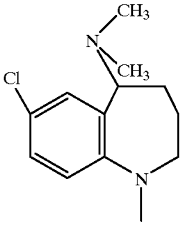

$R^2$: 2-$CH_3$ $R^3$ : 4-NHCO 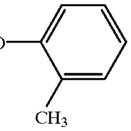

Crystalline form: Colorless amorphous
NMR analysis: 216)
Form: Free

TABLE 8-continued

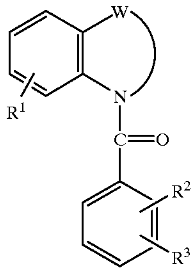

Example 1041

Structure

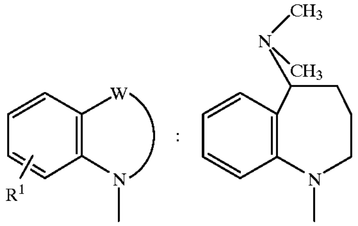

$R^2$: H $R^3$ : 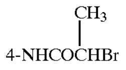

Crystalline form: White powder
Recrystallization solvent: Methanol/diethyl ether
Melting Point: 147–151° C.
Form: Free Example 1042

Structure

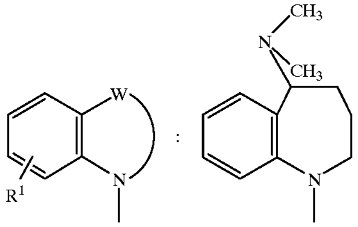

$R^2$: H $R^3$ : 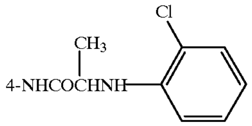

Crystalline form: White powder
Recrystallization solvent: Methanol/n-hexane
Melting Point: 127–129° C.
Form: Free TABLE 8-continued

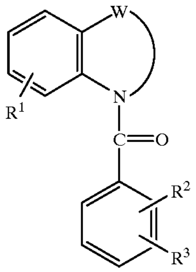

Example 1043

Structure

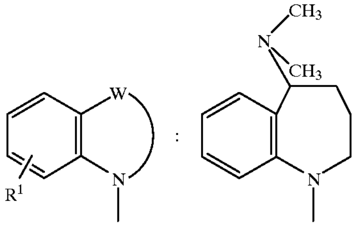

$R^2$: H $R^3$ : 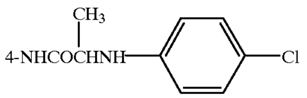

Crystalline form: White powder
Recrystallization solvent: Methanol/n-hexane
Melting Point: 109–112° C.
Form: Free Example 1044

Structure

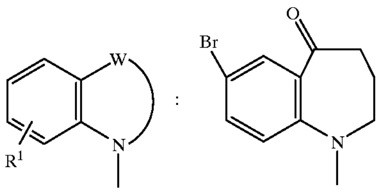

$R^2$: H $R^3$ : 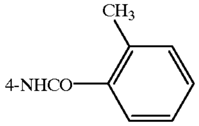

Crystalline form: White powder
Recrystallization solvent: Methanol/diethyl ether
Melting Point: 198–200° C.
Form: Free TABLE 8-continued

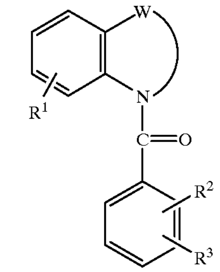

Example 1045

Structure

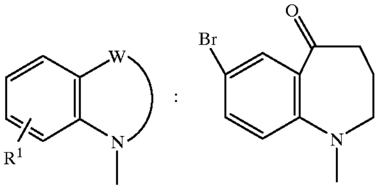

$R^2$: H $R^3$ : 4-NHCO 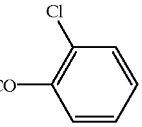

Crystalline form: White powder
Recrystallization solvent: Methanol/diethyl ether
Melting Point: 210–211° C.
Form: Free Example 1046

Structure

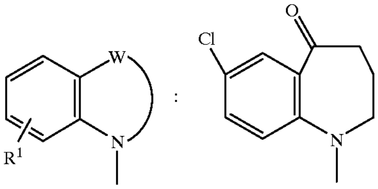

$R^2$: 2-$CH_3$ $R^3$ : 4-NHCO 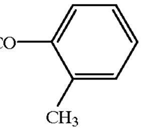

Crystalline form: Colorless amorphous
NMR analysis: 217)
Form: Free

TABLE 8-continued

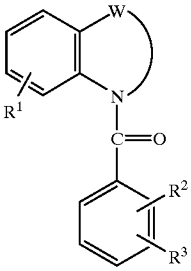

Example 1047

Structure

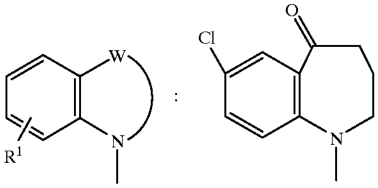

$R^2$: 2-$CH_3$ $R^3$ : 4-NHCO 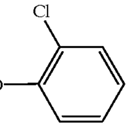

Crystalline form: Colorless amorphous
NMR analysis: 218)
Form: Free

Example 1048

Structure

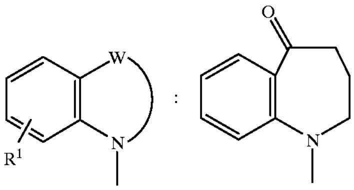

$R^2$: H $R^3$ : 4-NHCO 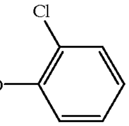

Crystalline form: Colorless amorphous
NMR analysis: 219)
Form: Free

TABLE 8-continued

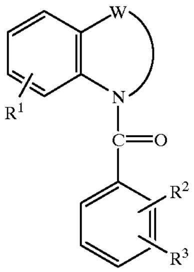

Example 1049

Structure

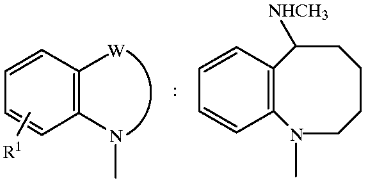

R$^2$: H

R$^3$ : 4-NHCO

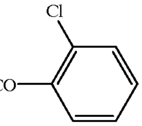

Crystalline form: Colorless needles
Recrystallization solvent: Ethanol
Melting Point: 243–243.5° C.
Form: Free Example 1050

Structure

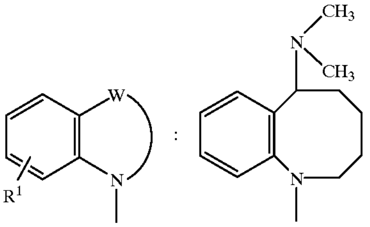

R$^2$: H

R$^3$ : 4-NHCO

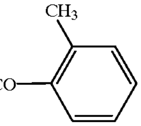

Crystalline form: Colorless prisms
Recrystallization solvent: Ethanol/petroleum ether
Melting Point: 207–209° C.
Form: Free TABLE 8-continued

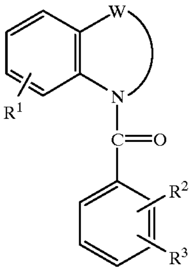

Example 1051

Structure

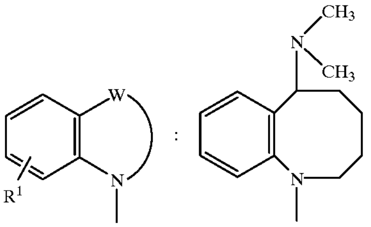

R$^2$: H

R$^3$ : 4-NHCO

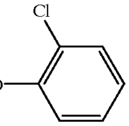

Crystalline form: Colorless needles
Recrystallization solvent: Ethanol/petroleum ether
Melting Point: 239–241° C.
Form: Free Example 1052

Structure

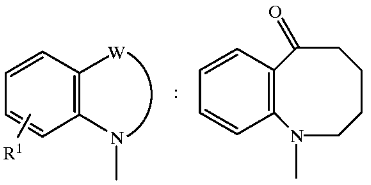

R$^2$: 2-Cl

R$^3$ : 4-NHCO

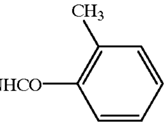

Crystalline form: Colorless amorphous
NMR analysis: 220)
Form: Free

Example 1053

Structure

TABLE 8-continued

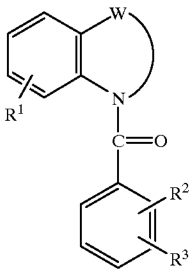

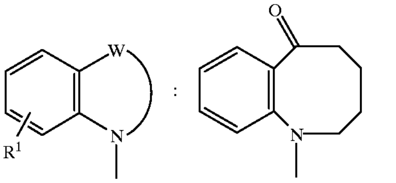

R$^2$: 2-Cl

R$^3$ : 4-NHCO— 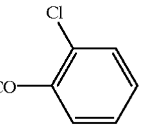

Crystalline form: Colorless amorphous
NMR analysis: 221)
Form: Free

Example 1054

Structure

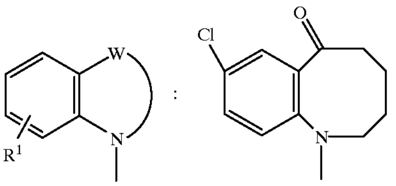

R$^2$: 2-Cl

R$^3$ : 4-NHCO— 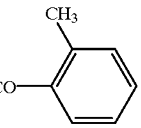

Crystalline form: Light yellow amorphous
NMR analysis: 222)
Form: Free

Example 1055

Structure

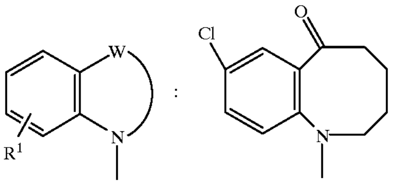

R$^2$: 2-Cl

TABLE 8-continued

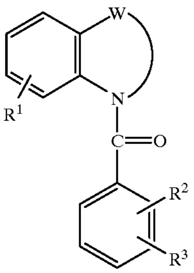

R$^3$ : 4-NHCO— 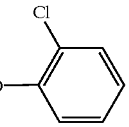

Crystalline form: Light yellow amorphous
NMR analysis: 223)
Form: Free

Example 1056

Structure

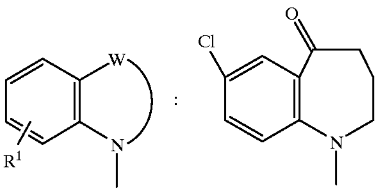

R$^2$: 2-Cl

R$^3$ : 4-NHCO— 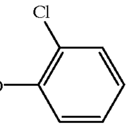

Crystalline form: White powder
Recrystallization solvent: Diethyl ether/dichloromethane
Melting Point: 169.5–173° C.
Form: Free Example 1057

Structure

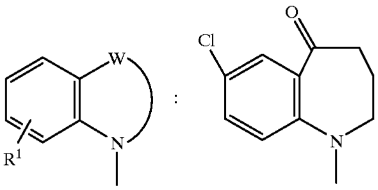

R$^2$: 2-Cl

R$^3$ : 4-NHCO— 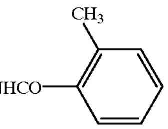

Crystalline form: Colorless amorphous

TABLE 8-continued

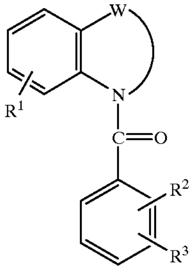

NMR analysis: 224)
Form: Free

Example 1058

Structure

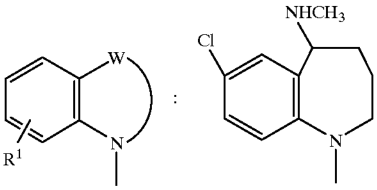

$R^2$: 2-Cl $R^3$ : 4-NHCO 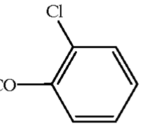

Crystalline form: Colorless amorphous
NMR analysis: 225)

Example 1059

Structure

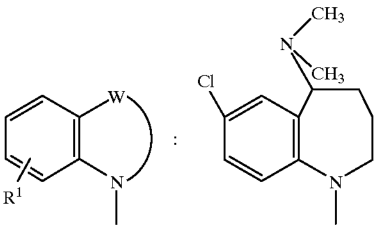

$R^2$: 2-Cl $R^3$ : 4-NHCO 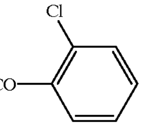

Crystalline form: Colorless amorphous
NMR analysis: 226)
Form: Free

TABLE 8-continued

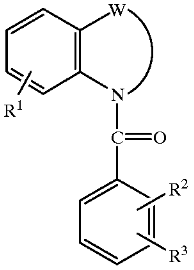

Example 1060

Structure

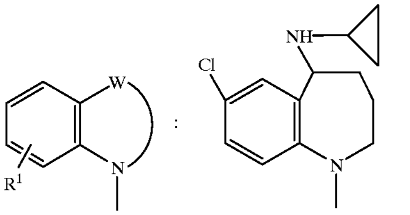

$R^2$: 2-Cl $R^3$ : 4-NHCO 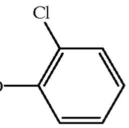

Crystalline form: Colorless amorphous
NMR analysis: 227)
Form: Free

Example 1061

Structure

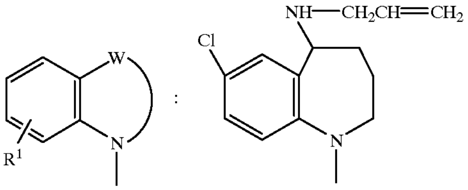

$R^2$: 2-Cl $R^3$ : 4-NHCO 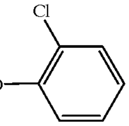

Crystalline form: Colorless amorphous
NMR analysis: 228)
Form: Free

TABLE 8-continued

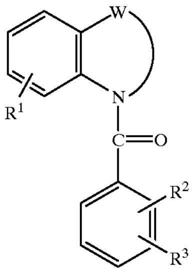

Example 1062

Structure

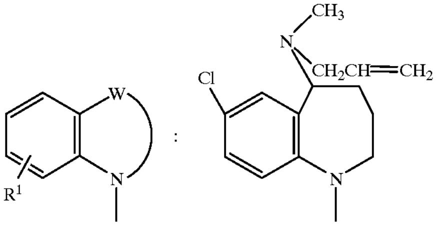

R$^2$: 2-Cl

R$^3$ : 4-NHCO 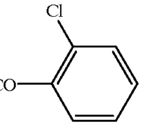

Crystalline form: Colorless amorphous
NMR analysis: 229)
Form: Free

Example 1063

Structure

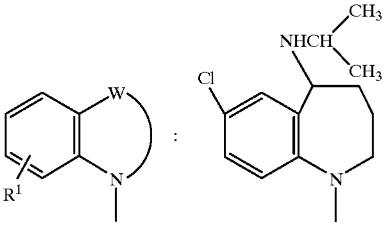

R$^2$: 2-Cl

R$^3$ : 4-NHCO 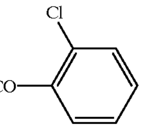

Crystalline form: Colorless amorphous
NMR analysis: 230)
Form: Free

TABLE 8-continued

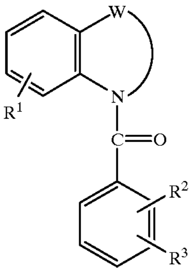

Example 1064

Structure

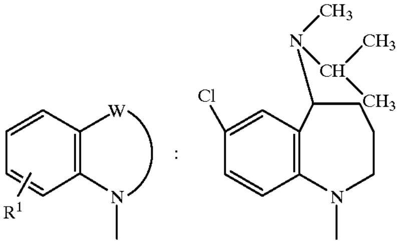

R$^2$: 2-Cl

R$^3$ : 4-NHCO 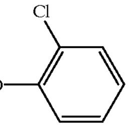

Crystalline form: Colorless amorphous
NMR analysis: 231)
Form: Free

Example 1065

Structure

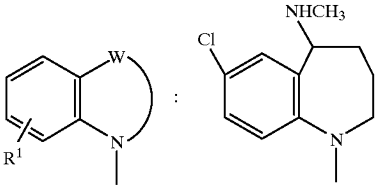

R$^2$: 2-Cl

R$^3$ : 4-NHCO 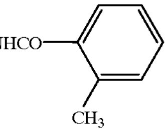

Crystalline form: Colorless amorphous
NMR analysis: 232)
Form: Free

TABLE 8-continued

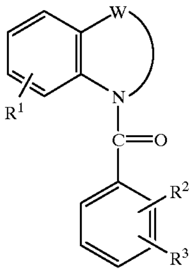

Example 1066

Structure

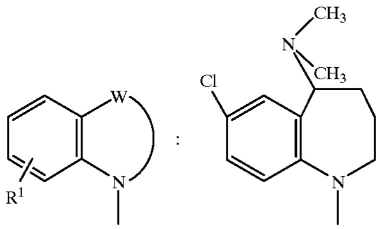

$R^2$: 2-Cl $R^3$ : 4-NHCO 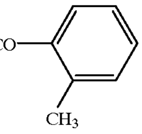

Crystalline form: Colorless amorphous
NMR analysis: 233)
Form: Free

Example 1067

Structure

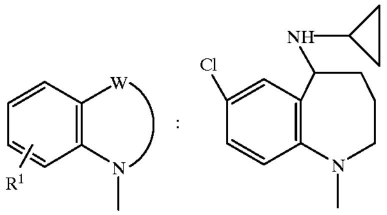

$R^2$: 2-Cl $R^3$ : 4-NHCO 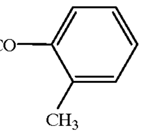

Crystalline form: Colorless amorphous
NMR analysis: 234)
Form: Free

TABLE 8-continued

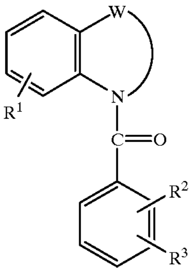

Example 1068

Structure

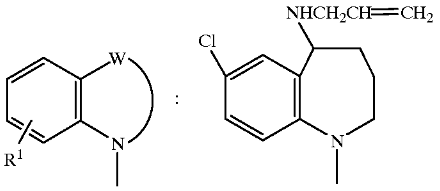

$R^2$: 2-Cl $R^3$ : 4-NHCO 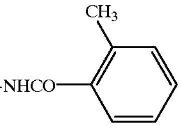

Crystalline form: Colorless amorphous
NMR analysis: 235)
Form: Free

Example 1069

Structure

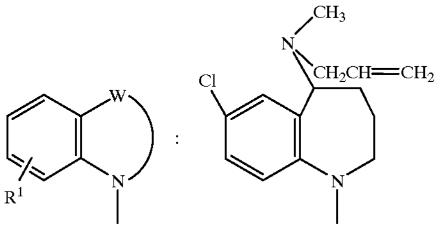

$R^2$: 2-Cl $R^3$ : 4-NHCO 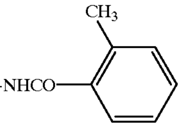

TABLE 8-continued

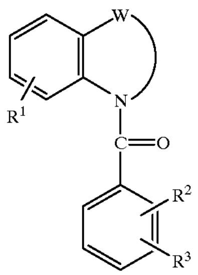

Example 1070

Structure

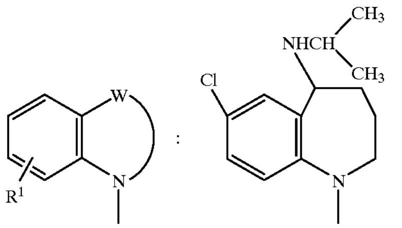

$R^2$: 2-Cl $R^3$ : 4-NHCO— 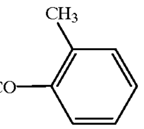

Crystalline form: Colorless amorphous
NMR analysis: 237)
Form: Free

196) $^1$H-NMR($CDCl_3$)δ; 2.14(2H, brs), 2.33(3H, s), 2.46(3H, s), 2.85(2H, t, J=6.1Hz), 4.83(2H, brs), 6.64(1H, d, J=8.1Hz), 7.07(1H, d, J=8.0Hz), 7.21–7.48(8H, m), 7.65(1H, m), 7.74(1H, brs)

197) $^1$H-NMR($CDCl_3$)δ; 2.12(2H, brs), 2.33(3H, s), 2.85(2H, t, J=6.2Hz), 2.88–5.28(2H, m), 6.63(1H, d, J=8.1Hz), 7.06(1H, dd, J=1.7Hz, 8.1Hz), 7.19–7.69(9H, m), 8.26(1H, brs)

198) $^1$H-NMR($CDCl_3$)δ; 0.49(4H, m), 1.25–5.13(9H, m), 2.33(3H, s), 2.45 (3H, s), 6.53(1H, m), 6.79(1H, m), 7.07–7.42(9H, m), 7.73(1H, m)

199) $^1$H-NMR($CDCl_3$)δ; 2.04(2H, brs), 2.29(3H, s), 2.82(2H, t, J=5.9Hz), 2.85–5.29(2H, m), 6.82–7.69(10H, m), 8.31(1H, brs)

200) $^1$H-NMR($CDCl_3$)δ; 2.05(2H, brs), 2.29(3H, s), 2.44(3H, s), 2.79(2H, t, J=5.5Hz), 2.82–5.28(2H, m), 6.82–8.12(11H, m)

201) $^1$H-NMR($CDCl_3$)δ; 1.40–4.85(11H, m), 2.51(3H, s), 6.78–7.63(10H, m), 8.64(1H, brs)

202) $^1$H-NMR($CDCl_3$)δ; 1.40–4.85(11H, m), 2.45(3H, s), 2.50(3H, s), 6.78–7.55(10H, m), 8.10(1H, brs)

203) $^1$H-NMR($CDCl_3$)δ; 0.49(4H, m), 1.25–4.85(9H, m), 2.28(3H, s), 6.77–7.62(10H, m), 8.64(1H, brs)

204) $^1$H-NMR($CDCl_3$)δ; 0.48(4H, m), 1.26–4.85(9H, m), 2.29(3H, s), 2.44 (3H, s), 6.78–7.58(10H, m), 8.18(1H, brs)

205) $^1$H-NMR($CDCl_3$)δ; 1.14(6H, d, J=6.3Hz), 1.52–2.20(7H, m), 2.20–2.60 (1H, m), 2.64–3.66(10H, m), 4.00–4.50(4H, m), 4.50–5.23(2H, m), 6.57–7.90 (11H, m), 8.10–8.30(1H, m), 9.97(1H, s)

206) $^1$H-NMR($CDCl_3$)δ; 1.24–2.08(4H, m), 2.08–2.26(3H, m), 2.26–3.16 (4H, m), 3.47–4.03(4H, m), 4.18–4.92(1H, m), 6.40–7.94(10H, m), 8.45–9.03 (1H, m)

207) $^1$H-NMR($CDCl_3$)δ; 1.26–2.10(4H, m), 2.10–2.28(3H, m), 2.28–3.20 (1H, m), 3.43–4.06(4H, m), 4.20–4.93(1H, m), 6.40–8.00(10H, m), 8.78–9.30 (1H, m)

208) $^1$H-NMR($CDCl_3$)δ; 1.10–1.98(4H, m), 1.98–3.10(7H, m), 3.30–3.90 (4H, m), 3.90–5.10(1H, m), 6.45–8.25(12H, m)

209) $^1$H-NMR($CDCl_3$)δ; 1.06–1.94(4H, m), 1.94–3.19(10H, m), 3.19–3.90 (4H, m), 3.90–5.10(1H, m), 6.44–8.60(11H, m)

210) $^1$H-NMR($CDCl_3$)δ; 1.06–1.97(4H, m), 1.97–3.20(7H, m), 3.20–3.92 (4H, m), 3.92–5.10(1H, m), 6.44–8.55(11H, m)

TABLE 8-continued

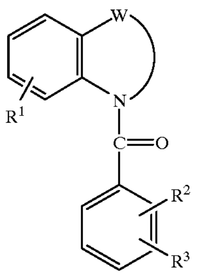

211) $^1$H-NMR($CDCl_3$)δ; 1.07–1.98(4H, m), 1.98–3.10(10H, m), 3.37–5.20 (8H, m), 6.44–6.86(3H, m), 6.97–7.60(6H, m), 8.13(1H, s), 8.19–8.38(1H, m)

212) $^1$H-NMR($CDCl_3$)δ; 1.08–1.99(4H, m), 1.99–3.13(7H, m), 3.33–5.14 (8H, m), 6.40–6.90(3H, m), 6.95–7.56(5H, m), 7.63–7.87(1H, m), 8.17–8.37 (1H, m), 8.60(1H, s)

213) $^1$H-NMR($CDCl_3$)δ; 0.30–0.64(4H, m), 0.70–3.42(9H, m), 3.42–5.10 (5H, m), 6.40–8.70(11H, m)

214) $^1$H-NMR($CDCl_3$)δ; 0.30–0.76(4H, m), 0.80–3.43(6H, m), 3.50–5.00 (5H, m), 6.40–9.04(11H, m)

215) $^1$H-NMR($CDCl_3$)δ; 1.25–3.25(14H, m), 3.55–5.06(2H, m), 6.43–7.00 (2H, m), 7.00–7.71(8H, m), 7.91–8.45(1H, m)

216) $^1$H-NMR($CDCl_3$)δ; 1.11–3.20(17H, m), 3.28–5.12(2H, m), 6.41–7.01 (2H, m), 7.02–7.63(8H, m), 7.76–8.21(1H, m)

217) $^1$H-NMR($CDCl_3$)δ; 1.92–2.29(2H, m), 2.36(3H, s), 2.45(3H, s), 2.84 (2H, t, J=6.3Hz), 3.32–4.64(2H, m), 6.40–8.10(11H, m)

218) $^1$H-NMR($CDCl_3$)δ; 1.92–2.25(2H, m), 2.34(3H, s), 2.83(2H, t, J=6.3Hz), 3.21–4.52(2H, m), 6.39–7.97(10H, m), 8.43(1H, brs)

219) $^1$H-NMR($CDCl_3$)δ; 1.7–2.15(4H, m), 2.5–5.2(4H, m), 6.75–6.9(1H, m), 7.27–7.6(9H, m), 7.65–7.85(1H, m), 7.9–8.15(2H, m)

220) $^1$H-NMR($CDCl_3$)δ; 1.65–2.1(4H, m), 2.44(3H, s), 2.8–4.5(4H, m), 6.75–8.0(12H, m)

221) $^1$H-NMR($CDCl_3$)δ; 1.65–2.3(4H, m), 2.7–4.8(4H, m), 6.75–8.4(12H, m)

222) $^1$H-NMR($CDCl_3$)δ; 1.45–2.15(4H, m), 2.45–2.55(3H, m), 2.85–4.6(4H, m), 6.8–8.25(11H, m)

223) $^1$H-NMR($CDCl_3$)δ; 1.5–2.2(4H, m), 2.8–4.7(4H, m), 6.8–8.4(11H, m)

224) $^1$H-NMR($CDCl_3$)δ; 1.75–2.25(2H, m), 2.30–2.70(3H, m), 2.70–2.95 (2H, m), 3.20–5.10(2H, m), 6.70–8.40(11H, m)

225) $^1$H-NMR($CDCl_3$)δ; 1.20–2.60(8H, m), 2.60–5.10(3H, m), 6.80–7.90 (10H, m), 8.20–8.60(1H, m)

226) $^1$H-NMR($CDCl_3$)δ; 1.20–2.60(10H, m), 2.60–5.10(3H, m), 6.80–8.15 (11H, m)

227) $^1$H-NMR($CDCl_3$)δ; 0.30–0.70(4H, m), 1.20–2.45(6H, m), 2.60–5.10 (3H, m), 6.80–7.95(10H, m), 8.15–8.50(1H, m)

228) $^1$H-NMR($CDCl_3$)δ; 1.20–2.40(5H, m), 2.60–5.35(7H, m), 5.80–6.15 (1H, m), 6.75–7.95(10H, m), 8.20–8.70(1H, m)

229) $^1$H-NMR($CDCl_3$)δ; 1.20–2.55(7H, m), 2.60–5.35(7H, m), 5.85–6.05 (1H, m), 6.70–7.10(2H, m), 7.10–7.90(8H, m), 8.15–8.60(1H, m)

230) $^1$H-NMR($CDCl_3$)δ; 1.00–1.20(6H, m), 1.00–2.40(5H, m), 2.60–5.10 (4H, m), 6.80–8.00(10H, m), 8.15–8,65(1H, m)

231) $^1$H-NMR($CDCl_3$)δ; 0.80–2.50(13H, m), 2.60–5.10(4H, m), 6.70–8.85 (10H, m), 8.25–8.60(1H, m)

232) $^1$H-NMR($CDCl_3$)δ; 1.30–2.60(11H, m), 2.60–5.10(3H, m), 6.80–8.15 (11H, m)

233) $^1$H-NMR($CDCl_3$)δ; 1.10–2.50(13H, m), 2.50–5.10(3H, m), 6.75–8.40 (11H, m)

234) $^1$H-NMR($CDCl_3$)δ; 0.30–0.65(4H, m), 1.20–2.30(6H, m), 2.35–2.55 (3H, m), 2.60–5.10(3H, m), 6.75–8.35(11H, m)

235) $^1$H-NMR($CDCl_3$)δ; 1.20–2.60(8H, m), 2.60–5.40(7H, m), 5.80–6.15 (1H, m), 6.80–8.20(11H, m)

236) $^1$H-NMR($CDCl_3$)δ; 1.25–2.60(10H, m), 2.60–5.40(7H, m), 5.75–6.10 (1H, m), 6.75–7.10(2H, m), 7.10–8.40(9H, m)

237) $^1$H-NMR($CDCl_3$)δ; 0.95–1.20(6H, m), 0.95–2.25(5H, m), 2.40–2.60 (3H, m), 2.60–5.10(4H, m), 6.75–7.05(2H, m), 7.10–8.30(9H, m)

REFERENCE EXAMPLE 22

Using the suitable starting materials, the following compounds are obtained in the same manner as in Reference Example 1.

8-Chloro-6-oxo-1-(4-nitrobenzoyl)-1,2,3,4,5,6-hexahydrobenzazocine, yellow prisms $^1$H-NMR (DMSO-$d_6$) δ; 1.3–2.2 (4H, m), 2.6–5.0 (4H, m), 7.05–8.5 (7H, m)

5-Oxo-7-methyl-1-(2-chloro-4-nitrobenzoyl)-2,3,4,5-tetrahydro-1H-benzazepine, light yellow amorphous $^1$H-NMR ($CDCl_3$) δ; 1.71–2.32 (2H, m), 2.29 (3H, s), 2.86 (2H, t, J=6.3 Hz), 3.10–5.30 (2H, m), 6.84–8.38 (6H, m)

5-Oxo-7-methyl-1-(3-methoxy-4-nitrobenzoyl)- 2,3,4,5-tetrahydro-1H-benzazepine, light yellow amorphous $^1$H-NMR ($CDCl_3$) δ; 2.17 (2H, brs), 2.34 (3H, s), 2.84 (2H, t, J=6.0 Hz), 3.10–5.29 (2H, m), 3.77 (3H, s), 6.67 (1H, d, J=7.9 Hz), 6.85 (2H, m), 7.10 (1H, d, J=8.0 Hz), 7.57–7.65 (2H, m)

5-Oxo-7-dimethylamino-1-(2-chloro-4-nitrobenzoyl)-2,3,4,5-tetrahydro-1H-benzazepine, yellow powder $^1$H-NMR ($CDCl_3$) δ; 1.66–2.38 (2H, m), 2.65–2.88 (2H, m), 2.92 (6H, s), 3.08–3.64, 4.58–5.01 (total 2H, m), 6.49 (1H, dd, J=3.1, 8.7 Hz), 6.82 (1H, d, J=8.7 Hz), 6.90 (1H, d, J=3.1 Hz), 7.02–7.37 (1H, m), 7.94 (1H, dd, J=1.9, 8.4 Hz), 8.08 (1H, d, J=1.9 Hz)

REFERENCE EXAMPLE 23

Using the suitable starting materials, the following compounds are obtained in the same manner as in Reference Example 2.

8-Chloro-6-oxo-1-(4-aminobenzoyl)-1,2,3,4,5,6-hexahydrobenzazocine, light yellow amorphous $^1$H-NMR ($CDCl_3$) δ; 1.7–2.2 (4H, m), 2.3–4.8 (6H, m), 6.4–6.6 (2H, m), 6.74 (1H, d, J=8.5 Hz), 7.1–7.4 (3H, m), 7.99 (1H, d, J=2.6 Hz)

8-Methyl-6-oxo-(2-chloro-4-aminobenzoyl)-1,2,3,4,5,6-hexahydrobenzazocine, colorless amorphous $^1$H-NMR ($CDCl_3$) δ; 1.4–2.1 (4H, m), 2.15–2.6 (3H, m), 2.7–4.4 (6H, m), 6.15–6.35 (1H, m), 6.51 (1H, s), 6.6–6.85 (1H, m), 6.9–7.25 (2H, m), 7.72 (1H, s)

8-Methoxy-6-oxo-(2-chloro-4-aminobenzoyl)-1,2,3,4,5,6-hexahydrobenzazocine, light yellow amorphous $^1$H-NMR ($CDCl_3$) δ; 1.4–2.2 (4H, m), 2.7–5.0 (9H, m), 6.25 (1H, dd, J=8.3 Hz, 2.2 Hz), 6.51 (1H, d, J=2.2 Hz), 6.66 (1H, d, J=8.3 Hz), 6.88 (1H, dd, J=8.6 Hz, 3.0 Hz), 7.23 (1H, d, J=8.6 Hz), 7.43 (1H, d, J=3.0 Hz)

5-Oxo-7-chloro-1-(2-methoxy-4-aminobenzoyl)-2,3,4,5-tetrahydro-1H-benzazepine, colorless particles (recrystallized from methanol/diethyl ether), m.p. 206–208° C.

5-Oxo-7-methyl-1-(2-chloro-4-aminobenzoyl)-2,3,4,5-tetrahydro-1H-benzazepine, light yellow amorphous $^1$H-NMR ($CDCl_3$) δ; 2.09 (2H, brs), 2.29 (3H, s), 3.10–5.00 (2H, m), 3.78 (2H, brs), 6.34–7.54 (6H, m)

5-Oxo-7-methyl-1-(3-methoxy-4-aminobenzoyl)-2,3,4,5-tetrahydro-1H-benzazepine, light yellow amorphous $^1$H-NMR ($CDCl_3$) δ; 2.12 (2H, brs), 2.32 (3H, s), 2.85 (2H, t, J=5.9 Hz), 3.30–5.00 (2H, m), 3.65 (3H, s), 3.98 (2H, brs), 6.40 (1H, d, J=8.1 Hz), 6.64–6.76 (3H, m), 7.06 (1H, dd, J=1.6, 8.1 Hz), 7.63 (1H, d, J=2.0 Hz)

5-Oxo-7-dimethylamino-1-(2-chloro-4-aminobenzoyl)-2,3,4,5-tetrahydro-1H-benzazepine, yellow amorphous $^1$H-NMR ($CDCl_3$) δ; 1.60–2.32 (2H, m), 2.67–5.13 (4H, m), 2.92 (6H, s), 3.75 (2H, s), 6.31 (1H, dd, J=2.1, 8.3 Hz), 6.46 (1H, d, J=2.1 Hz), 6.48 (1H, dd, J=3.1, 8.7 Hz), 6.66–6.89 (2H, m), 6.95 (1H, d, J=3.1 Hz)

Using the stuitable starting materials, the compounds of the following Table 9 are obtained in the same manner as in above Examples 1 and 382.

TABLE 9

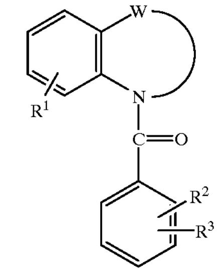

Example 1071

Structure

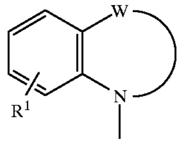
:

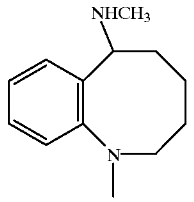
$R^2$: 2-Cl $R^3$: 4-NHCO
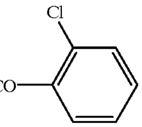

Crystalline form: Colorless prisms
Recrystallization solvent: Ethanol
Melting Point: 227–230° C.
Form: Free Example 1072

Structure

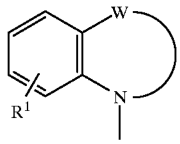
:

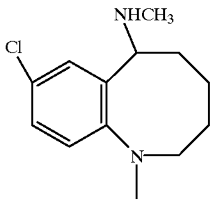
$R^2$: 2-H $R^3$: 4-NHCO
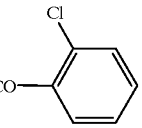

TABLE 9-continued

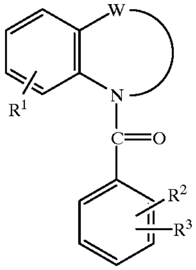

Crystalline form: Colorless needles
Recrystallization solvent: Ethanol/petroleum ether
Melting Point: 216–218° C.
Form: Free Example 1073

Structure

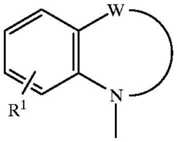
:

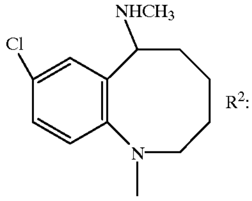
$R^2$: 2-H $R^3$: 4-NHCO 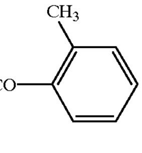

Crystalline form: Colorless prisms
Recrystallization solvent: Ethyl acetate/n-hexane
Melting Point: 227–228° C.
Form: Free Example 1074

Structure

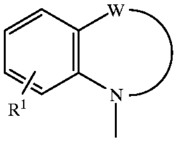
:

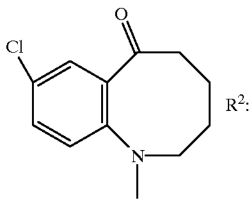
$R^2$: H

TABLE 9-continued

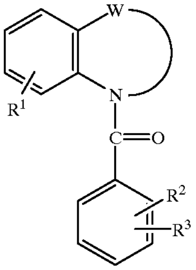

$R^3$: 4-NHCO 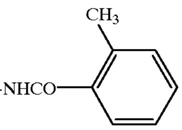

Crystalline form: White powder
NMR analysis: 238)
Form: Free

Example 1075

Structure

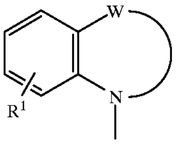
:

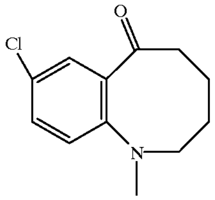
$R^2$: H $R^3$: 4-NHCO 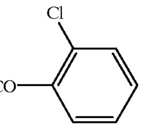

Crystalline form: White powder
NMR analysis: 239)
Form: Free

Example 1076

Structure

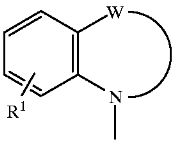
:

TABLE 9-continued

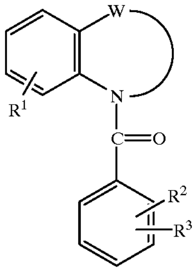

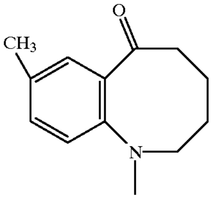
$R^2$: 2-Cl $R^3$: 4-NHCO 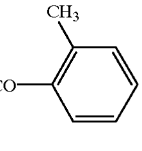

Crystalline form: Light yellow amorphous
NMR analysis: 240)
Form: Free

Example 1077

Structure

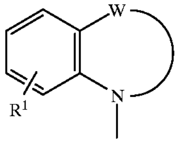 :

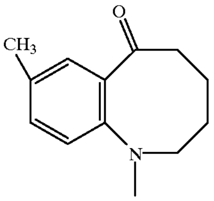
$R^2$: 2-Cl $R^3$: 4-NHCO 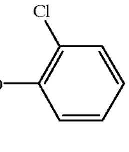

Crystalline form: Light yellow amorphous
NMR analysis: 241)
Form: Free

TABLE 9-continued

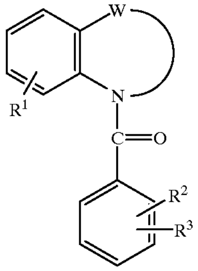

Example 1078

Structure

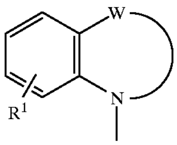 :

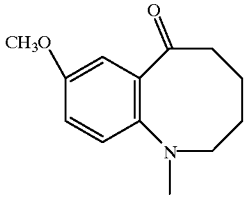
$R^2$: 2-Cl $R^3$: 4-NHCO 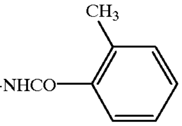

Crystalline form: Colorless amorphous
NMR analysis: 242)
Form: Free

Example 1079

Structure

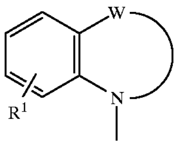 :

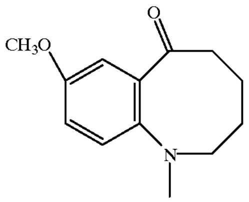
$R^2$: 2-Cl $R^3$: 4-NHCO 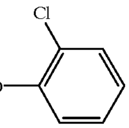

Crystalline form: Colorless amorphous

TABLE 9-continued

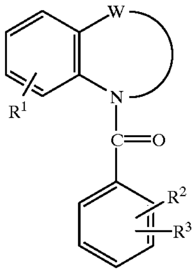

NMR analysis: 243)
Form: Free

Example 1080

Structure

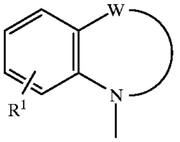 :

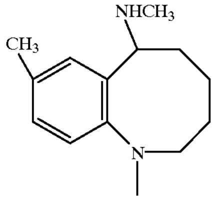 $R^2$: 2-Cl $R^3$: 4-NHCO 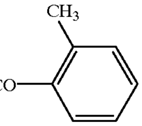

Crystalline form: Light yellow powder
Recrystallization solvent: Ethyl acetate/diethyl ether
Melting Point: 179–181° C.
Form: Free Example 1081

Structure

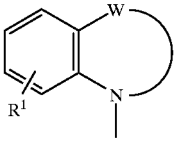 :

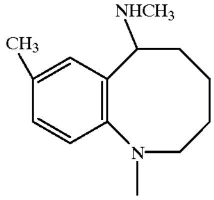 $R^2$: 2-Cl

TABLE 9-continued

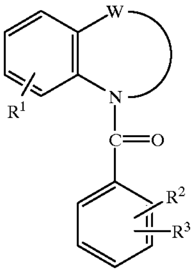

$R^3$: 4-NHCO 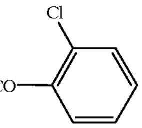

Crystalline form: White powder
Recrystallization solvent: Ethyl acetate/diethyl ether
Melting Point: 213–216° C.
Form: Free Example 1082

Structure

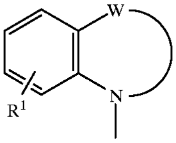 :

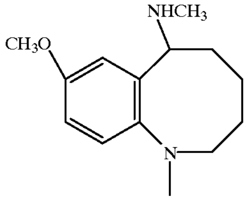 $R^2$: 2-Cl $R^3$: 4-NHCO 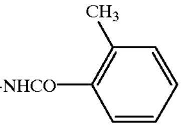

Crystalline form: Light yellow powder
Recrystallization solvent: Ethyl acetate/diethyl ether
Melting Point: 185–187° C.
Form: Free Example 1083

Structure

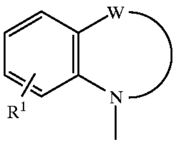 :

TABLE 9-continued

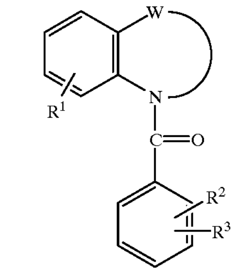

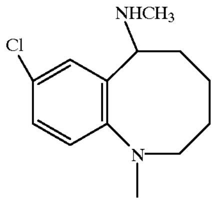

$R^2$: 2-H $R^3$: 4-NHCO—
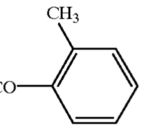

Crystalline form: Colorless prisms
Recrystallization solvent: Ethanol
Melting Point: 249–251° C.
Form: Free Example 1084

Structure

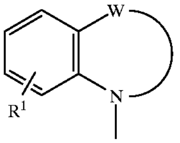
:

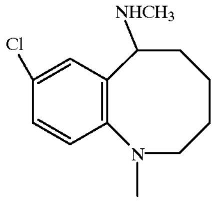

$R^2$: 2-H $R^3$: 4-NHCO—
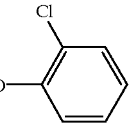

Crystalline form: Colorless needles
Recrystallization solvent: Ethanol
Melting Point: 239–241° C.
Form: Free TABLE 9-continued

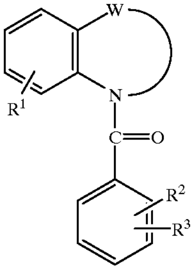

Example 1085

Structure

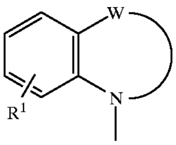
:

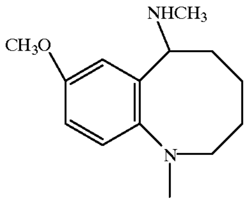

$R^2$: 2-Cl $R^3$: 4-NHCO—
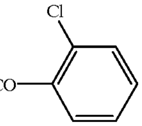

Crystalline form: White powder
Recrystallization solvent: Ethyl acetate/diethyl ether
Melting Point: 208–210° C.
Form: Free Example 1086

Structure

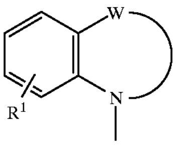
:

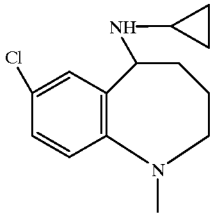

$R^2$: 2-$OCH_3$ $R^3$: 4-NHCO—
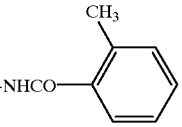

TABLE 9-continued

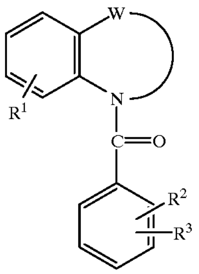

Crystalline form: White powder
Recrystallization solvent: Methanol/n-hexane
Melting Point: 178–108.5° C.
Form: Free Example 1087

Structure

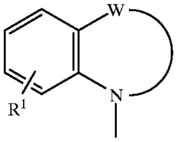
:

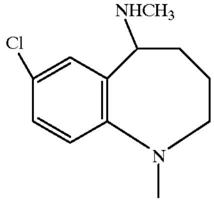
$R^2$: 2-OCH$_3$ $R^3$: 4-NHCO 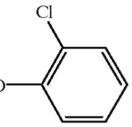

Crystalline form: Colorless amorphous
NMR analysis: 244)
Form: Free

Example 1088

Structure

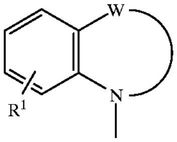
:

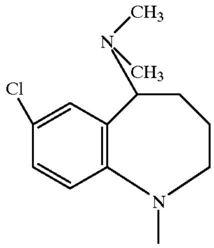
$R^2$: 2-OCH$_3$

TABLE 9-continued

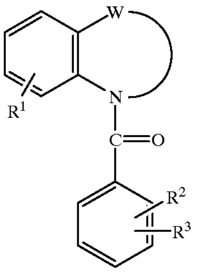

$R^3$: 4-NHCO 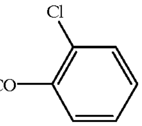

Crystalline form: Colorless amorphous
NMR analysis: 245)
Form: Free

Example 1089

Structure

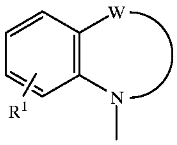
:

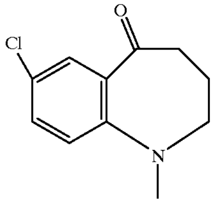
$R^2$: 2-OCH$_3$ $R^3$: 4-NHCOO—CH$_2$— 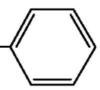

Crystalline form: White powder
Recrystallization solvent: Methanol/diethyl ether
NMR analysis: 246)
Form: Free Example 1090

Structure

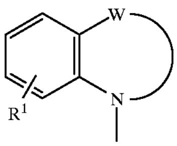
:

TABLE 9-continued
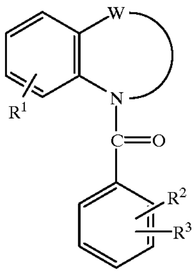
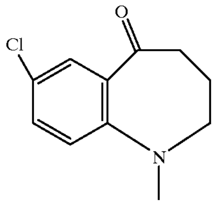
R$^2$: 2-OCH$_3$
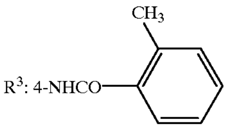
Crystalline form: Colorless amorphous
NMR analysis: 247)
Form: Free
Example 1091
Structure
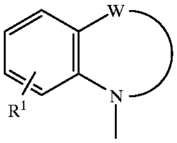
:
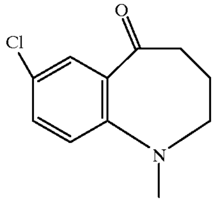
R$^2$: 2-OCH$_3$
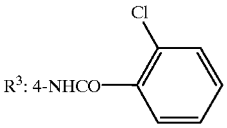
Crystalline form: Colorless amorphous
NMR analysis: 248)
Form: Free
TABLE 9-continued
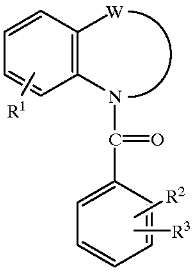
Example 1092
Structure
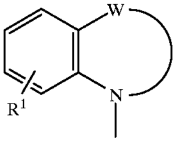
:
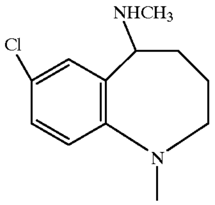
R$^2$: 2-OCH$_3$
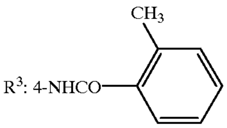
Crystalline form: Colorless amorphous
NMR analysis: 249)
Form: Free
Example 1093
Structure
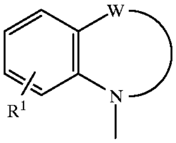
:
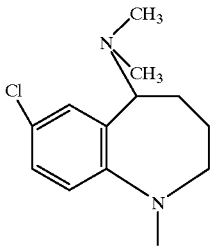
R$^2$: 2-OCH$_3$ TABLE 9-continued

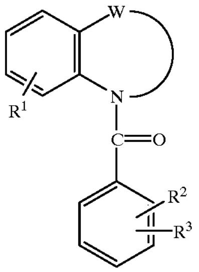

$R^3$: 4-NHCO

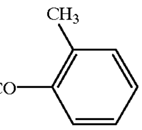

Crystalline form: White powder
Recrystallization solvent: Methanol/diethyl ether
Melting Point: 205–206° C.
Form: Free Example 1094

Structure

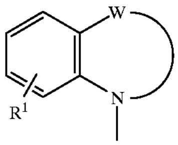

:

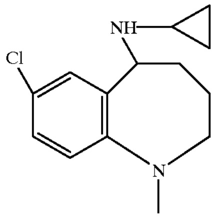

$R^2$: 2-$OCH_3$ $R^3$: 4-NHCO

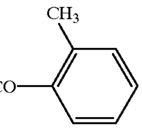

Crystalline form: Colorless amorphous
NMR analysis: 250)
Form: Free

Example 1095

Structure

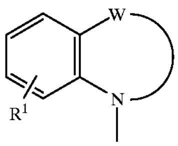

:

TABLE 9-continued

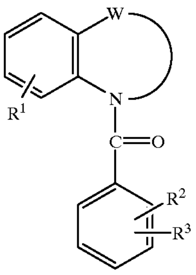

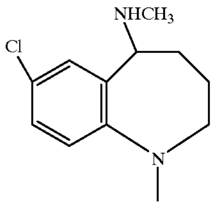

$R^2$: 2-$OCH_3$ $R^3$: 4-NHCO

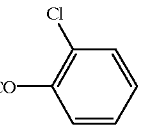

Crystalline form: White powder
Recrystallization solvent: Methanol/n-hexane
Melting Point: 172.5–174° C.
Form: Free Example 1096

Structure

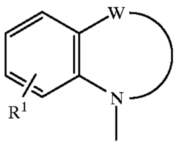

:

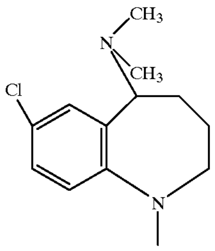

$R^2$: 2-$OCH_3$ $R^3$: 4-NHCO

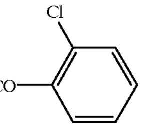

Crystalline form: White powder
Recrystallization solvent: Methanol/diethyl ether
Melting Point: 215–216.5° C.
Form: Free TABLE 9-continued

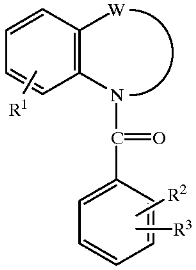

Example 1097

Structure

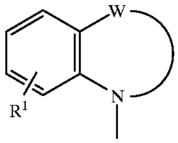 :

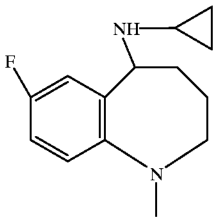

$R^2$: H $R^3$: 4-NHCO 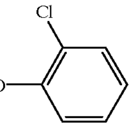

Crystalline form: White powder
Recrystallization solvent: Methanol/diethyl ether
Melting Point: 133–136° C.
Form: Free Example 1098

Structure

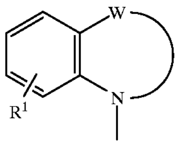 :

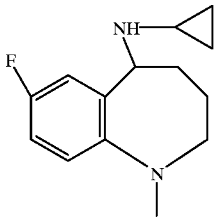

$R^2$: 2-Cl

TABLE 9-continued

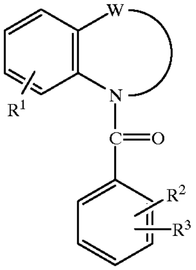

$R^3$: 4-NHCO 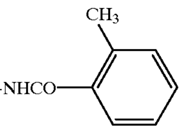

Crystalline form: Colorless amorphous
NMR analysis: 251)
Form: Free

Example 1099

Structure

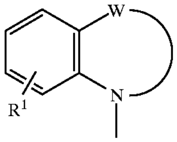 :

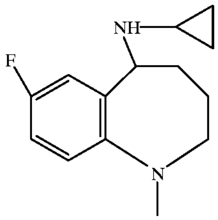

$R^2$: 2-Cl $R^3$: 4-NHCO 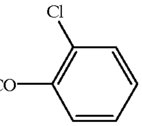

Crystalline form: White powder
Recrystallization solvent: Methanol/n-hexane
Melting Point: 179–180° C.
Form: Free Example 1100

Structure

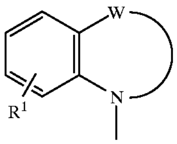 :

TABLE 9-continued

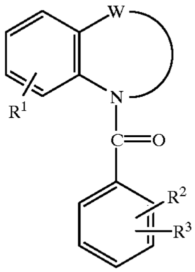

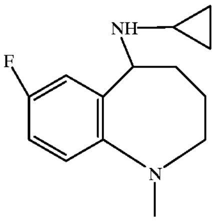

$R^2$: 3-$OCH_3$ $R^3$: 4-NHCO 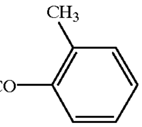

Crystalline form: White powder
Recrystallization solvent: Methanol/n-hexane
Melting Point: 167.5–169.5° C.
Form: Free Example 1101

Structure

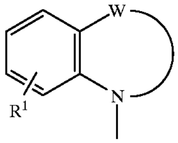 :

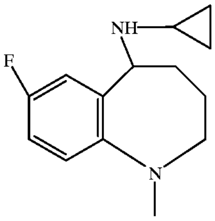

$R^2$: 3-$OCH_3$ $R^3$: 4-NHCO 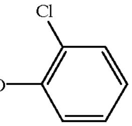

Crystalline form: White powder
Recrystallization solvent: Methanol/diethyl ether
Melting Point: 176–178° C.
Form: Free TABLE 9-continued

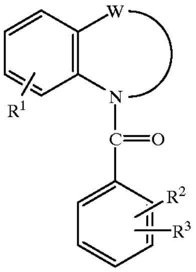

Example 1102

Structure

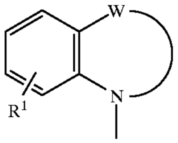 :

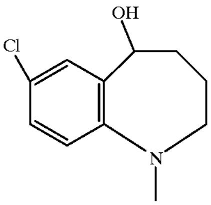

$R^2$: 2-$OCH_3$ $R^3$: 4-NHCO 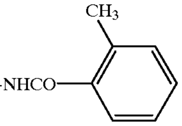

Crystalline form: Colorless amorphous
NMR analysis: 252)
Form: Free

Example 1103

Structure

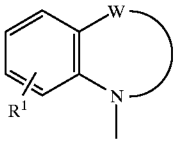 :

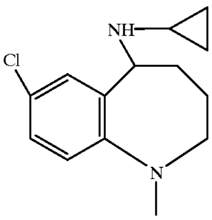

$R^2$: 2-$OCH_3$ $R^3$: 4-NHCO 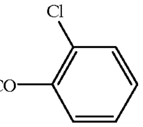

TABLE 9-continued

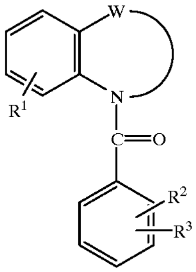

Crystalline form: White powder
Recrystallization solvent: Methanol/diethyl ether
Melting Point: 185–188° C.
Form: Free Example 1104

Structure

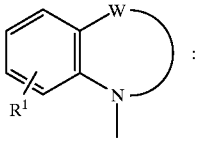

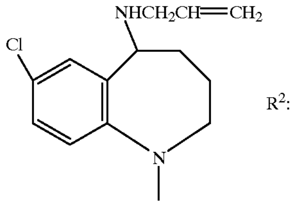

$R^2$: H $R^3$: 4-NHCO

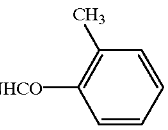

Crystalline form: White powder
Recrystallization solvent: Methanol/diethyl ether
Melting Point: 180–181.5° C.
Form: Free Example 1105

Structure

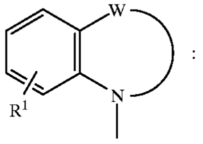

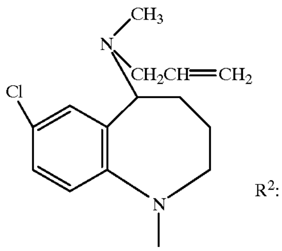

$R^2$: H

TABLE 9-continued

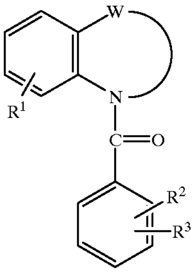

$R^3$: 4-NHCO

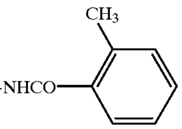

Crystalline form: White powder
Recrystallization solvent: Methanol/diethyl ether
Melting Point: 181–184° C.
Form: Free Example 1106

Structure

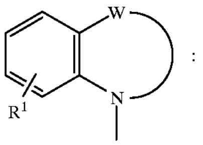

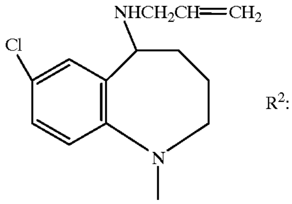

$R^2$: H $R^3$: 4-NHCO

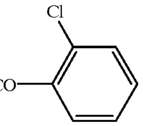

Crystalline form: White powder
Recrystallization solvent: Methanol/diethyl ether
Melting Point: 186.5–187° C.
Form: Free Example 1107

Structure

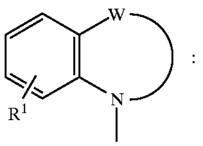

TABLE 9-continued

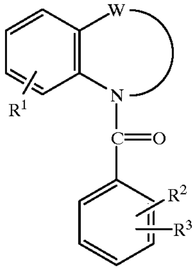

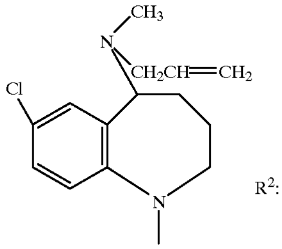

$R^2$: H $R^3$: 4-NHCO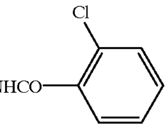

Crystalline form: White powder
Recrystallization solvent: Methanol/diethyl ether
Melting Point: 183–184° C.
Form: Free Example 1108

Structure

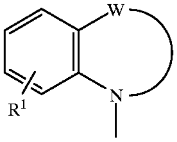 :

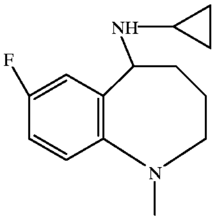

$R^2$: H $R^3$: 4-NHCO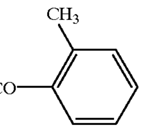

Crystalline form: White powder
Recrystallization solvent: Methanol/diethyl ether
Melting Point: 151–153° C.
Form: Free TABLE 9-continued

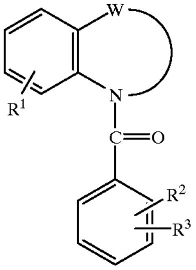

Example 1109

Structure

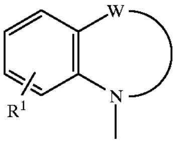 :

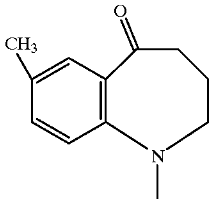

$R^2$: 3-$OCH_3$ $R^3$: 4-NHCO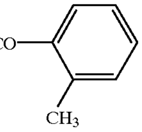

Crystalline form: Colorless amorphous
NMR analysis: 253)
Form: Free

Example 1110

Structure

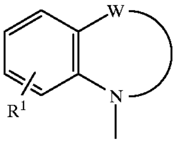 :

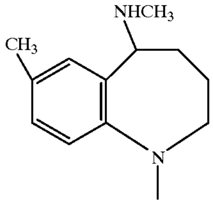

$R^2$: H $R^3$: 4-NHCO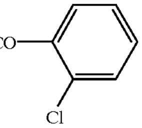

TABLE 9-continued

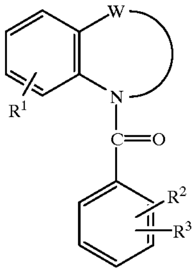

Crystalline form: Colorless amorphous
NMR analysis: 254)
Form: Free

Example 1111

Structure

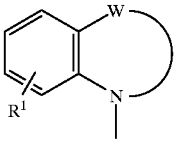

:

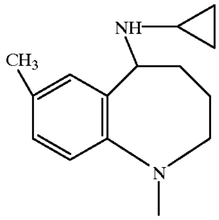

$R^2$: H $R^3$: 4-NHCO

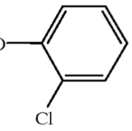

Crystalline form: White needles
Recrystallization solvent: Ethanol/n-hexane
Melting Point: 191–195° C.
Form: Free Example 1112

Structure

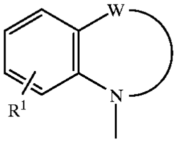

:

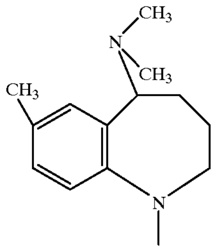

$R^2$: H

TABLE 9-continued

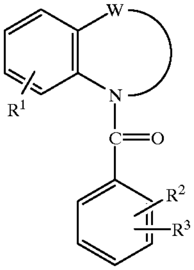

$R^3$: 4-NHCO

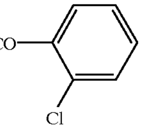

Crystalline form: White powder
Recrystallization solvent: Diethyl ether/n-hexane
Melting Point: 227–230° C.
Form: Free Example 1113

Structure

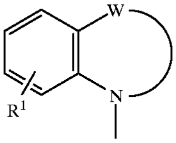

:

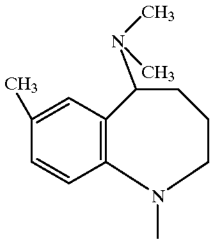

$R^2$: 2-Cl $R^3$: 4-NHCO

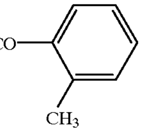

Crystalline form: Colorless amorphous
NMR analysis: 289)
Form: Free

Example 1114

Structure

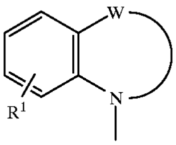

:

TABLE 9-continued

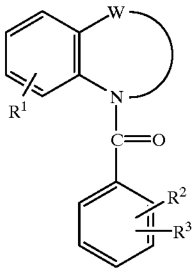

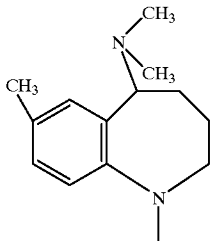

$R^2$: 2-Cl $R^3$: 4-NHCO 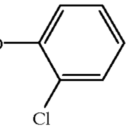

Crystalline form: Light yellow amorphous

NMR analysis: 255)

Example 1115

Structure

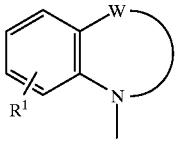 :

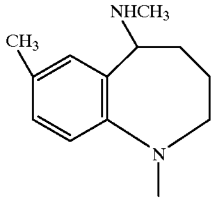

$R^2$: 3-$OCH_3$ $R^3$: 4-NHCO 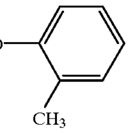

Crystalline form: White powder

Recrystallization solvent: Diethyl ether/n-hexane

Melting Point: 172–174° C.

Form: Free

TABLE 9-continued

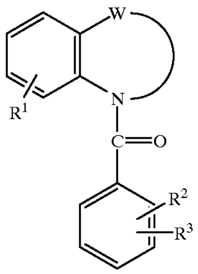

Example 1116

Structure

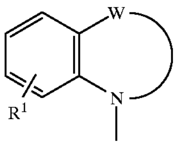 :

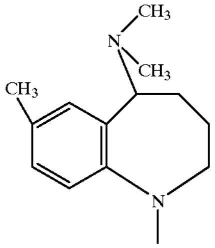

$R^2$: 3-$OCH_3$ $R^3$: 4-NHCO 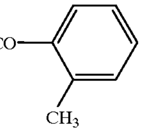

Crystalline form: Colorless amorphous

NMR analysis: 305)

Form: Free

Example 1117

Structure

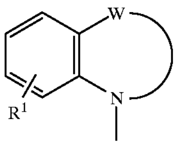 :

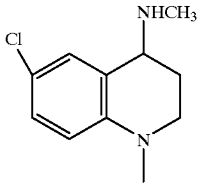

$R^2$: 2-$CH_3$ $R^3$: 4-NHCO 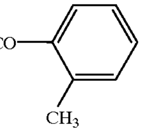

TABLE 9-continued

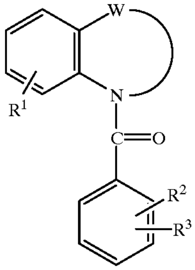

Crystalline form: Colorless amorphous
NMR analysis: 290)
Form: Free

Example 1118

Structure

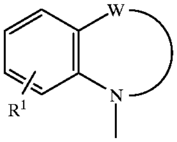
:

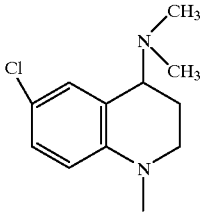

$R^2$: 2-$CH_3$ $R^3$: 4-NHCO
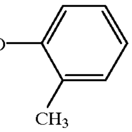

Crystalline form: Colorless amorphous
NMR analysis: 291)
Form: Free

Example 1119

Structure

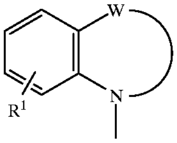
:

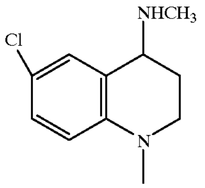

$R^2$: H

TABLE 9-continued

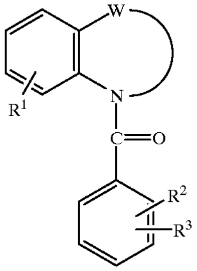

$R^3$: 4-NHCO
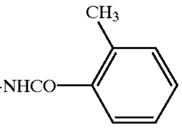

Crystalline form: Colorless amorphous
NMR analysis: 264)
Form: Free

Example 1120

Structure

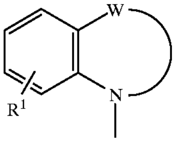
:

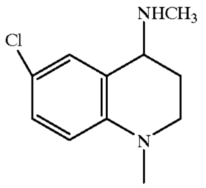

$R^2$: H $R^3$: 4-NHCO
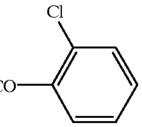

Crystalline form: Colorless amorphous
NMR analysis: 265)
Form: Free

Example 1121

Structure

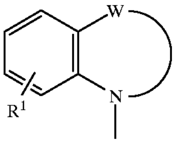
:

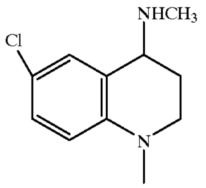

$R^2$: 2-Cl

TABLE 9-continued

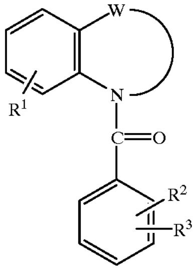

$R^3$: 4-NHCO

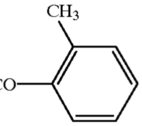

Crystalline form: Colorless amorphous
NMR analysis: 266)
Form: Free

Example 1122

Structure

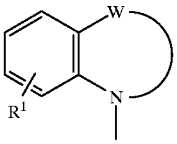

:

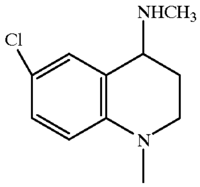

$R^2$: 2-Cl $R^3$: 4-NHCO

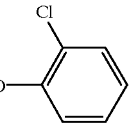

Crystalline form: Colorless amorphous
NMR analysis: 267)
Form: Free

Example 1123

Structure

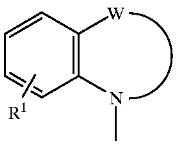

:

TABLE 9-continued

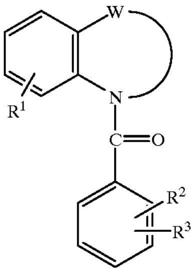

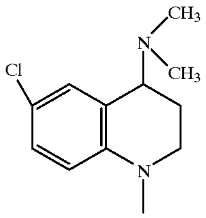

$R^2$: H $R^3$: 4-NHCO

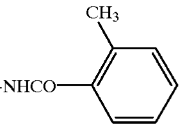

Crystalline form: Colorless amorphous
NMR analysis: 268)
Form: Free

Example 1124

Structure

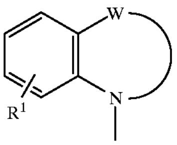

:

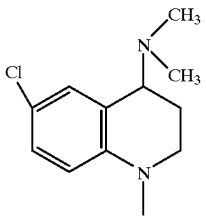

$R^2$: H $R^3$: 4-NHCO

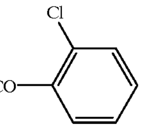

Crystalline form: Colorless amorphous
NMR analysis: 269)
Form: Free

TABLE 9-continued
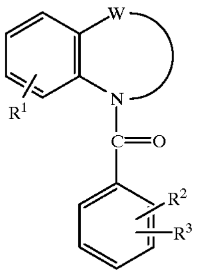
Example 1125
Structure
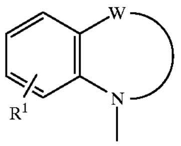 :
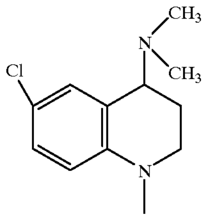
$R^2$: Cl
$R^3$: 4-NHCO 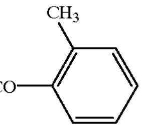
Crystalline form: Colorless amorphous
NMR analysis: 270)
Form: Free
Example 1126
Structure
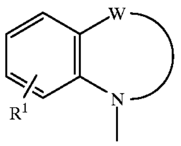 :
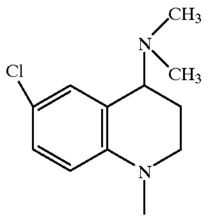
$R^2$: Cl
$R^3$: 4-NHCO 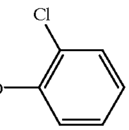
TABLE 9-continued
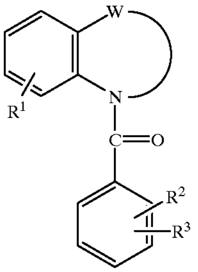
Crystalline form: Colorless amorphous
NMR analysis: 271)
Form: Free
Example 1127
Structure
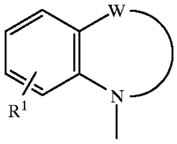 :
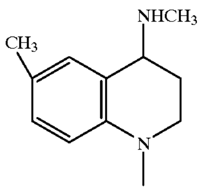
$R^2$: H
$R^3$: 4-NHCO 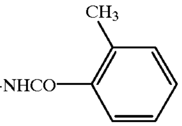
Crystalline form: Colorless amorphous
NMR analysis: 272)
Form: Free
Example 1128
Structure
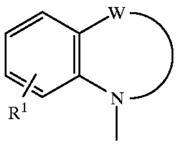 :
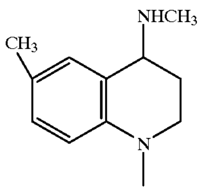
$R^2$: H TABLE 9-continued

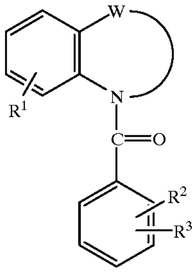

$R^3$: 4-NHCO 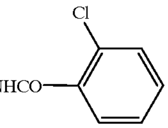

Crystalline form: Colorless amorphous
NMR analysis: 273)
Form: Free

Example 1129

Structure

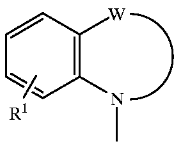 :

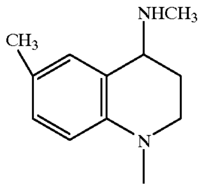 $R^2$: 2-Cl $R^3$: 4-NHCO 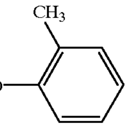

Crystalline form: Colorless amorphous
NMR analysis: 274)
Form: Free

Example 1130

Structure

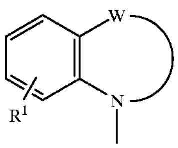 :

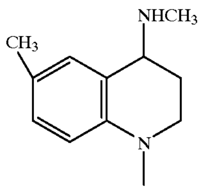 $R^2$: 2-Cl

TABLE 9-continued

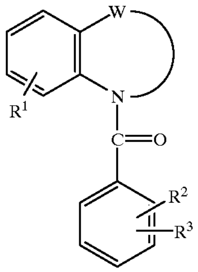

$R^3$: 4-NHCO 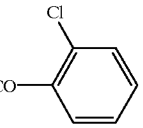

Crystalline form: Colorless amorphous
NMR analysis: 275)
Form: Free

Example 1131

Structure

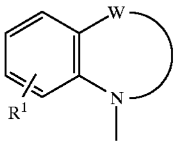 :

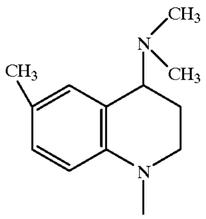 $R^2$: H $R^3$: 4-NHCO 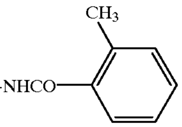

Crystalline form: Colorless amorphous
NMR analysis: 276)
Form: Free

Example 1132

Structure

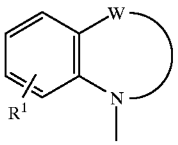 :

TABLE 9-continued
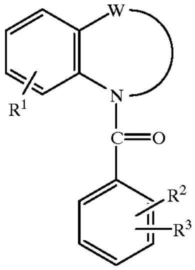
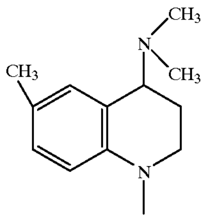
$R^2$: H
$R^3$: 4-NHCO 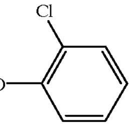
Crystalline form: Colorless amorphous
NMR analysis: 277)
Form: Free
Example 1133
Structure
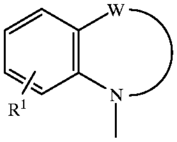 :
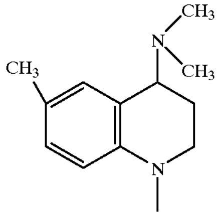
$R^2$: 2-Cl
$R^3$: 4-NHCO 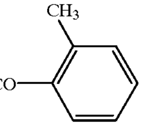
Crystalline form: Colorless amorphous
NMR analysis: 278)
Form: Free
TABLE 9-continued
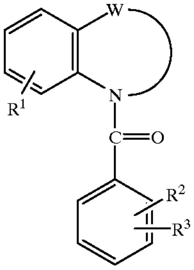
Example 1134
Structure
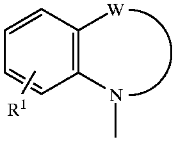 :
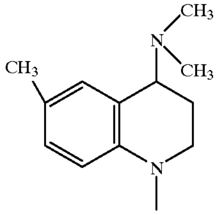
$R^2$: 2-Cl
$R^3$: 4-NHCO 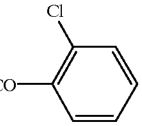
Crystalline form: Colorless amorphous
NMR analysis: 279)
Form: Free
Example 1135
Structure
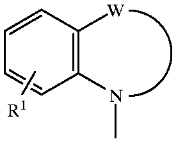 :
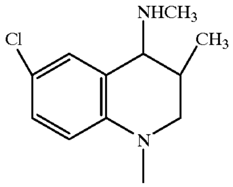
$R^2$: H
$R^3$: 4-NHCO 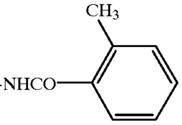
NMR analysis: 280)

TABLE 9-continued
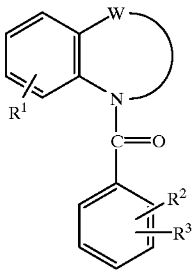
Form: Free
Example 1136
Structure
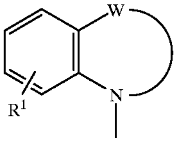 :
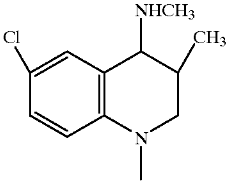
$R^2$: H
$R^3$: 4-NHCO 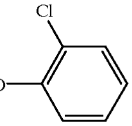
NMR analysis: 281)
Form: Free
Example 1137
Structure
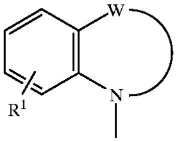 :
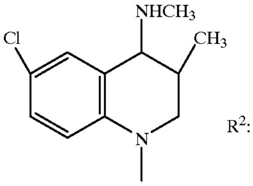
$R^2$: 2-Cl
$R^3$: 4-NHCO 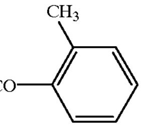
NMR analysis: 282)
Form: Free
TABLE 9-continued
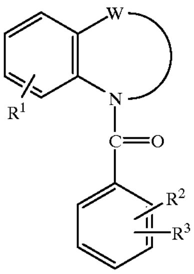
Example 1138
Structure
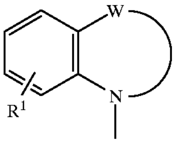 :
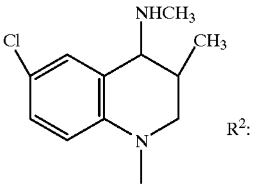
$R^2$: 2-Cl
$R^3$: 4-NHCO 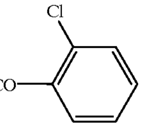
NMR analysis: 283)
Form: Free
Example 1139
Structure
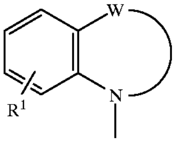 :
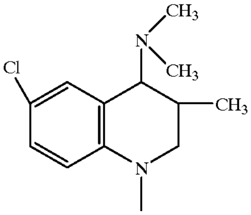
$R^2$: 2-Cl
$R^3$: 4-NHCO 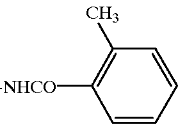
NMR analysis: 306)
Form: Free TABLE 9-continued
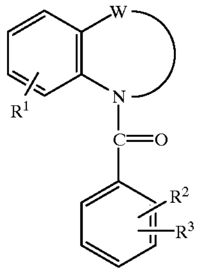
Example 1140
Structure
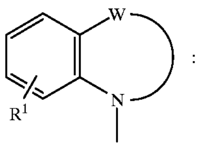
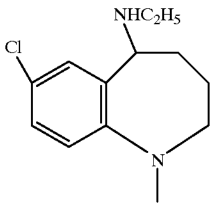
$R^2$: 2-Cl
$R^3$: 4-NHCO—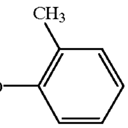
Crystalline form: Colorless amorphous
NMR analysis: 284)
Form: Free
Example 1141
Structure
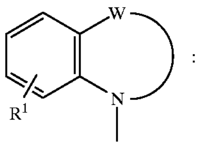
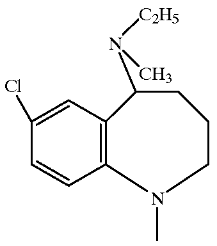
$R^2$: 2-Cl
TABLE 9-continued
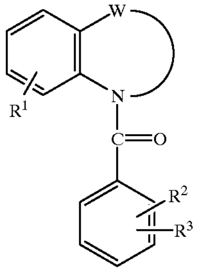
$R^3$: 4-NHCO—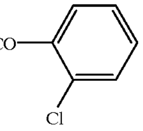
Crystalline form: Colorless amorphous
NMR analysis: 285)
Form: Free
Example 1142
Structure
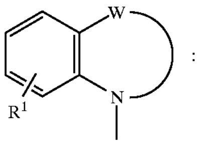
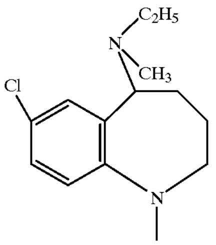
$R^2$: 2-Cl
$R^3$: 4-NHCO—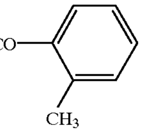
Crystalline form: Colorless amorphous
NMR analysis: 286)
Form: Free
Example 1143
Structure
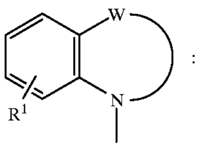

TABLE 9-continued

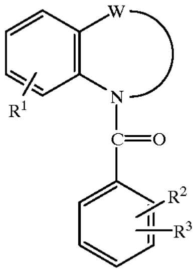

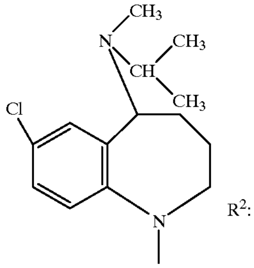

$R^2$: 2-Cl $R^3$: 4-NHCO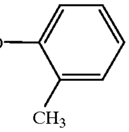

Crystalline form: Colorless amorphous
NMR analysis: 287)
Form: Free

Example 1144

Structure

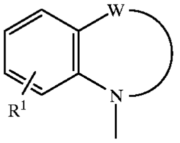 :

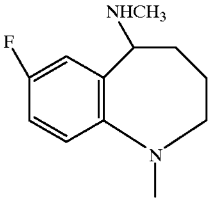

$R^2$: H $R^3$: 4-NHCO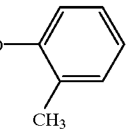

Crystalline form: White powder
Recrystallization solvent: Dichloromethane/diethyl ether
Melting Point: 203–207° C.
Form: Free Example 1145

Structure

TABLE 9-continued

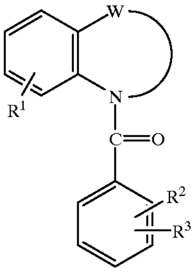

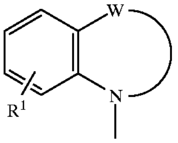 :

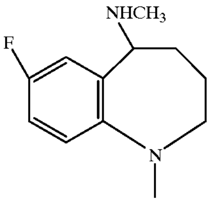

$R^2$: H $R^3$: 4-NHCO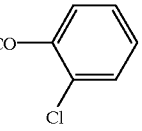

Crystalline form: White powder
Recrystallization solvent: Dichloromethane/diethyl ether
Melting Point: 199–203° C.
Form: Free Example 1146

Structure

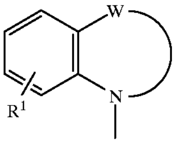 :

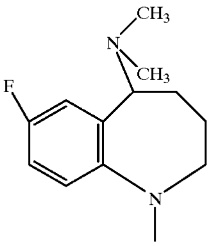

$R^2$: H $R^3$: 4-NHCO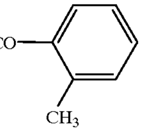

Crystalline form: White powder

TABLE 9-continued

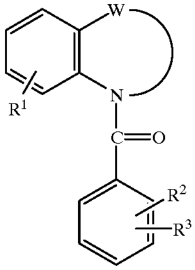

Recrystallization solvent: Dichloromethane/diethyl ether
Melting Point: 210–212° C.
Form: Free Example 1147

Structure

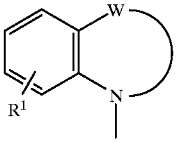
:

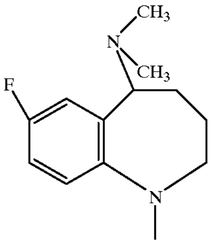
$R^2$: H $R^3$: 4-NHCO
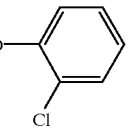

Crystalline form: White powder
Recrystallization solvent: Dichloromethane/diethyl ether
Melting Point: 211–214° C.
Form: Free Example 1148

Structure

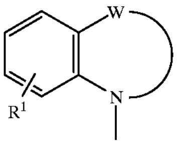
:

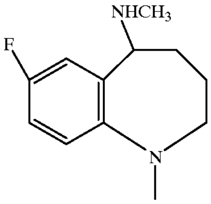
$R^2$: 2-Cl

TABLE 9-continued

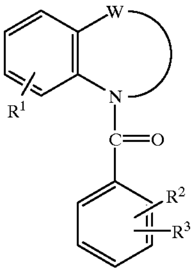

$R^3$: 4-NHCO
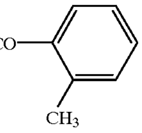

Crystalline form: White powder
Recrystallization solvent: Dichloromethane/diethyl ether
Melting Point: 186–189° C.
Form: Free Example 1149

Structure

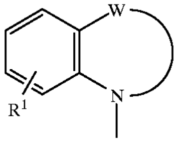
:

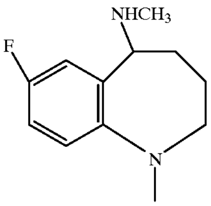
$R^2$: 2-Cl $R^3$: 4-NHCO
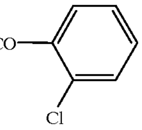

Crystalline form: Colorless amorphous
NMR analysis: 288)
Form: Free

Example 1150

Structure

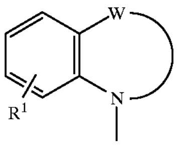
:

TABLE 9-continued

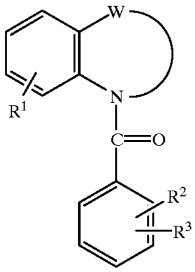

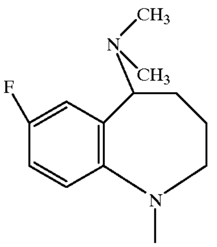

$R^2$: 2-Cl $R^3$: 4-NHCO—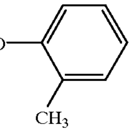

Crystalline form: Colorless amorphous
NMR analysis: 292)
Form: Free

Example 1151

Structure

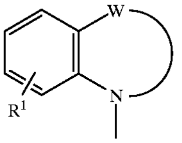 :

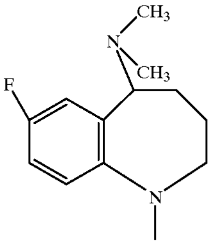

$R^2$: 2-Cl $R^3$: 4-NHCO—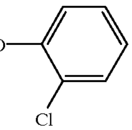

Crystalline form: Colorless amorphous
NMR analysis: 293)
Form: Free

TABLE 9-continued

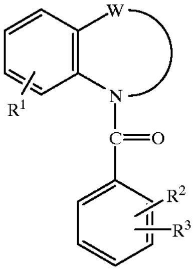

Example 1152

Structure

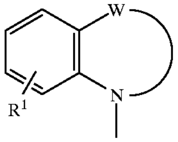 :

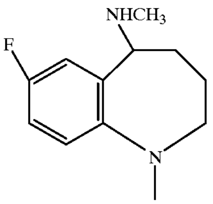

$R^2$: 3-$OCH_3$ $R^3$: 4-NHCO—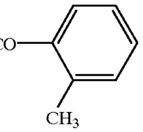

Crystalline form: White powder
Recrystallization solvent: Dichloromethane/diethyl ether
Melting Point: 144–145° C.
Form: Free Example 1153

Structure

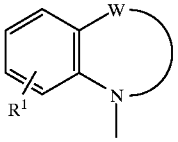 :

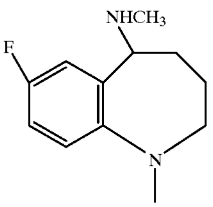

$R^2$: 3-$OCH_3$ $R^3$: 4-NHCO—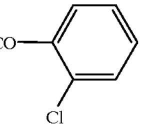

TABLE 9-continued

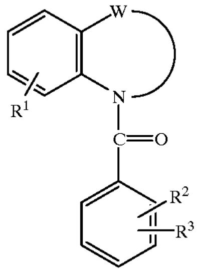

Crystalline form: White powder
Recrystallization solvent: Dichloromethane/diethyl ether
Melting Point: 149–150° C.
Form: Free Example 1154

Structure

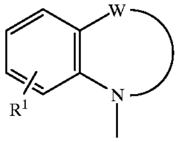 :

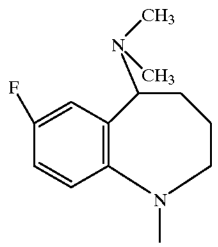 $R^2$: 3-$OCH_3$ $R^3$: 4-NHCO 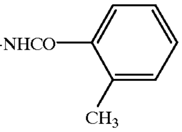

Crystalline form: Colorless amorphous
NMR analysis: 294)
Form: Free

Example 1155

Structure

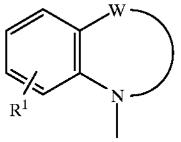 :

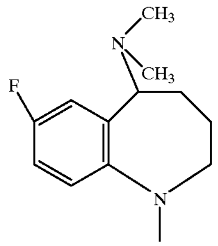 $R^2$: 3-$OCH_3$

TABLE 9-continued

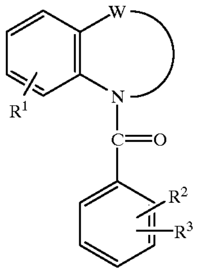

$R^3$: 4-NHCO 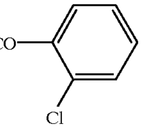

Crystalline form: Colorless amorphous
NMR analysis: 295)
Form: Free

Example 1156

Structure

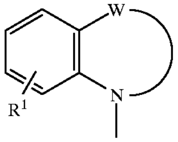 :

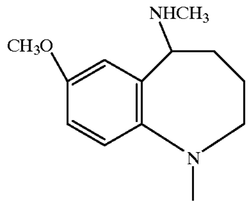 $R^2$: 2-$CH_3$ $R^3$: 4-NHCO 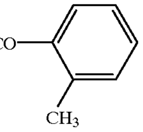

Crystalline form: Colorless amorphous
NMR analysis: 301)
Form: Free

Example 1157

Structure

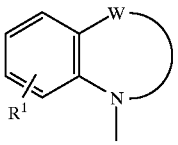 :

TABLE 9-continued
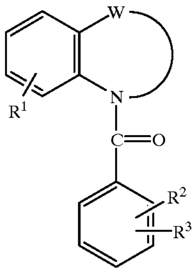
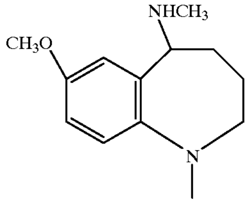
$R^2$: 2-$CH_3$
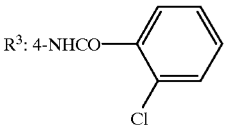
Crystalline form: Colorless amorphous
NMR analysis: 302)
Form: Free
Example 1158
Structure
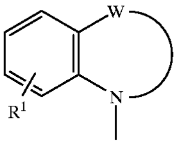 :
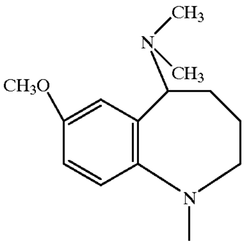
$R^2$: 2-$CH_3$
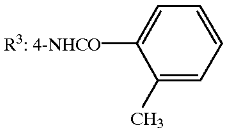
Crystalline form: Colorless amorphous
NMR analysis: 303)
Form: Free
TABLE 9-continued
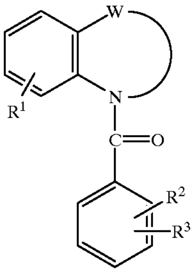
Example 1159
Structure
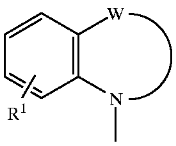 :
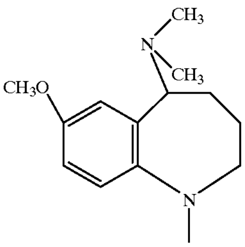
$R^2$: 2-$CH_3$
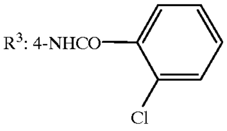
Crystalline form: Colorless amorphous
NMR analysis: 304)
Form: Free
Example 1160
Structure
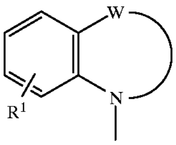 :
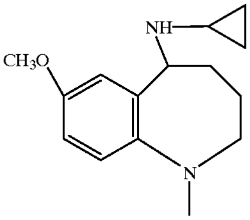
$R^2$: H TABLE 9-continued

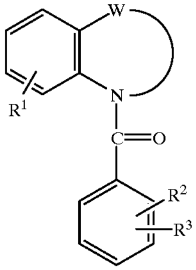

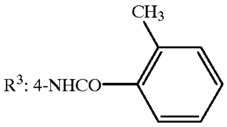

Crystalline form: White powder
Recrystallization solvent: Ethyl acetate/diisopropyl ether
Melting Point: 191–193° C.
Form: Free
Example 1161

Structure

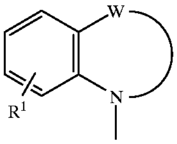

:

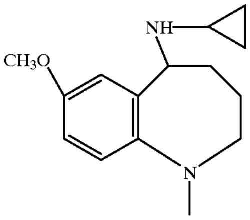

$R^2$: H

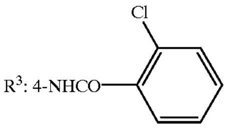

Crystalline form: White powder
Recrystallization solvent: Ethyl acetate/diisopropyl ether
Melting Point: 221–223° C.
Form: Free
Example 1162

Structure

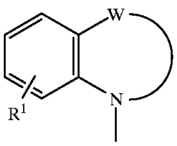

:

TABLE 9-continued

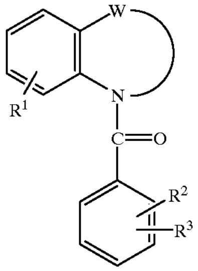

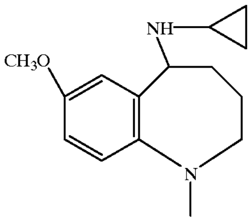

$R^2$: 3-$OCH_3$

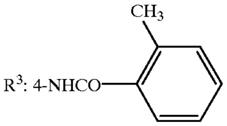

Crystalline form: White powder
Recrystallization solvent: Ethyl acetate/n-hexane
Melting Point: 159–161° C.
Form: Free
Example 1163

Structure

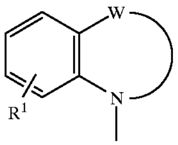

:

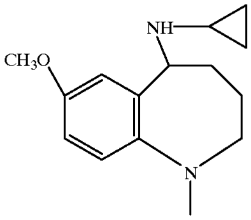

$R^2$: 3-$OCH_3$

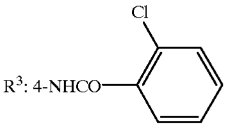

Crystalline form: White powder
Recrystallization solvent: Ethyl acetate/n-hexane
Melting Point: 174–175° C.
Form: Free TABLE 9-continued

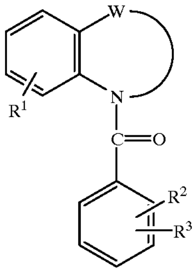

Example 1164

Structure

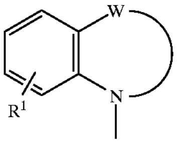 :

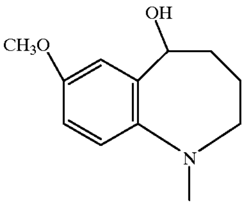 $R^2$: 2-Cl $R^3$: 4-NHCO 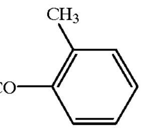

Crystalline form: Colorless amorphous
NMR analysis: 256)
Form: Free

Example 1165

Structure

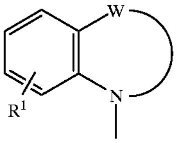 :

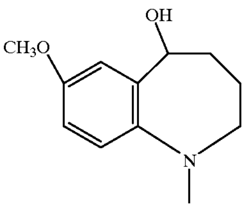 $R^2$: 2-Cl $R^3$: 4-NHCO 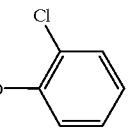

Crystalline form: Colorless amorphous

TABLE 9-continued

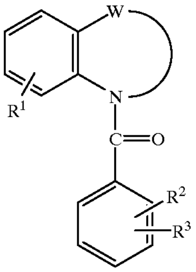

NMR analysis: 257)
Form: Free

Example 1166

Structure

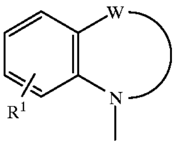 :

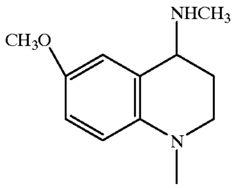 $R^2$: H $R^3$: 4-NHCO 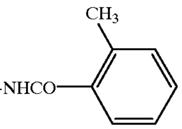

Crystalline form: Colorless amorphous
NMR analysis: 258)
Form: Free

Example 1167

Structure

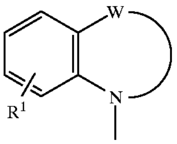 :

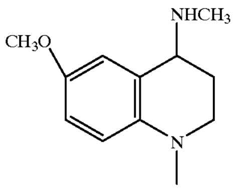 $R^2$: 2-Cl $R^3$: 4-NHCO 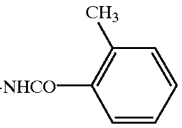

TABLE 9-continued

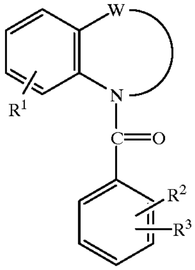

Crystalline form: Colorless amorphous
NMR analysis: 259)
Form: Free

Example 1168

Structure

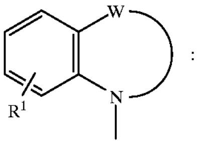

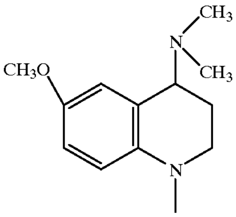

$R^2$: H $R^3$: 4-NHCO

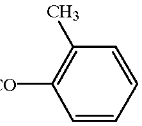

Crystalline form: Colorless amorphous
NMR analysis: 260)
Form: Free

Example 1169

Structure

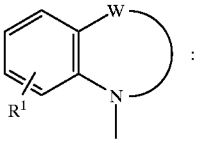

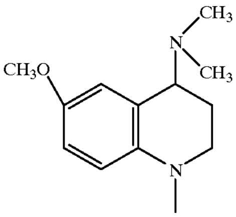

$R^2$: 2-Cl

TABLE 9-continued

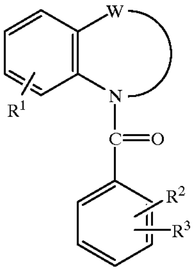

$R^3$: 4-NHCO

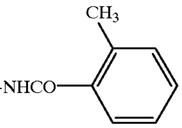

Crystalline form: Colorless amorphous
NMR analysis: 261)
Form: Free

Example 1170

Structure

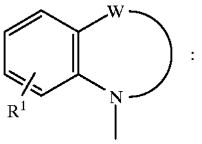

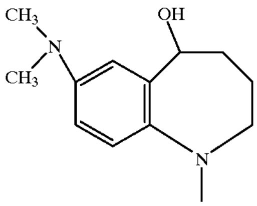

$R^2$: H $R^3$: 4-NHCO

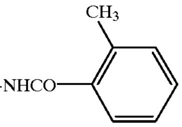

Crystalline form: Colorless amorphous
NMR analysis: 296)
Form: Free

Example 1171

Structure

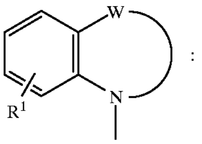

TABLE 9-continued

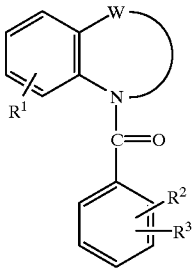

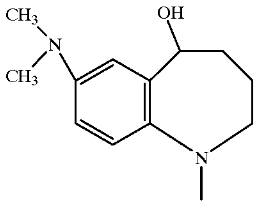

$R^2$: 2-Cl $R^3$: 4-NHCO 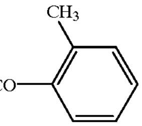

Crystalline form: White powder

Recrystallization solvent: Ethanol/diethyl ether/n-hexane

Melting Point: 159–162° C.

Form: Free

Example 1172

Structure

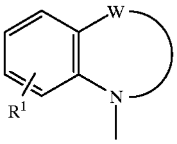 :

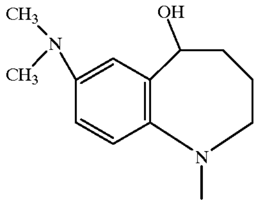

$R^2$: 2-Cl $R^3$: 4-NHCO 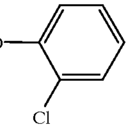

Crystalline form: Colorless needles

Recrystallization solvent: Ethanol/diethyl ether/n-hexane

Melting Point: 221–224° C.

Form: Free

TABLE 9-continued

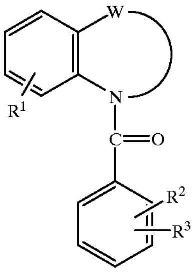

Example 1173

Structure

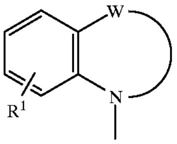 :

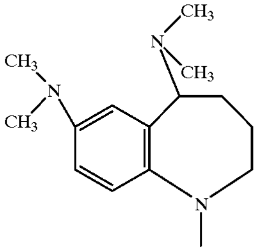

$R^2$: 2-Cl $R^3$: 4-NHCO 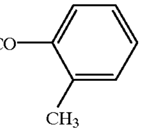

Crystalline form: Colorless prisms

Recrystallization solvent: Ethanol/diethyl ether

Melting Point: 199–202° C.

Form: Free

Example 1174

Structure

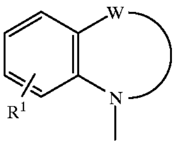 :

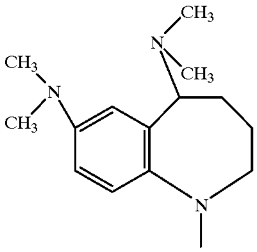

$R^2$: 2-Cl

TABLE 9-continued

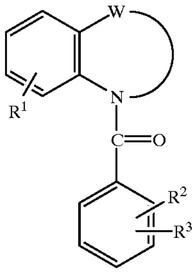

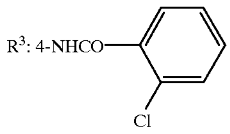

Crystalline form: Colorless prisms
Recrystallization solvent: Ethanol/diethyl ether
Melting Point: 215–218° C.
Form: Free Example 1175

Structure

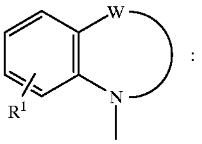

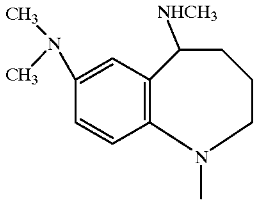

$R^2$: 2-Cl

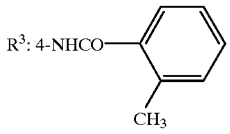

Crystalline form: Colorless needles
Recrystallization solvent: Ethanol/diethyl ether/n-hexane
Melting Point: 167–170° C.
Form: Free Example 1176

Structure

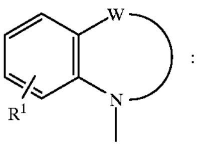

TABLE 9-continued

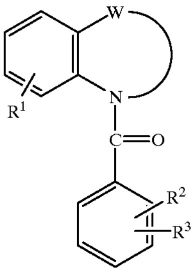

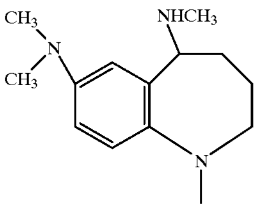

$R^2$: 2-Cl

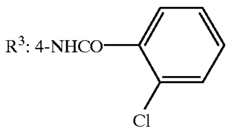

Crystalline form: White powder
Recrystallization solvent: Ethanol/diethyl ether/n-hexane
Melting Point: 191–193° C.
Form: Free Example 1177

Structure

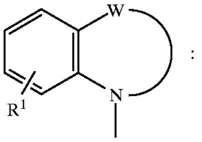

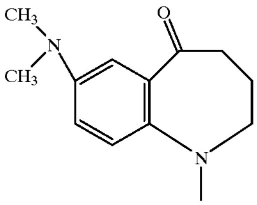

$R^2$: 2-Cl

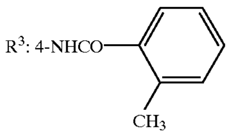

Crystalline form: Light yellow amorphous
NMR analysis: 262)
Form: Free

TABLE 9-continued
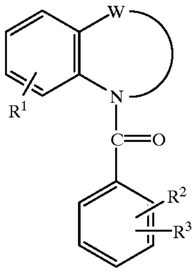
Example 1178
Structure
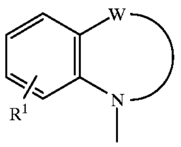
:
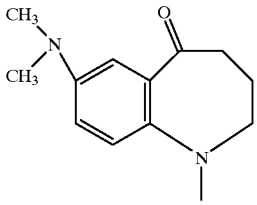
$R^2$: 2-Cl
$R^3$: 4-NHCO
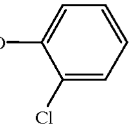
Crystalline form: Light yellow amorphous
NMR analysis: 263)
Form: Free
Example 1179
Structure
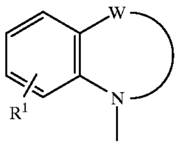
:
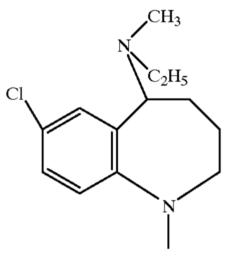
$R^2$: 3-$OCH_3$
TABLE 9-continued
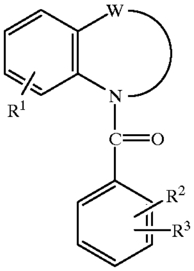
$R^3$: 4-NHCO
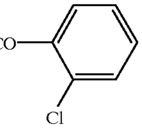
Crystalline form: Colorless amorphous
NMR analysis: 297)
Form: Free
Example 1180
Structure
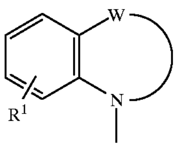
:
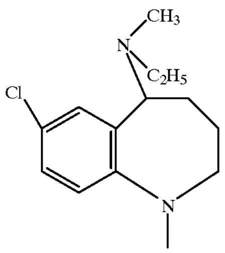
$R^2$: 3-$OCH_3$
$R^3$: 4-NHCO
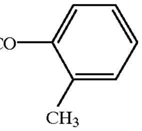
Crystalline form: Colorless amorphous
NMR analysis: 298)
Form: Free
Example 1181
Structure
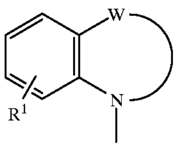
:

TABLE 9-continued
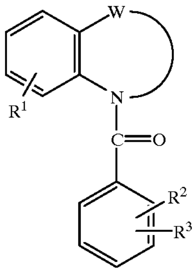
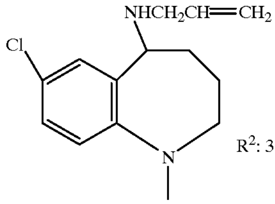
R$^2$: 3-$OCH_3$
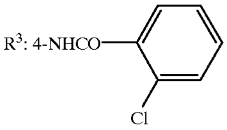
Crystalline form: Colorless amorphous
NMR analysis: 299)
Form: Free
Example 1182
Structure
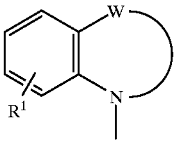
:
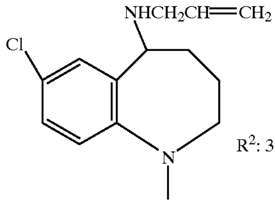
R$^2$: 3-$OCH_3$
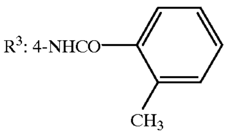
Crystalline form: Colorless amorphous
NMR analysis: 300)
Form: Free
TABLE 9-continued
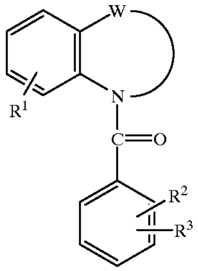
Example 1183
Structure
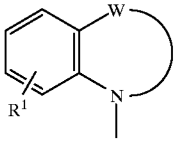
:
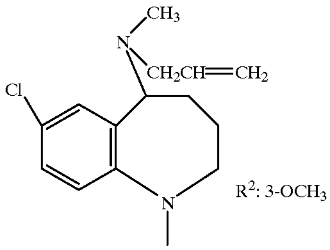
R$^2$: 3-$OCH_3$
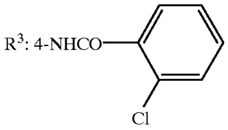
Crystalline form: Colorless amorphous
NMR analysis: 307)
Form: Free
Example 1184
Structure
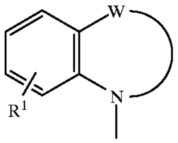
:
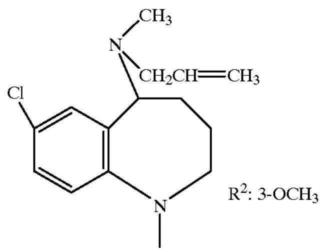
R$^2$: 3-$OCH_3$ TABLE 9-continued

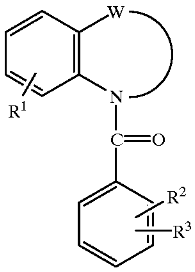

R[3]: 4-NHCO 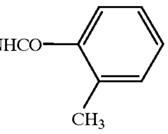

Crystalline form: Colorless amorphous
NMR analysis: 308)
Form: Free

Example 1185

Structure

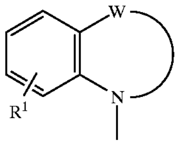 :

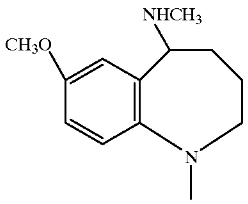 R[2]: 2-OCH3

R[3]: 4-NHCO 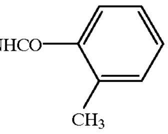

Crystalline form: Colorless amorphous
NMR analysis: 309)
Form: Free

Example 1186

Structure

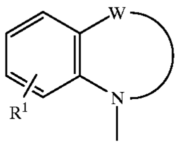 :

TABLE 9-continued

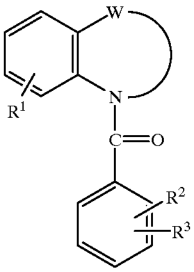

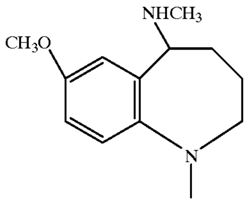 R[2]: 2-OCH3

R[3]: 4-NHCO 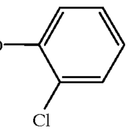

Crystalline form: Colorless amorphous
NMR analysis: 310)
Form: Free

Example 1187

Structure

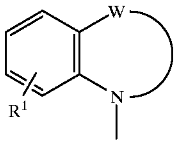 :

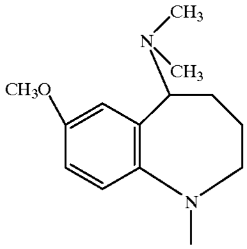 R[2]: 2-OCH3

R[3]: 4-NHCO 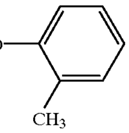

Crystalline form: Colorless amorphous
NMR analysis: 311)
Form: Free

TABLE 9-continued

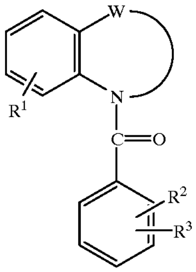

Example 1188

Structure

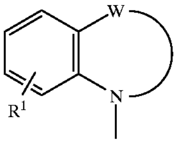
:

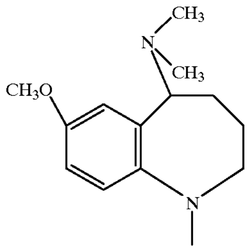

$R^2$: 2-$OCH_3$ $R^3$: 4-NHCO

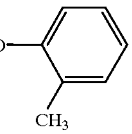

Crystalline form: Colorless amorphous
NMR analysis: 312
Form: Free

238) $^1$H-NMR(DMSO-d$_6$)δ; 1.4–2.1(4H, m), 2.34(3H, s), 2.8–5.4(4H, m), 7.09(1H, d, J=8.4Hz), 7.15–7.7 (9H, m), 7.76(1H, d, J=2.6Hz), 10.41(1H, s)

239) $^1$H-NMR(DMSO-d$_6$)δ; 1.5–2.2(4H, m), 2.8–5.2(4H, m), 7.09(1H, d, J=8.4Hz), 7.2–7.7(9H, m), 7.76 (1H, d, J=2.6Hz), 10.63(1H, s)

240) $^1$H-NMR(CDCl$_3$)δ; 1.65–2.2(4H, m), 2.25–2.65(6H, m), 2.75–4.6(4H, m), 6.8–8.15(11H, m)

241) $^1$H-NMR(CDCl$_3$)δ; 1.4–2.25(4H, m), 2.25–2.55(3H, m), 2.7–4.8(4H, m), 6.8–8.3(11H, m)

242) $^1$H-NMR(CDCl$_3$)δ; 1.4–2.1(4H, m), 2.35–2.6(3H, m), 2.8–5.2(7H, m), 6.8–8.05(11H, m)

243) $^1$H-NMR(CDCl$_3$)δ; 1.4–2.15(4H, m), 2.4–5.2(7H, m), 6.8–7.85(10H, m), 7.9–8.3(1H, m)

244) $^1$H-NMR(CDCl$_3$)δ; 1.20–2.38(11H, m), 2.98–5.10 (3H, m), 6.45–7.04(2H, m), 7.05–7.86(8H, m), 8.00–8.50(1H, m)

245) $^1$H-NMR(CDCl$_3$)δ; 1.05–2.78(14H, m), 2.78–5.18 (2H, m), 6.36–7.03(2H, m), 7.06–7.90(8H, m), 7.98–8.39(1H, m)

246) $^1$H-NMR(CDCl$_3$)δ; 1.75–2.54(2H, m), 2.60–4.03 (4H, m), 3.37(3H, brs), 5.17(2H, s), 6.60–6.83 (3H, m), 6.90–7.07(1H, m), 7.07–7.20(1H, m), 7.22–7.50(6H, m), 7.73–7.84(1H, m)

247) $^1$H-NMR(CDCl$_3$)δ; 1.60–2.40(2H, m), 2.45(3H, s), 2.65–3.06(2H, m), 3.06–5.28(2H, m), 3.35(3H, brs, 6.59–7.60(9H, m), 7.67–7.88(1H, m), 8.12 (1H, brs)

TABLE 9-continued

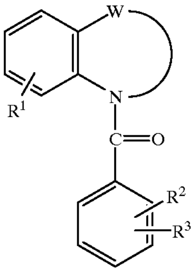

248) $^1$H-NMR(CDCl$_3$)δ; 1.60–2.52(2H, m), 2.64–5.32 (4H, m), 3.37(3H, brs), 6.60–7.98(10H, m), 8.50 (1H, brs)

249) $^1$H-NMR(CDCl$_3$)δ; 1.18–3.15(12H, m), 3.40–4.38 (5H, m), 6.58–7.75(10H, m), 8.30–8.71(1H, m)

250) $^1$H-NMR(CDCl$_3$)δ; 0.26–0.71(4H, m), 1.15–3.29 (10H, m), 3.40–4.95(5H, m), 6.60–7.85(10H, m), 8.18–8.68(1H, m)

251) $^1$H-NMR(CDCl$_3$)δ; 0.25–0.72(4H, m), 1.16–2.35 (6H, m), 2.35–3.30(4H, m), 3.43–4.98(2H, m), 6.57–7.94(10H, m), 8.22–8.89(1H, m)

252) $^1$H-NMR(CDCl$_3$)δ; 0.69–2.90(9H, m), 2.90–5.10 (5H, m), 6.40–7.85(10H, m), 8.25–8.54(1H, m)

253) $^1$H-NMR(CDCl$_3$)δ; 2.17(2H, brs), 2.34(3H, s), 2.49(3H, s), 2.87(2H, t, J=6.0Hz), 3.10–5.00 (2H, m), 3.70(3H, s), 6.67(1H, d, J=8.0Hz), 6.85–6.88(2H, m), 7.09(1H, dd, J=1.5, 8.0Hz), 7.21–7.50(4H, m), 7.64(1H, d, J=1.9Hz), 8.11 (1H, m), 8.33(1H, d, J=8.8Hz)

254) $^1$H-NMR(CDCl$_3$)δ; 1.42–5.06(13H, m), 6.51(1H, d, J=7.8Hz), 6.76(1H, m), 7.01–7.63(10H, m), 8.53 (1H, m)

255) $^1$H-NMR(CDCl$_3$)δ; 1.26–4.93(16H, m), 6.69–7.73 (10H, m), 8.62–8.84(1H, m)

256) $^1$H-NMR(CDCl$_3$)δ; 1.45–1.90(2H, m), 1.90–2.33 (2H, m), 2.33–3.25(4H, m), 3.60–3.93(3H, m), 4.45–5.15(2H, m), 6.40–8.25(11H, m)

257) $^1$H-NMR(CDCl$_3$)δ; 1.49–1.97(2H, m), 1.97–3.10 (3H, m), 3.58–3.98(3H, m), 4.60–5.26(2H, m), 6.44–8.36(11H, m)

258) $^1$H-NMR(CDCl$_3$)δ; 1.82–2.13(1H, m), 2.13–2.43 (1H, m), 2.50(3H, s), 2.57(3H, s), 3.69–4.06(3H, m), 3.78(3H, s), 6.45–6.80(2H, m), 6.85–7.00(1H, m), 7.18–7.80(9H, m)

259) $^1$H-NMR(CDCl$_3$)δ; 1.72–2.05(1H, m), 2.11–2.40 (1H, m), 2.51(3H, s), 2.57(2H, s), 3.40–4.20(3H, m), 3.77(3H, s), 6.35–6.64(1H, m), 6.79–6.96(1H, m), 7.15–8.13(9H, m)

260) $^1$H-NMR(CDCl$_3$)δ; 1.71–2.05(1H, m), 2.07–2.32 (1H, m), 2.33(6H, s), 2.47(3H, s), 3.50–3.80(2H, m), 3.76(3H, s), 3.95–4.17(1H, m), 6.40–6.70(2H, m), 6.90–7.03(1H, m), 7.14–7.77(8H, m), 7.90–8.14 (1H, m)

261) $^1$H-NMR(CDCl$_3$)δ; 1.76–2.70(2H, m), 2.30(6H, s), 2.47(3H, s), 3.23–4.40(3H, m), 3.73(3H, s), 6.30–6.65(2H, m), 6.65–8.76(9H, m)

262) $^1$H-NMR(CDCl$_3$)δ; 1.68–2.35(2H, m), 2.36–5.11 [13H, m, 2.45(3H, s), 2.92(6H, s)], 6.56(1H, dd, J=3.1, 8.7Hz), 6.87–7.06(2H, m), 6.82(1H, d, J=8.7Hz), 7.11–7.68(6H, m), 7.97(1H, brs)

263) $^1$H-NMR(CDCl$_3$)δ; 1.69–2.30(2H, m), 2.59–5.10 [10H, m, 2.92(6H, s)], 6.56(1H, dd, J=3.1, 8.8 Hz), 6.72–7.90(9H, m), 8.42(1H, brs)

264) $^1$H-NMR(CDCl$_3$)δ; 1.49(1H, brs), 182–2.01(1H, m), 2.03–2.26(1H, m), 2.46(3H, s), 2.54(3H, s), 3.67–3.76(1H, m), 3.86(2H, t, J=6.8Hz), 6.67 (1H, d, J=8.6Hz), 6.93(1H, dd, J=8.6, 2.5Hz), 7.13–7.43(9H, m), 8.15(1H, brs)

265) $^1$H-NMR(CDCl$_3$)δ; 1.58(1H, brs), 1.86–2.03(1H, m), 2.08–2.30(1H, m), 2.56(3H, s), 3.69–3.78(1H, m), 3.91(2H, t, J=6.5Hz), 6.69(1H, d, J=8.7Hz), 6.94(1H, dd, J=8.6, 2.5Hz), 7.33–7.47(6H, m), 7.54–7.63(2H, m), 7.67–7.77(1H, m), 8.16(1H, brs)

TABLE 9-continued

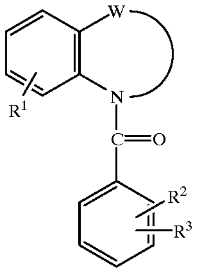

266) $^1$H-NMR($CDCl_3$)δ; 1.50(1H, brs), 1.76–2.23(2H, m), 2.42(3H, s), 2.47(3H, s), 3.55–3.94(3H, m), 6.28–7.78(10H, m), 8.91(1H, brs)

267) $^1$H-NMR($CDCl_3$)δ; 1.46(1H, brs), 1.82–2.28(2H, m), 2.50(3H, s), 3.52–4.08(3H, m), 6.34–7.75 (10H, m), 8.61(1H, brs)

268) $^1$H-NMR($CDCl_3$)δ; 1.80–2.31(2H, m), 2.32(3H, s), 2.48(3H, s), 3.51–3.82(2H, m), 3.95–4.15(1H, m), 6.59(1H, d, J=8.6Hz), 6.90(1H, dd, J=8.6, 2.5 Hz), 7.16–7.61(9H, m), 7.88(1H, brs) 3.52–4.08(3H, m), 6.34–7.75 (10H, m), 8.61(1H, brs)

269) $^1$H-NMR($CDCl_3$)δ; 1.86–2.04(1H, m), 2.13–2.31 (1H, m), 2.33(3H, s), 3.53–3.62(1H, m), 3.76(1H, dt, J=12.8, 6.4Hz), 6.60(1H, d, J=8.7Hz), 6.91 (1H, dd, J=8.7, 2.5Hz), 7.33–7.52(6H, m), 7.54–7.66(2H, m), 7.73–7.82(1H, m), 8.07(1H, brs)

270) $^1$H-NMR($CDCl_3$)δ; 1.65–2.27(2H, m), 2.28(6H, s), 2.48(3H, s), 3.37–4.07(3H, m), 6.33–7.91(10H, m), 8.20(1H, brs)

271) $^1$H-NMR($CDCl_3$)δ; 1.71–2.26(2H, m), 2.28(6H, s), 3.36–4.10(3H, m), 6.35–7.95(10H, m), 8.59(1H, brs)

272) $^1$H-NMR($CDCl_3$)δ; 2.02–2.23(2H, m), 2.28(3H, s), 2.47(3H, s), 2,56(3H, s), 3.73–4.07(3H, m), 4.68 (1H, brs), 6.61(1H, d, J=8.1Hz), 6.72–6.83(1H, m), 7.17–7.63(11H, m), 8.03(1H, brs)

273) $^1$H-NMR($CDCl_3$)δ; 1.61(1H, brs), 1.87–2.25(2H, m), 2.29(3H, s), 2.56(3H, s), 3.67–3.78(1H, m), 3.91(2H, t, J=6.9Hz), 6.52–6.79(2H, m), 7.09–7.15(1H, m), 7.30–7.90(8H, m), 8.23(1H, brs)

274) $^1$H-NMR($CDCl_3$)δ; 1.58(1H, brs), 1.82–2.23(2H, m), 2.27(3H, s), 2.48(3H, s), 2.50(3H, s), 3.47–4.05(3H, m), 6.23–6.83(2H, m), 7.00–7.50(7H, m), 7.53–7.74(1H, m), 8.28(1H, brs)

275) $^1$H-NMR($CDCl_3$)δ; 1.60(1H, brs), 1.82–2.35(5H, m), 2.49(3H, s), 3.41–4.08(3H, m), 6.30–6.80(1H, m), 6.98–7.68(8H, m), 7.31–7.82(1H, m), 8.77(1H, brs)

276) $^1$H-NMR($CDCl_3$)δ; 1.76–2.03(2H, m), 2.27(3H, s), 2.32(6H, s), 2.47(3H, s), 3.48–3.58(1H, m), 3.66 (1H, dt, J=12.7, 6.1Hz), 3.97–4.14(1H, m), 6.48 (1H, d, J=8.2Hz), 6.65–6.77(1H, m), 7.14–7.59 (9H, m), 7.96(1H, brs)

277) $^1$H-NMR($CDCl_3$)δ; 1.75–2.04(2H, m), 2.27(3H, s), 2.33(6H, s), 3.48–3.58(1H, m), 3.67(1H, dt, J=12.7, 6.1Hz), 3.98–4.16(1H, m), 6.48(1H, d, J=8.2Hz), 6.72(1H, dd, J=8.2, 1.9Hz), 7.16(1H, d, J=1.9Hz), 7.27–7.91(8H, m), 8.31(1H, brs)

278) $^1$H-NMR($CDCl_3$)δ; 1.72–2.05(2H, m), 2.28(9H, s), 2.47(3H, s), 3.16–4.34(3H, m), 6.38–7.79(10H, m), 8.37(1H, brs)

279) $^1$H-NMR($CDCl_3$)δ; 1.65–2.07(2H, m), 2.28(9H, s), 3.26–4.38(3H, m), 6.34–8.06(10H, m), 8.53(1H, brs)

280) Two stereoisomers: Both colorless amorphous

Isomer A:

$[\alpha]_D^{22}$ = 0° (chloroform, c=1.0)
$^1$H-NMR($CDCl_3$)δ; 1.04(3H, d, J=6.9Hz), 1.59 (1H, brs), 2.25–2.45(1H, m), 2.49(3H, s), 2.52 (3H, s), 3.53–3.69(2H, m), 3.91(1H, abq, J=7.2, 12.9Hz), 6.60(1H, d, J=8.6Hz), 6.93(1H, dd, J=8.6, 2.5Hz), 7.18–7.60(9H, m), 7.76(1H, brs)

TABLE 9-continued

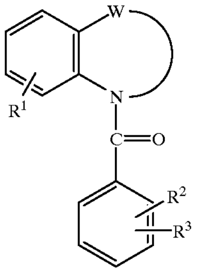

Isomer B:

$[\alpha]_D^{22}$ = 0° (chloroform, c=1.0)
$^1$H-NMR($CDCl_3$)δ; 1.06(3H, d, J=6.9Hz), 1.60 (1H, brs), 2.21–2.43(1H, m), 2.47(3H, s), 2.52 (3H, s), 3.51–3.66(2H, m), 3.93(1H, abq, J=7.5, 12.9Hz), 6.60–6.68(1H, m), 6.95(1H, dt, J=7.5, 1.8Hz), 7.03(1H, dt, J=7.4, 1.4Hz), 7.17–7.55 (8H, m), 7.81(1H, brs)

281) Two stereoisomers: Both colorless amorphous

Isomer A:

$[\alpha]_D^{22}$ = 0° (chloroform, c=1.0)
$^1$H-NMR($CDCl_3$)δ; 1.04(3H, d, J=6.9Hz), 1.55 (1H, brs), 2.23–2.46(1H, m), 2.53(3H, s), 3.53–3.67(2H, m), 3.91(1H, abq, J=7.1, 12.9Hz), 6.61 (1H, d, J=8.6Hz), 6.93(1H, dd, J=8.6, 2.5Hz), 7.28–7.52(6H, m), 7.54–7.65(2H, m), 7.70–7.79 (1H, m), 8.16(1H, brs)

Isomer B:

$[\alpha]_D^{22}$ = 0° (chloroform, c=1.0)
$^1$H-NMR($CDCl_3$)δ; 1.06(3H, d, J=6.9Hz), 1.61 (1H, brs), 2.21–2.42(1H, m), 2.51(3H, s), 3.48–3.67(2H, m), 3.90(1H, abq, J=7.4, 12.9Hz), 6.59–6.67(1H, m), 6.94(1H, dt, J=7.5, 1.9Hz), 7.03 (1H, dt, J=7.4, 1.4Hz), 7.23–7.75(8H, m), 8.41 (1H, brs)

282) Two stereoisomers: Both colorless amorphous

Isomer A:

$[\alpha]_D^{22}$ = 0° (chloroform, c=1.0)
$^1$H-NMR($CDCl_3$)δ; 0.99(3H, d, J=6.5Hz), 1.37 (1H, brs), 2.61–2.40(1H, m), 2.46(3H, s), 2.48 (3H, s), 3.38–3.96(3H, m), 6.30–7.28(10H, m), 8.26(1H, brs)

Isomer B:

$[\alpha]_D^{22}$ = 0° (chloroform, c=1.0)
$^1$H-NMR($CDCl_3$)δ; 1.03(3H, d, J=6.7Hz), 1.44(1H, brs), 2.17–2.40(1H, m), 2.45(3H, s), 2.47(3H, s), 3.40–3.98(3H, m), 6.47–7.73(10H, m), 8.23 (1H, brs)

283) Two stereoisomers: Both colorless amorphous

Isomer A:

$[\alpha]_D^{22}$ = 0° (chloroform, c=1.0)
$^1$H-NMR($CDCl_3$)δ; 1.00(3H, d, J=6.6Hz), 1.40 (1H, brs), 2.18–2.42(1H, m), 2.47(3H, s), 3.36–4.02(3H, m), 6.32–7.78(10H, m), 8.55(1H, brs)

Isomer B:

$[\alpha]_D^{22}$ = 0° (chloroform, c=1.0)
$^1$H-NMR($CDCl_3$)δ; 1.03(3H, d, J=6.5Hz), 1.39 (1H, brs), 2.14–2.39(1H, m), 2.45(3H, s). 3.34–3.98(3H, m), 6.53–7.98(10H, m), 8.78(1H, brs)

284) $^1$H-NMR($CDCl_3$)δ; 1.05–1.25(3H, m), 1.25–2.80 (10H, m), 3.00–5.10(3H, m), 6.75–8.40(11H, m)

285) $^1$H-NMR($CDCl_3$)δ; 1.00–2.80(12H, m), 3.00–5.10 (3H, m), 6.70–7.80(10H, m), 8.03–8.80(1H, m)

286) $^1$H-NMR($CDCl_3$)δ; 0.95–2.80(15H, m), 2.80–5.15 (3H, m), 6.70–7.05(2H, m), 7.10–7.80(10H, m), 7.95–8.45(1H, m)

287) $^1$H-NMR($CDCl_3$)δ; 0.80–2.60(16H, m), 2.60–5.05

TABLE 9-continued

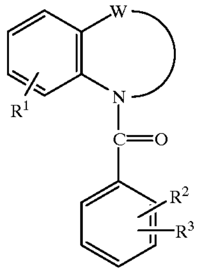

| | |
|---|---|
| | (4H, m), 6.70–7.70(10H, m), 7.85–8.40(1H, m) |
| 288) | $^1$H-NMR($CDCl_3$)δ; 1.30–2.60(8H, m), 2.60–5.10 (3H, m), 6.60–7.95(10H, m), 8.25–8.70(1H, m) |
| 289) | $^1$H-NMR($CDCl_3$)δ; 1.27–4.91(19H, m), 6.68–7.73 (10H, m), 8.40–8.71(1H, m) |
| 290) | $^1$H-NMR($CDCl_3$)δ; 1.81–2.54(6H, m), 2.15(3H, s), 2.41(3H, s), 2.46(3H, s), 3.61–3.71(3H, m), 6.91–7.43(10H, m), 8.06(1H, s) |
| 291) | $^1$H-NMR($CDCl_3$)δ; 1.86–2.50(3H, m), 2.28(9H, s), 2.49(3H, s), 6.60–7.47(10H, m), 7.75(1H, m) |
| 292) | $^1$H-NMR($CDCl_3$)δ; 1.15–2.55(13H, m), 2.55–5.10 (3H, m) 6.60–8.40(11H, m) |
| 293) | $^1$H-NMR($CDCl_3$)δ; 1.15–2.45(10H, m), 2.55–5.10 (3H, m), 6.60–7.80(10H, m), 8.30–8.70(1H, m) |
| 294) | $^1$H-NMR($CDCl_3$)δ; 1.10–2.60(4H, m), 2.41(6H, s), 2.49(3H, s), 3.76(3H, s), 2.60–5.20(3H, m), 6.50–6.80(3H, m), 6.90–7.60(6H, m), 8.13(1H, s), 8.30(1H, d, J=8.5Hz) |
| 295) | $^1$H-NMR($CDCl_3$)δ; 1.15–2.50(4H, m), 2.41(6H, s), 2.60–5.20(3H, m), 3.77(3H, s), 6.50–7.50(8H, m), 7.65–7.80(1H, m), 8.31(1H, d, J=8.4Hz), 8.61 (1H, s) |
| 296) | $^1$H-NMR($CDCl_3$)δ; 1.55–3.13(12H, m), 2.44(3H, s), 4.60–5.14(2H, m), 6.28(1H, dd, J=2.5, 8.5 Hz), 6.48(1H, d, J=8.5Hz), 6.99(1H, d, J=2.5 Hz), 7.07–7.58(8H, m), 7.80(1H, brs) |
| 297) | $^1$H-NMR($CDCl_3$)δ; 1.01–2.88, 3.22–4.41, 4.90–5.28 [total 18H, 1.17(3H, t, J=7.2Hz), 2.40(3H, s), 3.77(3H, s)], 6.55(1H, d, J=8.1Hz), 6.60–7.98 (8H, m), 8.23–8.75(2H, m) |
| 298) | $^1$H-NMR($CDCl_3$)δ; 1.00–3.04, 3.24–4.45. 4.91–5.27 [total 21H, m, 1.17(3H, t, J=7.0Hz), 2.39(3H, s), 2.50(3H, s), 3.75(3H, s)], 8.56(1H, d, J=8.3 Hz), 6.69(1H, d, J=8.3Hz), 6.82–7.75(7H, m), 8.05–8.49(2H, m) |
| 299) | $^1$H-NMR($CDCl_3$)δ; 1.21–4.62, 4.90–5.43(total 15H, m), 5.70–6.11(1H, m), 6.35–7.90(9H, m), 8.07–8.92 (2H, m) |
| 300) | $^1$H-NMR($CDCl_3$)δ; 1.20–4.68, 5.01–5.3[total 18H, m, 2.50(3H, s)], 5.72–6.14(1H, m), 6.49–7.69(9H, m), 8.01–8.58(2H, m) |
| 301) | $^1$H-NMR($CDCl_3$)δ; 1.25–2.80(14H, m), 3.00–5.10 (6H, m), 6.40–8.00(11H, m) |
| 302) | $^1$H-NMR($CDCl_3$)δ; 1.30–2.90(11H, m), 3.00–5.10 (6H, m), 6.40–7.80(10H, m), 8.00–8.35(1H, m) |
| 303) | $^1$H-NMR($CDCl_3$)δ; 1.10–2.80(16H, m), 2.85–5.15 (6H, m), 6.40–7.80(11H, m) |
| 304) | $^1$H-NMR($CDCl_3$)δ; 1.10–2.80(13H, m), 2.90–5.10 (6H, m), 6.40–7.85(10H, m), 7.90–8.20(1H, m) |
| 305) | $^1$H-NMR($CDCl_3$)δ; 1.27–5.28(19H, m), 3.75(3H, s), 6.51(1H, d, J=7.9Hz), 6.69–6.81(2H, m), 7.05–7.49(6H, m), 8.14(1H, m), 8.27(1H, d, J=8.4 Hz) |
| 306) | Two stereoisomers: Both colorless amorphous<br>Isomer A:<br>$[\alpha]_D^{22}$ = 0° (chloroform, c=1.0)<br>$^1$H-NMR($CDCl_3$)δ; 0.78–1.02(3H, m), 2.23–2.52 (1H, m) 2.39(6H, s), 2.48(3H, s), 3.17–4.30(3H, m), 6.85–7.84(10H, m), 8.17(1H, brs)<br>Isomer B:<br>$[\alpha]_D^{22}$ = 0° (chloroform, c=1.0)<br>$^1$H-NMR($CDCl_3$)δ; 0.73–1.00(3H, m), 2.17–2.52 |

TABLE 9-continued

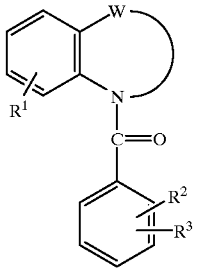

| | |
|---|---|
| | (1H, m) 2.39(6H, s), 2.49(3H, s), 3.15–4.33(3H, m), 6.36–7.55(8H, m), 7.58–7.83(2H, m), 8.19(1H, brs) |
| 307) | $^1$H-NMR($CDCl_3$)δ; 1.25–4.44, 4.98–5.41 [total 17H, m, 2.40(3H, s), 3.76(3H, s)], 5.72–6.13(1H, m), 6.56(1H, d, J=8.4Hz), 6.69(1H, d, J=7.9Hz), 6.77–7.93(7H, m), 8.32(1H, d, J=8.3Hz), 8.49–8.95(1H, m) |
| 308) | $^1$H-NMR($CDCl_3$)δ; 1.23–5.42(20H, m), 5.78–6.09 (1H, m), 6.56(1H, d, J=8.3Hz), 6.61–7.82(8H, m), 8.14(1H, s), 8.30(1H, d, J=8Hz) |
| 309) | $^1$H-NMR($CDCl_3$)δ; 1.20–2.70(11H, m), 2.80–4.90 (9H, m), 6.40–7.70(10H, m), 8.30–8.70(1H, m) |
| 310) | $^1$H-NMR($CDCl_3$)δ; 1.20–2.80(8H, m), 2.85–5.05 (9H, m), 6.40–7.80(10H, m), 8.10–8.50(1H, m) |
| 311) | $^1$H-NMR($CDCl_3$)δ; 1.20–2.75(13H, m), 2.80–5.10 (9H, m), 6.40–8.00(11H, m) |
| 312) | $^1$H-NMR($CDCl_3$)δ; 1.20–2.80(10H, m), 2.90–5.10 (9H, m), 6.40–7.80(10H, m), 8.00–8.40(1H, m) |

EXAMPLE 1189

By using di-p-toluoyl-L-tartaric acid monohydride or di-p-toluoyl-D-tartaric acid monohydride, the compound obtained in above Example 408 is optically resolved to give the following compounds.

(+)-5-Dimethylamino-1-[4-(2-methylbenzoylamino) benzoyl]-2,3,4,5-tetrahydro-1H-benzazepine hydrochloride White amorphous $[\alpha]_D^{25}$=+234° (methanol, c=0.2)

Purity; more than 99% ee, determined by HPLC using an optical acitive column

HPLC conditions;

Mobile phase; n-hexane:ethanol:diethylamine=950:50:1

Flow rate; 1.0 ml/min.

Column; CHIRALCEL OD, 25 cm×0.46 cm (manufactured by Daicel Chemical Ind. Ltd.)

Concentration of sample; 0.1% in methanol

Retention time; 34 minutes $^1$H-NMR (DMSO-$d_6$) δ; 0.85–1.20, 1.56–4.06, 4.94–5.21 (total 13H, m), 2.36 (3H, s), 6.79 (1H, d, J=7.6 Hz), 7.12–7.60 (8H, m), 7.62 (2H, d, J=8.4 Hz), 8.00 (1H, d, J=7.6 Hz), 10.43 (1H, s), 11.80 (1H, brs)

(−)-5-Dimethylamino-1-[4-(2-methylbenzoylamino) benzoyl]-2,3,4,5-tetrahydro-1H-benzazepine hydrochloride White amorphous $[\alpha]_D^{25}$=−23.1° (methanol, c=0.2)

Purity; more than 99% ee, determined by HPLC using an optical active column, and the conditions are the same as above except that the retention time is 40 minutes.

$^1$H-NMR (DMSO-$d_6$) δ; 0.83–1.19, 1.55–4.06, 4.94–5.20 (total 13H, m), 2.36 (3H, s), 6.80 (1H, d, J=7.8 Hz), 7.12–7.60 (8H, m), 7.63 (2H, d, J=8.5 Hz), 8.00 (1H, d, J=7.8 Hz), 10.44 (1H, s), 11.74 (1H, brs)

Pharmacological Test

Experiment 1: $V_1$ receptor binding assay

Using rat liver plasma membrane preparations prepared according to Ichihara's method [cf: Akira Ichihara, J. Bio. Chem., 258, 9283 (1983)], the plasma membrane (50000 dpm, $2\times10^{-10}$ M) of [$^3$H]-Arg-vasopressin and a test compound (60 $\mu$g, $10^{-8}$–$10^{-4}$ M) are incubated at 37° C. for 10 minutes in 100 mM Tris-HCl buffer (pH: 8.0, 250 $\mu$l) containing 5 mM $MgCl_2$, 1 mM EDTA and 0.1% BSA. After incubation, the mixture is filtered three times using the glass filter (GF/F) so as to separate the membrane preparation combined with vasopressin and then washed with the buffer (5 ml). This glass filter is taken out and mixed with liquid scintillation cocktail. The amount of [$^3$H]-vasopressin combined with the membrane is measured by liquid scintillation counter and the rate of the inhibitory effect of the test compound is estimated according to the following equation.

$$\text{Rate of the inhibitory effect (\%)} = 100 - \frac{C_1 - B_1}{C_0 - B_1} \times 100$$

$C^1$: The amount of [$^3$H]-vasopressin combined with the membrane in the presence of the test compound (in prescribed amount).

$C^0$: The amount of [$^3$H]-vasopressin combined with the membrane in the absence of the test compound.

$B^1$: The amount of [$^3$H]-vasopressin combined with the membrane in the presence of the excess amount of vasopressin ($10^{-6}$ M).

The results are expressed as $IC_{50}$ values, which is the concentration of the test compound required to achieve the inhibitory effect in the rate of 50%.

The results are shown in the following Table 10.

Test compound 1. 1-(4-Benzoylaminobenzoyl)-1,2,3,4-tetrahydroquinoline
2. 1-[4-(3-Chlorobenzoylamino)benzoyl]-1,2,3,4-tetrahydroquinoline
3. 1-[4-(3-Methoxybenzoylamino)benzoyl]-1,2,3,4-tetrahydroquinoline
4. 1-[4-(3-Cyanobenzoylamino)benzoyl]-1,2,3,4-tetrahydroquinoline
5. 1-[4-(3-Aminobenzoylamino)benzoyl]-1,2,3,4-tetrahydroquinoline
6. 1-[4-(2,3-Dimethylbenzoylamino)benzoyl]-1,2,3,4-tetrahydroquinoline
7. 1-[4-(2-Methylbenzoylamino)benzoyl]-1,2,3,4-tetrahydroquinoline
8. 1-[4-(2-Trifluoromethylbenzoylamino)benzoyl]-1,2,3,4-tetrahydroquinoline
9. 1-[4-(2-Nitrobenzoylamino)benzoyl]-1,2,3,4-tetrahydroquinoline
10. 1-[4-(3,5-Dichlorobenzoylamino)benzoyl]-1,2,3,4-tetrahydroquinoline
11. 1-[4-(3,3-Dimethylbutyrylamino)benzoyl]-1,2,3,4-tetrahydroquinoline
12. 1-[4-(2-Cyclohexylacetylamino)benzoyl]-1,2,3,4-tetrahydroquinoline
13. 1-[4-(2-Phenylacetylamino)benzoyl]-1,2,3,4-tetrahydroquinoline
14. 1-(4-Cyclohexylcarbonylaminobenzoyl)-1,2,3,4-tetrahydroquinoline
15. 1-(4-Cycloheptylcarbonylaminobenzoyl)-1,2,3,4-tetrahydroquinoline
16. 1-(4-Cyclooctylcarbonylaminobenzoyl)-1,2,3,4-tetrahydroquinoline
17. 1-(4-Tricyclo[3.3.1.1]decanylcarbonylaminobenzoyl)-1,2,3,4-tetrahydroquinoline
18. 1-[4-(α-Naphthylcarbonylamino)benzoyl]-1,2,3,4-tetrahydroquinoline
19. 1-[4-(3-Thenoyl)benzoyl]-1,2,3,4-tetrahydroquinoline
20. 1-[2-(β-Naphthylcarbonylamino)benzoyl]-1,2,3,4-tetrahydroquinoline
21. 1-[4-(4-Methoxyanilinocarbonyl)benzoyl]-1,2,3,4-tetrahydroquinoline
22. 1-[4-(2-Methylanilinocarbonyl)benzoyl]-1,2,3,4-tetrahydroquinoline
23. 1-[4-(3-Chloroanilinocarbonyl)benzoyl]-1,2,3,4-tetrahydroquinoline
24. 1-[4-(3,5-Dichloroanilinocarbonyl)benzoyl]-1,2,3,4-tetrahydroquinoline
25. 1-(4-Cyclohexylaminocarbonylbenzoyl)-1,2,3,4-tetrahydroquinoline
26. 1-(4-Cyclohexylcarbonylaminobenzoyl)-2,3,4,5-tetrahydro-1H-benzazepine
27. 1-(4-Benzoylaminobenzoyl)-2,3,4,5-tetrahydro-1H-benzazepine
28. 1-[4-(2-Methylbenzoylamino)benzoyl]-2,3,4,5-tetrahydro-1H-benzazepine
29. 1-[4-(3-Methoxybenzoylamino)benzoyl]-2,3,4,5-tetrahydro-1H-benzazepine
30. 1-[4-(3-Chlorobenzoylamino)benzoyl]-2,3,4,5-tetrahydro-1H-benzazepine
31. 1-[4-(3-Cyanobenzoylamino)benzoyl]-2,3,4,5-tetrahydro-1H-benzazepine
32. 1-[4-(3,5-Dichlorobenzoylamino)benzoyl]-2,3,4,5-tetrahydro-1H-benzazepine
33. 1-[4-(2,3-Dimethylbenzoylamino)benzoyl]-2,3,4,5-tetrahydro-1H-benzazepine
34. 1-(4-Cyclohexylcarbonylaminobenzoyl)-1,2,3,4,5,6-hexahydrobenzazocine
35. 1-(4-Benzoylaminobenzoyl)-1,2,3,4,5,6-hexahydrobenzazocine
36. 1-[4-(2-Methylbenzoylamino)benzoyl]-1,2,3,4,5,6-hexahydrobenzazocine
37. 1-[4-(3-Methoxybenzoylamino)benzoyl]-1,2,3,4,5,6-hexahydrobenzazocine
38. 1-[4-(2,3-Dimethylbenzoylamino)benzoyl]-1,2,3,4,5,6-hexahydrobenzazocine
39. 1-[4-(3,5-Dichlorobenzoylamino)benzoyl]-1,2,3,4,5,6-hexahydrobenzazocine
40. 1-(4-Cyclohexylcarbonylaminobenzoyl)-1,2,3,5-tetrahydro-4,1-benzoxazepine
41. 1-[4-(3-Methylbenzoylamino)benzoyl]-1,2,3,5-tetrahydro-4,1-benzoxazepine
42. 1-[4-(2,3-Dimethylbenzoylamino)benzoyl]-1,2,3,5-tetrahydro-4,1-benzoxazepine
43. 1-[4-(3,5-Dichlorobenzoylamino)benzoyl]-1,2,3,5-tetrahydro-4,1-benzoxazepine
44. 3-Methyl-1-(4-cyclohexylcarbonylaminobenzoyl)-1,2,3,4-tetrahydroquinoline
45. 3-Methyl-1-(4-benzoylaminobenzoyl)-1,2,3,4-tetrahydroquinoline
46. 3-Methyl-1-[4-(2-methylbenzoylamino)benzoyl]-1,2,3,4-tetrahydroquinoline
47. 3-Methyl-1-[4-(3-methoxybenzoylamino)benzoyl]-1,2,3,4-tetrahydroquinoline
48. 3-Methyl-1-[4-(2,3-dimethylbenzoylamino)benzoyl]-1,2,3,4-tetrahydroquinoline
49. 3-Methyl-1-[4-(3,5-dichlorobenzoylamino)benzoyl]-1,2,3,4-tetrahydroquinoline
50. 4-Methyl-1-(4-cyclohexylcarbonylaminobenzoyl)-1,2,3,4-tetrahydroquinoxaline 51. 4-Methyl-1-[4-(2-methylbenzoylamino)benzoyl]-1,2,3,4-tetrahydroquinoxaline 52. 4-Methyl-1-[4-(2,3-dimethylbenzoylamino)benzoyl]-1,2,3,4-tetrahydroquinoxaline 53. 4-Methyl-1-[4-(3,5-dichlorobenzoylamino)benzoyl]-1,2,3,4-tetrahydroquinoxaline 54. 2-Methyl-1-[4-(3,5-dichlorobenzoylamino)benzoyl]-1,2,3, 4-tetrahydroquinoline 55. 4-Methyl-1-[4-(3,5-dichlorobenzoylamino)benzoyl]-1,2,3,4-tetrahydroquinoline 56. 1-[4-(2-Bromobenzoylamino)benzoyl]-2,3,4,5-tetrahydro-1H-benzazepine 57. 1-[4-(3-Nitrobenzoylamino)benzoyl]-2,3,4,5-tetrahydro-1H-benzazepine 58. 1-[4-(3-Trifluoromethylbenzoylamino)benzoyl]-2,3,4,5-tetrahydro-1H-benzazepine 59. 1-[4-(3-Ethoxybenzoylamino)benzoyl]-2,3,4,5-tetrahydro-1H-benzazepine 60. 1-[4-(3,5-Dimethoxybenzoylamino)benzoyl]-2,3,4,5-tetrahydro-1H-benzazepine 61. 1-[4-(2-Chloro-4-nitrobenzoylamino)benzoyl]-2,3,4,5-tetrahydro-1H-benzazepine 62. 1-[4-(2,4-Dichlorobenzoylamino)benzoyl]-2,3,4,5-tetrahydro-1H-benzazepine 63. 1-[4-(2-Chloro-6-fluorobenzoylamino)benzoyl]-2,3,4,5-tetrahydro-1H-benzazepine 64. 1-[4-(2,6-Dimethylbenzoylamino)benzoyl]-2,3,4,5-tetrahydro-1H-benzazepine 65. 1-[4-(2-Chloro-4-aminobenzoylamino)benzoyl]-2,3,4,5-tetrahydro-1H-benzazepine 66. 1-[4-(2-Chloro-4-acetylaminobenzoylamino)benzoyl]-2,3,4,5-tetrahydro-1H-benzazepine 67. 1-[4-(3-Aminobenzoylamino)benzoyl]-2,3,4,5-tetrahydro-1H-benzazepine 68. 1-{4-[2-(4-Isopropylaminobutoxy)benzoylamino]benzoyl}-2,3,4,5-tetrahydro-1H-benzazepine hydrochloride 69. 1-[4-(3-Hydroxybenzoylamino)benzoyl]-2,3,4,5-tetrahydro-1H-benzazepine 70. 1-{4-[2-(4-Aminobutoxy)benzoylamino]benzoyl}-2,3,4,5-tetrahydro-1H-benzazepine 71. 1-{4-[2-(2-Diethylaminoethoxy)benzoylamino]benzoyl}-2,3,4,5-tetrahydro-1H-benzazepine hydrochloride 72. 1-{4-[2-(4-Acetylaminobutoxy)benzoylamino]benzoyl}-2,3,4,5-tetrahydro-1H-benzazepine 73. 1-{4-[2-(6-Phthalimidohexyloxy)benzoylamino]benzoyl}-2,3,4,5-tetrahydro-1H-benzazepine 74. 1-{4-[2-(6-Morpholinohexyloxy)benzoylamino]benzoyl}-2,3,4,5-tetrahydro-1H-benzazepine 75. 1-{4-[2-(6-[4-Methyl-1-piperazinyl]hexyloxy)benzoylamino]benzoyl}-2,3,4,5-tetrahydro-1H-benzazepinedihydrochloride 76. 1-(3-Methoxy-4-cyclohexylcarbonylaminobenzoyl)-2,3,4,5-tetrahydro-1H-benzazepine 77. 1-(3-methoxy-4-benzoylamino)benzoyl]-2,3,4,5-tetrahydro-1H-benzazepine 78. 1-[3-Methyl-4-(2-methylbenzoylamino)benzoy]-2,3,4,5-tetrahydro-1H-benzazepine 79. 4-Methyl-1-(4-cyclohexylcarbonylaminobenzoyl)-2,3,4,5-tetrahydro-1H-1,4-benzodiazepine hydrochloride 80. 4-Methyl-1-[4-(3,5-dichlorobenzoylamino)benzoyl]-2,3,4,5-tetrahydro-1H-l,4-benzodiazepine hydrochloride 81. 4-Methyl-1-[4-(2,3-dimethylbenzoylamino)benzoyl]-2,3,4,5-tetrahydro-1H-1,4-benzodiazepine hydrochloride 82. 4-Methyl-1-[4-(2-methylbenzoylamino)benzoyl]-2,3,4,5-tetrahydro-1H-1,4-benzodiazepine hydrochloride 83. 4-Methyl-1-[4-(3-methoxybenzoylamino)benzoyl]-2,3,4,5-tetrahydro-1H-1,4-benzodiazepine 84. 4-Methyl-1-[4-(3-chlorobenzoylamino)benzoyl]-2,3,4,5-tetrahydro-1H-1,4-benzodiazepine 85. 4-Methyl-1-[4-(2,3,5-trichlorobenzoylamino)benzoyl]-2,3,4,5-tetrahydro-1H-1,4-benzodiazepine 86. 4-Propyl-1-[4-(2,3-dimethylbenzoylamino)benzoyl]-2,3,4,5-tetrahydro-1H-1,4-benzodiazepine hydrochloride 87. 5-Methyl-1-(4-benzoylaminobenzoyl)-2,3,4,5-tetrahydro-1H-1,5-benzodiazepine 88. 5-Methyl-1-(4-cyclohexylcarbonylaminobenzoyl)-2,3,4,5-tetrahydro-1H-1,5-benzodiazepine 89. 5-Methyl-1-[4-(3,5-dichlorobenzoylamino)benzoyl]-2,3,4,5-tetrahydro-1H-1,5-benzodiazepine 90. 5-Methyl-1-[4-(2-methylbenzoylamino)benzoyl]-2,3,4,5-tetrahydro-1H-1,5-benzodiazepine 91. 5-Methyl-1-[4-(2,3-dimethylbenzoylamino)benzoyl]-2,3,4,5-tetrahydro-1H-1,5-benzodiazepine 92. 4-Methyl-1-[3-methoxy-4-(3,5-dichlorobenzoylamino)benzoyl]-2,3,4,5-tetrahydro-1H-1,4-benzodiazepine 93. 3-(1-Pyrrolidinyl)-1-[4-(2,3-dimethylbenzoylamino)benzoyl]-1,2,3,4-tetrahydroquinoline 94. 6-Methyl-1-[4-(3,5-dichlorobenzoylamino)benzoyl]-1,2,3,4-tetrahydroquinoline 95. 6-Methoxy-1-[4-(3,5-dichlorobenzoylamino)benzoyl]-1,2,3,4-tetrahydroquinoline 96. 3-Hydroxymethyl-1-(4-(3,5-dichlorobenzoylamino)benzoyl]-1,2,3,4-tetrahydroquinoline 97. 4-Methylamino-1-[4-(3,5-dichlorobenzoylamino)benzoyl]-1,2,3,4-tetrahydroquinoline 98. 3-Amino-1-[4-(3,5-dichlorobenzoylamino)benzoyl]-1,2,3,4-tetrahydroquinoline 99. 3-Acetylamino-1-[4-(3,5-dichlorobenzoylamino)benzoyl]-1,2,3,4-tetrahydroquinoline 100. 4-Dimethylamino-1-[4-(3,5-dichlorobenzoylamino)benzoyl]-1,2,3,4-tetrahydroquinoline 101. 1-[4-(2-t-Butylaminoacetylamino)benzoyl]-2,3,4,5-tetrahydroquinoline-1H-benzazepine 102. 1-{4-[2-(N-Cyclohexyl-N-ethyl)acetylamino]benzoyl}-2,3,4,5-tetrahydro-1H-benzazepine 103. 1-{4-[2-(1-Piperidinyl)acetylamino]benzoyl}-2,3,4,5-tetrahydro-1H-benzazepine 104. 1-[4-(2-Phenoxyacetylamino)benzoyl]-2,3,4,5-tetrahydro-1H-benzazepine 105. 1-[4-(2-Phthalimidoacetylamino)benzoyl]-2,3,4,5-tetrahydro-1H-benzazepine 106. 1-{4-[2-(1,1-Dimethyl-2-phenoxyethyl)aminoacetylamino]benzoyl}-2,3,4,5-tetrahydro-1H-benzazepine 107. 1-{4-[2-(3-Methylphenoxy)acetylamino]benzoyl}-2,3,4,5-tetrahydro-1H-benzazepine 108. 1-{4-[2-(3-Methoxyanilino)acetylamino]benzoyl}-2,3,4,5-tetrahydro-1H-benzazepine 109. 1-{4-[2-(β-Naphthyloxy)acetyamino]benzoyl}-2,3,4,5-tetrahydro-1H-benzazepine 110. 1-{4-[2-(4-Methylanilino)acetylamino]benzoyl}-2,3,4,5-tetrahydro-1H-benzazepine 111. 1-{4-(2-(3-Methoxyphenoxy)acetylamino]benzoyl}-2,3,4,5-tetrahydro-1H-benzazepine 112. 1-[4-(4-Pyridylcarbonylaminobenzoyl]-2,3,4,5-tetrahydro-1H-benzazepine 113. 1-{4-[2-(2,4-Dimethylanilino)acetylamino]benzoyl}-2,3,4,5-tetrahydro-1H-benzazepine 114. 1-{4-[2-(N-Ethylanilino)acetylamino]benzoyl}-2,3,4,5-tetrahydro-1H-benzazepine 115. 1-{4-[2-(N-Allylanilino)acetylamino]benzoyl}-2,3,4,5-tetrahydro-1H-benzazepine 116. 1-{4-[2-(2-Chloroanilino)acetylamino]benzoyl}-2,3,4,5-tetrahydro-1H-benzazepine 117. 1-{4-[2-(4-Acetyloxybutoxy)benzoylamino]benzoyl}-2,3,4,5-tetrahydro-1H-benzazepine 118. 1-[4-(2-Carboxymethoxybenzoylamino)benzoyl]-2,3,4,5-tetrahydro-1H-benzazepine 119. 1-[4-(2-Carbamoylmethoxybenzoylamino)benzoyl]-2,3,4,5-tetrahydro-1H-benzazepine 120. 1-{4-[2-(4-Hydroxybutoxy)benzoylamino]benzoyl}-2,3,4,5-tetrahydro-1H-benzazepine 121. 1-[4-(2-Ethoxycarbonylmethoxybenzoylamino)benzoyl]-2,3,4,5-tetrahydro-1H-benzazepine 122. 6-Fluoro-1-[4-(3,5-dichlorobenzoylamino)benzoyl]-1,2,3,4-tetrahydroquinoline 123. 6-Fluoro-1-{4-[di-(3,5-dichlorobenzoyl)amino]benzoyl}-1,2,3,4-tetrahydroquinoline 124. 1-[4-(2-Diethylaminocarbonylmethoxybenzoylamino)benzoyl]-2,3,4,5-tetrahydro-1H-benzazepine 125. 1-{4-[2-(2-[(N-(2-hydroxyethyl)-N-methylamino]ethoxy)benzoylamino]benzoyl}-2,3,4,5-tetrahydro-1H-benzoazepine hydrochloride 126. 1-[4-(2-Methylanilinocarbonylamino)benzoyl]-2,3,4,5-tetrahydro-1H-benzazepine 127. 1-[4-(2-Chlorophenylsulfonylamino)benzoyl]-2,3,4,5-tetrahydro-1H-benzazepine 128. 1-{4-[2-(4-Aminomethylanilino)acetylamino]benzoyl}-2,3,4,5-tetrahydro-1H-benzazepine 129. 1-{4-[2-(N-Phenyl-N-(3-acetylaminopropyl)amino)acetylamino]benzoyl}-2,3,4,5-tetrahydro-1H-benzazepine 130. 1-{4-[2-(N-Phenyl-N-propargylamino)acetylamino]benzoyl}-2,3,4,5-tetrahydro-1H-benzazepine 131. 4-(N-Methyl-N-ethylamino)-1-[4-(3,5-dichlorobenzoylamino)benzoyl]-1,2,3,4-tetrahydroquinoline 132. 5-Dimethylamino-1-[4-(2,4-dichlorobenzoylamino)benzoyl]-2,3,4,5-tetrahydro-1H-benzazepine 133. 4-Dimethylamino-1-[3-methoxy-4-(2-methylbenzoylamino)benzoyl]-1,2,3,4-tetrahydroquinoline 134. 5-Dimethylamino-1-[3-methoxy-4-(2-chlorobenzoylamino)benzoyl]-2,3,4,5-tetrahydro-1H-benzazepine 135. 1-[4-(2,3-Dimethylbenzoylamino)benzoyl]-4-ethyl-2,3,4,5-tetrahydro-1H-1,4-benzodiazepine 136. 1-[4-(3,5-Dichlorobenzoylamino)benzoyl]-4-isopropyl-2,3,4,5-tetrahydro-1H-1,4-benzodiazepine 137. 1-[4-(2-Methylbenzoylamino)benzoyl]-5-methyl-1,2,3,4,5,6-hexahydro-1,5-benzodiazocine 138. 1-[4-(2-Methylbenzoylamino)benzoyl]-1,2,3,4-tetrahydro-5,1-benzoxazepine 139. 5-Oxo-1-[4-(3,5-dichlorobenzoylamino)benzoyl]-2,3,4,5-tetrahydro-1H-benzazepine 140. 4-Methyl-1-[2-chloro-4-(3,5-dichlorobenzoylamino)benzoyl]-2,3,4,5-tetrahydro-1H-1,4-benzodiazepine 141. 5-Methylamino-1-[4-(3,5-dichlorobenzoylamino)benzoyl]-2,3,4,5-tetrahydro-1H-benzazepine 142. 5-(N-Acetyl-N-methylamino)-1-[4-(3,5-dichlorobenzoylamino)benzoyl]-2,3,4,5-tetrahydro-1H-benzazepine 143.5-Hydroxy-1-[4-(2-methylbenzoylamino)benzoyl]-2,3,4,5-tetrahydro-1H-benzazepine 144. 4-Dimethylamino-1-[3-methoxy-4-(2,3-dimethylbenzoylamino)benzoyl]-1,2,3,4-tetrahydroquinoline 145. 4-Dimethylaminomethyl-1-[4-(2-methylbenzoylamino)benzoyl]-1,2,3,4-tetrahydroquinoline 146. 4-Dimethylaminomethyl-1-[4-(3,5-dichlorobenzoylamino)benzoyl]-1,2,3,4-tetrahydroquinoline 147. 5-Methoxy-1-[4-(2-methylbenzoylamino)benzoyl]-2,3,4,5-tetrahydro-1H-benzazepine 148. 4-Methyl-1-[3-methyl-4-(2,4-dichlorobenzoylamino)benzoyl]-2,3,4,5-tetrahydro-1H-1,4-benzodiazepine 149. 5-Methoxy-1-[4-(2,4-dichlorobenzoylamino)benzoyl]-2,3,4,5-tetrahydro-1H-benzazepine 150. 4-Dimethylamino-1-[4-(2-chlorobenzoylamino)benzoyl]- 2,3,4,5-tetrahydro-1H-benzazepine 151. 4-Acetyloxy-1-[4-(2-methylbenzoylamino)benzoyl]-1,2,3,4-tetrahydroquinoline 152. 5-Hydroxyimino-1-[4-(3,5-dichlorobenzoylamino)benzoyl]-2,3,4,5-tetrahydro-1H-benzazepine 153. 5-Acetyloxy-1-[4-(2-chlorobenzoylamino)benzoyl]-2,3,4,5-tetrahydro-1H-benzazepine 154. 5-Ethoxycarbonylmethoxy-1-[4-(2,4-dichlorobenzoylamino)benzoyl]-2,3,4,5-tetrahydro-1H-benzazepine 155. 4-Allylamino-1-[4-(3,5-dichlorobenzoylamino)benzoyl]-2,3,4,5-tetrahydro-1H-benzazepine 156. 5-Dimethylamino-1-[3-methoxy-4-(2,3,5-trichlorobenzoylamino)benzoyl]-2,3,4,5-tetrahydro-1H-benzazepine 157. 4-[4-(2-Methylbenzoylamino)benzoyl]-3,4-dihydro-2H-1,4-benzothiazine 158. 5-Dimethylamino-1-[2-chloro-4-(2-methylbenzoylamino)benzoyl]-2,3,4,5-tetrahydro-1H-benzazepine 159. 5-Dimethylamino-1-[4-(2-methylanilinocarbonyl)benzoyl]-2,3,4,5-tetrahydro-1H-benzazepine 160. 5-Ethoxycarbonylmethoxy-1-[4-(2-methylbenzoylamino)benzoyl]-2,3,4,5-tetrahydro-1H-benzazepine 161. 5-(4-dimethylaminobutoxy)-1-[4-(2-methylbenzoylamino)benzoyl]-2,3,4,5-tetrahydro-1H-benzazepine 162. 5-Carboxymethoxy-1-[4-(2-chlorobenzoylamino)benzoyl]-2,3,4,5-tetrahydro-1H-benzazepine 163. 5-Dimethylaminocarbonylmethoxy-1-[4-(2-methylbenzoylamino)benzoyl]-2,3,4,5-tetrahydro-1H-benzazepine 164. 5-Carbamoylmethoxy-1-[4-(2-chlorobenzoylamino)benzoyl]-2,3,4,5-tetrahydro-1H-benzazepine 165. 5-Dimethylamino-1-[3-ethoxy-4-(2-methyl-benzoylamino)benzoyl]-2,3,4,5-tetrahydro-1H-benzazepine 166. 5-[4-(2-Methylbenzoylamino)benzoyl]-2,3,4,5-tetrahydro-1,5-benzothiazepine 167. 5-Amino-1-[4-(2-methylbenzoylamino)benzoyl]-2,3,4,5-tetrahydro-1H-benzazepine 168. 5-Dimethylamino-1-[3-hydroxy-4-[2-methylbenzoylamino)benzoyl]-2,3,4,5-tetrahydro-1H-benzazepine 169. 5-n-Propylamino-1-[4-(2,4-dichlorobenzoylamino)benzoyl]-2,3,4,5-tetrahydro-1H-benzazepine 170. 5-Dimethylamino-1-[3-benzyloxy-4-(2-methylbenzoylamino)benzoyl]-2,3,4,5-tetrahydro-1H-benzazepine 171. 5-[4-(2-Methylbenzoylamino)benzoyl]-2,3,4,5-tetrahydro-1,5-benzothiazepin-1-oxide 172. 5-[3-(Phthalimid-1-yl)-propoxy]-1-[4-(2-methylbenzoylamino)benzoyl]-2,3,4,5-tetrahydro-1H-benzazepine 173. 5-(3-Aminopropoxy)-1-[4-(2-methylbenzoylamino)benzoyl]-2,3,4,5-tetrahydro-1H-benzazepine 174. 5-(3-Acetylaminopropoxy)-1-[4-(2-methylbenzoylamino)benzoyl]-2,3,4,5-tetrahydro-1H-benzazepine 175. 5-Dimethylamino-1-[2-chloro-4-(2-t-butylbenzoylamino)benzoyl]-2,3,4,5-tetrahydro-1H-benzazepine 176. 5-Methylamino-1-[2-chloro-4-(2-chlorobenzoylamino)benzoyl]-2,3,4,5-tetrahydro-1H-benzazepine 177. 5-Dimethylamino-1-[2-methoxy-4-(2-chlorobenzoylamino)benzoyl]-2,3,4,5-tetrahydro-1H-benzazepine 178. 5-Hydroxy-1-[4-(3,5-dichlorobenzoylamino)benzoyl]-2,3,4,5-tetrahydro-1H-benzazepine 179. 5-Dimethylamino-1-[4-(2-methylbenzoylamino)benzoyl]-2,3,4,5-tetrahydro-1H-benzazepine 180. 5-Dimethylamino-1-[4-(2-chlorobenzoylamino)benzoyl]-2,3,4,5-tetrahydro-1H-benzazepine 181. 5-Methylamino-1-[4-(2-chlorobenzoylamino)benzoyl]-2,3,4,5-tetrahydro-1H-benzazepine 182. 5-Methylamino-1-[2-chloro-4-(2-methylbenzoylamino)benzoyl]-2,3,4,5-tetrahydro-1H-benzazepine 183. 5-Dimethylamino-1-[2-methoxy-4-(2-methylbenzoylamino)benzoyl]-2,3,4,5-tetrahydro-1H-benzazepine 184. 5-Dimethylamino-1-[2-chloro-4-(2-chlorobenzoylamino)benzoyl]-2,3,4,5-tetrahydro-1H-benzazepine 185. 5-Methylamino-1-[2-chloro-4-(2-methylbenzoylamino)benzoyl-2,3,4,5-tetrahydro-1H-benzazepine 186. 5-Cyclopropylamino-1-[2-chloro-4-(2,4-dichlorobenzoylamino)benzoyl]-2,3,4,5-tetrahydro-1H-benzazepine 187. 5-Dimethylaminocarbonyloxy-1-[4-(2-methylbenzoylamino)benzoyl]-2,3,4,5-tetrahydro-1H-benzazepine 188. 5-Dimethylamino-1-[4-(2-trifluoromethylbenzoylamino)benzoyl]-2,3,4,5-tetrahydro-1H-benzazepine 189. 5-Dimethylamino-1-[3-(2-chlorobenzoyloxy)-4-(2-chlorobenzoylamino)benzoyl]-2,3,4,5-tetrahydro-1H-benzazepine 190. 5-(N-Methyl-N-Allylamino)-1-[2-chloro-4-(2-methylbenzoylamino)benzoyl]-2,3,4,5-tetrahydro-1H-benzazepine 191. 5-Carbamoyloxy-1-[4-(2-methylbenzoylamino)benzoyl]-2,3,4,5-tetrahydro-1H-benzazepine 192. 1-[4-(2-Methylbenzoylamino)benzoyl]-1,2,3,5-tetrahydro-4,1-benzothiazepine 193. 4-Oxo-1-[4-(2-methylbenzoylamino)benzoyl]-2,3,4,5-tetrahydro-1H-benzazepine 194. 1-[4-(2-Methylbenzoylamino)benzoyl]-1,2,3,5-tetrahydro-4,1-benzothiazepine-1,1-dioxide 195. 5-Methylaminocarbonylmethoxy-1-[4-(2-chlorobenzoylamino)benzoyl]-2,3,4,5-tetrahydro-1H-benzazepine 196. 5-Methylaminocarbonyloxy-1-[4-(2-methylbenzoylamino)benzoyl]-2,3,4,5-tetrahyro-1H-benzazepine 197. 5-Dimethylamino-1-[2-dimethylamino-4-(2-methylbenzoylamino)benzoyl]-2,3,4,5-tetrahydro-1H-benzazepine 198. 5-Methylamino-1-[2-chloro-4-(2-trifluoromethylbenzoylamino)benzoyl]-2,3,4,5-tetrahydro-1H-benzazepine 199. 5-Cycloropropylamino-1-[2-chloro-4-(2-methylbenzoylamino)benzoyl]-2,3,4,5-tetrahydro-1H-benzazepine 200. 5-Cyclopropylamino-1-[2-chloro-4-(2-chlorobenzoylamino)benzoyl]-2,3,4,5-tetrahydro-1H-benzazepine 201. 5-Allylamino-1-[2-chloro-4-(2-methylbenzoylamino)benzoyl]-2,3,4,5-tetrahydro-1H-benzazepine 202. 5-(1-Piperidinyl)-1-[4-(2-chlorobenzoylamino)benzoyl]-2,3,4,5-tetrahydro-1H-benzazepine 203. 5-(4-Benzyl-1-piperazinyl)-1-[4-(2-chlorobenzoylamino)benzoyl]-2,3,4,5-tetrahydro-1H-benzazepine 204. 5-(1-Pyrrolidinyl)-1-[4-(2-chlorobenzoylamino)benzoyl]-2,3,4,5-tetrahydro-1H-benzazepine 205. 5-(4-Acetyl-1-pipetazinyl)-1-[4-(2-chlorobenzoylamino)benzoyl]-2,3,4,5-tetrahydro-1H-benzazepine 206. 5-(4-Methyl-1-piperazinyl)-1-[4-(2-chlorobenzoylamino)benzoyl]-2,3,4,5-tetrahydro-1H-benzazepine 207. 1-[4-(2-Chlorobenzoylamino)benzoyl]-2,3-dihydro-1H-benzazepine 208. 5-Methyl-1-[4-(2-methylbenzoylamino)benzoyl]-2,3,4,5-tetrahydro-1H-benzazepine 209. 5-Methylidene-1-[4-(2-methylbenzoylamino)benzoyl]-2,3,4,5-tetrahydro-1H-benzazepine 210. 5-Hydroxy-1-[2-chloro-4-(2-methylbenzoylamino)benzoyl]-2,3,4,5-tetrahydro-1H-benzazepine 211. 5-(1-Morpholino)-1-[4-(2-chlorobenzoylamino)benzoyl]-2,3,4,5-tetrahydro-1H-benzazepine 212. 5-Dimethylamino-1-[4-(2-fluorobenzoylamino)benzoyl]-2,3,4,5-tetrahydro-1H-benzazepine 213. 5-Dimethylamino-1-[4-(2,4-difluorobenzoylamino)benzoyl]-2,3,4,5-tetrahydro-1H-benzazepine 214. 4-Hydroxy-1-[4-(2-methylbenzoylamino)benzoyl]-2,3,4,5-tetrahydro-1H-benzazepine 215. 5-Hydroxymethyl-1-[4-(2-methylbenzoylamino)benzoyl]-2,3,4,5-tetrahydro-1H-benzazepine 216. 5-Dimethylamino-4-hydroxy-1-[4-(2-chlorobenzoylamino)benzoyl]-2,3,4,5-tetrahydro-1H-benzazepine 217. 1-[4-(2-Methylbenzoylamino)benzoyl]-1,2-dihydroquinoline 218. 5-Dimethylamino-1–12-methyl-4-(2-methylbenzoylamino)benzoyl]-2,3,4,5-tetrahydro-1H-benzazepine (the compound of Example 979)

219. 5-Dimethylamino-1-[2-methyl-4-(2-chlorobenzoylamino)benzoyl]-2,3,4,5-tetrahydro-1H-benzazepine 220. 5-Dimethylamino-1-[2-methyl-4-(2,4-dichlorobenzoylamino)benzoyl]-2,3,4,5-tetrahydro-1H-benzazepine 221. 5-Methylamino-1-{2-chloro-4-(2-(N-ethylanilino)acetylamino]benzoyl}-2,3,4,5-tetrahydro-1H-benzazepine 222. 5-Hydroxy-1-{2-chloro-4-[2-(N-ethylanilino)acetylamino]benzoyl}-2,3,4,5-tetrahydro-1H-benzazepine 223. 5-Dimethylamino-1-[2-fluoro-4-(2-chlorobenzoylamino)benzoyl]- 2,3,4,5-tetrahydro-1H-benzazepine 224. 5-Methylamino-4-hydroxy-1-[2-chloro-4-(2-chlorobenzoylamino)benzoyl]-2,3,4,5-tetrahydro-1H-benzazepine hydrochloride 225. 5-Hydroxymethyl-5-hydroxy-1-[2-chloro-4-(2-methylbenzoylamino)benzoyl]-2,3,4,5-tetrahydro-1H-benzazepine 226. 5-Dimethylamino-1-[2-fluoro-4-(2-methylbenzoylamino)benzoyl]-2,3,4,5-tetrahydro-1H-benzazepine 227. 5-Dimethylamino-1-[3-methyl-4-(2,4-dichlorobenzoylamino)benzoyl]-2,3,4,5-tetrahydro-1H-benzazepine 228. 5-(N-Methyl-N-ethylamino)-1-[4-(2-methylbenzoylamino)benzoyl]-2,3,4,5-tetrahydro-1H-benzazepine 229. 5-Ethylamino-1-[4-(2-methylbenzoylamino)benzoyl]-2,3,4,5-tetrahydro-1H-benzazepine 230. 5-Dimethylamino-1-[4-(3,5-difluorobenzoylamino)benzoyl]-2,3,4,5-tetrahydro-1H-benzazepine 231. 5-Acetyloxymethyl-1-[4-(2-methylbenzoylamino)benzoyl]-2,3,4,5-tetrahydro-1H-benzazepine 232. 5-Dimethylamino-1-[3-fluoro-4-(2-methylbenzoylamino)benzoyl]-2,3,4,5-tetrahydro-1H-benzazepine 233. 4,4-Dimethoxy-1-[4-(2-methylbenzoylamino)benzoyl]-2,3,4,5-tetrahydro-1H-benzazepine 234. 5-Acetyloxyimino-1-[4-(2-chlorobenzoylamino)benzoyl]-2,3,4,5-tetrahydro-1H-benzazepine 235. 5-Methylsulfonyloxymethyl-1-[4-(2-methylbenzoylamino)benzoyl]- 2,3,4,5-tetrahydro-1H-benzazepine 236. 5,5-Epoxy-1-[4-(2-methylbenzoylamino)benzoyl]-2,3,4,5-tetrahydro-1H-benzazepine 237. 5-Hydroxymethyl-5-hydroxy-1-[4-(2-methylbenzoylamino)benzoyl]-2,3,4,5-tetrahydro-1H-benzazepine 238. 5-Hydroxy-1-[2-methoxy-4-(2-methylbenzoylamino)benzoyl]-2,3,4,5-tetrahydro-1H-benzazepine 239. 5-Dimethylamino-1-[4-(2-carbamoylmethoxybenzoylamino)benzoyl]-2,3,4,5-tetrahydro-1H-benzazepine 240. 5-Hydroxy-6-methyl-1-[2-chloro-4-(2-methylbenzoylamino)benzoyl]-2,3,4,5-tetrahydro-1H-benzazepine 241. 5-(2-Dimethylaminoethyl)amino-1-[2-chloro-4-(2-methylbenzoylamino)benzoyl]-2,3,4,5-tetrahydro-1H-benzazepine 242. 5-Hydroxymethyl-5-methylamino-1-[4-(2-methylbenzoylamino)benzoyl]-2,3,4,5-tetrahydro-1H-benzazepine 243. 5-Methylaminomethyl-5-hydroxy-1-[4-(2-methylbenzoylamino)benzoyl]-2,3,4,5-tetrahydro-1H-benzazepine 244. 5-Aminomethyl-1-[4-(2-methylbenzoylamino)benzoyl]-2,3,4,5-tetrahydro-1H-benzazepine 245. 5-[N-Methyl-N-(3-methoxy-2-hydroxypropyl)amino]-1-[4-(2-methylbenzoylamino)benzoyl]-2,3,4,5-tetrahydro-1H-benzazepine 246. 5-[N-Methyl-N-(3-diethylamino-2-hydroxypropyl)amino]-1-[4-(2-methylbenzoylamino)benzoyl]-2,3,4,5-tetrahydro-1H-benzazepine 247. 5-Dimethylamino-1-[3-methoxy-4-(2-methylbenzoylamino)benzoyl]-2,3,4,5-tetrahydro-1H-benzazepine 248. 5-Dimethylamino-1-(3-methoxy-4-(2,4-dichlorobenzoylamino)benzoyl]-2,3,4,5-tetrahydro-1H-benzazepine 249. 5-Dimethylamino-1-[4-(2-methylbenzoylamino)benzoyl]-2,3,4,5-tetrahydro-1H-benzazepine.hydrochloride 250. 5-Azidomethyl-1-[4-(2-methylbenzoylamino)benzoyl]-2,3,4,5-tetrahydro-1H-benzazepine 251. 7-[4-(2-Chlorobenzoylamino)benzoyl]-1-methyl-1,2,3,4a,5,6,7,11b-octahydro-3-oxo[1]benzazepino[4,5-b]-[1,4]oxazine 252. 5-Benzylamino-1-[4-(2-chlorobenzoylamino)benzoyl]-2,3,4,5-tetrahydro-1H-benzazepine 253. 5-Amino-1-[4-(2-chlorobenzoylamino)benzoyl]-2,3,4,5-tetrahydro-1H-benzazepine 254. 5-Dimethylamino-4-methyl-1-[4-(2-methylbenzoylamino)benzoyl]-2,3,4,5-tetrahydro-1H-benzazepine 255. 5-Acetylaminomethyl-1-[4-(2-methylbenzoylamino)benzoyl]-2,3,4,5-tetrahydro-1H-benzazepine 256. 5-Hydroxy-4-methyl-1-[4-(2-methylbenzoylamino)benzoyl]-2,3,4,5-tetrahydro-1H-benzazepine 257. 5-[2-(2-Pyridyl)ethylamino]-1-[4-(2-chlorobenzoylamino)benzoyl]-2,3,4,5-tetrahydro-1H-benzazepine 258. 5-(N-Methyl-N-methanesulfonylamino)-1-[4-(2-methylbenzoylamino)benzoyl]-2,3,4,5-tetrahydro-1H-benzazepine 259. 5-(N-Methyl-N-benozylamino)-1-[4-(2-methylbenzoylamino)benzoyl]-2,3,4,5-tetrahydro-1H-benzazepine 260. 5-Ethoxycarbonylamino-1-[4-(2-methylbenzoylamino)benzoyl]-2,3,4,5-tetrahydro-1H-benzazepine 261. 5-Methyl-5-hydroxy-1-[4-(2-methylbenzoylamino)benzoyl]-2,3,4,5-tetrahydro-1H-benzazepine 262. 5-(N-Methyl-N-ethoxycarbonylmethylamino)-1-[4-(2-methylbenzoylamino)benzoyl]-2,3,4,5-tetrahydro-1H-benzazepine 263. 5-Cyclopentylamino-1-[2-chloro-4-(2-methylbenzoylamino)benzoyl]-2,3,4,5-tetrahydro-1H-benzazepine 264. 5-[N-Methyl-N-(2,3-dihydroxypropyl)amino]-1-[4-(2-methylbenzoylamino)benzoyl]-2,3,4,5-tetrahydro-1H-benzazepine 265. 5-(N-Methyl-N-cyanomethylamino)-1-[4-(2-methylbenzoylamino)benzoyl]-2,3,4,5-tetrahydro-1H-benzazepine 266. 5-(N-Methyl-N-carbamoylmethylamino)-1-[4-(2-methylbenzoylamino)benzoyl]-2,3,4,5-tetrahydro-1H-benzazepine 267. 5-{N-Methyl-N-[3-(3,4,5,6-tetrahydro-2H-pyran-2-yloxy)propyl]amino}-1-[4-(2-methylbenzoylamino)benzoyl]-2,3,4,5-tetrahydro-1H-benzazepine 268. 5-Dimethylaminomethyl-1-[4-(2-methylbenzoylamino)benzoyl]-2,3,4,5-tetrahydro-1H-benzazepine 269. 5-Formylaminomethyl-1-[4-(2-methylbenzoylamino)benzoyl]-2,3,4,5-tetrahydro-1H-benzazepine 270. 5-[N-Methyl-N-(3-acetyloxypropyl)amino]-1-[4-(2-methylbenzoylamino)benzoyl]-2,3,4,5-tetrahydro-1H-benzazepine 271. 5-[N-Methyl-N-(3-hydroxypropyl)amino]-1-[4-(2-methylbenzoylamino)benzoyl]-2,3,4,5-tetrahydro-1H-benzazepine 272. Potassium {1-[2-chloro-4-(2-methylbenzoylamino)benzoyl]-2,3,4,5-tetrahydro-1H-benzazepin-5-yl}imino-o-sulfonate 273. 5-Dimethylamino-1-(4-benzoylaminobenzoyl)-2,3,4,5-tetrahydro-1H-benzazepine 274. 5-(1-Benzyl-4-piperidinyl)amino-1-[4-(2-methylbenzoylamino)benzoyl]-2,3,4,5-tetrahydro-1H-benzazepine 275. 5-(2-Dimethylaminoacetyloxy)-1-[4-(2-methylbenzoylamino)benzoyl]-2,3,4,5-tetrahydro-1H-benzazepine 276. 5-Dimethylamino-1-[4-(3-methoxybenzoylamino)benzoyl]-2,3,4,5-tetrahydro-1H-benzazepine 277. 5-((4-Methyl-1-piperazinyl)carbonylmethoxy]-1-[4-(2-methylbenzoylamino)benzoyl]-2,3,4,5-tetrahydro-1H-benzazepine 278. 5-Morpholinocarbonylmethoxy-1-[4-(2-methylbenzoylamino)benzoyl]-2,3,4,5-tetrahydro-1H-benzazepine 279. 5-Thiomorpholinocarbonylmethoxy-1-[4-(2-methylbenzoylamino)benzoyl]-2,3,4,5-tetrahydro-1H-benzazepine 280. 5-Anilinocarbonylamino-1-[4-(2-methylbenzoylamino)benzoyl]-2,3,4,5-tetrahydro-1H-benzazepine 281. 5-(1-Oxothiomorpholino)carbonylmethoxy-1-[4-(2-methylbenzoylamino)benzoyl]-2,3,4,5-tetrahydro-1H-benzazepine 282. 5-Hydrazino-1-[4-(2-methylbenzoylamino)benzoyl]-2,3,4,5-tetrahydro-1H-benzazepine 283. 5-Methylaminocarbonylamino-1-[4-(2-methylbenzoylamino)benzoyl]-2,3,4,5-tetrahydro-1H-benzazepine 284. 5-[(2-a-Carbamoyl-1-pyrrolidinyl)carbonylmethoxy]-1-[4-(2-methylbenzoylamino)benzoyl]-2,3,4,5-tetrahydro-1H-benzazepine 285. -5-(Carbamoylmethylaminocarbonylmethoxy)-1-[4-(2-methylbenzoylamino)benzoyl]-2,3,4,5-tetrahydro-1H-benzazepine 286. 5-(1,1-Dioxothiomorpholino)carbonylmethoxy-1-[4-(2-methylbenzoylamino)benzoyl]-2,3,4,5-tetrahydro-1H-benzazepine 287. 7-Chloro-5-methylamino-1-[4-(2-methylbenzoylamino)benzoyl]-2,3,4,5-tetrahydro-1H-benzazepine 288. 5-[(4-Acetyl-1-piperazinyl)carbonylmethoxy]-1-[4-(2-methylbenzoylamino)benzoyl]-2,3,4,5-tetrahydro-1H-benzazepine 289. 5-Dimethylamino-1-[4-(3-nitrobenzoylamino)benzoyl]-2,3,4,5-tetrahydro-1H-benzazepine 290. 5-[(4-Pyridyl)methylaminocarbonylmethoxy]-1-[4-(2-methylbenzoylamino)benzoyl]-2,3,4,5-tetrahydro-1H-benzazepine 291. 5-[2-(Methylamino)acetylamino]-1-[4-(2-methylbenzoylamino)benzoyl]-2,3,4,5-tetrahydro-1H-benzazepine 292. 5-Dimethylamino-1-[4-(3-aminobenzoylamino)benzoyl]-2,3,4,5-tetrahydro-1H-benzazepine 293. 5-{[N-Methyl-N-(2-hydroxyethyl)amino]carbonylmethoxy}-1-[4-(2-methylbenzoylamino)benzoyl]-2,3,4,5-tetrahydro-1H-benzazepine 294. 5-Dimethylamino-1-[3-(2-diethylaminoethoxy)-4-(2-methylbenzoylamino)benzoyl]-2,3,4,5-tetrahydro-1H-benzazepine 295. 5-[N-Methyl-N-(dimethylaminocarbonylmethyl)amino]-1-[4-(2-methylbenzoylamino)benzoyl]-2,3,4,5-tetrahydro-1H-benzazepine 296. Potassium 2-[N-methyl-N-{1-[4-(2-methylbenzoylamino)benzoyl]-2,3,4,5-tetrahydro-1H-benzazepin-5-yl}amine]acetate 297. 5-(N-Methyl-N-[2-(1-imidazolyl)acetyl]amino}-1-[4-(2-methylbenzoylamino)benzoyl]-2,3,4,5-tetrahydro-1H-benzazepine 298. 5-Dimethylamino-1-[4-(2-dimethylaminobenzoylamino)benzoyl]-2,3,4,5-tetrahydro-1H-benzazepine 299. 5-[(2-Aminoacetyl)amino]-1-[4-(2-methylbenzoylamino)benzoyl]-2,3,4,5-tetrahydro-1H-benzazepine 300. 5-Dimethylamino-1-[4-(3-acetylaminobenzoylamino)benzoyl]-2,3,4,5-tetrahydro-1H-benzazepine 301. 5-(2-t-Butoxycarbonylaminoacetylamino)-1-[4-(2-methylbenzoylamino)benzoyl]-2,3,4,5-tetrahydro-1H-benzazepine 302. 5-Methylamino-7-chloro-1-[4-(2-chlorobenzoylamino)benzoyl]-2,3,4,5-tetrahydro-1H-benzazepine 303. 5-Dimethylamino-7-chloro-1-[4-(2-methylbenzoylamino)benzoyl]-2,3,4,5-tetrahydro-1H-benzazepine 304. 5-Dimethylamino-7-chloro-1-[4-(2-chlorobenzoylamino)benzoyl]-2,3,4,5-tetrahydro-1H-benzazepine 305. 5-Dimethylamino-1-[4-(phenylacetylamino)benzoyl]-2,3,4,5-tetrahydro-1H-benzazepine 306. 5-Dimethylamino-1-[4-(3-phenylpropionylamino)benzoyl]-2,3,4,5-tetrahydro-1H-benzazepine 307. 5-Methylamino-7-chloro-1-{4-[(N-ethylanilino)acetylamino]benzoyl}-2,3,4,5-tetrahydro-1H-benzazepine 308. 5-Dimethylamino-7-chloro-1-{4-[(N-ethylanilino)acetylamino]benzoyl}-2,3,4,5-tetrahydro-1H-benzazepine 309. 5-Dimethylamino-1-[4-(2-bromobenzoylamino)benzoyl]-2,3,4,5-tetrahydro-1H-benzazepine 310. 5-Cyclopropylamino-7-chloro-1-[4-(2-methylbenzoylamino)benzoyl]-2,3,4,5-tetrahydro-1H-benzazepine 311. 5-Cyclopropylamino-7-chloro-1-[4-(2-chlorobenzoylamino)benzoyl]-2,3,4,5-tetrahydro-1H-benzazepine 312. 5-hydroxy-1-{4-[2-(4-isopropylaminobutoxy)benzoylamino]benzoyl}-2,3,4,5-tetrahydro-1H-benzazepine 313. 5-Dimethylaminocarbonylmethoxy-1-{4-[(N-ethylanilino)acetylamino]benzoyl}-2,3,4,5-tetrahydro-1H-benzazepine 314. 5-(N-Methyl-N-ethylamino)-1-[2-chloro-4-(2-chlorobenzoylamino)benzoyl]-2,3,4,5-tetrahydro-1H-benzazepine 315. 5-Dimethylamino-1-{4-[(2-chloroanilino)acetylamino]benzoyl}-2,3,4,5-tetrahydro-1H-benzazepine 316. 5-Dimethylamino-1-{4-[(2-methylanilino)acetylamino]benzoyl}-2,3,4,5-tetrahydro-1H-benzazepine 317. 5-Dimethylamino-1-{4-[(N-methyl-2-methylanilino)acetylamino]benzoyl}-2,3,4,5-tetrahydro-1H-benzazepine 318. 5-Methylamino-9-chloro-1-[4-(2-methylbenzoylamino)benzoyl]-2,3,4,5-tetrahydro-1H-benzazepine 319. 5-Dimethylamino-1-[4-(phenoxyacetylamino)benzoyl]-2,3,4,5-tetrahydro-1H-benzazepine 320. 6-Methylamino-1-[4-(2-methylbenzoylamino)benzoyl]-1,2,3,4,5,6-hexahydrobenzazocine 321. 5-Methylamino-7-chloro-1-[3-methoxy-4-(2-chlorobenzoylamino)benzoyl]-2,3,4,5-tetrahydro-1H-benzazepine 322. 5-Cyclopropylamino-7-chloro-1-[3-methoxy-4-(2-chlorobenzoylamino)benzoyl]-2,3,4,5-tetrahydro-1H-benzazepine 323. 5-Methylamino-7-chloro-1-[3-methoxy-4-(2-methylbenzoylamino)benzoyl]-2,3,4,5-tetrahydro-1H-benzazepine

TABLE 10

| Test Comp. No. | $IC_{50}$ ($\mu$M) | Test Comp. No. | $IC_{50}$ ($\mu$M) |
|---|---|---|---|
| 26 | 0.071 | 78 | 0.10 |
| 27 | 0.095 | 88 | 0.34 |
| 28 | 0.056 | 90 | 0.38 |
| 29 | 0.15 | 114 | 0.011 |
| 30 | 0.15 | 115 | 0.012 |

TABLE 10-continued

| Test Comp. No. | $IC_{50}$ ($\mu$M) | Test Comp. No. | $IC_{50}$ ($\mu$M) |
|---|---|---|---|
| 32 | 0.30 | 116 | 0.04 |
| 33 | 0.092 | 117 | 0.22 |
| 36 | 0.41 | 119 | 0.049 |
| 46 | 0.40 | 120 | 0.29 |
| 56 | 0.025 | 121 | 0.45 |
| 57 | 0.46 | 124 | 0.15 |
| 58 | 0.40 | 125 | 0.091 |
| 59 | 0.31 | 130 | 0.023 |
| 60 | 0.18 | 143 | 0.15 |
| 62 | 0.098 | 147 | 0.28 |
| 63 | 0.14 | 161 | 0.14 |
| 64 | 0.069 | 163 | 0.22 |
| 67 | 0.34 | 164 | 0.15 |
| 68 | 0.013 | 172 | 0.26 |
| 69 | 0.066 | 173 | 0.15 |
| 70 | 0.041 | 174 | 0.14 |
| 71 | 0.18 | 187 | 0.45 |
| 72 | 0.12 | 188 | 0.47 |
| 74 | 0.10 | 192 | 0.054 |
| 75 | 0.069 | 193 | 0.17 |
| 76 | 0.042 | 195 | 0.17 |
| 77 | 0.085 | 196 | 0.40 |
| 207 | 0.16 | 284 | 0.29 |
| 208 | 0.11 | 285 | 0.18 |
| 209 | 0.074 | 286 | 0.40 |
| 214 | 0.27 | 287 | 0.064 |
| 215 | 0.13 | 288 | 0.26 |
| 222 | 0.096 | 290 | 0.21 |
| 231 | 0.16 | 293 | 0.19 |
| 235 | 0.088 | 298 | 0.29 |
| 236 | 0.16 | 302 | 0.071 |
| 238 | 0.39 | 303 | 0.19 |
| 244 | 0.23 | 304 | 0.21 |
| 250 | 0.19 | 307 | 0.024 |
| 252 | 0.36 | 308 | 0.11 |
| 255 | 0.046 | 309 | 0.43 |
| 256 | 0.049 | 310 | 0.065 |
| 266 | 0.29 | 311 | 0.078 |
| 269 | 0.48 | 312 | 0.056 |
| 274 | 0.11 | 313 | 0.032 |
| 275 | 0.18 | 315 | 0.38 |
| 277 | 0.23 | 316 | 0.47 |
| 278 | 0.30 | 321 | 0.059 |
| 279 | 0.15 | 322 | 0.044 |
| 280 | 0.47 | 323 | 0.064 |
| 281 | 0.18 | | |

Pharmacological Test

Experiment 2: $V_2$ receptor binding assay

Using rat kidney plasma membrane preparations prepared according to 0. Hechter's method [cf: J. Bio. Chem., 253, 3211 (1978)], the plasma membrane (100000 dpm, $4\times10^{-10}$ M) of [$^3$H]-Arg-vasopressin and a test compound (0.6 mg, $10^{-10}$–$10^{-5}$ M) are incubated at 4° C. for 3 hours in 100 mM Tris-HCl buffer (pH: 8.0, 250 $\mu$l) containing 5 mM $MgCl_2$, 1 mM EDTA and 0.1% BSA. After incubation, the mixture is filtered using the glass filter (GF/F) so as to separate the membrane preparation combined with vasopressin and then washed twice with the buffer (5 ml). This glass filter is taken out and mixed with liquid scintillation cocktail. The amount of [$^3$H]-vasopressin combined with the membrane is measured by liquid scintillation counter and the rate of the inhibitory effect of the test compound is estimated according to the following equation.

$$\text{Rate of the inhibitory effect (\%)} = 100 - \frac{C_1 - B_1}{C_0 - B_1} \times 100$$

$C^1$: The amount of [$^3$H]-vasopressin combined with the membrane in the presence of the test compound (in prescribed amount).

$C^0$: The amount of [$^3$H]-vasopressin combined with the membrane in the absence of the test compound.

$B^1$: The amount of [$^3$H]-vasopressin combined with the membrane in the presence of the excess amount of vasopressin ($10^{-6}$ M).

The results are expressed as $IC_{50}$ values, which is the concentration of the test compound required to achieve the inhibitory effect in the rate of 50%.

The results are shown in the following Table 11.

TABLE 11

| Test Comp. No. | $IC_{50}$ ($\mu$M) | Test Comp. No. | $IC_{50}$ ($\mu$M) |
|---|---|---|---|
| 1 | 0.98 | 28 | 0.018 |
| 2 | 0.20 | 29 | 0.069 |
| 3 | 0.40 | 30 | 0.029 |
| 4 | 0.58 | 31 | 0.098 |
| 5 | 1.2 | 32 | 0.016 |
| 6 | 0.076 | 33 | 0.007 |
| 7 | 0.20 | 34 | 0.049 |
| 8 | 0.32 | 35 | 0.20 |
| 9 | 0.53 | 36 | 0.028 |
| 10 | 0.082 | 37 | 0.16 |
| 11 | 1.05 | 38 | 0.029 |
| 12 | 1.97 | 39 | 0.071 |
| 13 | 1.02 | 40 | 0.33 |
| 14 | 0.23 | 41 | 0.20 |
| 15 | 0.13 | 42 | 0.063 |
| 16 | 0.17 | 43 | 0.17 |
| 17 | 0.23 | 44 | 0.050 |
| 18 | 1.0 | 45 | 0.19 |
| 19 | 1.7 | 46 | 0.018 |
| 20 | 1.4 | 47 | 0.20 |
| 21 | 1 | 48 | 0.021 |
| 22 | 0.33 | 49 | 0.063 |
| 23 | 1.07 | 50 | 1.3 |
| 24 | 1.09 | 51 | 0.40 |
| 25 | 1.67 | 52 | 0.32 |
| 26 | 0.025 | 53 | 1.6 |
| 27 | 0.070 | 54 | 0.11 |
| 55 | 0.091 | 86 | 0.58 |
| 56 | 0.037 | 87 | 0.046 |
| 57 | 0.16 | 88 | 0.021 |
| 58 | 0.14 | 89 | 0.035 |
| 59 | 0.24 | 90 | 0.014 |
| 60 | 0.15 | 91 | 0.005 |
| 61 | 0.090 | 92 | 0.41 |
| 62 | 0.023 | 93 | 0.52 |
| 63 | 0.046 | 94 | 0.095 |
| 64 | 0.007 | 95 | 0.089 |
| 65 | 0.081 | 96 | 0.039 |
| 66 | 0.45 | 97 | 0.024 |
| 67 | 0.050 | 98 | 0.45 |
| 68 | 0.19 | 99 | 1.6 |
| 69 | 0.12 | 100 | 0.011 |
| 70 | 0.012 | 101 | 0.60 |
| 71 | 0.085 | 102 | 0.29 |
| 72 | 0.16 | 103 | 0.54 |
| 74 | 0.51 | 104 | 0.37 |
| 75 | 0.30 | 105 | 0.72 |
| 76 | 0.017 | 106 | 0.44 |
| 77 | 0.090 | 107 | 0.032 |
| 78 | 0.084 | 108 | 0.12 |
| 79 | 0.53 | 109 | 0.49 |
| 80 | 0.070 | 110 | 0.044 |
| 81 | 0.15 | 111 | 0.087 |

TABLE 11-continued

| Test Comp. No. | $IC_{50}$ ($\mu$M) | Test Comp. No. | $IC_{50}$ ($\mu$M) |
|---|---|---|---|
| 82 | 0.17 | 112 | 0.29 |
| 83 | 0.73 | 113 | 0.28 |
| 84 | 0.11 | 114 | 0.006 |
| 85 | 0.068 | 115 | 0.006 |
| 116 | 0.039 | 146 | 0.056 |
| 117 | 0.24 | 147 | 0.009 |
| 118 | 0.55 | 148 | 0.34 |
| 119 | 0.059 | 149 | 0.004 |
| 120 | 0.28 | 150 | 0.14 |
| 121 | 0.18 | 151 | 0.18 |
| 122 | 0.10 | 152 | 0.039 |
| 123 | 0.10 | 153 | 0.063 |
| 124 | 0.13 | 154 | 0.063 |
| 125 | 0.28 | 155 | 0.028 |
| 126 | 0.062 | 156 | 0.15 |
| 127 | 0.99 | 157 | 0.38 |
| 128 | 0.23 | 158 | 0.018 |
| 129 | 0.29 | 159 | 0.020 |
| 130 | 0.007 | 160 | 0.020 |
| 131 | 0.027 | 161 | 0.009 |
| 132 | 0.013 | 162 | 0.059 |
| 133 | 0.022 | 163 | 0.009 |
| 134 | 0.048 | 164 | 0.010 |
| 135 | 0.081 | 165 | 0.098 |
| 136 | 0.18 | 166 | 0.070 |
| 137 | 0.41 | 167 | 0.032 |
| 138 | 0.11 | 168 | 0.083 |
| 139 | 0.10 | 169 | 0.071 |
| 140 | 0.024 | 170 | 0.25 |
| 141 | 0.010 | 171 | 0.87 |
| 142 | 0.008 | 172 | 0.023 |
| 143 | 0.008 | 173 | 0.008 |
| 144 | 0.02 | 174 | 0.007 |
| 145 | 0.06 | 175 | 0.038 |
| 176 | 0.004 | 206 | 0.088 |
| 177 | 0.15 | 207 | 0.045 |
| 178 | 0.012 | 208 | 0.007 |
| 179 | 0.040 | 209 | 0.004 |
| 180 | 0.034 | 210 | 0.004 |
| 181 | 0.038 | 211 | 0.12 |
| 182 | 0.005 | 212 | 0.035 |
| 183 | 0.26 | 213 | 0.033 |
| 184 | 0.023 | 214 | 0.058 |
| 185 | 0.005 | 215 | 0.006 |
| 186 | 0.030 | 216 | 0.91 |
| 187 | 0.029 | 217 | 0.37 |
| 188 | 0.039 | 218 | 0.022 |
| 189 | 0.087 | 219 | 0.023 |
| 190 | 0.082 | 220 | 0.026 |
| 191 | 0.009 | 221 | 0.024 |
| 192 | 0.011 | 222 | 0.010 |
| 193 | 0.036 | 223 | 0.022 |
| 194 | 0.21 | 224 | 0.38 |
| 195 | 0.010 | 225 | 0.030 |
| 196 | 0.013 | 226 | 0.019 |
| 197 | 0.99 | 227 | 0.029 |
| 198 | 0.040 | 228 | 0.029 |
| 199 | 0.019 | 229 | 0.029 |
| 200 | 0.024 | 230 | 0.020 |
| 201 | 0.023 | 231 | 0.007 |
| 202 | 0.14 | 232 | 0.020 |
| 203 | 0.070 | 233 | 0.15 |
| 204 | 0.11 | 234 | 0.14 |
| 205 | 0.074 | 235 | 0.006 |
| 236 | 0.006 | 267 | 0.12 |
| 237 | 0.041 | 268 | 0.018 |
| 238 | 0.020 | 269 | 0.003 |
| 239 | 0.17 | 270 | 0.046 |
| 240 | 0.022 | 271 | 0.030 |
| 241 | 0.006 | 272 | 0.40 |
| 242 | 0.17 | 273 | 0.027 |
| 243 | 0.40 | 274 | 0.024 |
| 244 | 0.018 | 275 | 0.018 |
| 245 | 0.059 | 276 | 0.032 |
| 246 | 0.027 | 277 | 0.016 |

TABLE 11-continued

| Test Comp. No. | $IC_{50}$ ($\mu$M) | Test Comp. No. | $IC_{50}$ ($\mu$M) |
|---|---|---|---|
| 247 | 0.048 | 278 | 0.013 |
| 248 | 0.060 | 279 | 0.008 |
| 250 | 0.12 | 280 | 0.045 |
| 251 | 0.094 | 281 | 0.011 |
| 252 | 0.063 | 282 | 0.38 |
| 253 | 0.052 | 283 | 0.096 |
| 254 | 0.016 | 284 | 0.019 |
| 255 | 0.005 | 285 | 0.008 |
| 256 | 0.004 | 286 | 0.019 |
| 257 | 0.045 | 287 | 0.007 |
| 258 | 0.20 | 288 | 0.015 |
| 259 | 0.25 | 289 | 0.071 |
| 260 | 0.13 | 290 | 0.021 |
| 261 | 0.011 | 291 | 0.13 |
| 262 | 0.029 | 292 | 0.18 |
| 263 | 0.053 | 293 | 0.065 |
| 264 | 0.030 | 294 | 0.33 |
| 265 | 0.025 | 295 | 0.026 |
| 266 | 0.013 | 296 | 0.25 |
| 297 | 0.051 | 311 | 0.013 |
| 298 | 0.10 | 312 | 0.29 |
| 299 | 0.22 | 313 | 0.012 |
| 300 | 0.48 | 314 | 0.096 |
| 301 | 0.14 | 315 | 0.025 |
| 302 | 0.011 | 316 | 0.060 |
| 303 | 0.025 | 317 | 0.072 |
| 304 | 0.024 | 318 | 0.060 |
| 305 | 0.038 | 319 | 0.058 |
| 306 | 0.077 | 320 | 0.039 |
| 307 | 0.010 | 321 | 0.012 |
| 308 | 0.023 | 322 | 0.025 |
| 309 | 0.015 | 323 | 0.014 |
| 310 | 0.008 | | |

Experiment 3: Anti-antidiuretic activity (effect on endogenous ADH)

A test compound or solvent (dimethylformamide) is administered into a caudal vein of untreated, unrestrained SD rats (male, weight: 300–350 g) and the amount of urine, which is spontaneously excreted for a period of 2 hours thereafter, is collected and measured by using a metabolic gauge. During this measurement, the rats are allowed to take water and feed freely.

The amount of urine of control rats (solvent-treated group) is regarded as 100%, and the results are expressed as $ED_3$ value, which is the dose of the test compound to be required to excrete the urine by three times than that of the control rats. The results are shown in the following Table 12.

TABLE 12

| Test compound No. | $ED_3$ (mg/kg) |
|---|---|
| 6 | 10 |
| 33 | 1.9 |
| 178 | 4.2 |
| 249 | 0.4*) |

*) Physicological saline solution was used as a solvent instead of dimethylformamide.

Using the suitable starting materials, the compounds of the following Table 13 are obtained in the same manner as in Examples 1 and 382.

TABLE 13

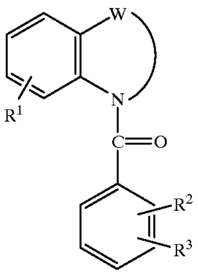

Example 1190
Structure

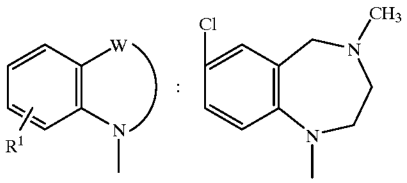

$R^2$: 2-$OCH_3$

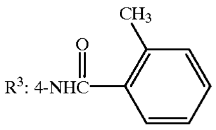

Crystalline form: White powder
Recrystallization solvent: Dichloromethane/diethyl ether
Melting Point: 210–213° C.
Form: Free
Example 1191
Structure

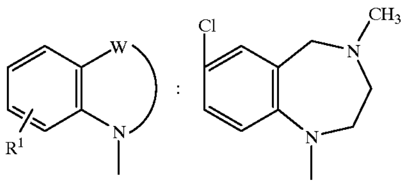

$R^2$: 2-$CH_3$

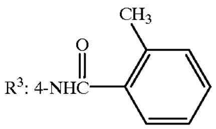

Crystalline form: White powder
Recrystallization solvent: Dichloromethane/diethyl ether
Melting Point: 184.5–186° C.
Form: Free
Example 1192
Structure

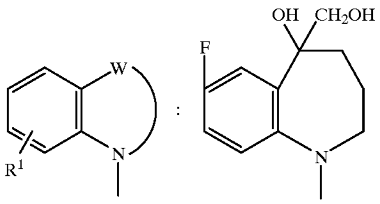

$R^2$: H

TABLE 13-continued

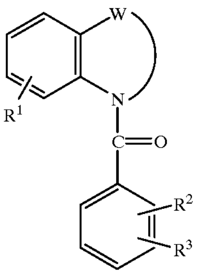

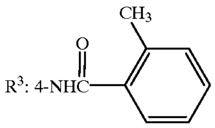

Crystalline form: White powder
Recrystallization solvent: Dichloromethane/diethyl ether
Melting Point: 201.5–202.5° C.
Form: Free
Example 1193
Structure

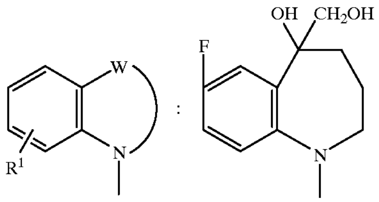

$R^2$: 2-Cl

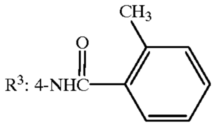

Crystalline form: White powder
Recrystallization solvent: Dichloromethane/diethyl ether
Melting Point: 159–162° C. (decomposed)
Form: Free
Example 1194
Structure

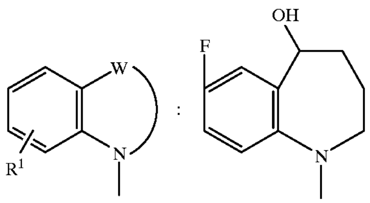

$R^2$: 2-$OCH_3$

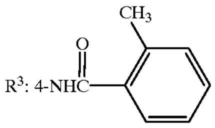

Crystalline form: White powder
Recrystallization solvent: Diethyl ether/dichloromethane
Melting Point: 237–240° C.
Form: Free TABLE 13-continued

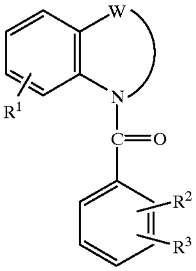

Example 1195
Structure

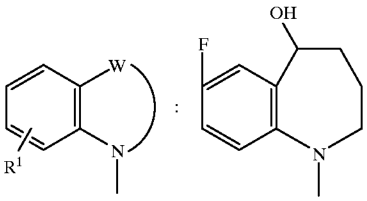

$R^2$: 2-$OCH_3$

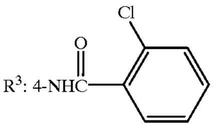

Crystalline form: White powder
Recrystallization solvent: Diethyl ether/dichloromethane
Melting Point: 269–272.5° C.
Form: Free
Example 1196
Structure

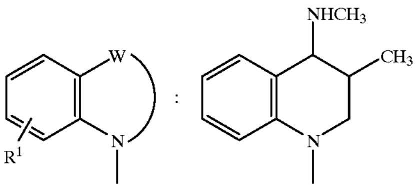

$R^2$: H

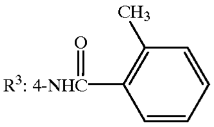

Crystalline form: Colorless prisms
Recrystallization solvent: Ethanol/dichloromethane
Melting Point: 201–202° C.
Form: Free
Example 1197
Structure

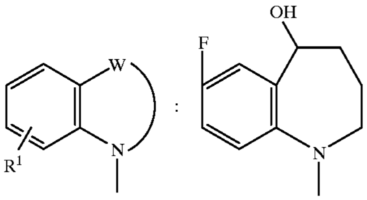

$R^2$: 2-$CH_3$

TABLE 13-continued

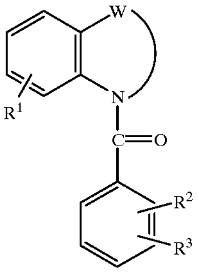

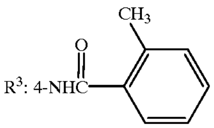

Crystalline form: White powder
Recrystallization solvent: Methanol
Melting Point: 204–206° C.
Form: Free
Example 1198
Structure

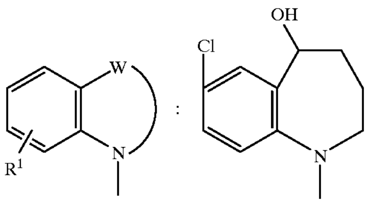

$R^2$: 2-Cl

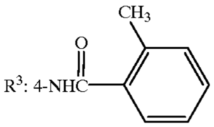

Crystalline form: Colorless amorphous
NMR analysis: 313)
Form: Free
Example 1199
Structure

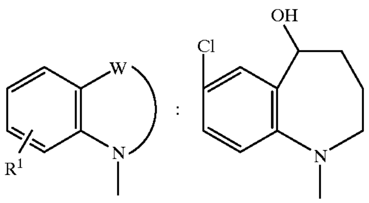

$R^2$: 2-$CH_3$

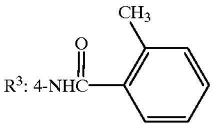

Crystalline form: Colorless amorphous
NMR analysis: 314)
Form: Free

TABLE 13-continued

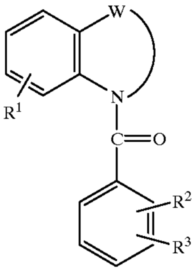

Example 1200

Structure $R^2$: 2-$CH_3$

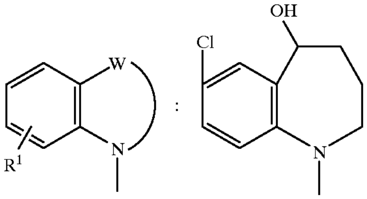

$R^3$: 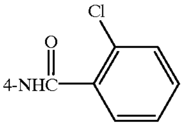

Crystalline form: Colorless amorphous

NMR analysis: 315)

Form: Free

Example 1201

Structure $R^2$: 2-$OCH_3$

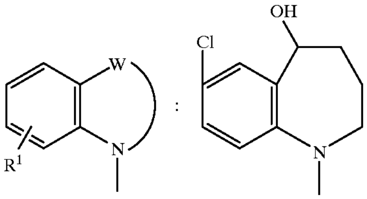

$R^3$: 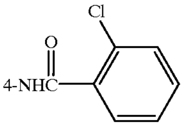

Crystalline form: Colorless amorphous

NMR analysis: 316)

Form: Free

Example 1202

Structure $R^2$: 2-Cl

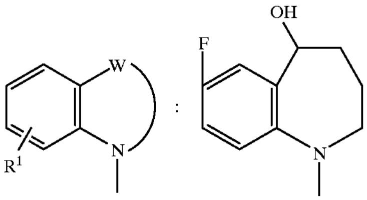

TABLE 13-continued

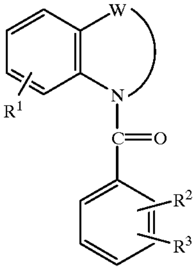

$R^3$: 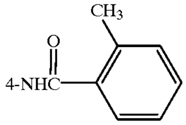

Crystalline form: Colorless amorphous

NMR analysis: 317)

Form: Free

Example 1203

Structure $R^2$: 2-$OCH_3$

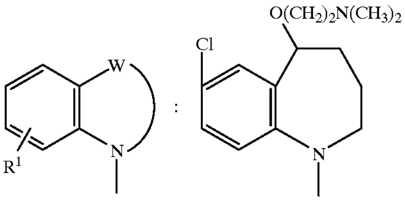

$R^3$: 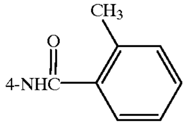

Crystalline form: Light brown amorphous

NMR analysis: 318)

Form: Hydrochloride

Example 1204

Structure $R^2$: 2-$OCH_3$

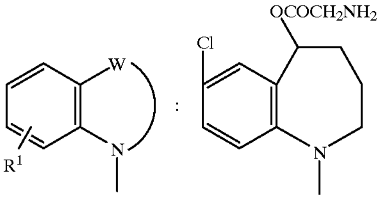

$R^3$: 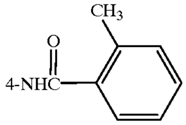

TABLE 13-continued

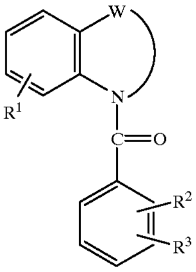

Example 1205

Structure

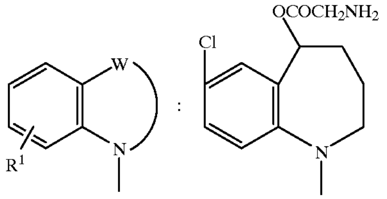

$R^2$: 2-$CH_3$

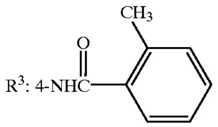

Crystalline form: Colorless amorphous

NMR analysis: 320)

Form: Hydrochloride

Example 1206

Structure

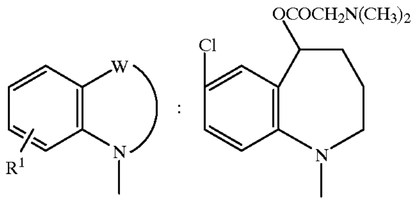

$R^2$: 2-$CH_3$

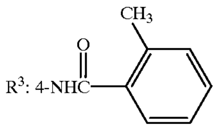

Crystalline form: Colorless amorphous

NMR analysis: 321)

Form: Hydrochloride

Example 1207

Structure

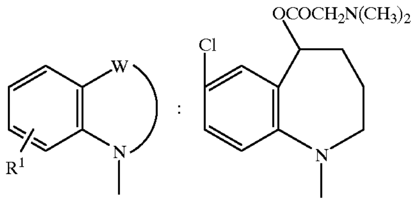

$R^2$: 2-$OCH_3$

TABLE 13-continued

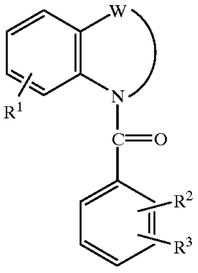

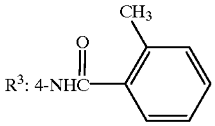

Crystalline form: Colorless amorphous

NMR analysis: 322)

Form: Free

Example 1208

Structure

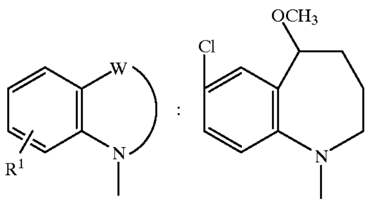

$R^2$: 2-$OCH_3$

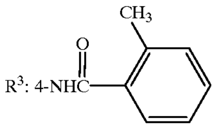

Crystalline form: Light yellow prisms

Recrystallization solvent: Ethyl acetate/n-hexane

Melting Point: 187–189° C.

Form: Free

Example 1209

Structure

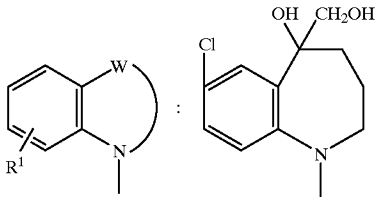

$R^2$: H

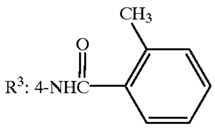

Crystalline form: White powder

Recrystallization solvent: Methanol/diethyl ether

Melting Point: 227–231° C.

Form: Free

TABLE 13-continued

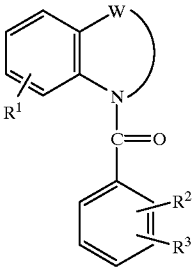

Example 1210
Structure

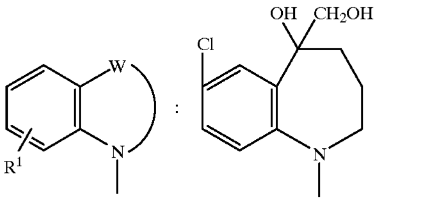

$R^2$: 2-$CH_3$

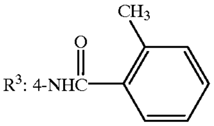

Crystalline form: White powder
Recrystallization solvent: Methanol/diethyl ether
Melting Point: 191–192° C.
Form: Free
Example 1211
Structure

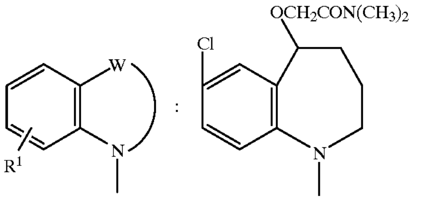

$R^2$: 2-$CH_3$

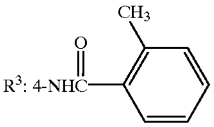

Crystalline form: Colorless amorphous
NMR analysis: 323)
Form: Free
Example 1212
Structure

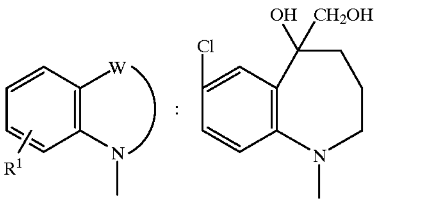

$R^2$: 2-$CH_3$

TABLE 13-continued

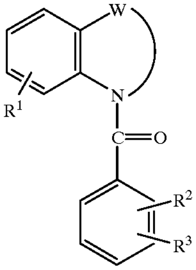

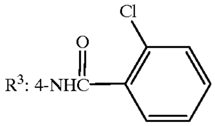

Crystalline form: Colorless amorphous
NMR analysis: 324)
Form: Free
Example 1213
Structure

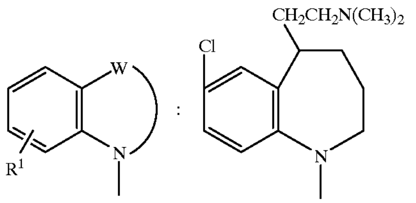

$R^2$: 2-$CH_3$

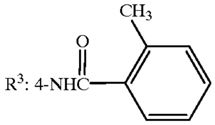

Crystalline form: White amorphous
NMR analysis: 325)
Form: Hydrochloride

313) $^1$H-NMR ($CDCl_3$) δ; 1.40–2.30(4H, m), 2.36(3H, s), 2.60–2.92(2H, m), 4.35–5.18(2H, m), 6.69–6.87(1H, m), 6.87–7.04(1H, m), 7.05–8.06(8H, m), 8.25–8.60(1H, m)
314) $^1$H-NMR ($CDCl_3$) δ; 1.43–2.26(4H, m), 2.38(3H, s), 2.42(3H, s), 2.61–2.91(1H, m), 2.91–3.40(1H, m), 4.49–5.08(2H, m), 6.40–7.68(10H, m), 7.68–7.93(1H, m)
315) $^1$H-NMR ($CDCl_3$) δ; 1.32–2.25(4H, m), 2.25–2.54(3H, m), 2.59–3.42 (2H, m), 4.45–5.08(2H, m), 6.40–7.80(10H, m), 8.00–8.38(1H, m)
316) $^1$H-NMR ($CDCl_3$) δ; 1.42–1.89(2H, m), 1.90–2.30(2H, m), 2.57–2.95 (2H, m), 3.36–3.64(3H, m), 4.51–5.17(2H, m), 6.52–7.80(10H, m), 8.11–8.41 (1H, m)
317) $^1$H-NMR ($CDCl_3$) δ; 1.18–2.25(4H, m), 2.25–2.59(3H, m), 2.59–2.88 (1H, m), 2.88–4.32(1H, m), 4.32–5.05(2H, m), 6.44–8.08(10H, m), 8.52–9.00 (1H, m)
318) $^1$H-NMR (DMSO-$d_6$) δ; 1.35–2.45(7H, m), 2.6–3.0(8H, m), 3.2–4.2(6H, m), 4.45–4.85(2H, m), 6.75–7.7(11H, m)
319) $^1$H-NMR ($CDCl_3$) δ; 1.20–2.89, 3.22–4.33, 4.48–5.05, 5.75–6.32 [total 17H, m {2.45 (s)}], 6.52–7.78(10H, m), 8.10–8.71(1H, m)
320) $^1$H-NMR (DMSO-$d_6$) δ; 1.49–3.05[11H, m{2.35(s), 2.40(s)}], 3.71–5.04(3H, m), 5.28–5.88(1H, m), 6.64–7.98(10H, m), 8.58(3H, brs), 10.32, 10.48(total 1H, each s)
321) $^1$H-NMR (DMSO-$d_6$) δ; 1.50–3.70[17H, m{2.36, 2.40(each s), 2.87, 2.89, 2.94(each s)}], 4.05–5.08(3H, m), 5.90–6.28(1H, m), 6.62–7.98(10H, m), 10.36, 10.52(total 1H, each brs), 10.94(1H, brs)
322) $^1$H-NMR ($CDCl_3$) δ; 1.53–2.91[14H, m{2.42, 2.47(each s)}], 3.09–4.27 (5H, m), 4.70–5.12(1H, m), 5.89–6.36(1H, m), 6.57–7.94(11H, m)
323) $^1$H-NMR ($CDCl_3$) δ; 1.32–2.23(2H, m), 2.23–2.68(7H, m), 2.68–3.84 (8H, m), 3.84–5.23(4H, m), 6.47–7.88(11H, m)
324) $^1$H-NMR ($CDCl_3$) δ; 1.45–2.32(5H, m), 2.44(3H, s), 2.63–3.21(1H, m), 3.40–5.01(4H, m), 6.28–7.93(10H, m), 8.10–8.43(1H, m)

TABLE 13-continued

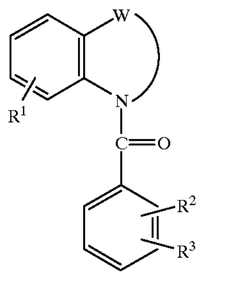

325) $^1$H-NMR (DMSO-$d_6$) δ; 0.71–3.46, 4.15–4.44[total 23H, 2.35(s), 2.42 (s), 2.86(s)], 6.71–7.88(10H, m), 10.16–10.58(2H, m)

What is claimed is:

1. A method for antagonizing vasopressin which comprises administering to a subject a therapeutically effective amount of a benzoheterocyclic compound of the formula:

(1)

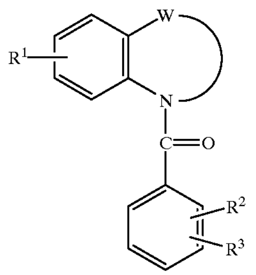

wherein $R^1$ is a hydrogen atom, a halogen atom, a $C_1$–$C_6$ alkyl, an amino having optionally a $C_1$–$C_6$ alkyl substituent, or a $C_1$–$C_6$ alkoxy;

$R^2$ is a hydrogen atom, a halogen atom, a $C_1$–$C_6$ alkoxy, a phenyl-($C_1$–$C_6$) alkoxy, hydroxy, a $C_1$–$C_6$ alkyl, an amino having optionally a $C_1$–$C_6$ alkyl substituent, a carbamoyl-substituted $C_1$–$C_6$ alkoxy, an amino-substituted $C_1$–$C_6$ alkoxy having optionally a $C_1$–$C_6$ alkyl substituent, or a benzoyloxy which has optionally a halogen substituent on the phenyl ring;

$R^3$ is a group of the formula:

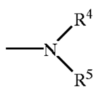

or a group of the formula:

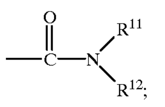

$R^4$ is a hydrogen atom, a benzoyl which has optionally a halogen substituent on the phenyl ring or a $C_1$–$C_6$ alkyl;

$R^5$ is a group of the formula:

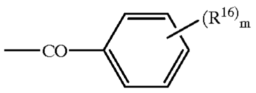

wherein $R^{16}$ is a halogen atom, a $C_1$–$C_6$ alkyl which has optionally a substituent selected from a halogen atom and hydroxy, hydroxy, a $C_1$–$C_6$ alkoxy, a $C_1$–$C_6$ alkanoyloxy, a $C_1$–$C_6$ alkylthio, a $C_1$–$C_6$ alkanoyl, carboxy, a $C_1$–$C_6$ alkoxycarbonyl, a cyano; a nitro, an amino which has optionally a substituent selected from a $C_1$–$C_6$ alkyl and a $C_1$–$C_6$ alkanoyl, a phenyl, a $C_3$–$C_8$ cycloalkyl, a $C_2$–$C_6$ alkanoyloxy-substituted $C_1$–$C_6$ alkoxy, a carboxy-substituted $C_1$–$C_6$ alkoxy, a halogen-substituted $C_1$–$C_6$ alkoxy, a carbamoyl-substituted $C_1$–$C_6$ alkoxy, a hydroxy-substituted $C_1$–$C_6$ alkoxy, a $C_1$–$C_6$ alkoxycarbonyl-substituted $C_1$–$C_6$ alkoxy, a phthalimido-substituted $C_1$–$C_6$ alkoxy; an aminocarbonyl-($C_1$–$C_6$) alkoxy having a $C_1$–$C_6$ alkyl substituent; or a group of the formula:

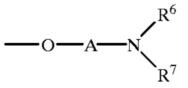

wherein A is a $C_1$–$C_6$ alkylene, and $R^6$ and $R^7$ are the same or different and are each a hydrogen atom, a $C_1$–$C_6$ alkyl having optionally a hydroxy substituent, a $C_1$–$C_6$ alkanoyl or benzoyl, or $R^6$ and $R^7$ may bind together with the nitrogen atom to which they are bonded to form a 5- or 6-membered saturated heterocyclic group with or without an intervening nitrogen or oxygen atom wherein the heterocyclic group is one member selected from the group consisting of pyrrolidinyl, piperidinyl, piperazinyl and morpholino, and has optionally a substituent selected from piperidinyl and a $C_1$–$C_6$ alkyl; and m is an integer of 0 to 3, or $R^5$ is a phenyl-($C_1$–$C_6$) alkoxycarbonyl, a $C_1$–$C_6$ alkanoyl, a phenyl-($C_2$–$C_6$) alkanoyl, a $C_3$–$C_8$ cycloalkyl-($C_2$–$C_6$) alkanoyl, a $C_3$–$C_8$ cycloalkylcarbonyl, tricyclo(3.3.1.1)decanylcarbonyl, naphthylcarbonyl, pyridylcarbonyl, fulroyl, thenoyl, a phenoxy-($C_2$–$C_6$) alkanoyl which phenyl ring has optionally 1 to 3 substituents selected from a $C_1$–$C_6$ alkyl, a $C_1$–$C_6$ alkoxy and an amino having optionally a $C_1$–$C_6$ alkanoyl substituent, a phthalimido-substituted $C_2$–$C_6$ alkanoyl, a $C_1$–$C_6$ alkoxycarbonyl-($C_2$–$C_6$) alkanoyl, a carboxy-($C_2$–$C_6$) alkanoyl, a naphthyloxy-($C_2$–$C_6$) alkanoyl, a halogen-substituted $C_1$–$C_6$ alkanoyl, a group of the formula:

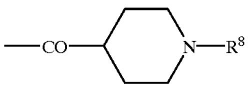

wherein $R^8$ is a hydrogen atom, a $C_1$–$C_6$ alkyl, a phenyl-($C_1$–$C_6$) alkoxycarbonyl, a carbamoyl-($C_1$–$C_6$) alkyl, an amino-($C_2$–$C_6$) alkanoyl having optionally a $C_1$–$C_6$ alkyl substituent, or a $C_1$–$C_6$ alkanoyl, an anilinocarbonyl which has optionally a $C_1$–$C_6$ alkyl substituent on the phenyl ring, phenoxycarbonyl, a phenylsulfonyl which has optionally a substituent selected from a halogen atom and a $C_1$–$C_6$ alkyl on the phenyl ring, quinolylsulfonyl, or a group of the formula:

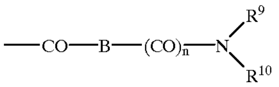

wherein B is a $C_1$–$C_6$ alkylene, n is an integer of 0 or 1, and $R^9$ and $R^{10}$ are the same or different and are each a hydrogen atom, a $C_1$–$C_6$ alkyl having optionally a hydroxy substituent, a $C_3$–$C_8$ cycloalkyl, a phenyl-($C_1$–$C_6$) alkyl, a $C_1$–$C_6$ alkanoyl, a $C_2$–$C_6$ alkenyl, a phenoxy-($C_1$–$C_6$) alkyl, a phenyl which has optionally 1 to 3 substituents selected from an amino-($C_1$–$C_6$) alkyl having optionally a $C_1$–$C_6$ alkanoyl substituent, a $C_1$–$C_6$ alkyl, a $C_1$–$C_6$ alkoxy and a halogen atom, a phthalimido-substituted $C_1$–$C_6$ alkyl, an amino-($C_1$–$C_6$) alkyl having optionally a $C_1$–$C_6$ alkanoyl substituent, a $C_2$–$C_6$ alkynyl, or an amino-($C_1$–$C_6$) alkyl having optionally a $C_1$–$C_6$ alkyl substituent, or $R^9$ and $R^{10}$ may bind together with the nitrogen atom to which they are bonded to form a 5- or 6-membered saturated heterocyclic group with or without being intervened with a nitrogen or an oxygen atom wherein the heterocyclic group is one member selected from the group consisting of pyrrolidinyl, piperidinyl, piperazinyl and morpholino, and has optionally a substituent selected from a $C_1$–$C_6$ alkyl, a $C_1$–$C_6$ alkoxycarbonyl and piperidinyl, $R^{11}$ is a hydrogen atom or a $C_1$–$C_6$ alkyl, $R^{12}$ is a $C_3$–$C_8$ cycloalkyl, or a phenyl which has optionally 1 to 3 substituents selected from a $C_1$–$C_6$ alkoxy, a $C_1$–$C_6$ alkyl and a halogen atom, W is a group of the formula: $—(CH_2)_p—$ wherein p is an integer of 3 to 5, or a group of the formula: $—CH{=}CH—(CH_2)_q—$ wherein q is an integer of 1 to 3, wherein one of the $CH_2$ groups associated with the formula $CH_2$ associated with the $—(CH_2)_p—$ and the $—CH{=}CH—(CH_2)_q—$ is replaced by a group of the formula:

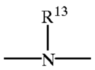

wherein $R^{13}$ is a hydrogen atom, a $C_3$–$C_8$ cycloalkyl, or a $C_1$–$C_6$ alkyl, and further said $—(CH_2)_p—$ group and said $—CH{=}CH—(CH_2)_q—$ group having optionally 1 to 3 substituents selected from a $C_1$–$C_6$ alkyl having optionally a hydroxy substituent, a $C_1$–$C_6$ alkoxycarbonyl, carboxy, hydroxy, oxo, a $C_1$–$C_6$ alkanoyloxy having optionally a halogen substituent, an amino-($C_1$–$C_6$) alkyl having optionally a substituent selected from a $C_1$–$C_6$ alkyl and a $C_1$–$C_6$ alkanoyl, a $C_1$–$C_6$ alkanoyloxy-substituted $C_1$–$C_6$ alkyl, a $C_1$–$C_6$ alkylsulfonyloxy-($C_1$–$C_6$) alkyl, an azido-($C_1$–$C_6$) alkyl, a group of the formula:

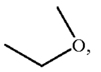, an aminocarbonyloxy having optionally a $C_1$–$C_6$ alkyl substituent, a $C_1$–$C_6$ alkoxy, a $C_1$–$C_6$ alkoxycarbonyl-substituted $C_1$–$C_6$ alkoxy, a carboxy-substituted $C_1$–$C_6$ alkoxy, an aminocarbonyl-($C_1$–$C_6$) alkoxy having optionally a $C_1$–$C_6$ alkyl substituent, an amino-($C_1$–$C_6$) alkoxy having optionally a substituent selected from a $C_1$–$C_6$ alkyl and a $C_1$–$C_6$ alkanoyl, a phthalimido-substituted $C_1$–$C_6$ alkoxy, hydroxyimino, a $C_1$–$C_6$ alkanoyloxy-imino, a $C_1$–$C_6$ alkylidene, a halogen atom, azido, sulfoxyimino, a group of the formula:

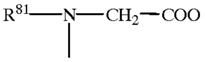

wherein $R^{81}$ is a hydrogen atom or a $C_1$–$C_6$ alkyl, provided that said

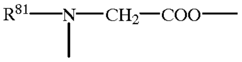

binds to said $—(CH_2)_p—$ or said $—CH{=}CH—(CH_2)_q—$ to form a 6-membered ring, a group of the formula:

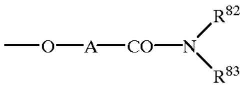

wherein A is as defined above in this claim, and $R^{82}$ and $R^{83}$ are the same or different and are each a hydrogen atom, a $C_1$–$C_6$ alkyl, a carbamoyl-substituted $C_1$–$C_6$ alkyl, a hydroxy-substituted $C_1$–$C_6$ alkyl, or a pyridyl-($C_1$–$C_6$) alkyl, or $R^{82}$ and $R^{83}$ may bind together with the nitrogen atom to which they are bonded to form a 5- or 6-membered saturated heterocyclic group with or without being intervened with a nitrogen, oxygen or sulfur atom wherein the heterocyclic group is one member selected from the group consisting of pyrrolidinyl, piperidinyl, piperazinyl, morpholino, and thiomorpholino, and has optionally a substituent selected from oxo, a $C_1$–$C_6$ alkyl, a $C_1$–$C_6$ alkanoyl, and carbamoyl, and a group of the formula:

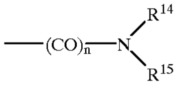

wherein n is as defined above in this claim, and $R^{14}$ and $R^{15}$ are the same or different and are each a hydrogen atom, a $C_1$–$C_6$ alkyl, a $C_2$–$C_6$ alkenyl, a $C_1$–$C_6$ alkanoyl, a $C_3$–$C_8$ cycloalkyl, an oxiranyl-substituted $C_1$–$C_6$ alkyl, a $C_1$–$C_6$ alkyl having 1 to 2 substituents selected from a $C_1$–$C_6$ alkoxy, hydroxy and an amino having optionally a $C_1$–$C_6$ alkyl substituent, a phenyl-($C_1$–$C_6$) alkyl, a pyridyl-($C_1$–$C_6$) alkyl, a $C_1$–$C_6$ alkylsulfonyl, benzoyl, a $C_1$–$C_6$ alkoxycarbonyl, anilinocarbonyl, an aminocarbonyl having optionally a $C_1$–$C_6$ alkyl substituent, a cyano-substituted $C_1$–$C_6$ alkyl, a $C_1$–$C_6$ alkoxycarbonyl-substituted $C_1$–$C_6$ alkyl, a carbamoyl-substituted $C_1$–$C_6$ alkyl, a carboxy-substituted $C_1$–$C_6$ alkyl, a tetrahydropyranyloxy-substituted $C_1$–$C_6$ alkyl, a $C_1$–$C_6$ alkanoyloxy-substituted $C_1$–$C_6$ alkyl, a piperidinyl having optionally a phenyl-($C_1$–$C_6$) alkyl substituent on the piperidine ring, a halogen substituted $C_1$–$C_6$ alkanoyl, an imidazolyl-substituted $C_2$–$C_6$ alkanoyl, an amino-($C_2$–$C_6$) alkanoyl having optionally a substituent selected from a $C_1$–$C_6$ alkyl and a $C_1$–$C_6$ alkoxycarbonyl, an aminocarbonyl-($C_1$–$C_6$) alkyl having optionally a $C_1$–$C_6$ alkyl substituent, or a phenyl-($C_1$–$C_6$) alkoxycarbonyl, or $R^{14}$ or $R^{15}$ may bind together with the nitrogen atom to which they are bonded to form a 5- or 6-membered saturated heterocyclic group with or without being intervened with a nitrogen or oxygen atom, wherein the heterocyclic group is one member selected from the group consisting of pyrrolidinyl, piperidinyl, piperazinyl, and morpholino, and may optionally have a substituent selected from a $C_1$–$C_6$ alkyl, a phenyl-($C_1$–$C_6$) alkyl or a $C_1$–$C_6$ alkanoyl, and a pharmaceutically acceptable salt thereof.

2. The method according to claim 1, wherein W is a group of the formula: $-(CH_2)_p-$ wherein p is an integer of 3 to 5, and one of the $CH_2$ groups is replaced by a group of the formula:

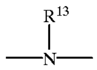

wherein $R^{13}$ is a hydrogen atom, a $C_3$–$C_8$ cycloalkyl, or a $C_1$–$C_6$ alkyl.

3. The method according to claim 1, wherein W is a group of the formula: $-CH{=}CH-(CH_2)_q-$ wherein q is an integer of 1–3 and one of the $CH_2$ groups is replaced by a group of the formula:

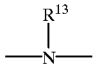

wherein $R^{13}$ is a hydrogen atom, a $C_3$–$C_8$ cycloalkyl, or a $C_1$–$C_6$ alkyl.

4. The method according to claim 2, wherein p in the group of the formula: $-(CH_2)_p-$ is 3.

5. The method according to claim 2, wherein p in the group of the formula: $-(CH_2)_p-$ is 4.

6. The method according to claim 2, wherein p in the group of the formula: $-(CH_2)_p-$ is 5.

7. The method according to claim 5, wherein the heterocyclic group of the formula:

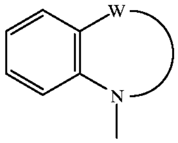

is 2,3,4,5-tetrahydro-1H-1,4-benzodiazepine.

8. The method according to claim 1, wherein the benzoheterocyclic compound is 1-[4-(2-mehtylbenzoylamino) benzoyl]-4-methyl-2,3,4,5-tetrahydro-1H-benzodiazepine.

9. The method according to claim 1, wherein the heterocyclic group of the formula:

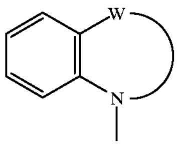

is 2,3,4,5-tetrahydro-1H-1,5-benzodiazepine.

* * * * *

UNITED STATES PATENT AND TRADEMARK OFFICE

CERTIFICATE OF CORRECTION

PATENT NO. : 5,985,869 Page 1 of 1
APPLICATION NO. : 08/893925
DATED : November 16, 1999
INVENTOR(S) : Hidenori Ogawa et al.

It is certified that error appears in the above-identified patent and that said Letters Patent is hereby corrected as shown below:

In the first line of the Specification:
This is a divisional of application Ser. No. 08/474,544 filed Jun. 7, 1995 (now U.S. Pat. No. 5,753,677 issued May 19, 1998), which is a divisional of application Ser. No. 08/076,804 filed Jun. 10, 1993 (now U.S. Pat. No. 5,559,230 issued Sep. 24, 1996), which is a Divisional of application Ser. No. 07/851,541 filed Mar. 13, 1992 (now U.S. Pat. No. 5,258,510 issued Nov. 2, 1993), which is a Continuation-In-Part of application Ser. No. 07/762,015 filed Jun. 19, 1991 (now Abandoned) which is a national stage of PCT/~~JP80~~JP90/01340, filed Oct. 18, 1990, each of which is incorporated in its entirety by reference.

Signed and Sealed this

Seventeenth Day of April, 2007

JON W. DUDAS
*Director of the United States Patent and Trademark Office*